(12) United States Patent
Wei et al.

(10) Patent No.: US 8,946,439 B2
(45) Date of Patent: Feb. 3, 2015

(54) AMIDE COMPOUNDS, COMPOSITIONS AND USES THEREOF

(75) Inventors: Zhi-Liang Wei, Foster City, CA (US); Sumithra Gowlugari, Hayward, CA (US); Carl Kaub, San Diego, CA (US); Zhan Wang, Palo Alto, CA (US); Yeyu Cao, Foster City, CA (US); John Kincaid, Hayward, CA (US)

(73) Assignee: Evotec AG, Hamburg (DE)

( * ) Notice: Subject to any disclaimer, the term of this patent is extended or adjusted under 35 U.S.C. 154(b) by 555 days.

(21) Appl. No.: 12/312,749

(22) PCT Filed: Feb. 27, 2009

(86) PCT No.: PCT/US2009/001249
§ 371 (c)(1),
(2), (4) Date: Nov. 19, 2010

(87) PCT Pub. No.: WO2009/110985
PCT Pub. Date: Sep. 11, 2009

(65) Prior Publication Data
US 2011/0065681 A1 Mar. 17, 2011

Related U.S. Application Data

(60) Provisional application No. 61/067,590, filed on Feb. 29, 2008, provisional application No. 61/124,531, filed on Apr. 17, 2008, provisional application No. 61/116,290, filed on Nov. 19, 2008, provisional application No. 61/156,905, filed on Feb. 26, 2009.

(51) Int. Cl.
| | | |
|---|---|---|
| *C07D 401/12* | (2006.01) | |
| *C07D 401/14* | (2006.01) | |
| *A61K 31/166* | (2006.01) | |
| *A61K 31/40* | (2006.01) | |
| *A61K 31/4427* | (2006.01) | |
| *A61K 31/444* | (2006.01) | |
| *A61P 19/02* | (2006.01) | |
| *C07D 213/56* | (2006.01) | |
| *C07D 277/30* | (2006.01) | |
| *C07D 205/04* | (2006.01) | |
| *C07D 317/48* | (2006.01) | |
| *C07D 213/61* | (2006.01) | |
| *C07D 333/54* | (2006.01) | |

(Continued)

(52) U.S. Cl.
CPC .......... *C07D 213/643* (2013.01); *C07D 213/56* (2013.01); *C07D 277/30* (2013.01); *C07D 205/04* (2013.01); *C07D 401/12* (2013.01); *C07D 317/48* (2013.01); *C07D 213/61* (2013.01); *C07D 333/54* (2013.01); *C07D 231/12* (2013.01); *C07D 241/12* (2013.01); *C07D 265/36* (2013.01); *C07D 239/47* (2013.01); *C07D 249/08* (2013.01); *C07D 239/26* (2013.01); *C07D 471/04* (2013.01); *C07D 263/56* (2013.01); *C07D 401/14* (2013.01); *C07D 413/04* (2013.01); *C07D 231/16* (2013.01); *C07D 239/34* (2013.01); *C07D 403/12* (2013.01); *C07D 489/04* (2013.01); *C07D 295/104* (2013.01); *C07D 417/12* (2013.01); *C07D 215/12* (2013.01)
USPC ........... 546/340; 564/151; 514/357; 514/277; 514/615

(58) Field of Classification Search
USPC ............ 546/340; 564/161; 514/357, 277, 615
See application file for complete search history.

(56) References Cited

U.S. PATENT DOCUMENTS

| | | |
|---|---|---|
| 2,731,469 A | 1/1956 | Krimmel |
| 4,916,145 A | 4/1990 | Tilley et al. |

(Continued)

FOREIGN PATENT DOCUMENTS

| | | |
|---|---|---|
| JP | 64-013082 | 1/1989 |
| JP | 64-013083 | 1/1989 |

(Continued)

OTHER PUBLICATIONS

Wolff Manfred E. "Burger's Medicinal Chemistry, 5ed, Part 1", John Wiley & Sons, 1995, pp. 975-977.*

(Continued)

*Primary Examiner* — Venkataraman Balasubramanian
(74) *Attorney, Agent, or Firm* — Klauber & Jackson LLC

(57) ABSTRACT

Compounds are provided according to formula 1:

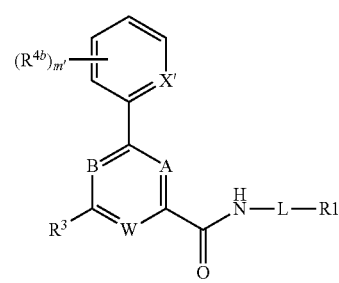

where A, B, W, X', L, $R^1$, $R^3$, $R^{4b}$, and m' are as defined herein. Provided compounds and pharmaceutical compositions thereof are useful for the prevention and treatment of a variety of conditions in mammals including humans, including by way of non-limiting example, pain, inflammation, cognitive disorders, anxiety, depression, and others.

25 Claims, No Drawings

(51) Int. Cl.

| | | |
|---|---|---|
| *C07D 231/12* | (2006.01) | |
| *C07D 241/12* | (2006.01) | |
| *C07D 265/36* | (2006.01) | |
| *C07D 239/47* | (2006.01) | |
| *C07D 249/08* | (2006.01) | |
| *C07D 239/26* | (2006.01) | |
| *C07D 471/04* | (2006.01) | |
| *C07D 263/56* | (2006.01) | |
| *C07D 413/04* | (2006.01) | |
| *C07D 231/16* | (2006.01) | |
| *C07D 239/34* | (2006.01) | |
| *C07D 403/12* | (2006.01) | |
| *C07D 489/04* | (2006.01) | |
| *C07D 213/643* | (2006.01) | |
| *C07D 295/104* | (2006.01) | |
| *C07D 417/12* | (2006.01) | |
| *C07D 215/12* | (2006.01) | |

(56) References Cited

U.S. PATENT DOCUMENTS

| | | |
|---|---|---|
| 2010/0152203 A1 | 6/2010 | Chen et al. |
| 2010/0168070 A1 | 7/2010 | Heine et al. |
| 2010/0324056 A1 | 12/2010 | Broka et al. |
| 2010/0324069 A1 | 12/2010 | Chen et al. |

FOREIGN PATENT DOCUMENTS

| | | |
|---|---|---|
| WO | 9725310 | 7/1997 |
| WO | 9725351 | 7/1997 |
| WO | WO 97/25310 | 7/1997 |
| WO | WO 02/22584 | 3/2002 |
| WO | 02070469 | 9/2002 |
| WO | WO 02/070469 | 9/2002 |
| WO | 02904767 | 11/2002 |
| WO | WO02/094767 | 11/2002 |
| WO | 03045913 | 6/2003 |
| WO | 03097617 | 11/2003 |
| WO | 2004052921 | 6/2004 |
| WO | 2005/032471 | 4/2005 |
| WO | 2005113484 | 12/2005 |
| WO | WO 2005/113484 | 12/2005 |
| WO | 2006114774 | 11/2006 |
| WO | 2007020194 | 2/2007 |
| WO | WO 2007/017510 | 2/2007 |
| WO | WO 2007/017511 | 2/2007 |
| WO | WO2007/020194 | 2/2007 |
| WO | 2007061930 | 5/2007 |
| WO | 2007115408 | 10/2007 |
| WO | WO2007/115408 | 10/2007 |
| WO | 2008000645 | 1/2008 |
| WO | 2008011131 | 1/2008 |
| WO | 2008023159 | 2/2008 |
| WO | 2008044217 | 4/2008 |
| WO | WO2008/055840 | 5/2008 |
| WO | WO 2008/119773 | 10/2008 |
| WO | 2009/058298 | 5/2009 |
| WO | WO2009/058298 | 5/2009 |
| WO | WO 2009/058299 | 5/2009 |
| WO | 2009/077385 | 6/2009 |
| WO | 2009077365 A1 | 6/2009 |
| WO | 2009077367 A1 | 6/2009 |
| WO | WO 2009/077366 | 6/2009 |
| WO | WO 2009/077371 | 6/2009 |
| WO | 2010051188 | 5/2010 |
| WO | 2010111058 A1 | 9/2010 |
| WO | 2010111059 A1 | 9/2010 |
| WO | 2010111060 A1 | 9/2010 |
| WO | 2010149541 | 12/2010 |

OTHER PUBLICATIONS

Banker, G.S. et al, "Modern Pharmaceutices, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Hulikal, V. Deuterium Labeled Compounds in Drug Discovery Process, 2010. Abstract provided-see also www. hwb.gov.in/htmldocs/nahwd201 O/L15.pdf.*
Pimlott SL., Nucl. Med. Commun. 26(3): 183-188, 2005 (PubMed Abstract provided).*
Geyer et al., British Journal of Pharmacology (2010), 160, 1387-1398.*
Sitkovsky et al., British Journal of Pharmacology, 153, 5457-5464, 2008.*
Baraldi et al., European Journal of Medicinal Chemistry 38: 367-382, 2003.*
Gao et al., Expert. Opin. Emerging Drugs 12(3): 479-492, 2008.*
Cecil Textbook of Medicine, edited by Bennet, J.C., and Plum F., 20th edition, vol. 1, 1004-101 O, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Registry Copyright (C) 2008 ACS Nos. 1069724-13-5; 1069510-47-9; 1067071-28-6; and 1066932-79-3.
Myakushkene, et al., Pharmaceutical Chemistry Journal (Translation of Khimiko-Farmatsevticheskii Zhurnal), "Synthesis and Antiinflammatory Activity of 4,6-Diphenyl-2-Pyrimidinecarboxylic Acid Amides," 1999; 33(1): 24-26.
Giardina, et al., Il Farmaco, "Replacement of the quinoline system in 2-phenyl-4-quinolinecarboxamide NK-3 receptor antagonists," 1999; 54(6): 364-374.
Miyasaka, et al., Journal of the Chemical Society, Transactions 1: Oraganic and Bio-Organic Chemistry, "Synthesis of Novel Streptonigrin 2-Amide Derivatives with 3,3'-(Phenylphosphoryl)bis(1,3-thiazolidine-2-thione)," 1986; 1986(3): 479-482.
Carrion, et al., Tetrahedron, "Cyclization of 2-dicyanomethylene-1,2-dihydropyridine-3-carbonitriles with amines: a mechanistic rationalization," 2007; 63(1): 215-223.
Severina, et al., European Journal of Pharmacology, "Antitumor antibiotic streptonigrin and its derivatives as inhibitors of nitric oxide-dependent activation of soluble guanylyl cyclase," 2004; 483(2-3): 127-132.

* cited by examiner

AMIDE COMPOUNDS, COMPOSITIONS AND USES THEREOF

RELATED APPLICATIONS

The present application is a National Stage application claiming the priority of PCT/US2009/001249 filed Feb. 27, 2009 which in turn claims the benefit under 35 U.S.C. §119 of U.S. Provisional Application Ser. No. 61/155,905, filed Feb. 26, 2009, Ser. No. 61/116,290, filed Nov. 19, 2008; Ser. No. 61/124,531, filed Apr. 17, 2008; and Ser. No. 61/067,590 filed Feb. 29, 2009. Applicants claim the benefit of all applications, and the contents of all of said applications are hereby incorporated herein by reference in their entireties.

FIELD

Provided herein are biphenyl and pyridylphenyl amide compounds, and pharmaceutical compositions comprising such compounds. Also provided are methods for preventing and/or treating conditions in mammals, such as (but not limited to) arthritis, Parkinson's disease, Alzheimer's disease, asthma, myocardial infarction, pain syndromes (acute and chronic or neuropathic), neurodegenerative disorders, schizophrenia, cognitive disorders, anxiety, depression, inflammatory bowel disease and autoimmune disorders, and promoting neuroprotection, using the compounds and pharmaceutical compositions provided herein.

BACKGROUND

Therapeutic strategies for the effective management of pain and central nervous system disorders or diseases are sought.

International Patent Application, Publication Number WO 08/000,645 discloses tetrazole-substituted arylamides and related compounds which are said to be $P2X_2$ and $P2X_{2/3}$ receptor modulators.

International Patent Application, Publication Number WO 08/055,840 discloses thiazole and oxazole substituted arylamides and related compounds which are said to be $P2X_2$ and $P2X_{2/3}$ receptor modulators.

US 2007049609, US 2007049610, US 2007049758, and US 2007049534 describe certain diaminopyrimidines as $P2X_3$ and $P2X_{2/3}$ modulators.

US 2007037974 describes heterocyclic inhibitors of $P2X_3$ useful for treating pain, genitourinary, gastrointestinal, and respiratory disorders.

WO 06/119504 describes fused heterocyclic compounds as $P2X_3$ and $P2X_{2/3}$ modulators for use in the treatment of various diseases. WO04/56774 describes certain substituted biphenyl-4-carboxylic acid arylamide analogues having possible application as receptor modulators.

WO 08/119,773 describes amide derivatives as inhibitors of aspartyl proteases and their use in the treatment of Alzheimer's disease.

WO 05/065195 describes certain phenylamides and pyridylamides as β-secretase inhibitors.

WO 02/070469 describes certain substituted sulfonylalkylcarboxamides as selective pde3b inhibitors WO 04/039753 describes certain benzoic acids and related compounds as EP1 receptor antagonists for the treatment of prostaglandin mediated diseases.

Also, WO03/104230 describes certain bicyclic pyrimidine derivatives, and US Published Application Serial No. 20030092908 and WO02/087513 describe fused heterocyclic PDE7 inhibitors.

U.S. Pat. Nos. 3,424,760 and 3,424,761 both describe a series of 3-ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively. International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fluorophenyl)-N-isoquinolin-5-yl-5-methyl-1H-pyrazole-3-carboxamide, 1-(2-chloro-5-trifluoromethylphenyl)-N-isoquinolin-5-yl-5-methyl-1N-pyrazole-3-carboxamide, 5-methyl-N-(3-methylisoquinolin-5-yl)-1-[3-(trifluoromethyl)phenyl]-1N-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino)ethyl]-1,2-dihydro-4-methyl-2-oxo-7-quinolinyl]-4-phenyl-1-piperazinecarboxamide.

SUMMARY

Biphenyl and pyridylphenyl amide compounds, and pharmaceutical compositions thereof, having potency and selectivity in the prevention and treatment of conditions that have been associated with neurological and inflammatory disorders and dysfunctions are provided herein.

In particular, compounds, pharmaceutical compositions and methods provided are useful to treat, prevent or ameliorate a range of conditions in mammals such as, but not limited to, pain of various genesis or etiology, for example acute, chronic, inflammatory and neuropathic pain, dental pain and headache (such as migraine, cluster headache and tension headache). In some embodiments, compounds, pharmaceutical compositions and methods provided are useful for the treatment of inflammatory pain and associated hyperalgesia and allodynia. In some embodiments, compounds, pharmaceutical compositions and methods provided are useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). In some embodiments, compounds, pharmaceutical compositions and methods provided are useful as anti-inflammatory agents for the treatment of arthritis, and as agents to treat Parkinson's Disease, Alzheimer's Disease, asthma, myocardial infarction, neurodegenerative disorders, inflammatory bowel disease and autoimmune disorders, renal disorders, obesity, gating disorders, cancer, schizophrenia, epilepsy, sleeping disorders, cognitive disorders, depression, anxiety, blood pressure, and lipid disorders.

Accordingly, in one aspect, compounds are provided that have formula 1:

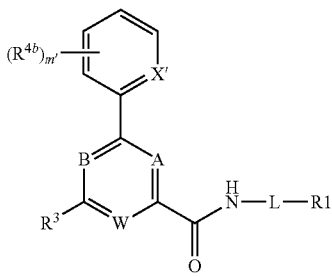

1 wherein
each of A, B, and W are independently selected from $CR^4$;
X' is selected from $CR^{4a}$ and N;
L is $-C(R^{2a}R^{2b})-$;
$R^1$ is selected from substituted or unsubstituted aryl, substituted or unsubstituted heteroaryl, hydroxy $C_1$-$C_4$ alkyl, $C_3$-$C_7$ cycloalkyl-$C_1$-$C_4$ alkyl, or 4-7 membered heterocycloalkyl-$C_1$-$C_4$ alkyl;
each of $R^{2a}$ and $R^{2b}$ is independently selected from hydrogen, $C_1$-$C_4$ alkyl, or hydroxy $C_1$-$C_4$ alkyl;
$R^3$ is substituted or unsubstituted $C_1$-$C_6$ alkyl; CH(OH)$R^{3a}$, $OR^{3a}$, CN, $COR^{3a}$, $COOR^{3a}$, $SOR^{3a}$, $SO_2R^{3a}$, $CONR^{3a}R^{3b}$, $SONR^{3a}R^{3b}$, or $SO_2NR^{3a}R^{3b}$;
$R^{3a}$ is H, substituted or unsubstituted alkyl, substituted or unsubstituted cycloalkyl, substituted or unsubstituted heterocycloalkyl, substituted or unsubstituted aryl, or substituted or unsubstituted heteroaryl;
$R^{3b}$ is H, substituted or unsubstituted $C_1$-$C_6$ alkyl; or $R^{3a}$ and $R^{3b}$ join together to form a cycloheteroalkyl ring of 3-7 atoms;
each $R^4$ is independently selected from H, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, halo, nitro, and thiol;
each $R^{4a}$, and $R^{4b}$ is independently selected from H, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxy, substituted or unsubstituted alkoxycarbonyl, substituted or unsubstituted alkylarylamino, substituted or unsubstituted arylalkyloxy, substituted or unsubstituted amino, substituted or unsubstituted aryl, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol;
and subscript m' is selected from 0-4;
provided that
i) when $R^3$ is $CO_2Me$, $SO_2Ph$, or $OR^{3a}$; then $R^1$ is other than unsubstituted phenyl;
ii) when $R^3$ is $SO_2$-(4-methylpiperazin-1-yl) or is $SO_2$-(thiomorpholin-1-yl); and X' is CH; then $R^{4b}$ is other than H;
iii) when $R^3$ is Me, or methyl substituted with alkoxy; then $R^1$ is other than substituted phenyl;
iv) when $R^3$ is $CO_2H$; then $R^{4b}$ is Cl, F, Br, Me, Et, OMe, or $CF_3$;
v) when X' is $CR^{4a}$; $R^3$ is $CONR^{3a}R^{3b}$; and $R^{3a}$ IS H; then $R^{3b}$ is other than substituted n-pentyl, substituted pentynyl, substituted benzyl, substituted phenethyl, substituted thiophenylethyl, or substituted thiazolylethyl; and
vi) when $R^1$ is 5-6 membered heterocycloalkylmethyl, and $R^3$ is $CO_2Me$ or n-Pr; then $R^{4b}$ is other than Cl or 4-F;
or a pharmaceutically acceptable salt, N-oxide, solvate, prodrug, stereoisomer, tautomer or isotopic variant thereof.

In one particular embodiment, with respect to formula 1, each A, B, and W is CH.

In one particular embodiment, with respect to formula 1, L is selected from $-CH_2-$, $-CHMe-$, $-CMe_2-$, $-CH(CH_2OH)-$, and $-CH(CH_2CH_2OH)-$.

In one particular embodiment, with respect to formula 1, L is selected from $-CH_2-$, and $-CHMe-$.

In one particular embodiment, with respect to formula 1, the compound is according to formula 2a, 2b, 2c, 2d, 2e, 2f, 2g, 2h, or 2i:

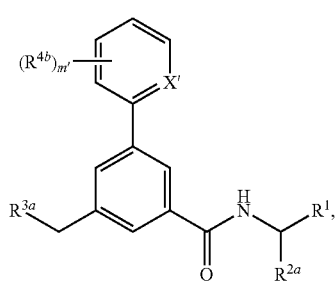

2a

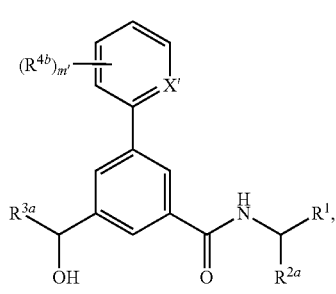

2b

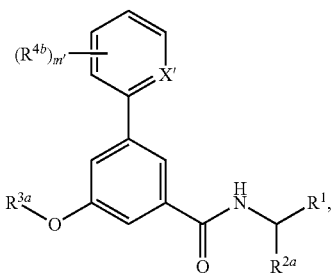

wherein

X', R¹, R³ᵃ, R³ᵇ, R⁴ᵃ; R⁴ᵇ, and m' are as in formula 1; and R²ᵃ is H, Me, CH₂OH, or CH₂CH₂OH.

or a pharmaceutically acceptable salt, solvate, N-oxide, prodrug, stereoisomer, tautomer or isotopic variant thereof.

In another aspect, pharmaceutical compositions are provided comprising a biphenyl and pyridylphenyl amide provided herein, and a pharmaceutical carrier, excipient or diluent. The pharmaceutical composition can comprise one or more of the compounds described herein.

It will be understood that compounds provided herein useful in the pharmaceutical compositions and treatment methods disclosed herein, can be pharmaceutically acceptable as prepared and used.

In another aspect, methods are provided for preventing, treating or ameliorating a condition from among those listed herein, and particularly, such condition as may be associated with, e.g., arthritis, asthma, myocardial infarction, lipid disorders, cognitive disorders, anxiety, schizophrenia, depression, memory dysfunctions such as Alzheimers disease, inflammatory bowel disease and autoimmune disorders, which method comprises administering to a mammal in need thereof an amount of one or more of the compounds as provided herein, or pharmaceutical composition thereof, effective to prevent, treat or ameliorate the condition.

In yet another aspect, methods are provided for preventing, treating or ameliorating a condition that gives rise to pain responses or that relates to imbalances in the maintenance of basal activity of sensory nerves in a mammal. The compounds provided herein have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-mastectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In one aspect, methods are provided for preventing, treating or ameliorating a neurodegenerative disease or disorder in a mammal. A neurodegenerative disease or disorder can, for example, be Parkinson's disease, Alzheimer's disease and multiple sclerosis; diseases and disorders which are mediated by or result in neuroinflammation such as, for example, encephalitis; centrally-mediated neuropsychiatric diseases and disorders such as, for example, depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders; itch/pruritus such as, for example, psoriasis; obesity; lipid disorders; cancer; and renal disorders Typically, the methods comprise administering an effective condition-treating or condition-preventing amount of one or more of the compounds as provided herein, or pharmaceutical composition thereof, to the mammal in need thereof.

In addition to the methods of treatment set forth above, the present invention extends to the use of any of the compounds of the invention for the preparation of medicaments, or as medicaments that may be administered for such treatments, as well as to such compounds for the treatments disclosed and specified.

In additional aspects, methods are provided for synthesizing the compounds described herein, with representative synthetic protocols and pathways described below. In certain embodiments, provided are methods of making enantiomerically pure compounds according to formula 1 by asymmetric synthesis. In certain embodiments, provided are methods of making enantiomerically pure compounds according to formula 1 by chiral resolution.

Other objects and advantages will become apparent to those skilled in the art from a consideration of the ensuing detailed description.

DETAILED DESCRIPTION OF THE PREFERRED EMBODIMENTS

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' or 'Alkanoyl' refers to a radical —C(O)$R^{20}$, where $R^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—$(CH_2)_t(C_6$-$C_{10}$ aryl), —C(O)—$(CH_2)_t$(5-10 membered heteroaryl), —C(O)—$(CH_2)_t(C_3$-$C_{10}$ cycloalkyl), and —C(O)—$(CH_2)_t$(4-10 membered heterocycloalkyl), wherein t is an integer from 0 to 4.

'Substituted Acyl' or 'Substituted Alkanoyl' refers to a radical —C(O)$R^{21}$, wherein $R^{21}$ is independently
  $C_1$-$C_8$ alkyl, substituted with halo or hydroxy; or
  $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted alkoxy, unsubstituted $C_1$-$C_4$ haloalkyl, unsubstituted hydroxyalkyl, or unsubstituted haloalkoxy or hydroxy.

'Acylamino' refers to a radical —$NR^{22}$C(O)$R^{23}$, where $R^{22}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl and $R^{23}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino. Particular exemplary 'acylamino' groups are —$NR^{24}$C(O)—$C_1$-$C_8$ alkyl, $NR^{24}$C(O)—$(CH_2)_t(C_6$-$C_{10}$ aryl), —$NR^{24}$C(O)—$(CH_2)_t$(5-10 membered heteroaryl), —$NR^{24}$C(O)—$(CH_2)_t$($C_3$-$C_{10}$ cycloalkyl), and —$(CH_2)_t$(4-10 membered heterocycloalkyl), wherein t is an integer from 0 to 4, and each $R^{24}$ independently represents H or $C_1$-$C_8$ alkyl.

'Substituted Acylamino' refers to a radical —$NR^{25}$C(O)$R^{26}$, wherein:
  $R^{25}$ is independently
    H, $C_1$-$C_8$ alkyl, substituted with halo or hydroxy; or
    $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and
  $R^{26}$ is independently
    H, $C_1$-$C_8$ alkyl, substituted with halo or hydroxy; or
    $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl;
  provided at least one of $R^{25}$ and $R^{26}$ is other than H.

'Acyloxy' refers to a radical —OC(O)$R^{27}$, where $R^{27}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—$(CH_2)_t$($C_6$-$C_{10}$ aryl), —C(O)—$(CH_2)_t$(5-10 membered heteroaryl), —C(O)—$(CH_2)_t$($C_3$-$C_{10}$ cycloalkyl), and —C(O)—$(CH_2)_t$(4-10 membered heterocycloalkyl), wherein t is an integer from 0 to 4.

'Substituted Acyloxy' refers to a radical —OC(O)$R^{28}$, wherein $R^{28}$ is independently $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkoxy' refers to the group —$OR^{29}$ where $R^{29}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of 'substituted' herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—$(CH_2)_t$($C_6$-$C_{10}$ aryl), —O—$(CH_2)_t$(5-10 membered heteroaryl), —O—$(CH_2)_t$($C_3$-$C_{10}$ cycloalkyl), and —O—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are $OCF_3$, $OCH_2CF_3$, $OCH_2Ph$, $OCH_2$-cyclopropyl, $OCH_2CH_2OH$, and $OCH_2CH_2NMe_2$.

'Alkoxycarbonyl' refers to a radical —C(O)—$OR^{30}$ where $R^{30}$ represents an $C_1$-$C_8$ alkyl, $C_3$-$C_{10}$ cycloalkyl, $C_3$-$C_{10}$ cycloalkylalkyl, 4-10 membered heterocycloalkylalkyl, aralkyl, or 5-10 membered heteroarylalkyl as defined herein. Exemplary "alkoxycarbonyl" groups are C(O)O—$C_1$-$C_8$ alkyl, —C(O)O—$(CH_2)_t$($C_6$-$C_{10}$ aryl), —C(O)O—$(CH_2)_t$(5-10 membered heteroaryl), —C(O)O—$(CH_2)_t$($C_3$-$C_{10}$ cycloalkyl), and —C(O)O—$(CH_2)_t$(4-10 membered heterocycloalkyl), wherein t is an integer from 1 to 4.

'Substituted Alkoxycarbonyl' refers to a radical —C(O)—$OR^{31}$ where $R^{31}$ represents:

$C_1$-$C_8$ alkyl, $C_3$-$C_{10}$ cycloalkyl, $C_3$-$C_{10}$ cycloalkylalkyl, or 4-10 membered heterocycloalkylalkyl, each of which is substituted with halo, substituted or unsubstituted amino, or hydroxy; or $C_6$-$C_{10}$ aralkyl, or 5-10 membered heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Aryloxycarbonyl' refers to a radical —C(O)—$OR^{32}$ where $R^{32}$ represents an $C_6$-$C_{10}$ aryl, as defined herein. Exemplary "aryloxycarbonyl" groups is —C(O)O—($C_6$-$C_{10}$ aryl).

'Substituted Aryloxycarbonyl' refers to a radical —C(O)—$OR^{33}$ where $R^{33}$ represents $C_6$-$C_{10}$ aryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Heteroaryloxycarbonyl' refers to a radical —C(O)—$OR^{34}$ where $R^{34}$ represents a 5-10 membered heteroaryl, as defined herein. An exemplary "aryloxycarbonyl" group is —C(O)O-(5-10 membered heteroaryl).

'Substituted Heteroaryloxycarbonyl' refers to a radical —C(O)—$OR^{35}$ where $R^{35}$ represents:

5-10 membered heteroaryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Alkoxycarbonylamino' refers to the group —$NR^{36}$C(O)$OR^{37}$, where $R^{36}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein, and $R^{37}$ is $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl, n-propyl, and n-butyl. Branched means that one or more lower alkyl groups such as methyl, ethyl, propyl or butyl is attached to a linear alkyl chain, exemplary branched chain groups include isopropyl, isobutyl, t-butyl and isoamyl.

'Substituted alkyl' refers to an alkyl group as defined above substituted with one or more of those groups recited in the definition of 'substituted' herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)$R^{20}$), alkoxy, alkoxycarbonyl, alkoxycarbonylamino (—NR"-alkoxycarbonyl or —NH—C(O)—$OR^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'''SO$_2$R", —SO$_2$NR"R", —C(O)R", —C(O)OR", —OC(O)R", —NR'''C(O)R", —C(O)NR"R''', —NR"R''', or —(CR'''R''')$_m$OR'''; wherein each R" is independently selected from H, $C_1$-$C_8$ alkyl, —$(CH_2)_t$($C_6$-$C_{10}$ aryl), —$(CH_2)_t$(5-10 membered heteroaryl), —$(CH_2)_t$($C_3$-$C_{10}$ cycloalkyl), and —$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted hydroxyalkyl, or unsubstituted haloalkoxy or hydroxy. Each of R''' and R'''' independently represents H or $C_1$-$C_8$ alkyl.

'Alkylene' refers to divalent saturated alkene radical groups having 1 to 11 carbon atoms and more particularly 1 to 6 carbon atoms which can be straight-chained or branched. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

'Substituted alkylene' refers to those groups recited in the definition of 'substituted' herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenyl' refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═$CH_2$), n-propenyl (—$CH_2$CH═$CH_2$), isopropenyl (—C($CH_3$)═$CH_2$), vinyl and substituted vinyl, and the like.

'Substituted alkenyl' refers to those groups recited in the definition of 'substituted' herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—, 'Alkenylene' refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═$CHCH_2$— and —C($CH_3$)═CH— and —CH═C($CH_3$)—) and the like.

'Alkynyl' refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—$CH_2$C≡CH), and the like.

'Substituted alkynyl' refers to those groups recited in the definition of 'substituted' herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Amino' refers to the radical —$NH_2$.

'Substituted amino' refers to an amino group substituted with one or more of those groups recited in the definition of 'substituted' herein, and particularly refers to the group —N($R^{38}$)$_2$ where each $R^{38}$ is independently selected from:

hydrogen, $C_1$-$C_8$ alkyl, $C_6$-$C_{10}$ aryl, 5-10 membered heteroaryl, 4-10 membered heterocycloalkyl, or $C_3$-$C_{10}$ cycloalkyl; or $C_1$-$C_8$ alkyl, substituted with halo or hydroxy; or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl) or —(CH$_2$)$_t$(4-10 membered heterocycloalkyl) wherein t is an integer between 0 and 8, each of which is substituted by unsubstituted $C_1$-$C_4$ alkyl, halo, unsubstituted $C_1$-$C_4$ alkoxy, unsubstituted haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

When both $R^{38}$ groups are hydrogen, —N($R^{38}$)$_2$ is an amino group. Exemplary 'substituted amino' groups are —$NR^{39}$—$C_1$-$C_8$ alkyl, —$NR^{39}$—(CH$_2$)$_t$($C_6$-$C_{10}$ aryl), —$NR^{39}$—(CH$_2$)$_t$(5-10 membered heteroaryl), —$NR^{39}$—(CH$_2$)$_t$($C_3$-$C_{10}$ cycloalkyl), and —$NR^{39}$—(CH$_2$)$_t$(4-10 membered heterocycloalkyl), wherein t is an integer from 0 to 4, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino and substituted dialkylamino as defined below.

'Alkylamino' refers to the group —$NHR^{40}$, wherein $R^{40}$ is $C_1$-$C_8$ alkyl.

'Substituted Alkylamino' refers to the group —$NHR^{41}$, wherein $R^{41}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted haloalkyl, unsubstituted $C_1$-$C_4$ hydroxyalkyl, or unsubstituted haloalkoxy or hydroxy.

'Alkylarylamino' refers to the group —$NR^{42}R^{43}$, wherein $R^{42}$ is aryl and $R^{43}$ is $C_1$-$C_8$ alkyl.

'Substituted Alkylarylamino' refers to the group —$NR^{44}R^{45}$, wherein $R^{44}$ is aryl and $R^{45}$ is $C_1$-$C_8$ alkyl; and the alkyl group is substituted with halo, substituted or unsubstituted amino, hydroxy, $C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Arylamino' means a radical —$NHR^{46}$ where $R^{46}$ is selected from $C_6$-$C_{10}$ aryl and 5-10 membered heteroaryl as defined herein.

'Substituted Arylamino' refers to the group —NHR$^{47}$, wherein R$^{47}$ is independently selected from C$_6$-C$_{10}$ aryl and 5-10 membered heteroaryl; and any aryl or heteroaryl groups present, may themselves be substituted by unsubstituted C$_1$-C$_4$ alkyl, halo, cyano, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Dialkylamino' refers to the group —NR$^{48}$R$^{49}$, wherein each of R$^{48}$ and R$^{49}$ are independently selected from C$_1$-C$_8$ alkyl.

'Substituted Dialkylamino' refers to the group —NR$^{50}$R$^{51}$, wherein each of R$^{59}$ and R$^{51}$ are independently selected from C$_1$-C$_8$ alkyl; and at least one of the alkyl groups is independently substituted with halo, hydroxy, C$_3$-C$_{10}$ cycloalkyl, 4-10 membered heterocycloalkyl, C$_6$-C$_{10}$ aryl, 5-10 membered heteroaryl, aralkyl or heteroaralkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_{1-4}$ haloalkyl, unsubstituted C$_1$-C$_4$ hydroxyalkyl, or unsubstituted C$_1$-C$_4$ haloalkoxy or hydroxy.

'Diarylamino' refers to the group —NR$^{52}$R$^{53}$, wherein each of R$^{52}$ and R$^{53}$ are independently selected from C$_6$-C$_{10}$ aryl.

'Aminosulfonyl' or 'Sulfonamide' refers to the radical —S(O$_2$)NH$_2$.

'Substituted aminosulfonyl' or 'substituted sulfonamide' refers to a radical such as —S(O$_2$)N(R$^{54}$)$_2$ wherein each R$^{54}$ is independently selected from:

H, C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy;

provided that at least one R$^{54}$ is other than H.

Exemplary 'substituted aminosulfonyl' or 'substituted sulfonamide' groups are —S(O$_2$)N(R$^{55}$)—C$_1$-C$_8$ alkyl, —S(O$_2$)N(R$^{55}$)—(CH$_2$)$_t$(C$_6$-C$_{10}$ aryl), —S(O$_2$)N(R$^{55}$)—(CH$_2$)$_t$(5-10 membered heteroaryl), —S(O$_2$)N(R$^{55}$)—(CH$_2$)$_t$(C$_3$-C$_{10}$ cycloalkyl), and —S(O$_2$)N(R$^{55}$)—(CH$_2$)$_t$(4-10 membered heterocycloalkyl), wherein t is an integer from 0 to 4; each R$^{55}$ independently represents H or C$_1$-C$_8$ alkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted C$_1$-C$_4$ alkyl, halo, cyano, unsubstituted C$_1$-C$_4$ alkoxy, unsubstituted haloalkyl, unsubstituted C$_1$-C$_4$ hydroxyalkyl, or unsubstituted haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

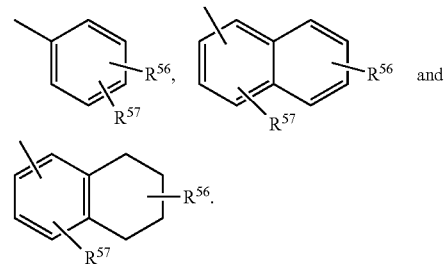

In these formulae one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocycloalkyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O or S. R$^{60}$ and R$^{61}$ are independently hydrogen, C$_1$-C$_8$ alkyl, C$_1$-C$_4$ haloalkyl, C$_3$-C$_{10}$ cycloalkyl, 4-10 membered heterocycloalkyl, C$_6$-C$_{10}$ aryl, substituted aryl, 5-10 membered heteroaryl.

'Fused Aryl' refers to an aryl having two of its ring carbon in common with a second aryl ring or with an aliphatic ring.

'Arylalkyloxy' refers to an —O-alkylaryl radical where alkylaryl is as defined herein.

'Substituted Arylalkyloxy' refers to an —O-alkylaryl radical where alkylaryl is as defined herein; and any aryl groups present, may themselves be substituted by unsubstituted C$_1$-C$_4$ alkyl, halo, cyano, unsubstituted C$_1$-C$_4$ alkoxy, unsubstituted C$_{1-4}$ haloalkyl, unsubstituted C$_1$-C$_4$ hydroxyalkyl, or unsubstituted C$_1$-C$_4$ haloalkoxy or hydroxy.

'Azido' refers to the radical —N$_3$.

'Carbamoyl or amido' refers to the radical —C(O)NH$_2$.

'Substituted Carbamoyl or substituted amido' refers to the radical —C(O)N(R$^{62}$)$_2$ wherein each R$^{62}$ is independently H, $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy;

provided that at least one $R^{62}$ is other than H.

Exemplary 'Substituted Carbamoyl' groups are —C(O)NR$^{64}$—$C_1$-$C_8$ alkyl, —C(O)NR$^{64}$—(CH$_2$)$_t$($C_6$-$C_{10}$ aryl), —C(O)N$^{64}$—(CH$_2$)$_t$(5-10 membered heteroaryl), —C(O)NR$^{64}$—(CH$_2$)$_t$($C_3$-$C_{10}$ cycloalkyl), and —C(O)NR$^{64}$—(CH$_2$)$_t$(4-10 membered heterocycloalkyl), wherein t is an integer from 0 to 4, each $R^{64}$ independently represents H or $C_1$-$C_8$ alkyl and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted haloalkoxy or hydroxy.

'Carboxy' refers to the radical —C(O)OH.

'Cycloalkyl' refers to cyclic non-aromatic hydrocarbyl groups having from 3 to 10 carbon atoms. Such cycloalkyl groups include, by way of example, single ring structures such as cyclopropyl, cyclobutyl, cyclopentyl, and cyclooctyl.

'Substituted cycloalkyl' refers to a cycloalkyl group as defined above substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g. cycloheteroalkenyl, and the like having from 1 to 5, and particularly from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

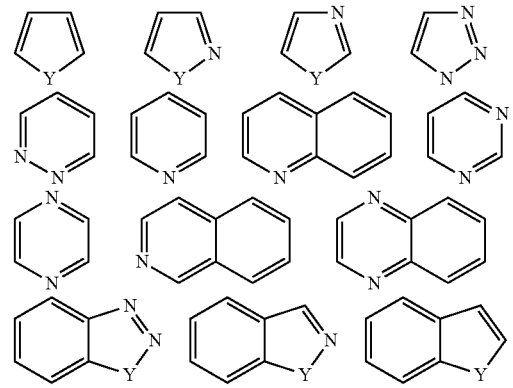

wherein each Y is selected from carbonyl, N, NR$^{65}$, O and S; and R$^{65}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative aryl having hetero atoms containing substitution include the following:

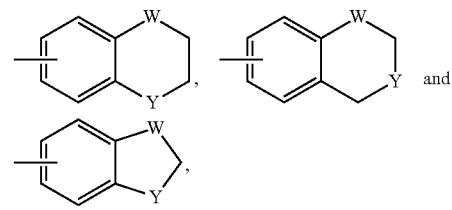

wherein each W is selected from C(R$^{66}$)$_2$, NR$^{66}$, O and S; and each Y is selected from carbonyl, NR$^{66}$, O and S; and R$^{66}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

As used herein, the term 'heterocycloalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

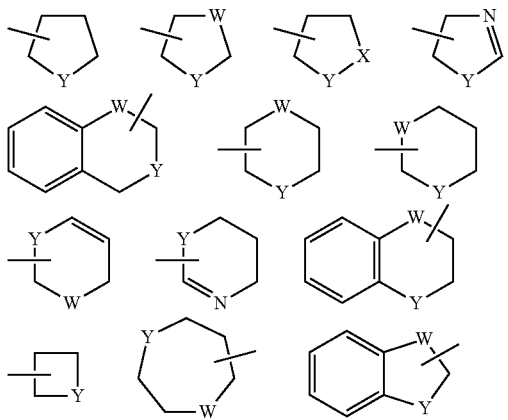

wherein each W is selected from $CR^{67}$, $C(R^{67})_2$, $NR^{67}$, O and S; and each Y is selected from $NR^{67}$, O and S; and $R^{67}$ is independently hydrogen, $C_1$-$C_8$ alkyl, $C_3$-$C_{10}$ cycloalkyl, 4-10 membered heterocycloalkyl, $C_6$-$C_{10}$ aryl, 5-10 membered heteroaryl, These heterocycloalkyl rings may be optionally substituted with one or more groups selected from the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

'Hydroxy' refers to the radical —OH.

'Nitro' refers to the radical —$NO_2$.

'Substituted' refers to a group in which one or more hydrogen atoms are each independently replaced with the same or different substituent(s). Typical substituents may be selected from the group consisting of:
halogen, —$R^{68}$, —O$^-$, =O, —$OR^{68}$, —$SR^{68}$, —$S^-$, =S, —$NR^{68}R^{69}$, =$NR^{68}$, —$CCl_3$, —$CF_3$, —CN, —OCN, —SCN, —NO, —$NO_2$, =$N_2$, —$N_3$, —$S(O)_2O^-$, —$S(O)_2$OH, —$S(O)_2R^{68}$, -$OS(O_2)O^-$, —$OS(O)_2R^{68}$, —$P(O)(O^-)_2$, —$C(O)(OR^{68})(O^-)$, —$OP(O)(OR^{68})(OR^{69})$, —$C(O)R^{68}$, —$C(S)R^{68}$, —$C(O)OR^{68}$, —$C(O)NR^{68}R^{69}$, —$C(O)O^-$, —$C(S)OR^{68}$, —$NR^{70}C(O)NR^{68}R^{69}$, $NR^{70}C(O)NR^{68}R^{69}$, —$NR^{71}C(NR^{70})NR^{68}R^{69}$ and —$C(NR^{70})NR^{68}R^{69}$;

wherein each $R^{68}$, $R^{69}$, $R^{70}$ and $R^{71}$ are independently:
hydrogen, $C_1$-$C_8$ alkyl, $C_6$-$C_{10}$ aryl, arylallyl, $C_3$-$C_{10}$ cycloalkyl, 4-10 membered heterocycloalkyl, 5-10 membered heteroaryl, heteroarylalkyl; or
$C_1$-$C_8$ alkyl substituted with halo or hydroxy; or
$C_6$-$C_{10}$ aryl, 5-10 membered heteroaryl, $C_6$-$C_{10}$ cycloalkyl or 4-10 membered heterocycloalkyl each of which is substituted by unsubstituted $C_1$-$C_4$ alkyl, halo, unsubstituted $C_1$-$C_4$ alkoxy, unsubstituted $C_1$-$C_4$ haloalkyl, unsubstituted hydroxyalkyl, or unsubstituted $C_1$-$C_4$ haloalkoxy or hydroxy.

In a particular embodiment, substituted groups are substituted with one or more substituents, particularly with 1 to 3 substituents, in particular with one substituent group. In a further particular embodiment the substituent group or groups are selected from halo, cyano, nitro, trifluoromethyl, trifluoromethoxy, azido, —$NR^{72}SO_2R^{73}$, —$SO_2NR^{73}R^{72}$, —$C(O)R^{73}$, —$C(O)OR^{73}$, —$OC(O)R^{73}$, —$NR^{72}C(O)R^{73}$, —$C(O)NR^{73}R^{72}$, —$NR^{73}R^{72}$, —$(CR^{72}R^{72})_mOR^{72}$, wherein, each $R^{73}$ is independently selected from H, $C_1$-$C_8$ alkyl, —$(CH_2)_t(C_6$-$C_{10}$ aryl), —$(CH_2)_t$(5-10 membered heteroaryl), —$(CH_2)_t(C_3$-$C_{10}$ cycloalkyl), and —$(CH_2)_t$(4-10 membered heterocycloalkyl), wherein t is an integer from 0 to 4; and any alkyl groups present, may themselves be substituted by halo or hydroxy; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each R" independently represents H or $C_1$-$C_6$alkyl.

'Substituted sulfanyl' refers to the group —$SR^{74}$, wherein $R^{74}$ is selected from:

$C_1$-$C_8$ alkyl, $C_3$-$C_{10}$ cycloalkyl, 4-10 membered heterocloalkyl, $C_6$-$C_{10}$ aryl, aralkyl, 5-10 membered heteroaryl, and heteroaralkyl; or $C_1$-$C_8$ alkyl substituted with halo, substituted or unsubstituted amino, or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted haloalkyl, unsubstituted $C_1$-$C_4$ hydroxyalkyl, or unsubstituted haloalkoxy or hydroxy.

Exemplary 'substituted sulfanyl' groups are —S—($C_1$-$C_8$ alkyl) and —S—($C_3$-$C_{10}$ cycloalkyl), —S—($CH_2)_t(C_6$-$C_{10}$ aryl), —S—($CH_2)_t$(5-00 membered heteroaryl), —S—($CH_2)_t(C_3$-$C_{10}$ cycloalkyl), and —S—($CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted haloalkoxy or hydroxy. The term 'substituted sulfanyl' includes the groups 'alkylsulfanyl' or 'alkylthio', 'substituted alkylthio' or 'substituted alkylsulfanyl', 'cycloalkylsulfanyl' or 'cycloalkylthio', 'substituted cycloalkylsulfanyl' or 'substituted cycloalkylthio', 'arylsulfanyl' or 'arylthio' and 'heteroarylsulfanyl' or 'heteroarylthio' as defined below.

'Alkylthio' or 'Alkylsulfanyl' refers to a radical —$SR^{75}$ where $R^{75}$ is a $C_1$-$C_8$ alkyl or group as defined herein. Representative examples include, but are not limited to, methylthio, ethylthio, propylthio and butylthio.

'Substituted Alkylthio' or 'substituted alkylsulfanyl' refers to the group —$SR^{76}$ where $R^{76}$ is a $C_1$-$C_8$ alkyl, substituted with halo, substituted or unsubstituted amino, or hydroxy.

'Cycloalkylthio' or 'Cycloallylsulfanyl' refers to a radical —$SR^{77}$ where $R^{77}$ is a $C_3$-$C_{10}$ cycloalkyl or group as defined herein. Representative examples include, but are not limited to, cyclopropylthio, cyclohexylthio, and cyclopentylthio.

'Substituted cycloalkylthio' or 'substituted cycloalkylsulfanyl' refers to the group —$SR^{78}$ where $R^{78}$ is a $C_3$-$C_{10}$ cycloalkyl, substituted with halo, substituted or unsubstituted amino, or hydroxy.

'Arylthio' or 'Arylsulfanyl' refers to a radical —$SR^{79}$ where $R^{79}$ is a $C_6$-$C_{10}$ aryl group as defined herein.

'Heteroarylthio' or 'Heteroarylsulfanyl' refers to a radical —$SR^{80}$ where $R^{80}$ is a 5-10 membered heteroaryl group as defined herein.

'Substituted sulfinyl' refers to the group —$S(O)R^{81}$, wherein $R^{81}$ is selected from:
- $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
- $C_1$-$C_8$ alkyl substituted with halo, substituted or unsubstituted amino, or hydroxy; or
- $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfinyl' groups are —$S(O)$—($C_1$-$C_8$ alkyl) and —$S(O)$—($C_3$-$C_{10}$ cycloalkyl), —$S(O)$—$(CH_2)_t(C_6$-$C_{10}$ aryl), —$S(O)$—$(CH_2)_t$(5-10 membered heteroaryl), —$S(O)$—$(CH_2)_t(C_3$-$C_{10}$ cycloalkyl), and —$S(O)$—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfinyl includes the groups 'alkylsulfinyl', 'substituted alkylsulfinyl', 'cycloalkylsulfinyl', 'substituted cycloalkylsulfinyl', 'arylsulfinyl' and 'heteroarylsulfinyl' as defined herein.

'Alkylsulfinyl' refers to a radical —$S(O)R^{82}$ where $R^{82}$ is a $C_1$-$C_8$ alkyl group as defined herein. Representative examples include, but are not limited to, methylsulfinyl, ethylsulfinyl, propylsulfinyl and butylsulfinyl.

'Substituted Alkylsulfinyl' refers to a radical —$S(O)R^{83}$ where $R^{83}$ is a $C_1$-$C_8$ alkyl group as defined herein, substituted with halo, substituted or unsubstituted amino, or hydroxy.

'Cycloalkylsulfinyl' refers to a radical —$S(O)R^{84}$ where $R^{84}$ is a $C_3$-$C_{10}$ cycloalkyl or group as defined herein. Representative examples include, but are not limited to, cyclopropylsulfinyl, cyclohexylsulfinyl, and cyclopentylsulfinyl. Exemplary 'cycloalkylsulfinyl' groups are $S(O)$—$C_3$-$C_{10}$ cycloalkyl.

'Substituted cycloalkylsulfinyl' refers to the group —$S(O)R^{85}$ where $R^{85}$ is a $C_3$-$C_{10}$ cycloalkyl, substituted with halo, substituted or unsubstituted amino, or hydroxy.

'Arylsulfinyl' refers to a radical —$S(O)R^{86}$ where $R^{86}$ is a $C_6$-$C_{10}$ aryl group as defined herein.

'Heteroarylsulfinyl' refers to a radical —$S(O)R^{87}$ where $R^{87}$ is a 5-10 membered heteroaryl group as defined herein.

'Substituted sulfonyl' refers to the group —$S(O)_2R^{88}$, wherein $R^{88}$ is selected from:
- $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
- $C_1$-$C_8$ alkyl substituted with halo, substituted or unsubstituted amino, or hydroxy; or
- $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted haloalkyl, unsubstituted $C_1$-$C_4$ hydroxyalkyl, or unsubstituted $C_1$-$C_4$ haloalkoxy or hydroxy.

Exemplary 'substituted sulfonyl' groups are —$S(O)_2$—($C_1$-$C_8$ alkyl) and —$S(O)_2$—($C_3$-$C_{10}$ cycloalkyl), —$S(O)_2$—$(CH_2)_t(C_6$-$C_{10}$ aryl), —$S(O)_2$—$(CH_2)_t$(5-10 membered heteroaryl), —$S(O)_2$—$(CH_2)_t(C_3$-$C_{10}$ cycloalkyl), and —$S(O)_2$—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfonyl includes the groups alkylsulfonyl, substituted alkylsulfonyl, cycloalkylsulfonyl, substituted cycloalkylsulfonyl, arylsulfonyl and heteroarylsulfonyl.

'Alkylsulfonyl' refers to a radical —$S(O)_2R^{89}$ where $R^{89}$ is an $C_1$-$C_8$ alkyl group as defined herein. Representative examples include, but are not limited to, methylsulfonyl, ethylsulfonyl, propylsulfonyl and butylsulfonyl.

'Substituted Alkylsulfonyl' refers to a radical —$S(O)_2R^{90}$ where $R^{90}$ is an $C_1$-$C_8$ alkyl group as defined herein, substituted with halo, substituted or unsubstituted amino, or hydroxy.

'Cycloalkylsulfonyl' refers to a radical —$S(O)_2R^{91}$ where $R^{91}$ is a $C_3$-$C_{10}$ cycloalkyl or group as defined herein. Representative examples include, but are not limited to, cyclopropylsulfonyl, cyclohexylsulfonyl, and cyclopentylsulfonyl.

'Substituted cycloalkylsulfonyl' refers to the group —$S(O)_2R^{92}$ where $R^{92}$ is a $C_3$-$C_{10}$ cycloalkyl, substituted with halo, substituted or unsubstituted amino, or hydroxy.

'Arylsulfonyl' refers to a radical —$S(O)_2R^{93}$ where $R^{93}$ is an $C_6$-$C_{10}$ aryl group as defined herein.

'Heteroarylsulfonyl' refers to a radical —$S(O)_2R^{94}$ where $R^{94}$ is an 5-10 membered heteroaryl group as defined herein.

'Sulfo' or 'sulfonic acid' refers to a radical such as —$SO_3H$.

'Substituted sulfo' or 'sulfonic acid ester' refers to the group —$S(O)_2OR^{95}$, wherein $R^{95}$ is selected from:
- $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
- $C_1$-$C_8$ alkyl substituted with halo, substituted or unsubstituted amino, or hydroxy; or
- $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted haloalkoxy or hydroxy.

Exemplary 'Substituted sulfo' or 'sulfonic acid ester' groups are —$S(O)_2$—$O$—($C_1$-$C_8$ alkyl) and —$S(O)_2$—$O$—($C_3$-$C_{10}$ cycloalkyl), —$S(O)_2$—$O$—$(CH_2)_t(C_6$-$C_{10}$ aryl), —$S(O)_2$—$O$—$(CH_2)_t$(5-10 membered heteroaryl), —$S(O)_2$—$O$—$(CH_2)_t(C_3$-$C_{10}$ cycloalkyl), and —$S(O)_2$—$O$—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Thiol' refers to the group —SH.

'Aminocarbonylamino' refers to the group —NR$^{96}$C(O) NR$^{96}$R$^{96}$ where each R$^{96}$ is independently hydrogen $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl, as defined herein; or where two R$^{96}$ groups, when attached to the same N, are joined to form an alkylene group.

'Bicycloaryl' refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

'Bicycloheteroaryl' refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

'Compounds of the present invention', and equivalent expressions, are meant to embrace the compounds as hereinbefore described, in particular compounds according to any of the formulae herein recited and/or described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

'Cycloalkylalkyl' refers to a radical in which a cycloalkyl group is substituted for a hydrogen atom of an alkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

'Heterocycloalkylalkyl' refers to a radical in which a heterocycloalkyl group is substituted for a hydrogen atom of an alkyl group. Typical heterocycloalkylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

'Cycloalkenyl' refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

'Substituted cycloalkenyl' refers to those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Fused Cycloalkenyl' refers to a cycloalkenyl having two of its ring carbon atoms in common with a second aliphatic or aromatic ring and having its olefinic unsaturation located to impart aromaticity to the cycloalkenyl ring.

'Ethenyl' refers to substituted or unsubstituted —(C═C)—.

'Ethylene' refers to substituted or unsubstituted —(C—C)—.

'Ethynyl' refers to —(C≡C)—.

'Hydrogen bond donor' group refers to a group containing O—H, or N—H functionality. Examples of 'hydrogen bond donor' groups include —OH, —NH$_2$, and —NH—R$^{97}$ and wherein R$^{97}$ is alkyl, acyl, cycloalkyl, aryl, or heteroaryl.

'Dihydroxyphosphoryl' refers to the radical —PO(OH)$_2$.

'Substituted dihydroxyphosphoryl' refers to those groups recited in the definition of 'substituted' herein, and particularly refers to a dihydroxyphosphoryl radical wherein one or both of the hydroxyl groups are substituted. Suitable substituents are described in detail below.

'Aminohydroxyphosphoryl' refers to the radical —PO(OH)NH$_2$.

'Substituted aminohydroxyphosphoryl' refers to those groups recited in the definition of 'substituted' herein, and particularly refers to an aminohydroxyphosphoryl wherein the amino group is substituted with one or two substituents. Suitable substituents are described in detail below. In certain embodiments, the hydroxyl group can also be substituted.

'Nitrogen-Containing Heterocycloalkyl' group means a 4 to 7 membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

'Thioketo' refers to the group ═S.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject not yet exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

'Compounds of the present invention', and equivalent expressions, are meant to embrace compounds of the Formula (e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

When ranges are referred to herein, for example but without limitation, $C_1$-$C_8$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

THE COMPOUNDS

In certain aspects, provided herein are compounds useful for preventing and/or treating a broad range of conditions, among them, arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders or conditions in mammals.

In one aspect, provided herein are compounds according to formula 1:

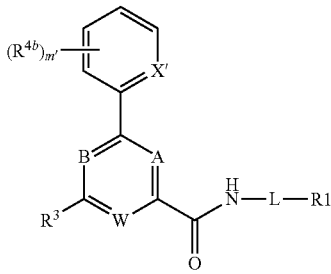

wherein
each of A, B, and W are independently selected from $CR^4$;
$X'$ is selected from $CR^{4a}$ and N;
L is $—C(R^{2a}R^{2b})—$;
$R^1$ is selected from substituted or unsubstituted aryl, substituted or unsubstituted heteroaryl, hydroxy $C_1$-$C_4$ alkyl, $C_3$-$C_7$ cycloalkyl-$C_1$-$C_4$ alkyl, or 4-7 membered heterocycloalkyl-$C_1$-$C_4$ alkyl;
each of $R^{2a}$ and $R^{2b}$ is independently selected from hydrogen, $C_1$-$C_4$ alkyl, or hydroxy $C_1$-$C_4$ alkyl;
$R^3$ is substituted or unsubstituted $C_1$-$C_6$ alkyl; CH(OH)$R^{3a}$, $OR^{3a}$, CN, $COR^{3a}$, $COOR^{3a}$, $SOR^{3a}$, $SO_2R^{3a}$, $CONR^{3a}R^{3b}$, $SONR^{3a}R^{3b}$, or $SO_2NR^{3a}R^{3b}$;
$R^{3a}$ is H, substituted or unsubstituted alkyl, substituted or unsubstituted cycloalkyl, substituted or unsubstituted heterocycloalkyl, substituted or unsubstituted aryl, or substituted or unsubstituted heteroaryl;
$R^{3b}$ is H, substituted or unsubstituted $C_1$-$C_6$ alkyl; or $R^{3a}$ and $R^{3b}$ join together to form a cycloheteroalkyl ring of 3-7 atoms;
each $R^4$ is independently selected from H, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, halo, nitro, and thiol;
each $R^{4a}$, and $R^{4b}$ is independently selected from H, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxy, substituted or unsubstituted alkoxycarbonyl, substituted or unsubstituted alkylarylamino, substituted or unsubstituted arylalkyloxy, substituted or unsubstituted amino, substituted or unsubstituted aryl, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol;
and subscript m' is selected from 0-4;
provided that
i) when $R^3$ is $CO_2Me$, $SO_2Ph$, or $OR^{3a}$; then $R^1$ is other than unsubstituted phenyl;
ii) when $R^3$ is $SO_2$-(4-methylpiperazin-1-yl) or is $SO_2$-(thiomorpholin-1-yl); and $X'$ is CH; then $R^{4b}$ is other than H;
iii) when $R^3$ is Me, or methyl substituted with alkoxy; then $R^1$ is other than substituted phenyl;
iv) when $R^3$ is $CO_2H$; then $R^{4b}$ is Cl, F, Br, Me, Et, OMe, or $CF_3$;
v) when $X'$ is $CR^{4a}$; $R^3$ is $CONR^{3a}R^{3b}$; and $R^{3a}$ is H; then $R^{3b}$ is other than substituted n-pentyl, substituted pentynyl, substituted benzyl, substituted phenethyl, substituted thiophenylethyl, or substituted thiazolylethyl; and
vi) when $R^1$ is 5-6 membered heterocycloalkylmethyl, and $R^3$ is $CO_2Me$ or n-Pr; then $R^{4b}$ is other than Cl or 4-F;
or a pharmaceutically acceptable salt, N-oxide, solvate, prodrug, stereoisomer, tautomer or isotopic variant thereof.

In another aspect, provided herein are pharmaceutical composition of compounds according to formula 1:

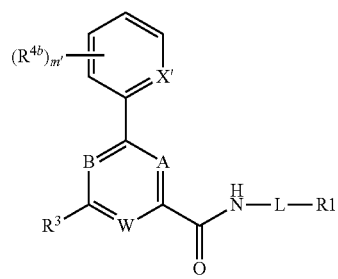

wherein A, B, W, $X'$, L, $R^1$, $R^3$, $R^{4b}$, and m' are as described above;
provided that
i) when $R^3$ is $CO_2Me$, $SO_2Ph$, or $OR^{3a}$; then $R^1$ is other than unsubstituted phenyl;
ii) when $R^3$ is $SO_2$-(4-methylpiperazin-1-yl) or is $SO_2$-(thiomorpholin-1-yl); and $X'$ is CH; then $R^{4b}$ is other than H;
iii) when $R^3$ is Me, or methyl substituted with alkoxy; then $R^1$ is other than substituted phenyl;
iv) when $R^3$ is $CO_2H$; then $R^{4b}$ is Cl, F, Br, Me, Et, OMe, or $CF_3$;
v) when $X'$ is $CR^{4a}$; $R^3$ is $CONR^{3a}R^{3b}$; and $R^{3a}$ is H; then $R^{3b}$ is other than substituted n-pentyl, substituted pentynyl, substituted benzyl, substituted phenethyl, substituted thiophenylethyl, or substituted thiazolylethyl; and
vi) when $R^1$ is 5-6 membered heterocycloalkylmethyl, and $R^3$ is $CO_2Me$ or n-Pr; then $R^{4b}$ is other than Cl or 4-F;
or a pharmaceutically acceptable salt, N-oxide, solvate, prodrug, stereoisomer, tautomer or isotopic variant thereof.

In another aspect, provided herein are pharmaceutical composition of compounds according to formula 1; wherein A, B, W, X', L, $R^1$, $R^{3a}$, $R^{4b}$, and m' are as described above; $R^3$ is $CO_2Me$, $SO_2Ph$, or $OR^{3a}$; and $R^1$ is unsubstituted phenyl.

In another aspect, provided herein are pharmaceutical composition of compounds according to formula 1; wherein A, B, W, L, $R^{3a}$, and m' are as described above; $R^3$ is $SO_2$-(4-methylpiperazin-1-yl), or is $SO_2$-(thiomorpholin-1-yl); X' is CH; and $R^{4b}$ is H.

In another aspect, provided herein are pharmaceutical composition of compounds according to formula 1; wherein A, B, W, X', L, $R^{3a}$, $R^{4b}$, and m' are as described above; $R^3$ is Me, or methyl substituted with alkoxy; and $R^1$ is substituted phenyl.

In another aspect, provided herein are pharmaceutical composition of compounds according to formula 1; wherein A, B, W, X', L, $R^1$, $R^{3a}$, and m' are as described above; $R^3$ is $CO_2H$; and $R^{4b}$ is other than Cl, F, Br, Me, Et, OMe, or $CF_3$.

In another aspect, provided herein are pharmaceutical composition of compounds according to formula 1; wherein A, B, W, L, $R^1$, $R^3$, $R^{3a}$, $R^{4b}$, and m' are as described above; X' is $CR^{4a}$; $R^3$ is $CONR^{3a}R^{3b}$; $R^{3a}$ is H; and $R^{3b}$ is substituted n-pentyl, substituted pentynyl, substituted benzyl, substituted phenethyl, substituted thiophenylethyl, or substituted thiazolylethyl;

In another aspect, provided herein are pharmaceutical composition of compounds according to formula 1; wherein A, B, W, X', L, $R^{3a}$, and m' are as described above; $R^1$ is 5-6 membered heterocycloalkylmethyl, $R^3$ is $CO_2Me$ or n-Pr, and $R^{4b}$ is Cl or 4-F.

In one particular embodiment, with respect to formula 1, each A, B, and W is CH.

In one particular embodiment, with respect to formula 1, L is selected from —$CH_2$—, —CHMe—, —$CMe_2$-, —CH($CH_2OH$)—, and —CH($CH_2CH_2OH$)—.

In one particular embodiment, with respect to formula 1, L is selected from —$CH_2$—, and —CHMe—.

In one particular embodiment, with respect to formula 1, the compound is according to formula 2a, 2b, 2c, 2d, 2e, 2f, 2g, 2h, 2i, 2j, 2k, 2l, 2m, or 2n:

2a
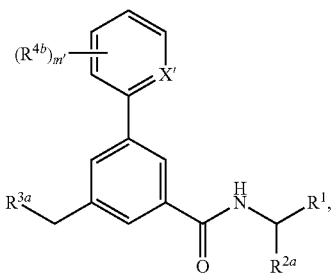

2b
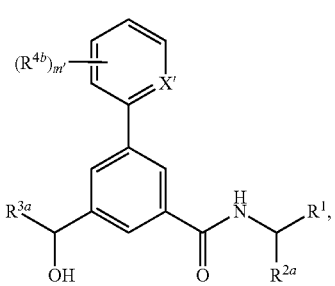

-continued

2c
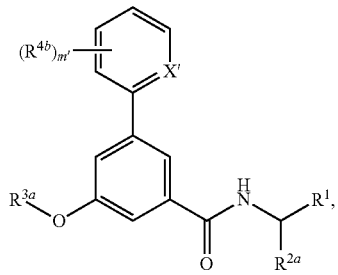

2d
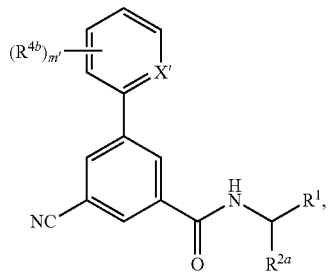

2e
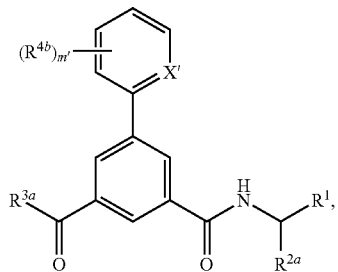

2f
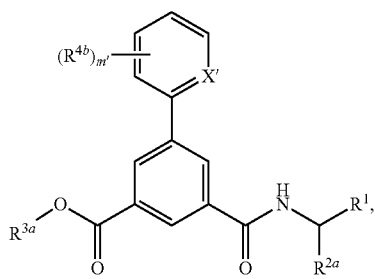

2g
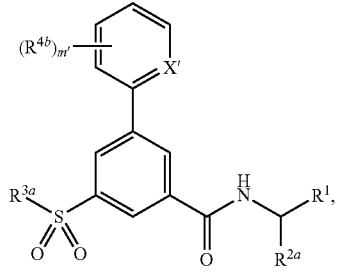

-continued

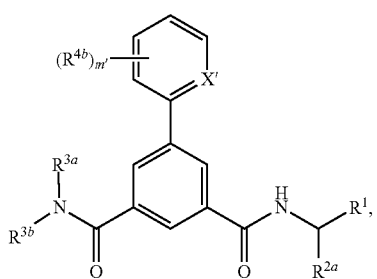
2h

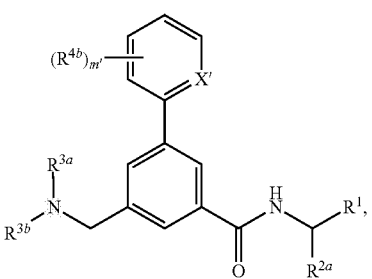
2m

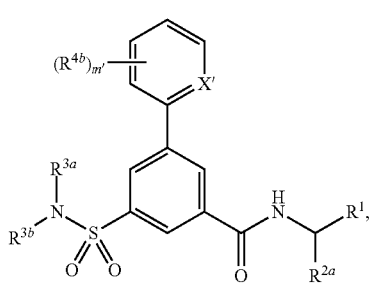
2i

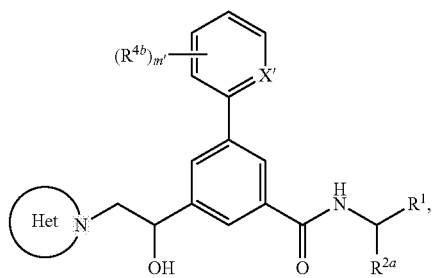
2n

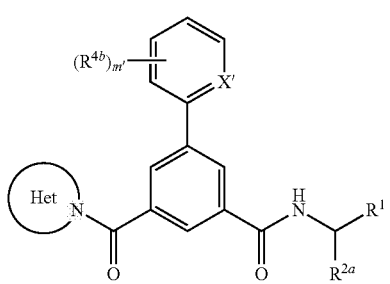
2j

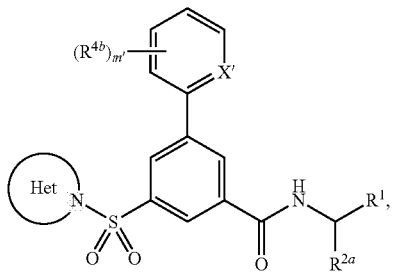
2k wherein
X', R¹, R³ᵃ; R³ᵇ, R⁴ᵃ; R⁴ᵇ, and m' are as described for formula 1; R²ᵃ is H, Me, CH₂OH, or CH₂CH₂OH; Het is substituted or unsubstituted heterocycloalkyl; or a pharmaceutically acceptable salt, solvate, N-oxide, prodrug, stereoisomer, tautomer or isotopic variant thereof.

In one particular embodiment, with respect to formula 1-2n, subscript the m' is 1, 2 or 3.

In one particular embodiment, with respect to formula 1-2n, subscript the m' is 1.

In one particular embodiment, with respect to formula 1-2n, each R⁴ᵇ is independently H, C₁-C₄ alkyl, halo C₁-C₄ alkyl, CN, NO₂, or halo.

In one particular embodiment, with respect to formula 1, the compound is according to formula 3a, 3b, 3c, 3d, 3e, 3f, 3g, 3h, 3i, 3j, 3k, 3l, or 3m:

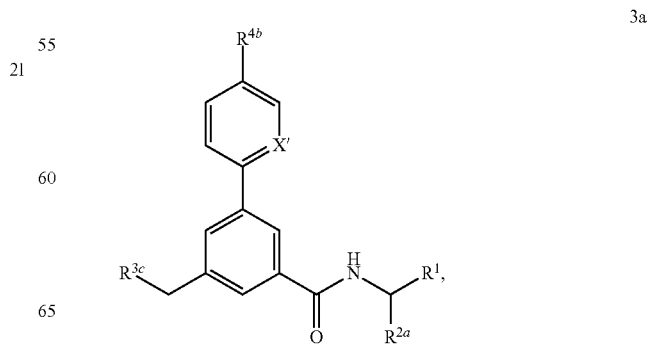
3a

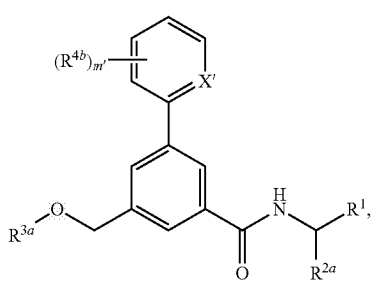
2l

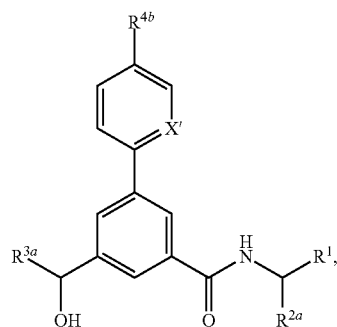
3b
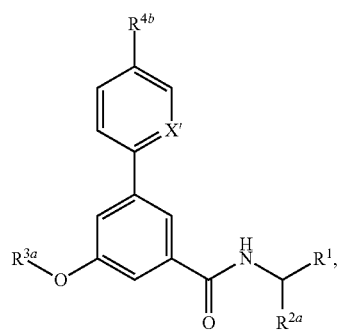
3c
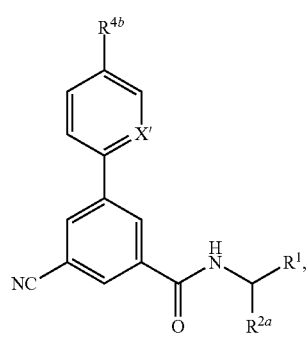
3d
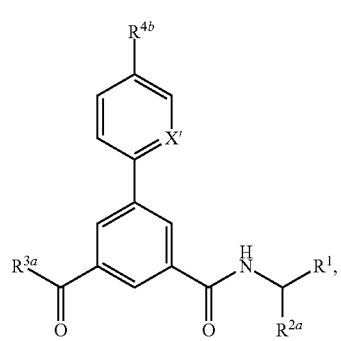
3e
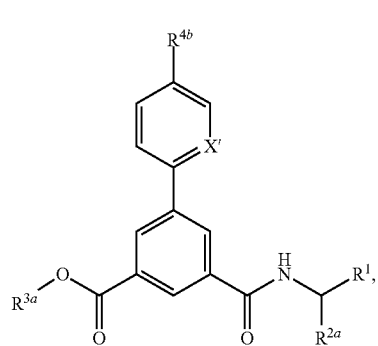
3f
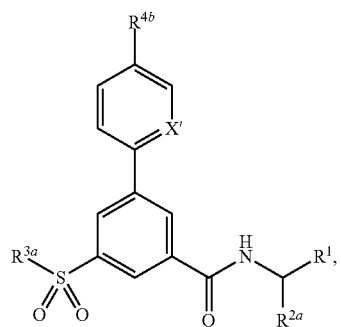
3g
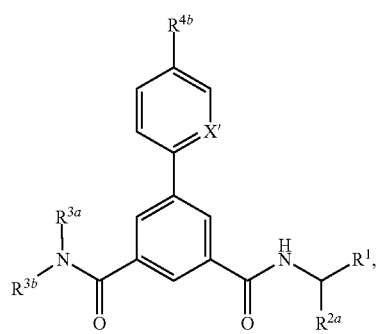
3h
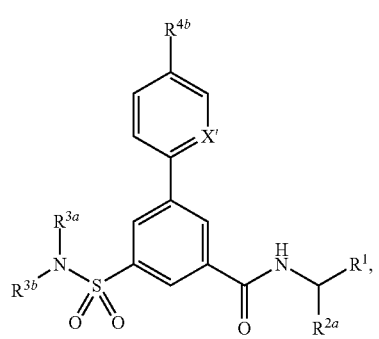
3i
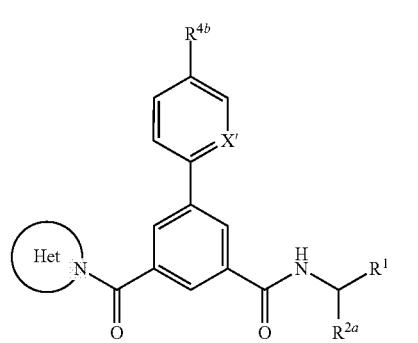 or
3j
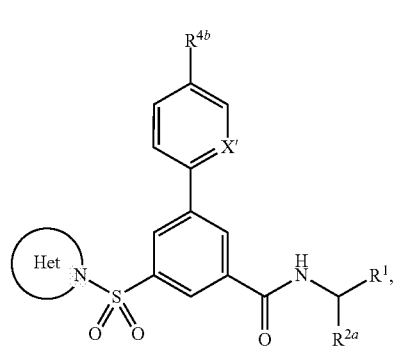
3k

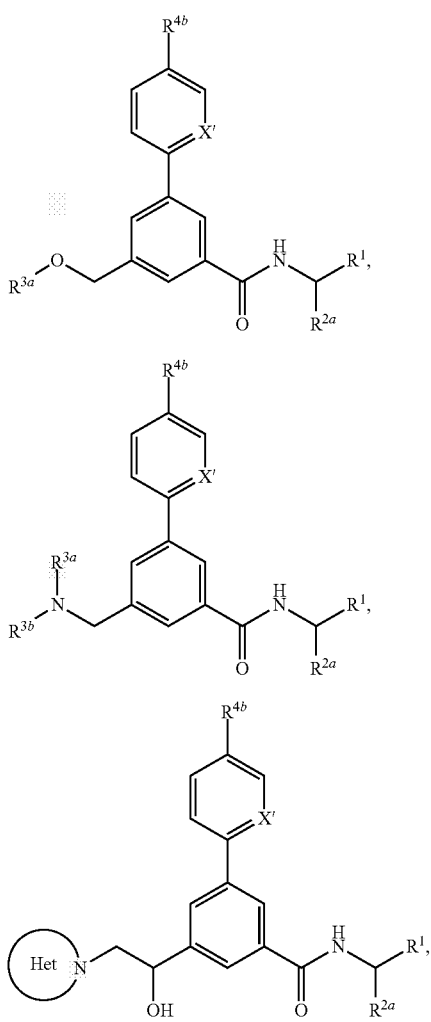

wherein

X', R¹, R³ᵃ; R³ᵇ; R⁴ᵃ; R⁴ᵇ, and are as described for formula 1; R²ᵃ is H, Me, CH₂OH, or CH₂CH₂OH; Het is substituted or unsubstituted heterocycloalkyl; or a pharmaceutically acceptable salt, solvate, N-oxide, prodrug, stereoisomer, tautomer or isotopic variant thereof.

In one particular embodiment, with respect to formula 1, the compound is according to formulae 2b, 2c, 2h, 2i, 3b, 3c, 3h, or 3i; and R³ᵃ is H.

In one particular embodiment, with respect to formula 1-3n, R³ᵃ is substituted or unsubstituted alkyl.

In one particular embodiment, with respect to formula 1-3n, R³ᵃ is Me, Et, i-Pr, n-Pr, i-Bu, t-Bu, CF₃, CH₂CF₃, or benzyl.

In one particular embodiment, with respect to formula 1-3n, R³ᵃ is substituted methyl.

In one particular embodiment, with respect to formula 1-3n, R³ᵃ is methoxymethyl, methoxyethyl, dimethylaminomethyl, or dimethylaminoethyl.

In one particular embodiment, with respect to formula 1-3n, R³ᵃ is heteroarylmethyl, or heterocycloallylmethyl.

In one particular embodiment, with respect to formula 1-3n, R³ᵃ is heteroarylethyl, or heterocycloalkylethyl.

In one particular embodiment, with respect to formula 1-3n, R³ᵃ is pyridylmethyl.

In one particular embodiment, with respect to formula 1-3n, R³ᵃ is piperidinylmethyl, piperazinylmethyl, pyrrolidinylmethyl, or morpholinylmethyl.

In one particular embodiment, with respect to formula 1-3n, R³ᵃ is pyridylethyl, piperidinylethyl, piperazinylethyl, pyrrolidinylethyl, or morpholinylethyl.

In another particular embodiment, with respect to formula 1-3n, the compound is of formula 3b, and R³ᵃ is piperidinylmethyl, piperazinylmethyl, pyrrolidinylmethyl, or morpholinylmethyl.

In one particular embodiment, with respect to formula 1-3n, R³ᵃ is cyclopropyl, cyclopenyl, cyclopropylmethyl, or cyclopentylmethyl.

In one particular embodiment, with respect to formula 1-3n, R³ᵃ is substituted or unsubstituted heteroaryl.

In one particular embodiment, with respect to formula 1-3n, R³ᵃ is substituted or unsubstituted pyridyl, pyrazinyl or pyrimidinyl.

In one particular embodiment, with respect to formula 1-3n, R³ᵃ is substituted or unsubstituted phenyl.

In one particular embodiment, with respect to formula 1-3n, R³ᵃ is pyrrolyl, furanyl, thiophenyl, pyrazolyl, imidazolyl, oxazolyl, thiazolyl, triazolyl, thiadiazolyl, unsubstituted or substituted with alkyl or haloalkyl.

In one particular embodiment, with respect to formula 1-3n, R³ᵃ is selected from substituted or unsubstituted quinolinyl, isoquinolinyl, methylenedioxyphenyl, imidazopyridyl, benzoxazolyl, benzothiazolyl, and indolyl.

In one particular embodiment, with respect to formula 1-3n, R³ᵃ is

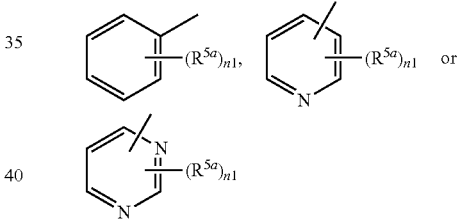

and wherein subscript n1 is selected from 1-5 and each R⁵ᵃ is independently selected from hydrogen, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, sulfo, substituted sulfo, substituted sulfinyl, substituted sulfonyl, substituted sulfanyl, substituted or unsubstituted aminosulfonyl, substituted or unsubstituted allylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol.

In one particular embodiment, with respect to formula 1-3n, R³ᵇ is H or alkyl.

In one particular embodiment, with respect to formula 1-3n, $R^{3b}$ is H, Me, Et, or i-Pr. In one particular embodiment, with respect to formula 1-3k, $R^{3b}$ is H.

In one particular embodiment, with respect to formula 2j, 2k, 2j, 3k, or 3n, Het is azetidin-1-yl, pyrrolidin-1-yl, piperidin-1-yl, morpholin-1-yl, piperazin-1-yl, and azepin-1-yl, unsubstituted or substituted with one or more groups selected from alkyl, alkoxy, dialkylamino, halo, haloalkyl, hydroxy, or hydroxyalkyl.

In one particular embodiment, with respect to formula 2j, 2k, 2j, 3k, or 3n, Het is azetidin-1-yl, pyrrolidin-1-yl, piperidin-1-yl, morpholin-1-yl, piperazin-1-yl, and azepin-1-yl, unsubstituted or substituted with one or more groups selected from Me, Et, i-Pr, OMe, $NMe_2$, Cl, F, OH, or $CF_3$.

In one particular embodiment, with respect to formula 21 or 31, $R^{3a}$ is Me, Et, i-Pr, n-Pr, i-Bu, t-Bu, $CF_3$, $CH_2CF_3$, or benzyl.

In one particular embodiment, with respect to formula 21 or 31, $R^{3a}$ is Me.

In one particular embodiment, with respect to formula 2m or 3m, $R^{3a}$ is Me, Et, or i-Pr.

In one particular embodiment, with respect to formula 2m or 3m, $R^{3b}$ is Me, Et, or i-Pr.

In one particular embodiment, with respect to formula 2m or 3m, each $R^{3a}$ and $R^{3b}$ is independently Me, Et, or i-Pr.

In one particular embodiment, with respect to formula 2m or 3m, each $R^{3a}$ and $R^{3b}$ is Me.

In another embodiment, with respect to formula 1, the compound is according to formula 4, 5, 6, 7, 8, or 9:

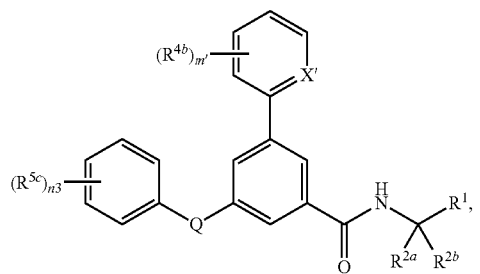

4

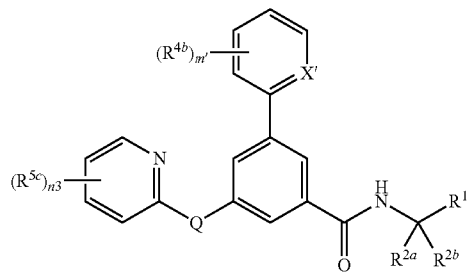

5

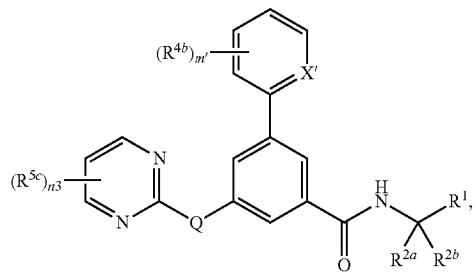

6

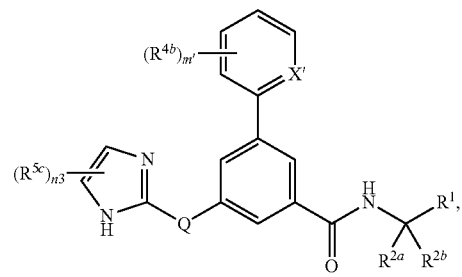

7

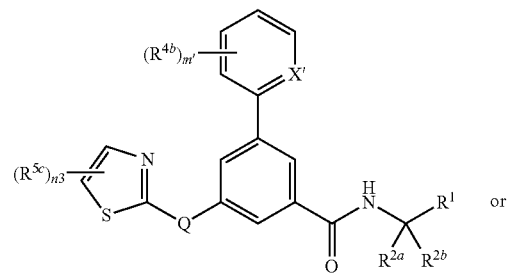

8

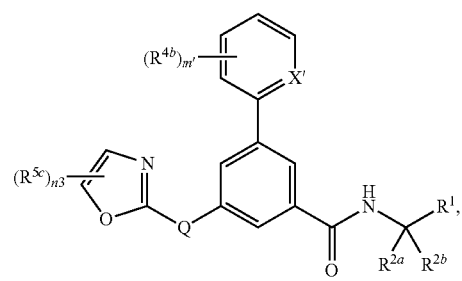

9 wherein
X', $R^1$, $R^{4b}$; and m' are as described for formula 1; $R^{5c}$ is $R^{5a}$; the subscript n3 is 1, 2, or 3; and $R^{5a}$ is as described above;
each of $R^{2a}$ and $R^{2b}$ is independently selected from hydrogen, $C_1$-$C_4$ alkyl, or hydroxy $C_1$-$C_4$ alkyl; and Q is —O—, or —C(OH)H—;
or a pharmaceutically acceptable salt, solvate, prodrug, stereoisomer, tautomer or isotopic variant thereof.

In one embodiment, with respect to formulae 4-9, the subscript m' is 1, 2 or 3.

In another embodiment, with respect to formulae 4-9, the subscript m' is 1.

In another embodiment, with respect to formula 1, the compound is according to formula 10, 11, 12, 13, 14, or 15:

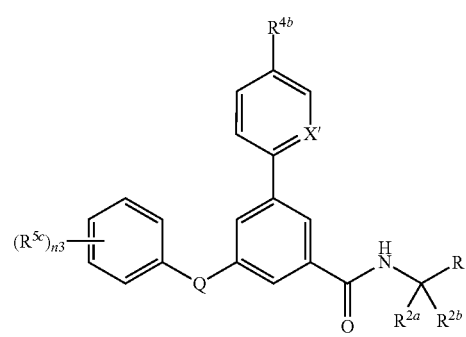

10

-continued

11
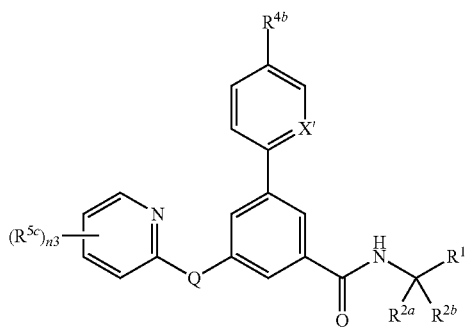

12
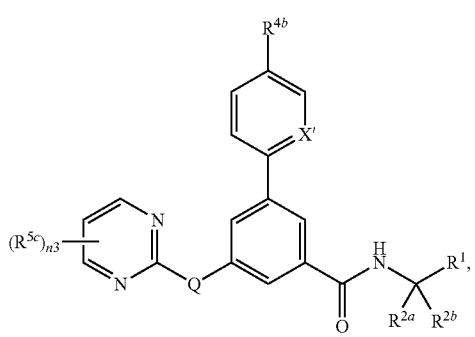

13
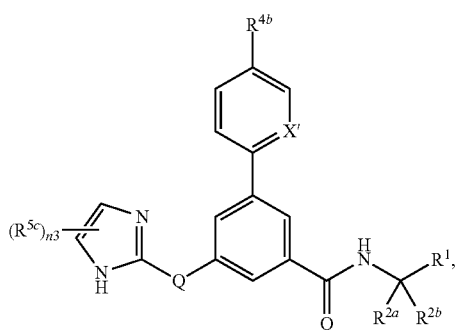

14
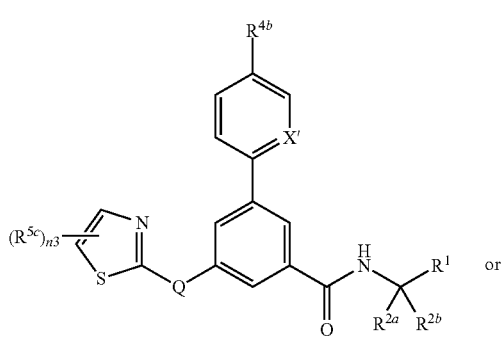

or

-continued

15
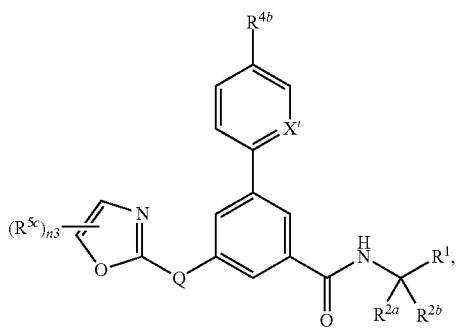

wherein

X', $R^1$, $R^{4a}$, and $R^{4b}$, are as described for formula 1; $R^{5c}$ is $R^{5a}$; the subscript n3 is 1, 2, or 3; and $R^{5a}$ is as described above;

each of $R^{2a}$ and $R^{2b}$ is independently selected from hydrogen, $C_1$-$C_4$ alkyl, or hydroxy $C_1$-$C_4$ alkyl;

or $R^{2a}$ and $R^{2b}$ join together to form a cycloalkyl or cycloheteroalkyl ring of 3-7 atoms; and Q is —O—, or —C(OH)H—;

or a pharmaceutically acceptable salt, solvate, prodrug, stereoisomer, tautomer or isotopic variant thereof.

In one embodiment, with respect to formulae 4-15, Q is —O—.

In another embodiment, with respect to formulae 4-15, Q is —C(OH)H—.

In one embodiment, with respect to formulae 4-15, $R^{2a}$ is H, Me, $CH_2OH$, or $CH_2CH_2OH$.

In one embodiment, with respect to formulae 4-15, $R^{2b}$ is H.

In one embodiment, with respect to formulae 4-15, n3 is 1 or 2.

In one embodiment, with respect to formulae 4-15, $R^{5c}$ is independently selected from H, alkyl, halo, cyano, alkoxy, and haloalkyl.

In one embodiment, with respect to formulae 4-15, $R^{5c}$ is from H, Cl, F, Me, OMe, or $CF_3$.

In one particular embodiment, with respect to formula 1, 2a-2n, 3a-3n, and 4-15, X' is $CR^{4a}$; and $R^{4a}$ is H, $C_1$-$C_4$ alkyl, halo $C_1$-$C_4$ alkyl, CN, $NO_2$, or halo.

In one particular embodiment, with respect to formula 1, 2a-2n, 3a-3n, and 4-15, X' is $CR^{4a}$; and $R^{4a}$ is H, Me, $CF_3$, Cl, F, CN or $NO_2$.

In one particular embodiment, with respect to formula 1, 2a-2n, 3a-3n, and 4-15, X' is $CR^{4a}$; and $R^{4a}$ is CN.

In one particular embodiment, with respect to formula 1, 2a-2n, 3a-3n, and 4-15, X' is N.

In one particular embodiment, with respect to formula 1, 2a-2n, 3a-3n, and 4-15, $R^{4b}$ is H, $C_1$-$C_4$ alkyl, halo $C_1$-$C_4$ alkyl or halo.

In one particular embodiment, with respect to formula 1, 2a-2n, 3a-3n, and 4-15, $R^{4b}$ is H, Me, $CF_3$, Cl, Br, or F.

In one particular embodiment, with respect to formula 1, 2a-2n, 3a-3n, and 4-15, $R^1$ is substituted or unsubstituted aryl or heteroaryl.

In one particular embodiment, with respect to formula 1, 2a-2n, 3a-3n, and 4-15, $R^1$ is substituted or unsubstituted bicycloaryl, bicycloalkyl, or bicycloheteroaryl.

In one particular embodiment, with respect to formula 1, 2a-2n, 3a-3n, and 4-15, $R^1$ is substituted or unsubstituted phenyl.

In one particular embodiment, with respect to formula 1, 2a-2n, 3a-3n, and 4-15, $R^1$ is substituted or unsubstituted pyridyl, pyrazinyl, thiazolyl, or pyrimidinyl.

In one particular embodiment, with respect to formula 1, 2a-2n, 3a-3n, and 4-15, $R^1$ is substituted or unsubstituted pyridyl.

In one particular embodiment, with respect to formula 1, 2a-2n, 3a-3n, and 4-15, $R^1$ is substituted or unsubstituted pyrimidyl.

In one particular embodiment, with respect to formula 1, 2a-2n, 3a-3n, and 4-15, wherein $R^1$ is selected from substituted or unsubstituted quinolinyl, isoquinolinyl, methylenedioxyphenyl, imidazopyridyl, benzoxazolyl, benzothiazolyl, and indolyl.

In one particular embodiment, with respect to formula 1, 2a-2n, 3a-3n, and 4-15, $R^1$ is

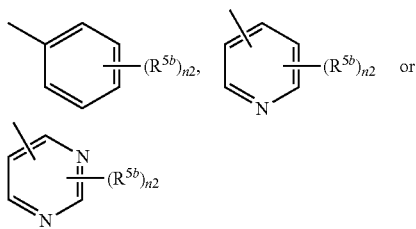

and wherein subscript n2 is selected from 1-5 and each $R^{5b}$ is independently selected from hydrogen, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, sulfo, substituted sulfo, substituted sulfinyl, substituted sulfonyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol.

In one particular embodiment, with respect to formula 1, 2a-2n, 3a-3n, and 4-15, subscript n2 is 1, 2 or 3.

In one particular embodiment, with respect to formula 1, 2a-2n, 3a-3n, and 4-15, subscript n2 is 1 or 2.

In one particular embodiment, with respect to formula 1, 2a-2n, 3a-3n, and 4-15, $R^1$ is

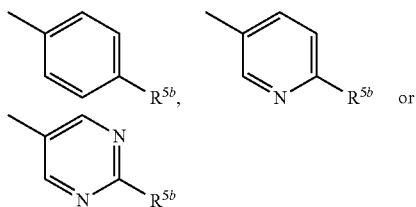

and wherein $R^{5b}$ is as described above.

In one particular embodiment, with respect to formula 1, 2a-2n, 3a-3n, and 4-15, each $R^{5b}$ is independently selected from H, alkyl, halo, cyano, alkoxy, and haloalkyl.

In one particular embodiment, with respect to formula 1, 2a-2n, 3a-3n, and 4-15, each $R^{5b}$ is independently selected from H, Me, Et, n-Pr, iso-Pr, Ph, Cl, F, Br, CN, OH, OMe, OEt, OPh, COPh, $CO_2Me$, $CH_2$—N-morpholino, $CH_2$—N-(4-Me-piperidino), $NH_2$, $CONH_2$, $CF_3$, $CHF_2$, $OCF_3$, $OCHF_2$, t-Bu, SMe, CH=CH—$CO_2H$, SOMe, $SO_2Me$, $SO_2CF_3$, $SO_2NH_2$, $SO_3H$, $SO_3Me$, cyclopropyl, triazolyl, morpholinyl, and pyridyl.

In one particular embodiment, with respect to formula 1, 2a-2n, 3a-3n, and 4-15, each $R^{5b}$ is independently selected from H, Cl, F, Me, OMe, or $CF_3$.

In one particular embodiment, with respect to formula 1, 2a-2n, 3a-3n, and 4-15, each $R^{5b}$ is Me.

In one particular embodiment, with respect to formula 1, 2a-2n, 3a-3n, and 4-15, each $R^{5b}$ is OMe.

In one particular embodiment, with respect to formula 1, 2a-2n, 3a-3n, and 4-15, each $R^{5b}$ is $CF_3$.

In one particular embodiment, with respect to formula 1, 2a-2n, 3a-3n, and 4-15, $R^1$ is selected from hydroxy $C_1$-$C_4$ alkyl, $C_3$-$C_7$ cycloalkyl-$C_1$-$C_4$ alkyl, or 4-7 membered heterocycloalkyl-$C_1$-$C_4$ alkyl.

In one particular embodiment, with respect to formula 1, 2a-2n, 3a-3n, and 4-15, $R^1$ is selected from hydroxymethyl, 1-hydroxyethyl, and 2-hydroxyethyl.

In one particular embodiment, with respect to formula 1, 2a-2n, 3a-3n, and 4-15, $R^1$ is selected from piperidin-1-ylmethyl, piperazin-1-ylmethyl, and morpholin-1-ylmethyl.

In one particular embodiment, with respect to formula 1, 2a-2n, 3a-3n, and 4-15, $R^{2a}$ is hydrogen.

In one particular embodiment, with respect to formula 1, 2a-2n, 3a-3n, and 4-15, $R^{2a}$ is methyl, hydroxymethyl or hydroxyethyl.

In one particular embodiment, with respect to formula 1, 2a-2n, 3a-3n, and 4-15, $R^{2a}$ is methyl.

In one particular embodiment, with respect to formula 1, the compound is according to formula 3g; and X' is CH.

In one particular embodiment, with respect to formula 1, the compound is according to formula 3g; and X' is C—CN.

In one particular embodiment, with respect to formula 1, the compound is according to formula 3g; and X' is N.

In one particular embodiment, with respect to formula 1, the compound is according to formula 3g; and $R^{2a}$ is methyl, hydroxymethyl or hydroxyethyl.

In one particular embodiment, with respect to formula 1, the compound is according to formula 3g; and $R^{4b}$ is methyl.

In one particular embodiment, with respect to formula 1, the compound is according to formula 3g; $R^1$ is

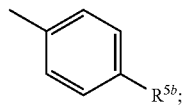

and wherein $R^{5b}$ is Me, $CF_3$, or OMe.

In one particular embodiment, with respect to formula 1, the compound is according to formula 3g; $R^1$ is

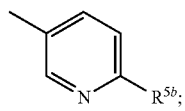

and wherein $R^{5b}$ is Me, $CF_3$, or OMe.

In one particular embodiment, with respect to formula 1, the compound is according to formula 3g; $R^1$ is

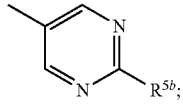

and wherein $R^{5b}$ is Me, $CF_3$, or OMe.

In one particular embodiment, with respect to formula 1, the compound is according to formula 3g; X', $R^1$, $R^{2a}$, and $R^{4b}$ are as described in preceding paragraphs, and $R^{3a}$ is Me, or Et.

In one particular embodiment, with respect to formula 1, the compound is according to formula 3g; X', $R^1$, $R^{2a}$, and $R^{4b}$ are as described in preceding paragraphs, and $R^{3a}$ is Me.

In another embodiment, with respect to formula 1, the compound is according to formula 16, 17, 18, 19, 20, or 21:

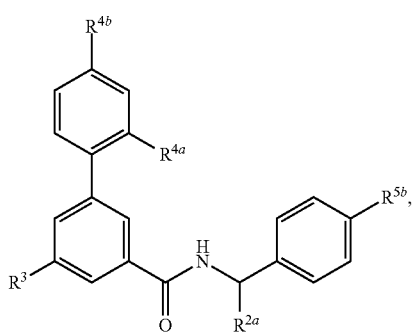

16

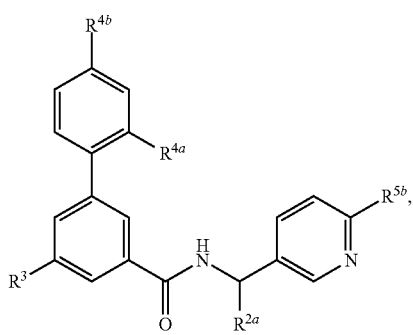

17

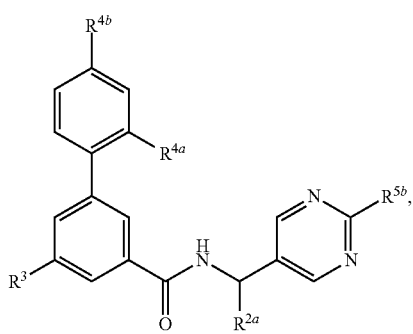

18

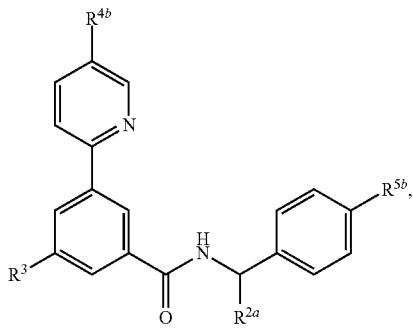

19

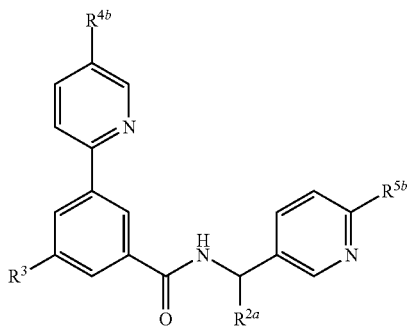

20

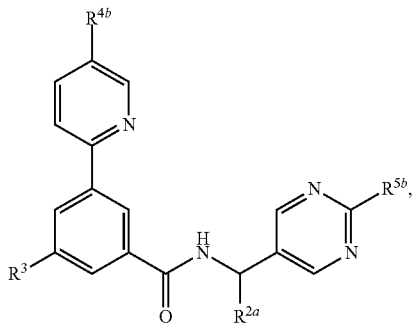

21 wherein $R^{2a}$ is H, Me, $CH_2OH$, or $CH_2CH_2OH$; $R^{4a}$ is H, or CN; $R^{5b}$ is F, Cl, Br, Me, or $CF_3$; $R^{5b}$ is F, Cl, Br, Me, OMe, or $CF_3$;

$R^3$ is i) $CH_2R^{3c}$; ii) C(OH)(H)$R^{3a}$; iii) C(OH)(Me)$R^{3a}$; iv) $OR^{3a}$; v) C(=O)$R^{3a}$; vi) C(=O)$OR^{3a}$; vii) S(O)$_2R^{3a}$; viii) C(=O)$NR^{3a}R^{3b}$; ix) S(O)$_2NR^{3a}R^{3b}$; x) C(=O)—Het; xi) S(O)$_2$-Het; xii) $CH_2OR^{3a}$; xiii) $CH_2NR^{3a}R^{3b}$; and xiv) C(OH)(H)$CH_2$-Het;

and $R^{3a}$, $R^{3b}$, $R^{3c}$, and Het are as described for formulae 2a-3n;

or a pharmaceutically acceptable salt, solvate, prodrug, stereoisomer, tautomer or isotopic variant thereof.

In one embodiment, with respect to formulae 16-21, $R^{5b}$ is Me.

In one embodiment, with respect to formulae 16-21, $R^{5b}$ is $CF_3$.

In one embodiment, with respect to formulae 16-21, $R^{5b}$ is OMe.

In another embodiment, with respect to formula 1, the compound is according to formula 22, or 23:

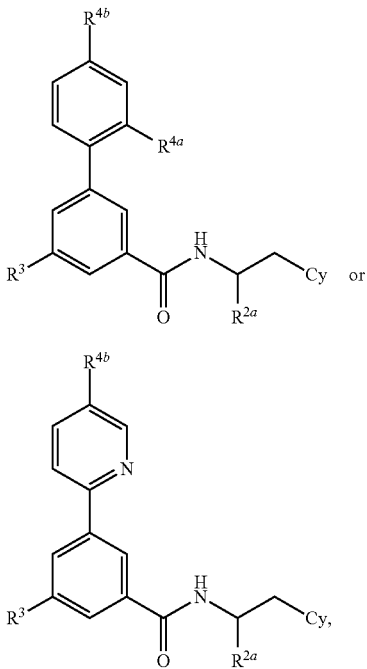

wherein

Cy is substituted or unsubstituted 4-7 membered N-containing heterocyclalkyl;

$R^{2a}$ is H, Me, $CH_2OH$, or $CH_2CH_2OH$; $R^{4a}$ is H, or CN; $R^{4b}$ is F, Cl, Br, Me, or $CF_3$;

$R^3$ is i) $CH_2R^{3c}$; ii) $C(OH)(H)R^{3a}$; iii) $C(OH)(Me)R^{3a}$; iv) $OR^{3a}$; v) $C(=O)R^{3a}$; vi) $C(=O)OR^{3a}$; vii) $S(O)_2R^{3a}$; viii) $C(=O)NR^{3a}R^{3b}$; ix) $S(O)_2NR^{3a}R^{3b}$; x) $C(=O)$—Het; xi) $S(O)_2$-Het; xii) $CH_2OR^{3a}$; xiii) $CH_2NR^{3a}R^{3b}$; or xiv) $C(OH)(H)CH_2$-Het;

and $R^{3a}$, $R^{3b}$, $R^{3c}$, and Het are as described for formulae 2a-3n;

or a pharmaceutically acceptable salt, solvate, prodrug, stereoisomer, tautomer or isotopic variant thereof.

In one embodiment, with respect to formulae 22-23, Cy is morpholin-1-yl.

In one embodiment, with respect to formulae 16-23, $R^{2a}$ is H.

In one embodiment, with respect to formulae 16-23, $R^{2a}$ is Me.

In one embodiment, with respect to formulae 16-23, $R^{2a}$ is $CH_2OH$.

In one embodiment, with respect to formulae 16-18 and 22, $R^{4a}$ is H.

In one embodiment, with respect to formulae 16-18 and 22, $R^{4a}$ is CN.

In one embodiment, with respect to formulae 16-23, $R^{4b}$ is Me.

In one particular embodiment, with respect to formulae 16-23, $R^{3a}$ is Me, Et, i-Pr, n-Pr, i-Bu, t-Bu, $CF_3$, $CH_2CF_3$, or benzyl.

In one particular embodiment, with respect to formulae 16-23, $R^{3a}$ is methoxymethyl, methoxyethyl, dimethylaminomethyl, or dimethylaminoethyl.

In one particular embodiment, with respect to formulae 16-23, $R^{3a}$ is piperidinylmethyl, piperazinylmethyl, pyrrolidinylmethyl, or morpholinylmethyl.

In one particular embodiment, with respect to formulae 16-23, $R^{3a}$ is pyridylmethyl, pyridylethyl, piperidinylethyl, piperazinylethyl, pyrrolidinylethyl, or morpholinylethyl.

In one particular embodiment, with respect to formulae 16-23, $R^{3a}$ is cyclopropyl, cyclopenyl, cyclopropylmethyl, or cyclopentylmethyl.

In one particular embodiment, with respect to formulae 16-23, $R^{3a}$ is substituted or unsubstituted phenyl, pyridyl, pyrazinyl or pyrimidinyl.

In one particular embodiment, with respect to formulae 16-23, $R^{3a}$ is pyrrolyl, furanyl, thiophenyl, pyrazolyl, imidazolyl, oxazolyl, thiazolyl, triazolyl, thiadiazolyl, unsubstituted or substituted with alkyl or haloalkyl.

In one particular embodiment, with respect to formulae 16-23, $R^{3a}$ is quinolinyl, isoquinolinyl, methylenedioxyphenyl, imidazopyridyl, benzoxazolyl, benzothiazolyl, and indolyl.

In one particular embodiment, with respect to formulae 16-23, $R^{3b}$ is H, Me, Et, or i-Pr.

In one particular embodiment, with respect to formulae 16-23, $R^{3b}$ is H.

In one particular embodiment, with respect to formulae 16-23, Het is azetidin-1-yl, pyrrolidin-1-yl, piperidin-1-yl, morpholin-1-yl, piperazin-1-yl, and azepin-1-yl, unsubstituted or substituted with one or more groups selected from Me, Et, i-Pr, OMe, $NMe_2$, Cl, F, OH, or $CF_3$.

In one particular embodiment, with respect to formula 1, the compound is selected from the compounds exemplified in Table 1.

In one particular embodiment, with respect to formula 1, the compound is selected from 4'-Methyl-5-(propane-1-sulfonyl)-biphenyl-3-carboxylic acid ((S)-2-hydroxy-1-methyl-ethyl)-amide;

2,4'-Dimethyl-5-(pyrrolidine-1-sulfonyl)-biphenyl-3-carboxylic acid (2-methyl-pyrimidin-5-ylmethyl)-amide;

2'-Cyano-4'-methyl-5-(pyrrolidine-1-sulfonyl)-biphenyl-3-carboxylic acid [(R)-1-(2-methyl-pyrimidin-5-yl)-ethyl]-amide;

2'-Cyano-4'-methyl-5-(pyrrolidine-1-sulfonyl)-biphenyl-3-carboxylic acid (6-methyl-pyridin-3-ylmethyl)-amide;

4'-Methyl-5-(2-methyl-propane-1-sulfonyl)-biphenyl-3-carboxylic acid ((S)-2-hydroxy-1-methyl-ethyl)-amide;

5-Cyclopentanesulfonyl-4'-methyl-biphenyl-3-carboxylic acid ((S)-2-hydroxy-1-methyl-ethyl)-amide;

4'-Methyl-5-(propane-2-sulfonyl)-biphenyl-3-carboxylic acid ((S)-2-hydroxy-1-methyl-ethyl)-amide;

3-Methanesulfonyl-5-(5-methyl-pyridin-2-yl)-N-(2-methyl-pyrimidin-5-ylmethyl)-benzamide;

3-(4-Hydroxy-pyrrolidin-3-yloxy)-5-(5-methyl-pyridin-2-yl)-N—[(R)-1-(2-methyl-pyrimidin-5-yl)-ethyl]-benzamide;

5-(2-Dimethylamino-1-hydroxy-ethyl)-4'-methyl-biphenyl-3-carboxylic acid (6-methyl-pyridin-3-ylmethyl)-amide;

4'-Methyl-5-(4-methyl-3-oxo-piperazine-1-carbonyl)-biphenyl-3-carboxylic acid (2-methyl-pyrimidin-5-ylmethyl)-amide;

4'-Methyl-5-(2-methyl-aziridine-1-carbonyl)-biphenyl-3-carboxylic acid (2-methyl-pyrimidin-5-ylmethyl)-amide;

4'-Methyl-5-(pyrrolidine-1-carbonyl)-biphenyl-3-carboxylic acid ((S)-1-methyl-2-morpholin-4-yl-ethyl)-amide;

5-[1-Hydroxy-2-(4-methyl-piperazin-1-yl)-ethyl]-4'-methyl-biphenyl-3-carboxylic acid (6-methyl-pyridin-3-ylmethyl)-amide; and 5-{1-Hydroxy-2-[(2-hydroxy-ethyl)-methyl-amino]-ethyl}-4'-methyl-biphenyl-3-carboxylic acid (6-methyl-pyridin-3-ylmethyl)-amide;

or a pharmaceutically acceptable salt, solvate, prodrug, stereoisomer, tautomer or isotopic variant thereof.

In one particular embodiment, with respect to formula 1, the compound is selected from 4'-Methyl-biphenyl-3,5-dicarboxylic acid 5-[(6-chloro-pyridin-3-ylmethyl)-amide]3-(isobutyl-methyl-amide);
4'-Methyl-biphenyl-3,5-dicarboxylic acid 3-(isobutyl-methyl-amide)5-[(2-methyl-pyrimidin-5-ylmethyl)-amide];
4'-Methyl-biphenyl-3,5-dicarboxylic acid 3-(isobutyl-methyl-amide)5-{[(R)-1-(2-methyl-pyrimidin-5-yl)-ethyl]-amide};
4'-Methyl-5-[(2-methyl-pyrimidin-5-ylmethyl)-carbamoyl]-biphenyl-3-carboxylic acid ethyl ester;
5-(3,3-Difluoro-azetidine-1-carbonyl)-4'-methyl-biphenyl-3-carboxylic acid (2-methyl-pyrimidin-5-ylmethyl)-amide;
4'-Methyl-5-(piperidine-1-carbonyl)-biphenyl-3-carboxylic acid (2-methyl-pyrimidin-5-ylmethyl)-amide;
5-(Azepane-1-carbonyl)-4'-methyl-biphenyl-3-carboxylic acid (2-methyl-pyrimidin-5-ylmethyl)-amide;
4'-Methyl-5-(pyrrolidine-1-carbonyl)-biphenyl-3-carboxylic acid (2-methyl-pyrimidin-5-ylmethyl)-amide;
5-Methanesulfonyl-4'-methyl-biphenyl-3-carboxylic acid [1-(4-chloro-3-methanesulfonyl-phenyl)-ethyl]-amide;
5-(3-Hydroxy-azetidine-1-carbonyl)-4'-methyl-biphenyl-3-carboxylic acid (2-methyl-pyrimidin-5-ylmethyl)-amide;
5-(Azetidine-1-carbonyl)-4'-methyl-biphenyl-3-carboxylic acid (2-methyl-pyrimidin-5-ylmethyl)-amide;
5-(3-Methoxy-pyrrolidine-1-carbonyl)-4'-methyl-biphenyl-3-carboxylic acid (2-methyl-pyrimidin-5-ylmethyl)-amide;
4'-Methyl-5-(2-trifluoromethyl-pyrrolidine-1-carbonyl)-biphenyl-3-carboxylic acid (2-methyl-pyrimidin-5-ylmethyl)-amide;
5-(3,3-Difluoro-pyrrolidine-1-carbonyl)-4'-methyl-biphenyl-3-carboxylic acid (2-methyl-pyrimidin-5-ylmethyl)-amide;
5-Methanesulfonyl-4'-methyl-biphenyl-3-carboxylic acid [(R)-1-(6-trifluoromethyl-pyridin-3-yl)-ethyl]-amide;
5-Methanesulfonyl-4'-methyl-biphenyl-3-carboxylic acid 3-methanesulfonyl-4-methyl-benzylamide;
2'-Cyano-4'-methyl-5-(pyrrolidine-1-carbonyl)-biphenyl-3-carboxylic acid (2-methyl-pyrimidin-5-ylmethyl)-amide;
4'-Methyl-5-(propane-1-sulfonyl)-biphenyl-3-carboxylic acid 3-methanesulfonyl-4-methyl-benzylamide;
4'-Methyl-5-(propane-1-sulfonyl)-biphenyl-3-carboxylic acid (2-methyl-pyrimidin-5-ylmethyl)-amide;
4'-Methyl-5-(pyrrolidine-1-carbonyl)-biphenyl-3-carboxylic acid (2-methoxy-pyrimidin-5-ylmethyl)-amide;
4'-Methyl-5-(pyrrolidine-1-carbonyl)-biphenyl-3-carboxylic acid (imidazo[1,2-a]pyridin-7-ylmethyl)-amide;
4'-Methyl-5-(pyrrolidine-1-carbonyl)-biphenyl-3-carboxylic acid (5-methyl-pyrazin-2-ylmethyl)-amide;
4'-Methyl-5-(pyrrolidine-1-carbonyl)-biphenyl-3-carboxylic acid [(R)-1-(2-methyl-pyrimidin-5-yl)-ethyl]-amide;
4'-Methyl-5-(propane-1-sulfonyl)-biphenyl-3-carboxylic acid [(R)-1-(2-methyl-pyrimidin-5-yl)-ethyl]-amide;
4'-Methyl-5-(propane-1-sulfonyl)-biphenyl-3-carboxylic acid (6-methyl-pyridin-3-ylmethyl)-amide;
4'-Methyl-5-(propane-1-sulfonyl)-biphenyl-3-carboxylic acid (imidazo[1,2-a]pyridin-7-ylmethyl)-amide;
5-Methanesulfonyl-4'-methyl-biphenyl-3-carboxylic acid (6-methyl-pyridin-3-ylmethyl)-amide;
4'-Methyl-5-(pyrrolidine-1-carbonyl)-biphenyl-3-carboxylic acid (6-methyl-pyridin-3-ylmethyl)-amide;
2'-Cyano-4'-methyl-5-(pyrrolidine-1-carbonyl)-biphenyl-3-carboxylic acid (6-methyl-pyridin-3-ylmethyl)-amide;
2'-Cyano-5-(3-hydroxy-azetidine-1-carbonyl)-4'-methyl-biphenyl-3-carboxylic acid (6-methyl-pyridin-3-ylmethyl)-amide;
2'-Cyano-5-(3-hydroxy-azetidine-1-carbonyl)-4'-methyl-biphenyl-3-carboxylic acid (6-trifluoromethyl-pyridin-3-ylmethyl)-amide;
2'-Cyano-4'-methyl-5-(pyrrolidine-1-carbonyl)-biphenyl-3-carboxylic acid (6-chloro-pyridin-3-ylmethyl)-amide;
4'-Methyl-5-(pyrrolidine-1-carbonyl)-biphenyl-3-carboxylic acid 3-methanesulfonyl-4-methyl-benzylamide;
4'-Methyl-5-(pyrrolidine-1-carbonyl)-biphenyl-3-carboxylic acid (1,1-dioxo-2,3-dihydro-1H-benzo[b]thiophen-6-ylmethyl)-amide;
4'-Methyl-5-(pyrrolidine-1-carbonyl)-biphenyl-3-carboxylic acid (3-chloro-5-trifluoromethyl-pyridin-2-ylmethyl)-amide;
5-(Azetidine-1-carbonyl)-4'-methyl-biphenyl-3-carboxylic acid [(R)-1-(6-trifluoromethyl-pyridin-3-yl)-ethyl]amide;
5-(3-Hydroxy-azetidine-1-carbonyl)-4'-methyl-biphenyl-3-carboxylic acid [(R)-1-(2-methyl-pyrimidin-5-yl)-ethyl]-amide;
5-(Azetidine-1-carbonyl)-4'-methyl-biphenyl-3-carboxylic acid [(R)-1-(2-methoxy-pyrimidin-5-yl)-ethyl]-amide;
5-(Azetidine-1-carbonyl)-4'-methyl-biphenyl-3-carboxylic acid [(R)-1-(2-methyl-pyrimidin-5-yl)-ethyl]-amide;
4'-Methyl-5-(pyrrolidine-1-carbonyl)-biphenyl-3-carboxylic acid (3,5-dichloro-pyridin-2-ylmethyl)-amide;
5-(3-Hydroxy-azetidine-1-carbonyl)-4'-methyl-biphenyl-3-carboxylic acid [(R)-1-(6-trifluoromethyl-pyridin-3-yl)-ethyl]-amide;
4'-Methyl-5-(pyrrolidine-1-carbonyl)-biphenyl-3-carboxylic acid [(S)-1-(6-difluoromethyl-pyridin-3-yl)-2-hydroxy-ethyl]-amide;
4'-Methyl-5-(pyrrolidine-1-carbonyl)-biphenyl-3-carboxylic acid (benzooxazol-5-ylmethyl)-amide;
4'-Methyl-5-(pyrrolidine-1-carbonyl)-biphenyl-3-carboxylic acid (6-chloro-pyridin-3-ylmethyl)-amide;
4'-Methyl-5-(pyrrolidine-1-carbonyl)-biphenyl-3-carboxylic acid [(S)-2-hydroxy-1-(6-trifluoromethyl-pyridin-3-yl)-ethyl]-amide;
5-((R)-3-Hydroxy-pyrrolidine-1-carbonyl)-4'-methyl-biphenyl-3-carboxylic acid (6-methyl-pyridin-3-ylmethyl)-amide;
4'-Methyl-5-(pyrrolidine-1-carbonyl)-biphenyl-3-carboxylic acid [(S)-2-hydroxy-1-(2-methyl-pyrimidin-5-yl)-ethyl]-amide;
4'-Methyl-5-(pyrrolidine-1-carbonyl)-biphenyl-3-carboxylic acid 4-chloro-3-[1,2,4]triazol-4-yl-benzylamide;
4'-Methyl-5-(pyrrolidine-1-carbonyl)-biphenyl-3-carboxylic acid [1-(6-methyl-pyridin-3-yl)-ethyl]-amide;
4'-Methyl-5-(pyrrolidine-1-sulfonyl)-biphenyl-3-carboxylic acid (6-methyl-pyridin-3-ylmethyl)-amide;
3-(5-Methyl-pyridin-2-yl)-N-(6-methyl-pyridin-3-ylmethyl)-5-(pyrrolidine-1-sulfonyl)-benzamide;
4'-Methyl-5-(pyrrolidine-1-carbonyl)-biphenyl-3-carboxylic acid [(R)-1-(5-chloro-1-methyl-1H-pyrazol-4-yl)-ethyl]-amide;
5-Methanesulfonyl-4'-methyl-biphenyl-3-carboxylic acid [(R)-1-(2-methyl-pyrimidin-5-yl)-ethyl]amide;
3-(5-Methyl-pyridin-2-yl)-N-[1-(6-methyl-pyridin-3-yl)-ethyl]-5-(pyrrolidine-1-carbonyl)-benzamide;
3-(5-Methyl-pyridin-2-yl)-N-(6-methyl-pyridin-3-ylmethyl)-5-(pyrrolidine-1-carbonyl)-benzamide;
3-(5-Methyl-pyridin-2-yl)-5-(pyrrolidine-1-carbonyl)-N-(6-trifluoromethyl-pyridin-3-ylmethyl)-benzamide;

5-(Hexahydro-pyrrolo[1,2-a]pyrazine-2-carbonyl)-4'-methyl-biphenyl-3-carboxylic acid (6-methyl-pyridin-3-ylmethyl)-amide;
5-(3-Hydroxy-azetidine-1-carbonyl)-4'-methyl-biphenyl-3-carboxylic acid (3-chloro-5-trifluoromethyl-pyridin-2-ylmethyl)-amide;
5-(3-Hydroxy-azetidine-1-carbonyl)-4'-methyl-biphenyl-3-carboxylic acid (6-trifluoromethyl-pyridin-3-ylmethyl)-amide;
5-(3-Hydroxy-azetidine-1-carbonyl)-4'-methyl-biphenyl-3-carboxylic acid (6-chloro-pyridin-3-ylmethyl)-amide;
5-(3-Hydroxy-azetidine-1-carbonyl)-4'-methyl-biphenyl-3-carboxylic acid (6-methyl-pyridin-3-ylmethyl)-amide;
5-(3-Hydroxy-azetidine-1-carbonyl)-4'-methyl-biphenyl-3-carboxylic acid (3,5-dichloro-pyridin-2-ylmethyl)-amide;
3-(5-Methyl-pyridin-2-yl)-5-(pyrrolidine-1-carbonyl)-N—[(R)-1-(6-trifluoromethyl-pyridin-3-yl)-ethyl]-benzamide;
3-((R)-3-Hydroxy-pyrrolidine-1-carbonyl)-5-(5-methyl-pyridin-2-yl)-N-(6-trifluoromethyl-pyridin-3-ylmethyl)-benzamide;
3-((R)-3-Hydroxy-pyrrolidine-1-carbonyl)-5-(5-methyl-pyridin-2-yl)-N—[(R)-1-(6-trifluoromethyl-pyridin-3-yl)-ethyl]-benzamide;
4'-Methyl-5-(pyrrolidine-1-carbonyl)-biphenyl-3-carboxylic acid (6-methoxy-pyridin-3-ylmethyl)-amide;
5-((R)-3-Hydroxy-pyrrolidine-1-carbonyl)-4'-methyl-biphenyl-3-carboxylic acid [(R)-1-(2-methyl-pyrimidin-5-yl)-ethyl]-amide;
5-((R)-3-Hydroxy-pyrrolidine-1-carbonyl)-4'-methyl-biphenyl-3-carboxylic acid [(R)-1-(6-trifluoromethyl-pyridin-3-yl)-ethyl]-amide;
4'-Methyl-biphenyl-3,5-dicarboxylic acid 3-(methyl-pyridin-4-ylmethyl-amide)5-[(6-methyl-pyridin-3-ylmethyl)-amide];
4'-Methyl-biphenyl-3,5-dicarboxylic acid 5-[(6-methyl-pyridin-3-ylmethyl)-amide]3-[methyl-(2,2,2-trifluoro-ethyl)-amide];
5-Methanesulfonyl-4'-methyl-biphenyl-3-carboxylic acid [(R)-1-(6-methyl-pyridin-3-yl)-ethyl]-amide;
3-(5-Methyl-pyridin-2-yl)-N—[(R)-1-(6-methyl-pyridin-3-yl)-ethyl]-5-(pyrrolidine-1-carbonyl)-benzamide;
3-(5-Methyl-pyridin-2-yl)-N—[(R)-1-(2-methyl-pyrimidin-5-yl)-ethyl]-5-(pyrrolidine-1-carbonyl)-benzamide;
4'-Methyl-5-(pyrrolidine-1-carbonyl)-biphenyl-3-carboxylic acid [(R)-1-(6-methyl-pyridin-3-yl)-ethyl]-amide;
3-((R)-3-Hydroxy-pyrrolidine-1-carbonyl)-5-(5-methyl-pyridin-2-yl)-N—[(R)-1-(6-methyl-pyridin-3-yl)-ethyl]-benzamide;
3-((R)-3-Hydroxy-pyrrolidine-1-carbonyl)-5-(5-methyl-pyridin-2-yl)-N-(6-methyl-pyridin-3-ylmethyl)-benzamide;
4'-Methyl-5-(2-methyl-propane-1-sulfonyl)-biphenyl-3-carboxylic acid (6-methyl-pyridin-3-ylmethyl)-amide;
4'-Methyl-5-(2-methyl-propane-1-sulfonyl)-biphenyl-3-carboxylic acid (2-methyl-pyrimidin-5-ylmethyl)-amide;
5-(2,5-Dimethyl-pyrrolidine-1-carbonyl)-4'-methyl-biphenyl-3-carboxylic acid (6-methyl-pyridin-3-ylmethyl)-amide;
5-(Hexahydro-pyrrolo[1,2-a]pyrazine-2-carbonyl)-4'-methyl-biphenyl-3-carboxylic acid [(R)-1-(2-methyl-pyrimidin-5-yl)-ethyl]-amide;
5-(Hexahydro-pyrrolo[1,2-a]pyrazine-2-carbonyl)-4'-methyl-biphenyl-3-carboxylic acid [(R)-1-(6-methyl-pyridin-3-yl)-ethyl]-amide;
5-(7-Aza-bicyclo[2.2.1]heptane-7-carbonyl)-4'-methyl-biphenyl-3-carboxylic acid (6-methyl-pyridin-3-ylmethyl)-amide;
4'-Methyl-5-(2-methyl-propane-1-sulfonyl)-biphenyl-3-carboxylic acid [(R)-1-(2-methyl-pyrimidin-5-yl)-ethyl]-amide;
5-((2R,5R)-2,5-Dimethyl-pyrrolidine-1-carbonyl)-4'-methyl-biphenyl-3-carboxylic acid (6-methyl-pyridin-3-ylmethyl)-amide;
4'-Methyl-5-(propane-2-sulfonyl)-biphenyl-3-carboxylic acid [(R)-1-(6-methyl-pyridin-3-yl)-ethyl]amide;
4'-Methyl-5-(propane-2-sulfonyl)-biphenyl-3-carboxylic acid [(R)-1-(2-methyl-pyrimidin-5-yl)-ethyl]amide;
4'-Methyl-5-(propane-2-sulfonyl)-biphenyl-3-carboxylic acid (6-methyl-pyridin-3-ylmethyl)-amide;
4'-Bromo-5-(pyrrolidine-1-carbonyl)-biphenyl-3-carboxylic acid (6-methyl-pyridin-3-ylmethyl)-amide;
4'-Methyl-5-(propane-2-sulfonyl)-biphenyl-3-carboxylic acid (2-methyl-pyrimidin-5-ylmethyl)-amide;
5-Methanesulfonyl-4'-methyl-biphenyl-3-carboxylic acid [(R)-3-hydroxy-1-(6-methyl-pyridin-3-yl)-propyl]-amide;
5-Methanesulfonyl-4'-methyl-biphenyl-3-carboxylic acid [(S)-2-hydroxy-1-(6-methoxy-pyridin-3-yl)-ethyl]-amide;
5-Methanesulfonyl-4'-methyl-biphenyl-3-carboxylic acid [(S)-1-(6-difluoromethyl-pyridin-3-yl)-2-hydroxy-ethyl]-amide;
5-Ethanesulfonyl-4'-methyl-biphenyl-3-carboxylic acid [(R)-1-(6-methyl-pyridin-3-yl)-ethyl]-amide;
5-Ethanesulfonyl-4'-methyl-biphenyl-3-carboxylic acid [(R)-1-(2-methyl-pyrimidin-5-yl)-ethyl]-amide;
5-Ethanesulfonyl-4'-methyl-biphenyl-3-carboxylic acid (6-methyl-pyridin-3-ylmethyl)-amide;
5-Ethanesulfonyl-4'-methyl-biphenyl-3-carboxylic acid (2-methyl-pyrimidin-5-ylmethyl)-amide;
4'-Bromo-5-(pyrrolidine-1-carbonyl)-biphenyl-3-carboxylic acid [(R)-1-(2-methyl-pyrimidin-5-yl)-ethyl]amide;
4'-Bromo-5-(pyrrolidine-1-carbonyl)-biphenyl-3-carboxylic acid [(R)-1-(6-methyl-pyridin-3-yl)-ethyl]-amide;
5-Cyclopentanesulfonyl-4'-methyl-biphenyl-3-carboxylic acid [(R)-1-(6-methyl-pyridin-3-yl)-ethyl]amide;
5-Cyclopentanesulfonyl-4'-methyl-biphenyl-3-carboxylic acid [(R)-1-(2-methyl-pyrimidin-5-yl)-ethyl]amide;
5-Methanesulfonyl-4'-methyl-biphenyl-3-carboxylic acid [(S)-2-hydroxy-1-(2-methyl-pyrimidin-5-yl)-ethyl]-amide;
5-Methanesulfonyl-4'-methyl-biphenyl-3-carboxylic acid [(R)-3-hydroxy-1-(6-methoxy-pyridin-3-yl)-propyl]-amide;
4'-Methyl-5-(pyrrolidine-1-carbonyl)-biphenyl-3-carboxylic acid (6-methyl-1-oxy-pyridin-3-ylmethyl)-amide;
4'-Methyl-5-(pyrimidin-2-yloxy)-biphenyl-3-carboxylic acid [(R)-1-(6-methyl-pyridin-3-yl)-ethyl]amide;
4'-Methyl-5-(thiazol-2-yloxy)-biphenyl-3-carboxylic acid [(R)-1-(2-methyl-pyrimidin-5-yl)-ethyl]-amide;
4'-Methyl-5-(thiazol-2-yloxy)-biphenyl-3-carboxylic acid [(R)-1-(6-methyl-pyridin-3-yl)-ethyl]-amide;
5-(Hydroxy-pyridin-2-yl-methyl)-4'-methyl-biphenyl-3-carboxylic acid (6-methyl-pyridin-3-ylmethyl)-amide;
5-(Hydroxy-pyridin-2-yl-methyl)-4'-methyl-biphenyl-3-carboxylic acid [(R)-1-(6-methyl-pyridin-3-yl)-ethyl]-amide;
5-(2-Methoxy-ethoxy)-4'-methyl-biphenyl-3-carboxylic acid (6-methyl-pyridin-3-ylmethyl)-amide;
5-(2-Methoxy-ethoxy)-4'-methyl-biphenyl-3-carboxylic acid [(R)-1-(6-methyl-pyridin-3-yl)-ethyl]-amide;
5-(2-Methoxy-ethoxy)-4'-methyl-biphenyl-3-carboxylic acid [(R)-1-(2-methyl-pyrimidin-5-yl)-ethyl]-amide;
2'-Cyano-5-(2-methoxy-ethoxy)-4'-methyl-biphenyl-3-carboxylic acid [(R)-1-(6-methyl-pyridin-3-yl)-ethyl]amide;

2'-Cyano-5-(2-methoxy-ethoxy)-4'-methyl-biphenyl-3-carboxylic acid [(R)-1-(2-methyl-pyrimidin-5-yl)-ethyl]-amide;
2'-Cyano-4'-methyl-5-(thiazol-2-yloxy)-biphenyl-3-carboxylic acid [(R)-1-(2-methyl-pyrimidin-5-yl)-ethyl]-amide;
2'-Cyano-4'-methyl-5-(thiazol-2-yloxy)-biphenyl-3-carboxylic acid [(R)-1-(6-methyl-pyridin-3-yl)-ethyl]-amide;
5-Methanesulfonyl-4'-methyl-biphenyl-3-carboxylic acid (6-methyl-1-oxy-pyridin-3-ylmethyl)-amide;
5-Methanesulfonyl-4'-methyl-biphenyl-3-carboxylic acid [(S)-2-hydroxy-1-(6-methyl-pyridin-3-yl)-ethyl]-amide;
2'-Cyano-4'-methyl-5-(pyridin-2-yloxy)-biphenyl-3-carboxylic acid [(R)-1-(6-methyl-pyridin-3-yl)-ethyl]-amide;
3-(5-Methyl-pyridin-2-yl)-N—[(R)-1-(6-methyl-pyridin-3-yl)-ethyl]-5-(thiazol-2-yloxy)-benzamide;
5-(Hydroxy-pyridin-2-yl-methyl)-4'-methyl-biphenyl-3-carboxylic acid (2-methyl-pyrimidin-5-ylmethyl)-amide;
5-(Hydroxy-pyridin-2-yl-methyl)-4'-methyl-biphenyl-3-carboxylic acid [(R)-1-(2-methyl-pyrimidin-5-yl)-ethyl]-amide;
3-(5-Methyl-pyridin-2-yl)-N—[(R)-1-(2-methyl-pyrimidin-5-yl)-ethyl]-5-(thiazol-2-yloxy)-benzamide;
3-(5-Methyl-pyridin-2-yl)-N—[(R)-1-(2-methyl-pyrimidin-5-yl)-ethyl]-5-(pyridin-2-yloxy)-benzamide;
3-(5-Methyl-pyridin-2-yl)-N—[(R)-1-(6-methyl-pyridin-3-yl)-ethyl]-5-(pyridin-2-yloxy)-benzamide;
3-(Hydroxy-phenyl-methyl)-5-(5-methyl-pyridin-2-yl)-N—[(R)-1-(6-methyl-pyridin-3-yl)-ethyl]-benzamide;
3-(Hydroxy-phenyl-methyl)-5-(5-methyl-pyridin-2-yl)-N—[(R)-1-(2-methyl-pyrimidin-5-yl)-ethyl]-benzamide;
2'-Cyano-5-(hydroxy-phenyl-methyl)-4'-methyl-biphenyl-3-carboxylic acid [(R)-1-(2-methyl-pyrimidin-5-yl)-ethyl]-amide;
2'-Cyano-5-(hydroxy-phenyl-methyl)-4'-methyl-biphenyl-3-carboxylic acid [(R)-1-(6-methyl-pyridin-3-yl)-ethyl]-amide;
5-(Hydroxy-thiazol-2-yl-methyl)-4'-methyl-biphenyl-3-carboxylic acid [(R)-1-(6-methyl-pyridin-3-yl)-ethyl]amide;
5-(Hydroxy-thiazol-2-yl-methyl)-4'-methyl-biphenyl-3-carboxylic acid [(R)-1-(2-methyl-pyrimidin-5-yl)-ethyl]-amide;
2'-Cyano-5-(hydroxy-pyridin-2-yl-methyl)-4'-methyl-biphenyl-3-carboxylic acid [(R)-1-(6-methyl-pyridin-3-yl)-ethyl]-amide;
2'-Cyano-5-(hydroxy-pyridin-2-yl-methyl)-4'-methyl-biphenyl-3-carboxylic acid [(R)-1-(2-methyl-pyrimidin-5-yl)-ethyl]-amide;
3-(Hydroxy-pyridin-2-yl-methyl)-5-(5-methyl-pyridin-2-yl)-N—[(R)-1-(2-methyl-pyrimidin-5-yl)-ethyl]-benzamide;
3-(Hydroxy-pyridin-2-yl-methyl)-5-(5-methyl-pyridin-2-yl)-N—[(R)-1-(6-methyl-pyridin-3-yl)-ethyl]-benzamide;
5-(1,2-Dihydroxy-ethyl)-4'-methyl-biphenyl-3-carboxylic acid [(R)-1-(6-methyl-pyridin-3-yl)-ethyl]amide;
2'-Cyano-5-hydroxymethyl-4'-methyl-biphenyl-3-carboxylic acid [(R)-1-(6-methyl-pyridin-3-yl)-ethyl]amide;
3-(Hydroxy-thiazol-2-yl-methyl)-5-(5-methyl-pyridin-2-yl)-N—[(R)-1-(6-methyl-pyridin-3-yl)-ethyl]-benzamide;
3-(Hydroxy-thiazol-2-yl-methyl)-5-(5-methyl-pyridin-2-yl)-N—[(R)-1-(2-methyl-pyrimidin-5-yl)-ethyl]-benzamide;
2'-Cyano-5-(hydroxy-thiazol-2-yl-methyl)-4'-methyl-biphenyl-3-carboxylic acid [(R)-1-(2-methyl-pyrimidin-5-yl)-ethyl]-amide;
2'-Cyano-5-(hydroxy-thiazol-2-yl-methyl)-4'-methyl-biphenyl-3-carboxylic acid [(R)-1-(6-methyl-pyridin-3-yl)-ethyl]-amide;
T-Cyano-4'-methyl-5-(2,2,2-trifluoro-1-hydroxy-ethyl)-biphenyl-3-carboxylic acid [(R)-1-(6-methyl-pyridin-3-yl)-ethyl]-amide;
2'-Cyano-4'-methyl-5-(2,2,2-trifluoro-1-hydroxy-ethyl)-biphenyl-3-carboxylic acid (6-methyl-pyridin-3-ylmethyl)-amide;
2'-Cyano-5-(1,2-dihydroxy-ethyl)-4'-methyl-biphenyl-3-carboxylic acid [(R)-1-(6-methyl-pyridin-3-yl)-ethyl]-amide;
5-(2-Methoxy-1-methyl-ethoxy)-4'-methyl-biphenyl-3-carboxylic acid [(R)-1-(6-methyl-pyridin-3-yl)-ethyl]amide;
5-(2-Methoxy-1-methyl-ethoxy)-4'-methyl-biphenyl-3-carboxylic acid (6-methyl-pyridin-3-ylmethyl)-amide;
5-(2-Hydroxy-ethoxy)-4'-methyl-biphenyl-3-carboxylic acid [(R)-1-(6-methyl-pyridin-3-yl)-ethyl]-amide;
2'-Cyano-5-(2-hydroxy-ethoxy)-4'-methyl-biphenyl-3-carboxylic acid [(R)-1-(6-methyl-pyridin-3-yl)-ethyl]amide;
4'-Methyl-5-(tetrahydro-furan-3-yloxy)-biphenyl-3-carboxylic acid [(R)-1-(6-methyl-pyridin-3-yl)-ethyl]amide;
4'-Methyl-5-(tetrahydro-furan-2-ylmethoxy)-biphenyl-3-carboxylic acid [(R)-1-(6-methyl-pyridin-3-yl)-ethyl]-amide;
2'-Cyano-5-(1-hydroxy-ethyl)-4'-methyl-biphenyl-3-carboxylic acid [(R)-1-(6-methyl-pyridin-3-yl)-ethyl]amide;
2'-Cyano-4'-methyl-5-(tetrahydro-furan-2-ylmethoxy)-biphenyl-3-carboxylic acid [(R)-1-(6-methyl-pyridin-3-yl)-ethyl]-amide;
2'-Cyano-4'-methyl-5-(tetrahydro-furan-3-ylmethoxy)-biphenyl-3-carboxylic acid [(R)-1-(6-methyl-pyridin-3-yl)-ethyl]-amide;
2'-Cyano-4'-methyl-5-(tetrahydro-furan-3-yloxy)-biphenyl-3-carboxylic acid [(R)-1-(6-methyl-pyridin-3-yl)-ethyl]-amide;
2'-Cyano-5-(2-methoxy-1-methyl-ethoxy)-4'-methyl-biphenyl-3-carboxylic acid [(R)-1-(6-methyl-pyridin-3-yl)-ethyl]-amide;
2'-Cyano-5-([1,4]dioxan-2-ylmethoxy)-4'-methyl-biphenyl-3-carboxylic acid [(R)-1-(6-methyl-pyridin-3-yl)-ethyl]-amide;
5-(2,3-Dihydroxy-propoxy)-4'-methyl-biphenyl-3-carboxylic acid [(R)-1-(6-methyl-pyridin-3-yl)-ethyl]-amide;
5-(1-Hydroxy-ethyl)-4'-methyl-biphenyl-3-carboxylic acid [(R)-1-(6-methyl-pyridin-3-yl)-ethyl]amide;
5-(1-Hydroxymethyl-2-methoxy-ethoxy)-4'-methyl-biphenyl-3-carboxylic acid [(R)-1-(6-methyl-pyridin-3-yl)-ethyl]-amide;
3-(2-Methoxy-1-methyl-ethoxy)-5-(5-methyl-pyridin-2-yl)-N—[(R)-1-(6-methyl-pyridin-3-yl)-ethyl]-benzamide;
5-[Hydroxy-(3-methyl-3H-imidazol-4-yl)-methyl]-4'-methyl-biphenyl-3-carboxylic acid [(R)-1-(6-methyl-pyridin-3-yl)-ethyl]-amide;
3-(1-Hydroxy-ethyl)-5-(5-methyl-pyridin-2-yl)-N—[(R)-1-(6-methyl-pyridin-3-yl)-ethyl]-benzamide;
3-(5-Methyl-pyridin-2-yl)-N—[(R)-1-(6-methyl-pyridin-3-yl)-ethyl]-5-(tetrahydro-furan-3-yloxy)-benzamide;
3-(5-Methyl-pyridin-2-yl)-N—[(R)-1-(6-methyl-pyridin-3-yl)-ethyl]-5-(tetrahydro-furan-3-ylmethoxy)-benzamide;
3-(5-Methyl-pyridin-2-yl)-N—[(R)-1-(6-methyl-pyridin-3-yl)-ethyl]-5-(tetrahydro-furan-2-ylmethoxy)-benzamide;
5-(4-Hydroxy-tetrahydro-furan-3-yloxy)-4'-methyl-biphenyl-3-carboxylic acid [(R)-1-(6-methyl-pyridin-3-yl)-ethyl]-amide;

T-Cyano-5-(4-hydroxy-tetrahydro-furan-3-yloxy)-4'-methyl-biphenyl-3-carboxylic acid [(R)-1-(6-methyl-pyridin-3-yl)-ethyl]-amide;
3-(2-Hydroxy-1-methyl-ethoxy)-5-(5-methyl-pyridin-2-yl)-N—[(R)-1-(6-methyl-pyridin-3-yl)-ethyl]-benzamide;
5-(2-Hydroxy-1-methyl-ethoxy)-4'-methyl-biphenyl-3-carboxylic acid [(R)-1-(6-methyl-pyridin-3-yl)-ethyl]-amide;
3-(2-Hydroxy-1-methoxymethyl-ethoxy)-5-(5-methyl-pyridin-2-yl)-N—[(R)-1-(6-methyl-pyridin-3-yl)-ethyl]-benzamide;
2'-Cyano-4'-methyl-5-(2,2,2-trifluoro-1-hydroxy-ethyl)-biphenyl-3-carboxylic acid [(R)-1-(2-methyl-pyrimidin-5-yl)-ethyl]-amide;
5-[Hydroxy-(3-methyl-3H-imidazol-4-yl)-methyl]-4'-methyl-biphenyl-3-carboxylic acid [(R)-1-(2-methyl-pyrimidin-5-yl)-ethyl]-amide;
2'-Cyano-4'-methyl-5-(tetrahydro-furan-3-yloxy)-biphenyl-3-carboxylic acid [(R)-1-(2-methyl-pyrimidin-5-yl)-ethyl]-amide;
4'-Methyl-5-(tetrahydro-furan-3-yloxy)-biphenyl-3-carboxylic acid [(R)-1-(2-methyl-pyrimidin-5-yl)-ethyl]-amide;
5-(4-Hydroxy-tetrahydro-furan-3-yloxy)-4'-methyl-biphenyl-3-carboxylic acid [(R)-1-(2-methyl-pyrimidin-5-yl)-ethyl]-amide;
2'-Cyano-5-(4-hydroxy-tetrahydro-furan-3-yloxy)-4'-methyl-biphenyl-3-carboxylic acid [(R)-1-(2-methyl-pyrimidin-5-yl)-ethyl]-amide;
5-(1-Hydroxy-2-morpholin-4-yl-ethyl)-4'-methyl-biphenyl-3-carboxylic acid (6-methyl-pyridin-3-ylmethyl)-amide;
3-(5-Hydroxymethyl-thiazol-2-yloxy)-5-(5-methyl-pyridin-2-yl)-N—[(R)-1-(6-methyl-pyridin-3-yl)-ethyl]-benzamide;
2'-Cyano-4'-methyl-5-(4-methyl-thiazol-2-yloxy)-biphenyl-3-carboxylic acid [(R)-1-(6-methyl-pyridin-3-yl)-ethyl]-amide;
3-(5-Methyl-pyridin-2-yl)-N—[(R)-1-(6-methyl-pyridin-3-yl)-ethyl]-5-(4-methyl-thiazol-2-yloxy)-benzamide;
3-(Benzothiazol-2-yloxy)-5-(5-methyl-pyridin-2-yl)-N—[(R)-1-(6-methyl-pyridin-3-yl)-ethyl]-benzamide;
2'-Cyano-5-(2-hydroxy-1-methyl-ethoxy)-4'-methyl-biphenyl-3-carboxylic acid [(R)-1-(6-methyl-pyridin-3-yl)-ethyl]-amide;
2'-Cyano-5-(1-hydroxymethyl-2-methoxy-ethoxy)-4'-methyl-biphenyl-3-carboxylic acid [(R)-1-(6-methyl-pyridin-3-yl)-ethyl]-amide;
5-(1-Hydroxy-propyl)-4'-methyl-biphenyl-3-carboxylic acid [(R)-1-(6-methyl-pyridin-3-yl)-ethyl]amide;
5-(1,2-Dimethoxy-ethyl)-4'-methyl-biphenyl-3-carboxylic acid [(R)-1-(6-methyl-pyridin-3-yl)-ethyl]-amide; and
3-(4-Chloro-thiazol-2-yloxy)-5-(5-methyl-pyridin-2-yl)-N—[(R)-1-(6-methyl-pyridin-3-yl)-ethyl]-benzamide;
or a pharmaceutically acceptable salt, solvate, prodrug, stereoisomer, tautomer or isotopic variant thereof.

Additional embodiments within the scope provided herein are set forth in non-limiting fashion elsewhere herein and in the examples. It should be understood that these examples are for illustrative purposes only and are not to be construed as limiting in any manner.

In certain aspects, provided herein are prodrugs and derivatives of the compounds according to the formulae above. Prodrugs are derivatives of the compounds provided herein, which have metabolically cleavable groups and become by solvolysis or under physiological conditions the compounds provided herein, which are pharmaceutically active, in vivo. Such examples include, but are not limited to, choline ester derivatives and the like, N-alkylmorpholine esters and the like.

Certain compounds provided herein have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy) alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

Pharmaceutical Compositions

When employed as pharmaceuticals, the compounds provided herein are typically administered in the form of a pharmaceutical composition. Such compositions can be prepared in a manner well known in the pharmaceutical art and comprise at least one active compound.

Generally, the compounds provided herein are administered in a therapeutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The above-described components for orally administrable, injectable or topically administrable compositions are merely representative. Other materials as well as processing techniques and the like are set forth in Part 8 of Remington's The Science and Practice of Pharmacy, 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1

Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2

Capsules

A compound of the invention may be admixed as a dry powder with a starch diluent in an approximate 1:1 weight ratio. The mixture is filled into 250 mg capsules (125 mg of active compound per capsule).

Formulation 3

Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4

Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

A compound of the invention may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

Methods of Treatment

The present compounds are used as therapeutic agents for the treatment of conditions in mammals. Accordingly, the compounds and pharmaceutical compositions provided herein find use as therapeutics for preventing and/or treating neurodegenerative, autoimmune and inflammatory conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

In a method of treatment aspect, provided herein is a method of treating a mammal susceptible to or afflicted with a condition associated with arthritis, asthma, myocardial infarction, inflammatory bowel disease and autoimmune disorders, which method comprises administering an effective amount of one or more of the pharmaceutical compositions just described.

In yet another method of treatment aspect, provided herein is a method of treating a mammal susceptible to or afflicted with a condition that gives rise to pain responses or that relates to imbalances in the maintenance of basal activity of sensory nerves. The present compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Bane syndrome, fibromyalgia, phantom limb pain, post-mastectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, provided herein are methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders; itch/pruritus such as, for example psoriasis; obesity; lipid disorders; cancer; and renal disorders method comprises administering an effective condition-treating or condition-preventing amount of one or more of the pharmaceutical compositions just described.

As a further aspect there is provided the present compounds for use as a pharmaceutical especially in the treatment or prevention of the aforementioned conditions and diseases. We also provide the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds provided herein will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds provided herein can be administered as the sole active agent or they can be administered in combination with other agents, including other active amines and derivatives. Administration in combination can proceed by any technique apparent to those of skill in the art including, for example, separate, sequential, concurrent and alternating administration.

General Synthetic Procedures

The compounds provided herein can be prepared from readily available starting materials using the following general methods and procedures. See, e.g., Synthetic Schemes 1-11 below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein, for example, may be prepared by the reaction of a carboxylic acid with an appropriately substituted amine and the product isolated and purified by known standard procedures. Such procedures include (but are not limited to) recrystallization, column chromatography or HPLC. The following schemes are presented with details as to the preparation of representative substituted biarylamides that have been listed herein. The compounds provided herein may be prepared from known or commercially available starting materials and reagents by one skilled in the art of organic synthesis.

The enantiomerically pure compounds provided herein may be prepared according to any techniques known to those of skill in the art. For instance, they may be prepared by chiral or asymmetric synthesis from a suitable optically pure precursor or obtained from a racemate by any conventional technique, for example, by chromatographic resolution using a chiral column, TLC or by the preparation of diastereoisomers, separation thereof and regeneration of the desired enantiomer. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, *Tetrahedron,* 2725 (1977); E. L. Eliel *Stereochemistry of Carbon Compounds* (McGraw-Hill, NY, 1962); and S. H. Wilen *Tables of Resolving Agents and Optical Resolutions* 268 (E. L. Eliel ed., Univ. of Notre Dame Press, Notre Dame, Ind., 1972, Stereochemistry of Organic Compounds, Ernest L. Eliel, Samuel H. Wilen and Lewis N. Manda (1994 John Wiley & Sons, Inc.), and *Stereoselective Synthesis A Practical Approach*, Mihály Nógrádi (1995 VCH Publishers, Inc., NY, N.Y.).

In certain embodiments, an enantiomerically pure compound of formula 1 may be obtained by reaction of the racemate with a suitable optically active acid or base. Suitable acids or bases include those described in Bighley et al., 1995, *Salt Forms of Drugs and Adsorption*, in *Encyclopedia of Pharmaceutical Technology*, vol. 13, Swarbrick & Boylan, eds., Marcel Dekker, New York; ten Hoeve & H. Wynberg, 1985, *Journal of Organic Chemistry* 50:4508-4514; Dale & Mosher, 1973, *J. Am. Chem. Soc.* 95:512; and *CRC Handbook of Optical Resolution via Diastereomeric Salt Formation*, the contents of which are hereby incorporated by reference in their entireties.

Enantiomerically pure compounds can also be recovered either from the crystallized diastereomer or from the mother liquor, depending on the solubility properties of the particular acid resolving agent employed and the particular acid enantiomer used. The identity and optical purity of the particular compound so recovered can be determined by polarimetry or other analytical methods known in the art. The diasteroisomers can then be separated, for example, by chromatography or fractional crystallization, and the desired enantiomer regenerated by treatment with an appropriate base or acid. The other enantiomer may be obtained from the racemate in a similar manner or worked up from the liquors of the first separation.

In certain embodiments, enantiomerically pure compound can be separated from racemic compound by chiral chromatography. Various chiral columns and eluents for use in the separation of the enantiomers are available and suitable conditions for the separation can be empirically determined by methods known to one of skill in the art. Exemplary chiral columns available for use in the separation of the enantiomers provided herein include, but are not limited to CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

Various substituted biarylamides can be prepared using general procedures or synthetic schemes described below.

General Synthetic Schemes

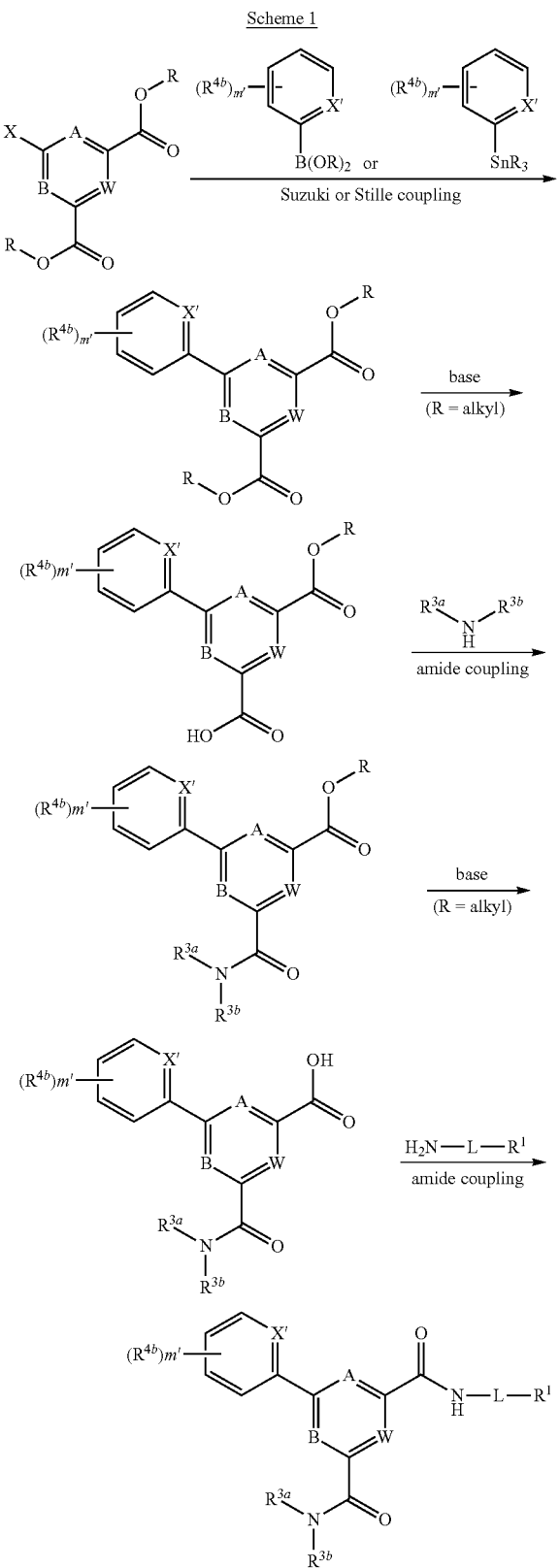

Scheme 1

Scheme 2
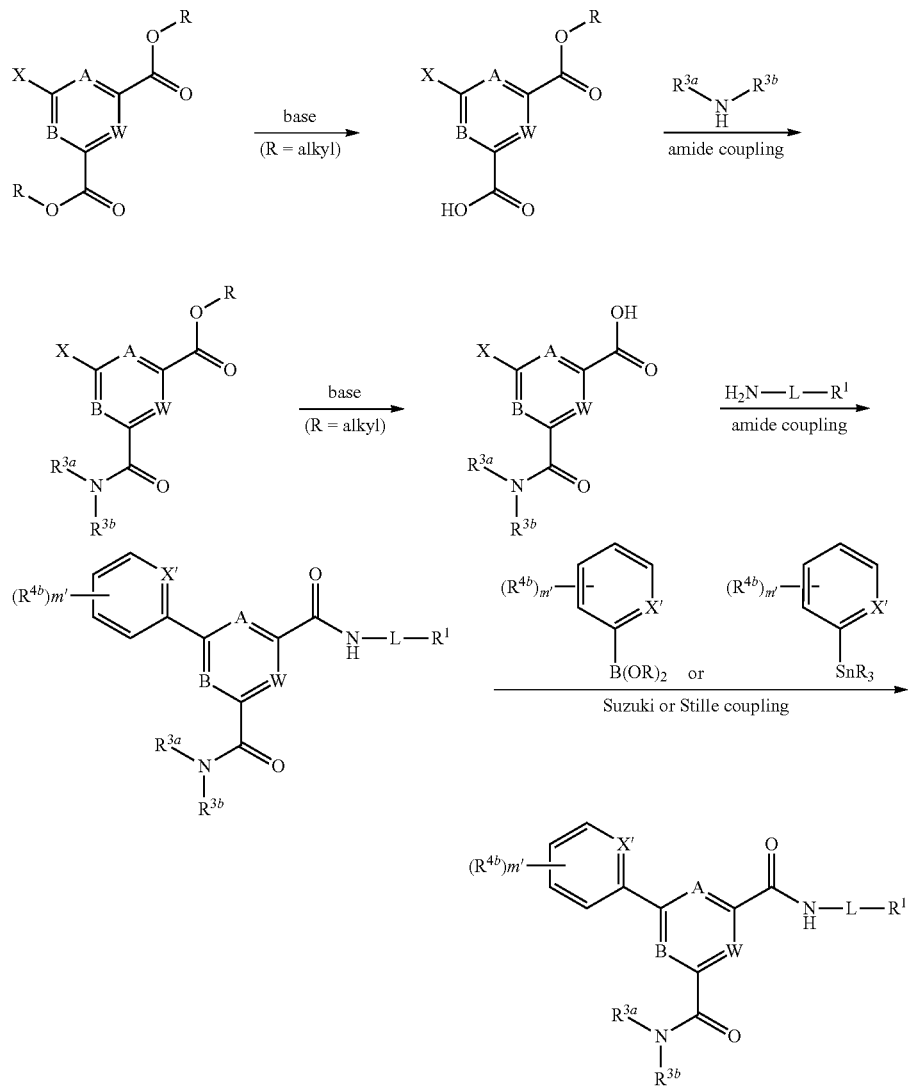
Scheme 3
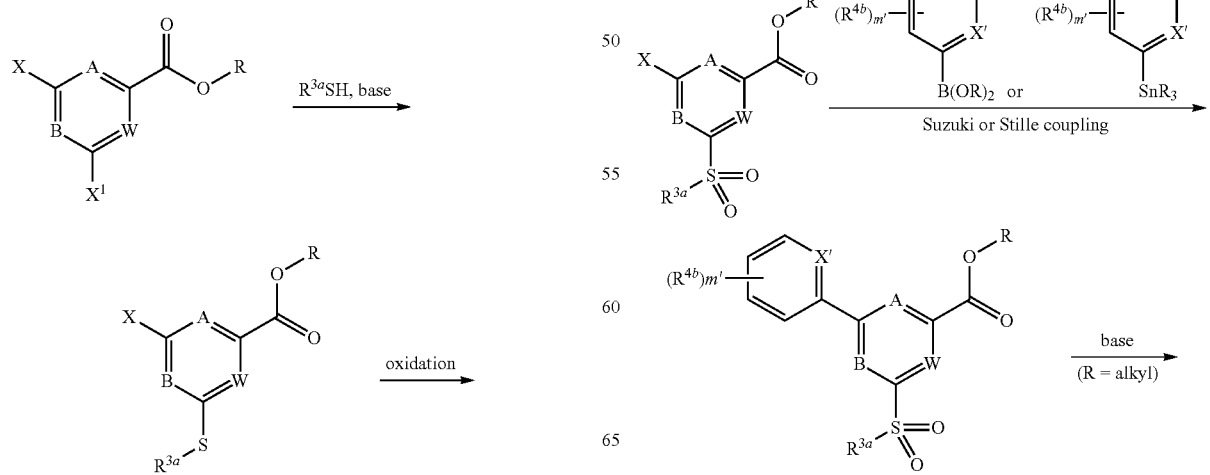

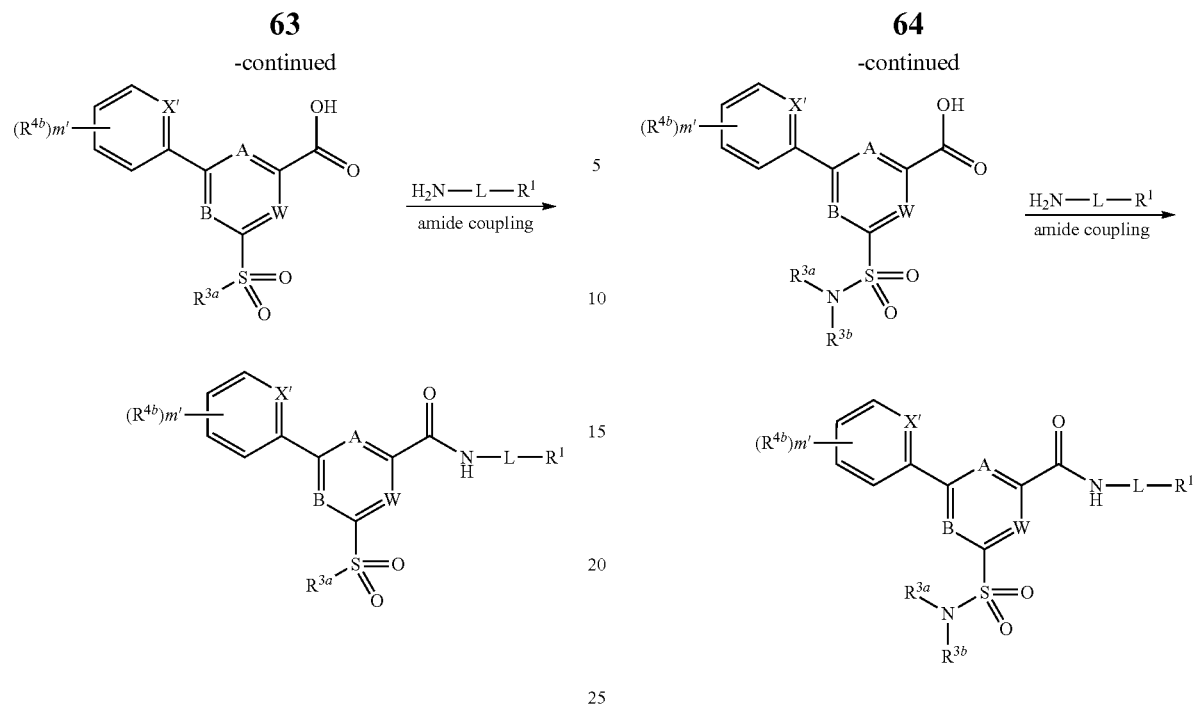
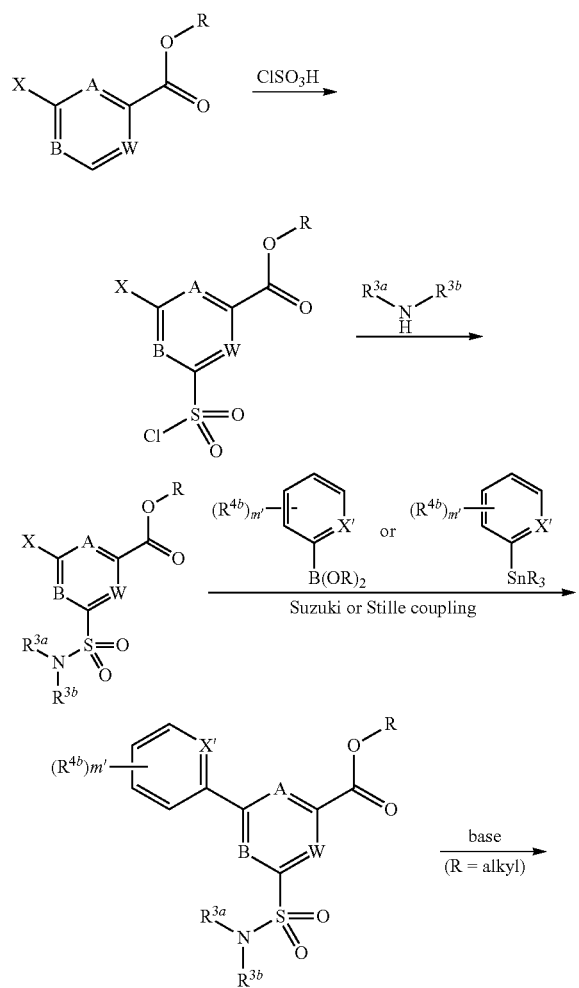
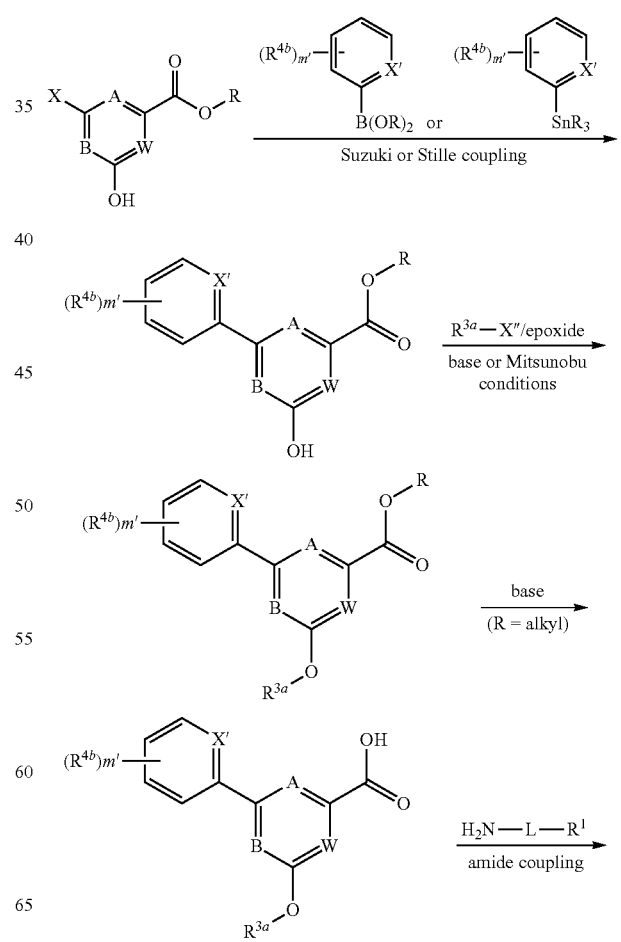

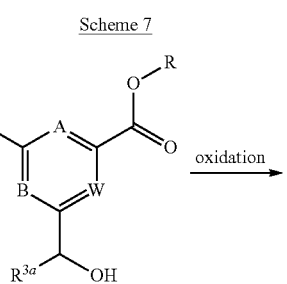
Scheme 7
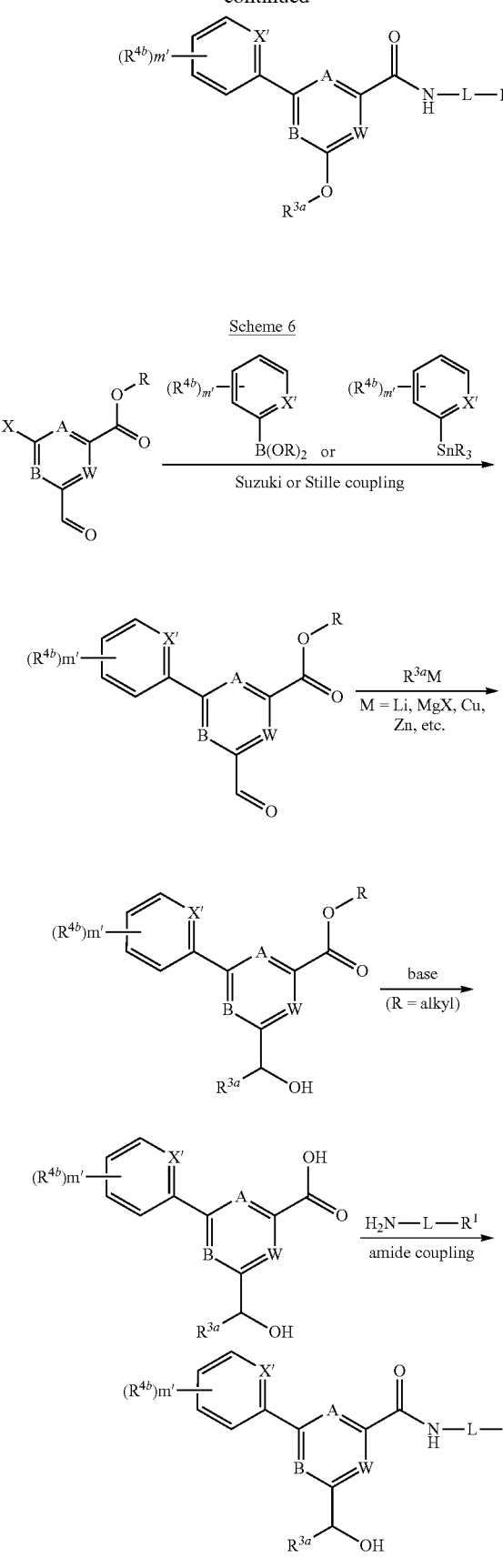
Scheme 6
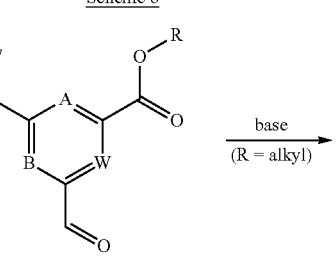
Scheme 8

67
-continued
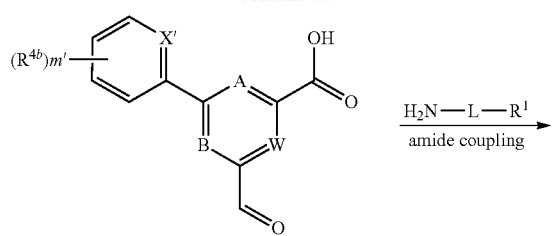
H$_2$N—L—R$^1$
amide coupling
→
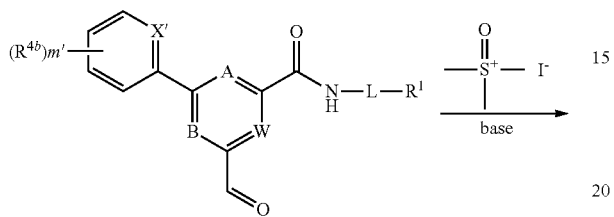
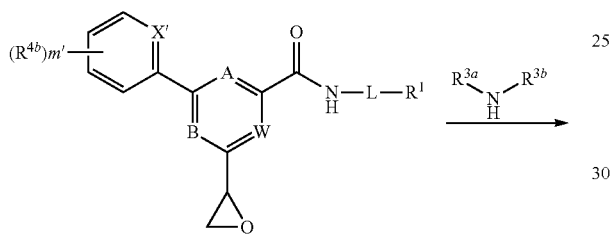
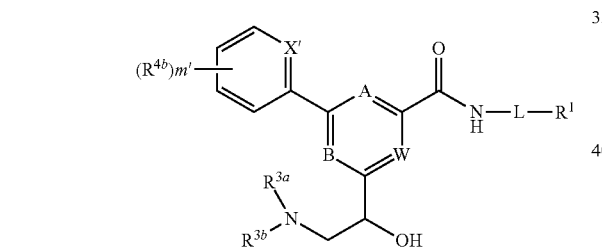
Scheme 9
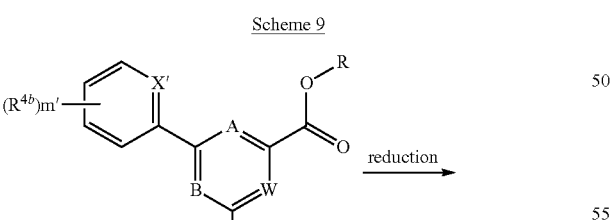
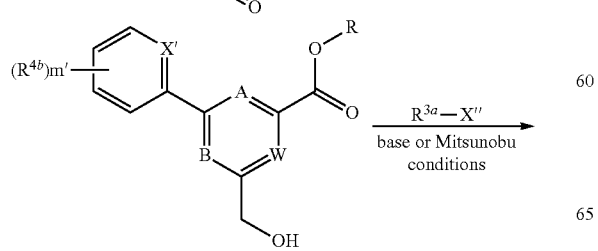
68
-continued
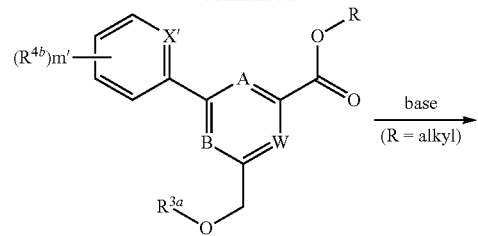
base
(R = alkyl)
→
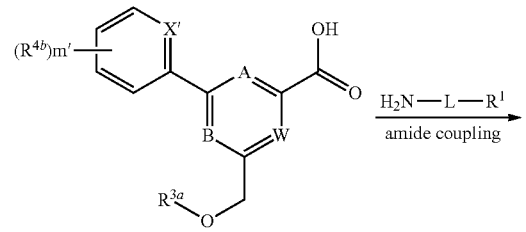
H$_2$N—L—R$^1$
amide coupling
→
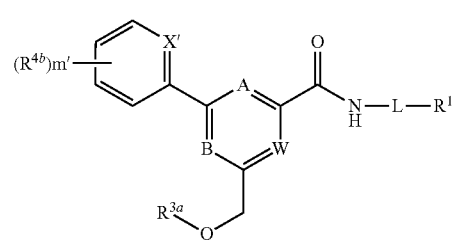
Scheme 10
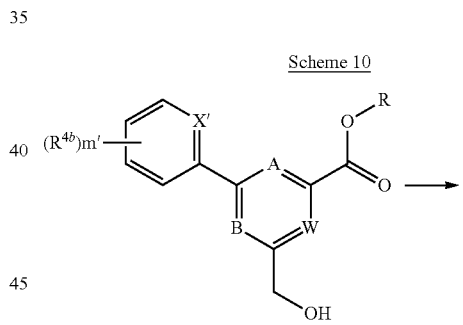
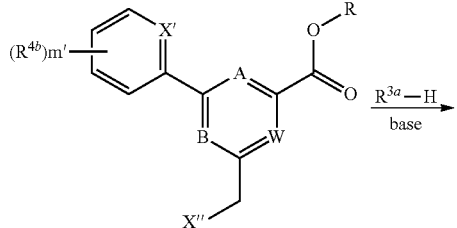
R$^{3a}$—H
base
→
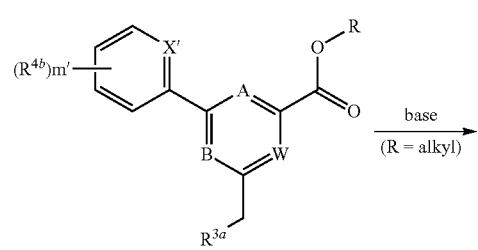
base
(R = alkyl)
→

Scheme 11

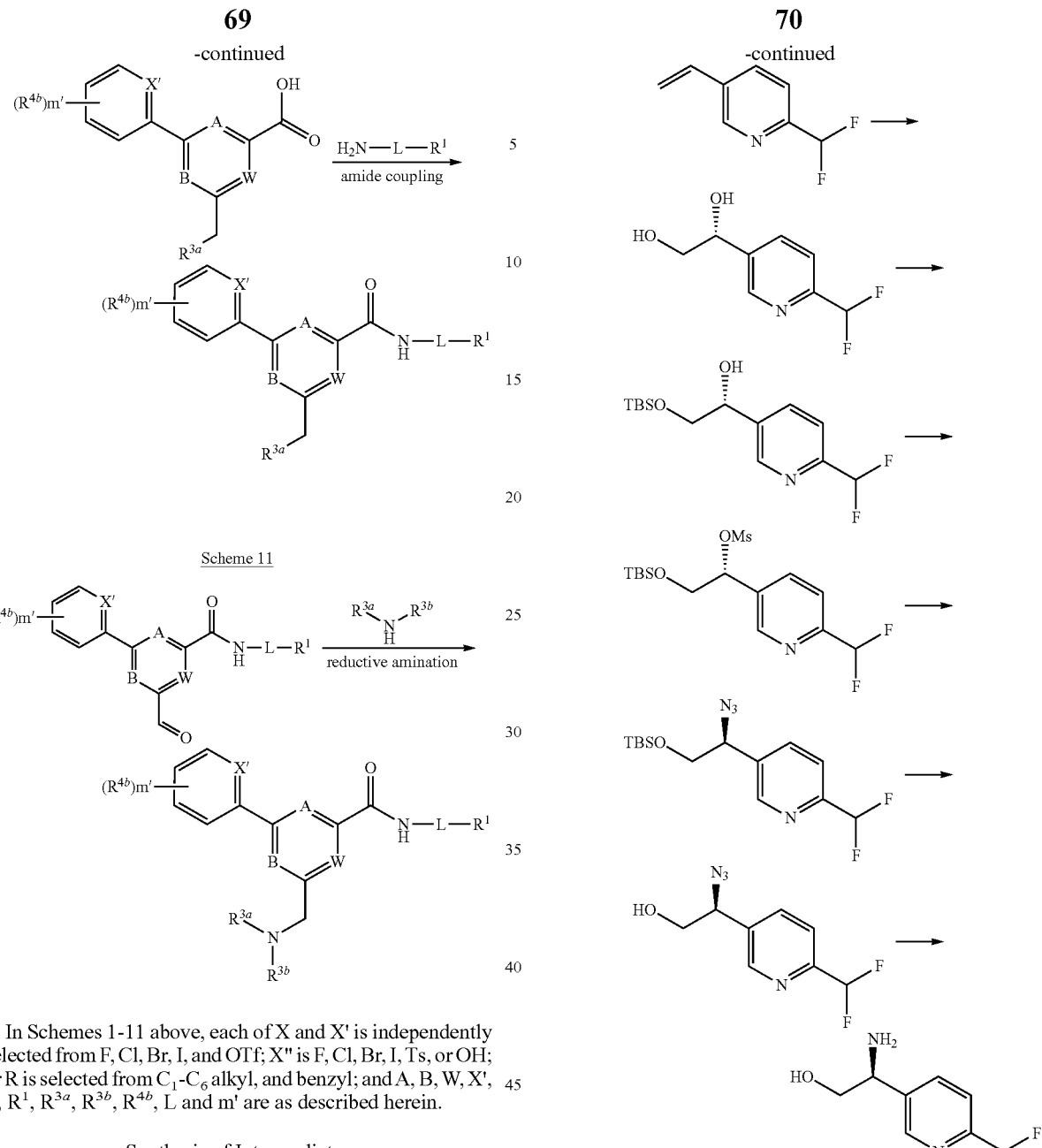

In Schemes 1-11 above, each of X and X' is independently selected from F, Cl, Br, I, and OTf; X" is F, Cl, Br, I, Ts, or OH; or R is selected from $C_1$-$C_6$ alkyl, and benzyl; and A, B, W, X', L, $R^1$, $R^{3a}$, $R^{3b}$, $R^{4b}$, L and m' are as described herein.

Synthesis of Intermediates

Intermediate 1

(S)-2-Amino-2-(6-(difluoromethyl)pyridin-3-yl)ethanol

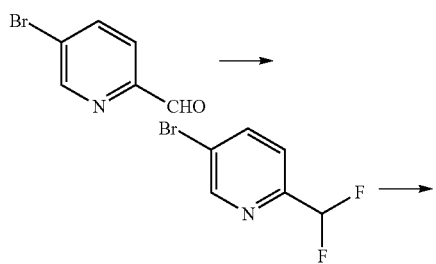

A) 5-Bromo-2-(difluoromethyl)pyridine

A stirred solution of 5-bromo-2-picolinaldehyde (10 g, 54 mmol) (*Org. Lett.* 2004, 6, 4905) in dry $CH_2Cl_2$ (100 mL) at −78° C. was treated with DAST (9.2 g, 70 mmol) and the resulting reaction mixture was allowed to warm to room temperature over a period 5 h. After completion of the reaction, the reaction mixture was quenched by ice-cold water and extracted with $CH_2Cl_2$. The organic layer was dried over anhydrous $Na_2SO_4$ and the solvents were evaporated in vacuo. The residue was purified by column chromatography ($SiO_2$, 5% $Et_2O$/pet. ether) to afford the title compound (6 g, 54% yield). MS: 210 [M+1]$^+$; $^1$H-NMR (300 MHz, $CDCl_3$): δ 8.72 (s, 1H), 7.93 (d, 1H, J=8.3 Hz), 7.54 (d, 1H, J=8.3 Hz), 6.60 (t, 1H, J=55.1 Hz).

B) 2-(Difluoromethyl)-5-vinylpyridine

To a stirred suspension of potassium vinyltrifluoroborate (3.32 g, 24.8 mmol), $PdCl_2$ (0.1 g, 0.56 mmol) and $PPh_3$ (0.45 g, 1.71 mmol) in 60 mL of $THF—H_2O$ (9:1) were added $Cs_2CO_3$ (20.2 g, 62 mmol) and 5-bromo-2-(difluoromethyl)pyridine (4.3 g, 20.7 mmol). The resulting reaction mixture was heated to 80° C. and stirred for 16 h. After completion of the reaction, the reaction mixture was cooled to room temperature, treated with water and extracted with $CH_2Cl_2$. The organic layer was dried over anhydrous $Na_2SO_4$ and the solvents were evaporated in vacuo. The residue was purified by column chromatography ($SiO_2$, 5% $Et_2O$/pentane) to afford the title compound (2.46 g, 75% yield). MS: 156 $[M+1]^+$; $^1$H-NMR (300 MHz, $CDCl_3$): δ 8.64 (s, 1H), 7.86 (d, 1H, J=8.3 Hz), 7.60 (d, 1H, J=8.3 Hz), 6.74 (dd, 1H, J=18, 11.2 Hz), 6.63 (t, 1H, J=55.6 Hz), 5.91 (d, 1H, J=18 Hz), 5.48 (d, 1H, J=11.2 Hz).

C) (R)-1-(6-(Difluoromethyl)pyridin-3-yl)ethane-1,2-diol

To a stirred suspension of AD-mix-β (21.67 g) in 30 mL t-BuOH—$H_2O$ (1:1) at 0° C. was added 2-(difluoromethyl)-5-vinylpyridine (2.4 g, 15.5 mmol) and the resulting reaction mixture was stirred at 0° C. for 5 h and then at room temperature. After 16 h, the reaction mixture was treated with $Na_2SO_3$ solution and then extracted with EtOAc (3×). The combined organic layers were dried over anhydrous $Na_2SO_4$ and the solvents were evaporated in vacuo to afford the title compound (2.6 g, 87% yield). MS: 190 $[M+1]^+$; $^1$H-NMR (300 MHz, $CDCl_3$): 8.64 (s, 1H), 7.89 (d, 1H, J=7.8 Hz), 7.64 (d, 1H, J=7.8 Hz), 6.64 (t, 1H, J=55.4 Hz), 4.91-4.96 (m 1H), 3.84 (dd, 1H, J=11, 3.6 Hz), 3.67 (dd, 1H, J=11, 7.8 Hz).

D) (R)-2-(tert-Butyldimethylsilyloxy)-1-(6-(difluoromethyl)pyridin-3-yl)ethanol To a stirred solution of (R)-1-(6-(difluoromethyl)pyridin-3-yl)ethane-1,2-diol (2.5 g, 13.2 mmol) in dry $CH_2Cl_2$ at room temperature were added tert-butyldimethylsilyl chloride (2.19 g, 14.5 mmol) and imidazole (0.99 g, 14.5 mmol). The resulting reaction mixture was stirred for 16 h. After completion of the reaction, the reaction mixture was treated with water and extracted with $CH_2Cl_2$. The organic layer was dried over anhydrous $Na_2SO_4$ and the solvents were evaporated in vacuo. The residue was purified by column chromatography ($SiO_2$, 20% EtOAc/pet. ether) to afford the title compound (3g, 75% yield). MS: 304 $[M+1]^+$; $^1$H-NMR (300 MHz, $CDCl_3$): 8.63 (s, 1H), 7.89 (d, 1H, J=8.2 Hz), 7.63 (d, 1H, J=8.2 Hz), 6.64 (t, 1H, J=55.4 Hz), 4.82-4.86 (m, 1H), 3.82 (dd, 1H, J=10.1, 3.7 Hz), 3.58 (dd, 1H, J=10.1, 7.8 Hz), 0.9 (s, 9H), 0.06 (s, 6H).

E) (R)-2-(tert-Butyldimethylsilyloxy)-1-(6-(difluoromethyl)pyridin-3-yl)ethyl methanesulfonate To a stirred solution of (R)-2-(tert-butyldimethylsilyloxy)-1-(6-(difluoromethyl)pyridin-3-yl)ethanol (3.0 g, 9.90 mmol) in dry $CH_2Cl_2$ at 0° C. was added $MeSO_2Cl$ (1.2 g, 10.9 mmol) and $Et_3N$ (1.3 g, 12.9 mmol). The resulting reaction mixture was warmed to room temperature over a period of 2 h. After completion of the reaction, the reaction mixture was treated with water and extracted with $CH_2Cl_2$. The organic layer was dried over anhydrous $Na_2SO_4$ and the solvents were evaporated in vacuo. The residue was purified by column chromatography ($SiO_2$, 10% EtOAc/pet. ether) to afford the title compound (2.26 g, 60% yield). MS: 381 $[M+1]^+$; $^1$H-NMR (300 MHz, $CDCl_3$): 8.67 (s, 1H), 7.90 (d, 1H, J=8.3 Hz), 7.68 (d, 1H, J=8.3 Hz), 6.65 (t, 1H, J=55.2 Hz), 5.62-5.66 (m, 1H), 3.98 (dd, 1H, J=11.2, 6.8 Hz), 3.87 (dd, 1H, J=11.2, 4.9 Hz), 3.028 (s, 3H), 0.87 (s, 9H), 0.04-0.05 (m, 6H).

F) (S)-5-(1-Azido-2-(tert-butyldimethylsilyloxy)ethyl)-2-(difluoromethyl)pyridine To a stirred solution of (R)-2-(tert-Butyldimethylsilyloxy)-1-(6-(difluoromethyl)pyridin-3-yl)ethyl methanesulfonate (2.24 g, 5.87 mmol) in dry DMF (15 mL) was added $NaN_3$ (0.45 g, 7.05 mmol) and the resulting reaction mixture was heated at 60° C. for 2 h. After completion of the reaction the reaction mixture was treated with ice-cold water and extracted with $Et_2O$. The organic layer was dried over anhydrous $Na_2SO_4$ and the solvents were evaporated in vacuo to afford the title compound (1.63 g, 85% yield). MS: 328 $[M+1]^+$; $^1$H-NMR (300 MHz, $CDCl_3$): 8.60 (s, 1H), 7.82 (d, 1H, J=8.3 Hz), 7.64 (d, 1H, J=8.3 Hz), 6.64 (t, 1H, J=55.7 Hz), 4.65-4.70 (m 1H), 3.80-3.86 (m, 2H), 0.89 (s, 9H), 0.04-0.06 (m, 61-1).

G) (S)-2-Azido-2-(6-(difluoromethyl)pyridin-3-yl)ethanol

To a stirred solution of (S)-5-(1-azido-2-(tert-butyldimethylsilyloxy)ethyl)-2-(difluoromethyl)pyridine (1.9 g, 5.79 mmol) in 20 mL of EtOH at 0° C. was added 5 mL 6N HCl and the resultant reaction mixture was slowly warmed to room temperature over a period of 2 h. The solvents were evaporated and the residue was separated between 10% $NaHCO_3$ solution and $CH_2Cl_2$. The organic layer was dried over anhydrous $Na_2SO_4$ and the solvents were evaporated in vacuo to afford the title compound (1.1 g, 89% yield). MS: 215 $[M+1]^+$; $^1$H-NMR (300 MHz, $CDCl_3$): 8.63 (s, 1H), 7.86 (d, 1H, J=8.3 Hz), 7.68 (d, 1H, J=8.3 Hz), 6.65 (t, 1H, J=55.2 Hz), 4.75-4.79 (m 1H), 3.70-3.90 (m, 2H).

H) (S)-2-Amino-2-(6-(difluoromethyl)pyridin-3-yl)ethanol

To a stirred solution of (S)-2-azido-2-(6-(difluoromethyl)pyridin-3-yl)ethanol (1 g, 4.67 mmol) in 15 mL of THF was added $PPh_3$ (2.45 g, 9.39 mmol). The resulting reaction mixture was stirred for 3 h, treated with 0.5 mL of water and stirred for 16 h. After completion of the reaction, the reaction mixture was treated with 2N HCl (15 mL) and extracted with EtOAc. The aqueous layer was treated with aq. $NH_3$ and the volatiles were evaporated to afford a residue. Purification of the residue by column chromatography (small pad of neutral $Al_2O_3$, aq. $NH_3$/MeOH/$CH_2Cl_2$, 1:14:85) afforded the title compound (0.74 g, 85% yield). MS: 189 $[M+1]^+$; $^1$H-NMR (300 MHz, $CD_3OD$): 8.72 (s, 1H), 8.09 (d, 1H, J=8.3 Hz), 7.75 (d, 1H, J=8.3 Hz), 6.73 (t, 1H, J=55.0 Hz), 4.39-4.43 (m 1H), 3.90 (dd, 1H, J=10.9, 4.7 Hz), 3.80 (dd, 1H, J=10.9, 6.2 Hz).

Intermediate 2

(S)-2-Amino-2-(6-(trifluoromethyl)pyridin-3-yl)ethanol

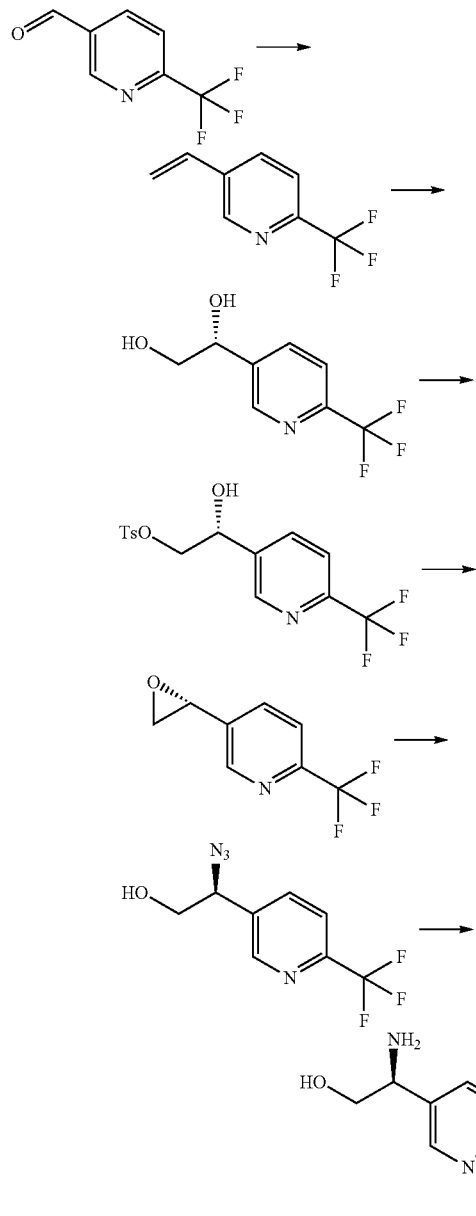

A) 2-(Trifluoromethyl)-5-vinylpyridine

A suspension of methyltriphenylphosphonium bromide (24.4 g, 68.4 mmol) in THF (150 mL) at −78° C. under an atmosphere of nitrogen was added 2.5 M of n-butyllithium in hexane (27 mL, 67.5 mmol) during a period of 12 mins. The reaction was warmed to room temperature to give a deep red ylide solution. To the ylide solution, cooled in ice, was introduced a solution of 6-(trifluoromethyl)nicotinaldehyde (10 g, 57 mmol) in THF (50 mL). The reaction mixture was warmed to room temperature and stirred for 3 hours. The result suspension was heated to 60° C. over 30 minutes and then stirred at 60° C. for 1 hour. After cooling, the mixture was diluted with water (400 mL), and extracted with EtOAc. The organic layer was washed with brine, dried (MgSO$_4$), and concentrated. The residue was purified by silica gel column (0-10% EtOAc/hexane) to afford title compound.

B) (R)-1-(6-(Trifluoromethyl)pyridin-3-yl)ethane-1,2-diol

A 100 mL flask was charged with tert-butyl alcohol (49 mL), water (49 mL), and AD-mix-β (13.78 g). Stirring at room temperature produced two clear phases. The mixture was cooled to 0° C. and 2-(trifluoromethyl)-5-vinylpyridine (1.7 g, 9.8 mmol) was added at once. The heterogeneous slurry was stirred vigorously at −20° C. overnight. TLC indicated completion of the reaction. While the mixture was stirred at 0° C., solid sodium sulfite (15 g, 0.12 mol) was added and the mixture was allowed to warm to rt and stirred for 1 hour. EtOAc was added to the reaction mixture, and after separation of the layers, the aqueous phase was further extracted with EtOAc. The combined organic layers were dried over anhydrous MgSO$_4$ and concentrated in vacuo. The residue was purified by silica gel column (MeOH/CH$_2$Cl$_2$: 0-10%) to afford the title compound as a white solid.

C) (R)-2-Hydroxy-2-(6-(trifluoromethyl)pyridin-3-yl)ethyl 4-methylbenzenesulfonate To a stirred solution of (R)-1-(6-(trifluoromethyl)pyridin-3-yl)ethane-1,2-diol (6.4 g, 31 mmol) and pyridine (20 mL) in CH$_2$Cl$_2$ (200 mL) at 0° C. was added p-toluenesulfonyl chloride (7.0 g, 37 mmol) in small portions. The mixture was slowly warmed to rt and stirred for 40 hours, and then diluted with CH$_2$Cl$_2$ (100 mL). The organic phase was washed with aq. NaHCO$_3$, brine, and dried (Na$_2$SO$_4$), and concentrated to yield the crude title compound.

D) (R)-5-(Oxiran-2-yl)-2-(trifluoromethyl)pyridine

To a stirred solution of (R)-2-hydroxy-2-(6-(trifluoromethyl)pyridin-3-yl)ethyl 4-methylbenzenesulfonate (1.0 g, 2.77 mmol) in THF (50 mL) was added powder potassium hydroxide (464 mg, 8.28 mmol) in small portions. The mixture was stirred for 40 minutes and TLC indicated completion of the reaction. The mixture was filtered through Celite and the filter cake was washed with acetonitrile (50 mL). The filtrate was carefully concentrated to a half volume and the obtained expoxide solution was used directly for the next step reaction.

E) (S)-2-Azido-2-(6-(trifluoromethyl)pyridin-3-yl)ethanol

To a stirred solution of (R)-5-(oxiran-2-yl)-2-(trifluoromethyl)pyridine (2.72 g, 14.4 mmol) in acetonitrile (200 mL) were added lithium perchlorate (20 g, 0.19 mol) and sodium azide (3.7 g, 57 mmol). The mixture was stirred at 60° C. overnight and TLC indicated completion of the reaction. After cooling, the mixture was filtered through Celite and the filtrate was concentrated. The residue was treated with water and extracted with EtOAc. The combined organic layers were dried, and concentrated. The residue was purified by silica gel column to afford the title compound.

F) (S)-2-Amino-2-(6-(trifluoromethyl)pyridin-3-yl)ethanol

A mixture of (S)-2-azido-2-(6-(trifluoromethyl)pyridin-3-yl)ethanol (604 mg, 2.60 mmol) in ethyl acetate (28 mL) and 10% Pd—C (70 mg) was stirred under H$_2$ (1 atm) for 1 hr. The catalyst was filtered off and the filtrate was concentrated to afford the title compound. $^1$H-NMR (300 MHz, CDCl$_3$): 8.64 (s, 1H), 7.86 (d, 1H, J=8.1 Hz), 7.60 (d, 1H, J=8.1 Hz), 4.16 (m, 1H), 3.73 (dd, 1H, J=10.5, 4.2 Hz), 3.56 (dd, 1H, J=10.4, 7.2 Hz).

Intermediate 3

C-(1,1-Dioxo-2,3-dihydro-1H-benzo[b]thiophen-6-yl)-methylamine

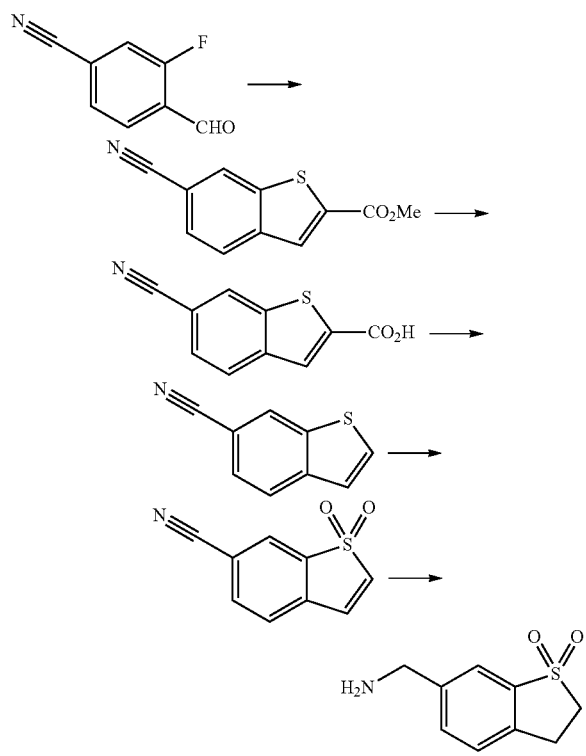

A) Methyl 6-cyanobenzo[b]thiophene-2-carboxylate

A round bottom flask was charged with 3-fluoro-4-formyl-benzonitrile (9.00 g, 60.4 mmol), dimethyl sulfoxide (90 mL), triethylamine (18.0 mL, 129 mmol), and subsequently methyl 2-mercaptoacetate (5.40 mL, 60.4 mmol). The reaction mixture was heated at 80° C. for 2 hours. After cooling, the reaction mixture was poured into water and the precipitated product was collected by filtration, dried and used in the next step without further purification.

B) 6-Cyanobenzo[b]thiophene-2-carboxylic acid

A round bottom flask was charged with methyl 6-cyanobenzo[b]thiophene-2-carboxylate (4.00 g, 17.9 mmol), methanol (130 mL), and sodium hydroxide (23 g, 0.58 mol) in water (200 mL). The reaction was stirred at room temperature for 20 minutes. The reaction was concentrated to half of the volume and acidified with 6 N aq. HCl. The mixture was extracted with CHCl$_3$/i-PrOH (90:10) and the organic phase was concentrated under reduced pressure to get the title compound as a brown solid.

C) Benzo[b]thiophene-6-carbonitrile

A microwave vial was charged with 6-cyanobenzo[b]thiophene-2-carboxylic acid (1.90 g, 9.35 mmol), 1,8-diazabicyclo[5.4.0]undec-7-ene (5.6 mL, 37.4 mmol) and N,N-dimethylacetamide (15 mL) and the reaction was subjected to microwave irradiation at 190° C. for 1 hour. After cooling, the reaction mixture was poured into 1N aq. HCl and extracted with ethyl acetate. The organic phase was concentrated under reduced pressure to get the product as light brown solid.

D) 1,1-Dioxo-1H-benzo[b]thiophene-6-carbonitrile

A round bottom flask was charged with benzo[b]thiophene-6-carbonitrile (1.35 g, 8.48 mmol), methylene chloride (270 mL), and m-chloroperbenzoic acid (70% purity, 5.85 g, 23.73 mmol) was added in portions over 20 minutes. The reaction mixture was heated at 45° C. overnight. The reaction gave a mixture of sulfoxide and sulfones in 2:1 ratio. The reaction was diluted with ethyl acetate and quenched with saturated aqueous sodium thiosulfate and stirred for 1 hour. The mixture was then extracted with ethyl acetate and the organic phase was concentrated under reduced pressure. The residue was purified by flash chromatography to afford the title compound as a white solid.

E) C-(1,1-Dioxo-2,3-dihydro-1H-benzo[b]thiophen-6-yl)-methylamine

A hydrogenation par vessel was charged with 1,1-dioxo-1H-benzo[b]thiophene-6-carbonitrile (0.30 g, 1.57 mmol), ethanol (25 mL) and palladium hydroxide (66 mg). The vessel was put on a shaker under hydrogen at 40 Psi for 5 h. The reaction mixture was filtered through Celite and the filter cake was washed with methanol. The filtrate was concentrated to get the product as a white solid.

Intermediate 4

(S)-2-(tert-Butyldimethylsilyloxy)-1-(6-methylpyridin-3-yl)ethanamine

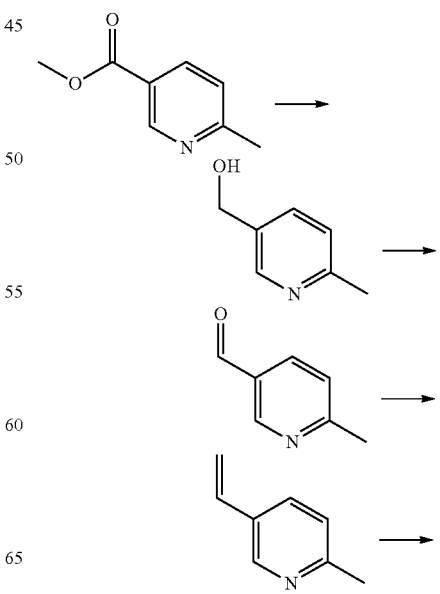

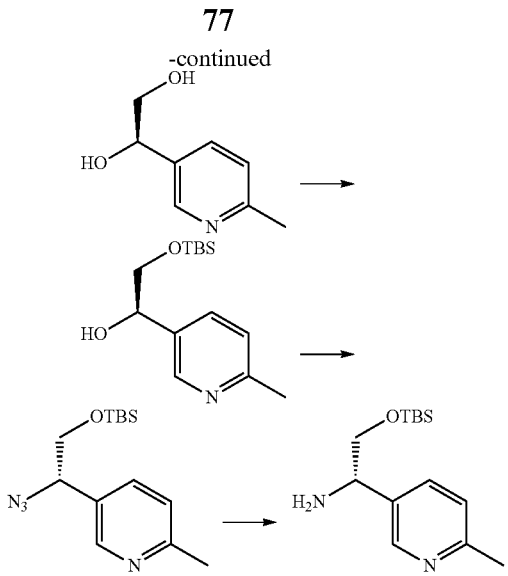

A) (6-Methyl-3-pyridyl)methanol

To a solution of methyl 6-methylnicotinate (25 g, 0.16 mol) in ethyl ether (620 mL) under nitrogen was added dropwise sodium bis(2-methoxyethoxy)aluminium hydride (Red-Al®) (65 wt. % in toluene, 110 mL, 0.37 mol) at room temperature. The mixture was then heated to reflux for 1.5 hr. After cooling, the reaction mixture was quenched with water (500 mL) at 0° C. and the aqueous layer was extracted with EtOAc. The combined organic layers were dried over anhydrous $MgSO_4$, filtered, and concentrated. The residue was purified by silica gel column to afford the title compound.

B) 6-Methylnicotinaldehyde

To a stirred solution of dimethyl sulfoxide (25.3 mL, 0.357 mol) and $CH_2Cl_2$ (600 mL) under nitrogen at −78° C. was slowly added oxalyl chloride (16 mL, 0.19 mol). After completion of the addition, the mixture was stirred for additional 10 min. To the resulting solution was added dropwise a solution of (6-methyl-3-pyridyl)methanol (20 g, 0.162 mol) in $CH_2Cl_2$ (10 mL), and then the mixture was stirred at −78° C. for 2.5 hr. Triethylamine (110 mL, 0.82 mol) was slowly added at −78° C. and then the mixture was slowly warmed to room temperature and stirred for another 1 hr. The mixture was treated with water and the aqueous phase was extracted with $CH_2Cl_2$ (3×500 mL). The combined organic layers were washed with brine, dried over anhydrous $MgSO_4$, filtered and concentrated. The residue was purified by silica gel column to afford the title compound.

C) 2-Methyl-5-vinylpyridine

To a suspension of methyltriphenylphosphonium bromide (62.54 g, 0.175 mol) in THF (150 mL) at −78° C. under nitrogen was added 2.5 M of n-butyllithium in hexane (69 mL, 0.17 mol) over a period of 1 hr. The mixture was warmed to room temperature to give a deep yellow ylide solution. To the ylide solution, cooled in ice, was introduced a solution of 6-methylnicotinaldehyde (18.63 g, 0.146 mol) in THF (50 mL). The reaction mixture was warmed to room temperature and stirred for 2 hours. The resulting suspension was heated to 60° C. over 30 minutes and stirred at 60° C. for 1 hour. After cooling, the reaction mixture was diluted with water and extracted with EtOAc. The organic layer was separated and washed with brine, dried ($MgSO_4$), and concentrated. The residue was purified by silica gel column (0-10% EtOAc/hexane) to afford the title compound.

D) (R)-1-(6-Methylpyridin-3-yl)ethane-1,2-diol

A 100 mL flask was charged with tert-butyl alcohol (480 mL), water (480 mL), and AD-mix-β (138 g). Stirring at room temperature produced two clear phases, and then the mixture was cooled to 0° C. 2-Methyl-5-vinylpyridine (11.72 g, 0.0934 mol) was added at once, and the heterogeneous slurry was stirred vigorously at −20° C. overnight. TLC indicated completion of the reaction. While the mixture was stirred at 0° C., solid sodium sulfite (117.8 g, 0.934 mol) was added and the mixture was warmed to rt and stirred for 1 hour. EtOAc was added, and after separation of the layers, the aqueous phase was extracted with EtOAc. The combined organic layers were dried over anhydrous $MgSO_4$ and concentrated in vacuo to get the diol as a brown oil.

E) (R)-2-(tert-Butyldimethylsilyloxy)-1-(6-methylpyridin-3-yl)ethanol

To a stirred mixture of (R)-1-(6-methylpyridin-3-yl)ethane-1,2-diol (13.72 g, 0.085 mol), 1H-imidazole (13.55 g, 0.197 mol), and $CH_2Cl_2$ (180 mL) at 0° C. was added tert-butyldimethylsilyl chloride (15.31 g, 0.098 mol). The reaction mixture was stirred at 0° C. for 30 minutes, then warmed to room temperature and stirred overnight. The mixture was washed with water (300 mL) and extracted with $CH_2Cl_2$. The combined organic layers were dried over sodium sulfate, and concentrated. The residue was purified by flash chromatography (0-50% EtOAc/hexane) to afford a colorless oil.

F) (S)-5-(1-Azido-2-(tert-butyldimethylsilyloxy)ethyl)-2-methylpyridine

To a stirred mixture of (R)-2-(tert-butyldimethylsilyloxy)-1-(6-methylpyridin-3-yl)ethanol (15.6 g, 0.055 mol) and diphenylphosphonic azide (62.8 mL, 0.292 mol) in toluene (200 mL) at 0° C. was added 1,8-diazabicyclo[5.4.0]undec-7-ene (44.5 mL, 0.292 mol). The mixture was stirred at 0° C. for 30 minutes and then heated at 60° C. overnight. After cooling, the mixture was washed with water. The organic layer was dried and concentrated in vacuo. The residue was purified by flash chromatography (0-15% EtOAc/hexane) to afford a colorless oil.

G) (S)-2-(tert-Butyldimethylsilyloxy)-1-(6-methylpyridin-3-yl)ethanamine

A mixture of (S)-5-(1-azido-2-(tert-butyldimethylsilyloxy)ethyl)-2-methylpyridine (11.21 g, 0.036 mol), ethyl acetate (400 mL), and 10% Pd—C (7 g) was stirred under $H_2$ (1 atm) for 1 hour. The catalyst was filtered off and the filtrate was concentrated to get the title product as an oil. $^1H$ NMR ($CD_3OD$, 400 MHz): 8.39 (d, 1H, J=2.0 Hz), 7.74 (dd, 1H, J=8.0, 2.4 Hz), 7.28 (d, J=8.0 Hz, 1H), 3.98 (t, 1H, J=6.0 Hz), 3.73 (d, 2H, J=6.0 Hz), 2.51 (s, 3H), 0.86 (s, 9H), −0.02 (s, 6H).

Intermediate 5

Imidazo[1,2-a]pyridin-7-ylmethanamine

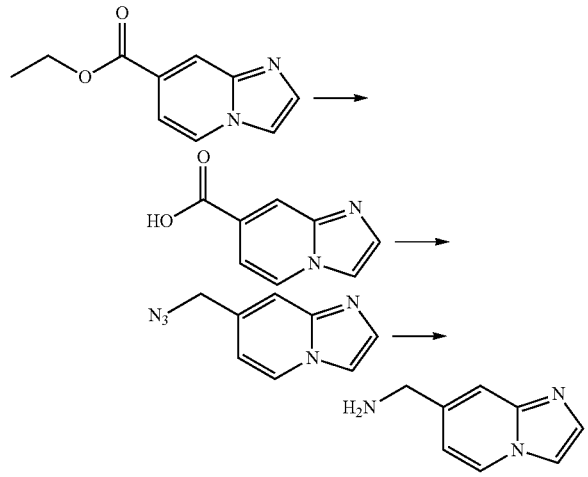

A) Imidazo[1,2-a]pyridin-7-ylmethanol

Lithium tetrahydroaluminate (0.50 g, 13.2 mmol) was slowly added in small portions to an ice-cooled solution of ethyl imidazo[1,2-a]pyridine-7-carboxylate (2.20 g, 11.6 mmol) in THF (150 mL). The mixture was slowly warmed to II and stirred at rt overnight. The solution was cooled to 0° C. and quenched carefully with 1N aq. HCl (10 mL). Solid $K_2CO_3$ and anhydrous $Na_2SO_4$ were added and the mixture was stirred at rt for 30 min. The mixture was filtered and the filter cake was washed with THF. The filtrate was concentrated to yield the crude product as a solid (1.68 g, 80% purity) which was used for the next step without further purification.

B) 7-(Azidomethyl)imidazo[1,2-a]pyridine

To a stirred solution of imidazo[1,2-a]pyridin-7-ylmethanol (80% purity, 1.68 g, 9.07 mmol) in toluene (40 mL) and $CH_2Cl_2$ (40 mL) at 0° C. was added diphenylphosphonic azide (3.5 mL, 16 mmol) followed by 1,8-diazabicyclo[5.4.0]undec-7-ene (2.5 mL, 17 mmol). The mixture was stirred at 0° C. for 2 h and then at rt for 16 h. The reaction mixture was diluted with water (200 mL) and $CH_2Cl_2$ (200 mL). The organic layer was separated and washed with brine, dried ($Mg_2SO_4$), filtered, and concentrated. The residue was purified by silica gel column to afford the title compound as a colorless oil (1.5 g, 75% yield for two steps).

C) Imidazo[1,2-a]pyridin-7-ylmethanamine

Into a round bottom flask were charged 7-(azidomethyl)imidazo[1,2-a]pyridine (1.5 g, 8.7 mmol), ethyl acetate (200 mL), and 10% Pd/C (250 mg). The mixture was stirred under hydrogen balloon at room temperature for 40 minutes. The mixture was filtered through Celite and the filtrate was concentrated to get the title product (1.2 g). $^1$H NMR (400 MHz, DMSO-d6): 8.48 (d, 1H, J=7.2 Hz), 7.88 (s, 1H), 7.52 (d, 1H, J=1.2 Hz), 7.51 (s, 1H), 6.89 (dd, 1H, J=7.2, 1.6 Hz), 3.83 (s, 2H).

Intermediate 6

(4-Methyl-3-(methylsulfonyl)phenyl)methanamine

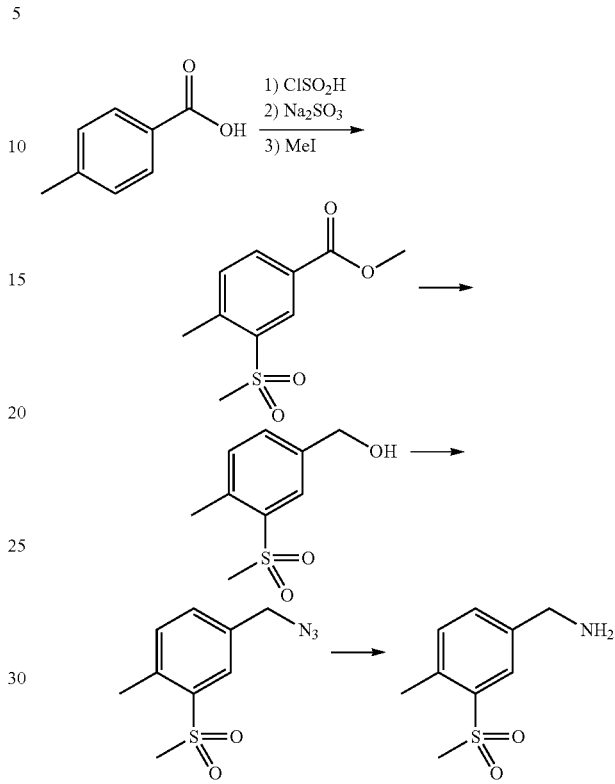

A) Methyl-4-methyl-3-(methylsulfonyl)benzoate

A round bottom flask was charged with chlorosulfonic acid (170 mL, 2.57 mol) at 0° C. and 4-methyl benzoic acid (50 g, 0.37 mol) was added portion wise. The reaction mixture was heated at 130° C. for 5 h. The reaction mixture was then poured over ice and stirred for 10 minutes. The solids formed were filtered, washed with cold water and dried to afford 4-methyl-3-(chlorosulfonyl)benzoic acid as a white powder. This compound (80 g, 0.34 mol) was then charged into a round bottom flask containing sodium sulfite (200 g, 2.05 mol) and water (80 mL) portion wise. Aqueous sodium hydroxide (6 N) was then added dropwise till the pH of the reaction mixture reaches 10 and the reaction was stirred overnight. The reaction was then made acidic (pH 2) by addition of 2N HCl. The solids formed were filtered and dried to get 4-methyl-3-sulfinobenzoic acid as a white solid. This compound (55 g, 0.275 mol) was charged into a round bottom flask containing potassium carbonate (75.8 g, 0.55 mol) and N,N-dimethylformamide (450 mL). Methyl iodide (68.1 mL, 1.10 mol) was added slowly and the reaction was stirred for 4 hours. The reaction mixture was then diluted with water and extracted with EtOAc. The solvents were removed under reduced pressure to get the title compound as a white solid.

B) (4-Methyl-3-(methylsulfonyl)phenyl)methanol

A round bottom flask was charged with methyl-4-methyl-3-(methylsulfonyl)benzoate (1.5 g, 7.0 mmol) and methanol (15 mL) at 0° C. Sodium borohydride (3.7 g, 100 mmol) was added in portions and the reaction was stirred for 12 h at room temperature. The reaction was quenched with ice and extracted with MTBE. The combined organic phases were concentrated under reduced pressure and the residue was purified by flash chromatography to get the title compound.

C) 4-(1-Azidomethyl)-1-methyl-2-(methylsulfonyl)benzene

A round bottom flask was charged with (4-methyl-3-(methylsulfonyl)phenyl)methanol (6.0 g, 30.14 mmol), toluene (70 mL). Diphenyl phosphoryl azide (7.8 mL, 36.1 mmol) and 1,8-diazabicyclo[5.4.0]undec-7-ene (5.3 mL, 36.1 mmol) were added at 0° C. and the reaction mixture was stirred over night at room temperature. The solvent was removed under reduced pressure and the residue was diluted with water and extracted with EtOAc. The combined organic phases were concentrated under reduced pressure and the residue was purified by column chromatography to get the title compound (4 g, 62% yield).

D) (4-Methyl-3-(methylsulfonyl)phenyl)methanamine

A round bottom flask was charged with 4-(1-azidomethyl)-1-methyl-2-(methylsulfonyl)benzene (5.0 g, 22.17 mmol), THF (40 mL), triphenylphosphine (6.4 g, 24.3 mmol) and water (1.6 mL, 34.2 mmol) at 0° C., and the reaction mixture was stirred at room temperature over night. The solvents were removed and the residue was dissolved in MTBE and 20% HCl in dioxane was added dropwise at 0° C. and the resulting salt was collected and washed with EtOAc. The salt was then neutralized with 6N aq. NaOH and extracted with $CH_2Cl_2$. The organic layers were concentrated under reduced pressure to get the title compound as a very thick oil. $^1H$ NMR (400 MHz, $CDCl_3$): 7.98 (s, 1H), 7.50 (d, 1H, J=8.0 Hz), 7.32 (d, 1H, J=8.0 Hz), 3.93 (s, 2H), 3.08 (s, 3H), 2.69 (s, 3H).

Intermediate 7

1-(4-Chloro-3-(methylsulfonyl)phenyl)ethanamine

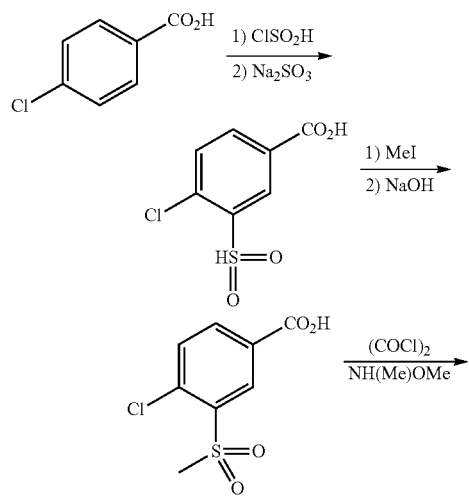

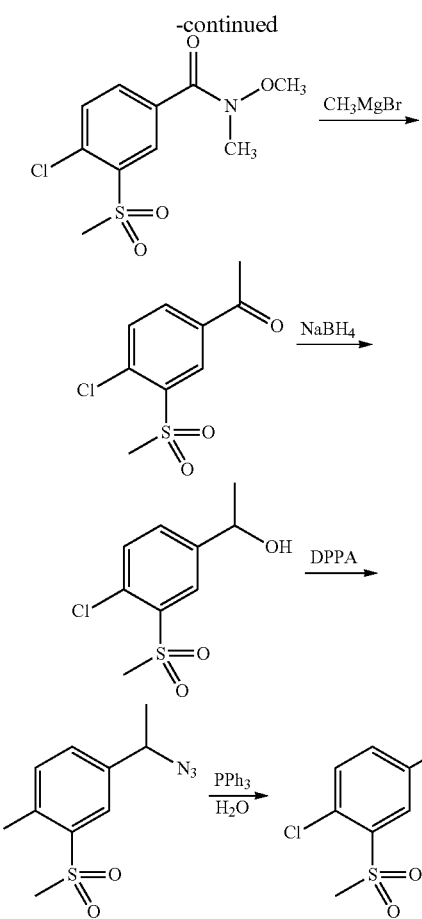

A) 4-Chloro-3-sulfinobenzoic acid

A round bottom flask was charged with chlorosulfonic acid (6.36 g, 96.0 mmol) at 0° C. and 4-chloro benzoic acid was added portion wise. The reaction mixture was heated at 130° C. for 5 h. The reaction mixture was then poured over ice and stirred for 10 minutes. The solids formed were filtered, washed with cold water and dried to afford 4-chloro-3-(chlorosulfonyl)benzoic acid as a white powder. This compound was then charged into a round bottom flask containing sodium sulfite (7.1 g, 56.4 mmol) and water (40 mL) portion wise. Aqueous sodium hydroxide (6 N) was then added drop wise till the pH of the reaction mixture reaches 10 and the reaction was stirred over night. The reaction was then made acidic (pH 2) by addition of 2N HCl. The solids formed were filtered and dried to get the title compound as a white solid.

B) 4-Chloro-3-(methylsulfonyl)benzoic acid

A round bottom flask was charged with 4-chloro-3-sulfinobenzoic acid (12 g, 54.0 mmol), potassium carbonate (15.4 g, 109 mmol) and N,N-dimethylformamide (170 mL). Methyl iodide (16.1 mL, 218 mmol) was added slowly and the reaction was stirred for 4 hours. The reaction mixture was then diluted with water and extracted with EtOAc. The combined organic layers were concentrated under reduced pressure to get the intermediate methyl-4-chloro-3-(methylsulfonyl)benzoate as an off white solid. This was dissolved in methanol (100 mL) and 6N sodium hydroxide (50 mL) was added and the reaction was stirred for 3 hours. Methanol was removed under reduced pressure and water was added to the residue. The resulting mixture was then acidified with 2N HCl at 0° C. and the solid formed was filtered and dried to get the title compound as a white solid.

C) 4-Chloro-N-methoxy-N-methyl-3-(methylsulfonyl)benzamide

A round bottom flask was charged with 4-chloro-3-(methylsulfonyl)benzoic acid (7.5 g, 30.24 mmol), dichloromethane (75 mL) and N,N-dimethylformamide (0.25 mL). Oxalyl chloride (4.0 mL, 45.36 mmol) was added slowly and the reaction mixture was stirred at room temperature for one hour. The solvent was removed to get the intermediate acid chloride which was dissolved in dichlormethane (50 mL) and N,O-dimethylhydroxylamine (10.0 g, 122.9 mmol) was added and the reaction mixture was stirred at room temperature over night. The solvent was removed under reduced pressure and the residue was purified by flash chromatography to get the title compound.

D) 1-(4-Chloro-3-(methylsulfonyl)phenyl)ethanone

A round bottom flask was charged with 4-chloro-N-methoxy-N-methyl-3-(methylsulfonyl)benzamide (18.0 g, 64.9 mmol) and tetrahydrofuran (200 mL) at 0° C. Methylmagnesiumbromide (1M solution in THF, 78 mL, 78 mmol) was added slowly and the reaction was stirred for 3 h at that temperature. The reaction was then quenched with aqueous ammonium chloride solution and extracted with ethyl acetate. The organic layers were concentrated under reduced pressure and the residue was purified by flash chromatography to get the title compound.

E) 1-(4-Chloro-3-(methylsulfonyl)phenyl)ethanol

A round bottom flask was charged with 1-(4-chloro-3-(methylsulfonyl)phenyl)ethanone (12.0 g, 50.0 mmol) and tetrahydrofuran (100 mL) at 0° C. Sodium borohydride (3.7 g, 100 mmol) was added in portions and the reaction was stirred for 12 h at room temperature. The reaction was quenched with ice and extracted with MTBE. The organic solvents were removed under reduced pressure and the residue was purified by flash chromatography to get the title compound.

F) 4-(1-Azidoethyl)-1chloro-2-(methylsulfonyl)benzene

A round bottom flask was charged with 1-(4-chloro-3-(methylsulfonyl)phenyl)ethanol (8.5 g, 32.44 mmol) and toluene (100 mL). Diphenyl phosphoryl azide (8.4 mL, 38.93 mmol) and 1,8-diazabicyclo[5.4.0]undec-7-ene (5.8 mL, 38.93 mmol) were added at 0° C. and the mixture was stirred over night at room temperature. The volatiles were removed under reduced pressure and the residue was diluted with water and extracted with EtOAc. The combined organic layers were concentrated under reduced pressure and the residue was purified by column chromatography to get the product (2.4 g, 28% yield).

G) 1-(4-Chloro-3-(methylsulfonyl)phenyl)ethanamine

A round bottom flask was charged with 4-(1-azidoethyl)-1chloro-2-(methylsulfonyl)benzene (2.1 g, 7.7 mmol), THF (20 mL), triphenylphosphine (2.4 g, 8.5 mmol) and water (0.6 mL, 34.2 mmol) at 0° C. and the reaction was stirred at room temperature over night. The solvents were removed and the residue was dissolved in MTBE and 20% HCl in dioxane was added dropwise at 0° C. The resulting salt was collected and washed with EtOAc. The salt was then neutralized with 6N NaOH and extracted with $CH_2Cl_2$. The combined organic layers were concentrated under reduced pressure to get the title compound as a very thick oil. $^1H$ NMR (400 MHz, $CDCl_3$): 8.14 (d, 1H, J=2.0 Hz), 7.63 (dd, 1H, J=8.4, 2.4 Hz), 7.52 (d, 1H, J=8.0 Hz), 4.24 (q, 1H, J=6.4 Hz), 3.28 (s, 3H), 1.40 (d, 3H, J=6.4 Hz).

Intermediate 8

5-(Aminomethyl)-2-chloro-N-cyclopropylbenzenesulfonamide

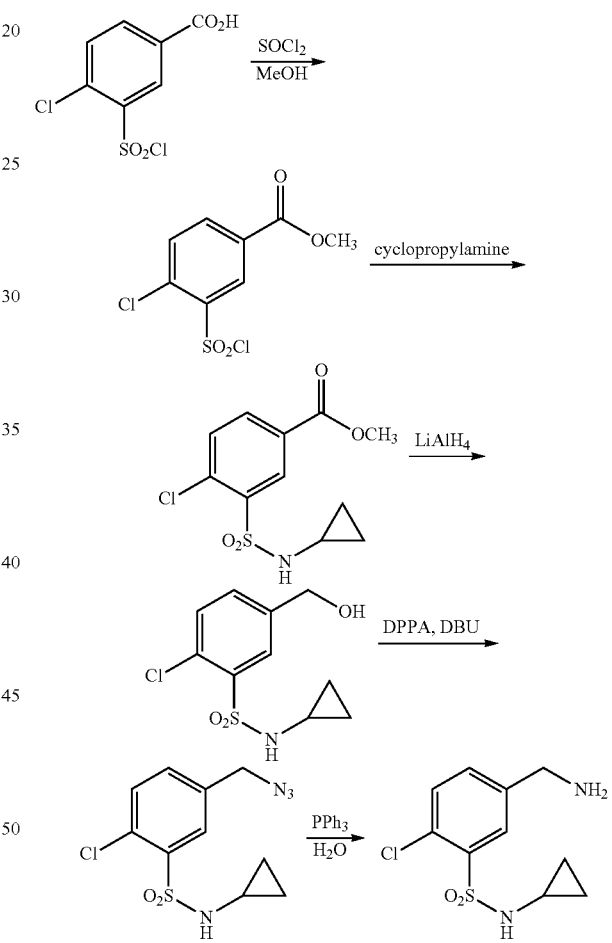

A) Methyl 4-chloro-3-(chlorosulfonyl)benzoate

A round bottom flask was charged with 4-chloro-3-(chlorosulfonyl)benzoic acid (16.0 g, 63.24 mmol) and methanol (100 mL), and thinoyl chloride (9.3 mL, 126.5 mmol) was added slowly at 0° C. The reaction mixture was then heated to reflux for 1.5 hours. The volatiles were removed under reduced pressure, and the residue was diluted with water and extracted with EtOAc. The solvents were removed under reduced pressure to get the title compound as a solid.

B) Methyl 4-chloro-3-(N-cyclopropylsulfamoyl)benzoate

A round bottom flask was charged with methyl 4-chloro-3-(chlorosulfonyl)benzoate (12.0 g, 44.32 mmol) and 1,4-dioxane (100 mL) at 0° C. Cyclopropyl amine (9.31 mL, 137.8 mmol) was added dropwise and the mixture was stirred at that temperature for 3 h. The solvent was removed and the residue was treated with EtOAc. The organic phase was washed with brine, dried, and concentrated to get the title compound (4.5 g, 32% yield).

C) 2-Chloro-N-cyclopropyl-5-(hydroxymethyl)benezenesulfonamide

A round bottom flask was charged with lithium aluminiumhydride (2.36 g, 62.2 mmol) under nitrogen and THF (50 mL) was added at 0° C. Methyl 4-chloro-3-(N-cyclopropylsulfamoyl)benzoate (4.5 g, 15.57 mmol) in THF (20 mL) was added slowly and the mixture was stirred for 3 h at that temperature. The reaction mixture was quenched with 1:1 mixture THF/H$_2$O and 6N NaOH and filtered through Celite. The filtrate was concentrated under reduced pressure and the residue was purified by flash chromatography to get the title compound (2.5 g, 63% yield) as a solid.

D) 5-(Azidomethyl)-2-chloro-N-cyclopropylbenzenesulfonamide

A round bottom flask was charged with 2-chloro-N-cyclopropyl-5-(hydroxymethyl)benezenesulfonamide (2.4 g, 10 mmol) and toluene (30 mL). Diphenyl phosphoryl azide (2.19 mL, 10.1 mmol) and 1,8-diazabicyclo[5.4.0]undec-7-ene (1.31 mL, 10.1 mmol) were added at 0° C. and the mixture was stirred over night at room temperature. The volatiles were removed under reduced pressure and the residue was diluted with water and extracted with EtOAc. The organic solvents were removed under reduced pressure and the residue was purified by column chromatography to get the title compound (1.4 g, 53% yield).

D) 5-(Aminomethyl)-2-chloro-N-cyclopropylbenzenesulfonamide

A round bottom flask was charged with 5-(azidomethyl)-2-chloro-N-cyclopropylbenzenesulfonamide (1.40 g, 4.87 mmol), THF (40 mL), triphenylphosphine (1.6 g, 6.43 mmol) and water (0.11 mL, 6.43 mmol) at 0° C. and the reaction was stirred at room temperature over night. The solvents were removed and the residue was dissolved in MTBE and 20% HCl in dioxane was added dropwise at 0° C. The resulting salt was collected and washed with EtOAc. The salt was then neutralized with 6N NaOH and extracted with CH$_2$Cl$_2$. The combined organic phases were concentrated under reduced pressure to get the title product as a very thick oil. $^1$H NMR (400 MHz, DMSO-d6): 8.00 (s, 1H), 7.58 (s, 2H), 3.78 (s, 2H), 2.18 (m, 1H), 0.50-0.35 (m, 4H).

Synthesis of Representative Compounds

Compound 1

(S)—N-(1-Hydroxypropan-2-yl)-N-isobutyl-N,4'-dimethylbiphenyl-3,5-dicarboxamide

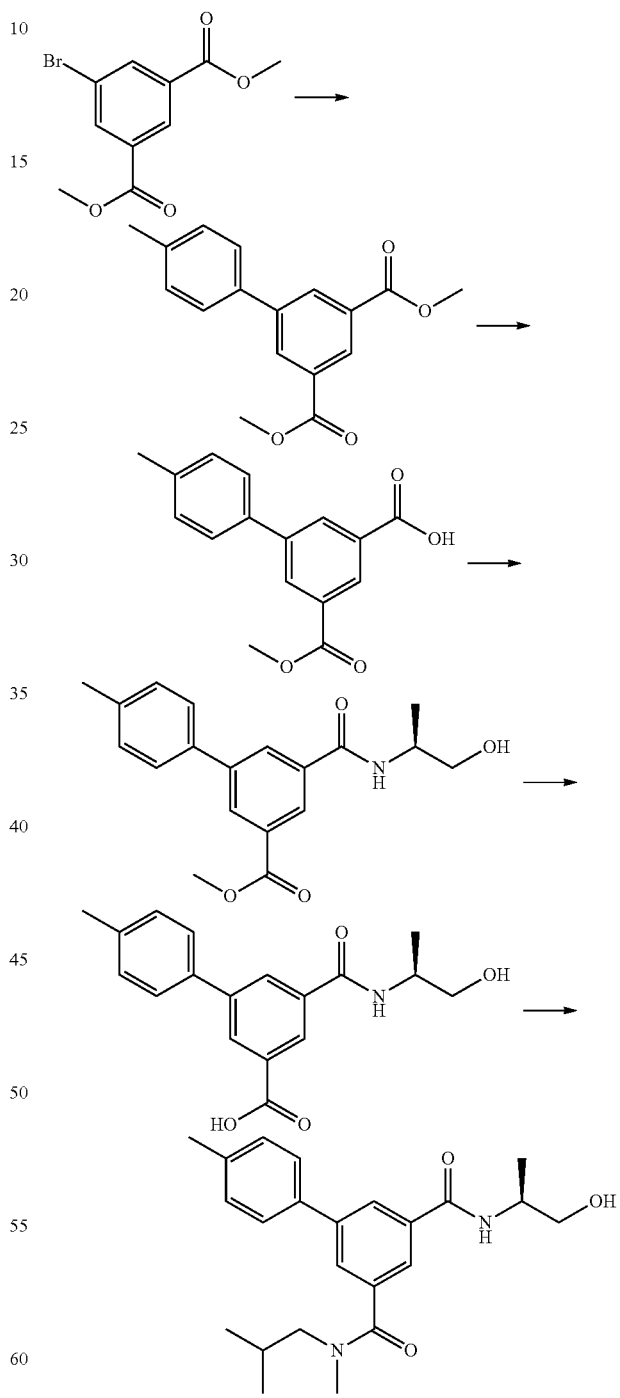

A) Dimethyl 4'-methylbiphenyl-3,5-dicarboxylate

To a mixture of dimethyl 5-bromoisophthalate (2.50 g, 9.15 mmol), p-tolylboronic acid (1.37 g, 10.1 mmol), toluene (50 mL), ethanol (10 mL), cesium carbonate (3.28 g, 10.1 mmol), and water (5 mL) under argon was added tetrakis(triphenylphosphine)-palladium(0) (529 mg, 0.458 mmol). The mixture was heated to reflux for 6 h, and then cooled to room temperature and filtered through Celite. The filtrate was concentrated and the residue was purified by silica gel column (0-50% EtOAc/hexane) to yield a white solid. $^1$H NMR (400 MHz, CDCl$_3$): δ 8.63 (s, 1H), 8.45 (s, 2H), 7.57 (d, 2H, J=8.0 Hz), 7.29 (d, 2H, J=8.0 Hz), 3.98 (s, 6H), 2.42 (s, 3H).

B) 5-(Methoxycarbonyl)-4'-methylbiphenyl-3-carboxylic acid

A mixture of dimethyl 4'-methylbiphenyl-3,5-dicarboxylate (1.70 g, 5.98 mmol), MeOH (100 mL) and 2N aq. NaOH (8 mL) was stirred at 60° C. until LC-MS indicated the diester was almost completely consumed. After cooling, the mixture was concentrated in vacuo and acidified with 1N aq. HCl to pH<4 and extracted with EtOAc (100 mL×3). The combined organic layers were washed with brine, dried (Na$_2$SO$_4$), and concentrated to yield a white solid (contained some dicarboxylic acid).

C) (S)-Methyl 5-(1-hydroxypropan-2-ylcarbamoyl)-4'-methylbiphenyl-3-carboxylate

To a mixture of 5-(methoxycarbonyl)-4'-methylbiphenyl-3-carboxylic acid (0.60 g, 2.2 mmol), N-(3-dimethylaminopropyl)-N'-ethylcarbodiimide hydrochloride (470 mg, 2.4 mmol), 1-hydroxybenzotriazole hydrate (340 mg, 2.2 mmol), and CH$_2$Cl$_2$ (5 mL) were added (S)-2-aminopropan-1-ol (180 mg, 2.4 mmol) and N,N-diisopropylethylamine (0.58 mL, 3.3 mmol). The mixture was stirred at room temperature overnight, and then diluted with EtOAc, washed with aq. NaHCO$_3$, brine, dried (Na$_2$SO$_4$), and concentrated. The residue was purified by silica gel column (0-80% EtOAc/hexane) to yield a white solid. LC-MS: 328.2 [M+1]$^+$; $^1$H NMR (400 MHz, DMSO-d6): δ 8.48 (d, 1H, J=8.0 Hz), 8.40 (t, 1H, J=1.6 Hz), 8.37 (t, 1H, J=1.6 Hz), 8.28 (t, 1H, J=1.6 Hz), 7.69 (d, 2H, J=8.0 Hz), 7.34 (d, 2H, J=8.0 Hz), 4.78 (t, 1H, J=5.6 Hz), 4.07 (m, 1H), 3.92 (s, 3H), 3.49 (m, 1H), 3.38 (m, 1H), 2.37 (s, 3H), 1.16 (d, 3H, J=6.8 Hz).

D) (S)-5-(1-Hydroxypropan-2-ylcarbamoyl)-4'-methylbiphenyl-3-carboxylic acid

A mixture of (S)-methyl 5-(1-hydroxypropan-2-ylcarbamoyl)-4'-methylbiphenyl-3-carboxylate (105 mg, 0.321 mmol), lithium hydroxide (9.98 mg, 0.417 mmol), THF (3 mL), and water (1 mL) was stirred at room temperature for 12 h. LC-MS indicated completion of the reaction. The reaction mixture was diluted with water (5 mL) and acidified with 1N aq. HCl to pH=3 and extracted with EtOAc (50 mL×3). The combined organic layers were washed with brine, dried (Na$_2$SO$_4$), and concentrated to yield a white solid. LC-MS: 314.4 [M+1]$^+$.

E) (S)—N-3-(1-Hydroxypropan-2-yl)-N-5-isobutyl-N5,4'-dimethylbiphenyl-3,5-dicarboxamide To a mixture of (S)-5-(1-hydroxypropan-2-ylcarbamoyl)-4'-methylbiphenyl-3-carboxylic acid (32 mg, 0.10 mmol), N-(3-dimethylaminopropyl)-N'-ethylcarbodiimide hydrochloride (29 mg, 0.15 mmol), 1-hydroxybenzotriazole hydrate (16 mg, 0.10 mmol), CH$_2$Cl$_2$ (3 mL), and DMF (0.5 mL) were added N-methylisobutylamine (13 mg, 0.15 mmol) and N,N-diisopropylethylamine (0.027 mL, 0.15 mmol). The mixture was stirred at room temperature overnight, and then diluted with EtOAc, washed with aq. NaHCO$_3$, brine, dried (Na$_2$SO$_4$), and concentrated. The residue was purified by preparative HPLC (100×21.2 mm C18 column, 40-80% MeCN/water [10 mM Et$_2$NH]) to yield a white foam.

LC-MS: 383.3 [M+1]$^+$; $^1$H NMR (400 MHz, CDCl$_3$): (rotamers) δ 8.00 (d, 1H, J=5.2 Hz), 7.66 (m, 2H), 7.50 (d, 2H, J=8.0 Hz), 7.27 (d, 2H, J=8.0 Hz), 6.52 (m, 1H), 4.30 (m, 1H), 3.81 (dd, 1H, J=11.2, 3.6 Hz), 3.67 (dd, 1H, J=11.2, 5.6 Hz), 3.41 (d, 1H, J=7.2 Hz), 3.11 (d, 1H, J=7.6 Hz), 3.08 and 2.95 (s, 3H), 2.41 (s, 3H), 2.10 and 1.94 (m, 1H), 1.31 (d, 3H, J=6.8 Hz), 1.01 and 0.77 (d, 6H, J=6.8 Hz).

Compound 2

(S)—N3-(1-Hydroxypropan-2-yl)-N5-isobutyl-4'-methylbiphenyl-3,5-dicarboxamide

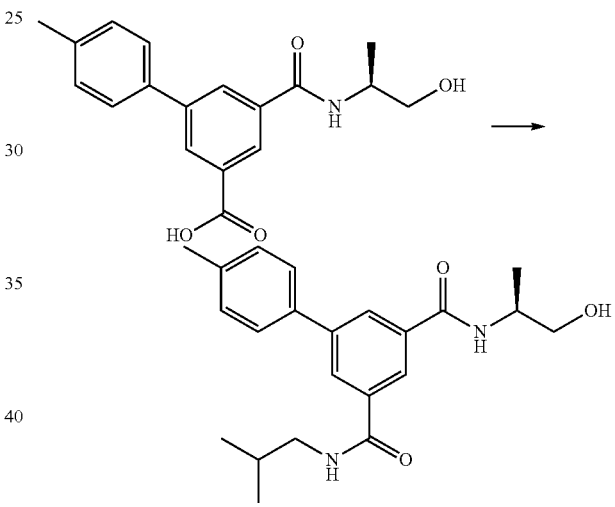

To a mixture of (S)-5-(1-hydroxypropan-2-ylcarbamoyl)-4'-methylbiphenyl-3-carboxylic acid (25 mg, 0.080 mmol), N-(3-dimethylaminopropyl)-N'-ethylcarbodiimide hydrochloride (30 mg, 0.16 mmol), 1-hydroxybenzotriazole hydrate (12 mg, 0.080 mmol), CH$_2$Cl$_2$ (3 mL), and DMF (0.5 mL) were added 2-methyl-1-propanamine (12 mg, 0.16 mmol) and N,N-diisopropylethylamine (0.021 mL, 0.12 mmol). The mixture was stirred at room temperature overnight, and then diluted with EtOAc, washed with aq. NaHCO$_3$, brine, dried (Na$_2$SO$_4$), and concentrated. The residue was purified by preparative HPLC (100×21.2 mm C18 column, 30-70% MeCN/water[10 mM Et$_2$NH]) to afford a white foam.

LC-MS: 369.1 [M+1]$^+$; $^1$H NMR (400 MHz, CDCl$_3$): 8.08 (m, 3H), 7.52 (m, 2H), 7.28 (m, 2H), 4.32 (m, 1H), 3.81 (dd, 1H, J=11.2, 3.6 Hz), 3.68 (dd, 1H, J=11.2, 5.6 Hz), 3.30 (d, 2H, J=6.4 Hz), 2.41 (s, 3H), 1.93 (m, 1H), 1.32 (d, 3H, J=6.8 Hz), 0.99 (d, 6H, J=6.4 Hz).

Compound 3

(S)—N-(1-hydroxypronan-2-yl)-4'-methyl-5-(methylsulfonyl)biphenyl-3-carboxamide

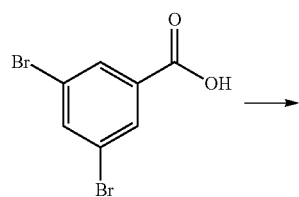

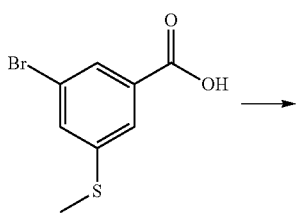

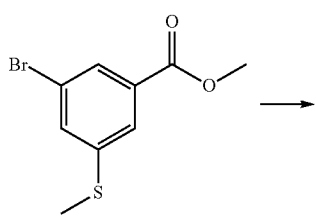

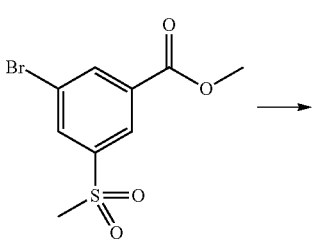

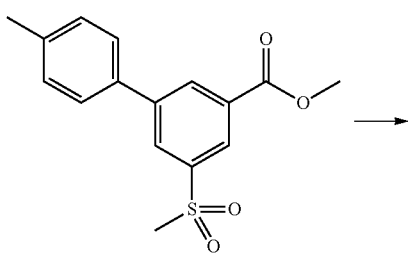

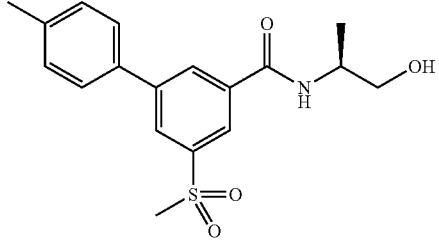

-continued

A) 3-Bromo-5-methylsulfanyl-benzoic acid

A mixture of 3,5-dibromobenzoic acid (2.5 g, 8.9 mmol), sodium methyl sulfide (1.4 g, 20 mmol), and dimethyl sulfoxide (10 mL) was sealed in a microwave tube and heated with an oil bath at 100° C. for 4 h. TLC indicated completion of the reaction. The reaction mixture was poured into water and extracted with EtOAc (3×50 mL). The combined organic layers were washed with brine, dried ($Na_2SO_4$), and concentrated. The residue was used for the next step reaction without purification. $^1$H NMR (400 MHz, $CDCl_3$): δ 7.97 (t, 1H, J=1.6 Hz), 7.87 (t, 1H, J=1.6 Hz), 7.57 (t, 1H, J=1.6 Hz), 2.53 (s, 3H).

B) Methyl 3-bromo-5-(methylthio)benzoate

To a stirred mixture of 3-bromo-5-methylsulfanyl-benzoic acid (2.2 g, 8.9 mmol), methylene chloride (100 mL), and DMF (5 drops) at 0° C. was added oxalyl chloride (1.0 mL, 12 mmol). The mixture was slowly warmed to room temperature and stirred at room temperature overnight. Methanol (5.0 mL, 120 mmol) and N,N-diisopropylethylamine (5.0 mL, 29 mmol) were added and the mixture stirred at room temperature for 3 h and then concentrated. The residue was purified by silica gel column (0-50% EtOAc/hexane) to yield an oil. $^1$H NMR (400 MHz, $CDCl_3$): δ 7.91 (t, 1H, J=1.6 Hz), 7.81 (t, 1H, J=1.6 Hz), 7.52 (t, 1H, J=1.6 Hz), 3.92 (s, 3H), 2.52 (s, 3H).

C) Methyl 3-bromo-5-(methylsulfonyl)benzoate

A mixture of methyl 3-bromo-5-(methylthio)benzoate (1.6 g, 6.1 mmol), m-chloroperbenzoic acid (75% purity, 4.2 g, 18 mmol), and methylene chloride (100 mL) was stirred at room temperature overnight. The reaction mixture was washed with aq. $Na_2CO_3$ solution and brine, dried ($Na_2SO_4$), and concentrated. The residue was purified by silica gel column (EtOAc/hexane: 0-70%) to yield a white solid. $^1$H NMR (400 MHz, $CDCl_3$): δ 8.52 (s, 1H), 8.44 (s, 1H), 8.27 (s, 1H), 3.98 (s, 3H), 3.10 (s, 3H).

D) Methyl 4'-methyl-5-(methylsulfonyl)biphenyl-3-carboxylate

To a mixture of methyl 3-bromo-5-(methylsulfonyl)benzoate (0.65 g, 2.2 mmol), p-tolylboronic acid (0.332 g, 2.44 mmol), toluene (10 mL), cesium carbonate (0.795 g, 2.44 mmol), and water (1 mL) under argon was added tetrakis(triphenylphosphine)-palladium(0) (128 mg, 0.111 mmol). The mixture was heated under reflux for 15 h. After cooling, the mixture was filtered through Celite and the filter cake was washed with EtOAc. The filtrate was washed with brine, dried ($Na_2SO_4$), and concentrated. The residue was purified by silica gel column (0-100% EtOAc/hexane) to yield a white solid. LC-MS: 3.26 min, 305.3 [M+1]+ (weak).

E) 4'-Methyl-5-(methylsulfonyl)biphenyl-3-carboxylic acid

A mixture of methyl 4'-methyl-5-(methylsulfonyl)biphenyl-3-carboxylate (0.55 g, 1.8 mmol), MeOH (50 mL) and 2N aq. NaOH (4 mL) was stirred at 50° C. for 3 h. After cooling the mixture was concentrated in vacuo and acidified with 1N aq. HCl to pH<4 and extracted with EtOAc (100 mL). The organic layer was washed with brine, dried ($Na_2SO_4$), and concentrated to yield a white solid. LC-MS: 289.3 [M−1]−; $^1$H NMR (400 MHz, $CDCl_3$): δ 8.61 (t, 1H, J=1.6 Hz), 8.59 (t, 1H, J=1.6 Hz), 8.39 (t, 1H, J=1.6 Hz), 7.58 (d, 2H, J=8.0 Hz), 7.33 (d, 2H, J=8.0 Hz), 3.15 (s, 3H), 2.44 (s, 3H).

F) (S)—N-(1-Hydroxypropan-2-yl)-4'-methyl-5-(methylsulfonyl)biphenyl-3-carboxamide To a mixture of 4'-methyl-5-(methylsulfonyl)biphenyl-3-carboxylic acid (50 mg, 0.17 mmol), N-(3-dimethylaminopropyl)-N'-ethylcarbodiimide hydrochloride (36 mg, 0.19 mmol), 1-hydroxybenzotriazole hydrate (26 mg, 0.17 mmol), and $CH_2Cl_2$ (2 mL) were added (S)-2-aminopropan-1-ol (19 mg, 0.26 mmol) and N,N-diisopropylethylamine (0.045 mL, 0.26 mmol). The mixture was stirred at room temperature overnight and then concentrated in vacuo. The residue was purified by preparative HPLC (100×20.2 mm, C18 column; 30-60% MeCN-water[10 mM $Et_2NH$]) to yield a white solid.

LC-MS: 348.2 [M+1]+; $^1$H NMR (400 MHz, DMSO-d6): δ 8.55 (d, 1H, J=8.0 Hz), 8.42 (t, 1H, J=1.6 Hz), 8.33 (t, 1H, J=1.6 Hz), 8.26 (t, 1H, J=1.6 Hz), 7.75 (d, 2H, J=8.0 Hz), 7.37 (d, 2H, J=8.0 Hz), 4.80 (bs, 1H), 4.08 (m, 1H), 3.49 (m, 1H), 3.39 (m, 1H), 2.50 (s, 3H), 2.38 (s, 3H), 1.17 (d, 3H, J=6.8 Hz).

Compound 6

(S)-Ethyl 5-(1-hydroxypropan-2-ylcarbamoyl)-4'-methylbiphenyl-3-carboxylate

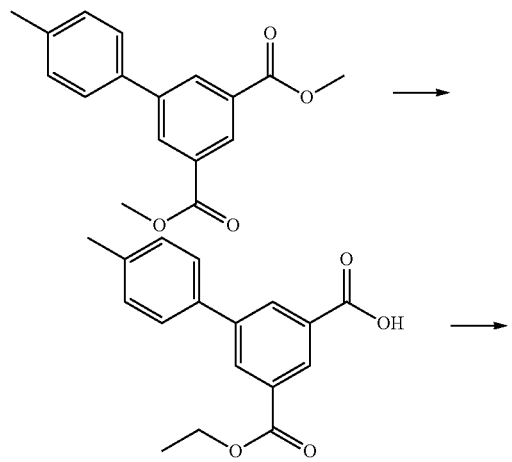

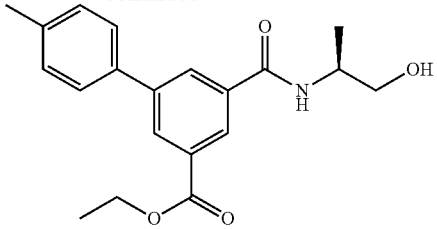

A) 5-(Ethoxycarbonyl)-4'-methylbiphenyl-3-carboxylic acid

Dimethyl 4'-methylbiphenyl-3,5-dicarboxylate (14.3 g, 50.3 mmol) was dissolved in 1,4-dioxane (160 mL) and ethanol (200 proof, 450 mL). To the stirred solution was added lithium hydroxide (2.41 g, 100 mmol) and the reaction mixture was stirred at room temperature and monitored with LC-MS. While about 90% of the dimethyl ester was consumed to give the major monoethyl ester and some dicarboxylic acid (5-10%), the mixture was cooled and neutralized with 2N aq. HCl and concentrated in vacuo to about 100 mL. The residue was treated with water (100 mL) and acidified with 2N aq. HCl to pH 2-3 and extracted with EtOAc (100 mL×3). The combined organic layers were washed with brine, dried ($Na_2SO_4$), and concentrated to give the crude monoethyl ester as a white solid. LC-MS: 283.1 [M−1]−.

B) (S)-Ethyl 5-(1-hydroxypropan-2-ylcarbamoyl)-4'-methylbiphenyl-3-carboxylate To a mixture of 5-(ethoxycarbonyl)-4'-methylbiphenyl-3-carboxylic acid (35 mg, 0.12 mmol), N-(3-dimethylaminopropyl)-N'-ethylcarbodiimide hydrochloride (47 mg, 0.25 mmol), 1-hydroxybenzotriazole hydrate (19 mg, 0.12 mmol), and $CH_2Cl_2$ (3 mL) were added (S)-2-aminopropan-1-ol (10 mg, 0.14 mmol) and N,N-diisopropylethylamine (0.032 mL, 0.18 mmol). The mixture was stirred at room temperature overnight, and then concentrated. The residue was purified by preparative HPLC (100×21.2 mm C18 column, 30-70% MeCN/water[10 mM $Et_2NH$]) to afford a white solid.

LC-MS: 342.4 [M+1]+; $^1$H NMR (400 MHz, $CDCl_3$): 8.38 (t, 1H, J=1.6 Hz), 8.29 (t, 1H, J=1.6 Hz), 8.24 (t, 1H, J=1.6 Hz), 7.55 (d, 2H, J=8.0 Hz), 7.29 (d, 2H, J=8.0 Hz), 4.44 (q, 2H, J=7.2 Hz), 4.34 (m, 1H), 3.83 (dd, 1H, J=11.2, 3.6 Hz), 3.70 (dd, 1H, J=11.2, 6.0 Hz), 2.41 (s, 3H), 1.43 (t, 3H, J=7.2 Hz), 1.34 (d, 3H, J=6.8 Hz).

Compound 7

(S)—N3-(2-hydroxy-1-(6-methoxypyridin-3-yl)ethyl)-N5-isobutyl-N5,4'-dimethyl-biphenyl-3,5-dicarboxamide

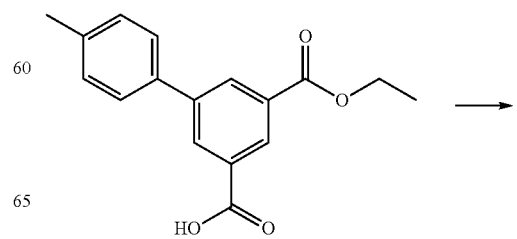

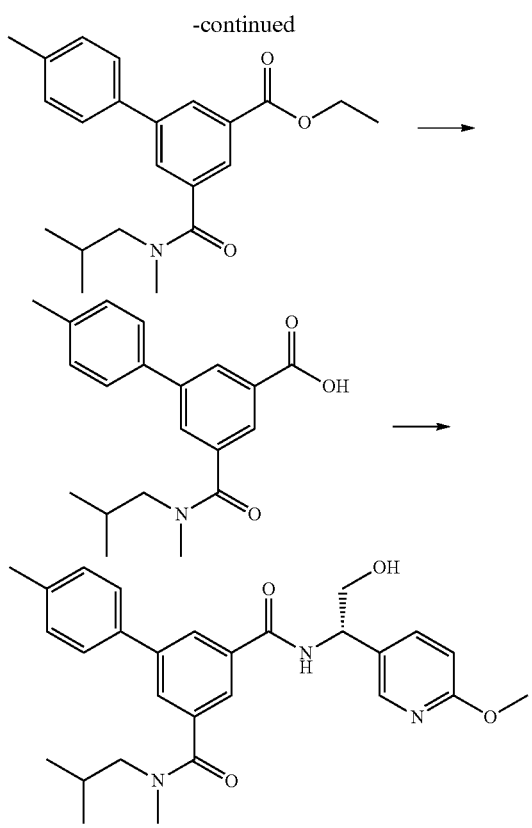

A) Ethyl 5-(isobutyl(methyl)carbamoyl)-4'-methylbiphenyl-3-carboxylate

To a mixture of 5-(ethoxycarbonyl)-4'-methylbiphenyl-3-carboxylic acid (260 mg, 0.91 mmol), N-(3-dimethylaminopropyl)-N'-ethylcarbodiimide hydrochloride (350 mg, 1.8 mmol), 1-hydroxybenzotriazole hydrate (140 mg, 0.91 mmol), CH$_2$Cl$_2$ (5 mL) were added N-methylisobutylamine (120 mg, 1.4 mmol) and N,N-diisopropylethylamine (0.24 mL, 1.4 mmol). The mixture was stirred at room temperature overnight, and then concentrated in vacuo. The residue was purified by silica gel column (0-60% EtOAc/hexane) to yield a syrup. LC-MS: 354.2 [M+1]$^+$.

B) 5-(Isobutyl(methyl)carbamoyl)-4'-methylbiphenyl-3-carboxylic acid

A mixture of ethyl 5-(isobutyl(methyl)carbamoyl)-4'-methylbiphenyl-3-carboxylate (165 mg, 0.467 mmol), lithium hydroxide (55 mg, 2.3 mmol), ethanol (10 mL), and water (1 mL) was stirred at room temperature for 5 h. LC-MS indicated completion of the reaction. The solvent was removed in vacuo and the residue was treated with water and acidified with 1N aq. HCl to pH=3 and extracted with EtOAc (50 mL×3). The combined organic layers were washed with brine, dried (Na$_2$SO$_4$), and concentrated to yield the product as white foam. LC-MS: 326.0 [M+1]$^+$.

C) (S)—N3-(2-Hydroxy-1-(6-methoxypyridin-3-yl)ethyl)-N5-isobutyl-N5,4'-dimethylbiphenyl-3,5-dicarboxamide To a mixture of 5-(isobutyl(methyl)carbamoyl)-4'-methylbiphenyl-3-carboxylic acid (35 mg, 0.11 mmol), N-(3-dim-ethylaminopropyl)-N'-ethylcarbodiimide hydrochloride (41 mg, 0.22 mmol), 1-hydroxybenzotriazole hydrate (16 mg, 0.11 mmol), CH$_2$Cl$_2$ (3 mL) were added (S)-2-amino-2-(6-methoxypyridin-3-yl)ethanol (27 mg, 0.16 mmol) (WO 2008/130481) and N,N-diisopropylethylamine (28 pt, 0.16 mmol). The mixture was stirred at room temperature overnight, and then concentrated in vacuo. The residue was purified by preparative HPLC (100×21.2 mm C18 column, 30-70% MeCN/water[10 mM Et$_2$NH]) to yield a white solid.

LC-MS: 476.4 [M+1]$^+$; $^1$H NMR (400 MHz, CD$_3$OD): (rotamers) 8.19 (m, 2H), 7.82-7.70 (m, 3H), 7.59 (m, 2H), 7.30 (d, 2H, J=8.0 Hz), 6.80 (d, 1H, J=8.4 Hz), 5.19 (t, 1H, J=6.4 Hz), 3.94-3.83 (m, 5H), 3.42 (d, 1H, J=7.6 Hz), 3.18 (d, 1H, J=7.6 Hz), 3.10 and 3.00 (s, 3H), 2.38 (s, 3H), 2.15 and 1.98 (m, 1H), 1.01 and 0.77 (d, 6H, J=6.8 Hz).

Compound 8

N3-Isobutyl-N3,4'-dimethyl-N-5-(1-(pyrazin-2-yl)ethyl)biphenyl-3,5-dicarboxamide

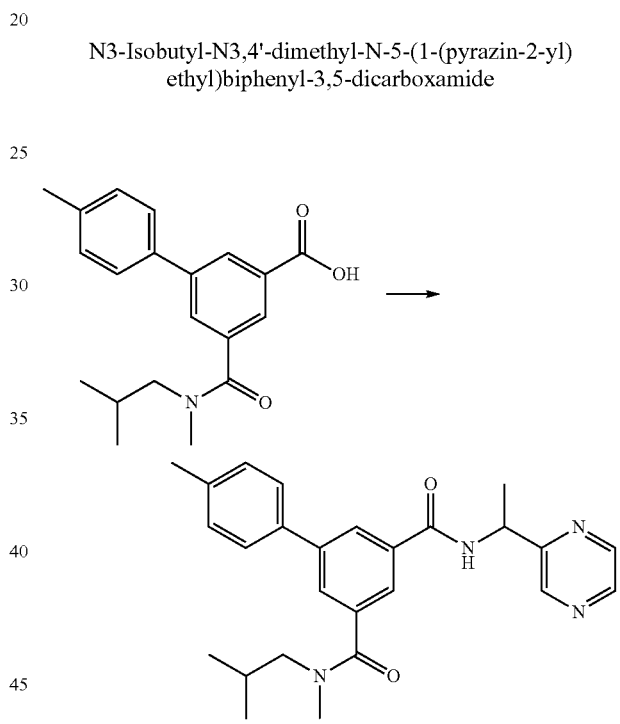

To a mixture of 5-(isobutyl(methyl)carbamoyl)-4'-methylbiphenyl-3-carboxylic acid (21 mg, 0.064 mmol), N-(3-dim-ethylaminopropyl)-N'-ethylcarbodiimide hydrochloride (25 mg, 0.13 mmol), 1-hydroxybenzotriazole hydrate (9.9 mg, 0.064 mmol), and CH$_2$Cl$_2$ (3 mL) were added 1-(pyrazin-2-yl)ethanamine (12 mg, 0.097 mmol) and N,N-diisopropylethylamine (17 μL, 0.097 mmol). The mixture was stirred at room temperature overnight, and then concentrated in vacuo. The residue was purified by preparative HPLC (100×21.2 mm C18 column, 30-70% MeCN/water[10 mM Et$_2$NH]) to afford a white foam.

LC-MS: 431.1 [M+1]$^+$; $^1$H NMR (400 MHz, CD$_3$OD): (rotamers) δ 8.70 (s, 1H), 8.59 (m, 1H), 8.49 (d, 1H, J=2.8 Hz), 8.20 (t, 1H, J=1.6 Hz), 7.84-7.75 (m, 2H), 7.62-7.57 (m, 2H), 7.30 (d, 2H, J=8.0 Hz), 5.36 (q, 1H, J=7.2 Hz), 3.42 (d, 1H, J=7.6 Hz), 3.19 (d, 1H, J=7.6 Hz), 3.10 and 3.01 (s, 3H), 2.39 (s, 3H), 2.15 and 1.98 (m, 1H), 1.66 (d, 3H, J=7.2 Hz), 1.02 and 0.78 (d, 6H, J=6.4 Hz).

Compound 9

N3-((6-Chloropyridin-3-yl)methyl)-N5-isobutyl-N5,4'-dimethylbiphenyl-3,5-dicarboxamide

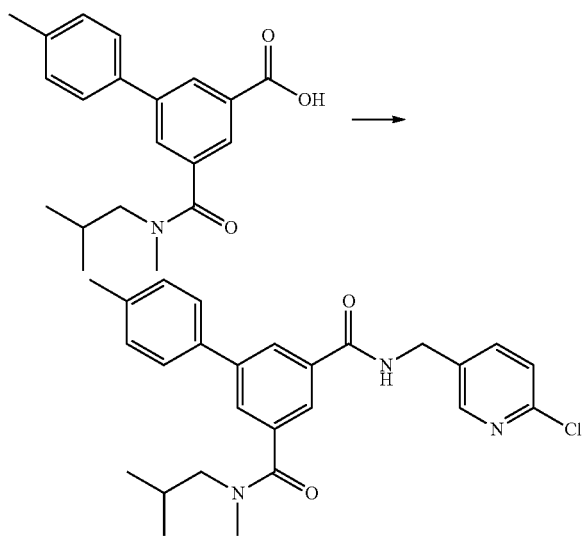

To a mixture of 5-(isobutyl(methyl)carbamoyl)-4'-methyl-biphenyl-3-carboxylic acid (21 mg, 0.064 mmol), N-(3-dimethylaminopropyl)-N'-ethylcarbodiimide hydrochloride (25 mg, 0.13 mmol), 1-hydroxybenzotriazole hydrate (9.9 mg, 0.064 mmol), and CH$_2$Cl$_2$ (3 mL) were added 2-chloro-5-aminomethylpyridine (14 mg, 0.097 mmol) and N,N-diisopropylethylamine (17 µL, 0.097 mmol). The mixture was stirred at room temperature overnight, and then concentrated in vacuo. The residue was purified by preparative HPLC (100×21.2 mm C18 column, 40-80% MeCN/water[10 mM Et$_2$NH]) to yield a white foam.

LC-MS: 450.4 [M+1]$^+$; $^1$H NMR (400 MHz, CD$_3$OD): (rotamers) δ 8.39 (d, 1H, J=2.0 Hz), 8.18 (m, 1H), 7.85 (dd, 1H, J=8.0, 2.4 Hz), 7.82-7.75 (m, 2H), 7.58 (m, 2H), 7.44 (d, 1H, J=8.0 Hz), 7.30 (d, 2H, J=7.6 Hz), 4.61 (s, 2H), 3.42 (d, 1H, J=7.6 Hz), 3.19 (d, 1H, J=7.2 Hz), 3.10 and 3.01 (s, 3H), 2.38 (s, 3H), 2.15 and 1.98 (m, 1H), 1.01 and 0.77 (d, 6H, J=6.8 Hz).

Compound 10

(R)—N3-Isobutyl-N3,4'-dimethyl-N5-(1-(6-(trifluoromethyl)pyridin-3-yl)ethyl)biphenyl-3,5-dicarboxamide

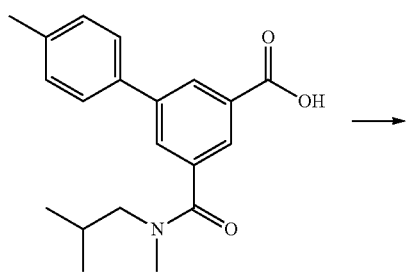

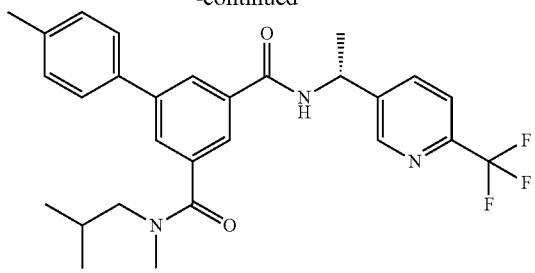

To a mixture of 5-(isobutyl(methyl)carbamoyl)-4'-methyl-biphenyl-3-carboxylic acid (21 mg, 0.064 mmol), N-(3-dimethylaminopropyl)-N'-ethylcarbodiimide hydrochloride (25 mg, 0.13 mmol), 1-hydroxybenzotriazole hydrate (9.9 mg, 0.064 mmol), and CH$_2$Cl$_2$ (3 mL) were added (R)-1-(6-(trifluoromethyl)pyridin-3-yl)ethanamine (18 mg, 0.097 mmol) (WO 2008/130481) and N,N-diisopropylethylamine (17 µL, 0.097 mmol). The mixture was stirred at room temperature overnight, and then concentrated in vacuo. The residue was purified by preparative HPLC (100×21.2 mm C18 column, 40-80% MeCN/water[10 mM Et$_2$NH]) to afford a white foam.

LC-MS: 498.6 [M+1]$^+$; $^1$H NMR (400 MHz, CD$_3$OD): (rotamers) δ 8.77 (d, 1H, J=1.6 Hz), 8.19 (t, 1H, J=1.6 Hz), 8.07 (dd, 1H, J=8.0, 2.0 Hz), 7.83-7.75 (m, 3H), 7.59 (m, 2H), 7.30 (d, 2H, J=8.4 Hz), 5.36 (q, 1H, J=6.4 Hz), 3.42 (d, 1H, J=7.6 Hz), 3.18 (d, 1H, J=7.6 Hz), 3.10 and 3.00 (s, 3H), 2.39 (s, 3H), 2.15 and 1.98 (m, 1H), 1.66 (d, 31-1, J=7.2 Hz), 1.01 and 0.77 (d, 6H, J=6.8 Hz).

Compound 11

N3-(Imidazo[1,2-a]pyridin-7-ylmethyl)-N5-isobutyl-N5,4'-dimethylbiphenyl-3,5-dicarboxamide

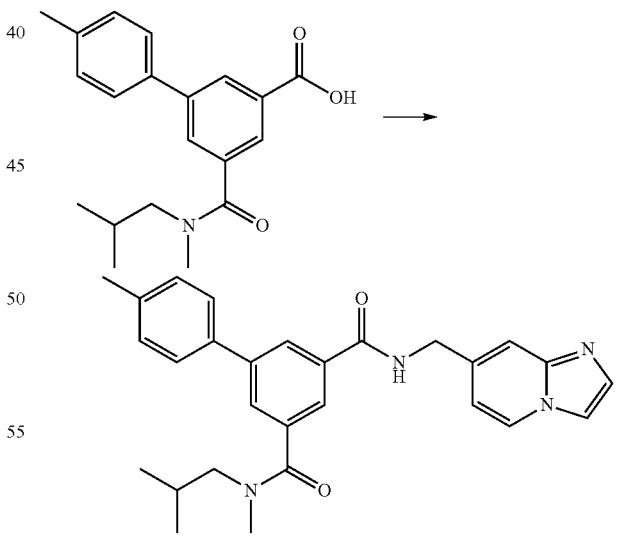

To a mixture of 5-(isobutyl(methyl)carbamoyl)-4'-methyl-biphenyl-3-carboxylic acid (15 mg, 0.046 mmol), N-(3-dimethylaminopropyl)-N'-ethylcarbodiimide hydrochloride (18 mg, 0.092 mmol), 1-hydroxybenzotriazole hydrate (7.0 mg, 0.046 mmol), and CH$_2$Cl$_2$ (2 mL) were added imidazo[1,2-a]pyridin-7-ylmethanamine (10 mg, 0.069 mmol) and N,N-diisopropylethylamine (12 µL, 0.069 mmol). The mixture was stirred at room temperature overnight, and then concentrated in vacuo. The residue was purified by preparative HPLC (100×21.2 mm C18 column, 40-70% MeCN/water[10 mM Et$_2$NH]) to afford a white foam.

LC-MS: 455.4 [M+1]$^+$; $^1$H NMR (400 MHz, CD$_3$OD): (rotamers) δ 8.40 (d, 1H, J=7.2 Hz), 8.22 (s, 1H), 7.87-7.76 (m, 3H), 7.62-7.57 (m, 2H), 7.52 (d, 1H, J=1.6 Hz), 7.49 (s, 1H), 7.30 (d, 2H, J=8.0 Hz), 6.96 (dd, 1H, J=7.2, 1.6 Hz), 4.66 (s, 2H), 3.43 (d, 1H, J=8.0 Hz), 3.20 (d, 1H, J=7.6 Hz), 3.10 and 3.02 (s, 3H), 2.39 (s, 3H), 2.15 and 1.98 (m, 1H), 1.01 and 0.78 (d, 6H, J=6.4 Hz).

Compound 12

N3-Isobutyl-N3,4'-dimethyl-N5-((2-methylpyrimidin-5-yl)methyl)biphenyl-3,5-dicarboxamide

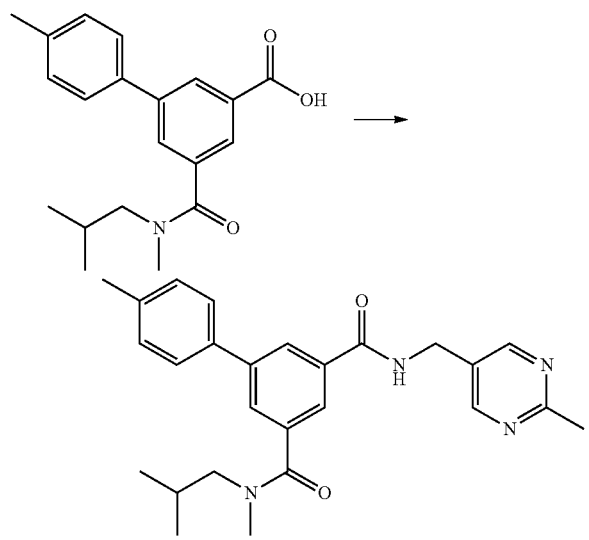

To a mixture of 5-(isobutyl(methyl)carbamoyl)-4'-methylbiphenyl-3-carboxylic acid (15 mg, 0.046 mmol), N-(3-dimethylaminopropyl)-N'-ethylcarbodiimide hydrochloride (18 mg, 0.092 mmol), 1-hydroxybenzotriazole hydrate (7.0 mg, 0.046 mmol), and CH$_2$Cl$_2$ (2 mL) were added (2-methylpyrimidin-5-yl)methanamine (8.5 mg, 0.069 mmol) (WO 2008/130481) and N,N-diisopropylethylamine (12 μL, 0.069 mmol). The mixture was stirred at room temperature overnight, and then concentrated in vacuo. The residue was purified by preparative HPLC (100×21.2 mm C18 column, 40-70% MeCN/water[10 mM Et$_2$NH]) to afford a white foam.

LC-MS: 431.3 [M+1]$^+$; $^1$H NMR (400 MHz, CD$_3$OD): (rotamers) δ 8.72 (s, 2H), 8.17 (s, 1H), 7.82-7.75 (m, 2H), 7.60-7.55 (m, 2H), 7.30 (d, 2H, J=8.4 Hz), 4.59 (s, 2H), 3.42 (d, 1H, J=7.6 Hz), 3.18 (d, 1H, J=7.6 Hz), 3.10 and 3.00 (s, 3H), 2.67 (s, 3H), 2.38 (s, 3H), 2.15 and 1.98 (m, 1H), 1.01 and 0.77 (d, 6H, J=6.4 Hz).

Compound 13

(R)—N3-(3-Hydroxy-1-(6-methylpyridin-3-yl)propyl)-N5-isobutyl-N5,4'-dimethylbiphenyl-3,5-dicarboxamide

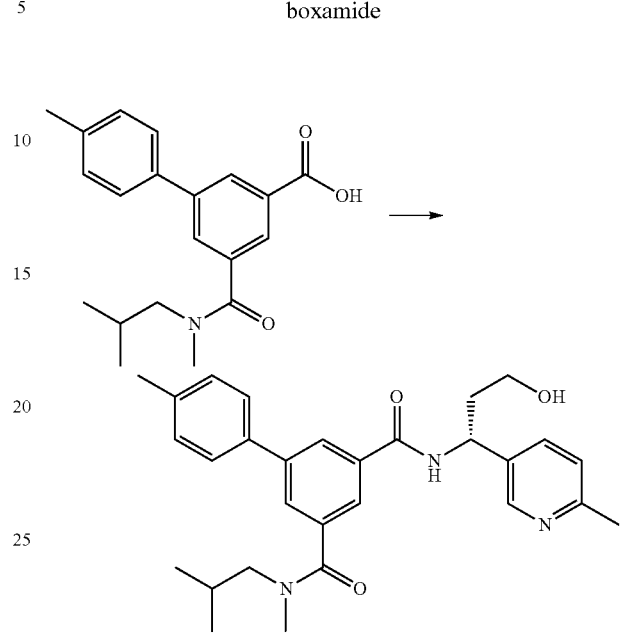

To a mixture of 5-(isobutyl(methyl)carbamoyl)-4'-methylbiphenyl-3-carboxylic acid (15 mg, 0.046 mmol), N-(3-dimethylaminopropyl)-N'-ethylcarbodiimide hydrochloride (18 mg, 0.092 mmol), 1-hydroxybenzotriazole hydrate (7.0 mg, 0.046 mmol), and CH$_2$Cl$_2$ (2 mL) were added (R)-3-amino-3-(6-methylpyridin-3-yl)propan-1-ol (11 mg, 0.069 mmol) (WO 2008/130481) and N,N-diisopropylethylamine (12 μL, 0.069 mmol). The mixture was stirred at room temperature overnight, and then concentrated in vacuo. The residue was purified by preparative HPLC (100×21.2 mm C18 column, 40-70% MeCN/water[10 mM Et$_2$NH]) to afford a white foam.

LC-MS: 474.6 [M+1]$^+$; $^1$H NMR (400 MHz, CD$_3$OD): (rotamers) δ 8.47 (d, 1H, J=1.6 Hz), 8.15 (s, 1H), 7.80-7.73 (m, 3H), 7.60-7.55 (m, 2H), 7.30 (d, 3H, J=8.0 Hz), 5.32 (m, 1H), 3.72-3.57 (m, 2H), 3.42 (d, 1H, J=7.6 Hz), 3.17 (d, 1H, J=7.6 Hz), 3.09 and 3.00 (s, 3H), 2.51 (s, 3H), 2.38 (s, 3H), 2.24-1.94 (m, 3H), 1.01 and 0.77 (d, 6H, J=6.4 Hz).

Compound 14

(R)—N3-Isobutyl-N3,4'-dimethyl-N5-(1-(2-methylpyrimidin-5-yl)ethyl)biphenyl-3,5-dicarboxamide

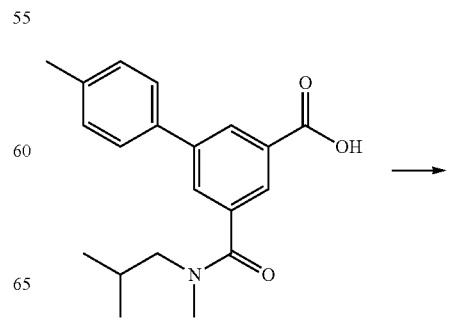

-continued

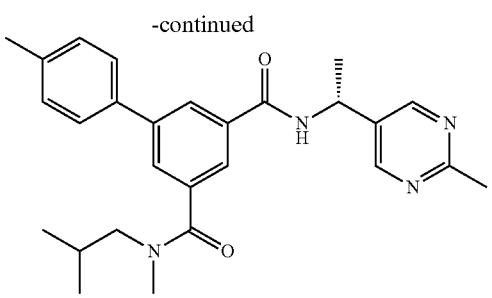

To a mixture of 5-(isobutyl(methyl)carbamoyl)-4'-methylbiphenyl-3-carboxylic acid (15 mg, 0.046 mmol), N-(3-dimethylaminopropyl)-N'-ethylcarbodiimide hydrochloride (18 mg, 0.092 mmol), 1-hydroxybenzotriazole hydrate (7.0 mg, 0.046 mmol), and CH$_2$Cl$_2$ (2 mL) were added (R)-1-(2-methylpyrimidin-5-yl)ethanamine (9.5 mg, 0.069 mmol) (WO 2008/130481) and N,N-diisopropylethylamine (12 µL, 0.069 mmol). The mixture was stirred at room temperature overnight, and then concentrated in vacuo. The residue was purified by preparative HPLC (100×21.2 mm C18 column, 40-70% MeCN/water[10 mM Et$_2$NH]) to afford a white foam.

LC-MS: 445.6 [M+1]$^+$; $^1$H NMR (400 MHz, CD$_3$OD): (rotamers) δ 8.77 (s, 2H), 8.17 (t, 1H, J=1.6 Hz), 7.81-7.74 (m, 2H), 7.61-7.55 (m, 2H), 7.30 (d, 2H, J=8.4 Hz), 5.27 (q, 1H, J=7.2 Hz), 3.42 (d, 1H, J=7.6 Hz), 3.18 (d, 1H, J=7.6 Hz), 3.09 and 3.00 (s, 3H), 2.67 (s, 3H), 2.39 (s, 3H), 2.15 and 1.98 (m, 1H), 1.65 (d, 3H, J=6.8 Hz), 1.01 and 0.77 (d, 6H, J=6.8 Hz).

Compound 15

Ethyl 4'-methyl-5-((2-methylpyrimidin-5-yl)methylcarbamoyl)biphenyl-3-carboxylate

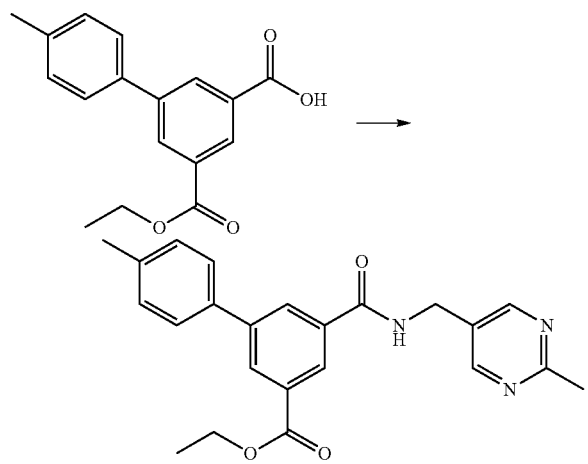

To a mixture of crude 5-(ethoxycarbonyl)-4'-methylbiphenyl-3-carboxylic acid (450 mg, 1.6 mmol), N-(3-dimethylaminopropyl)-N'-ethylcarbodiimide hydrochloride (610 mg, 3.2 mmol), 1-hydroxybenzotriazole hydrate (240 mg, 1.6 mmol), CH$_2$Cl$_2$ (5 mL) were added (2-methylpyrimidin-5-yl)methanamine (290 mg, 2.4 mmol) and N,N-diisopropylethylamine (0.41 mL, 2.4 mmol). The reaction mixture was stirred at room temperature overnight, and then diluted with aq. NaHCO$_3$ solution and EtOAc (100 mL). The organic layer was separated, washed with brine, dried over anhydrous sodium sulfate, and concentrated in vacuo. The residue was purified by silica gel column (0-20% MeOH/CH$_2$Cl$_2$) to afford the title product as a white foam.

LC-MS: 390.4 [M+1]$^+$; $^1$H NMR (400 MHz, CDCl$_3$): 8.73 (s, 2H), 8.40 (t, 1H, J=1.6 Hz), 8.29 (t, 1H, J=1.6 Hz), 8.26 (t, 1H, J=1.6 Hz), 7.54 (d, 2H, J=8.0 Hz), 7.28 (d, 2H, J=8.0 Hz), 6.72 (bs, 1H), 4.67 (d, 2H, J=6.0 Hz), 4.43 (q, 2H, J=7.2 Hz), 2.76 (s, 3H), 2.41 (s, 3H), 1.42 (t, 3H, J=7.2 Hz).

Compound 16

4'-Methyl-N3,N5-bis((2-methylpyrimidin-5-yl)methyl)biphenyl-3,5-dicarboxamide

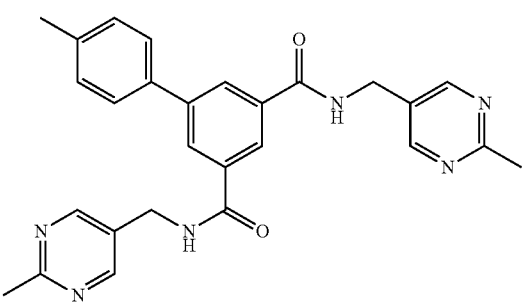

The title compound was isolated as a white foam from the preparation of compound 15 as the crude 5-(ethoxycarbonyl)-4'-methylbiphenyl-3-carboxylic acid contained some 4'-methylbiphenyl-3,5-dicarboxylic acid.

LC-MS: 467.4 [M+1]$^+$; $^1$H NMR (400 MHz, CDCl$_3$): 8.66 (s, 4H), 8.09 (s, 2H), 8.06 (s, 1H), 7.46 (d, 2H, J=8.4 Hz), 7.25 (d, 2H, J=8.8 Hz), 6.95 (t, 2H, J=5.6 Hz), 4.61 (d, 4H, J=6.0 Hz), 2.71 (s, 6H), 2.39 (s, 3H).

Compound 17

5-(3,3-Difluoroazetidine-1-carbonyl)-4'-methyl-N-((2-methylpyrimidin-5-yl)methyl)biphenyl-3-carboxamide

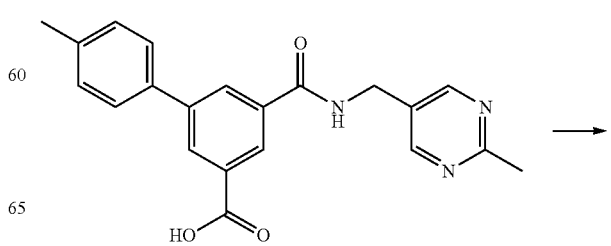

-continued

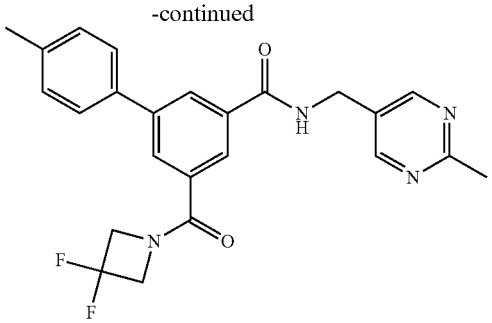

To a mixture of 4'-methyl-5-((2-methylpyrimidin-5-yl)methylcarbamoyl)biphenyl-3-carboxylic acid (11 mg, 0.030 mmol), N-(3-dimethylaminopropyl)-N'-ethylcarbodiimide hydrochloride (12 mg, 0.061 mmol), 1-hydroxybenzotriazole hydrate (4.7 mg, 0.030 mmol), $CH_2Cl_2$ (2 mL) were added 3,3-difluoroazetidine (4.2 mg, 0.046 mmol) and N,N-diisopropylethylamine (11 μL, 0.061 mmol). The mixture was stirred at room temperature overnight, and then concentrated in vacuo. The residue was purified by preparative HPLC (100×21.2 mm C18 column, 30-70% MeCN/water[10 mM $Et_2NH$]) to afford a white foam.

LC-MS: 437.3 $[M+1]^+$; $^1H$ NMR (400 MHz, $CD_3OD$): δ 8.73 (s, 2H), 8.26 (t, 1H, J=1.6 Hz), 8.06 (m, 2H), 7.60 (d, 2H, J=8.4 Hz), 7.31 (d, 2H, J=8.0 Hz), 4.77 (bs, 2H), 4.59 (s, 2H), 4.56 (bs, 2H), 2.67 (s, 3H), 2.38 (s, 3H).

Compound 18

4'-Methyl-N-((2-methylpyrimidin-5-yl)methyl)-5-(piperidine-1-carbonyl)biphenyl-3-carboxamide

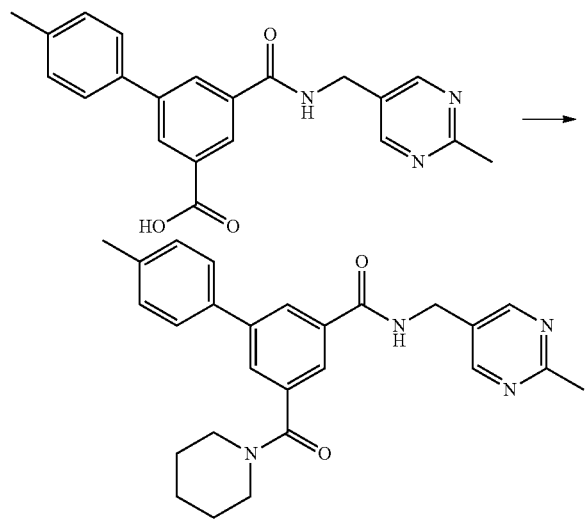

To a mixture of 4'-methyl-5-((2-methylpyrimidin-5-yl)methylcarbamoyl)biphenyl-3-carboxylic acid (11 mg, 0.030 mmol), N-(3-dimethylaminopropyl)-N'-ethylcarbodiimide hydrochloride (12 mg, 0.061 mmol), 1-hydroxybenzotriazole hydrate (4.7 mg, 0.030 mmol), and $CH_2Cl_2$ (2 mL) were added piperidine (3.9 mg, 0.046 mmol) and N,N-diisopropylethylamine (11 μL, 0.061 mmol). The mixture was stirred at room temperature overnight, and then concentrated in vacuo. The residue was purified by preparative HPLC (100×21.2 mm C18 column, 30-70% MeCN/water[10 mM $Et_2NH$]) to afford a white foam.

LC-MS: 429.3 $[M+1]^+$; $^1H$ NMR (400 MHz, $CD_3OD$): δ 8.72 (s, 2H), 8.17 (t, 1H, J=1.6 Hz), 7.80 (t, 1H, J=1.6 Hz), 7.78 (t, 1H, J=1.6 Hz), 7.58 (d, 2H, J=8.0 Hz), 7.30 (d, 2H, J=8.0 Hz), 4.58 (s, 2H), 3.74 (bs, 2H), 3.41 (bs, 2H), 2.67 (s, 3H), 2.38 (s, 3H), 1.71 (bs, 4H), 1.56 (bs, 2H).

Compound 19

5-(Azepane-1-carbonyl)-4'-methyl-N-((2-methylpyrimidin-5-yl)methyl)biphenyl-3-carboxamide

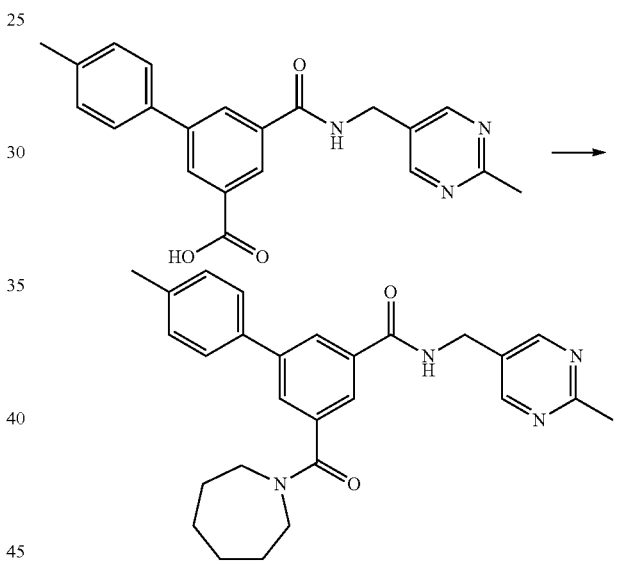

To a mixture of 4'-methyl-5-((2-methylpyrimidin-5-yl)methylcarbamoyl)biphenyl-3-carboxylic acid (11 mg, 0.030 mmol), N-(3-dimethylaminopropyl)-N'-ethylcarbodiimide hydrochloride (12 mg, 0.061 mmol), 1-hydroxybenzotriazole hydrate (4.7 mg, 0.030 mmol), and $CH_2Cl_2$ (2 mL) were added hexahydro-1H-azepine (4.5 mg, 0.046 mmol) and N,N-diisopropylethylamine (11 μL, 0.061 mmol). The mixture was stirred at room temperature overnight, and then concentrated in vacuo. The residue was purified by preparative HPLC (100×21.2 mm C18 column, 30-70% MeCN/water[10 mM $Et_2NH$]) to yield a white foam.

LC-MS: 443.5 $[M+1]^+$; $^1H$ NMR (400 MHz, $CD_3OD$): δ 8.72 (s, 2H), 8.17 (t, 1H, J=1.6 Hz), 7.80 (t, 1H, J=1.6 Hz), 7.77 (t, 1H, J=1.6 Hz), 7.58 (d, 2H, J=8.4 Hz), 7.30 (d, 2H, J=8.0 Hz), 4.58 (s, 2H), 3.70 (t, 2H, J=6.0 Hz), 3.45 (t, 2H, J=5.6 Hz), 2.67 (s, 3H), 2.38 (s, 3H), 1.90-1.80 (m, 2H), 1.73-1.58 (m, 6H).

Compound 20

4'-Methyl-N-((2-methylpyrimidin-5-yl)methyl)-5-(pyrrolidine-1-carbonyl)biphenyl-3-carboxamide

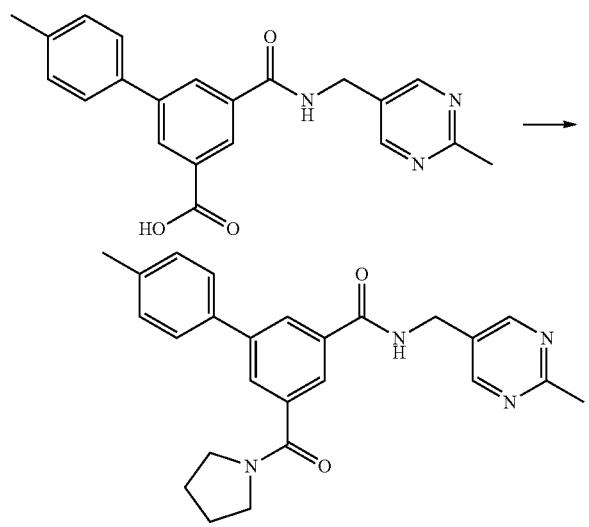

To a mixture of 4'-methyl-5-((2-methylpyrimidin-5-yl)methylcarbamoyl)-biphenyl-3-carboxylic acid (11 mg, 0.030 mmol), N-(3-dimethylaminopropyl)-N'-ethylcarbodiimide hydrochloride (12 mg, 0.061 mmol), 1-hydroxybenzotriazole hydrate (4.7 mg, 0.030 mmol), and CH$_2$Cl$_2$ (2 mL) were added pyrrolidine (3.2 mg, 0.046 mmol) and N,N-diisopropylethylamine (11 µL, 0.061 mmol). The mixture was stirred at room temperature overnight, and then concentrated in vacuo. The residue was purified by preparative HPLC (100× 21.2 mm C18 column, 30-70% MeCN/water[10 mM Et$_2$NH]) to afford a white foam.

LC-MS: 415.2 [M+1]$^+$; $^1$H NMR (400 MHz, DMSO-d6): 9.27 (t, 1H, J=5.6 Hz), 8.68 (s, 2H), 8.20 (t, 1H, J=1.6 Hz), 7.93 (t, 1H, J=1.4 Hz), 7.90 (t, 1H, J=1.5 Hz), 7.67 (d, 2H, J=8.1 Hz), 7.31 (d, 2H, J=8.0 Hz), 4.49 (d, 2H, J=5.6 Hz), 3.50 (t, 2H, J=6.7 Hz), 3.42 (t, 2H, J=6.4 Hz), 2.60 (s, 3H), 2.36 (s, 3H), 2.00-1.78 (m, 4H).

Compound 21

4'-Methyl-5-((2-methylpyrimidin-5-yl)methylcarbamoyl)biphenyl-3-carboxylic acid

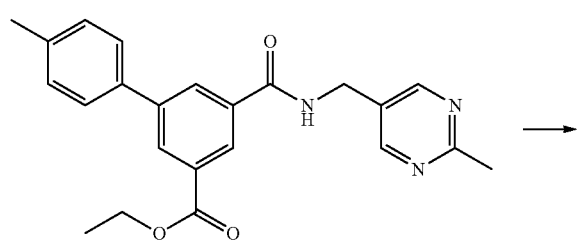

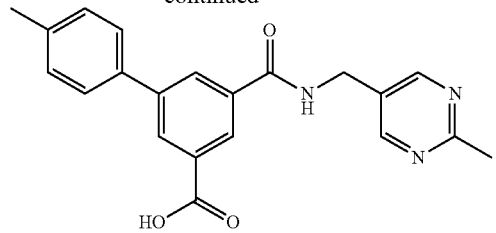

A mixture of ethyl 4'-methyl-5-((2-methylpyrimidin-5-yl)methylcarbamoyl)-biphenyl-3-carboxylate (275 mg, 0.706 mmol), lithium hydroxide (85 mg, 3.5 mmol), THF (10 mL), and water (1 mL) was stirred at room temperature for 5 h. LC-MS indicated completion of the reaction. The solvent was removed in vacuo and the residue was treated with water and acidified with 1N aq. HCl to pH=4-5. The precipitate was collected by filtration and dried to afford the title compound as a white solid. The filtrate was extracted with EtOAc (100 mL). The organic layer was washed with water and concentrated to afford some additional product.

LC-MS: 362.4 [M+1]$^+$; $^1$H NMR (400 MHz, DMSO-d6): δ 13.33 (s, 1H), 9.36 (t, 1H, J=5.6 Hz), 8.69 (s, 2H), 8.41 (t, 1H, J=1.6 Hz), 8.36 (t, 1H, J=1.6 Hz), 8.29 (t, 1H, J=1.6 Hz), 7.67 (d, 2H, J=8.0 Hz), 7.33 (d, 2H, J=8.0 Hz), 4.50 (d, 2H, J=5.6 Hz), 2.60 (s, 3H), 2.37 (s, 3H).

Compound 22

4'-Methyl-N-((2-methylpyrimidin-5-yl)methyl)-5-(methylsulfonyl)biphenyl-3-carboxamide

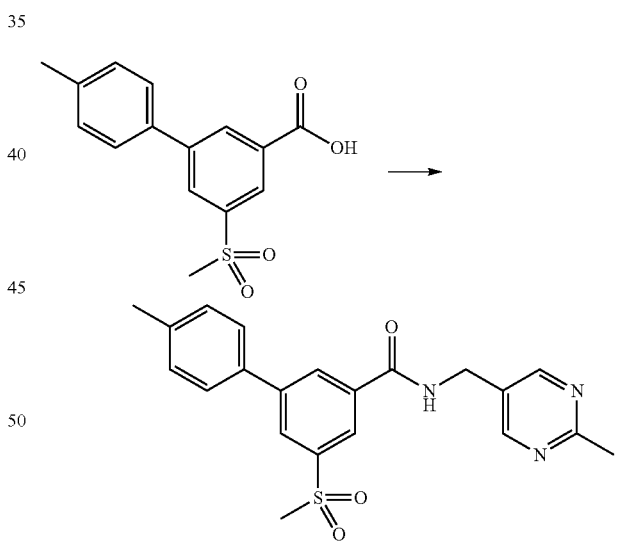

To a mixture of 4'-methyl-5-(methylsulfonyl)biphenyl-3-carboxylic acid (45 mg, 0.15 mmol), N-(3-dimethylaminopropyl)-N'-ethylcarbodiimide hydrochloride (59 mg, 0.31 mmol), 1-hydroxybenzotriazole hydrate (24 mg, 0.15 mmol), and CH$_2$Cl$_2$ (3 mL) were added (2-methylpyrimidin-5-yl)methanamine (29 mg, 0.23 mmol) and N,N-diisopropylethylamine (54 µL, 0.31 mmol). The mixture was stirred at room temperature overnight and then concentrated. The residue was purified by preparative HPLC (100×20.2 mm, C18 column; 30-60% MeCN-water[10 mM Et$_2$NH]) to afford a white solid.

LC-MS: 396.3 [M+1]+; 1H NMR (400 MHz, DMSO-d6): δ 9.45 (t, 1H, J=5.6 Hz), 8.70 (s, 2H), 8.45 (t, 1H, J=1.6 Hz), 8.33 (t, 1H, J=1.6 Hz), 8.29 (t, 1H, J=1.6 Hz), 7.75 (d, 2H, J=8.4 Hz), 7.36 (d, 2H, J=8.0 Hz), 4.52 (d, 2H, J=5.6 Hz), 2.60 (s, 3H), 2.50 (s, 3H), 2.38 (s, 3H).

Compound 28

3-(5-Methylpyridin-2-yl)-N-((2-methylpyrimidin-5-yl)methyl)-5-(pyrrolidine-1-carbonyl)benzamide

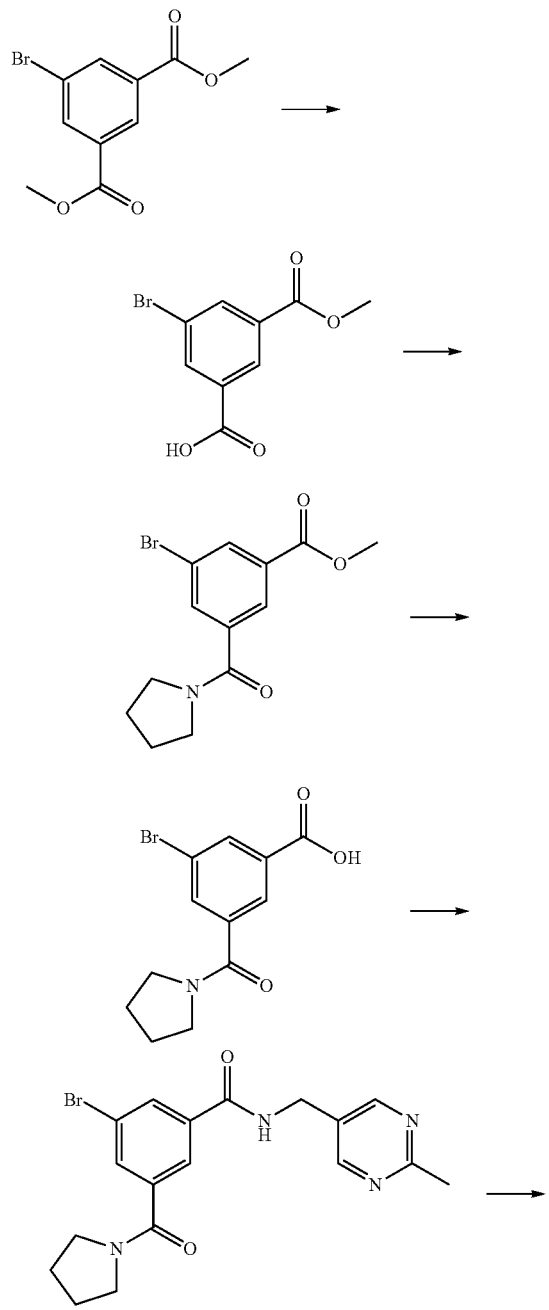

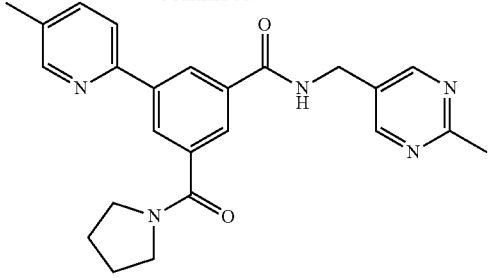

A) 3-Bromo-5-(methoxycarbonyl)benzoic acid

Into a round-bottom flask were charged with dimethyl 5-bromoisophthalate (0.50 g, 1.8 mmol), barium hydroxide octahydrate (0.43 g, 1.4 mmol) and methanol (10 mL). The mixture was stirred at room temperature overnight. HCl (2 N ethyl ether solution, 10 mL) was added and the volatiles were removed under reduced pressure. The residue was purified via flash chromatography to afford the desired product as a white solid. 1H NMR (400 MHz, DMSO-d6): 13.70 (br, 1H), 8.42 (t, J=1.5 Hz, 1H), 8.31-8.24 (m, 2H), 3.90 (s, 3H).

B) Methyl 3-bromo-5-(pyrrolidine-1-carbonyl)benzoate

To a mixture of 3-bromo-5-(methoxycarbonyl)benzoic acid (1.8 g, 5.6 mmol), N-(3-dimethylaminopropyl)-N'-ethylcarbodiimide hydrochloride (2.1 g, 11 mmol), 1-hydroxybenzotriazole hydrate (1.7 g, 11 mmol), methylene chloride (20 mL) were added pyrrolidine (0.58 g, 8.2 mmol) and N,N-diisopropylethylamine (1.9 mL, 11 mmol). The mixture was stirred at room temperature overnight, and then diluted with methylene chloride (200 mL). The organic phase was washed with aq. BaHCO3, and aq. K2HPO4, brine, dried over Na2SO4, and concentrated. The residue was purified via flash chromatography (silica gel column, 0-100 EtOAc/hexane) to afford the desired product as a clear oil. 1H NMR (400 MHz, DMSO-d6): 8.12 (t, J=1.8 Hz, 1H), 7.80-7.98 (m, 2H), 3.88 (s, 3H), 3.47 (t, J=6.7 Hz, 2H), 3.36 (t, J=6.5 Hz, 2H), 1.89-1.80 (m, 4H).

C) 3-Bromo-5-(pyrrolidine-1-carbonyl)benzoic acid

Into a round-bottom flask were charged methyl 3-bromo-5-(pyrrolidine-1-carbonyl)benzoate (0.86 g, 2.5 mmol), lithium hydroxide (0.071 g, 3.0 mmol), methanol (5 mL) and water (5 mL). The mixture was stirred at room temperature for 2 h. Methanol was removed under reduced pressure. The aqueous layer was acidified to pH=1 with 1N aq. HCl, and then extracted with CH2Cl2. The separated organic phase was dried over Na2SO4, filtered, and concentrated to dryness to afford the desired product as a white solid. 1H NMR (400 MHz, DMSO-d6): 13.54 (br, 1H), 8.09 (t, J=1.6 Hz, 1H), 7.98 (t, J=1.5 Hz, 1H), 7.94 (t, J=1.8 Hz, 1H), 3.47 (t, J=6.7 Hz, 2H), 3.37 (t, J=6.5 Hz, 2H), 1.90-1.80 (m, 4H).

D) 3-Bromo-N-((2-methylpyrimidin-5-yl)methyl)-5-(pyrrolidine-1-carbonyl)benzamide Into a round-bottom flask were charged 3-bromo-5-(pyrrolidine-1-carbonyl)benzoic acid (340 mg, 1.0 mmol), N-(3-dimethylaminopropyl)-N'-ethylcarbodiimide hydrochloride (0.39 g, 2.0 mmol), 1-hydroxybenzotriazole (0.30 g, 2.2 mmol), N,N-diisopropylethylamine (0.2 g, 1.5 mmol), methylene chloride (10 mL), 4-dimethylaminopyridine (5 mg, 0.04 mmol), and (2-methylpyrimidin-5-yl)methanamine (240 mg, 1.5 mmol). The mixture was stirred at room temperature overnight, and then diluted with $CH_2Cl_2$. The separated organic phase was washed with aq. $Na_2HPO_4$, brine, and dried over $Na_2SO_4$, and concentrated. The residue was purified via flash chromatography to afford the desired product as an oil. LC-MS: 404.8 [M+1]$^+$; $^1$H NMR (400 MHz, $CDCl_3$): 8.68 (s, 2H), 7.95 (t, J=1.6 Hz, 1H), 7.76 (t, J=1.3 Hz, 1H), 7.74-7.71 (m, 1H), 7.61 (t, J=1.5 Hz, 1H), 4.57 (d, J=5.8 Hz, 2H), 3.56 (t, J=6.8 Hz, 2H), 3.37 (t, J=6.4 Hz, 2H), 2.73 (s, 3H), 1.96-1.89 (m, 4H).

E) 3-(5-Methylpyridin-2-yl)-N-((2-methylpyrimidin-5-yl)methyl)-5-(pyrrolidine-1-carbonyl)benzamide A mixture of 3-bromo-N-((2-methylpyrimidin-5-yl)methyl)-5-(pyrrolidine-1-carbonyl)benzamide (25 mg, 0.059 mmol), 5-methyl-2-(tributylstannyl)pyridine (40 mg, 0.10 mmol), tetrakis(triphenylphosphine)palladium(0) (5 mg, 0.0043 mmol), and toluene (1 mL) under nitrogen was subjected to microwave irradiation at 120° C. for 1 hour. After cooling, the mixture was diluted with water and extracted with EtOAc. The combined organic layers were dried over $Na_2SO_4$, and concentrated. The residue was purified by flash chromatography to afford the title compound as a white solid.

LC-MS: 416.3 [M+1]$^+$; $^1$H NMR (400 MHz, DMSO-d6): 9.29 (t, J=5.4 Hz, 1H), 8.67 (s, 2H), 8.62 (t, J=1.7 Hz, 1H), 8.54 (d, J=2.2 Hz, 1H), 8.32 (t, J=1.6 Hz, 1H), 8.01-7.99 (m, 2H), 7.75 (dd, J=1.7, 8.0 Hz, 1H), 4.49 (d, J=5.6 Hz, 2H), 3.50 (t, J=6.7 Hz, 2H), 3.41 (t, J=6.3 Hz, 2H), 2.60 (s, 3H), 2.36 (s, 3H), 1.91-1.81 (m, 4H).

Compound 29

5-(3-Hydroxyazetidine-1-carbonyl)-4'-methyl-N-((2-methylpyrimidin-5-yl)methyl)biphenyl-3-carboxamide

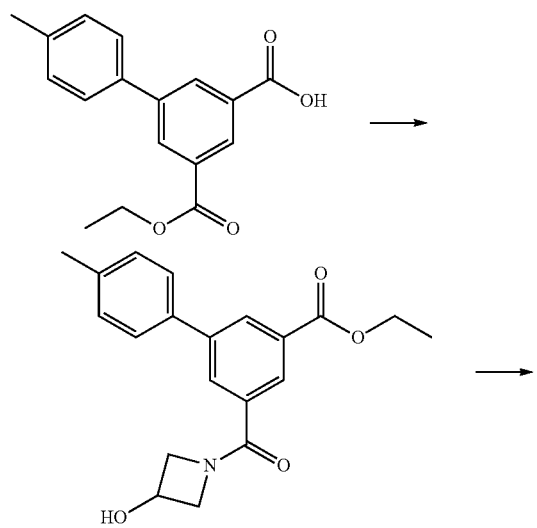

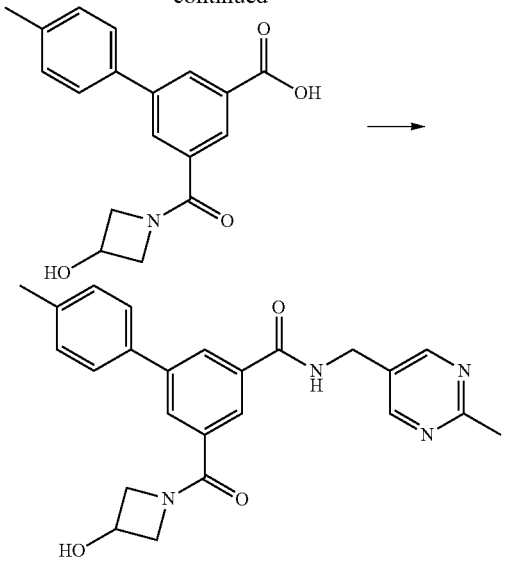

A) Ethyl 5-(3-hydroxyazetidine-1-carbonyl)-4'-methylbiphenyl-3-carboxylate

To a mixture of 5-(ethoxycarbonyl)-4'-methylbiphenyl-3-carboxylic acid (2.0 g, 7.0 mmol), N-(3-dimethylaminopropyl)-N'-ethylcarbodiimide hydrochloride (2.7 g, 14 mmol), 1-hydroxybenzotriazole hydrate (1.1 g, 7.0 mmol), and $CH_2Cl_2$ (50 mL) were added 3-hydroxyazetidine hydrochloride (1.2 g, 10 mmol) and N,N-diisopropylethylamine (3.7 mL, 21 mmol). The mixture was stirred at room temperature for 5 h, and then washed with brine and aq. $Na_2CO_3$ solution, dried ($Na_2SO_4$), and concentrated in vacuo. The residue was purified by silica gel column (0-10% MeOH/$CH_2Cl_2$) to afford a syrup. LC-MS: 340.4 [M+1]$^+$; $^1$H NMR (400 MHz, $CDCl_3$): 8.34 (t, 1H, J=1.6 Hz), 8.19 (t, 1H, J=1.6 Hz), 8.04 (t, 1H, J=1.6 Hz), 7.52 (d, 2H, J=8.4 Hz), 7.28 (d, 2H, J=8.4 Hz), 4.75 (bs, 1H), 4.50 (m, 2H), 4.41 (q, 2H, J=7.2 Hz), 4.25 (bs, 1H), 4.10 (bs, 1H), 2.82 (bs, 1H), 2.41 (s, 3H), 1.42 (t, 3H, J=7.2 Hz).

B) 5-(3-Hydroxyazetidine-1-carbonyl)-4'-methylbiphenyl-3-carboxylic acid

A mixture of ethyl 5-(3-hydroxyazetidine-1-carbonyl)-4'-methylbiphenyl-3-carboxylate (2.0 g, 5.9 mmol), lithium hydroxide (0.56 g, 24 mmol), methanol (100 mL), and water (10 mL) was stirred at rt for 4 h. LC-MS indicated completion of the reaction. The solvent was removed in vacuo and the residue was treated with water and acidified with 1N aq. HCl to pH 2-3 and extracted with EtOAc (50 mL×3). The combined organic layers were washed with brine, dried ($Na_2SO_4$), and concentrated to yield a white solid. LC-MS: 312.4 [M+1]$^+$; $^1$H NMR (400 MHz, DMSO-d6): 13.30 (bs, 1H), 8.26 (s, 1H), 8.09 (s, 1H), 8.03 (s, 1H), 7.64 (d, 2H, J=8.0 Hz), 7.32 (d, 2H, J=8.0 Hz), 5.79 (bs, 1H), 4.52 (s, 2H), 4.30 (bs, 1H), 4.10 (bs, 1H), 3.84 (d, 1H, J=9.6 Hz), 2.37 (s, 3H).

C) 5-(3-Hydroxyazetidine-1-carbonyl)-4'-methyl-N-((2-methylpyrimidin-5-yl)methyl)biphenyl-3-carboxamide To a mixture of 5-(3-hydroxyazetidine-1-carbonyl)-4'-methylbiphenyl-3-carboxylic acid (350 mg, 1.1 mmol), N-(3- dimethylaminopropyl)-N'-ethylcarbodiimide hydrochloride (430 mg, 2.2 mmol), 1-hydroxybenzotriazole hydrate (170 mg, 1.1 mmol), CH$_2$Cl$_2$ (50 mL) were added (2-methylpyrimidin-5-yl)methanamine (210 mg, 1.7 mmol) and N,N-diisopropylethylamine (0.39 mL, 2.2 mmol). The mixture was stirred at room temperature for 4 h, and then washed with water and aq. Na$_2$CO$_3$ solution, dried (Na$_2$SO$_4$), and concentrated in vacuo. The residue was purified by preparative HPLC (100×21.2 mm C18 column, 20-60% MeCN/water[10 mM Et$_2$NH]) to yield a white solid.

LC-MS: 417.5 [M+1]$^+$; $^1$H NMR (400 MHz, CD$_3$OD): 8.73 (s, 2H), 8.22 (t, 1H, J=1.6 Hz), 8.03 (t, 1H, J=1.6 Hz), 8.01 (t, 1H, J=1.6 Hz), 7.59 (d, 2H, J=8.0 Hz), 7.30 (d, 2H, J=8.0 Hz), 4.66-4.55 (m, 4H), 4.42 (m, 1H), 4.18 (m, 1H), 3.97 (m, 1H), 2.67 (s, 3H), 2.39 (s, 3H).

Compound 31

4'-Methyl-5-(2-methylaziridine-1-carbonyl)-N-((2-methylpyrimidin-5-yl)methyl)biphenyl-3-carboxamide

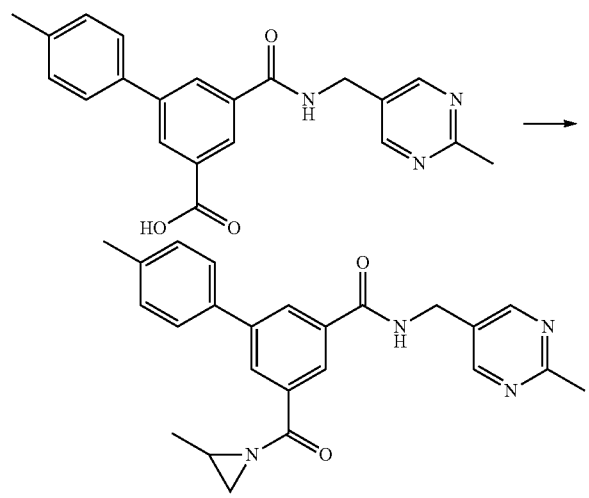

To a mixture of 4'-methyl-5-((2-methylpyrimidin-5-yl)methylcarbamoyl)-biphenyl-3-carboxylic acid (11 mg, 0.030 mmol), N-(3-dimethylaminopropyl)-N'-ethylcarbodiimide hydrochloride (12 mg, 0.061 mmol), 1-hydroxybenzotriazole hydrate (4.7 mg, 0.030 mmol), CH$_2$Cl$_2$ (2 mL) were added 2-methyl-aziridine (3.5 mg, 0.061 mmol) and N,N-diisopropylethylamine (11 µL, 0.061 mmol). The mixture was stirred at room temperature overnight, and then concentrated in vacuo. The residue was purified by preparative HPLC (100× 21.2 mm C18 column, 30-70% MeCN/water[10 mM Et$_2$NH]) to afford a white foam.

LC-MS: 401.3 [M+1]$^+$; $^1$H NMR (400 MHz, CD$_3$OD): 8.74 (s, 2H), 8.28-8.13 (m, 3H), 7.62 (m, 2H), 7.31 (d, 2H, J=8.4 Hz), 5.02 (m, 1H), 4.71 (m, 1H), 4.60 (s, 2H), 3.84 (m, 1H), 2.67 (s, 3H), 2.40 (s, 3H), 1.50 and 1.45 (d, 3H, J=6.8 Hz).

Compound 34

5-(3,3-Difluoropyrrolidine-1-carbonyl)-4'-methyl-N-((2-methylpyrimidin-5-yl)methyl)biphenyl-3-carboxamide

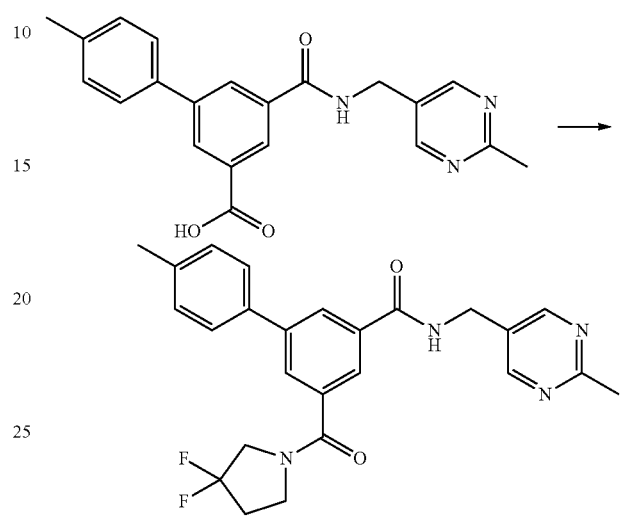

To a mixture of 4'-methyl-5-((2-methylpyrimidin-5-yl) methylcarbamoyl)-biphenyl-3-carboxylic acid (11 mg, 0.030 mmol), N-(3-dimethylaminopropyl)-N'-ethylcarbodiimide hydrochloride (12 mg, 0.061 mmol), 1-hydroxybenzotriazole hydrate (5 mg, 0.030 mmol), CH$_2$Cl$_2$ (2 mL) were added 3,3-difluoropyrrolidine hydrochloride (9 mg, 0.061 mmol) and N,N-diisopropylethylamine (21 µL, 0.12 mmol). The mixture was stirred at room temperature overnight, and then concentrated in vacuo. The residue was purified by preparative HPLC (100×21.2 mm C18 column, 30-70% MeCN/water[10 mM Et$_2$NH]) to afford a white foam.

LC-MS: 451.2 [M+1]$^+$; $^1$H NMR (400 MHz, CD$_3$OD): 8.73 (s, 2H), 8.22 (s, 1H), 7.94 (s, 2H), 7.60 (d, 2H, J=8.0 Hz), 7.30 (d, 2H, J=8.0 Hz), 4.59 (s, 2H), 4.03-3.75 (m, 4H), 2.67 (s, 3H), 2.45 (m, 2H), 2.38 (s, 3H).

Compound 37

4'-Methyl-5-(methylsulfonyl)-N-((6-(trifluoromethyl)pyridin-3-yl)methyl)biphenyl-3-carboxamide

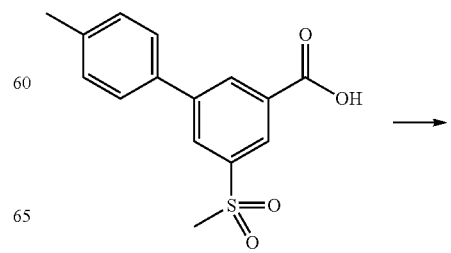

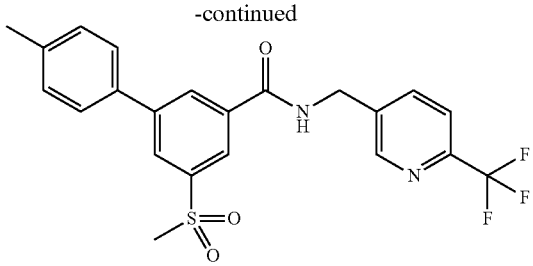

To a mixture of 4'-methyl-5-(methylsulfonyl)biphenyl-3-carboxylic acid (40 mg, 0.14 mmol), N-(3-dimethylaminopropyl)-N'-ethylcarbodiimide hydrochloride (53 mg, 0.28 mmol), 1-hydroxybenzotriazole hydrate (21 mg, 0.14 mmol), and CH$_2$Cl$_2$ (3 mL) were added C-(6-trifluoromethyl-pyridin-3-yl)-methylamine (36 mg, 0.21 mmol) and N,N-diisopropylethylamine (48 μL, 0.28 mmol). The mixture was stirred at room temperature overnight and then concentrated. The residue was purified by preparative HPLC (100×20.2 mm, C18 column; 40-80% MeCN-water[10 mM Et$_2$NH]) to afford a white solid.

LC-MS: 449.4 [M+1]$^+$; $^1$H NMR (400 MHz, CDCl$_3$): 8.77 (s, 1H), 8.35 (t, 1H, J=1.6 Hz), 8.28 (t, 1H, J=1.6 Hz), 8.21 (t, 1H, J=1.6 Hz), 7.95 (d, 1H, J=8.0 Hz), 7.70 (d, 1H, J=8.0 Hz), 7.55 (d, 2H, J=8.0 Hz), 7.31 (d, 2H, J=8.0 Hz), 6.89 (t, 1H, J=6.0 Hz), 4.78 (d, 2H, J=6.0 Hz), 3.12 (s, 3H), 2.42 (s, 3H).

Compound 39

2'-Cyano-4'-methyl-N-((2-methylpyrimidin-5-yl)methyl)-5-(pyrrolidine-1-carbonyl)biphenyl-3-carboxamide

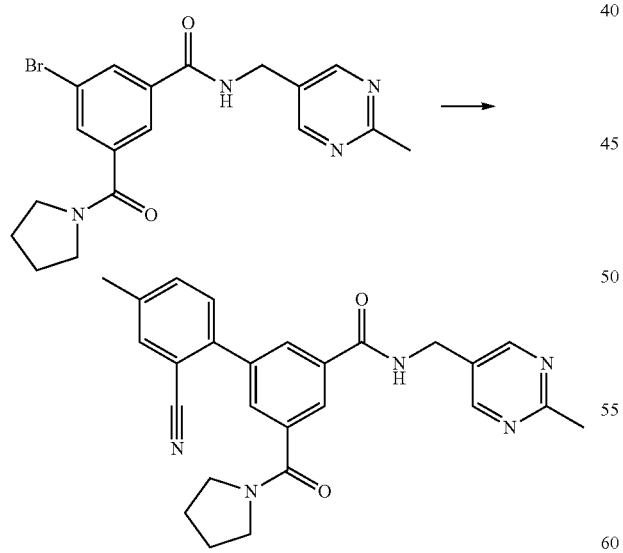

Into a Parr pressure reactor were charged 3-bromo-N-((2-methylpyrimidin-5-yl)methyl)-5-(pyrrolidine-1-carbonyl)benzamide (240 mg, 0.48 mmol), 5-methyl-2-(4,4,5,5-tetramethyl-1,3,2-dioxaborolan-2-yl)benzonitrile (160 mg, 0.58 mmol) (WO 2008/130481), toluene (5 mL), ethanol (1 mL), cesium carbonate (170 mg, 0.52 mmol), and water (0.5 mL). The mixture was degassed and purged with nitrogen several times and then tetrakis(triphenylphosphine)palladium(0) (28 mg, 0.024 mmol) was added. The tube was sealed and the mixture was heated at 90° C. overnight. After cooling, the mixture was filtered through Celite and the filtrate was concentrated. The residue was purified via flash chromatography and then preparative HPLC to afford the desired product as a white solid.

LC-MS: 440.3 [M+1]$^+$; 1H NMR (400 MHz, DMSO-d6): 9.26 (t, J=5.9 Hz, 1H), 8.67 (s, 2H), 8.10-8.07 (m, 2H), 7.83 (dd, J=1.6, 9.7 Hz, 2H), 7.62 (t, J=8.0 Hz, 2H), 4.48 (d, J=5.7 Hz, 2H), 3.51-3.43 (m, 4H), 2.59 (s, 3H), 2.41 (s, 3H), 1.90-1.82 (m, 4H).

Compound 45

N-(1-(4-Chloro-3-(methylsulfonyl)phenyl)ethyl)-4'-methyl-5-(pyrrolidine-1-carbonyl)biphenyl-3-carboxamide

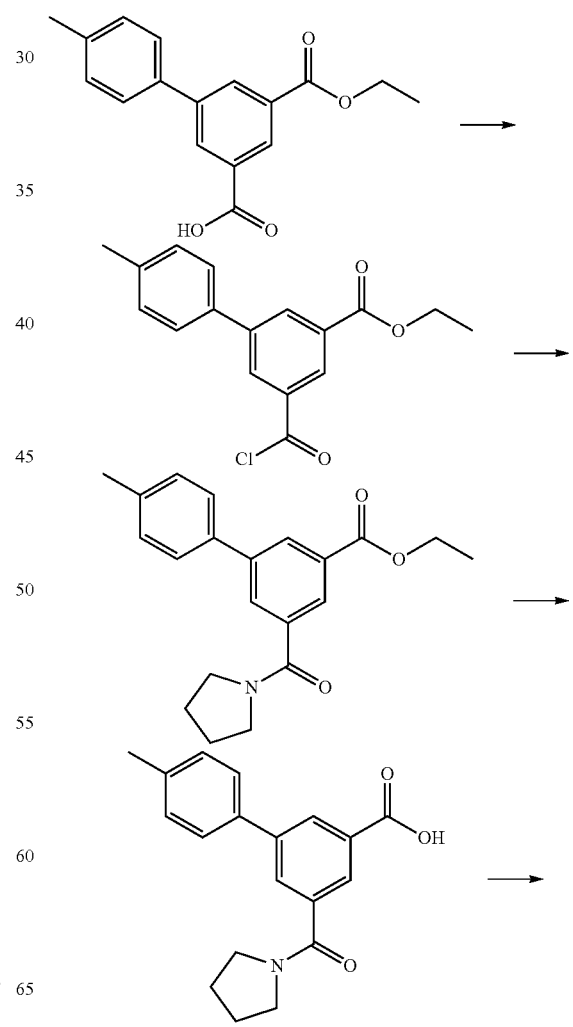

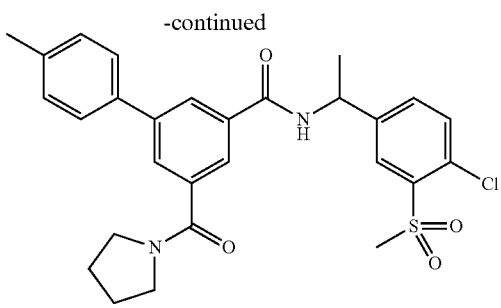

A) Ethyl 5-(chlorocarbonyl)-4'-methylbiphenyl-3-carboxylate

To a stirred solution of 5-(ethoxycarbonyl)-4'-methylbiphenyl-3-carboxylic acid (5.0 g, 18 mmol), DMF (0.05 mL), and CH$_2$Cl$_2$ (150 mL) at 0° C. was added oxalyl chloride (2.23 mL, 26.4 mmol). The mixture was stirred at room temperature for 6 h and then concentrated in vacuo to afford the crude acid chloride for the next step reaction.

B) Ethyl 4'-methyl-5-(pyrrolidine-1-carbonyl)biphenyl-3-carboxylate

To a stirred solution of ethyl 5-(chlorocarbonyl)-4'-methylbiphenyl-3-carboxylate (5.5 g, 18 mmol) in methylene chloride (100 mL) at 0° C. were slowly added pyrrolidine (2.6 g, 36 mmol) and triethylamine (7.6 mL, 54 mmol). The mixture was stirred at room temperature for 2 h, and then washed with brine, aq. Na$_2$CO$_3$ solution and water. The separated organic phase was dried (Na$_2$SO$_4$), and concentrated. The residue was purified by silica gel column (30-100% EtOAc/hexane) to afford the desired compound.

C) 4'-Methyl-5-(pyrrolidine-1-carbonyl)biphenyl-3-carboxylic acid

A mixture of ethyl 4'-methyl-5-(pyrrolidine-1-carbonyl)biphenyl-3-carboxylate (3.94 g, 11.7 mmol), lithium hydroxide (0.65 g, 27.1 mmol), MeOH (250 mL), and water (40 mL) was stirred at rt for 20 hr. LC-MS indicated completion of the reaction. The solvent was removed in vacuo and the residue was treated with water and acidified with 1N aq. HCl to pH=2-3. The aqueous phase was extracted with EtOAc (3×100 mL). The combined organic layers were washed with water, brine, dried and concentrated to yield the product as a white solid. LC-MS: 310.4 [M+1]$^+$; $^1$H NMR (400 MHz, DMSO-d6): 13.29 (s, 1H), 8.21 (t, 1H, J=1.6 Hz), 7.99 (t, 1H, J=1.6 Hz), 7.98 (t, 1H, J=1.5 Hz), 7.64 (d, 2H, J=8.2 Hz), 7.31 (d, 2H, J=7.9 Hz), 3.50 (t, 2H, J=6.7 Hz), 3.43 (t, 2H, J=6.5 Hz), 2.36 (s, 3H), 1.98-1.78 (m, 4H).

D) N-(1-(4-Chloro-3-(methylsulfonyl)phenyl)ethyl)-4'-methyl-5-(pyrrolidine-1-carbonyl)biphenyl-3-carboxamide To a solution of 4'-methyl-5-(pyrrolidine-1-carbonyl)biphenyl-3-carboxylic acid (17 mg, 0.055 mmol) in N,N-dimethylformamide (0.5 mL) were added 1-(4-chloro-3-(methylsulfonyl)phenyl)ethanamine (50 mg, 0.21 mmol), N,N,N',N'-tetramethyl-O-(7-azabenzotriazol-1-yl)uronium hexafluorophosphate (80 mg, 0.21 mmol) and N,N-diisopropylethylamine (80 µL, 0.46 mmol). The reaction mixture was stirred for 16 hours at 50° C. LC-MS indicated the reaction was complete. The mixture was purified by preparative HPLC to afford the final product as an off white solid.

LC-MS: 525.6 [M+1]$^+$; $^1$H NMR (400 MHz, DMSO-d6): 9.18 (d, 1H, J=7.3 Hz), 8.21 (s, 1H), 8.10 (d, 1H, J=1.8 Hz), 8.0-7.85 (m, 2H), 7.80-7.65 (m, 4H), 7.32 (d, 2H, J=7.9 Hz), 5.30-5.20 (m, 1H), 3.50 (t, 2H, J=6.5 Hz), 3.46-3.35 (m, 5H), 2.36 (s, 3H), 2.00-1.78 (m, 4H), 1.53 (d, 3H, J=7 Hz).

Compound 49

4'-Methyl-5-(pyrrolidine-1-carbonyl)-N-(quinolin-7-ylmethyl)biphenyl-3-carboxamide

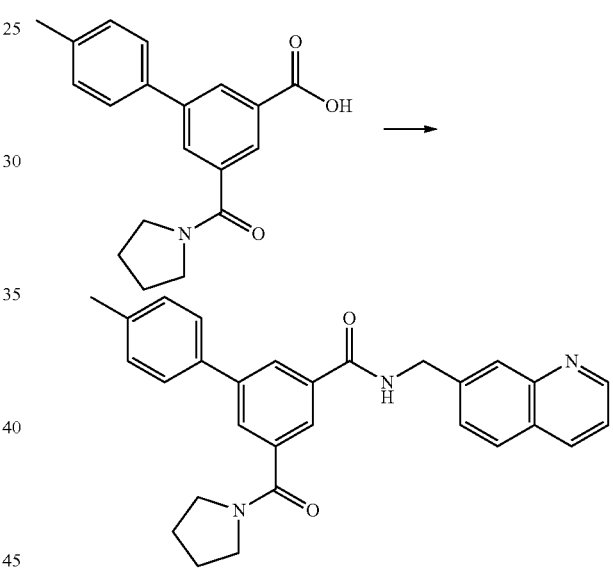

To a solution of 4'-methyl-5-(pyrrolidine-1-carbonyl)biphenyl-3-carboxylic acid (17 mg, 0.055 mmol) in N,N-dimethylformamide (0.5 mL) were added quinolin-7-ylmethanamine (34 mg, 0.22 mmol) (WO 2008/130481), N,N,N',N'-tetramethyl-O-(7-azabenzotriazol-1-yl)uronium hexafluorophosphate (80 mg, 0.21 mmol) and N,N-diisopropylethylamine (80 µL, 0.46 mmol). The reaction mixture was stirred at 50° C. for 16 hours. LC-MS indicated the reaction was complete. The reaction mixture was purified by preparative HPLC to afford the titile compound.

LC-MS: 450.5 [M+1]$^+$; $^1$H NMR (400 MHz, CDCl$_3$): 8.92 (dd, 1H, J=4.1, 1.4 Hz), 8.19 (d, 1H, J=8.1 Hz), 8.12 (t, 1H, J=1.7 Hz), 8.09 (s, 1H), 7.92-7.80 (m, 3H), 7.60 (dd, 1H, J=9.9, 1.4 Hz), 7.52 (d, 2H, J=8.1 Hz), 7.43 (dd, 1H, J=8.3, 4.3 Hz), 7.26 (d, 2H, J=7.8 Hz), 6.76 (t, 1H, J=5.7 Hz), 4.91 (d, 2H, J=5.8 Hz), 3.66 (t, 2H, J=6.9 Hz), 3.47 (t, 2H, J=6.6 Hz), 2.40 (s, 3H), 2.10-1.80 (m, 4H).

Compound 58

4'-Methyl-N-((6-methylpyridin-3-yl)methyl)-5-(methylsulfonyl)biphenyl-3-carboxamide

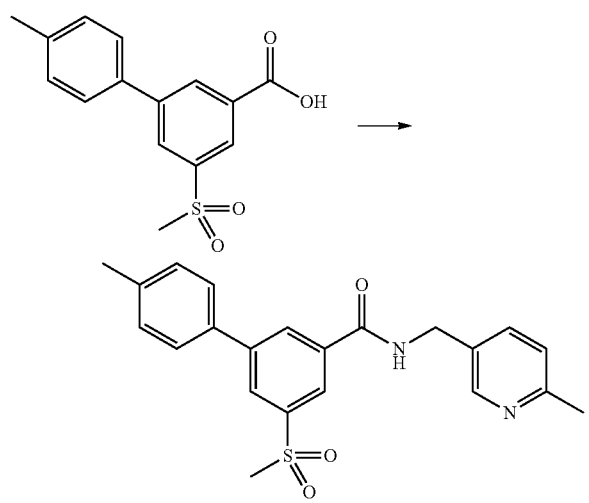

To a mixture of 4'-methyl-5-(methylsulfonyl)biphenyl-3-carboxylic acid (40 mg, 0.14 mmol), N-(3-dimethylaminopropyl)-N'-ethylcarbodiimide hydrochloride (53 mg, 0.28 mmol), 1-hydroxybenzotriazole hydrate (21 mg, 0.14 mmol), and CH$_2$Cl$_2$ (3 mL) were added (6-methylpyridin-3-yl)methanamine (25 mg, 0.21 mmol), and N,N-diisopropylethylamine (48 μL, 0.28 mmol). The mixture was stirred at room temperature overnight and then concentrated. The residue was purified by preparative HPLC (100×20.2 mm, C18 column; 30-80% CH$_3$CN-water[10 mM Et$_2$NH]) to afford a white solid.

LC-MS: 395.5 [M+1]$^+$; $^1$H NMR (400 MHz, CDCl$_3$): 8.52 (s, 1H), 8.34 (s, 1H), 8.26 (s, 1H), 8.18 (s, 1H), 7.65 (dd, 1H, J=8.0, 2.0 Hz), 7.54 (d, 2H, J=8.0 Hz), 7.30 (d, 2H, J=8.0 Hz), 7.17 (d, 1H, J=8.0 Hz), 6.73 (bs, 1H), 4.66 (d, 2H, J=5.6 Hz), 3.11 (s, 3H), 2.56 (s, 3H), 2.42 (s, 3H).

Compound 62

2'-Cyano-4'-methyl-5-(pyrrolidine-1-carbonyl)-N-((6-(trifluoromethyl)pyridin-3-yl)methyl)biphenyl-3-carboxamide

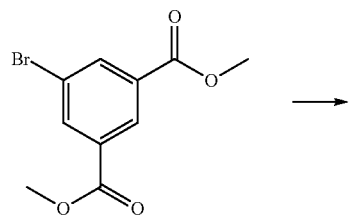

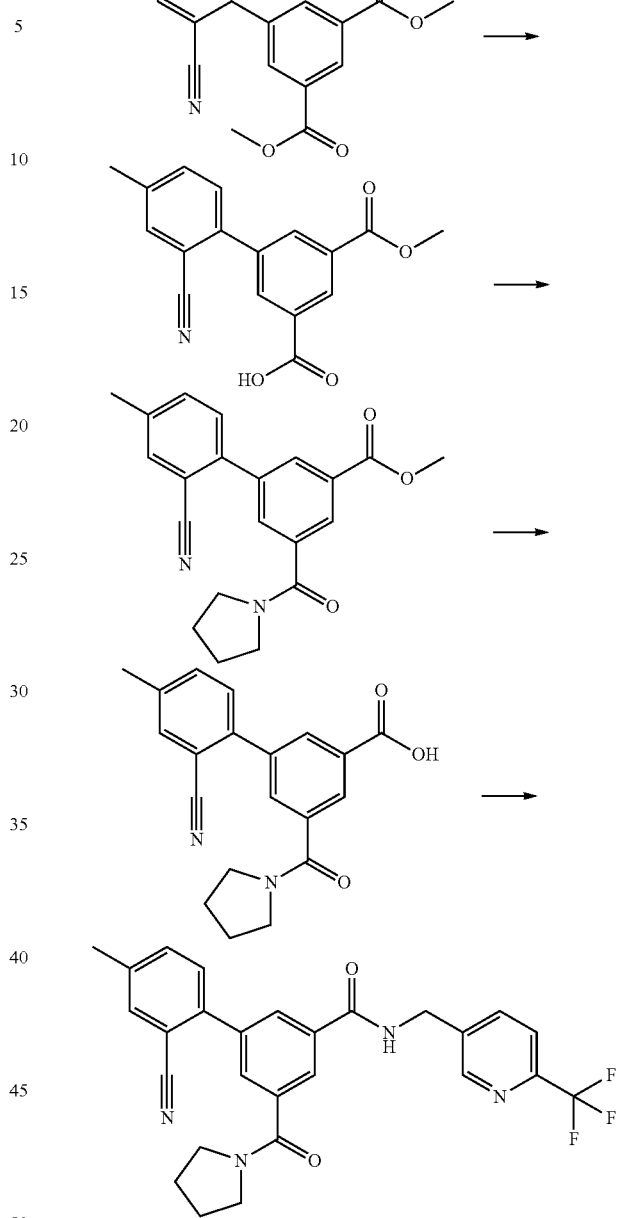

A) Dimethyl 2'-cyano-4'-methylbiphenyl-3,5-dicarboxylate

A Parr pressure reactor was charged with dimethyl 5-bromoisophthalate (1.3 g, 4.8 mmol), 5-methyl-2-(4,4,5,5-tetramethyl-1,3,2-dioxaborolan-2-yl)benzonitrile (2.0 g, 5.9 mmol), toluene (25 mL), ethanol (5 mL), cesium carbonate (1.7 g, 5.2 mmol), and water (2.5 mL). The mixture was degassed and purged with nitrogen several times before tetrakis(triphenylphosphine)-palladium(0) (280 mg, 0.24 mmol) was added. The tube was sealed and the mixture was heated at 90° C. overnight. After cooling, the mixture was diluted with EtOAc (200 mL), washed with brine, dried over Na$_2$SO$_4$, and concentrated. The residue was purified via flash chromatography to afford the desired product as a white solid.

LC-MS: 310.5 [M+1]+; 1H NMR (400 MHz, CDCl3): 8.75 (s, 1H), 8.39 (d, J=1.6 Hz, 2H), 7.61 (s, 1H), 7.49 (dd, J=1.1, 8.5 Hz, 1H), 7.43 (d, J=7.9 Hz, 1H), 3.98 (s, 6H), 2.46 (s, 3H).

B) 2'-Cyano-5-(methoxycarbonyl)-4'-methylbiphenyl-3-carboxylic acid

A round-bottom flask was charged with dimethyl 2'-cyano-4'-methylbiphenyl-3,5-dicarboxylate (1.5 g, 4.4 mmol), ethanol (100 mL), 1,4-dioxane (20 mL), and a solution of sodium hydroxide (0.17 g, 4.4 mmol) in water (10 mL). The mixture was stirred at room temperature for 3 h. The volatiles were removed under reduced pressure, and the residue was acidified with 1N aq. HCl to pH=4 and extracted with CH2Cl2. The combined organic layers were dried and concentrated. The residue was purified via flash chromatography to afford the desired product 2'-cyano-5-(methoxycarbonyl)-4'-methylbiphenyl-3-carboxylic acid as a white solid. 1H NMR (400 MHz, DMSO-d6): 13.58 (br, 1H), 8.56 (t, J=1.3 Hz, 1H), 8.34-8.31 (m, 2H), 7.85 (s, 1H), 7.65 (d, J=2.6 Hz, 2H), 3.92 (s, 3H), 2.42 (s, 3H). 3-Ethyl 5-methyl 2'-cyano-4'-methylbiphenyl-3,5-dicarboxylate was also isolated as a white solid.

C) Methyl 2'-cyano-4'-methyl-5-(pyrrolidine-1-carbonyl)biphenyl-3-carboxylate To a mixture of 2'-cyano-5-(methoxycarbonyl)-4'-methylbiphenyl-3-carboxylic acid (0.20 g, 0.68 mmol), N-(3-dimethylaminopropyl)-N'-ethylcarbodiimide hydrochloride (0.26 g, 1.4 mmol), 1-hydroxybenzotriazole hydrate (0.21 g, 1.4 mmol), and methylene chloride (10 mL) were added pyrrolidine (0.072 g, 1.0 mmol) and N,N-diisopropylethylamine (0.24 mL, 1.4 mmol). The mixture was stirred at room temperature overnight, and then concentrated. The residue was purified via flash chromatography (silica gel column, 0-100% EtOAc/hexane) to afford the desired product as a white solid.

LC-MS: 349.0 [M+1]+; 1H NMR (400 MHz, DMSO-d6) 8.14 (s, 1H), 8.12 (t, J=1.6 Hz, 1H), 7.96 (t, J=1.7 Hz, 1H), 7.83 (s, 1H), 7.66-7.60 (m, 2H), 3.91 (s, 3H), 3.52-3.43 (m, 4H), 2.42 (s, 3H), 1.90-1.81 (m, 4H).

B) 2'-Cyano-4'-methyl-5-(pyrrolidine-1-carbonyl)biphenyl-3-carboxylic acid

A round-bottom flask was charged with methyl 2'-cyano-4'-methyl-5-(pyrrolidine-1-carbonyl)biphenyl-3-carboxylate (0.17 g, 0.46 mmol), lithium hydroxide (17 mg, 0.70 mmol), methanol (5 mL), and water (1 mL). The mixture was stirred at room temperature overnight. The evolatiles were removed under reduced pressure and the residue was acidified with 1 N HCl, extracted with CH2Cl2. The combined organic layers were dried over Na2SO4, filtered, concentrated to afford the desired product as a white solid. LC-MS: 335.4 [M+1]+; 1H NMR (400 MHz, DMSO-d6): 8.14 (t, J=1.6 Hz, 1H), 8.10 (t, J=1.5 Hz, 1H), 7.93 (t, J=1.7 Hz, 1H), 7.83 (t, J=0.8 Hz, 1H), 7.66-7.60 (m, 2H), 3.51-3.42 (m, 4H), 2.42 (s, 3H), 1.91-1.83 (m, 4H).

C) 2'-Cyano-4'-methyl-5-(pyrrolidine-1-carbonyl)-N-((6-(trifluoromethyl)pyridin-3-yl)methyl)biphenyl-3-carboxamide A round-bottom flask was charged with 2'-cyano-4'-methyl-5-(pyrrolidine-1-carbonyl)biphenyl-3-carboxylic acid (50 mg, 0.1 mmol), N-(3-dimethylaminopropyl)-N'-ethylcarbodiimide hydrochloride (52 mg, 0.27 mmol), 1-hydroxybenzotriazole (36 mg, 0.27 mmol), N,N-diisopropylethylamine (35 mg, 0.27 mmol), methylene chloride (4 mL), 4-dimethylaminopyridine (1 mg), and C-(6-trifluoromethylpyridin-3-yl)-methylamine (47 mg, 0.27 mmol). The mixture was stirred at room temperature overnight, and then diluted with CH2Cl2, washed with aq. Na2HPO4, brine, and dried over Na2SO4, and concentrated. The residue was purified via preparative HPLC to afford the desired product as a white solid.

LC-MS: 493.2 [M+1]+; 1H NMR (400 MHz, CDCl3): 8.67 (s, 1H), 8.07 (dd, J=1.6 Hz, 6.0 Hz, 2H), 7.87 (dd, J=1.1, 8.4 Hz, 1H), 7.72-7.71 (m, 1H), 7.59-7.57 (m, 2H), 7.47 (dd, J=0.44, 8.1 Hz, 1H), 7.41 (d, J=8 Hz, 1H), 4.67 (s, 2H), 3.54-3.49 (m, 4H), 2.44 (s, 3H), 1.95-1.88 (m, 4H).

Compound 63

2'-Cyano-5-(3-hydroxyazetidine-1-carbonyl)-4'-methyl-N-((6-methylpyridin-3-yl)methyl)biphenyl-3-carboxamide

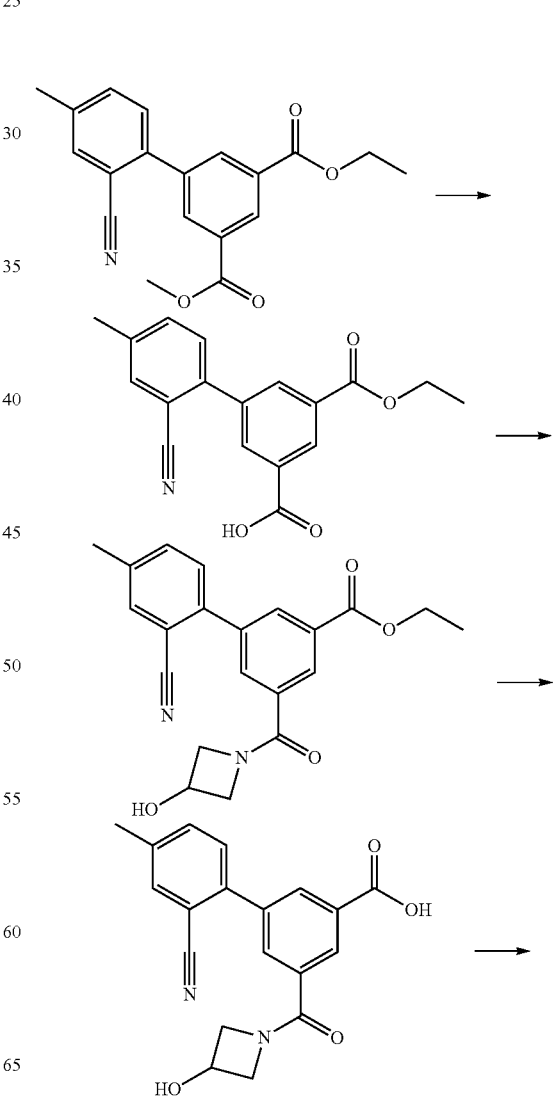

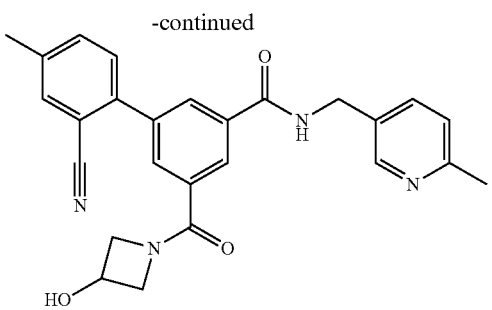

A) 2'-Cyano-5-(ethoxycarbonyl)-4'-methylbiphenyl-3-carboxylic acid

A round-bottom flask was charged with 3-ethyl 5-methyl 2'-cyano-4'-methylbiphenyl-3,5-dicarboxylate (0.12 g, 0.33 mmol), 1,4-dioxane (10 mL), and a solution of lithium hydroxide (9 mg, 0.4 mmol) in water (2 mL). The mixture was stirred at room temperature for 2 h. The volatiles were removed under reduced pressure and the residue was acidified with 1 N HCl, and extracted with $CH_2Cl_2$. The separated organic phase was dried and concentrated. The residue was purified via flash chromatography to afford the desired product as a white solid.

B) Ethyl 2'-cyano-5-(3-hydroxyazetidine-1-carbonyl)-4'-methylbiphenyl-3-carboxylate To a mixture of 2'-cyano-5-(ethoxycarbonyl)-4'-methylbiphenyl-3-carboxylic acid (90 mg, 0.29 mmol), N-(3-dimethylaminopropyl)-N'-ethylcarbodiimide hydrochloride (120 mg, 0.61 mmol), 1-hydroxybenzotriazole hydrate (93 mg, 0.61 mmol), and methylene chloride (5 mL) were added 3-hydroxyazetidine hydrochloride (67 mg, 0.61 mmol) and N,N-diisopropylethylamine (0.21 mL, 1.2 mmol). The mixture was stirred at room temperature overnight, and then concentrated under reduced pressure. The residue was purified via flash chromatography to afford the desired product as a white solid.

LC-MS: 365.4 [M+1]$^+$; $^1$H NMR (400 MHz, DMSO-d6): 8.24 (d, J=1.6 Hz, 1H), 8.18 (t, J=1.7 Hz, 1H), 8.00 (t, J=1.7 Hz, 1H), 7.84 (s, 1H), 7.64-7.61 (m, 2H), 5.79 (d, J=6.0 Hz, 1H), 4.54-4.52 (m, 2H), 4.37 (q, J=7.2 Hz, 2H), 4.35-4.34 (m, 1H), 4.29-4.27 (m, 1H), 3.84-3.82 (m, 1H), 2.42 (s, 3H), 1.35 (t, J=7.2 Hz, 3H).

C) 2'-Cyano-5-(3-hydroxyazetidine-1-carbonyl)-4'-methylbiphenyl-3-carboxylic acid A round-bottom flask was charged with ethyl 2'-cyano-5-(3-hydroxyazetidine-1-carbonyl)-4'-methylbiphenyl-3-carboxylate (25 mg, 0.066 mmol), sodium hydroxide (10 mg, 0.25 mmol), acetonitrile (2 mL) and water (2 mL). The mixture was stirred at room temperature overnight. 1N aq. HCl (3 mL) was added and the volatiles were removed under reduced pressure. The residue was extracted with $CH_2Cl_2$, and the $CH_2Cl_2$ layer was concentrated to dryness to afford the desired product as a white solid.

LC-MS: 337.5 [M+1]$^+$.

D) 2'-Cyano-5-(3-hydroxyazetidine-1-carbonyl)-4'-methyl-N-((6-methylpyridin-3-yl)methyl)biphenyl-3-carboxamide A round-bottom flask was charged with 2'-cyano-4'-methyl-5-((6-methylpyridin-3-yl)methylcarbamoyl)biphenyl-3-carboxylic acid (80 mg, 0.24 mmol), N-(3-dimethylaminopropyl)-N'-ethylcarbodiimide hydrochloride (80 mg, 0.42 mmol), 1-hydroxybenzotriazole hydrate (64 mg, 0.42 mmol), N,N-diisopropylethylamine (110 mg, 0.83 mmol), methylene chloride (5 mL) and 3-hydroxyazetidine hydrochloride (45 mg, 0.42 mmol). The mixture was stirred at room temperature overnight and then concentrated. The residue was purified via flash chromatography to afford the desired product as a white solid.

LC-MS: 441.5 [M+1]$^+$; $^1$H NMR (400 MHz, CDCl$_3$): 8.54 (s, 1H), 8.10 (d, J=8.3 Hz, 2H), 7.81 (s, 1H), 7.72 (d, J=7.9 Hz, 1H), 7.58 (s, 1H), 7.49-7.42 (m, 3H), 7.18 (d, J=7.9 Hz, 1H), 4.68-4.57 (m, 4H), 4.44-4.41 (m, 1H), 4.29-4.28 (m, 1H), 4.05-4.02 (m, 1H), 2.57 (s, 3H), 2.45 (s, 3H).

Compound 65

(R)-2,4'-Dimethyl-N-(1-(2-methylpyrimidin-5-yl)ethyl)-5-(pyrrolidin-1-ylsulfonyl)biphenyl-3-carboxamide

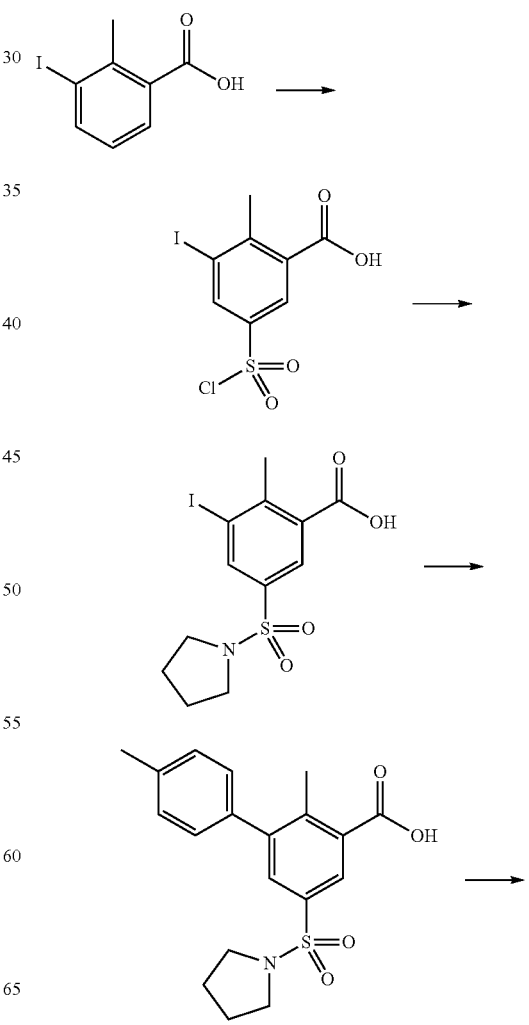

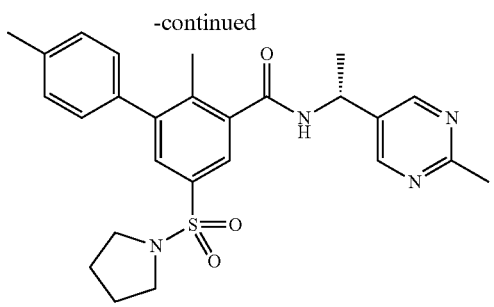

A) 5-(Chlorosulfonyl)-3-iodo-2-methylbenzoic acid

A round bottom flask was charged with chlorosulfonic acid (3.80 mL, 57.2 mmol), and 3-iodo-2-methylbenzoic acid (5.00 g, 19.1 mmol) was added in portions at 0° C. The reaction was heated at 95° C. for two hours and then stirred at room temperature overnight. The reaction mixture was poured onto ice and the solids formed were collected and dried to afford the desired product as a white solid.

B) 3-Iodo-2-methyl-5-(pyrrolidin-1-ylsulfonyl)benzoic acid

A round bottom flask was charged with 5-(chlorosulfonyl)-3-iodo-2-methylbenzoic acid (1.00 g, 2.77 mmol), pyrrolidine (0.278 mL, 3.33 mmol), 1,4-dioxane (4 mL) and pyridine (0.20 mL, 2.5 mmol). The mixture was stirred for 30 minutes. The solvent was removed and the residue was purified by flash chromatography to yield the compound as a yellow solid.

C) 2,4'-Dimethyl-5-(pyrrolidin-1-ylsulfonyl)biphenyl-3-carboxylic acid

To a mixture of 3-iodo-2-methyl-5-(pyrrolidin-1-ylsulfonyl)benzoic acid (1.00 g, 2.53 mmol), p-tolylboronic acid (0.378 g, 2.78 mmol), toluene (10 mL), ethanol (3 mL), cesium carbonate (0.907 g, 2.78 mmol), and water (1 mL) under argon was added tetrakis(triphenylphosphine)palladium(0) (146 mg, 0.126 mmol). The mixture was heated to reflux for 6 h, and then cooled to room temperature and filtered through Celite. The filtrate was concentrated and the residue was purified by silica gel column (0-50% EtOAc/hexane) to yield a yellow solid.

D) (R)-2,4'-Dimethyl-N-(1-(2-methylpyrimidin-5-yl)ethyl)-5-(pyrrolidin-1-ylsulfonyl)biphenyl-3-carboxamide A reaction vial was charged with 2,4'-dimethyl-5-(pyrrolidin-1-ylsulfonyl)biphenyl-3-carboxylic acid (40 mg, 0.11 mmol), (R)-1-(2-methylpyrimidin-5-yl)ethanamine (20 mg, 0.14 mmol), N,N,N',N'-tetramethyl-O-(7-azabenzotriazol-1-yl)uronium hexafluorophosphate (106 mg, 0.28 mmol), N,N-diisopropylethylamine (39 µL, 0.22 mmol) and N,N-dimethylformamide (1.33 mL), and the reaction mixture was stirred at room temperature overnight. The reaction mixture was purified by preparative HPLC to afford the compound as a light brown solid.

LC-MS: 479.4 [M+1]$^+$; $^1$H NMR (400 MHz, DMSO-d6): 9.13 (t, J=7.34 Hz, 1H), 8.73 (s, 2H), 7.61 (d, J=1.87 Hz, 1H), 7.54 (d, J=1.87 Hz, 1H), 7.31 (d, J=7.68 Hz, 2H), 7.25 (d, J=7.68 Hz, 2H), 5.15 (t, J=7.45 Hz, 1H), 3.16 (t, J=6.72 Hz, 4H), 2.60 (s, 3H), 2.37 (s, 3H), 2.18 (s, 3H), 1.70 (t, J=6.72 Hz, 4H), 1.50 (d, J=6.72 Hz, 3H).

Compound 67

2,4'-Dimethyl-N-((2-methylpyrimidin-5-yl)methyl)-5-(pyrrolidin-1-ylsulfonyl)biphenyl-3-carboxamide

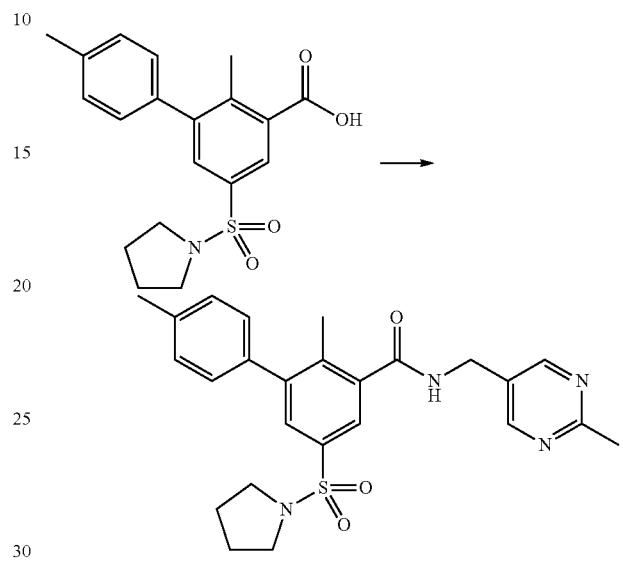

A reaction vial was charged with 2,4'-dimethyl-5-(pyrrolidin-1-ylsulfonyl)biphenyl-3-carboxylic acid (40 mg, 0.11 mmol), (2-methylpyrimidin-5-yl)methanamine (18 mg, 0.15 mmol), N,N,N',N'-tetramethyl-O-(7-azabenzotriazol-1-yl)uronium hexafluorophosphate (106 mg, 0.28 mmol), N,N-diisopropylethylamine (39 µL, 0.22 mmol) and N,N-dimethylformamide (1.33 mL), and the reaction mixture was stirred at room temperature overnight. The reaction mixture was purified by preparative HPLC to afford the compound as a white solid.

LC-MS: 465.3 [M+1]$^+$; $^1$H NMR (400 MHz, DMSO-d6): 9.14 (t, J=6.16 Hz, 1H), 8.69 (s, 2H), 7.65 (d, J=1.93 Hz, 1H), 7.54 (d, J=1.93 Hz, 1H), 7.30 (d, J=7.73 Hz, 2H), 7.26 (d, J=7.73 Hz, 2H), 4.46 (d, J=5.64 Hz, 2H), 3.16 (t, J=6.78 Hz, 4H), 2.60 (s, 3H), 2.37 (s, 3H), 2.22 (s, 3H), 1.70 (t, J=6.67 Hz, 4H).

Compound 73

N-(4-Chloro-3-(N-cyclopropylsulfamoyl)benzyl)-4'-methyl-5-(pyrrolidine-1-carbonyl)biphenyl-3-carboxamide

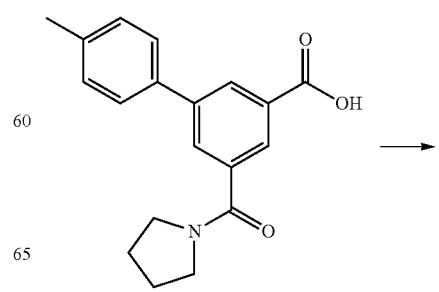

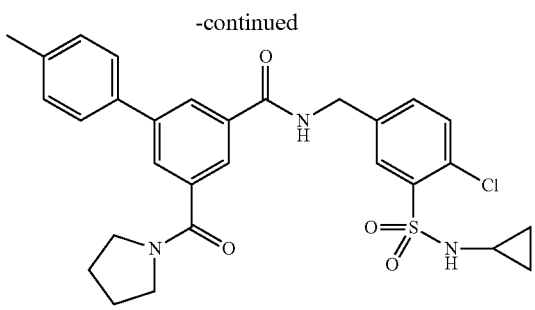

To a solution of 4'-methyl-5-(pyrrolidine-1-carbonyl)biphenyl-3-carboxylic acid (60 mg, 0.19 mmol) in N,N-dimethylformamide (1.0 mL) were added 5-(aminomethyl)-2-chloro-N-cyclopropylbenzenesulfonamide (80 mg, 0.31 mmol), N,N,N',N'-tetramethyl-O-(7-azabenzotriazol-1-yl)uronium hexafluorophosphate (150 mg, 0.39 mmol) and N,N-diisopropylethylamine (150 µL, 0.86 mmol). The reaction mixture was stirred for 16 hours at 50° C. The reaction mixture was purified by preparative HPLC to afford a light colour solid.

LC-MS: 552.6 [M+1]$^+$; $^1$NMR (400 MHz, DMSO-d6): 9.39 (t, 1H, J=5.9 Hz), 8.23 (t, 2H, J=1.4 Hz), 8.00 (d, 1H, J=1.6 Hz), 7.95 (t, 1H, J=1.3 Hz), 7.92 (t, 1H, J=1.5 Hz), 7.70-7.55 (m, 4H), 7.32 (d, 2H, J=8.0 Hz), 4.58 (d, 2H, J=5.8 Hz), 3.50 (t, 2H, J=6.5 Hz), 3.43 (t, 2H, J=6.4 Hz), 2.36 (s, 3H), 2.28-2.12 (m, 1H), 2.00-1.78 (m, 4H), 0.50-0.32 (m, 4H).

Compound 83

N-(3-Hydroxy-1-(6-(trifluoromethyl)pyridin-3-yl)propyl)-4'-methyl-5-(pyrrolidine-1-carbonyl)biphenyl-3-carboxamide

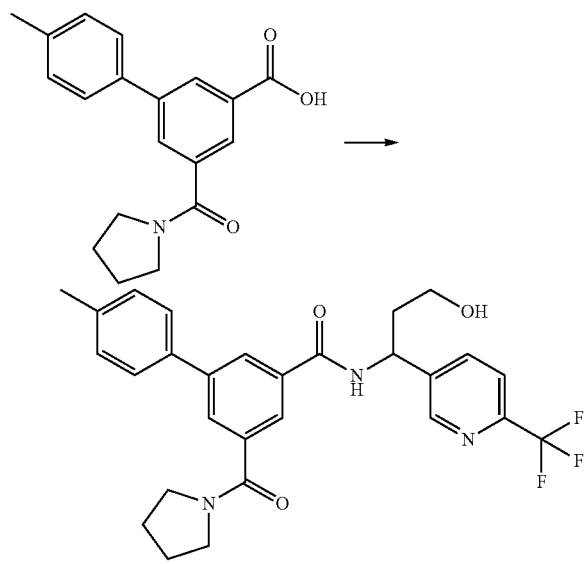

To a solution of 4'-methyl-5-(pyrrolidine-1-carbonyl)biphenyl-3-carboxylic acid (17 mg, 0.055 mmol) in N,N-dimethylformamide (0.5 mL) were added 3-amino-3-(6-(trifluoromethyl)pyridin-3-yl)propan-1-ol (47 mg, 0.21 mmol) (WO 2008/130481), N,N,N',N'-tetramethyl-O-(7-azabenzotriazol-1-yl)uronium hexafluorophosphate (80 mg, 0.21 mmol) and N,N-diisopropylethylamine (80 µL, 0.46 mmol). The reaction mixture was stirred for 16 hours at 30° C. The reaction mixture was purified by preparative HPLC to afford a white solid.

LC-MS: 512.4 [M+1]$^+$; $^1$H NMR (400 MHz, DMSO-d6): 9.15 (d, 1H, J=7.6 Hz), 8.81 (s, 1H), 8.19 (s, 1H), 8.09 (dd, 1H, J=8.0, 1.3 Hz), 8.0-7.85 (m, 3H), 7.66 (d, 2H, J=8.1 Hz), 7.32 (d, 2H, J=8.0 Hz), 5.4-5.25 (m, 1H), 4.71 (t, 1H, J=4.5 Hz), 3.60-3.35 (m, 6H), 2.36 (s, 3H), 2.25-2.10 (m, 1H), 2.05-1.95 (m, 1H), 1.94-1.78 (m, 4H).

Compound 86

4'-Methyl-N-((6-methylpyridin-3-yl)methyl)-5-(3-morpholinopyrrolidine-1-carbonyl)biphenyl-3-carboxamide

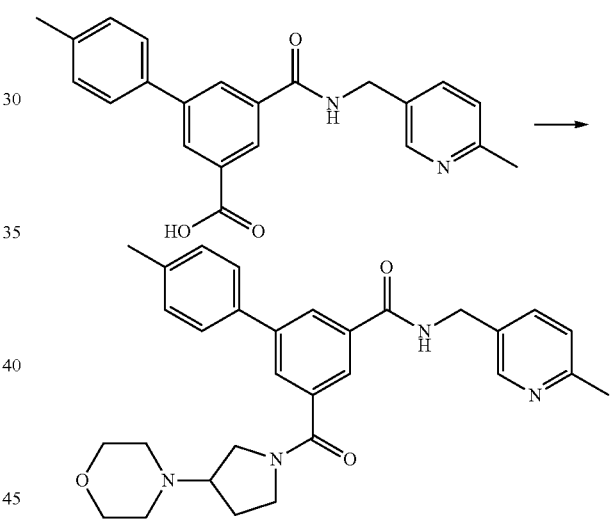

To a mixture of 4'-methyl-5-(((6-methylpyridin-3-yl)methylcarbamoyl)-biphenyl-3-carboxylic acid (55 mg, 0.15 mmol), N-(3-dimethylaminopropyl)-N'-ethylcarbodiimide hydrochloride (58 mg, 0.30 mmol), 1-hydroxybenzotriazole hydrate (23 mg, 0.15 mmol), and CH$_2$Cl$_2$ (3 mL) were added 4-(pyrrolidin-3-yl)morpholine (48 mg, 0.30 mmol) and N,N-diisopropylethylamine (53 µL, 0.30 mmol). The mixture was stirred at room temperature overnight, and then concentrated in vacuo. The residue was purified by preparative HPLC (100×21.2 mm C18 column, 30-60% MeCN/water[10 mM Et$_2$NH]) to afford a white foam.

LC-MS: 499.7 [M+1]$^+$; $^1$H NMR (400 MHz, CD$_3$OD): 8.43 (d, 1H, J=2.0 Hz), 8.19 (s, 1H), 7.92 (d, 2H, J=1.6 Hz), 7.76 (dd, 1H, J=8.0, 2.0 Hz), 7.59 (d, 2H, J=8.0 Hz), 7.31-7.27 (m, 3H), 4.59 (s, 2H), 3.95-3.20 (m, 8H), 2.90 (m, 1H), 2.65-2.10 (m, 11H), 1.85 (m, 1H).

Compound 87

4'-Methyl-5-((6-methylpyridin-3-yl)methylcarbamoyl)biphenyl-3-carboxylic acid

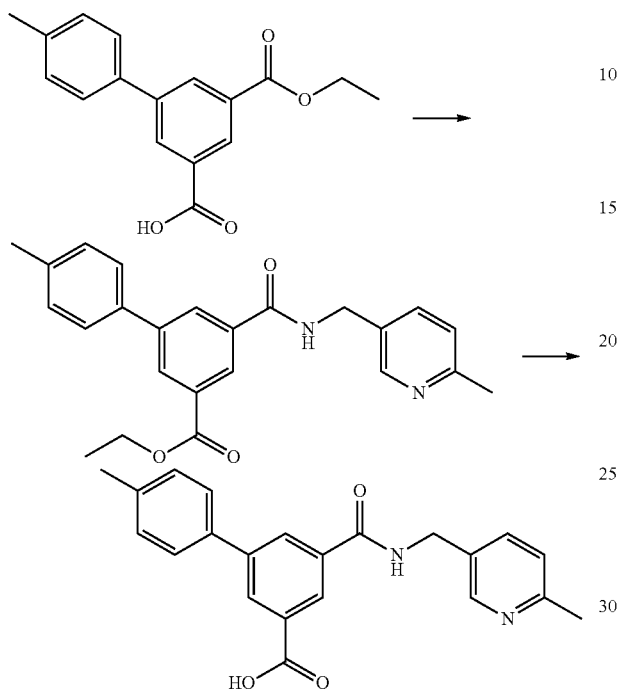

A) Ethyl 4'-methyl-5-((6-methylpyridin-3-yl)methylcarbamoyl)biphenyl-3-carboxylate To a mixture of 5-(ethoxycarbonyl)-4'-methylbiphenyl-3-carboxylic acid (1.5 g, 5.3 mmol), N-(3-dimethylaminopropyl)-N'-ethylcarbodiimide hydrochloride (2.0 g, 10 mmol), 1-hydroxybenzotriazole hydrate (0.32 g, 2.1 mmol), and $CH_2Cl_2$ (50 mL) were added (6-methylpyridin-3-yl)methanamine (0.97 g, 7.9 mmol) and N,N-diisopropylethylamine (1.8 mL, 10 mmol). The mixture was stirred at room temperature for 4 h, and then washed with water and aq. $Na_2CO_3$ solution, dried ($Na_2SO_4$), and concentrated in vacuo. The residue was purified by silica gel column to afford a white foam.

LC-MS: 389.4 [M+1]$^+$; $^1$H NMR (400 MHz, $CDCl_3$): 8.53 (d, 1H, J=2.0 Hz), 8.39 (t, 1H, J=1.6 Hz), 8.29 (t, 1H, J=1.6 Hz), 8.26 (t, 1H, J=1.6 Hz), 7.66 (dd, 1H, J=8.0, 2.0 Hz), 7.55 (d, 2H, J=8.4 Hz), 7.28 (d, 2H, J=8.0 Hz), 7.17 (d, 1H, J=8.0 Hz), 6.64 (m, 1H), 4.67 (d, 2H, J=5.6 Hz), 4.42 (q, 2H, J=7.2 Hz), 2.57 (s, 3H), 2.41 (s, 3H), 1.42 (t, 3H, J=7.2 Hz).

B) 4'-Methyl-5-((6-methylpyridin-3-yl)methylcarbamoyl)biphenyl-3-carboxylic acid A mixture of ethyl 4'-methyl-5-((6-methylpyridin-3-yl)methylcarbamoyl)biphenyl-3-carboxylate (1.02 g, 2.62 mmol), lithium hydroxide (310 mg, 13 mmol), EtOH (100 mL), and water (10 mL) was stirred at rt overnight. LC-MS indicated completion of the reaction. The solvent was removed in vacuo and the residue was treated with water (50 mL) and acidified with 1N aq. HCl to pH=4. The precipitated solids were collected by filtration, washed with water, and dried to yield a white solid.

LC-MS: 361.3 [M+1]$^+$; $^1$H NMR (400 MHz, DMSO-d6): 13.5 (bs, 1H), 9.34 (t, 1H, J=5.6 Hz), 8.44 (d, 1H, J=2.0 Hz), 8.41 (t, 1H, J=1.6 Hz), 8.34 (t, 1H, J=1.6 Hz), 8.29 (t, 1H, J=1.6 Hz), 7.67 (d, 2H, J=8.4 Hz), 7.64 (dd, 1H, J=8.0, 2.0 Hz), 7.33 (d, 2H, J=8.0 Hz), 7.22 (d, 1H, J=8.0 Hz), 4.49 (d, 2H, J=5.6 Hz), 2.44 (s, 3H), 2.37 (s, 3H).

Compound 94

(R)-5-(3-Hydroxypyrrolidine-1-carbonyl)-4'-methyl-N-((6-methylpyridin-3-yl)methyl)biphenyl-3-carboxamide

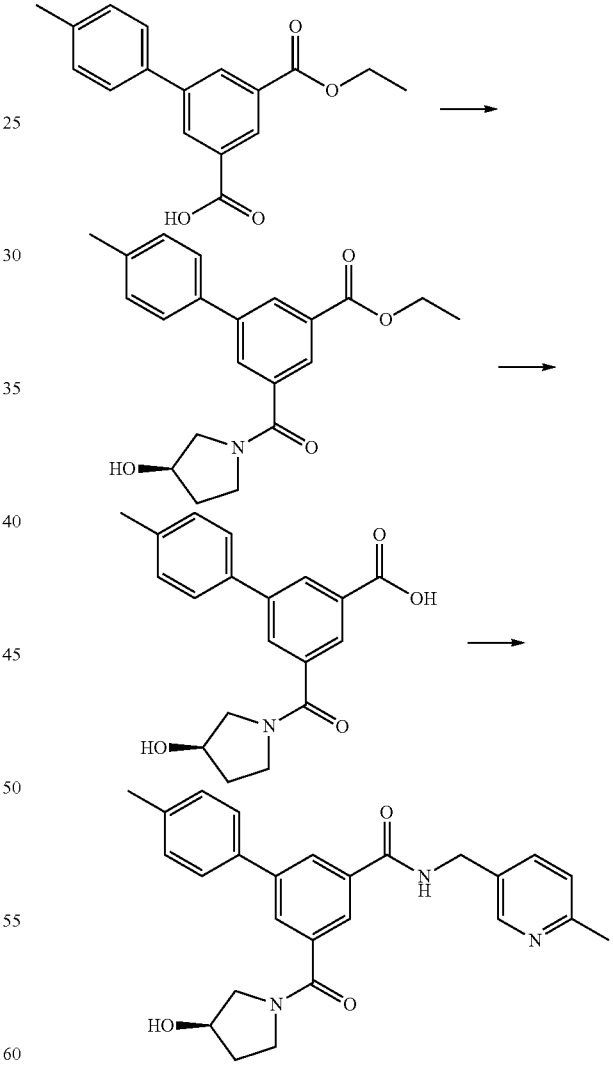

A) (R)-Ethyl 5-(3-hydroxypyrrolidine-1-carbonyl)-4'-methylbiphenyl-3-carboxylate To a mixture of 5-(ethoxycarbonyl)-4'-methylbiphenyl-3-carboxylic acid (1.50 g, 5.28 mmol), N-(3-dimethylaminopropyl)-N'-ethylcarbodiimide hydrochloride (2.0 g, 10 mmol), 1-hydroxybenzotriazole hydrate (0.404 g, 2.64 mmol), and CH$_2$Cl$_2$ (30 mL) were added (R)-3-hydroxypyrrolidine (0.92 g, 10 mmol) and N,N-diisopropylethylamine (1.8 mL, 10 mmol). The mixture was stirred at room temperature overnight, and then diluted with CH$_2$Cl$_2$ (100 mL), washed with aq. NaHCO$_3$, brine, dried (Na$_2$SO$_4$), and concentrated in vacuo. The residue was purified by silica gel column (100% EtOAc) to afford a white foam. LC-MS: 354.2 [M+1]$^+$; $^1$H NMR (400 MHz, CDCl$_3$): 8.32 (s, 1H), 8.16 and 8.12 (bs, 1H), 7.92 (m, 1H), 7.53 (d, 2H, J=7.6 Hz), 7.28 (d, 2H, J=8.4 Hz), 4.63 and 4.49 (bs, 1H), 4.41 (q, 2H, J=7.2 Hz), 3.95-3.40 (m, 4H), 2.41 (s, 3H), 2.20-1.90 (m, 2H), 1.41 (t, 3H, J=7.2 Hz).

B) (R)-5-(3-Hydroxypyrrolidine-1-carbonyl)-4'-methylbiphenyl-3-carboxylic acid

A mixture of (R)-ethyl 5-(3-hydroxypyrrolidine-1-carbonyl)-4'-methylbiphenyl-3-carboxylate (1.25 g, 3.54 mmol), lithium hydroxide (0.42 g, 18 mmol), methanol (50 mL), and water (5 mL) was stirred at rt for 4 h. LC-MS indicated completion of the reaction. The volatiles were removed in vacuo and the residue was treated with water and acidified with 1N aq. HCl to pH 2-3 and extracted with EtOAc (50 mL×3). The combined organic layers were washed with brine, dried (Na$_2$SO$_4$), and concentrated to afford a white foam. LC-MS: 326.3 [M+1]$^+$; $^1$H NMR (400 MHz, CD$_3$OD): 8.33 (m, 1H), 8.11 and 8.10 (t, 1H, J=1.6 Hz), 7.98 and 7.97 (t, 1H, J=1.6 Hz), 7.57 (d, 2H, J=7.6 Hz), 7.30 (d, 2H, J=8.0 Hz), 4.51 and 4.38 (m, 1H), 3.85-3.35 (m, 4H), 2.39 (s, 3H), 2.20-1.90 (m, 2H).

C) (R)-5-(3-Hydroxypyrrolidine-1-carbonyl)-4'-methyl-N-((6-methylpyridin-3-yl)methyl)biphenyl-3-carboxamide To a mixture of 4'-methyl-5-((6-methylpyridin-3-yl)methylcarbamoyl)-biphenyl-3-carboxylic acid (55 mg, 0.15 mmol), N-(3-dimethylaminopropyl)-N'-ethylcarbodiimide hydrochloride (58 mg, 0.30 mmol), 1-hydroxybenzotriazole hydrate (23 mg, 0.15 mmol), and CH$_2$Cl$_2$ (3 mL) were added (R)-3-hydroxypyrrolidine (26 mg, 0.30 mmol) and N,N-diisopropylethylamine (53 µL, 0.30 mmol). The mixture was stirred at room temperature overnight, and then concentrated in vacuo. The residue was purified by preparative HPLC (100×21.2 mm C18 column, 30-60% MeCN/water[10 mM Et$_2$NH]) and then silica gel column (0-20% MeOH/CH$_2$Cl$_2$) to afford a white foam.

LC-MS: 430.3 [M+1]$^+$; $^1$H NMR (400 MHz, CD$_3$OD): 8.44 (d, 1H, J=2.0 Hz), 8.19 (m, 1H), 7.95-7.90 (m, 2H), 7.77 (dd, 1H, J=8.0, 2.4 Hz), 7.59 (d, 2H, J=8.0 Hz), 7.29 (d, 3H, J=8.0 Hz), 4.59 (s, 2H), 4.50 and 4.37 (m, 1H), 3.85-3.30 (m, 4H), 2.51 (s, 3H), 2.38 (s, 3H), 2.20-1.90 (m, 2H).

Compound 95

(S)-5-(3-Hydroxypyrrolidine-1-carbonyl)-4'-methyl-N-((6-methylpyridin-3-yl)methyl)biphenyl-3-carboxamide

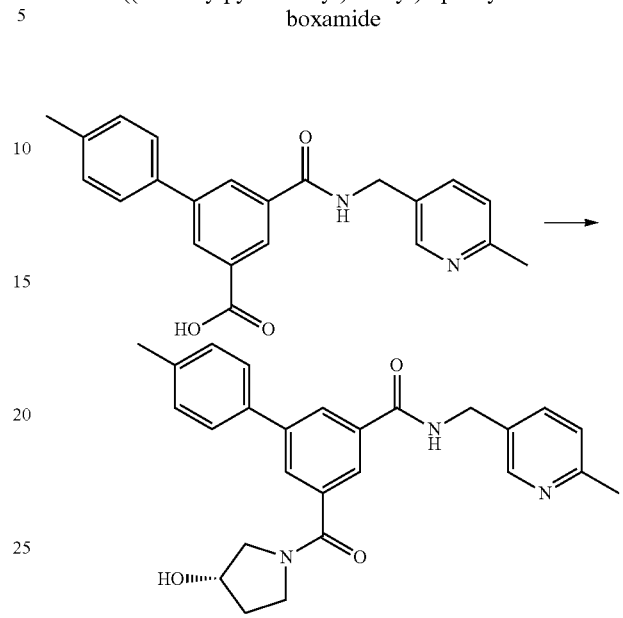

To a mixture of 4'-methyl-5-((6-methylpyridin-3-yl)methylcarbamoyl)-biphenyl-3-carboxylic acid (55 mg, 0.15 mmol), N-(3-dimethylaminopropyl)-N'-ethylcarbodiimide hydrochloride (58 mg, 0.30 mmol), 1-hydroxybenzotriazole hydrate (23 mg, 0.15 mmol), and CH$_2$Cl$_2$ (3 mL) were added (S)-3-hydroxypyrrolidine (26 mg, 0.30 mmol) and N,N-diisopropylethylamine (53 µL, 0.30 mmol). The mixture was stirred at room temperature overnight, and then concentrated in vacuo. The residue was purified by preparative HPLC (100×21.2 mm C18 column, 30-60% MeCN/water[10 mM Et$_2$NH]) and then by silica gel column (0-20% MeOH/CH$_2$Cl$_2$) to afford a white foam.

LC-MS: 430.3 [M+1]$^+$; $^1$H NMR (400 MHz, CD$_3$OD): 8.44 (d, 1H, J=2.0 Hz), 8.19 (m, 1H), 7.95-7.90 (m, 2H), 7.77 (dd, 1H, J=8.0, 2.4 Hz), 7.59 (d, 2H, J=8.0 Hz), 7.29 (d, 3H, J=8.0 Hz), 4.59 (s, 2H), 4.50 and 4.37 (m, 1H), 3.81-3.30 (m, 4H), 2.51 (s, 3H), 2.38 (s, 3H), 2.20-1.90 (m, 2H).

Compound 108

(R)—N-(1-(5-Chloro-1-methyl-1H-pyrazol-4-yl)ethyl)-4'-methyl-5-(pyrrolidine-1-carbonyl)biphenyl-3-carboxamide

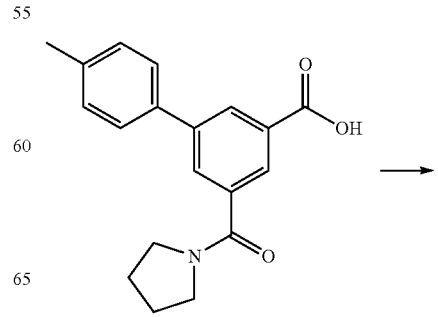

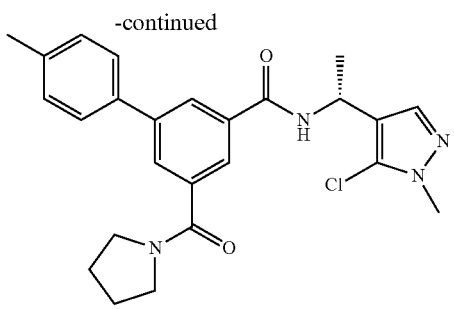

A 20 mL vial was charged with 4'-methyl-5-(pyrrolidine-1-carbonyl)biphenyl-3-carboxylic acid (30 mg, 0.097 mmol), (R)-1-(5-chloro-1-methyl-1H-pyrazol-4-yl)ethanamine hydrochloride (24 mg, 0.12 mmol), N,N,N',N'-tetramethyl-O-(7-azabenzotriazol-1-yl)uronium hexafluorophosphate (92 mg, 0.24 mmol), N,N-diisopropylethylamine (0.068 mL, 0.39 mmol), and N,N-dimethylformamide (1.0 mL) and the reaction mixture was stirred at room temperature overnight. The reaction mixture was purified by preparative HPLC to get the product as a light yellow solid.

LC-MS: 451.3 [M+1]$^+$; $^1$H NMR (DMSO-d6): 8.87 (d, J=7.77 Hz, 1H), 8.16 (t, J=1.83 Hz, 1H), 7.92 (t, J=1.61 Hz, 1H), 7.87 (t, J=1.61 Hz, 1H), 7.66 (d, J=8.22 Hz, 2H), 7.59 (s, 1H), 7.31 (d, J=8.22 Hz, 2H), 5.16-5.12 (m, 1H), 3.76 (s, 3H), 3.49 (t, J=6.70 Hz, 2H), 3.40 (t, J=6.70 Hz, 2H), 2.36 (s, 3H), 1.90-1.80 (m, 4H), 1.47 (d, J=7.45 Hz, 3H).

Compound 111

4'-Methyl-N-(1-(2-methylthiazol-4-yl)ethyl)-5-(pyrrolidine-1-carbonyl)biphenyl-3-carboxamide

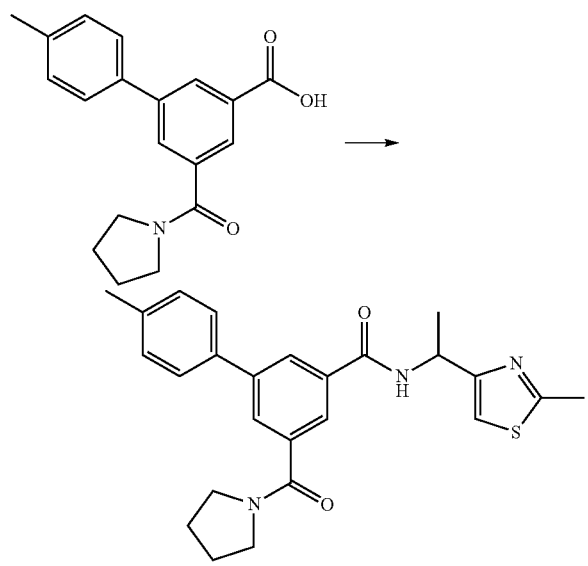

A 20 mL vial was charged with 4'-methyl-5-(pyrrolidine-1-carbonyl)biphenyl-3-carboxylic acid (30 mg, 0.097 mmol), 1-(2-Methylthiazol-4-yl)-ethylamine hydrochloride (22 mg, 0.12 mmol), N,N,N',N'-tetramethyl-O-(7-azabenzotriazol-1-yl)uronium hexafluorophosphate (92 mg, 0.24 mmol), N,N-diisopropylethylamine (0.068 mL, 0.39 mmol), and N,N-dimethylformamide (1.0 mL) and the reaction mixture was stirred at room temperature overnight. The reaction mixture was purified by preparative HPLC to get the product as a light peach colored solid.

LC-MS: 434.4 [M+1]$^+$; $^1$H NMR (DMSO-d6): 9.01 (d, J=8.50 Hz, 1H), 8.24 (t, J=1.59 Hz, 1H), 7.97 (t, J=1.99 Hz, 1H), 7.88 (t, J=1.99 Hz, 1H), 7.68 (d, J=8.35 Hz, 2H), 7.31 (d, J=7.95 Hz, 2H), 7.25 (d, J=0.99 Hz, 1H), 5.31-5.27 (m, 1H), 3.50 (t, J=6.53 Hz, 2H), 3.42 (t, J=6.53 Hz, 2H), 2.63 (s, 3H), 2.36 (s, 3H), 1.91-1.81 (m, 4H), 1.53 (d, J=7.26 Hz, 3H).

Compound 113

3-(5-Methylpyridin-2-yl)-N-((6-methylpyridin-3-yl)methyl)-5-(methylsulfonyl)benzamide

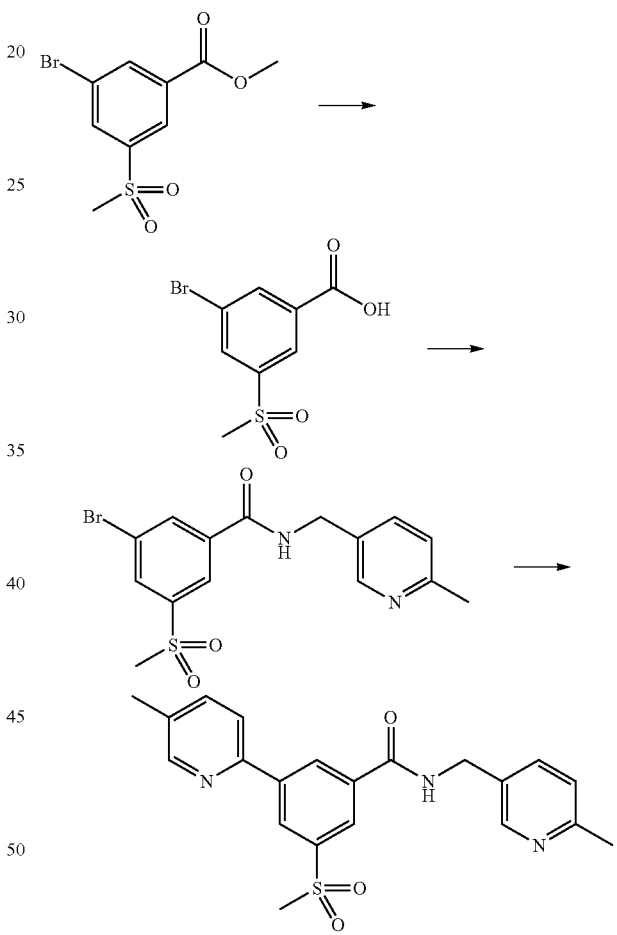

A) 3-Bromo-5-(methylsulfonyl)benzoic acid

A mixture of methyl 3-bromo-5-(methylsulfonyl)benzoate (0.65 g, 2.2 mmol), lithium hydroxide (0.26 g, 11 mmol), tetrahydrofuran (25 mL) and water (5 mL) was stirred at room temperature for 3 h. Water (50 mL) was added and the mixture was acidified with 1N aq. HCl to pH 2-3 and extracted with EtOAc (100 mL). The organic layer was separated, washed with brine, dried (Na$_2$SO$_4$), and concentrated to yield a white solid. LC-MS: 278.6 [M−1]$^−$; $^1$H NMR (400 MHz, CDCl$_3$): 8.59 (m, 1H), 8.50 (m, 1H), 8.33 (m, 1H), 3.13 (s, 3H).

B) 3-Bromo-N-((6-methylpyridin-3-yl)methyl)-5-(methylsulfonyl)benzamide

To a mixture of 3-bromo-5-(methylsulfonyl)benzoic acid (630 mg, 2.2 mmol), N-(3-dimethylaminopropyl)-N'-ethylcarbodiimide hydrochloride (860 mg, 4.5 mmol), 1-hydroxybenzotriazole hydrate (140 mg, 0.90 mmol), and $CH_2Cl_2$ (25 mL) were added (6-methylpyridin-3-yl)methanamine (550 mg, 4.5 mmol) and N,N-diisopropylethylamine (0.79 mL, 4.5 mmol). The mixture was stirred at room temperature overnight, and then diluted with $CH_2Cl_2$ (50 mL). The organic phase was washed with water and aq. $Na_2CO_3$ solution, dried ($Na_2SO_4$), and concentrated in vacuo. The residue was purified by silica gel column (50-100% EtOAc/hexane) to afford a white solid. LC-MS: 385.2 [M+1]$^+$; $^1$H NMR (400 MHz, CDCl$_3$): 8.51 (d, 1H, J=1.6 Hz), 8.28 (t, 1H, J=1.6 Hz), 8.23 (t, 1H, J=1.6 Hz), 8.19 (t, 1H, J=1.6 Hz), 7.66 (dd, 1H, J=8.0, 2.0 Hz), 7.19 (d, 1H, J=8.0 Hz), 6.93 (bs, 1H), 4.63 (d, 2H, J=5.6 Hz), 3.09 (s, 3H), 2.57 (s, 3H).

C) 3-(5-Methylpyridin-2-yl)-N-((6-methylpyridin-3-yl)methyl)-5-(methylsulfonyl)benzamide A mixture of 3-bromo-N-((6-methylpyridin-3-yl)methyl)-5-(methylsulfonyl)benzamide (71 mg, 0.18 mmol), 5-methyl-2-(tributylstannyl)pyridine (91 mg, 0.23 mmol), tetrakis(triphenylphosphine)palladium(0) (11 mg, 0.0093 mmol) and toluene (2.0 mL) under argon was subjected to microwave irradiation at 120° C. for 2 hours. The mixture was cooled to allow the product to precipitate. The solvent was discarded and the precipitated solids were rinsed with hexane and then purified by preparative HPLC (100×21.2 mm C18 column, 30-70% $CH_3CN$/water[10 mM $Et_2NH$]) to afford a white foam.

LC-MS: 396.4 [M+1]$^+$; $^1$H NMR (400 MHz, CDCl$_3$): 8.72 (t, 1H, J=1.6 Hz), 8.69 (t, 1H, J=1.6 Hz), 8.53 (m, 2H), 8.34 (t, 1H, J=1.6 Hz), 7.76 (d, 1H, J=8.0 Hz), 7.68-7.62 (m, 2H), 7.17 (d, 1H, J=8.0 Hz), 6.86 (bs, 1H), 4.67 (d, 2H, J=6.4 Hz), 3.13 (s, 3H), 2.57 (s, 3H), 2.41 (s, 3H).

Compound 116

(R)-4'-Methyl-N-(1-(2-methylpyrimidin-5-yl)ethyl)-5-(methylsulfonyl)biphenyl-3-carboxamide To a solution of 4'-methyl-5-(methylsulfonyl)biphenyl-3-carboxylic acid (1.0 g, 3.44 mmol) in N,N-dimethylformamide (10 mL) were added (R)-1-(2-methylpyrimidin-5-yl)ethanamine (900 mg, 5.58 mmol), N,N,N',N'-tetramethyl-O-(7-azabenzotriazol-1-yl)uronium hexafluorophosphate (3.0 g, 7.89 mmol) and N,N-diisopropylethylamine (3.0 mL, 17.22 mmol). The reaction mixture was stirred for 16 hours at 25° C. LC-MS indicated the reaction was complete. The reaction solution was diluted with EtOAc and washed with water, sat. aq. NaHCO$_3$, brine and dried over anhydrous MgSO$_4$. The residue was purified by silica gel column and preparative HPLC to afford the final product as a light color solid.

LC-MS: 410.1 [M+1]$^+$; $^1$H NMR (400 MHz, DMSO-d6): 9.26 (d, 1H, J=7.4 Hz), 8.75 (s, 2H), 8.44 (t, 1H, J=1.6 Hz), 8.33 (t, 1H, J=1.6 Hz), 8.28 (t, 1H, J=1.6 Hz), 7.75 (d, 2H, J=8.2 Hz), 7.37 (d, 2H, J=7.9 Hz), 5.22 (m, 1H), 3.34 (s, 3H), 2.60 (s, 3H), 2.38 (s, 3H), 1.58 (d, 3H, J=7.1 Hz).

Compound 122

3-(5-Methylpyridin-2-yl)-N-((6-methylpyridin-3-yl)methyl)-5-(pyrrolidine-1-carbonyl)benzamide

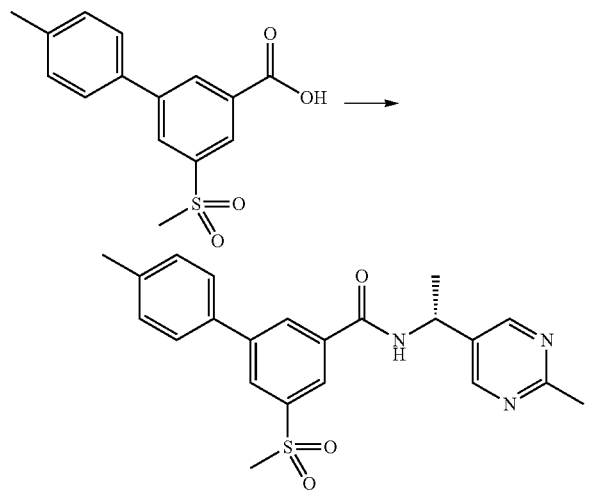

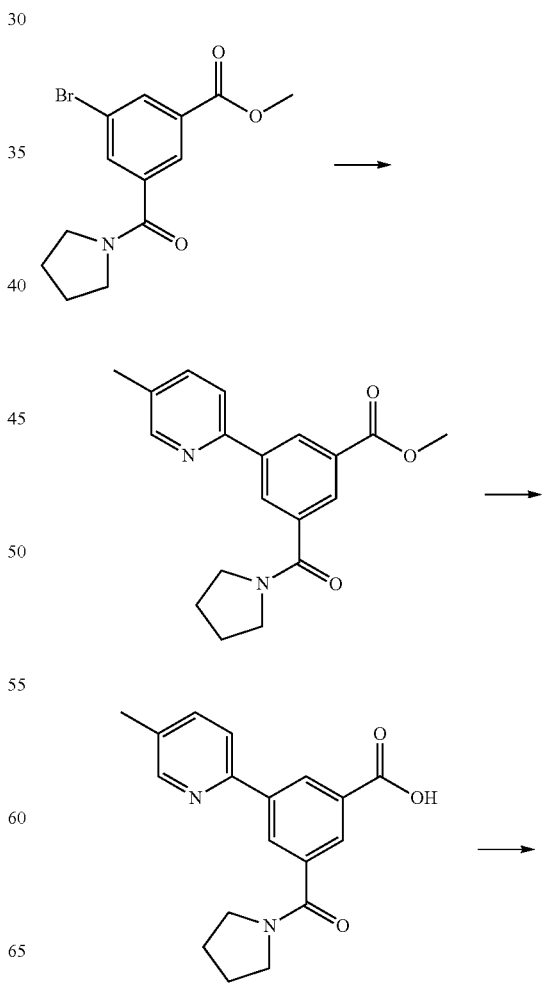

133

-continued

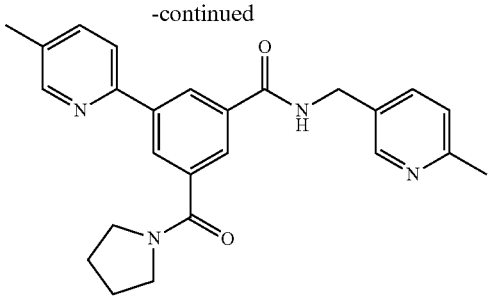

A) Methyl 3-(5-methylpyridin-2-yl)-5-(pyrrolidine-1-carbonyl)benzoate

A mixture of methyl 3-bromo-5-(pyrrolidine-1-carbonyl) benzoate (1.2 g, 3.8 mmol), 5-methyl-2-(tributylstannyl)pyridine (0.90 mL, 2.6 mmol), tetrakis(triphenylphosphine)palladium(0) (100 mg, 0.086 mmol) under argon was subjected to microwave irradiation at 120° C. for 2 hour. The mixture was cooled to room temperature and the precipitate was collected by filtration and rinsed with hexane to afford the title compound as a white solid. The filtrate was concentrated and purified via flash chromatography to afford another crop of the desired product. LC-MS: 325.1 [M+1]$^+$.

B) 3-(5-Methylpyridin-2-yl)-5-(pyrrolidine-1-carbonyl)benzoic acid

Into a round-bottom flask were charged methyl 3-(5-methylpyridin-2-yl)-5-(pyrrolidine-1-carbonyl)benzoate (0.80 g, 2.47 mmol), methanol (40 mL), sodium hydroxide (0.20 g, 5.0 mmol) and water (10 mL). The mixture was stirred at room temperature for 1 h. The volatiles were removed under reduced pressure. The residue was treated with 1N HCl (10 mL), concentrated, and purified via preparative HPLC to afford the desired product. LC-MS: 311.5 [M+1]$^+$; $^1$H NMR (400 MHz, DMSO-d6): 8.61 (t, J=1.7 Hz, 1H), 8.52 (t, J=0.8 Hz, 1H), 8.16 (t, J=1.8 Hz, 1H), 7.99 (t, J=1.5 Hz, 1H), 7.80 (d, J=8.2 Hz, 1H), 7.72-7.69 (m, 1H), 3.50 (t, J=6.7 Hz, 2H), 3.41 (t, J=6.5 Hz, 2H), 2.35 (s, 3H), 1.91-1.81 (m, 4H).

C) 3-(5-Methylpyridin-2-yl)-N-((6-methylpyridin-3-yl)methyl)-5-(pyrrolidine-1-carbonyl)benzamide Into a round-bottom flask were charged 3-(5-methylpyridin-2-yl)-5-(pyrrolidine-1-carbonyl)benzoic acid (80 mg, 0.26 mmol), (6-methylpyridin-3-yl)methanamine (60 mg, 0.49 mmol), N-(3-dimethylaminopropyl)-N'-ethylcarbodiimide hydrochloride (90 mg, 0.47 mmol), 1-hydroxybenzotriazole hydrate (80 mg, 0.52 mmol), N,N-diisopropylethylamine (80 mg, 0.62 mmol) and methylene chloride (5 mL). The mixture was stirred at room temperature overnight and then concentrated. The residue was purified via preparative HPLC to afford the desired product as a white solid.

LC-MS: 415.5 [M+1]$^+$; $^1$H NMR (400 MHz, CD$_3$OD): 8.56 (t, J=1.7 Hz, 1H), 8.53-8.52 (m, 1H), 8.46 (d, J=2.1 Hz, 1H), 8.29 (t, J=1.6 Hz, 1H), 8.04 (t, J=1.6 Hz, 1H), 7.89 (d, J=8.1 Hz, 1H), 7.81-7.77 (m, 2H), 7.32 (d, J=8.0 Hz, 1H), 4.63 (s, 2H), 3.66 (t, J=7.0 Hz, 2H), 3.54 (t, J=6.7 Hz, 2H), 2.54 (s, 3H), 2.43 (s, 3H), 2.05-1.94 (m, 4H).

134

Compound 127

4'-Methyl-N-((6-methylpyridin-3-yl)methyl)-5-(4-(thiazol-2-yl)piperazine-1-carbonyl)biphenyl-3-carboxamide

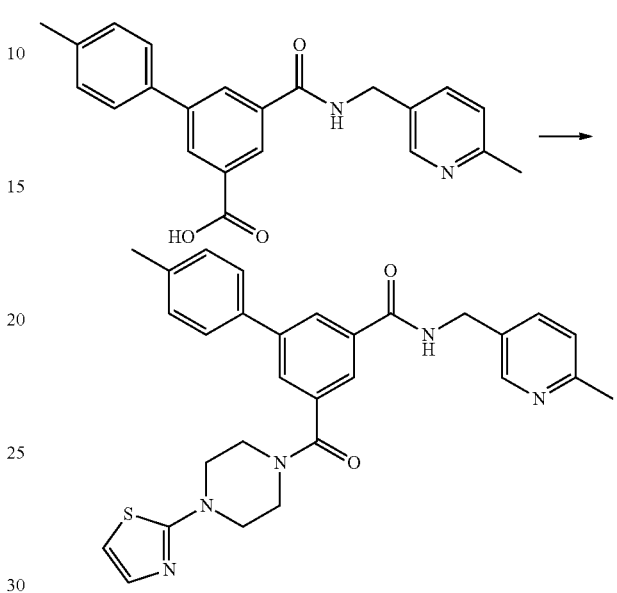

To a solution of 4'-methyl-5-(((6-methylpyridin-3-yl)methylcarbamoyl)biphenyl-3-carboxylic acid (30 mg, 0.083 mmol) in N,N-dimethylformamide (1 mL) were added 2-(piperazin-1-yl)thiazole (40 mg, 0.24 mmol), N,N,N',N'-tetramethyl-O-(7-azabenzotriazol-1-yl)uronium hexafluorophosphate (80 mg, 0.21 mol) and N,N-diisopropylethylamine (100 µL, 0.57 mmol). The reaction mixture was stirred for 16 hours at 25° C. The reaction mixture was purified by preparative HPLC to afford the final product as a white solid.

LC-MS: 512.4 [M+1]$^+$; $^1$H NMR (400 MHz, DMSO-d6): 9.27 (t, 1H, J=5.6 Hz), 8.44 (bs, 1H), 8.24 (bs, 1H), 7.90-7.84 (m, 2H), 7.70-7.60 (m, 3H), 7.32 (d, 2H, J=7.9 Hz), 7.22 (d, 1H, J=8.0 Hz), 7.19 (d, 1H, J=3.6 Hz), 6.89 (d, 1H, J=3.6 Hz), 4.49 (d, 2H, J=5.6 Hz), 3.90-3.70 (m, 2H), 3.60-3.40 (m, 6H), 2.44 (s, 3H), 2.36 (s, 3H).

Compound 130

5-(3-Hydroxyazetidine-1-carbonyl)-4'-methyl-N-((6-(trifluoromethyl)pyridin-3-yl)methyl)biphenyl-3-carboxamide

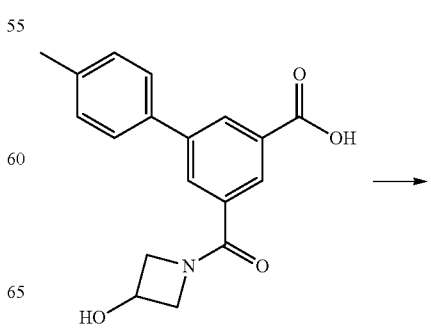

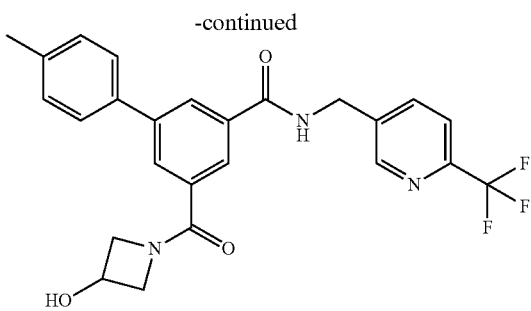

To a solution of 5-(3-hydroxyazetidine-1-carbonyl)-4'-methylbiphenyl-3-carboxylic acid (80 mg, 0.26 mmol) in N,N-dimethylformamide (1.5 mL) were added C-(6-trifluoromethyl-pyridin-3-yl)-methylamine (70 mg, 0.40 mmol), N,N,N',N'-tetramethyl-O-(7-azabenzotriazol-1-yl)uronium hexafluorophosphate (200 mg, 0.53 mmol), and N,N-diisopropylethylamine (200 pt, 1.15 mmol). The reaction mixture was stirred for 16 hours at 25° C. The reaction mixture was purified by preparative HPLC to afford a white solid.

LC-MS: 470.5 [M+1]$^+$; $^1$H NMR (400 MHz, DMSO-d6): 9.42 (t, 1H, J=5.7 Hz), 8.78 (d, 1H, J=1.3 Hz), 8.28 (t, 1H, J=1.6 Hz), 8.06 (t, 1H, J=1.4 Hz), 8.04 (dd, 1H, J=8.0, 1.5 Hz), 7.96 (t, 1H, J=1.5 Hz), 7.89 (d, 1H, J=8.1 Hz), 7.67 (d, 2H, J=8.2 Hz), 7.33 (d, 2H, J=8.0 Hz), 5.79 (d, 1H, J=5.7 Hz), 4.65 (d, 2H, J=5.7 Hz), 4.60-4.45 (m, 2H), 4.28 (m, 1H), 4.09 (m, 1H), 3.82 (m, 1H), 2.36 (s, 3H).

Compound 140

4'-Methyl-N-((6-methylpyridin-3-yl)methyl)-5-((3aR,6aS)-octahydropyrrolo[3,4-c]pyrrole-2-carbonyl)biphenyl-3-carboxamide

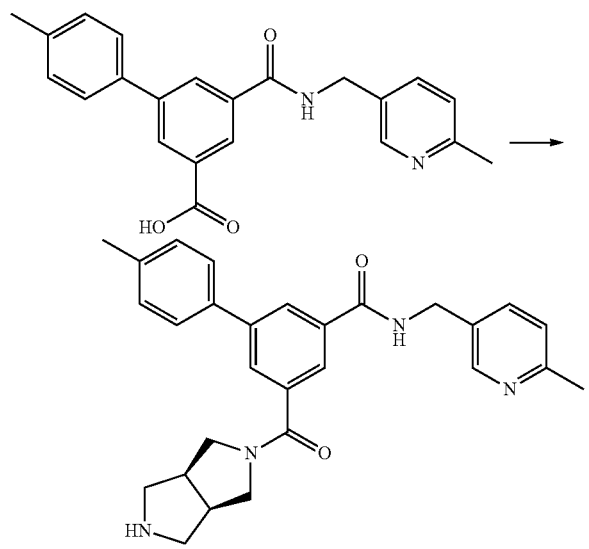

To a solution of 4'-methyl-5-((6-methylpyridin-3-yl)methylcarbamoyl)-biphenyl-3-carboxylic acid (25 mg, 0.069 mmol) in N,N-dimethylformamide (1 mL) were added (3aR,6aS)-tert-butyl hexahydropyrrolo[3,4-c]pyrrole-2(1H)-carboxylate (30 mg, 0.14 mmol), N,N,N',N'-tetramethyl-O-(7-azabenzotriazol-1-yl)uronium hexafluorophosphate (60 mg, 0.16 mmol) and N,N-diisopropylethylamine (100 μL, 0.57 mmol). The reaction mixture was stirred for 16 hours at 25° C. The reaction mixture was purified by preparative HPLC to yield Boc protected product as a white solid, which was dissolved in methylene chloride (3.0 mL) and trifluoroacetic acid (0.20 mL, 2.6 mmol) was added. The reaction mixture was stirred at rt overnight. The volatiles were removed in vacuo and the residue was purified by preparative HPLC (100×21.2 mm C18 column, 20-60% MeCN/water[10 mM Et$_2$NH]) to afford the product as a white foam.

LC-MS: 455.4 [M+1]$^+$; $^1$H NMR (400 MHz, DMSO-d6): 9.26 (t, 1H, J=5.3 Hz), 8.44 (bs, 1H), 8.21 (bs, 1H), 7.95-7.80 (m, 2H), 7.70-7.60 (m, 3H), 7.31 (d, 2H, J=7.9 Hz), 7.22 (d, 1H, J=7.9 Hz), 4.48 (d, 1H, J=5.5 Hz), 3.90-3.15 (m, 4H), 2.90 (m, 1H), 2.85-2.60 (m, 4H), 2.50-2.30 (m, 2H), 2.44 (s, 3H), 2.36 (s, 3H).

Compound 162

N3,4'-Dimethyl-N-5-((6-methylpyridin-3-yl)methyl)-N3-(pyridin-4-ylmethyl)biphenyl-3,5-dicarboxamide

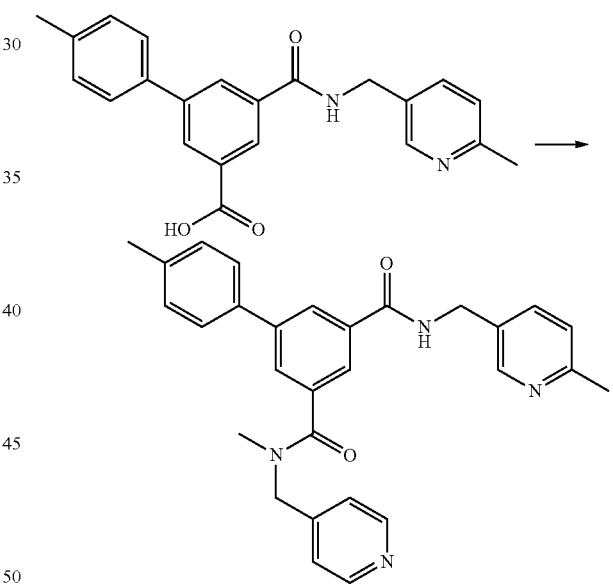

To a solution of 4'-methyl-5-((6-methylpyridin-3-yl)methylcarbamoyl)-biphenyl-3-carboxylic acid (60 mg, 0.16 mmol) in N,N-dimethylformamide (1 mL) were added methyl-pyridin-4-ylmethyl-amine (50 mg, 0.41 mmol), N,N,N',N'-tetramethyl-O-(7-azabenzotriazol-1-yl)uronium hexafluorophosphate (140 mg, 0.37 mmol) and N,N-diisopropylethylamine (140 μL, 0.80 mmol). The reaction mixture was stirred for 16 hours at 25° C. The reaction mixture was purified by preparative HPLC to afford the product as a light brown solid.

LC-MS: 465.5 [M+1]$^+$; $^1$H NMR (400 MHz, DMSO-d6): (rotomers) 9.29 (m, 1H), 8.57 (m, 2H), 8.44 (bs, 1H), 8.20 (m, 1H), 8.95-7.55 (m, 5H), 7.48-7.15 (m, 5H), 4.74 (bs, 1H), 4.60-4.40 (m, 3H), 3.00 and 2.94 (s, 3H), 2.44 (s, 3H), 2.37 and 2.33 (s, 3H).

Compound 163

N3,4'-Dimethyl-N5-((6-methylpyridin-3-yl)methyl)-N3-(pyridin-4-yl)biphenyl-3,5-dicarboxamide

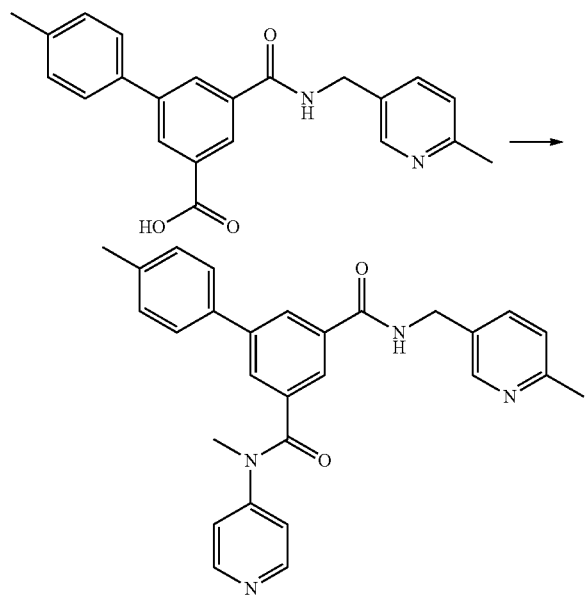

To a solution of 4'-methyl-5-((6-methylpyridin-3-yl)methylcarbamoyl)-biphenyl-3-carboxylic acid (50 mg, 0.134 mmol) in N,N-dimethylformamide (1 mL) were added N-methylpyridin-4-amine (40 mg, 0.37 mmol), N,N,N',N'-tetramethyl-O-(7-azabenzotriazol-1-yl)uronium hexafluorophosphate (120 mg, 0.32 mmol) and N,N-diisopropylethylamine (120 µL, 0.69 mmol). The reaction mixture was stirred for 16 hours at 25° C. The reaction mixture was purified by preparative HPLC to afford the final product as a light color solid.

LC-MS: 451.6 [M+1]+; 1H NMR (400 MHz, DMSO-d6): 9.20 (t, 1H, J=5.7 Hz), 8.48-8.38 (m, 3H), 8.12 (t, 1H, J=1.6 Hz), 7.87 (t, 1H, J=1.4 Hz), 7.65 (t, 1H, J=1.5 Hz), 7.59 (dd, 1H, J=8.0, 2.3 Hz), 7.42 (d, 2H, J=8.1 Hz), 7.30-7.15 (m, 5H), 4.45 (d, 2H, J=5.7 Hz), 3.45 (s, 3H), 2.44 (s, 3H), 2.33 (s, 3H).

Compound 165

(R)—N3,4'-Dimethyl-N5-((6-methylpyridin-3-yl)methyl)-N3-(pyrrolidin-3-yl)biphenyl-3,5-dicarboxamide

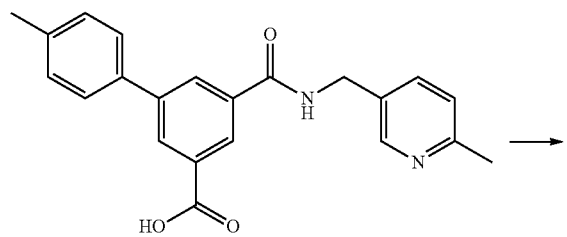

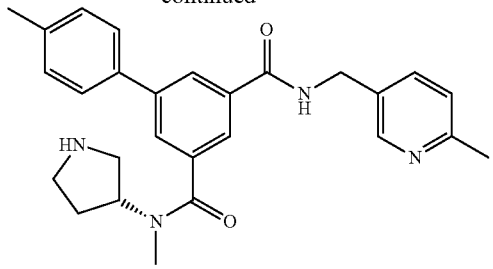

To a solution of 4'-methyl-5-((6-methylpyridin-3-yl)methylcarbamoyl)biphenyl-3-carboxylic acid (50 mg, 0.14 mmol) in N,N-dimethylformamide (1 mL) were added (R)—N-methylpyrrolidin-3-amine (50 mg, 0.50 mmol), N,N,N',N'-tetramethyl-O-(7-azabenzotriazol-1-yl)uronium hexafluorophosphate (120 mg, 0.32 mmol) and N,N-diisopropylethylamine (120 µL, 0.69 mmol). The reaction mixture was stirred for 16 hours at 25° C. The reaction solution was purified by preparative HPLC to afford the final product as a light color solid.

LC-MS: 443.5 [M+1]+; 1H NMR (400 MHz, DMSO-d6): 9.26 (t, 1H, J=5.8 Hz), 8.43 (bs, 1H), 8.22 (bs, 1H), 7.94 (bs, 1H), 7.88 (bs, 1H), 7.70-7.60 (m, 3H), 7.31 (d, 2H J=7.9 Hz), 7.21 (d, 1H, J=8.0 Hz), 4.48 (d, 2H, J=5.7 Hz), 3.65-3.05 (m, 5H), 2.44 (s, 3H), 2.36 (s, 3H), 2.29 and 2.17 (rotomers: s, 3H), 2.05-1.65 (m, 3H).

Compound 166

N3,N3,4'-Trimethyl-N5-((6-methylpyridin-3-yl)methyl)biphenyl-3,5-dicarboxamide

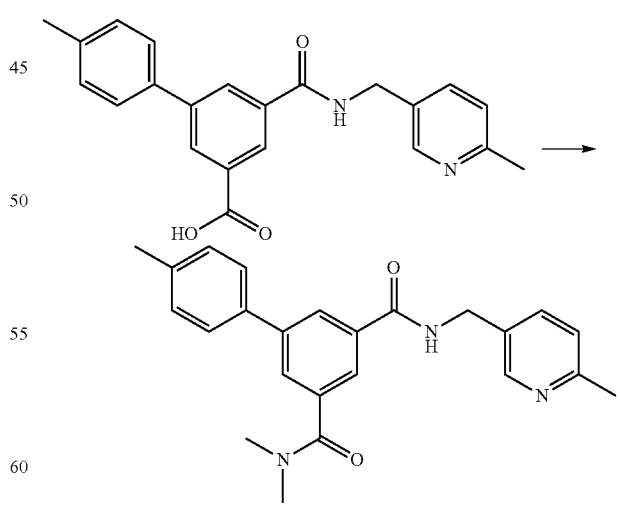

To a solution of 4'-methyl-5-((6-methylpyridin-3-yl)methylcarbamoyl)biphenyl-3-carboxylic acid (50 mg, 0.14 mmol)

in N,N-dimethylformamide (1 mL) were added dimethylamine hydrochloride (60 mg, 0.74 mmol), N,N,N',N'-tetramethyl-O-(7-azabenzotriazol-1-yl)uronium hexafluorophosphate (120 mg, 0.32 mmol) and N,N-diisopropylethylamine (0.50 mL, 2.87 mmol). The reaction mixture was stirred for 16 hours at 25° C. The reaction solution was purified by preparative HPLC to afford the final product as a light brown solid.

LC-MS: 388.5 [M+1]+; 1H NMR (400 MHz, DMSO-d6): 9.26 (t, 1H, J=5.8 Hz), 8.44 (bs, 1H), 8.21 (bs, 1H), 7.90-7.60 (m, 5H), 7.31 (d, 2H, J=7.3 Hz), 7.21 (d, 1H, J=8.0 Hz), 4.49 (d, 2H, J=4.9 Hz), 3.02 (s, 3H), 2.94 (s, 3H), 2.44 (s, 3H), 2.36 (s, 3H).

Compound 168

N3,4'-Dimethyl-N5-((6-methylpyridin-3-yl)methyl)-N3-(2,2,2-trifluoroethyl)biphenyl-3,5-dicarboxamide

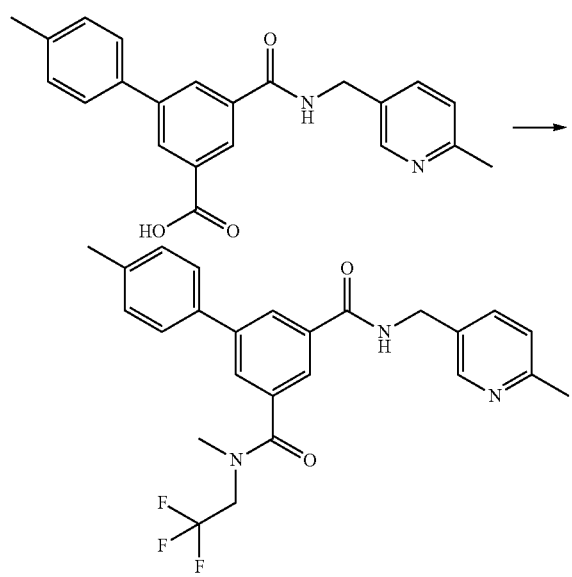

To a solution of 4'-methyl-5-((6-methylpyridin-3-yl)methylcarbamoyl)biphenyl-3-carboxylic acid (50 mg, 0.14 mmol) in N,N-dimethylformamide (1.5 mL) were added 2,2,2-trifluoro-N-methylethanamine hydrochloride (60 mg, 0.40 mmol), N,N,N',N'-tetramethyl-O-(7-azabenzotriazol-1-yl) uronium hexafluorophosphate (120 mg, 0.32 mmol) and N,N-diisopropylethylamine (0.50 mL, 2.87 mmol). The reaction mixture was stirred for 16 hours at 25° C. The reaction mixture was purified by preparative HPLC to afford the final product as a light yellow solid.

LC-MS: 456.3 [M+1]+; 1H NMR (400 MHz, DMSO-d6): 9.31 (bs, 1H), 8.44 (bs, 1H), 8.25 (bs, 1H), 7.90-7.60 (m, 5H), 7.32 (d, 2H, J=8.1 Hz), 7.21 (d, 1H, J=8.0 Hz), 4.49 (d, 2H, J=5.7 Hz), 4.45-4.10 (m, 2H), 3.07 (bs, 3H), 2.44 (s, 3H), 2.36 (s, 3H).

Compound 181

(R)-3-(5-Methylpyridin-2-yl)-5-(methylsulfonyl)-N-(1-(6-(trifluoromethyl)pyridin-3-yl)ethyl)benzamide

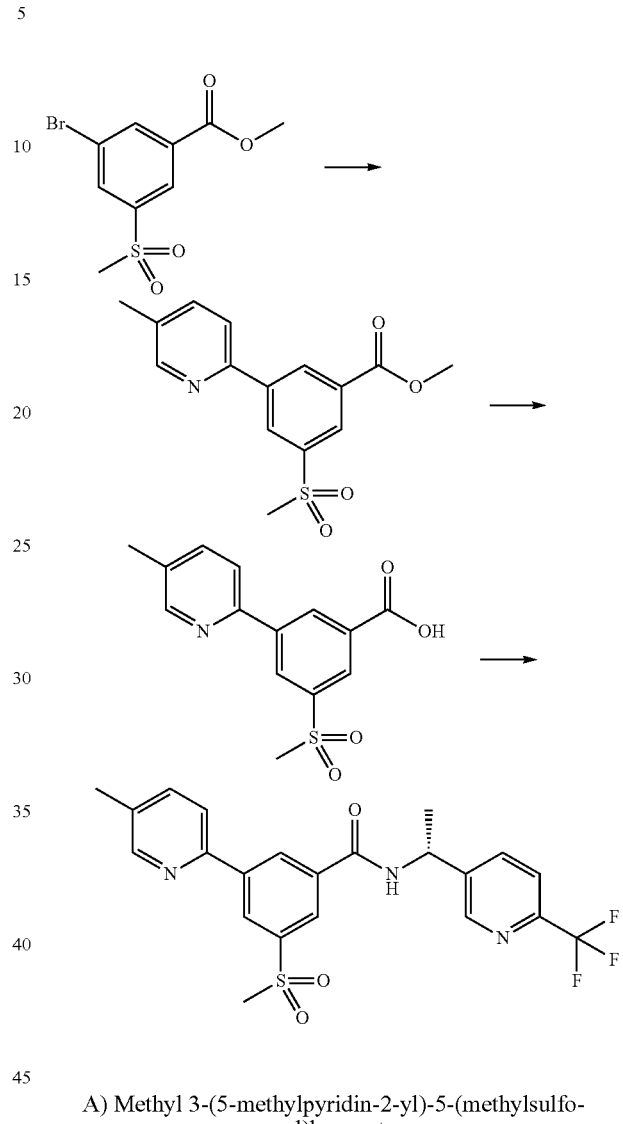

A) Methyl 3-(5-methylpyridin-2-yl)-5-(methylsulfonyl)benzoate

A mixture of methyl 3-bromo-5-(methylsulfonyl)benzoate (1.0 g, 3.4 mmol), 5-methyl-2-(tributylstannyl)pyridine (1.2 mL, 3.5 mmol), tetrakis(triphenylphosphine)palladium(0) (200 mg, 0.17 mmol), and toluene (10 mL) under argon was subjected to microwave irradiation at 120° C. for 2 hours. The mixture was cooled to room temperature. The precipitate was collected by filtration and rinsed with hexane to afford the title compound as a light brown solid (432 mg). The filtrate was concentrated and the residue was purified via flash chromatography to afford another crop of the product as a light yellow solid (200 mg). 1H NMR (400 MHz, CDCl3): 8.91 (t, J=1.4 Hz, 1H), 8.80 (d, J=1.7 Hz, 1H), 8.61 (s, 1H), 8.58 (d, J=0.8 Hz, 1H), 7.76 (d, J=8.1 Hz, 1H), 7.65 (d, J=8.1 Hz, 1H), 4.00 (s, 3H), 3.15 (s, 3H), 2.42 (s, 3H).

B) 3-(5-Methylpyridin-2-yl)-5-(methylsulfonyl)benzoic acid (HCl salt)

Into a round-bottom flask were charged methyl 3-(5-methylpyridin-2-yl)-5-(methylsulfonyl)benzoate (0.60 g, 1.96 mmol), barium hydroxide octahydrate (1.23 g, 3.90 mmol) and methanol (50 mL). The mixture was stirred at room temperature until the completion of the reaction. The mixture was acidified with HCl (2M ethyl ether solution, 20 mL). The mixture was concentrated to afford a mixture of the desired product and BaCl₂ as a white solid (1.4 g, 40% purity). LC-MS: 291.5 [M+1]; ¹H NMR (400 MHz, DMSO-d6): 8.90 (s, 1H), 8.80 (d, J=1.7 Hz, 1H), 8.63 (s, 1H), 8.43 (d, J=1.5 Hz, 1H), 8.16 (d, J=8.1 Hz, 1H), 7.89 (d, J=7.8 Hz, 1H), 7.64-7.55 (m, 1H), 3.38 (s, 3H), 2.40 (s, 3H).

C) (R)-3-(5-Methylpyridin-2-yl)-5-(methylsulfonyl)-N-(1-(6-(trifluoromethyl)pyridin-3-yl)ethyl)benzamide Into a round-bottom flask were charged 3-(5-methylpyridin-2-yl)-5-(methylsulfonyl)benzoic acid (40% mixture with BaCl₂, 250 mg, 0.34 mmol), (R)-1-(6-(trifluoromethyl)pyridin-3-yl)ethanamine (130 mg, 0.69 mmol), N-(3-dimethylaminopropyl)-N'-ethylcarbodiimide hydrochloride (130 mg, 0.69 mmol), 1-hydroxybenzotriazole hydrate (100 mg, 0.69 mmol), triethylamine (87 mg, 0.86 mmol) and CH₂Cl₂ (3 mL). The mixture was stirred at room temperature overnight and then concentrated. The residue was purified via flash chromatography to afford the desired product as a white solid.

LC-MS: 464.8 [M+1]⁺; ¹H NMR (400 MHz, DMSO-d6): 9.41 (d, J=7.3 Hz, 1H), 8.86 (t, J=1.6 Hz, 2H), 8.74 (t, J=1.6 Hz, 1H), 8.60 (d, J=2.2 Hz, 1H), 8.43 (t, J=1.6 Hz, 1H), 8.13-8.10 (m, 2H), 7.91 (d, J=8.1 Hz, 1H), 7.82 (dd, J=2.2, 8.7 Hz, 1H), 5.34 (p, J=7.1 Hz, 1H), 3.33 (s, 3H), 2.38 (s, 3H), 1.60 (d, J=7.1 Hz, 3H).

Compound 185

5-(Isoindoline-2-carbonyl)-4'-methyl-N-((6-methylpyridin-3-yl)methyl)biphenyl-3-carboxamide

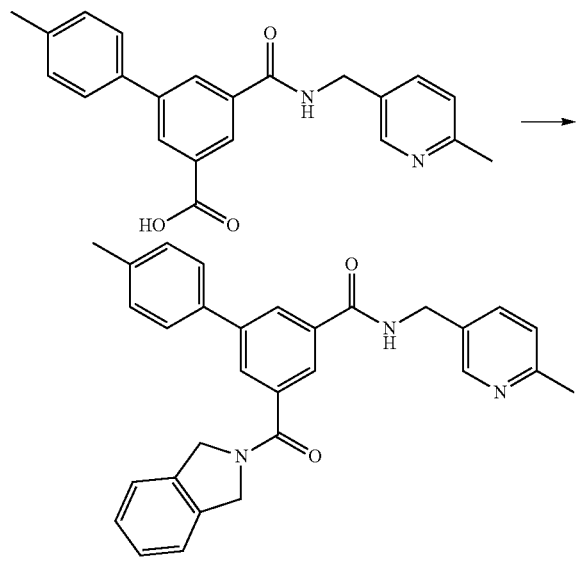

To a solution of 4'-methyl-5-((6-methylpyridin-3-yl)methylcarbamoyl)biphenyl-3-carboxylic acid (50 mg, 0.14 mmol) in N,N-dimethylformamide (1 mL) were added isoindoline (40 mg, 0.34 mmol), N,N,N',N'-tetramethyl-O-(7-azabenzotriazol-1-yl)uronium hexafluorophosphate (120 mg, 0.32 mmol) and N,N-diisopropylethylamine (120 μL, 0.69 mmol). The reaction mixture was stirred for 16 hours at 25° C. The reaction solution was purified by preparative HPLC to afford the final product as a yellow solid.

LC-MS: 461.9 [M+1]⁺; ¹H NMR (400 MHz, DMSO-d6): 9.27 (t, 1H, J=5.7 Hz), 8.45 (d, 1H, J=2.0 Hz), 8.26 (t, 1H, J=1.5 Hz), 8.02 (bs, 2H), 7.72-7.62 (m, 3H), 7.42 (d, 1H, J=7.2 Hz), 7.35-7.25 (m, 5H), 7.22 (d, 1H, J=8.0 Hz), 4.90 (s, 2H), 4.81 (s, 2H), 4.49 (d, 2H, J=5.7 Hz), 2.44 (s, 3H), 2.36 (s, 3H).

Compound 187

4'-Methyl-N-((6-methylpyridin-3-yl)methyl)-5-(1,2,3,4-tetrahydroisoquinoline-2-carbonyl)biphenyl-3-carboxamide

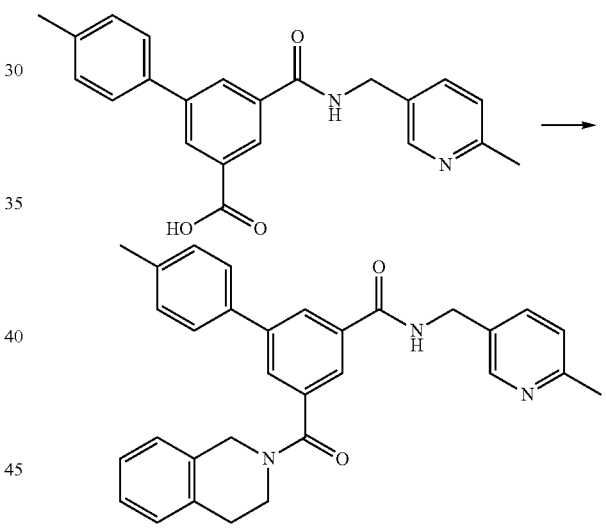

To a solution of 4'-methyl-5-((6-methylpyridin-3-yl)methylcarbamoyl)-biphenyl-3-carboxylic acid (50 mg, 0.14 mmol) in N,N-dimethylformamide (1 mL) were added 1,2,3,4-tetrahydroisoquinoline (50 mg, 0.38 mmol), N,N,N',N'-tetramethyl-O-(7-azabenzotriazol-1-yl)uronium hexafluorophosphate (120 mg, 0.32 mmol) and N,N-diisopropylethylamine (120 μL, 0.69 mmol). The reaction mixture was stirred for 16 hours at 25° C. The reaction solution was purified by preparative HPLC to afford the final product as a yellow solid.

LC-MS: 476 [M+1]⁺; ¹H NMR (400 MHz, DMSO-d6): 9.27 (t, 1H, J=5.6 Hz), 8.44 (d, 1H, J=1.8 Hz), 8.25 (bs, 1H), 7.88 (m, 2H), 7.72-7.62 (m, 3H), 7.35-7.00 (m, 7H), 4.81 and 4.61 (bs, 2H), 4.48 (d, 2H, J=5.7 Hz), 3.88 and 3.60 (bs, 2H), 2.85 (m, 2H), 2.44 (s, 3H), 2.36 (s, 3H).

Compound 191

4'-Methyl-N—((R)-1-(2-methylpyrimidin-5-yl)ethyl)-5-(octahydropyrrolo[1,2-a]pyrazine-2-carbonyl)biphenyl-3-carboxamide

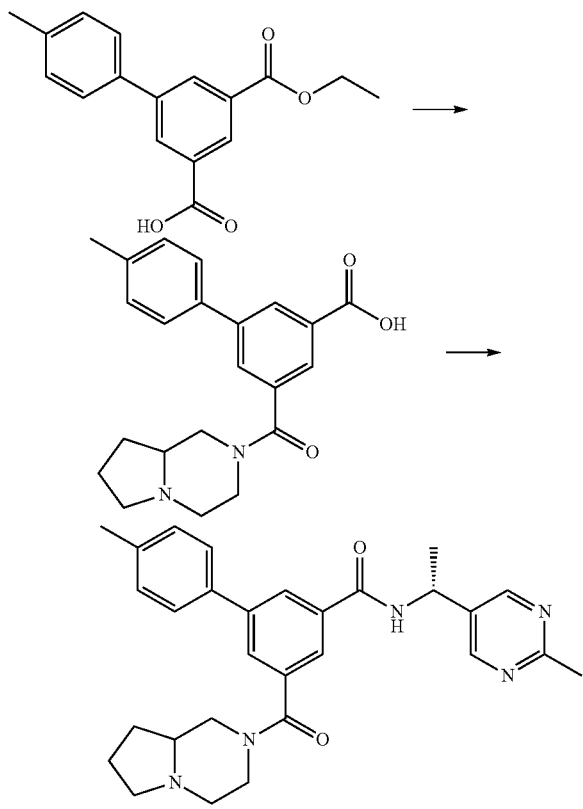

A) 4'-Methyl-5-(octahydropyrrolo[1,2-a]pyrazine-2-carbonyl)biphenyl-3-carboxylic acid To a solution of 5-(ethoxycarbonyl)-4'-methylbiphenyl-3-carboxylic acid (300 mg, 1.06 mmol) in N,N-dimethylformamide (6 mL) were added octahydropyrrolo[1,2-a]pyrazine (200 mg, 1.58 mmol), N,N,N',N'-tetramethyl-O-(7-azabenzotriazol-1-yl)uronium hexafluorophosphate (1.0 g, 2.63 mmol) and N,N-diisopropylethylamine (1.0 mL, 5.74 mmol). The reaction mixture was stirred for 16 hours at 25° C. LC-MS indicated completion of the reaction. The reaction mixture was diluted with EtOAc and washed with water, sat. aq. NaHCO₃, brine, dried over anhydrous MgSO₄, and concentrated. The residue was purified by silica-gel column to yield the ethyl ester product as a brown foam. A mixture of the obtained ethyl ester (480 mg, 1.22 mmol), lithium hydroxide (75 mg, 3.1 mmol), MeOH (25 mL), and water (4 mL) was stirred at rt for 20 hr. LC-MS indicated completion of the reaction. The volatiles were removed in vacuo and the residue was treated with water and acidified with 1N aq. HCl to pH=5. The aqueous phase was extracted with EtOAc (3×100 mL) and the combined organic layers were washed with brine, dried, and concentrated to yield the acid product as a light color solid.

B) 4'-Methyl-N—((R)-1-(2-methylpyrimidin-5-yl)ethyl)-5-(octahydropyrrolo[1,2-a]pyrazine-2-carbonyl)biphenyl-3-carboxamide To a solution of 4'-methyl-5-(octahydropyrrolo[1,2-a]pyrazine-2-carbonyl)biphenyl-3-carboxylic acid (50 mg, 0.14 mmol) in N,N-dimethylformamide (1.0 mL) were added (R)-1-(2-methylpyrimidin-5-yl)ethanamine (35 mg, 0.25 mmol), N,N,N',N'-tetramethyl-O-(7-azabenzotriazol-1-yl)uronium hexafluorophosphate (120 mg, 0.32 mmol) and N,N-diisopropylethylamine (120 µL, 0.69 mmol). The reaction mixture was stirred for 16 hours at 25° C. The reaction mixture was purified by preparative HPLC to afford the final product as a light yellow solid.

LC-MS: 484.1 [M+1]⁺; ¹H NMR (400 MHz, DMSO-d6): 9.07 (d, 1H, J=7.5 Hz), 8.73 (s, 2H), 8.19 (bs, 1H), 7.82 (bs, 1H), 7.77 (bs, 1H), 7.66 (d, 2H, J=7.8 Hz), 7.32 (d, 2H, J=8.0 Hz), 5.20 (m, 1H), 4.63 and 4.49 (bs, 1H), 3.70-2.80 (m, 4H), 2.64 (s, 3H), 2.36 (s, 3H), 2.20-1.10 (m, 8H), 1.55 (d, 3H, J=7.1 Hz).

Compound 200

4'-Bromo-N-((6-methylpyridin-3-yl)methyl)-5-(pyrrolidine-1-carbonyl)biphenyl-3-carboxamide

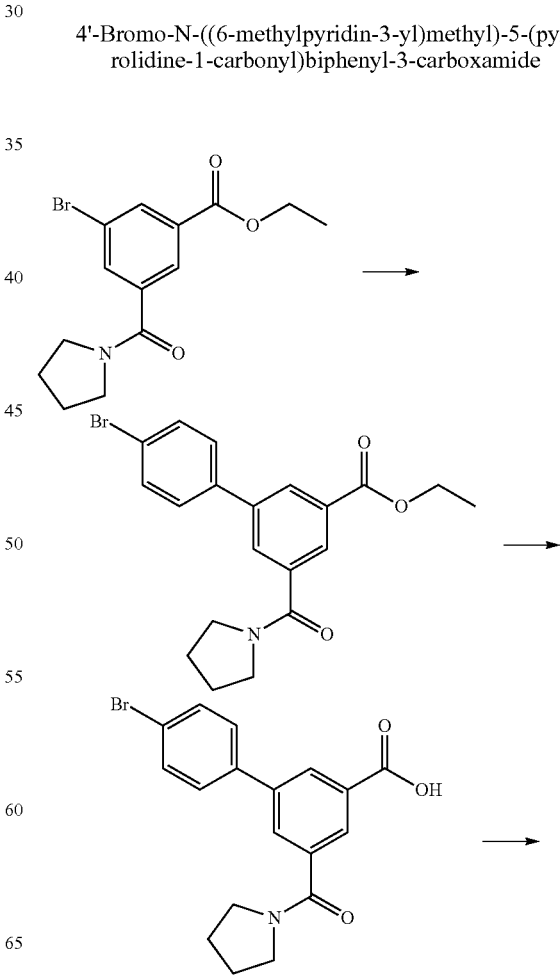

-continued

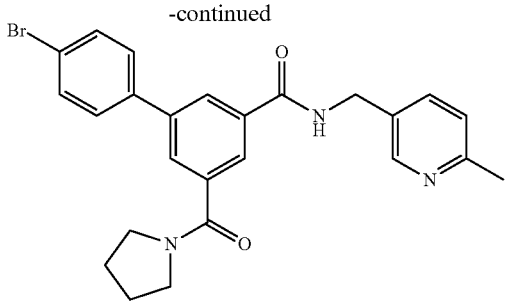

A) Ethyl 4'-bromo-5-(pyrrolidine-1-carbonyl)biphenyl-3-carboxylate

To a mixture of ethyl 3-bromo-5-(pyrrolidine-1-carbonyl)benzoate (3.20 g, 9.81 mmol), 4-bromophenylboronic acid (2.17 g, 10.8 mmol), toluene (40 mL), cesium carbonate (3.52 g, 10.8 mmol), and water (5 mL) under argon was added tetrakis(triphenylphosphine)palladium(0) (567 mg, 0.49 mmol). The mixture was heated under reflux for 15 h. After cooling, the mixture was filtered through Celite and the filter cake was washed with EtOAc. The filtrate was washed with brine, dried ($Na_2SO_4$), and concentrated. The residue was purified by silica gel column (0-80% EtOAc/hexane) to afford a syrup. LC-MS: 404.0 [M+1]$^+$.

B) 4'-Bromo-5-(pyrrolidine-1-carbonyl)-biphenyl-3-carboxylic acid

A mixture of ethyl 4'-bromo-5-(pyrrolidine-1-carbonyl)biphenyl-3-carboxylate (3.3 g, 8.2 mmol), MeOH (100 mL), water (20 mL), and lithium hydroxide (0.90 g, 38 mmol) was stirred at room temperature for 3 h. The mixture was concentrated in vacuo and the residue was acidified with 1N aq. HCl to pH 2-3 and extracted with EtOAc (2×100 mL). The combined organic layers were dried ($Na_2SO_4$) and concentrated to afford a white foam. LC-MS: 376.1 [M+1]$^+$.

C) 4'-Bromo-N-((6-methylpyridin-3-yl)methyl)-5-(pyrrolidine-1-carbonyl)biphenyl-3-carboxamide To a mixture of 4'-bromo-5-(pyrrolidine-1-carbonyl)-biphenyl-3-carboxylic acid (1.65 g, 4.41 mmol), N-(3-dimethylaminopropyl)-N'-ethylcarbodiimide hydrochloride (1.7 g, 8.8 mmol), 1-hydroxybenzotriazole hydrate (0.20 g, 1.3 mmol), and $CH_2Cl_2$ (50 mL) were added (6-methylpyridin-3-yl)methanamine (0.81 g, 6.6 mmol) and N,N-diisopropylethylamine (1.5 mL, 8.8 mmol). The mixture was stirred at room temperature overnight and then washed with water, dried ($Na_2SO_4$), and concentrated. The residue was purified by silica gel column (0-15% MeOH/$CH_2Cl_2$) and analytical sample was purified by preparative HPLC (100×20.2 mm, C18 column; 30-80% $CH_3CN$-water[10 mM $Et_2NH$]) to afford a white foam.

LC-MS: 480.1 [M+1]$^+$; $^1$H NMR (400 MHz, DMSO-d6): 9.26 (t, 1H, J=5.6 Hz), 8.44 (d, 1H, J=2.0 Hz), 8.23 (t, 1H, J=1.6 Hz), 7.99 (t, 1H, J=1.6 Hz), 7.94 (t, 1H, J=1.6 Hz), 7.77-7.66 (m, 4H), 7.63 (dd, 1H, J=8.0, 2.0 Hz), 7.22 (d, 1H, J=8.0 Hz), 4.49 (d, 2H, J=5.6 Hz), 3.50 (t, 2H, J=6.8 Hz), 3.42 (t, 2H, J=6.8 Hz), 2.44 (s, 3H), 1.93-1.79 (m, 4H).

Compound 203

4'-Methyl-d3-N-((6-methylpyridin-3-yl)methyl)-5-(pyrrolidine-1-carbonyl)biphenyl-3-carboxamide

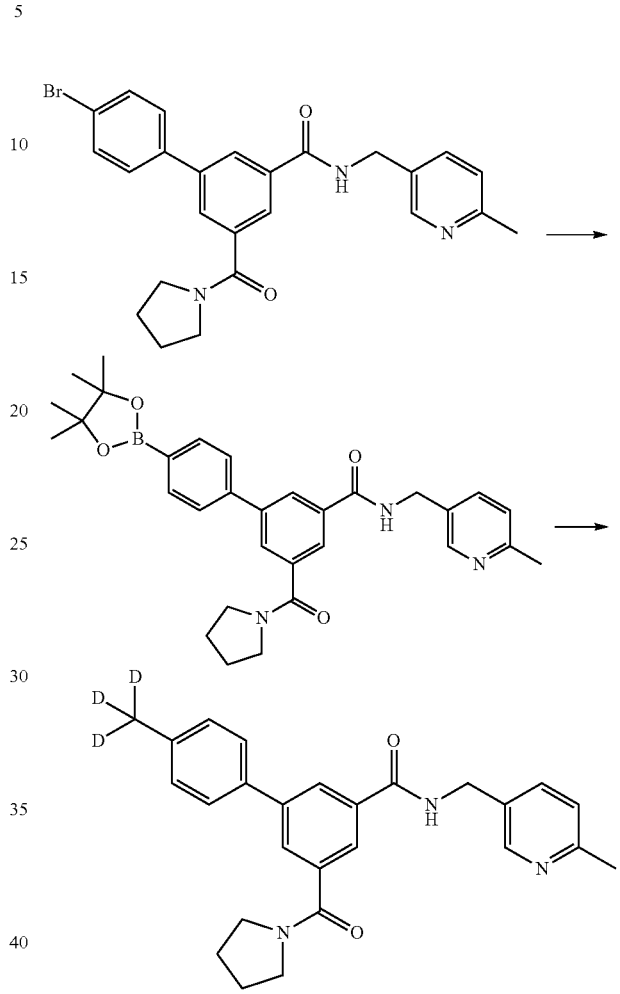

A) N-((6-Methylpyridin-3-yl)methyl)-5-(pyrrolidine-1-carbonyl)-4'-(4,4,5,5-tetramethyl-1,3,2-dioxaborolan-2-yl)biphenyl-3-carboxamide To a mixture of 4'-bromo-N-((6-methylpyridin-3-yl)methyl)-5-(pyrrolidine-1-carbonyl)biphenyl-3-carboxamide (0.47 g, 0.98 mmol), bis(pinacolato)diboron (0.37 g, 1.5 mmol), potassium acetate (0.29 g, 2.9 mmol), 1,4-dioxane (20 mL) and dimethyl sulfoxide (0.2 mL) under argon was added [1,1'-bis(diphenylphosphino)ferrocene]dichloropalladium(II), complex with dichloromethane (1:1) (24 mg, 0.029 mmol). The mixture was heated under argon at 85° C. overnight. After cooling, the mixture was filtered through Celite and the filter cake was washed with EtOAc. The filtrate was concentrated and the residue was purified by silica gel column (0-10% EtOH/$CH_2Cl_2$) to afford a brown foam. LC-MS: 526.2 [M+1]$^+$.

B) 4'-Methyl-d3-N-((6-methylpyridin-3-yl)methyl)-5-(pyrrolidine-1-carbonyl)biphenyl-3-carboxamide $K_3PO_4$ solution: 2.0 M aqueous $K_3PO_4$ solution was degassed and purged with argon. Boronate solution: N-((6- methylpyridin-3-yl)methyl)-5-(pyrrolidine-1-carbonyl)-4'-(4,4,5,5-tetramethyl-1,3,2-dioxaborolan-2-yl)biphenyl-3-carboxamide (100 mg, 0.19 mmol) was dissolved in DMF (0.8 mL). The solution was degassed and purged with argon. Catalyst solution: [1,1'-bis(diphenylphosphino)ferrocene]dichloropalladium(II), complex with dichloromethane (1:1) (10 mg, 0.012 mmol) was well dissolved in degassed N,N-dimethylformamide (5.0 mL). The solution was degassed and purged with argon. Reaction: Under argon at room temperature, a small reaction vial was charged with 1 mL of the orange-red catalyst solution (i.e. 2 mg of the catalyst was used) and iodomethane-d3 (55 mg, 0.38 mmol). Then the boronate solution (0.19 mmol) was added followed by 0.30 mL of 2.0 M aq. $K_3PO_4$ solution. The resulting reaction mixture was heated under argon in a 100° C. oil bath for 20 min. LC-MS indicated no boronate left. After cooling, the reaction was quenched with 1.0 mL of MeOH, and the resulting solution was filtered and purified by preparative HPLC (100×20.2 mm, C18 column; 30-80% MeCN-water[10 mM $Et_2NH$]; flow rate: 20 mL/min).

LC-MS: 417.2 [M+1]$^+$; $^1$H NMR (400 MHz, DMSO-d6): 9.25 (t, 1H, J=6.0 Hz), 8.44 (d, 1H, J=2.0 Hz), 8.21 (t, 1H, J=1.6 Hz), 7.94 (t, 1H, J=1.6 Hz), 7.89 (t, 1H, J=1.6 Hz), 7.67 (d, 2H, J=8.4 Hz), 7.63 (dd, 1H, J=8.0, 2.4 Hz), 7.31 (d, 2H, J=8.4 Hz), 7.22 (d, 1H, J=8.0 Hz), 4.48 (d, 2H, J=6.0 Hz), 3.50 (t, 2H, J=6.8 Hz), 3.42 (t, 2H, J=6.4 Hz), 2.44 (s, 3H), 1.93-1.78 (m, 4H).

Compound 206

(S)—N-(2-Hydroxy-1-(6-methoxypyridin-3-yl)ethyl)-4'-methyl-5-(methylsulfonyl)biphenyl-3-carboxamide

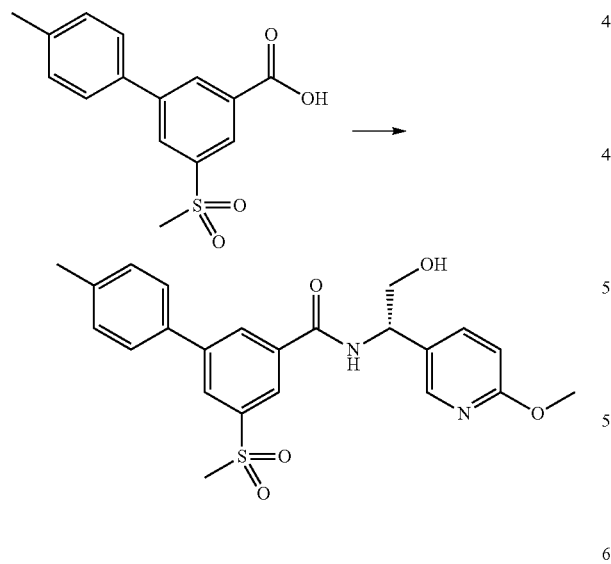

To a mixture of 4'-methyl-5-(methylsulfonyl)biphenyl-3-carboxylic acid (35 mg, 0.12 mmol), N-(3-dimethylaminopropyl)-N'-ethylcarbodiimide hydrochloride (46 mg, 0.24 mmol), 1-hydroxybenzotriazole hydrate (18 mg, 0.12 mmol), and $CH_2Cl_2$ (3 mL) were added (S)-2-amino-2-(6-methoxypyridin-3-yl)ethanol (30 mg, 0.18 mmol) and N,N-diisopropylethylamine (42 μL, 0.24 mmol). The mixture was stirred at room temperature overnight and then concentrated. The residue was purified by preparative HPLC (100×20.2 mm, C18 column; 30-80% $CH_3CN$-water[10 mM $Et_2NH$]) to afford a white foam.

LC-MS: 440.9 [M+1]$^+$; $^1$H NMR (400 MHz, CDCl$_3$): 8.32 (m, 1H), 8.27-8.23 (m, 3H), 7.65 (dd, 1H, J=8.4, 2.8 Hz), 7.53 (d, 2H, J=8.4 Hz), 7.30 (d, 2H, J=8.0 Hz), 7.16 (d, 1H, J=7.2 Hz), 6.77 (d, 1H, J=8.8 Hz), 5.26 (m, 1H), 4.11-4.00 (m, 2H), 3.93 (s, 3H), 3.13 (s, 3H), 2.42 (s, 3H).

Compound 219

(R)-5-(Cyclopentylsulfonyl)-4'-methyl-N-(1-(2-methylpyrimidin-5-yl)ethyl)biphenyl-3-carboxamide

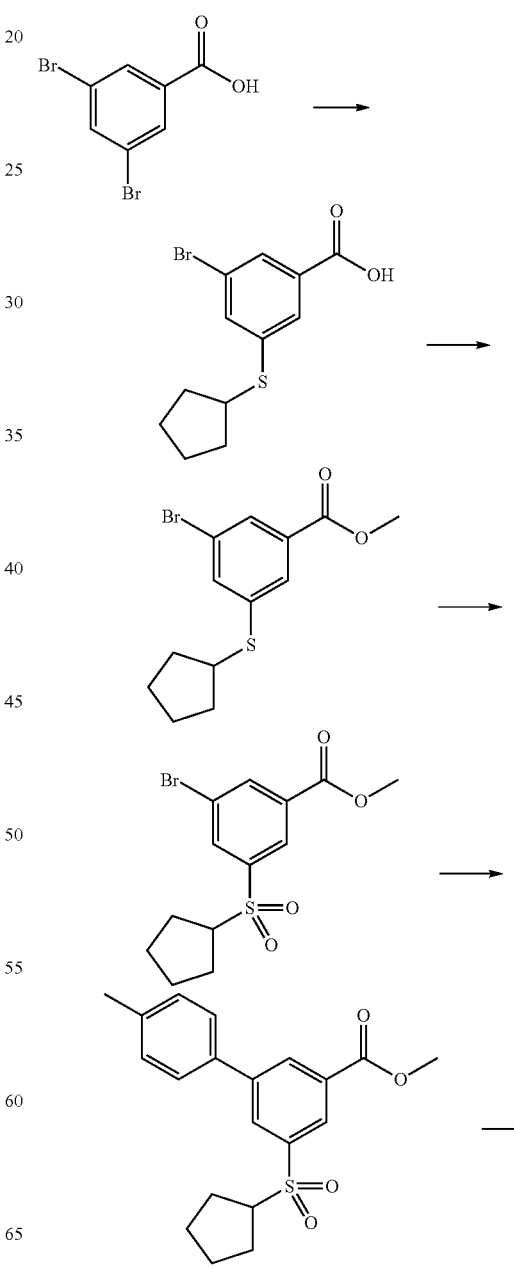

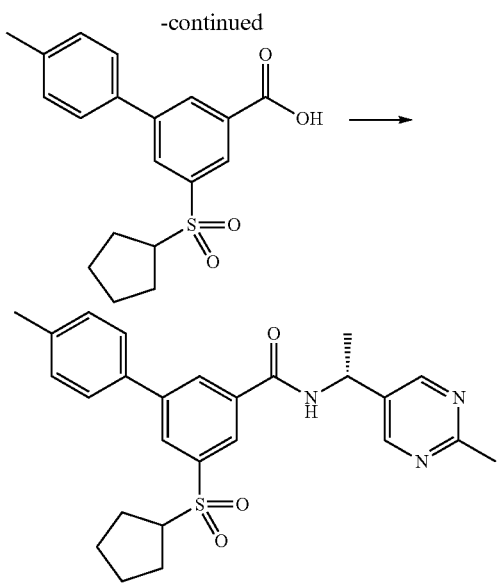

A) 3-Bromo-5-(cyclopentylthio)benzoic acid

To a stirred mixture of sodium hydride (60% in mineral oil, 0.82 g, 20.5 mmol) and DMSO (15 mL) in a sealable flask at 0° C. was slowly added cyclopentanethiol (1.23 mL, 11.9 mmol). The mixture was stirred at room temperature for 30 min and then a solution of 3,5-dibromobenzoic acid (2.5 g, 8.9 mmol) in DMSO (10 mL) was added. The reaction was sealed and stirred at 80° C. overnight. After cooling, the reaction mixture was poured into water and adjusted to pH 5-6 with 15% HCl (aq.) and extracted with EtOAc. The combined organic layers were washed with brine, dried over anhydrous $MgSO_4$, and concentrated to afford the crude product which was used for the next step reaction without further purification.

B) Methyl 3-bromo-5-(cyclopentylthio)benzoate

A solution of 3-bromo-5-(cyclopentylthio)benzoic acid (1.49 g, 4.95 mmol) in methanol (40 mL) was treated with acetyl chloride (3.87 mL, 54.4 mmol) at 0° C. The reaction mixture was heated to reflux overnight, and then concentrated under reduced pressure. The residue was purified by flash chromatography (0-20% EtOAc/hexane) to afford the title compound as a colorless oil.

C) Methyl 3-bromo-5-(cyclopentylsulfonyl)benzoate

To a stirred solution of methyl 3-bromo-5-(cyclopentylthio)benzoate (1.2 g, 3.8 mmol) in methylene chloride (20 mL) at 0° C. was slowly added m-chloroperbenzoic acid (70% purity, 2.35 g, 9.52 mmol) in portions. The mixture was slowly warmed to room temperature and stirred overnight. The reaction mixture was washed with aq. $Na_2CO_3$ solution and brine, dried over anhydrous $MgSO_4$, and concentrated. The residue was purified by silica gel column (EtOAc/hexane) to afford a colorless oil.

D) Methyl 5-(cyclopentylsulfonyl)-4'-methylbiphenyl-3-carboxylate

A microwave vial was charged with methyl 3-bromo-5-(cyclopentylsulfonyl)benzoate (0.50 g, 1.44 mmol), p-tolyl-boronic acid (0.44 g, 3.25 mmol), toluene (7 mL), and a solution of cesium carbonate (1.06 g, 3.26 mmol) in water (0.3 mL). The vial was degassed and purged with argon, and then tetrakis(triphenylphosphine)palladium(0) (0.16 g, 0.14 mmol) was added. The reaction mixture was subjected to microwave irradiation at 100° C. for 2 h. After cooling, the mixture was filtered and the filtrate was concentrated in vacuo. The residue was purified via flash column (0-25% EtOAc/hexane) to yield the title compound as a colorless oil.

E) 5-(Cyclopentylsulfonyl)-4'-methylbiphenyl-3-carboxylic acid

To a solution of methyl 5-(cyclopentylsulfonyl)-4'-methylbiphenyl-3-carboxylate (0.34 g, 0.95 mmol) in tetrahydrofuran (15 mL) was added 2.5 M aqueous lithium hydroxide solution (1.0 mL, 2.5 mmol). The reaction mixture was stirred at 60° C. overnight. The aqueous solution was acidified with 15% HCl (aq.) to pH=5, and extracted with EtOAc. The combined organic layers were concentrated in vacuo to afford the title compound as a white solid.

F) (R)-5-(Cyclopentylsulfonyl)-4'-methyl-N-(1-(2-methylpyrimidin-5-yl)ethyl)biphenyl-3-carboxamide To a solution of 5-(cyclopentylsulfonyl)-4'-methylbiphenyl-3-carboxylic acid (50 mg, 0.14 mmol) in N,N-dimethylformamide (1 mL) were added (R)-1-(2-methylpyrimidin-5-yl)ethanamine (40 mg, 0.29 mmol), N,N,N',N'-tetramethyl-O-(7-azabenzotriazol-1-yl)uronium hexafluorophosphate (120 mg, 0.32 mmol) and N,N-diisopropylethylamine (140 μL, 0.80 mmol). The reaction mixture was stirred for 16 hours at 25° C. The reaction mixture was purified by preparative HPLC to afford the final product as a light color solid.

LC-MS: 464.1 [M+1]$^+$; $^1$H NMR (400 MHz, DMSO-d6): 9.26 (d, 1H, J=7.4 Hz), 8.75 (s, 2H), 8.47 (t, 1H, J=1.5 Hz), 8.29 (t, 1H, J=1.5 Hz), 8.21 (t, 1H, J=1.6 Hz), 7.74 (d, 2H, J=8.2 Hz), 7.36 (d, 2H, J=8.0 Hz), 5.22 (m, 1H), 3.99 (m, 1H), 2.60 (s, 3H), 2.38 (s, 3H), 2.00-1.75 (m, 4H), 1.70-1.50 (m, 4H), 1.57 (d, 3H, J=7.1 Hz).

Compound 220

3-(5-Methylpyridin-2-yl)-N-((6-methylpyridin-3-yl)methyl)-5-(trifluoromethoxy)benzamide

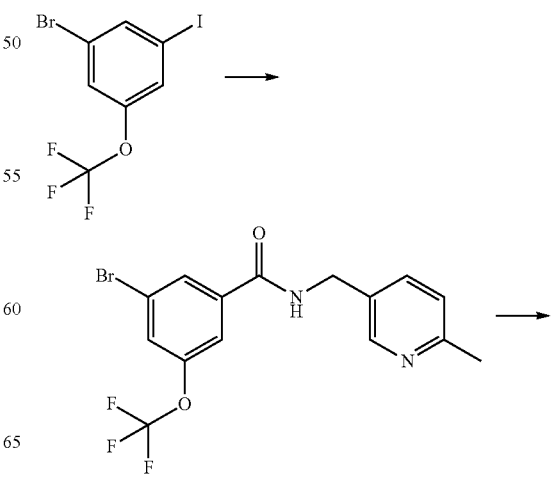

151

-continued

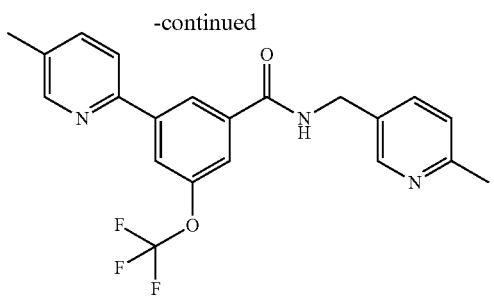

A) 3-Bromo-N-((6-methylpyridin-3-yl)methyl)-5-(trifluoromethoxy)benzamide

A 5 mL microwave vial was charged with 1-bromo-3-iodo-5-(trifluoromethoxy)benzene (98 mg, 0.27 mmol), (6-methylpyridin-3-yl)methanamine (50 mg, 0.41 mmol), molybdenum hexacarbonyl (160 mg, 0.61 mmol), palladium acetate (8 mg, 0.036 mmol), 1,8-diazabicyclo[5.4.0]undec-7-ene (120 mg, 0.79 mmol), and 1,4-dioxane (2 mL). The vial was sealed under nitrogen and the reaction was subjected to microwave irradiation at 120° C. for 20 minutes. After cooling, the mixture was purified via flash chromatography to afford the desired product as a white solid. LC-MS: 391.2 [M+1]+; 1H NMR (CDCl3, 400 MHz): 8.43 (d, J=2.1 Hz, 1H), 7.85 (t, J=1.5 Hz, 1H), 7.63-7.61 (m, 2H), 7.52 (s, 1H), 7.16 (d, J=8.0 Hz, 1H), 6.74 (br, 1H), 4.60 (d, J=5.8 Hz, 2H), 2.55 (s, 3H).

B) 3-(5-Methylpyridin-2-yl)-N-((6-methylpyridin-3-yl)methyl)-5-(trifluoromethoxy)benzamide A mixture of 3-bromo-N-((6-methylpyridin-3-yl)methyl)-5-(trifluoromethoxy)benzamide (60 mg, 0.15 mmol), 5-methyl-2-(tributylstannyl)pyridine (0.1 mL, 0.3 mmol), tetrakis(triphenylphosphine)palladium(0) (20 mg, 0.02 mmol) and toluene (4 mL) under argon was subjected to microwave irradiation at 120° C. for 2 hours. LC-MS indicated strong peak of starting material. The mixture was degassed with nitrogen and re-applied to microwave irradiation at 120° C. for 2 hours. The mixture was cooled to room temperature and concentrated in vacuo. The residue was purified via preparative HPLC (100×21.2 mm C18 column, CH3CN/water[10 mM Et2NH]) to afford the desired product as a white solid.

LC-MS: 401.7 [M+1]+; 1H NMR (DMSO-d6, 400 MHz): 9.36 (t, J=5.8 Hz, 1H), 8.60 (t, J=1.4 Hz, 1H), 8.56 (d, J=2.2 Hz, 1H), 8.45 (d, J=1.9 Hz, 1H), 8.21 (s, 1H), 8.04 (d, J=8.1 Hz, 1H), 7.85 (s, 1H), 7.78 (dd, J=1.6, 8.2 Hz, 1H), 7.65 (dd, J=2.4, 8.0 Hz, 1H), 7.22 (d, J=8.0 Hz, 1H), 4.49 (d, J=5.6 Hz, 2H), 2.44 (s, 3H), 2.36 (s, 3H).

Compound 221

(S)—N-(2-Hydroxy-1-(2-methylpyrimidin-5-yl)ethyl)-4'-methyl-5-(methylsulfonyl)biphenyl-3-carboxamide

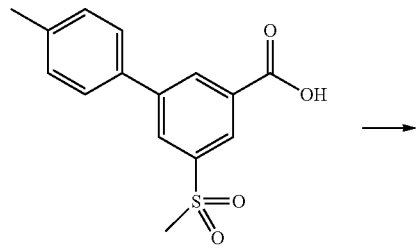

152

-continued

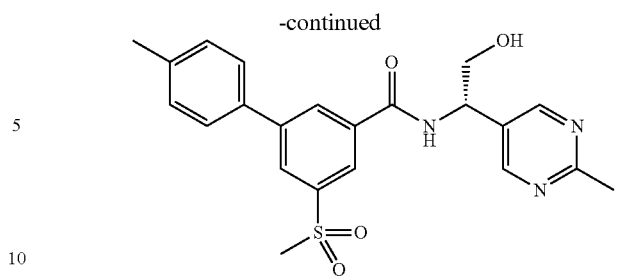

To a mixture of 4'-methyl-5-(methylsulfonyl)biphenyl-3-carboxylic acid (35 mg, 0.12 mmol), N-(3-dimethylaminopropyl)-N'-ethylcarbodiimide hydrochloride (46 mg, 0.24 mmol), 1-hydroxybenzotriazole hydrate (18 mg, 0.12 mmol), and CH2Cl2 (3 mL) were added (S)-2-(tert-butyldimethylsilyloxy)-1-(2-methylpyrimidin-5-yl)ethanamine (48 mg, 0.18 mmol) (WO 2008/130481) and N,N-diisopropylethylamine (42 μL, 0.24 mmol). The mixture was stirred at room temperature overnight and then concentrated. The residue was dissolved in MeOH (5 mL) and concentrated HCl solution (0.5 mL) was added. The mixture was stirred at room temperature for 2 h and then concentrated in vacuo. The residue was purified by preparative HPLC (100×20.2 mm, C18 column; 30-80% MeCN-water[10 mM Et2NH]) to afford a white solid.

LC-MS: 426 [M+1]+; 1H NMR (CDCl3, 400 MHz): 8.78 (s, 2H), 8.32 (t, 1H, J=1.6 Hz), 8.30-8.25 (m, 2H), 7.53 (d, 2H, J=8.0 Hz), 7.47 (d, 1H, J=7.2 Hz), 7.29 (d, 2H, J=8.0 Hz), 5.30 (m, 1H), 4.17 (dd, 1H, J=10.8, 4.0 Hz), 4.05 (dd, 1H, J=10.8, 4.8 Hz), 3.13 (s, 3H), 2.73 (s, 3H), 2.41 (s, 3H).

Compound 224

2-Methyl-5-((4'-methyl-5-(pyrrolidine-1-carbonyl)biphenyl-3-ylcarboxamido)methyl)pyridine 1-oxide

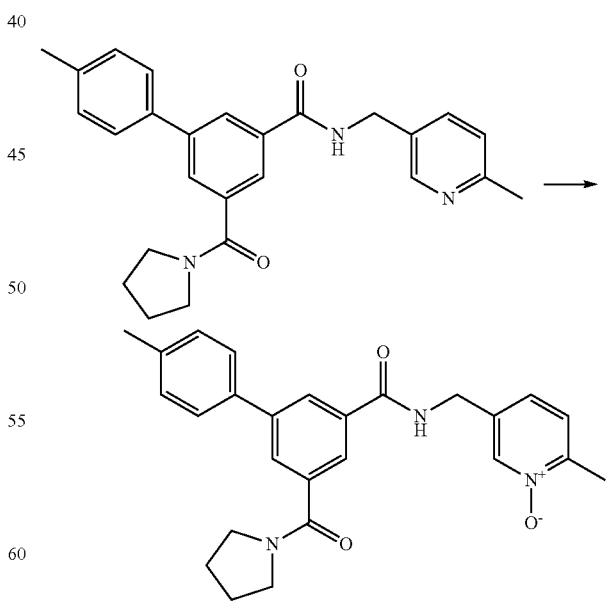

A 20 mL reaction vial was charged with 4'-methyl-N-((6-methylpyridin-3-yl)methyl)-5-(pyrrolidine-1-carbonyl)biphenyl-3-carboxamide (30 mg, 0.073 mmol) and methylene chloride (1.0 mL). The mixture was cooled to 0° C. and m-chloroperbenzoic acid (70% purity, 28 mg, 0.11 mmol) in water was added dropwise. The reaction mixture was allowed to stir for an additional 3 hr upon which water was added. The aqueous layer was extracted with dichloromethane and the combined organic layers were dried and concentrated. The resulting solid was purified by preparative HPLC to afford the title compound.

LC-MS: 429.6 [M+1]$^+$.

Compound 225

(R)-3-Methoxy-5-(5-methylpyridin-2-yl)-N-(1-(2-methylpyrimidin-5-yl)ethyl)benzamide

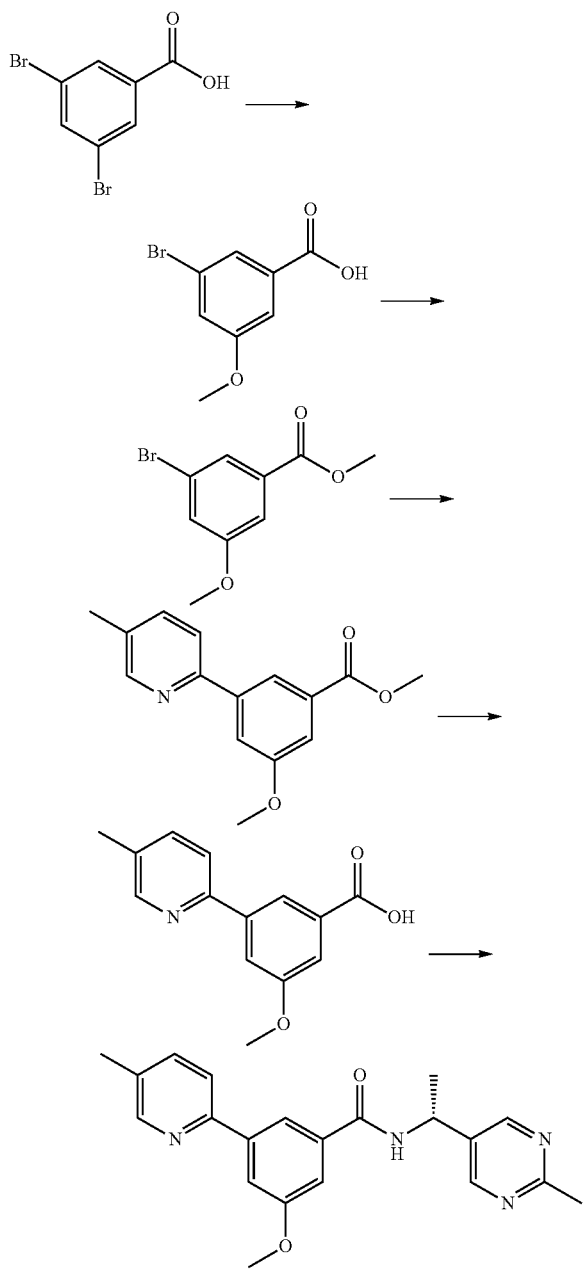

A) 3-Bromo-5-methoxybenzoic acid

A 3-necked flask was charged with 3,5-dibromobenzoic acid (1.0 g, 3.6 mmol), 4 M sodium methoxide solution in methanol (1.2 mL, 4.8 mmol), N,N-dimethylformamide (1.2 mL). The mixture was heated at 110° C. and then copper(I) bromide (51 mg, 0.36 mmol) was added. The mixture was stirred at 110° C. over 4 days. After cooling, the mixture was poured into 1N aq. HCl and adjusted to low pH, extracted with $CH_2Cl_2$. The organic layer was dried over $Na_2SO_4$, concentrated to dryness. The crude product was used for the next step reaction without further purification. LC-MS: 231.2 [M−1]$^-$.

B) Methyl 3-bromo-5-methoxybenzoate

To a stirred mixture of crude 3-bromo-5-methoxybenzoic acid (40% purity, 0.8 g, 1.4 mmol) in $CH_2Cl_2$ (50 mL) at 0° C. were added DMF (0.1 mL) and acetyl chloride (0.2 mL, 3 mmol). The mixture was slowly warmed to rt and stirred overnight. Then the mixture was cooled to 0° C. and methanol (2 mL) was slowly added. The mixture was stirred at rt for 3 h and then washed with aq. $Na_2CO_3$ solution, brine, dried ($Na_2SO_4$), and concentrated. The residue was purified via flash chromatography to afford the desired product as a white solid. $^1$H NMR (CDCl$_3$, 400 MHz): 7.76 (t, J=1.6 Hz, 1H), 7.49 (t, J=1.3 Hz, 1H), 7.24 (t, J=2.2 Hz, 1H), 3.92 (s, 3H), 3.84 (s, 3H).

C) Methyl 3-methoxy-5-(5-methylpyridin-2-yl)benzoate

A mixture of methyl 3-bromo-5-methoxybenzoate (0.1 g, 0.4 mmol), 5-methyl-2-(tributylstannyl)pyridine (0.1 mL, 0.3 mmol), tetrakis(triphenylphosphine)palladium(0) (20 mg, 0.02 mmol) and toluene (4 mL) under argon was subjected to microwave irradiation at 120° C. for 2 hours. The mixture was cooled to room temperature and purified via flash chromatography to afford the desired product as a light yellow oil. LC-MS: 257.9 [M+1]$^+$.

D) 3-Methoxy-5-(5-methylpyridin-2-yl)benzoic acid

Into a flask were charged methyl 3-methoxy-5-(5-methylpyridin-2-yl)benzoate (80 mg, 0.2 mmol), barium hydroxide octahydrate (300 mg, 0.95 mmol), and methanol (10 mL). The mixture was stirred at room temperature overnight. 2N HCl (ethyl ether solution, 30 mL) was added and the volatiles were removed under reduced pressure. LC-MS: 244.1 [M+1]$^+$.

E) (R)-3-Methoxy-5-(5-methylpyridin-2-yl)-N-(1-(2-methylpyrimidin-5-yl)ethyl)benzamide Into a round-bottom flask were charged 3-methoxy-5-(5-methylpyridin-2-yl)benzoic acid (26 mg, 0.11 mmol), (R)-1-(2-methylpyrimidin-5-yl)ethanamine (29 mg, 0.21 mmol), N-(3-dimethylaminopropyl)-N'-ethylcarbodiimide hydrochloride (41 mg, 0.21 mmol), 1-hydroxybenzotriazole hydrate (33 mg, 0.21 mmol), triethylamine (22 mg, 0.21 mmol) and methylene chloride (3 mL). The mixture was stirred at room temperature overnight, and then concentrated. The residue was purified via preparative HPLC (100×21.2 mm C18 column, CH$_3$CN/water[10 mM Et$_2$NH]) to afford the desired product as a white solid.

LC-MS: 363.1 [M+1]$^+$; $^1$H NMR (400 MHz, CD$_3$OD): 8.65 (s, 1H), 8.60 (s, 1H), 8.38 (d, J=1.9 Hz, 1H), 7.87 (t, J=1.5 Hz, 1H), 7.72 (d, J=8.1 Hz, 1H), 7.65 (dd, J=1.6, 8.1 Hz,

1H), 7.58 (dd, J=1.6, 2.4 Hz, 1H), 7.34 (dd, J=1.6, 2.4 Hz, 1H), 5.17 (q, J=7.1 Hz, 1H), 3.82 (s, 3H), 2.57 (s, 3H), 2.31 (s, 3H), 1.55 (d, J=7.1 Hz, 3H).

Compound 227

5-(Hydroxy(phenyl)methyl)-4'-methyl-N—((R)-1-(6-methylpyridin-3-yl)ethyl)biphenyl-3-carboxamide

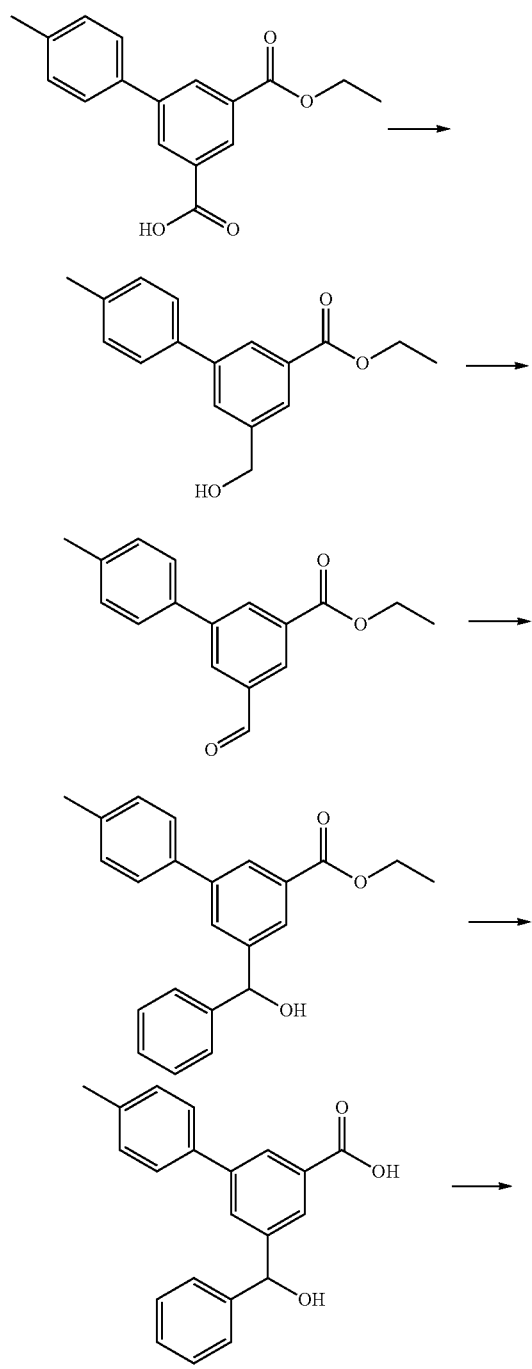

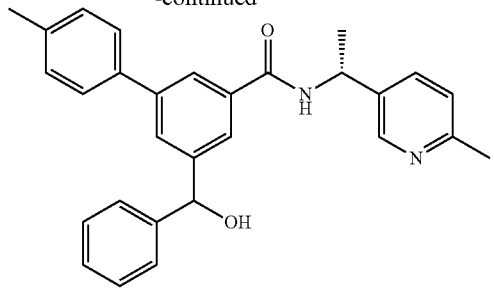

A) Ethyl 5-(hydroxymethyl)-4'-methylbiphenyl-3-carboxylate

To a stirred solution of 5-(ethoxycarbonyl)-4'-methylbiphenyl-3-carboxylic acid (2.66 g, 8.89 mmol) in dry tetrahydrofuran (40 mL) at 0° C. under an atmosphere of nitrogen was added 1 M of borane solution in tetrahydrofuran (20 mL, 20 mmol). The reaction was stirred at 0° C. for 30 minutes after the addition was complete, and then the cooling bath was removed. After being stirred for 2 hours at room temperature, the reaction mixture was cooled at 0° C. and quenched by addition of 2 M aq. HCl (30 mL). The mixture was stirred for 1 hour at room temperature, and then extracted with EtOAc (50 mL×3). The combined organic layers were washed with brine, dried over anhydrous MgSO$_4$, filtered, and concentrated. The residue was purified by silica gel column to afford the title compound.

B) Ethyl 5-formyl-4'-methylbiphenyl-3-carboxylate

A mixture of ethyl 5-(hydroxymethyl)-4'-methylbiphenyl-3-carboxylate (400 mg, 1.5 mmol) and manganese(IV) oxide (660 mg, 6.6 mmol) in methylene chloride (14 mL) was stirred at room temperature overnight. The reaction mixture was filtered through Celite and washed with methylene chloride. The filtrate was concentrated to afford the title compound.

C) Ethyl 5-(hydroxy(phenyl)methyl)-4'-methylbiphenyl-3-carboxylate

Phenylmagnesium bromide (850 mg, 4.7 mmol) was added to a solution of ethyl 5-formyl-4'-methylbiphenyl-3-carboxylate (360 mg, 1.3 mmol) in tetrahydrofuran (8 mL) at 0° C. The reaction mixture was stirred at room temperature for 3 h, and then water (10 mL) was added. The mixture was extracted with EtOAc (20 mL×2). The combined organic layers were dried over anhydrous MgSO$_4$ and concentrated. The residue was purified by silica gel column chromatography to afford the title compound.

D) 5-(Hydroxy(phenyl)methyl)-4'-methylbiphenyl-3-carboxylic acid

To a solution of ethyl 5-(hydroxy(phenyl)methyl)-4'-methylbiphenyl-3-carboxylate (230 mg, 0.66 mmol) in 1,4-dioxane (2 mL) and water (1 mL) was added lithium hydroxide (48 mg, 2 mmol). The reaction mixture was stirred at 60° C. overnight. After cooling, the mixture was acidified with 15% HCl (aq.) to pH=5, and extracted with EtOAc. The organic layer was dried and concentrated in vacuo to afford the title compound as a white solid. $^1$H NMR (300 MHz, acetone-d6):

8.14 (t, 1H, J=2.0 Hz), 8.09 (m, 1H), 7.97 (m, 1H), 7.60-7.47 (m, 4H), 7.37-7.19 (m, 5H), 6.00 (s, 1H), 2.37 (s, 3H).

E) 5-(Hydroxy(phenyl)methyl)-4'-methyl-N—((R)-1-(6-methylpyridin-3-yl)ethyl)biphenyl-3-carboxamide To a solution of 5-(hydroxy(phenyl)methyl)-4'-methylbiphenyl-3-carboxylic acid (50 mg, 0.16 mmol) in N,N-dimethylformamide (1 mL) were added (R)-1-(6-methylpyridin-3-yl)ethanamine dihydrochloride (70 mg, 0.34 mmol), N,N,N',N'-tetramethyl-O-(7-azabenzotriazol-1-yl)uronium hexafluorophosphate (120 mg, 0.32 mmol) and N,N-diisopropylethylamine (500 µL, 2.87 mmol). The reaction mixture was stirred for 16 hours at 30° C. The reaction mixture was purified by preparative HPLC (100×21.2 mm C18 column, CH$_3$CN/water[1 mM Et$_2$NH]) to afford a light color solid.

LC-MS: 437.2 [M+1]$^+$; $^1$H NMR (400 MHz, DMSO-d6): 8.92 (d, 1H, J=7.8 Hz), 8.47 (d, 1H, J=2.1 Hz), 7.98 (bs, 1H), 7.83 (bs, 1H), 7.79 (bs, 1H), 7.67 (dd, 1H, J=8.0, 2.2 Hz), 7.59 (d, 2H, J=8.1 Hz), 7.42 (d, 2H, J=7.3 Hz0, 7.35-7.25 (m, 4H), 7.23-7.15 (m, 2H), 6.04 (m, 1H), 5.82 (d, 1H, J=4.0 Hz), 5.17 (m, 1H), 2.43 (s, 3H), 2.35 (s, 3H), 1.50 (d, 3H, J=7.1 Hz).

Compound 229

(R)-5-Benzoyl-4'-methyl-N-(1-(6-methylpyridin-3-yl)ethyl)biphenyl-3-carboxamide

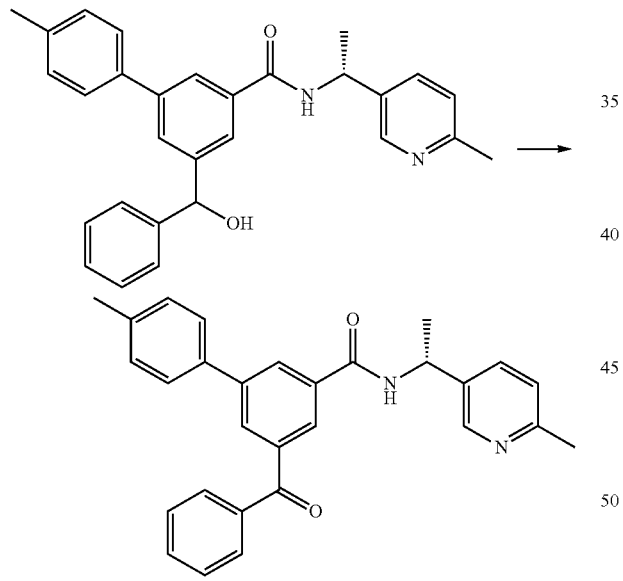

To a solution of 5-(hydroxy(phenyl)methyl)-4'-methyl-N—((R)-1-(6-methylpyridin-3-yl)ethyl)biphenyl-3-carboxamide (20 mg, 0.04 mmol) in methylene chloride (2.0 mL) was added Dess-Martin periodinane (26 mg, 0.061 mmol). The reaction mixture was stirred for 2 hours at 40° C., and LC-MS indicated the reaction was complete. The reaction solution was diluted with CH$_2$Cl$_2$, washed with 10% Na$_2$S$_2$O$_3$, sat. aq. NaHSO$_3$ and brine. The organic layer was dried over anhydrous MgSO$_4$ and concentrated. The residue was purified by silica gel column to afford a white solid.

LC-MS: 435.3 [M+1]$^+$; $^1$H NMR (400 MHz, DMSO-d6): 9.13 (d, 1H, J=7.7 Hz), 8.48 (d, 1H, J=2.2 Hz), 8.42 (t, 1H, J=1.5 Hz), 8.16 (bs, 1H), 8.06 (t, 1H, J=1.5 Hz), 7.85-7.55 (m, 8H), 7.33 (d, 2H, J=8.1 Hz), 7.21 (d, 1H, J=8.0 Hz), 5.20 (m, UT), 2.43 (s, 3H), 2.37 (s, 3H), 1.52 (d, 3H, J=7.1 Hz).

Compound 232

(R)-4'-Methyl-N-(1-(6-methylpyridin-3-yl)ethyl)-5-(pyrimidin-2-yloxy)biphenyl-3-carboxamide

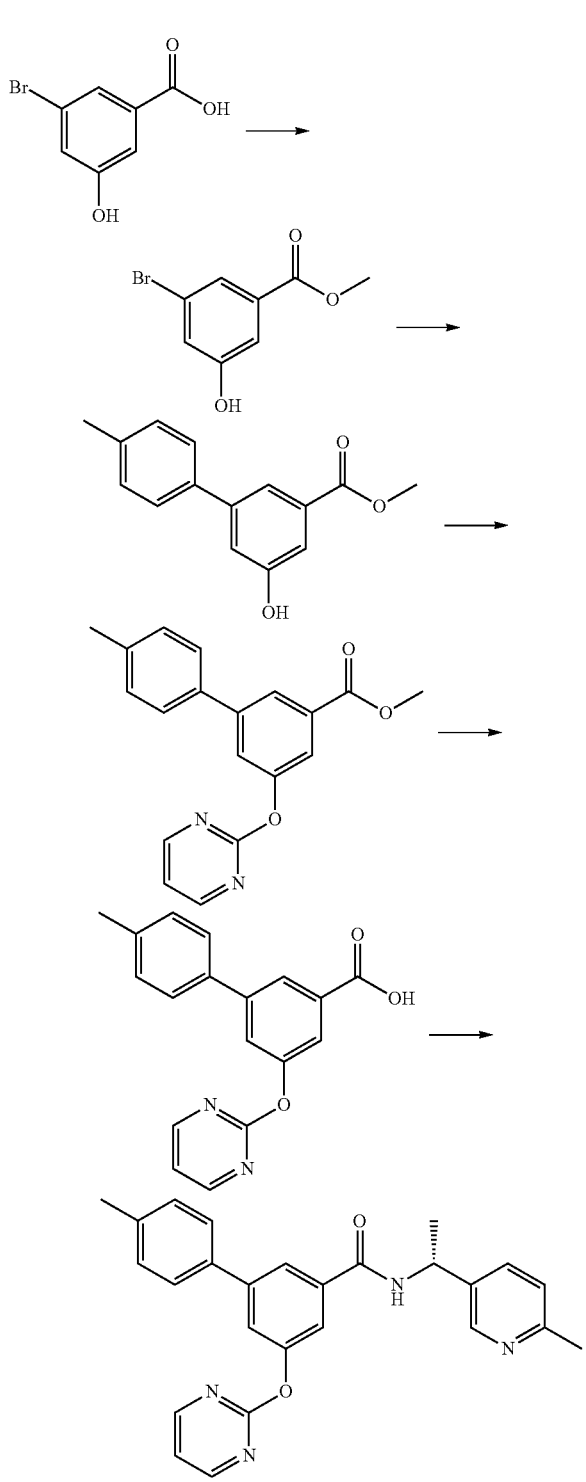

A) 3-Bromo-5-hydroxy-benzoic acid methyl ester

To a solution of 3-bromo-5-hydroxybenzoic acid (3.41 g, 15 mmol) (J. Chem. Soc. 1955, 463) in anhydrous methanol (80 mL) was added acetyl chloride (2.56 mL, 36 mmol) at 0° C. The mixture was then heated under reflux overnight. The volatiles were removed in vacuo to afford the title compound.

B) Methyl 5-hydroxy-4'-methylbiphenyl-3-carboxylate

To a stirred solution of 3-bromo-5-hydroxy-benzoic acid methyl ester (4.09 g, 17.7 mmol) and p-tolylboronic acid (2.86 g, 21 mmol) in toluene (36 mL) was added cesium carbonate (7.14 g, 22 mmol) in water (3.6 mL) at room temperature. The mixture was purged with nitrogen, and tetrakis(triphenylphosphine)palladium(0) (1.05 g, 0.906 mmol) was added. The reaction mixture was subjected to microwave irradiation at 110° C. for 1 hour. After cooling, the mixture was filtered through Celite and the filtrate was concentrated. The residue was purified by flash chromatography to afford the title compound.

C) Methyl 4'-methyl-5-(pyrimidin-2-yloxy)biphenyl-3-carboxylate

To a stirred solution of methyl 5-hydroxy-4'-methylbiphenyl-3-carboxylate (300 mg, 1.24 mmol) in tetrahydrofuran (20 mL) at 0° C. was added sodium hydride (60% in mineral oil, 55 mg, 1.37 mmol) over a period of 10 minutes. The reaction mixture was concentrated to afford a green solid. A microwave vial was charged with the resulting green solid, dimethyl sulfoxide (8 mL), and 2-chloropyrimidine (118 mg, 0.98 mmol). The mixture was subjected to microwave irradiation at 100° C. for 4 minutes. After cooling, the mixture was filtered through Celite and the filtrate was concentrated. The residue was purified by flash chromatography to afford the title compound.

D) 4'-Methyl-5-(pyrimidin-2-yloxy)biphenyl-3-carboxylic acid

To a stirred solution of methyl 4'-methyl-5-(pyrimidin-2-yloxy)biphenyl-3-carboxylate (60 mg, 0.19 mmol) in tetrahydrofuran (3 mL) was added 2.5 M aqueous lithium hydroxide solution (0.77 mL, 1.9 mmol). The mixture was stirred at room temperature overnight, and then acidified to pH=5 by addition of 2N aqueous HCl and extracted with EtOAc (50 mL). The organic layer was separated, dried over sodium sulfate, filtered and concentrated to afford the title product. $^1$H NMR (CD$_3$OD, 400 MHz): 8.63 (d, 2H, J=4.8 Hz), 8.16 (t, 1H, J=1.6 Hz), 7.74 (t, 1H, J=2.0 Hz), 7.65 (t, 1H, J=2.0 Hz), 7.56 (d, 2H, J=8.0 Hz), 7.29 (d, 2H, J=8.0 Hz), 7.24 (t, 1H, J=4.8 Hz), 2.39 (s, 3H).

E) (R)-4'-Methyl-N-(1-(6-methylpyridin-3-yl)ethyl)-5-(pyrimidin-2-yloxy)biphenyl-3-carboxamide To a solution of 4'-methyl-5-(pyrimidin-2-yloxy)biphenyl-3-carboxylic acid (20 mg, 0.065 mmol) in N,N-dimethylformamide (1 mL) were added (R)-1-(6-methylpyridin-3-yl)ethanamine dihydrochloride (30 mg, 0.143 mmol), N,N,N',N'-tetramethyl-O-(7-azabenzotriazol-1-yl)uronium hexafluorophosphate (60 mg, 0.16 mmol), and N,N-diisopropylethylamine (200 μL, 1.15 mmol). The reaction mixture was stirred at room temperature for 16 hours. LC-MS indicated the reaction was complete. The reaction mixture was purified by preparative HPLC (100×21.2 mm C18 column, CH$_3$CN/water[10 mM Et$_2$NH]) to afford a light color solid.

LC-MS: 425.1 [M+1]$^+$; $^1$H NMR (DMSO-d6, 400 MHz): 8.97 (d, 1H, J=7.8 Hz), 8.67 (d, 2H, J=4.8 Hz), 8.47 (d, 1H, J=2.2 Hz), 8.06 (t, 1H, J=1.4 Hz), 7.70-7.62 (m, 5H), 7.32-7.25 (m, 3H), 7.21 (d, 1H, J=8.0 Hz), 5.18 (m, 1H), 2.43 (s, 3H), 2.36 (s, 3H), 1.51 (d, 3H, J=7.1 Hz).

Compound 236

(R)-4'-Methyl-N-(1-(2-methylpyrimidin-5-yl)ethyl)-5-(thiazol-2-yloxy)biphenyl-3-carboxamide

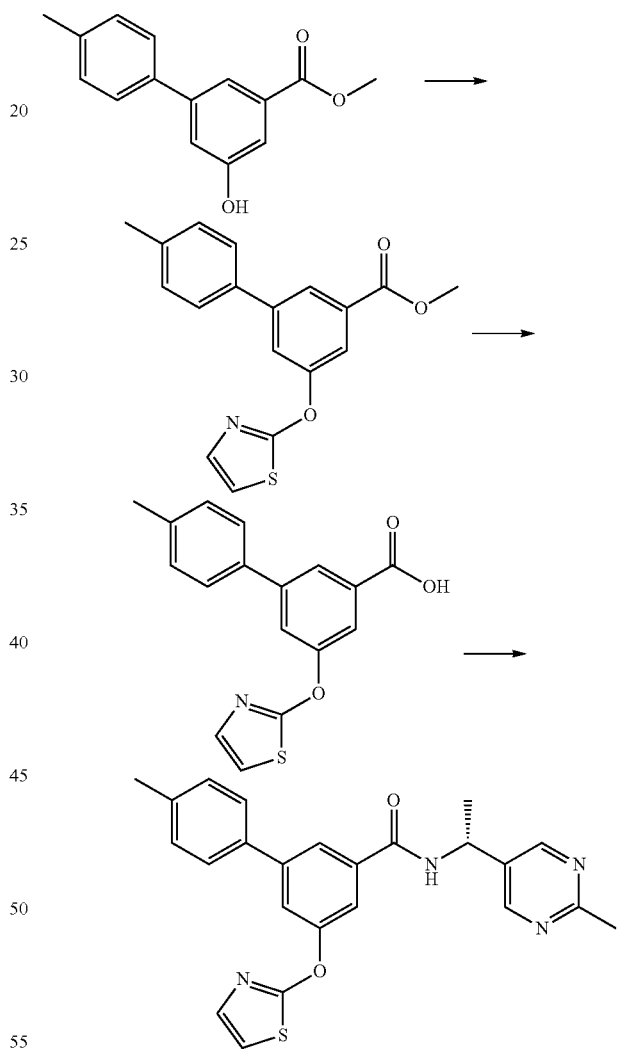

A) Methyl 4'-methyl-5-(thiazol-2-yloxy)biphenyl-3-carboxylate

A mixture of methyl 5-hydroxy-4'-methylbiphenyl-3-carboxylate (100 mg, 0.41 mmol), potassium carbonate (114 mg, 0.83 mmol), 2-bromothiazole (0.38 mL, 4.2 mmol), and dimethyl sulfoxide (2.5 mL) was stirred at 135° C. overnight. After cooling, the mixture was diluted with EtOAc and washed with aq. NaHCO$_3$ (sat.), dried over anhydrous MgSO₄, and concentrated. The residue was purified by flash chromatography (0-20% EtOAc/hexane) to afford the title compound.

B) 4'-Methyl-5-(thiazol-2-yloxy)biphenyl-3-carboxylic acid

To a stirred solution of methyl 4'-methyl-5-(thiazol-2-yloxy)biphenyl-3-carboxylate (560 mg, 1.6 mmol) in tetrahydrofuran (20 mL) was added 2.5 M aqueous lithium hydroxide solution (6.7 mL, 17 mmol). After being stirred at room temperature overnight, the mixture was acidified to pH=5 by addition of 2N aq. HCl and extracted with EtOAc. The organic layer was dried over sodium sulfate, and concentrated to afford the title product. ¹H NMR (CD₃OD, 400 MHz): 8.18 (t, 1H, J=1.6 Hz), 7.82 (dd, 1H, J=2.4, 1.2 Hz), 7.74 (t, 1H, J=2.0 Hz), 7.57 (d, 2H, J=8.0 Hz), 7.30 (d, 2H, J=8.4 Hz), 7.28 (d, 1H, J=4.0 Hz), 7.13 (d, 1H, J=4.0 Hz), 2.39 (s, 3H).

C) (R)-4'-Methyl-N-(1-(2-methylpyrimidin-5-yl)ethyl)-5-(thiazol-2-yloxy)biphenyl-3-carboxamide To a solution of 4'-methyl-5-(thiazol-2-yloxy)biphenyl-3-carboxylic acid (50 mg, 0.16 mmol) in N,N-dimethylformamide (1 mL) were added (R)-1-(2-methylpyrimidin-5-yl)ethanamine (45 mg, 0.33 mmol), N,N,N',N'-tetramethyl-O-(7-azabenzotriazol-1-yl)uronium hexafluorophosphate (150 mg, 0.39 mmol) and N,N-diisopropylethylamine (200 µL, 1.15 mmol). The reaction mixture was stirred at room temperature for 16 hours. LC-MS indicated the reaction was complete. The reaction mixture was purified by preparative HPLC (100×21.2 mm C18 column, CH₃CN/water[10 mM Et₂NH]) to afford a light color solid.

LC-MS: 431.2 [M+1]⁺; ¹H NMR (400 MHz, DMSO-d6): 9.07 (d, 1H, J=7.4 Hz), 8.73 (s, 2H), 8.10 (t, 1H, J=1.4 Hz), 7.82 (t, 1H, J=2.0 Hz), 7.76 (t, 1H, J=1.5 Hz), 7.68 (d, 2H, J=8.2 Hz), 7.35-7.25 (m, 4H), 5.18 (m, 1H), 2.59 (s, 3H), 2.36 (s, 3H), 1.55 (d, 3H, J=7.1 Hz).

Compound 240

5-(Hydroxy(pyridin-2-yl)methyl)-4'-methyl-N-((6-methylpyridin-3-yl)methyl)biphenyl-3-carboxamide

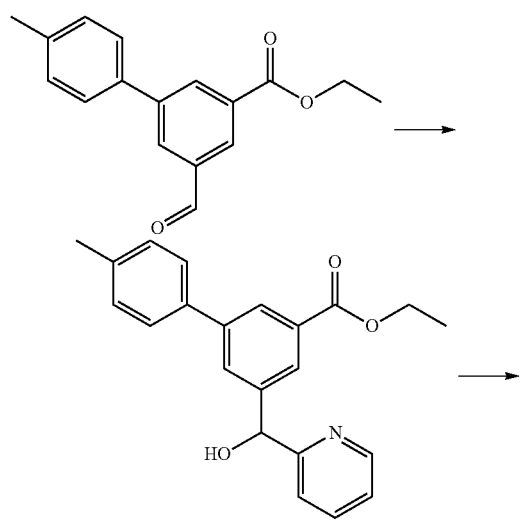

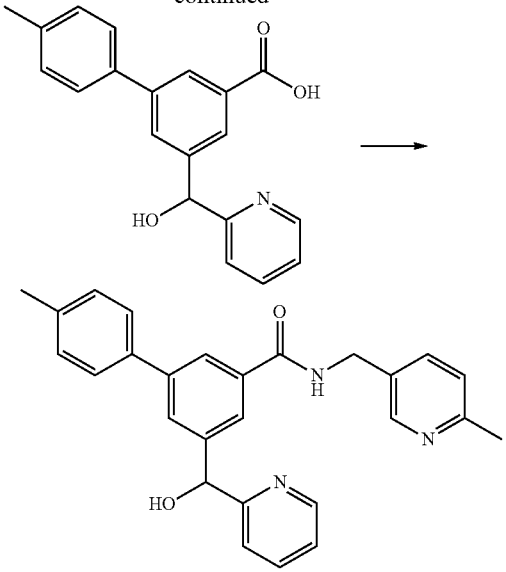

A) Ethyl 5-(hydroxy(pyridin-2-yl)methyl)-4'-methylbiphenyl-3-carboxylate

The Grignard reagent was generated by treatment of magnesium (100 mg, 4.3 mmol) with a solution of 2-bromopyridine (600 mg, 3.8 mmol) and iodine (30 mg) in tetrahydrofuran (5 mL) under nitrogen at 60° C. for 1 hour. The mixture was cooled at 0° C. and ethyl 5-formyl-4'-methylbiphenyl-3-carboxylate (332 mg, 1.24 mmol) was added. The reaction mixture was stirred at 0° C. for 2 h and then quenched by addition of 3 mL of 2 N aq. H₂SO₄. The mixture was extracted with EtOAc (20 mL×2). The combined organic layers were washed with 1 N aq. NaOH, brine, dried over anhydrous MgSO₄, filtered, and concentrated. The residue was chromatographed to yield a yellow oil.

B) 5-(Hydroxy-pyridin-2-yl-methyl)-4'-methyl-biphenyl-3-carboxylic acid

Ethyl 5-(hydroxy(pyridin-2-yl)methyl)-4'-methylbiphenyl-3-carboxylate (319 mg, 0.92 mmol) was dissolved in 1,4-dioxane (6 mL) and water (0.3 mL). To the stirred solution was added lithium hydroxide (120 mg, 5.0 mmol) and the reaction mixture was stirred at room temperature until the reaction was complete. The mixture was cooled and acidified with 2N aq. H₂SO₄ to pH 5-6 and extracted with EtOAc (20 mL×3). The combined organic layers were washed with brine, dried (MgSO₄), and concentrated to yield a light yellow solid. ¹H NMR (400 MHz, CD₃OD): 8.47 (m, 1H), 8.13 (t, 1H, J=1.6 Hz), 8.02 (t, 1H, J=1.6 Hz), 7.91 (t, 1H, J=1.6 Hz), 7.87 (td, 1H, J=7.6, 1.6 Hz), 7.71 (d, 1H, J=8.0 Hz), 7.51 (d, 2H, J=8.0 Hz), 7.31 (ddd, 1H, J=7.6, 5.2, 1.2 Hz), 7.27 (d, 2H, J=8.0 Hz), 5.93 (s, 1H), 2.37 (s, 3H).

C) 5-(Hydroxy(pyridin-2-yl)methyl)-4'-methyl-N-((6-methylpyridin-3-yl)methyl)biphenyl-3-carboxamide To a solution of 5-(hydroxy-pyridin-2-yl-methyl)-4'-methyl-biphenyl-3-carboxylic acid (35 mg, 0.11 mmol) in N,N-dimethylformamide (1 mL) were added (6-methylpyridin-3-yl)methanamine (40 mg, 0.33 mmol), N,N,N',N'-tetramethyl- O-(7-azabenzotriazol-1-yl)uronium hexafluorophosphate (100 mg, 0.26 mmol), and N,N-diisopropylethylamine (100 µL, 0.57 mmol). The reaction mixture was stirred for 16 hours at 25° C. The reaction mixture was purified by preparative HPLC (100×21.2 mm C18 column, CH$_3$CN/water[10 mM Et$_2$NH]) to afford a light color solid.

LC-MS: 424.1 [M+1]$^+$; $^1$H NMR (400 MHz, DMSO-d6): 9.15 (t, 1H, J=5.5 Hz), 8.46 (d, 1H, J=4.0 Hz), 8.41 (bs, 1H), 7.99 (bs, 1H), 7.88 (bs, 1H), 7.83 (bs, 1H), 7.79 (t, 1H, J=7.8 Hz), 7.65-7.55 (m, 4H), 7.30 (d, 2H, J=7.6 Hz), 7.22 (m, 2H), 6.26 (bs, 1H), 5.83 (bs, 1H), 4.45 (d, 2H, J=5.4 Hz), 2.43 (s, 3H), 2.35 (s, 3H).

Compound 241

5-(Hydroxy(pyridin-2-yl)methyl)-4'-methyl-N—((R)-1-(6-methylpyridin-3-yl)ethyl)biphenyl-3-carboxamide

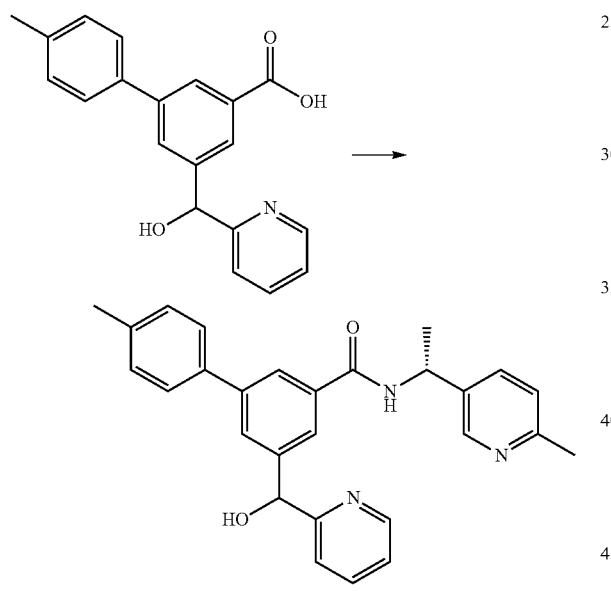

To a solution of 5-(hydroxy-pyridin-2-yl-methyl)-4'-methyl-biphenyl-3-carboxylic acid (25 mg, 0.078 mmol) in N,N-dimethylformamide (1 mL) were added (R)-1-(6-methylpyridin-3-yl)ethanamine dihydrochloride (35 mg, 0.17 mmol), N,N,N',N'-tetramethyl-O-(7-azabenzotriazol-1-yl) uronium hexafluorophosphate (50 mg, 0.13 mmol), and N,N-diisopropylethylamine (200 µL, 1.15 mmol). The reaction mixture was stirred for 16 hours at 25° C., and then purified by preparative HPLC (100×21.2 mm C18 column, CH$_3$CN/water[10 mM Et$_2$N11]) to afford a light color solid.

LC-MS: 438.1 [M+1]$^+$; $^1$H NMR (400 MHz, DMSO-d6): 8.92 (d, 1H, J=7.8 Hz), 8.45 (bs, 2H), 7.98 (bs, 1H), 7.85 (bs, 1H), 7.81 (bs, 1H), 7.79 (t, 1H, J=7.2 Hz), 7.70-7.55 (m, 4H), 7.30 (d, 2H, J=8.0 Hz), 7.22 (m, 2H), 6.25 (bs, 1H), 5.83 (s, 1H), 5.20-5.10 (m, 1H), 2.43 (s, 3H), 2.35 (s, 3H), 1.50 (d, 3H, J=7.1 Hz).

Compound 242

(R)-4'-Methyl-N-(1-(6-methylpyridin-3-yl)ethyl)-5-(pyridin-2-yloxy)biphenyl-3-carboxamide

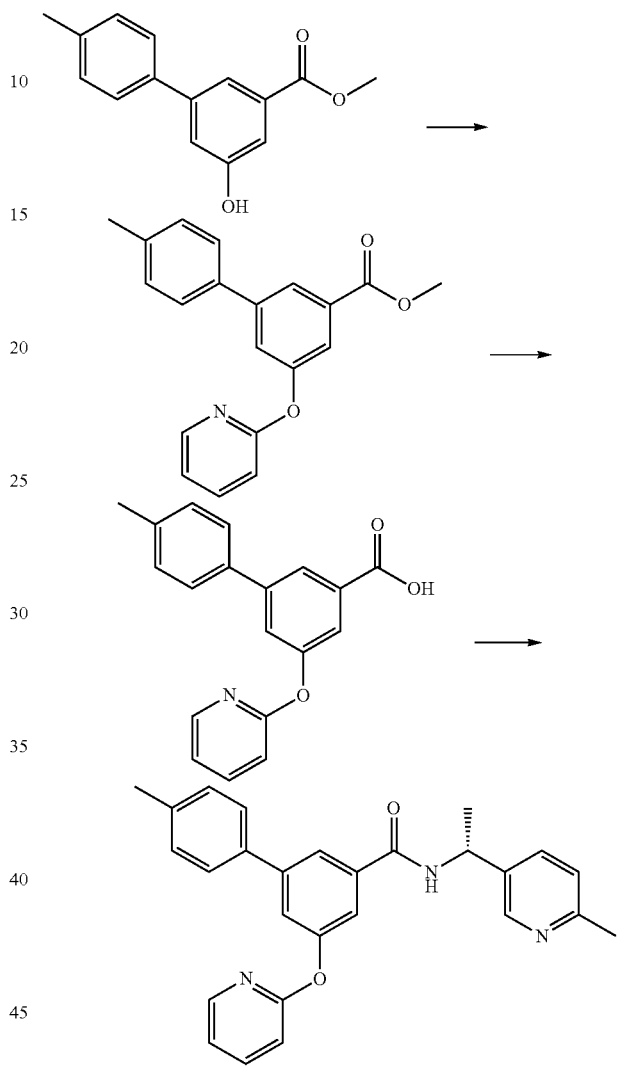

A) Methyl 4'-methyl-5-(pyridin-2-yloxy)biphenyl-3-carboxylate

A mixture of methyl 5-hydroxy-4'-methylbiphenyl-3-carboxylate (100 mg, 0.41 mmol), potassium carbonate (100 mg, 0.72 mmol), 2-bromopyridine (0.40 mL, 4.2 mmol), and dimethyl sulfoxide (2 mL) was stirred at 135° C. overnight. After cooling, the mixture was diluted with EtOAc and washed with aq. NaHCO$_3$ (sat.), dried over anhydrous MgSO$_4$, filtered, and concentrated. The residue was purified by flash chromatography (0-20% EtOAc/hexane) to afford the title compound.

B) 4'-Methyl-5-(pyridin-2-yloxy)biphenyl-3-carboxylic acid

To a stirred solution of methyl 4'-methyl-5-(pyridin-2-yloxy)biphenyl-3-carboxylate (460 mg, 1.4 mmol) in tetrahydrofuran (20 mL) was added 2.5 M aqueous lithium hydroxide solution (5.6 mL, 14 mmol). After being stirred at room temperature overnight, the mixture was acidified to pH=5 by addition of 2N aq. HCl and extracted with EtOAc. The organic layer was dried over sodium sulfate, filtered, and concentrated to afford the title compound. $^1$H NMR (CD$_3$OD, 300 MHz): 8.17 (d, 1H, J=3.2 Hz), 8.11 (s, 1H), 7.88 (td, 1H, J=8.0, 2.0 Hz), 7.65 (s, 1H), 7.58-7.52 (m, 3H), 7.29 (d, 2H, J=8.4 Hz), 7.16 (dd, 1H, J=7.2, 4.8 Hz), 7.06 (d, 1H, J=8.0 Hz), 2.38 (s, 3H).

C) (R)-4'-Methyl-N-(1-(6-methylpyridin-3-yl)ethyl)-5-(pyridin-2-yloxy)biphenyl-3-carboxamide To a solution of 4'-methyl-5-(pyridin-2-yloxy)biphenyl-3-carboxylic acid (50 mg, 0.16 mmol) in N,N-dimethylformamide (1 mL) were added (R)-1-(6-methylpyridin-3-yl)ethanamine dihydrochloride (70 mg, 0.34 mmol), N,N,N',N'-tetramethyl-O-(7-azabenzotriazol-1-yl)uronium hexafluorophosphate (150 mg, 0.39 mmol), and N,N-diisopropylethylamine (400 µL, 2.30 mmol). The reaction mixture was stirred for 16 hours at 25° C., and then purified by preparative HPLC to afford the final product as a light color solid.

LC-MS: 424.0 [M+1]$^+$; $^1$H NMR (400 MHz, DMSO-d6): 8.97 (d, 1H, J=7.7 Hz), 8.47 (bs, 1H), 8.15 (d, 1H, J=4.2 Hz), 8.02 (bs, 1H), 7.89 (t, 1H, J=8.5 Hz), 7.70-7.60 (m, 3H), 7.57 (bs, 2H), 7.30 (d, 2H, J=8.0 Hz), 7.25-7.05 (m, 3H), 5.18 (m, 1H), 2.43 (s, 3H), 2.35 (s, 3H), 1.51 (d, 3H, J=7.1 Hz).

Compound 248

5-(2-Methoxyethoxy)-4'-methyl-N-((6-methylpyridin-3-yl)methyl)biphenyl-3-carboxamide

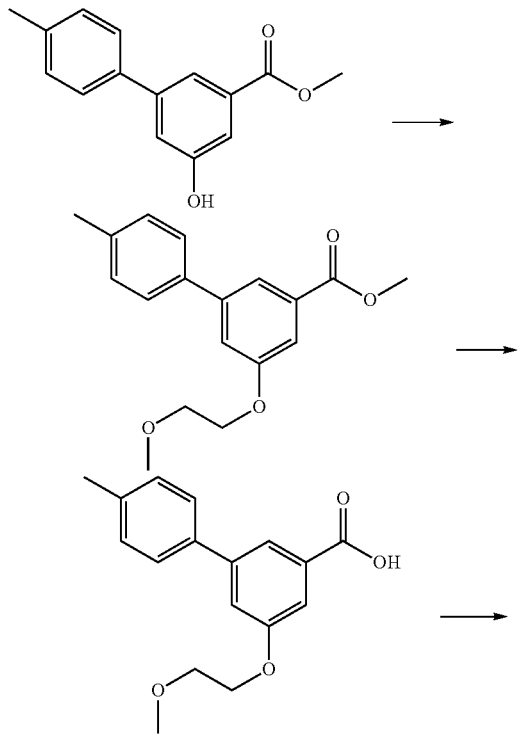

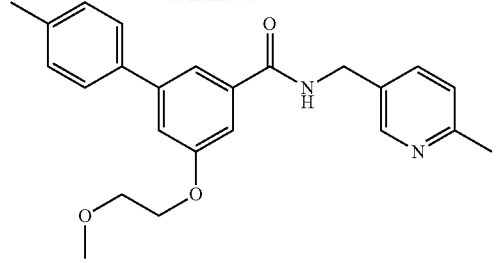

A) Methyl 5-(2-methoxyethoxy)-4'-methylbiphenyl-3-carboxylate

A mixture of methyl 5-hydroxy-4'-methylbiphenyl-3-carboxylate (400 mg, 1.65 mmol), 1-bromo-2-methoxyethane (436 mg, 3.14 mmol), potassium carbonate (434 mg, 3.14 mmol), and dimethyl sulfoxide (5 mL) was stirred at 135° C. overnight. After cooling, the mixture was diluted with EtOAc and washed with aq. NaHCO$_3$ (sat.), dried over anhydrous MgSO$_4$, filtered, and concentrated. The residue was purified by flash chromatography (0-100% EtOAc/hexane) to afford the title compound.

B) 5-(2-Methoxyethoxy)-4'-methylbiphenyl-3-carboxylic acid

To a stirred solution of methyl 5-(2-methoxyethoxy)-4'-methylbiphenyl-3-carboxylate (703 mg, 2.34 mmol) in tetrahydrofuran (40 mL) was added 2.5 M aqueous lithium hydroxide solution (9.6 mL, 24 mmol). After being stirred at room temperature overnight, the mixture was acidified to pH=5 by addition of 2N HCl and extracted with EtOAc. The organic layer was dried (Na$_2$SO$_4$) and concentrated to afford the title compound. $^1$H NMR (CD$_3$OD, 400 MHz): 7.84 (t, 1H, J=1.6 Hz), 7.55-7.51 (m, 3H), 7.34 (t, 1H, J=2.0 Hz), 7.27 (d, 2H, J=8.0 Hz), 4.22 (m, 2H), 3.79 (m, 2H), 3.45 (s, 3H), 2.38 (s, 3H).

C) 5-(2-Methoxyethoxy)-4'-methyl-N-((6-methylpyridin-3-yl)methyl)biphenyl-3-carboxamide To a solution of 5-(2-methoxyethoxy)-4'-methylbiphenyl-3-carboxylic acid (50 mg, 0.18 mmol) in N,N-dimethylformamide (1 mL) were added (6-methylpyridin-3-yl)methanamine (45 mg, 0.37 mmol), N,N,N',N'-tetramethyl-O-(7-azabenzotriazol-1-yl)uronium hexafluorophosphate (150 mg, 0.39 mmol) and N,N-diisopropylethylamine (150 µL, 0.86 mmol). The reaction mixture was stirred for 16 hours at 25° C. LC-MS indicated the reaction was complete. The reaction mixture was purified by preparative HPLC to afford the title product.

LC-MS: 391.5 [M+1]$^+$; $^1$H NMR (400 MHz, DMSO-d6): 9.13 (t, 1H, J=5.8 Hz), 8.42 (d, 1H, J=2.0 Hz), 7.74 (bs, 1H), 7.66-7.60 (m, 3H), 7.40 (bs, 1H), 7.34 (bs, 1H), 7.29 (d, 2H, J=8.0 Hz), 7.22 (d, 1H, J=8.0 Hz), 4.47 (d, 2H, J=5.8 Hz), 4.22 (t, 2H, J=4.4 Hz), 3.69 (t, 2H, J=4.4 Hz), 3.32 (s, 3H), 2.44 (s, 3H), 2.35 (s, 3H).

Compound 254

(R)-2'-Cyano-4'-methyl-N-(1-(2-methylpyrimidin-5-yl)ethyl)-5-(thiazol-2-yloxy)biphenyl-3-carboxamide

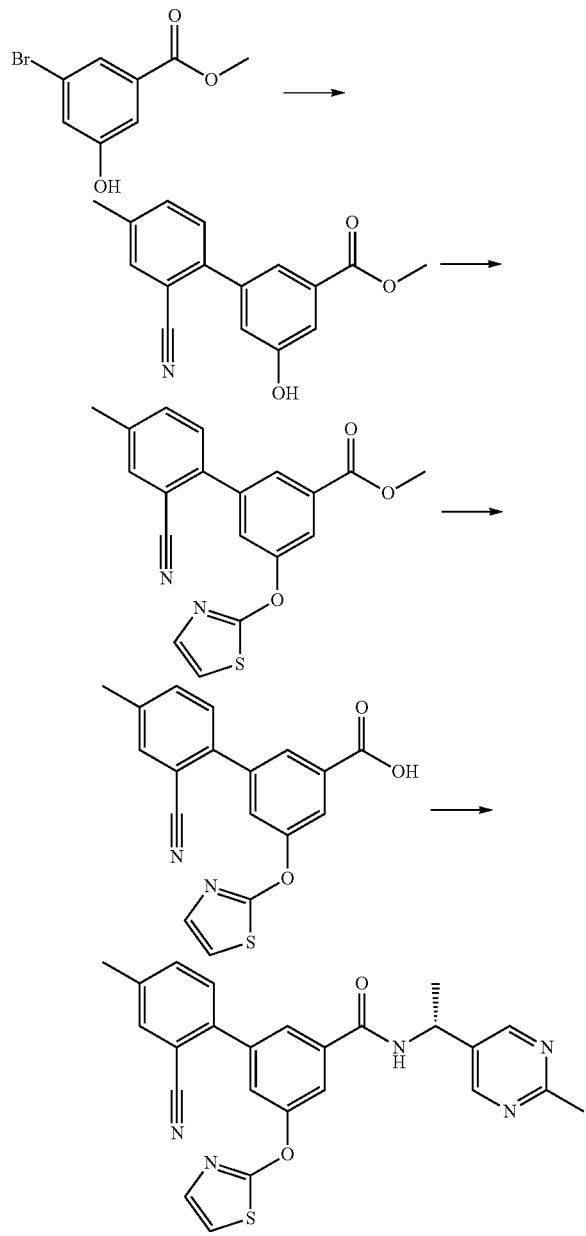

A) Methyl 2'-cyano-5-hydroxy-4'-methylbiphenyl-3-carboxylate

Under an atmosphere of nitrogen, a flask was charged with 5-methyl-2-(4,4,5,5-tetramethyl-1,3,2-dioxaborolan-2-yl)benzonitrile (2.1 g, 8.2 mmol), 3-bromo-5-hydroxy-benzoic acid methyl ester (1.5 g, 6.2 mmol), potassium phosphate (2.8 g, 13 mmol), tetrakis(triphenylphosphine)palladium(0) (400 mg, 0.35 mmol), 1,4-dioxane (90 mL), and water (20 mL). The reaction mixture was stirred at 85° C. overnight. After cooling, the mixture was filtered through Celite and the filter cake was washed with EtOAc. The filtrate was concentrated and the residue was purified by silica gel column to afford the title compound.

B) Methyl 2'-cyano-4'-methyl-5-(thiazol-2-yloxy)biphenyl-3-carboxylate

A stirred mixture of methyl 2'-cyano-5-hydroxy-4'-methylbiphenyl-3-carboxylate (350 mg, 1.2 mmol), potassium carbonate (363 mg, 2.63 mmol), 2-bromothiazole (431 mg, 2.63 mmol), and dimethyl sulfoxide (10 mL) was heated at 135° C. overnight. After cooling, the reaction mixture was diluted with EtOAc. The organic phase was washed with aq. $NaHCO_3$ (sat.), dried over anhydrous $MgSO_4$, filtered, and concentrated. The residue was purified by flash chromatography to afford the title compound.

C) 2'-Cyano-4'-methyl-5-(thiazol-2-yloxy)biphenyl-3-carboxylic acid

To a solution of methyl 2'-cyano-4'-methyl-5-(thiazol-2-yloxy)biphenyl-3-carboxylate (112 mg, 0.32 mmol) in tetrahydrofuran (2 mL) was added 2.5 M of aqueous lithium hydroxide solution (0.72 mL, 1.8 mmol). The reaction mixture was stirred at 60° C. overnight. The aqueous solution was acidified with 15% HCl (aq.) to pH=5, and extracted with EtOAc. The combined organic layers were concentrated in vacuo to get the title compound as a white solid.

D) (R)-2'-Cyano-4'-methyl-N-(1-(2-methylpyrimidin-5-yl)ethyl)-5-(thiazol-2-yloxy)biphenyl-3-carboxamide To a solution of 2'-cyano-4'-methyl-5-(thiazol-2-yloxy)biphenyl-3-carboxylic acid (30 mg, 0.089 mmol) in N,N-dimethylformamide (1 mL) were added (R)-1-(2-methylpyrimidin-5-yl)ethanamine (30 mg, 0.22 mmol), N,N,N',N'-tetramethyl-O-(7-azabenzotriazol-1-yl)uronium hexafluorophosphate (100 mg, 0.26 mmol), and N,N-diisopropylethylamine (100 μL, 0.57 mmol). The reaction mixture was stirred for 16 hours at 25° C., and then purified by preparative HPLC to afford a brown solid.

LC-MS: 455.9 [M+1]$^+$; $^1$H NMR (400 MHz, DMSO-d6): 9.07 (d, 1H, J=7.4 Hz), 8.71 (s, 2H), 8.00 (bs, 1H), 7.94 (t, 1H, J=1.8 Hz), 7.83 (bs, 1H), 7.76 (t, 1H, J=1.8 Hz), 7.68-7.60 (m, 2H), 7.32 and 7.30 (AB, 2H, J=3.7 Hz), 5.17 (m, 1H), 2.59 (s, 3H), 2.41 (s, 3H), 1.53 (d, 3H, J=7.1 Hz).

Compound 256

2-Methyl-5-((4'-methyl-5-(methylsulfonyl)biphenyl-3-ylcarboxamido)methyl)pyridine 1-oxide

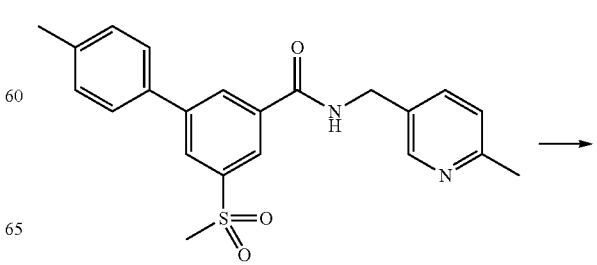

-continued

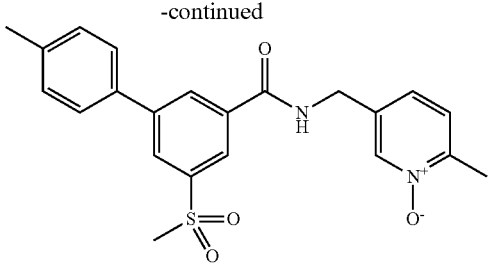

Into a 20 mL reaction vial were charged 4'-methyl-N-((6-methylpyridin-3-yl)methyl)-5-(methylsulfonyl)biphenyl-3-carboxamide (40 mg, 0.10 mmol), m-chloroperbenzoic acid (70% purity, 52 mg, 0.21 mmol), methylene chloride (3 mL), and water (1 mL). The reaction mixture was stirred at room temperature for 12 h. Saturated aq. sodium bicarbonate solution was added and the layers were separated. The organic layer was dried over sodium sulfate and concentrated in vacuo. The resulting oil was purified by flash chromatography (0-10% methanol/methylene chloride) to afford the title compound as a white solid.

LC-MS: 411.2 [M+1]$^+$; $^1$H NMR (400 MHz, DMSO-d6): 9.5 (t, 1H, J=5.8 Hz), 8.47 (t, 1H, J=1.5 Hz), 8.34 (t, 1H, J=1.5 Hz), 8.29 (t, 1H, J=1.5 Hz), 8.27 (s, 1H), 7.75 (d, 2H, J=8.1 Hz), 7.49 (d, 1H, J=8.1 Hz), 7.36 (d, 2H, J=8.1 Hz), 7.26 (d, 1H, J=8.5 Hz), 4.89 (d, 2H, J=5.8 Hz), 3.37 (s, 3H), 2.82 (s, 3H), 2.32 (s, 3H).

Compound 257

(S)—N-(2-Hydroxy-1-(6-methylpyridin-3-yl)ethyl)-4'-methyl-5-(methylsulfonyl)biphenyl-3-carboxamide

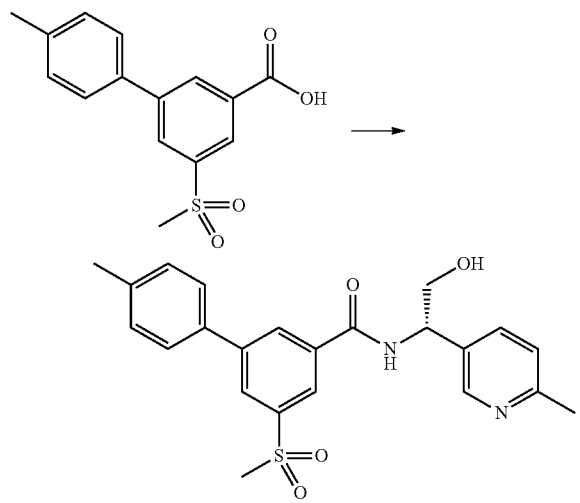

To a solution of 4'-methyl-5-(methylsulfonyl)biphenyl-3-carboxylic acid (37 mg, 0.12 mmol) in N,N-dimethylformamide (1 mL) were added (S)-2-(tert-butyldimethylsilyloxy)-1-(6-methylpyridin-3-yl)ethanamine (80 mg, 0.27 mmol), N,N,N',N'-tetramethyl-O-(7-azabenzotriazol-1-yl)uronium hexafluorophosphate (120 mg, 0.32 mmol) and N,N-diisopropylethylamine (120 µL, 0.69 mmol). The reaction mixture was stirred for 16 hours at 25° C. LC-MS indicated the reaction was complete. To the reaction mixture were added MeOH (2 mL) and 12N aq. HCl (0.5 mL). The mixture was stirred at rt for 2 hrs and then concentrated in vacuo. The residue was purified by preparative HPLC (100×21.2 mm C18 column, MeCN-water[10 mM Et$_2$NH]) to afford the final product as a light color solid.

LC-MS: 425 [M+1]$^+$; $^1$H NMR (400 MHz, DMSO-d6): 9.16 (d, 1H, J=8.0 Hz), 8.49 (d, 1H, J=2.1 Hz), 8.47 (t, 1H, J=1.6 Hz), 8.35 (t, 1H, J=1.6 Hz), 8.28 (t, 1H, J=1.6 Hz), 7.75 (d, 2H, J=8.2 Hz), 7.71 (dd, 1H, J=8.0, 2.2 Hz), 7.37 (d, 2H, J=8.0 Hz), 7.22 (d, 1H J=8.0 Hz), 5.20-5.05 (m, 2H), 3.85-3.65 (m, 2H), 3.35 (s, 3H), 2.44 (s, 3H), 2.39 (s, 3H).

Compound 264

(R)-3-(5-Methylpyridin-2-yl)-N-(1-(6-methylpyridin-3-yl)ethyl)-5-(thiazol-2-yloxy)benzamide

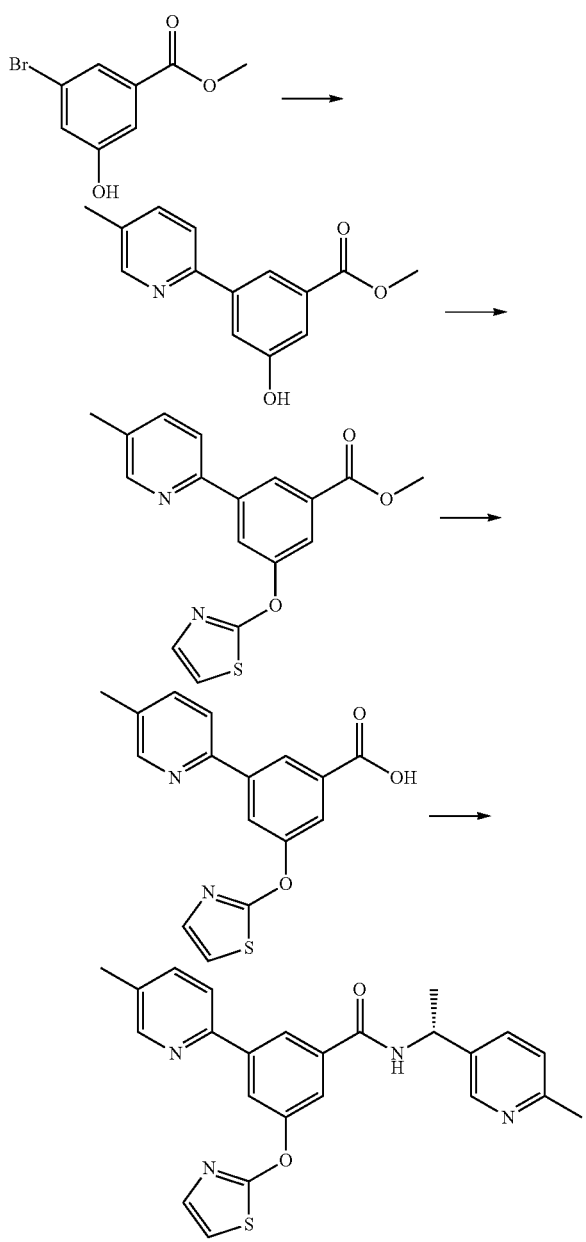

A) Methyl 3-hydroxy-5-(5-methylpyridin-2-yl)benzoate

A mixture of 3-bromo-5-hydroxy-benzoic acid methyl ester (1.47 g, 6.36 mmol), 5-methyl-2-(tributylstannyl)pyridine (3.0 g, 7.85 mmol), tetrakis(triphenylphosphine)-palladium(0) (300 mg, 0.26 mmol) in toluene (20 mL) and DMF (2 mL) was subjected to microwave irradiation at 110° C. for 1 hour. After cooling, the mixture was diluted with water and extracted with EtOAc. The combined organic layers were dried over anhydrous MgSO$_4$ and concentrated in vacuo. The residue was purified by flash chromatography to afford the title compound as a white solid.

B) Methyl 3-(5-methylpyridin-2-yl)-5-(thiazol-2-yloxy)benzoate

A stirred mixture of methyl 3-hydroxy-5-(5-methylpyridin-2-yl)benzoate (290 mg, 1.2 mmol), 2-bromothiazole (410 mg, 2.5 mmol), potassium carbonate (346 mg, 2.5 mmol), and dimethyl sulfoxide (5 mL) was heated at 135° C. overnight. The reaction mixture was then cooled to room temperature and diluted with EtOAc. The organic phase was washed with aq. NaHCO$_3$ (sat.), dried over anhydrous MgSO$_4$, filtered, and concentrated. The residue was purified by flash chromatography (0-30% EtOAc/hexane) to afford the title compound.

C) 3-(5-Methylpyridin-2-yl)-5-(thiazol-2-yloxy)benzoic acid

To a solution of methyl 3-(5-methylpyridin-2-yl)-5-(thiazol-2-yloxy)benzoate (240 mg, 0.74 mmol) in tetrahydrofuran (6 mL) was added 2.5 M of aqueous lithium hydroxide solution (1.6 mL, 4.1 mmol). The reaction mixture was stirred at 60° C. overnight. The aqueous solution was acidified with 15% HCl (aq.) to pH=5-6, and extracted with EtOAc. The combined organic layers were concentrated in vacuo to get the title compound as a white solid. $^1$H NMR (CDCl$_3$, 400 MHz): 8.77 (s, 1H), 8.70 (s, 1H), 8.08 (s, 1H), 8.04 (s, 1H), 7.71 (d, J=8.0 Hz, 1H), 7.64 (dd, J=8.0, 2.0 Hz, 1H), 7.25 (d, J=4.8 Hz, 1H), 6.85 (d, J=4.0 Hz, 1H), 2.41 (s, 3H).

D) (R)-3-(5-Methylpyridin-2-yl)-N-(1-(6-methylpyridin-3-yl)ethyl)-5-(thiazol-2-yloxy)benzamide To a solution of 3-(5-methylpyridin-2-yl)-5-(thiazol-2-yloxy)benzoic acid (40 mg, 0.13 mmol) in N,N-dimethylformamide (1 mL) were added (R)-1-(6-methylpyridin-3-yl)ethanamine dihydrochloride (60 mg, 0.29 mmol), N,N,N',N'-tetramethyl-O-(7-azabenzotriazol-1-yl)uronium hexafluorophosphate (120 mg, 0.32 mmol), and N,N-diisopropylethylamine (400 µL, 2.3 mmol). The reaction mixture was stirred for 16 hours at 25° C., and then purified by preparative HPLC to afford the final product as a light brown solid.

LC-MS: 431 [M+1]$^+$; $^1$H NMR (400 MHz, DMSO-d6): 9.08 (d, 1H, J=7.8 Hz), 8.55 (d, 1H, J=1.9 Hz), 8.49 (m, 2H), 8.19 (t, 1H, J=2.0 Hz), 8.01 (d, 1H, J=8.2 Hz), 7.85 (t, 1H, J=1.5 Hz), 7.77 (dd, 1H, J=8.2, 1.8 Hz), 7.69 (dd, 1H, J=8.0, 2.4 Hz), 7.33 and 7.30 (AB, 2H, J=3.8 Hz), 7.21 (d, 1H, J=8.0 Hz), 5.19 (m, 1H), 2.43 (s, 3H), 2.36 (s, 3H), 1.52 (d, 3H, J=7.1 Hz).

Compound 269

(R)-3-(5-Methylpyridin-2-yl)-N-(1-(2-methylpyrimidin-5-yl)ethyl)-5-(thiazol-2-yloxy)benzamide

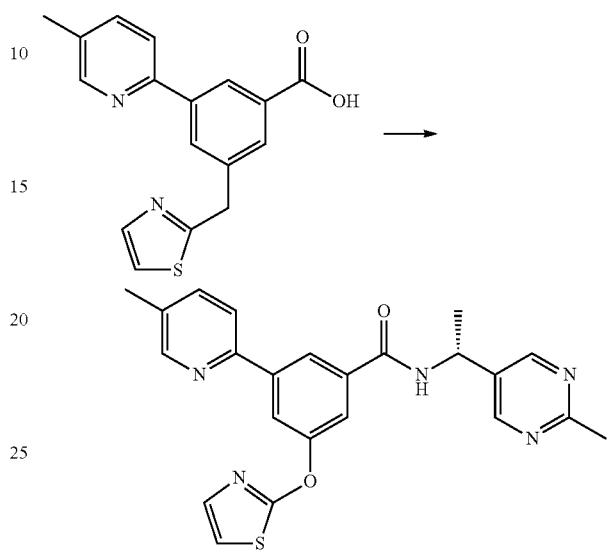

To a solution of 3-(5-methylpyridin-2-yl)-5-(thiazol-2-yloxy)benzoic acid (40 mg, 0.13 mmol) in N,N-dimethylformamide (1 mL) were added (R)-1-(2-methylpyrimidin-5-yl)ethanamine (40 mg, 0.29 mmol), N,N,N',N'-tetramethyl-O-(7-azabenzotriazol-1-yl)uronium hexafluorophosphate (120 mg, 0.32 mmol), and N,N-diisopropylethylamine (120 µL, 0.69 mmol). The reaction mixture was stirred for 16 hours at 25° C., and then purified by preparative HPLC to afford the product as a light color solid.

LC-MS: 432.2 [M+1]$^+$; $^1$H NMR (400 MHz, DMSO-d6): 9.12 (d, 1H, J=7.5 Hz), 8.73 (s, 2H), 8.55 (d, 1H, J=2.0 Hz), 8.49 (t, 1H, J=1.4 Hz), 8.19 (t, 1H, J=2.1 Hz), 8.01 (d, 1H, J=8.2 Hz), 7.84 (bs, 1H), 7.77 (dd, 1H, J=8.1, 1.7 Hz), 7.33 and 7.30 (AB, 2H, J=3.76 Hz), 5.19 (m, 1H), 2.59 (s, 3H), 2.36 (s, 3H), 1.56 (d, 3H, J=7.1 Hz).

Compound 274

(R)-3-(Methoxymethyl)-5-(5-methylpyridin-2-yl)-N-(1-(2-methylpyrimidin-5-yl)ethyl)benzamide

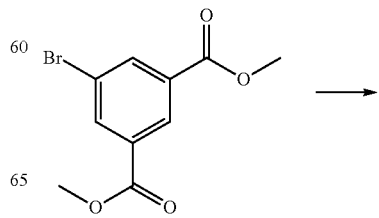

-continued

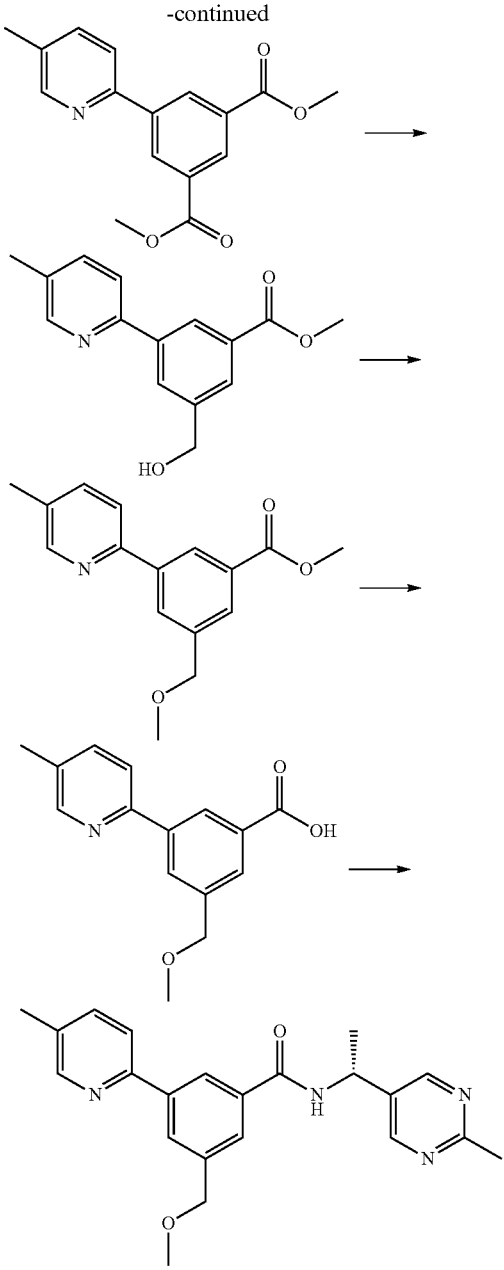

A) Dimethyl 5-(5-methylpyridin-2-yl)isophthalate

A mixture of dimethyl 5-bromoisophthalate (1.0 g, 3.66 mmol), 5-methyl-2-(tributylstannyl)pyridine (1.5 mL, 4.5 mmol), tetrakis(triphenylphosphine)palladium(0) (200 mg, 0.17 mmol), and toluene (10 mL) under nitrogen was subjected to microwave irradiation at 120° C. for 2 hour. The mixture was cooled to room temperature and the precipitate was collected via filtration and rinsed with hexane to afford a white solid which was the desired product. The filtrate was purified via flash chromatography to afford another crop of the desired product (0.8 g in total). LC-MS: 286.3 [M+1]+; $^1$H NMR (400 MHz, CDCl$_3$): 8.84 (d, J=1.6 Hz, 2H), 8.71 (t, J=1.6 Hz, 1H), 8.56 (t, J=0.8 Hz, 1H), 7.75 (d, J=8.0 Hz, 1H), 7.61 (dd, J=2.0, 8.1 Hz, 1H), 3.98 (s, 6H), 2.41 (s, 3H).

B) Methyl 3-(hydroxymethyl)-5-(5-methylpyridin-2-yl)benzoate

To a stirred solution of dimethyl 5-(5-methylpyridin-2-yl)isophthalate (1.78 g, 5.93 mmol) in methanol (100 mL) was added sodium tetrahydroborate (2.0 g, 0.053 mol) at 0° C. After 3 h, the reaction was treated with sat. aq. NH$_4$Cl and the volatiles were removed in vacuo. The residue was dissloved in water, basified to pH=9 by addition of NaHCO$_3$, and then extracted with CH$_2$Cl$_2$ (70 mL×3). The combined organic layers were dried over anhydrous MgSO$_4$ and concentrated. The residue was purified by flash chromatography to afford the title compound.

C) Methyl 3-(methoxymethyl)-5-(5-methylpyridin-2-yl)benzoate

To a stirred solution of methyl 3-(hydroxymethyl)-5-(5-methylpyridin-2-yl)benzoate (110 mg, 0.41 mmol) in N,N-dimethylformamide (2 mL) at 0° C. was added sodium hydride (60% in mineral oil, 21 mg, 0.52 mmol). After 30 minutes, methyl iodide (73 mg, 0.51 mmol) was added at 0° C. The mixture was warmed to room temperature and stirred for 30 minutes. The mixture was quenched with water (2 mL) and extracted with EtOAc. The combined organic layers were dried over anhydrous MgSO$_4$ and concentrated to get the tittle compound.

D) 3-(Methoxymethyl)-5-(5-methylpyridin-2-yl)benzoic acid

To a stirred solution of methyl 3-(methoxymethyl)-5-(5-methylpyridin-2-yl)benzoate (75 mg, 0.28 mmol) in 1,4-dioxane (3 mL) and water (0.3 mL) was added lithium hydroxide (66 mg, 2.8 mmol) and the reaction mixture was stirred at room temperature for 30 minutes. The reaction mixture was acidified with 2N aq. H$_2$SO$_4$ to pH=7-8, and then extracted with EtOAc (20 mL×3). The combined organic layers were washed with brine, dried (MgSO$_4$), and concentrated to afford the title compound. $^1$H NMR (D$_2$O, 400 MHz): 8.10 (s, 1H), 7.98 (s, 1H), 7.72 (s, 1H), 7.51 (s, 1H), 7.40 (d, J=8.0 Hz, 1H), 7.32 (d, J=8.4 Hz, 1H), 4.41 (s, 2H), 3.32 (s, 3H), 2.13 (s, 3H).

E) (R)-3-(Methoxymethyl)-5-(5-methylpyridin-2-yl)-N-(1-(2-methylpyrimidin-5-yl)ethyl)benzamide To a solution of 3-(methoxymethyl)-5-(5-methylpyridin-2-yl)benzoic acid (30 mg, 0.12 mmol) in N,N-dimethylformamide (1.5 mL) were added (R)-1-(2-methylpyrimidin-5-yl)ethanamine (40 mg, 0.29 mmol), N,N,N',N'-tetramethyl-O-(7-azabenzotriazol-1-yl)uronium hexafluorophosphate (100 mg, 0.26 mmol), and N,N-diisopropylethylamine (100 µL, 0.57 mmol). The reaction mixture was stirred for 16 hours at 25° C., and then purified by preparative HPLC to afford the final product.

LC-MS: 377.2 [M+1]+; $^1$H NMR (400 MHz, CDCl$_3$): 8.69 (s, 2H), 8.49 (d, 1H, J=1.1 Hz), 8.30 (bs, 1H), 8.07 (bs, 1H), 7.80 (bs, 1H), 7.69 (d, 1H, J=8.1 Hz), 7.58 (dd, 1H, J=8.1, 2.0 Hz), 6.79 (d, 1H, J=7.2 Hz), 5.34 (m, 1H), 4.56 (s, 2H), 3.43 (s, 3H), 2.72 (s, 3H), 2.38 (s, 3H), 1.65 (d, 3H, J=7.1 Hz).

Compound 280

5-(Hydroxy(thiazol-2-yl)methyl)-4'-methyl-N—((R)-1-(6-methylpyridin-3-yl)ethyl)biphenyl-3-carboxamide

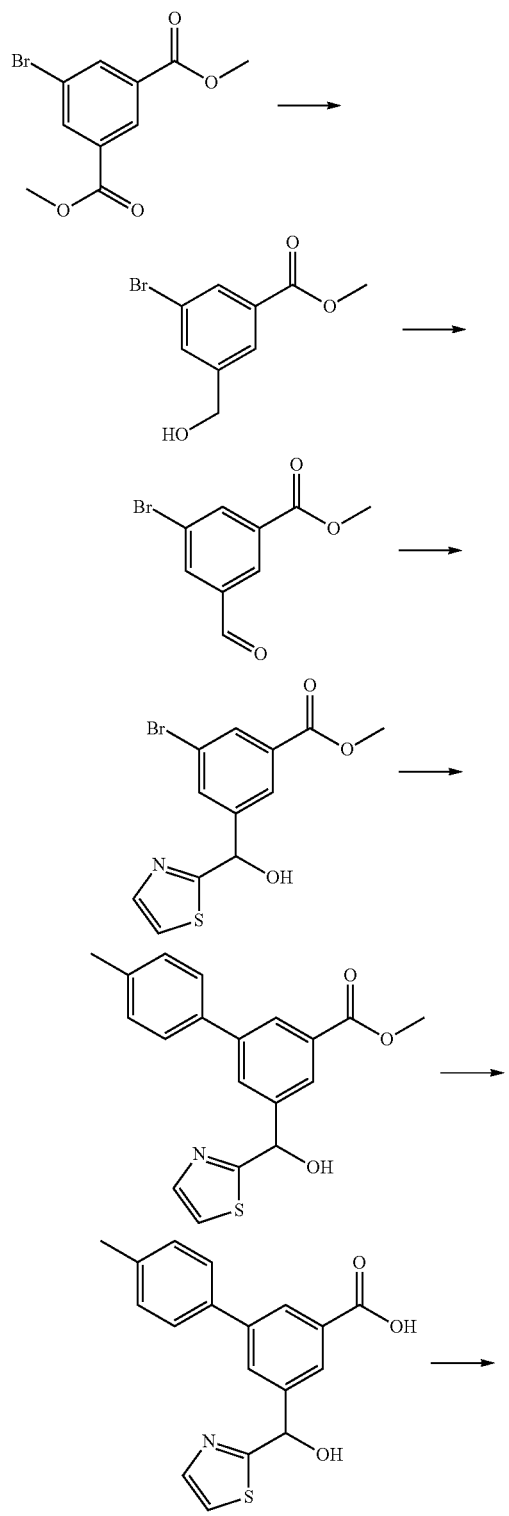

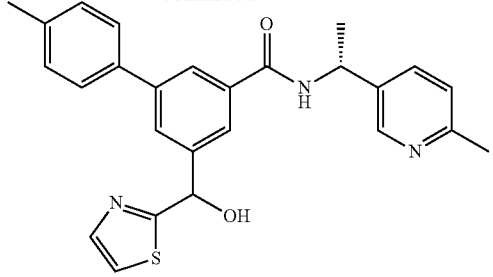

A) Methyl 3-bromo-5-(hydroxymethyl)benzoate

To a stirred solution of dimethyl 5-bromoisophthalate (5.4 g, 20 mmol) in methanol (300 mL) at 0° C. was slowly added sodium tetrahydroborate (10 g, 0.28 mol). The mixture was stirred at rt for 3 h, and then treated with water (300 mL). The volatiles were removed in vacuo and the aqueous phase was extracted with $CH_2Cl_2$ (100 mL×3). The combined organic layers were washed with brine, dried over anhydrous $MgSO_4$, and concentrated in vacuo. The resulting oil was purified by flash chromatography to afford the title compound.

B) Methyl 3-bromo-5-formylbenzoate

A mixture of methyl 3-bromo-5-(hydroxymethyl)benzoate (149 mg, 0.61 mmol) and manganese(IV) oxide (529 mg, 6.08 mmol), and $CH_2Cl_2$ (3 mL) was stirred at rt overnight. The mixture was filtered through Celite and the filter cake was washed with $CH_2Cl_2$. The filtrate was concentrated to afford the title compound.

C) Methyl 3-bromo-5-(hydroxy(thiazol-2-yl)methyl)benzoate

To a stirred solution of 2-bromothiazole (0.40 g, 24.4 mmol) in THF (60 mL) under nitrogen at rt was added 2M isopropylmagnesium chloride solution in THF (10 mL, 20 mmol). The mixture was stirred at rt for 1 h and then cooled to 0° C. Methyl 3-bromo-5-formylbenzoate (1.0 g, 4.1 mmol) was added and the reaction mixture was stirred at 0° C. for 30 minutes. The reaction mixture was quenched with water (30 mL) and extracted with $CH_2Cl_2$ (60 mL×3). The combined organic layers were dried over anhydrous $MgSO_4$ and concentrated. The residue was purified by flash chromatography to afford the title compound (0.90 g).

D) Methyl 5-(hydroxy(thiazol-2-yl)methyl)-4'-methylbiphenyl-3-carboxylate

To a mixture of methyl 3-bromo-5-(hydroxy(thiazol-2-yl)methyl)benzoate (320 mg, 0.98 mmol), p-tolylboronic acid (0.16 g, 1.2 mmol), potassium carbonate (0.20 g, 1.5 mmol), 1,4-dioxane (5 mL), and water (0.5 mL, 0.03 mol) under argon was added tetrakis(triphenylphosphine)palladium(0) (60 mg, 0.052 mmol). The reaction mixture was heated at 95° C. for 8 h. After cooling, the mixture was treated with water (15 mL) and extracted with EtOAc (20 mL×3). The combined organic layers were dried ($MgSO_4$) and concentrated. The residue was purified by flash chromatography to afford the title compound.

E) 5-(Hydroxy(thiazol-2-yl)methyl)-4'-methylbiphenyl-3-carboxylic acid

To a stirred solution of methyl 5-(hydroxy(thiazol-2-yl)methyl)-4'-methylbiphenyl-3-carboxylate (170 mg, 0.50 mmol) in 1,4-dioxane (1.5 mL) and water (1.5 mL) was added lithium hydroxide (42 mg, 1.8 mmol). After being stirred at rt for 4 h, the reaction mixture was treated with aq. NH$_4$Cl and extracted with EtOAc (15 mL×3). The combined organic layers were dried over anhydrous MgSO$_4$ and purified by silica gel column to afford the title compound. $^1$H NMR (CDCl$_3$, 400 MHz): 8.19 (s, 1H), 8.16 (s, 1H), 7.86 (s, 1H), 7.72 (d, J=2.4 Hz, 1H), 7.41 (d, J=7.6 Hz, 2H), 7.24 (m, 1H), 7.14 (d, J=7.6 Hz, 2H), 6.21 (s, 1H), 5.28 (s, 1H), 2.32 (s, 3H).

F) 5-(Hydroxy(thiazol-2-yl)methyl)-4'-methyl-N—((R)-1-(6-methylpyridin-3-yl)ethyl)biphenyl-3-carboxamide To a stirred solution of 5-(hydroxy(thiazol-2-yl)methyl)-4'-methylbiphenyl-3-carboxylic acid (31 mg, 0.095 mmol) in N,N-dimethylformamide (1 mL) were added (R)-1-(6-methylpyridin-3-yl)ethanamine dihydrochloride (50 mg, 0.24 mmol), N,N,N',N'-tetramethyl-O-(7-azabenzotriazol-1-yl) uronium hexafluorophosphate (100 mg, 0.26 mmol), and N,N-diisopropylethylamine (300 µL, 1.72 mmol). The reaction mixture was stirred for 16 hours at 25° C., and then purified by preparative HPLC to afford the final product as a light brown solid.

LC-MS: 444.1 [M+1]$^+$; $^1$H NMR (400 MHz, DMSO-d6): 8.96 (d, 1H, J=7.8 Hz), 8.47 (d, 1H, J=2.0 Hz), 8.05 (bs, 1H), 7.90 (bs, 1H), 7.85 (s, 1H), 7.72-7.58 (m, 5H), 7.31 (d, 2H, J=8.0 Hz), 7.21 (d, 1H, J=8.0 Hz), 6.95 (d, 1H, J=3.7 Hz), 6.08 (d, 1H, J=4.2 Hz), 5.18 (m, 1H), 2.43 (s, 3H), 2.36 (s, 3H), 1.51 (d, 3H, J=7.0 Hz).

Compound 290

(R)-2'-Cyano-5-(hydroxymethyl)-4'-methyl-N-(1-(6-methylpyridin-3-yl)ethyl)biphenyl-3-carboxamide

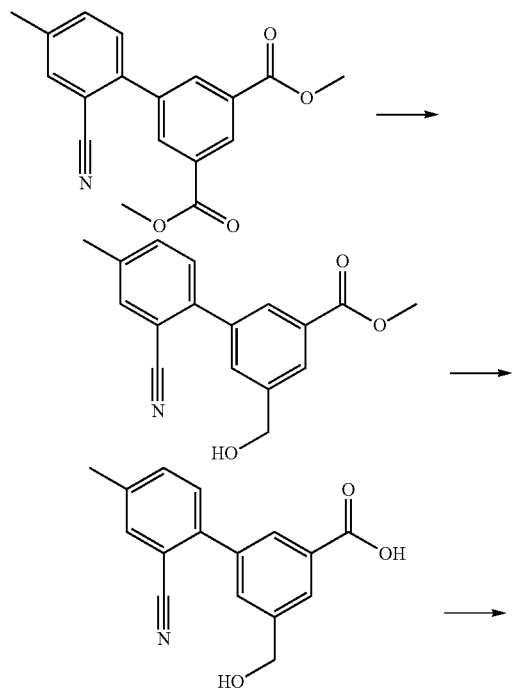

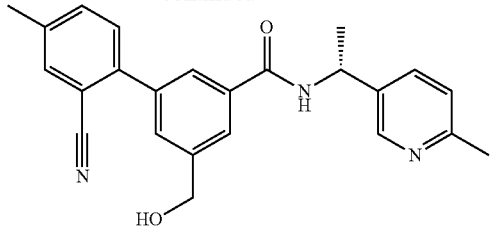

A) Methyl 2'-cyano-5-(hydroxymethyl)-4'-methylbiphenyl-3-carboxylate

A solution of dimethyl 2'-cyano-4'-methylbiphenyl-3,5-dicarboxylate (343 mg, 1.05 mmol) in methanol (20 mL) was cooled at 0° C. and sodium tetrahydroborate (0.60 g, 16 mmol) was added slowly. The mixture was stirred at rt for 6 h, and then treated with water (20 mL). The volatiles were removed in vacuo and the acqueous phase was extracted with CH$_2$Cl$_2$ (30 mL×3). The combined organic layers were washed with brine, dried over anhydrous MgSO$_4$, and concentrated in vacuo. The residue was purified by flash chromatography to afford the title compound.

B) 2'-Cyano-5-(hydroxymethyl)-4'-methylbiphenyl-3-carboxylic acid

To a stirred solution of methyl 2'-cyano-5-(hydroxymethyl)-4'-methylbiphenyl-3-carboxylate (220 mg, 0.78 mmol) in 1,4-dioxane (5 mL) and water (1 mL) was added lithium hydroxide (60 mg, 2.5 mmol). The reaction mixture was stirred at rt for 8 h, and then treated with aq. NH$_4$Cl and EtOAc. The organic layer was separated, dried over anhydrous MgSO$_4$, and concentrated. The residue was purified by silica gel chromatography to afford the title compound. $^1$H NMR (acetone-d6, 400 MHz): 8.16 (m, 1H), 8.11 (m, 1H), 7.81 (m, 1H), 7.73 (m, 1H), 7.65-7.61 (m, 1H), 7.56 (d, 1H, J=8.0 Hz), 4.81 (s, 2H), 2.46 (s, 3H).

C) (R)-2'-Cyano-5-(hydroxymethyl)-4'-methyl-N-(1-(6-methylpyridin-3-yl)ethyl)biphenyl-3-carboxamide To a stirred solution of 2'-cyano-5-(hydroxymethyl)-4'-methylbiphenyl-3-carboxylic acid (40 mg, 0.15 mmol) in N,N-dimethylformamide (1 mL) were added (R)-1-(6-methylpyridin-3-yl)ethanamine dihydrochloride (60 mg, 0.29 mmol), N,N,N',N'-tetramethyl-O-(7-azabenzotriazol-1-yl) uronium hexafluorophosphate (120 mg, 0.32 mmol), and N,N-diisopropylethylamine (400 µL, 2.3 mmol). The reaction mixture was stirred for 16 hours at 25° C., and then purified by preparative HPLC to afford the final product as a light color solid.

LC-MS: 386.4 [M+1]$^+$; $^1$H NMR (400 MHz, DMSO-d6): 8.93 (d, 1H, J=7.8 Hz), 8.47 (d, 1H, J=2.2 Hz), 7.93 (bs, 1H), 7.91 (bs, 1H), 7.81 (bs, 1H), 7.70-7.60 (m, 3H), 7.57 (d, 1H, J=8.0 Hz), 7.20 (d, 1H, J=8.0 Hz), 5.41 (t, 1H, J=5.7 Hz), 5.18 (m, 1H), 4.62 (d, 2H, J=5.7 Hz), 2.43 (s, 3H), 2.41 (s, 3H), 1.50 (d, 3H, J=7.1 Hz).

Compound 295

2'-Cyano-4'-methyl-N—((R)-1-(6-methylpyridin-3-yl)ethyl)-5-(2,2,2-trifluoro-1-hydroxyethyl)biphenyl-3-carboxamide

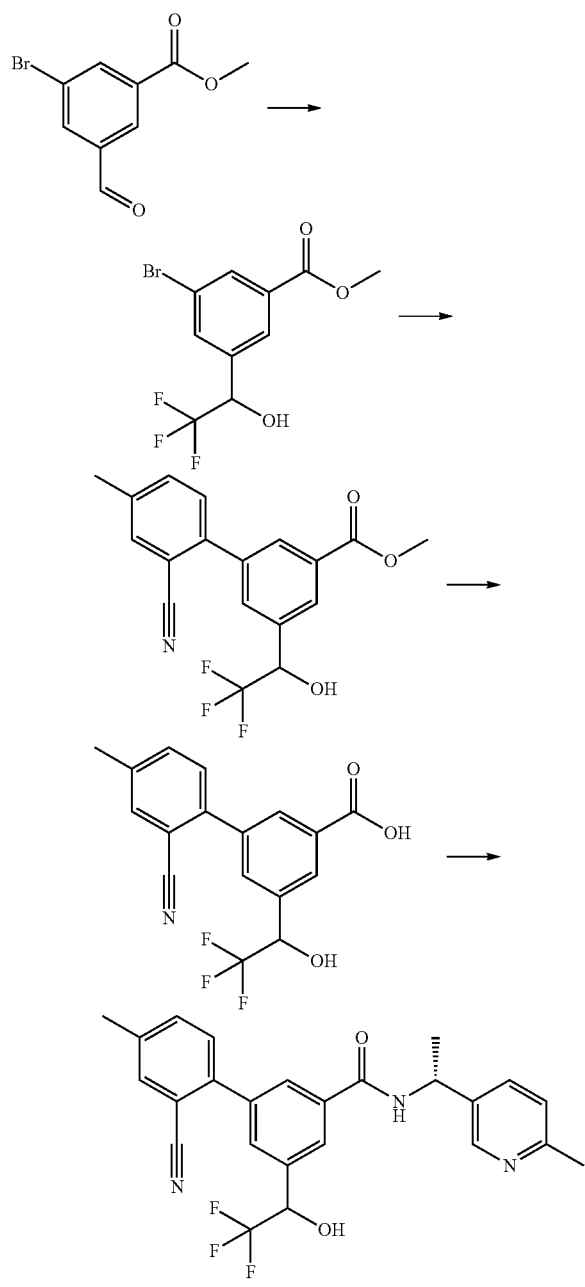

A) Methyl 3-bromo-5-(2,2,2-trifluoro-1-hydroxyethyl)benzoate

To a stirred mixture of methyl 3-bromo-5-formylbenzoate (0.60 g, 2.5 mmol), tetra-N-butylammonium bromide (0.90 g, 2.8 mol), potassium fluoride (10 mg, 0.17 mmol), and toluene (10 mL) at −20° C. was added (trifluoromethyl)trimethylsilane (0.74 mL, 5.0 mmol). The reaction mixture was stirred for 20 min, and then quenched with water. To the mixture were added 1 M HCl aqueous solution (2 mL) and 1,4-dioxane (12 mL), and the mixture was stirred for 30 min. The aqueous phase was extracted with EtOAc (3×20 mL). The combined organic layers were washed with brine, dried over anhydrous MgSO$_4$, and concentrated under reduced pressure. The residue was purified by flash column to afford the title compound.

B) Methyl 2'-cyano-4'-methyl-5-(2,2,2-trifluoro-1-hydroxyethyl)biphenyl-3-carboxylate A mixture of methyl 3-bromo-5-(2,2,2-trifluoro-1-hydroxyethyl)benzoate (300 mg, 0.96 mmol), 5-methyl-2-(4,4,5,5-tetramethyl-1,3,2-dioxaborolan-2-yl)benzonitrile (280 mg, 1.1 mmol), tetrakis(triphenylphosphine)palladium(0) (60 mg, 0.052 mmol) in N,N-dimethylformamide (0.75 mL) and toluene (1.5 mL) under nitrogen was subjected to microwave irradiation at 110° C. for 1 h. After cooling, the mixture was diluted with water (15 mL) and extracted with EtOAc (20 mL×3). The combined organic layers were washed with brine, dried over anhydrous MgSO$_4$, and concentrated. The residue was purified by flash chromatography to afford the title compound.

C) 2'-Cyano-4'-methyl-5-(2,2,2-trifluoro-1-hydroxyethyl)biphenyl-3-carboxylic acid To a stirred solution of methyl 2'-cyano-4'-methyl-5-(2,2,2-trifluoro-1-hydroxyethyl)biphenyl-3-carboxylate (250 mg, 0.72 mmol) in 1,4-dioxane (5 mL) and water (2.5 mL) was added lithium hydroxide (50 mg, 2.1 mmol). The reaction mixture was stirred at rt for 4 h, and then treated with aq. NH$_4$Cl and EtOAc. The organic layer was separated, dried over anhydrous MgSO$_4$, and concentrated. The residue was purified by silica gel chromatography to afford the title compound. $^1$H NMR (CDCl$_3$, 400 MHz): 8.27 (s, 1H), 8.24 (s, 1H), 7.95 (s, 1H), 7.58 (s, 1H), 7.48 and 7.43 (AB, J=8.0 Hz, 2H), 5.17 (q, J=6.4 Hz, 1H), 2.43 (s, 3H).

D) 2'-Cyano-4'-methyl-N—((R)-1-(6-methylpyridin-3-yl)ethyl)-5-(2,2,2-trifluoro-1-hydroxyethyl)biphenyl-3-carboxamide To a solution of 2'-cyano-4'-methyl-5-(2,2,2-trifluoro-1-hydroxyethyl)biphenyl-3-carboxylic acid (32 mg, 0.095 mmol) in N,N-dimethylformamide (1 mL) were added (R)-1-(6-methylpyridin-3-yl)ethanamine dihydrochloride (50 mg, 0.24 mmol), N,N,N',N'-tetramethyl-O-(7-azabenzotriazol-1-yl)uronium hexafluorophosphate (100 mg, 0.26 mmol), and N,N-diisopropylethylamine (300 μL, 1.72 mmol). The reaction mixture was stirred for 16 hours at 25° C., and then purified by preparative HPLC to afford the final product as a light color solid.

LC-MS: 454.3 [M+1]$^+$; $^1$H NMR (400 MHz, DMSO-d6): 9.00 (d, 1H, J=7.7 Hz), 8.48 (d, 1H, J=2.1 Hz), 8.09 (s, 2H), 7.83 (s, 2H), 7.70-7.55 (m, 3H), 7.21 (d, 1H, J=8.0 Hz), 7.07 (d, 1H, J=5.6 Hz), 5.35 (m, 1H), 5.19 (m, 1H), 2.43 (s, 3H), 2.42 (s, 3H), 1.51 (d, 3H, J=7.1 Hz).

Compound 297

2'-Cyano-5-(1,2-dihydroxyethyl)-4'-methyl-N-((6-methylpyridin-3-yl)methyl)biphenyl-3-carboxamide

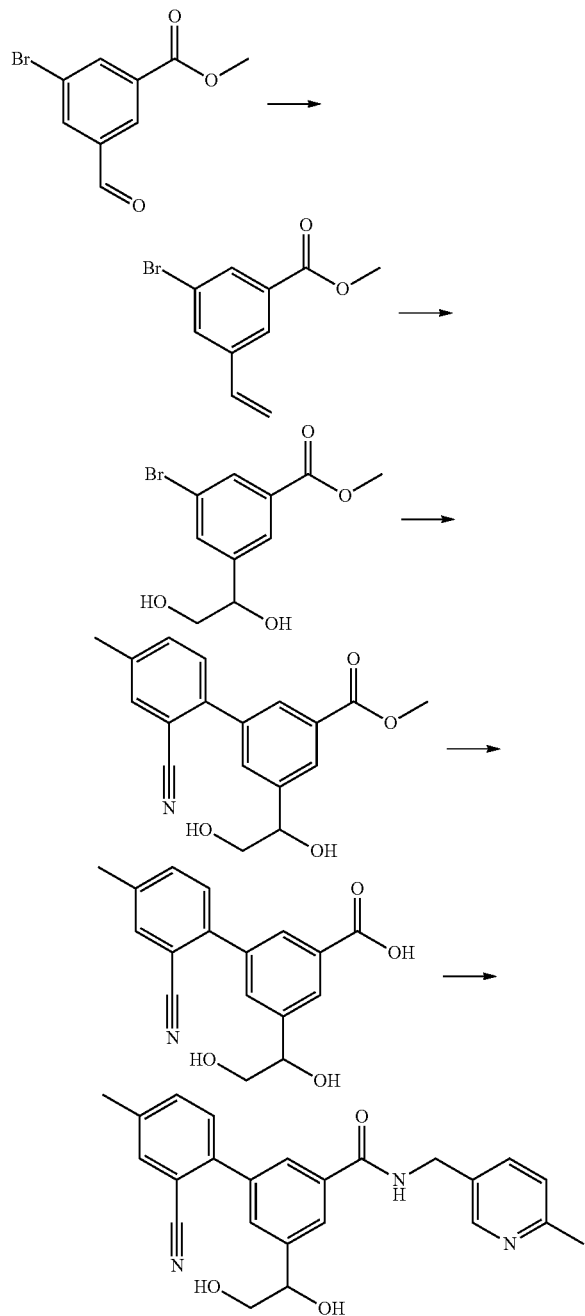

A) Methyl 3-bromo-5-vinylbenzoate

To a stirred solution of methyltriphenylphosphonium bromide (350 mg, 0.97 mmol) in THF (3 mL) at −78° C. under nitrogen was added dropwise 2.5 M of n-butyllithium in tetrahydrofuran (0.31 mL, 0.78 mmol). The mixture was gradually warmed until a yellow color persisted. The mixture was cooled to 0° C. and a solution of methyl 3-bromo-5-formylbenzoate (157 mg, 0.65 mmol) in THF (2 mL) was added dropwise. After being stirred for 20 min at 0° C., the mixture was quenched with saturated aq. NH₄Cl and extracted with EtOAc. The organic layer was separated and washed with brine, dried, and concentrated. The residue was purified by flash column to afford the title compound.

B) Methyl 3-bromo-5-(1,2-dihydroxyethyl)benzoate

To a stirred solution of methyl 3-bromo-5-vinylbenzoate (1.6 g, 6.6 mmol) and N-methylmorpholine N-oxide (2.0 g, 17.1 mmol) in acetone (40 mL) and water (10 mL) was added dropwise a 5% solution of osmium tetraoxide in water (0.50 g, 0.10 mmol). The reaction mixture was stirred at rt for 3 h, and then a saturated aq. $Na_2S_2O_3$ solution was added. After being stirred for 30 min, the reaction mixture was extracted with EtOAc (100 mL×3). The combined organic layers were washed with water and brine, dried, and concentrated. The residue was purified by flash column to afford the title compound.

C) Methyl 2'-cyano-5-(1,2-dihydroxyethyl)-4'-methylbiphenyl-3-carboxylate

A mixture of methyl 3-bromo-5-(1,2-dihydroxyethyl)benzoate (100 mg, 0.36 mmol), 5-methyl-2-(4,4,5,5-tetramethyl-1,3,2-dioxaborolan-2-yl)benzonitrile (130 mg, 0.54 mmol), tetrakis(triphenylphosphine)palladium(0) (40 mg, 0.035 mmol), potassium carbonate (75 mg, 0.54 mmol), N,N-dimethylformamide (0.5 mL), and toluene (1 mL) under nitrogen was subjected to microwave irradiation at 110° C. for 1 h. After cooling, the mixture was diluted with water (5 mL) and extracted with EtOAc (15 mL×3). The combined organic layers were washed with brine, dried over anhydrous $MgSO_4$, and concentrated in vacuo. The residue was purified by flash column to afford the title compound.

D) 2'-Cyano-5-(1,2-dihydroxyethyl)-4'-methylbiphenyl-3-carboxylic acid

To a stirred solution of methyl 2'-cyano-5-(1,2-dihydroxyethyl)-4'-methylbiphenyl-3-carboxylate (140 mg, 0.45 mmol) in 1,4-dioxane (5 mL) and water (2 mL) was added lithium hydroxide (40 mg, 1.67 mmol). The reaction mixture was stirred at rt for 6 h, and then treated with aq. NH₄Cl and extracted with EtOAc (3×). The combined organic layers were dried over anhydrous $MgSO_4$, and concentrated to afford the title compound. ¹H NMR (400 MHz, acetone-d6): 8.21 (m, 1H), 8.13 (m, 1H), 7.87 (m, 1H), 7.73 (s, 1H), 7.66-7.61 (m, 1H), 7.58 (d, 1H, J=7.6 Hz), 4.91 (dd, 1H, J=7.2, 4.4 Hz), 3.75 (dd, 1H, J=11.2, 4.4 Hz), 3.65 (dd, 1H, J=11.2, 7.2 Hz), 2.47 (s, 3H).

E) 2'-Cyano-5-(1,2-dihydroxyethyl)-4'-methyl-N-((6-methylpyridin-3-yl)methyl)biphenyl-3-carboxamide To a solution of 2'-cyano-5-(1,2-dihydroxyethyl)-4'-methylbiphenyl-3-carboxylic acid (30 mg, 0.10 mmol) in N,N-dimethylformamide (1 mL) were added (6-methylpyridin-3-yl)methanamine (35 mg, 0.26 mmol), N,N,N',N'-tetramethyl-O-(7-azabenzotriazol-1-yl)uronium hexafluorophosphate (100 mg, 0.26 mmol), and N,N-diisopropylethylamine (100 µL, 0.57 mmol). The reaction mixture was stirred for 16 hours at 25° C., and then purified by preparative HPLC to afford the final product as a light color solid.

LC-MS: 402.1 [M+1]+; 1H NMR (400 MHz, DMSO-d6): 9.14 (m, 1H), 8.47 (bs, 1H), 7.94 (m, 2H), 7.79 (bs, 1H), 7.70-7.50 (m, 4H), 7.20 (m, 1H), 5.46 (bs, 1H), 4.80 (bs, 1H), 4.66 (bs, 1H), 4.46 (bs, 2H), 3.49 (bs, 2H), 2.43 (s, 3H), 2.40 (s, 3H).

Compound 308

4'-Methyl-N—((R)-1-(6-methylpyridin-3-yl)ethyl)-5-(tetrahydrofuran-3-yloxy)biphenyl-3-carboxamide

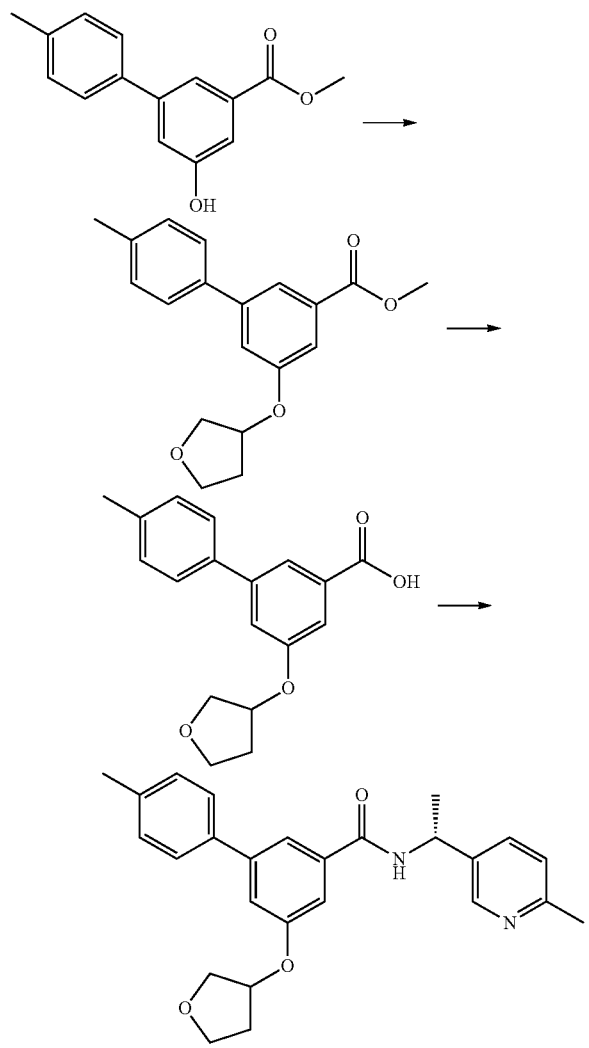

A) Methyl 4'-methyl-5-(tetrahydrofuran-3-yloxy)biphenyl-3-carboxylate

To a stirred solution of methyl 5-hydroxy-4'-methylbiphenyl-3-carboxylate (120 mg, 0.47 mmol), triphenylphosphine (120 mg, 0.47 mmol), 3-hydroxytetrahydrofuran (45 mg, 0.50 mmol) in CH$_2$Cl$_2$ (7 mL) at rt was slowly added a solution of diisopropyl azodicarboxylate (100 mg, 0.50 mmol) in CH$_2$Cl$_2$ (2 mL). The mixture was stirred at rt overnight, and then concentrated in vacuo. The residue was purified by flash chromatography to afford the title compound.

B) 4'-Methyl-5-(tetrahydrofuran-3-yloxy)biphenyl-3-carboxylic acid

To a stirred solution of methyl 4'-methyl-5-(tetrahydrofuran-3-yloxy)biphenyl-3-carboxylate (150 mg, 0.46 mmol) in 1,4-dioxane (5 mL) and water (0.5 mL) was added lithium hydroxide (55 mg, 2.3 mmol). The reaction mixture was stirred at room temperature for 2 hours, and then acidified with 2N aq. H$_2$SO$_4$ to pH 4-5 and concentrated in vacuo. The residue was treated with water and extracted with CH$_2$Cl$_2$ (10 mL×3). The combined organic layers were dried (MgSO$_4$), and concentrated to afford the title compound. 1H NMR (CD$_3$OD, 400 MHz): 7.85 (t, J=1.6 Hz, 1H), 7.52 (d, 2H, J=8.4 Hz), 7.48 (dd, 1H=2.4, 1.2 Hz), 7.34 (dd, 1H, J=2.4, 1.6 Hz), 7.28 (d, 2H, J=8.4 Hz), 5.15 (m, 1H), 4.05-3.87 (m, 4H), 2.38 (s, 3H), 2.36-2.27 (m, 1H), 2.20-2.11 (m, 1H).

C) 4'-Methyl-N—((R)-1-(6-methylpyridin-3-yl)ethyl)-5-(tetrahydrofuran-3-yloxy)biphenyl-3-carboxamide To a solution of 4'-methyl-5-(tetrahydrofuran-3-yloxy)biphenyl-3-carboxylic acid (40 mg, 0.13 mmol) in N,N-dimethylformamide (1 mL) were added (R)-1-(6-methylpyridin-3-yl)ethanamine dihydrochloride (60 mg, 0.29 mmol), N,N,N',N'-tetramethyl-O-(7-azabenzotriazol-1-yl)uronium hexafluorophosphate (120 mg, 0.32 mmol), and N,N-diisopropylethylamine (400 μL, 2.3 mmol). The reaction mixture was stirred for 16 hours at 25° C., and then purified by preparative HPLC to afford the final product as a light color solid.

LC-MS: 417.1 [M+1]+; 1H NMR (400 MHz, DMSO-d6): 8.90 (d, 1H, J=7.7 Hz), 8.47 (d, 1H, J=2.2 Hz), 7.73 (bs, 1H), 7.70-7.60 (m, 3H), 7.35 (bs, 1H), 7.32-7.25 (m, 3H), 7.21 (d, 1H, J=8.0 Hz), 5.20 (m, 2H), 4.00-3.70 (m, 4H), 2.43 (s, 3H), 2.35 (s, 3H), 2.25 (m, 1H), 2.00 (m, 1H), 1.51 (d, 3H, J=7.1 Hz).

Compound 310

4'-Methyl-N—((R)-1-(6-methylpyridin-3-yl)ethyl)-5-((tetrahydrofuran-2-yl)methoxy)biphenyl-3-carboxamide

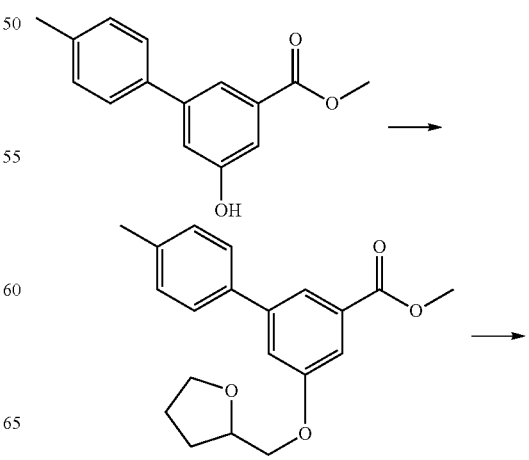

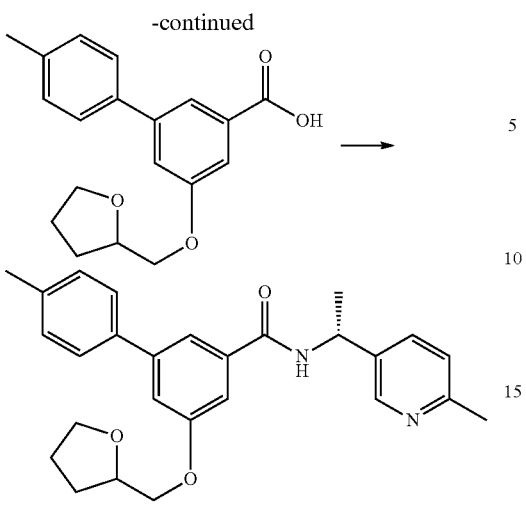

A) Methyl 4'-methyl-5-((tetrahydrofuran-2-yl)methoxy)biphenyl-3-carboxylate

To a stirred solution of methyl 5-hydroxy-4'-methylbiphenyl-3-carboxylate (150 mg, 0.59 mmol), triphenylphosphine (150 mg, 0.59 mmol), tetrahydro-2-furanmethanol (60 mg, 0.59 mmol) in CH$_2$Cl$_2$ (8 mL) at rt was slowly added a solution of diisopropyl azodicarboxylate (200 mg, 1.0 mmol) in CH$_2$Cl$_2$ (3 mL). The mixture was stirred at room temperature overnight, and then concentrated in vacuo. The residue was purified by flash chromatography to afford the title compound.

B) 4'-Methyl-5-((tetrahydrofuran-2-yl)methoxy)biphenyl-3-carboxylic acid

To a stirred solution of methyl 4'-methyl-5-((tetrahydrofuran-2-yl)methoxy)biphenyl-3-carboxylate (130 mg, 0.40 mmol) in 1,4-dioxane (5 mL) and water (0.5 mL) was added lithium hydroxide (50 mg, 2.1 mmol). The reaction mixture was stirred at room temperature for 2 hours, and then acidified with 2N aq. H$_2$SO$_4$ to pH 4-5 and concentrated in vacuo. The residue was treated with water and extracted with CH$_2$Cl$_2$ (10 mL×3). The combined organic layers were dried (MgSO$_4$) and concentrated to afford the title compound. $^1$H NMR (CD$_3$OD, 400 MHz): 7.84 (t, J=1.6 Hz, 1H), 7.54-7.50 (m, 3H), 7.38 (dd, 1H, J=2.8, 1.6 Hz), 7.27 (d, 2H, J=8.0 Hz), 4.34-4.27 (m, 1H), 4.12 (dd, 1H, J=10.0, 3.6 Hz), 4.04 (dd, 1H, J=10.0, 6.4 Hz), 3.97-3.80 (m, 2H), 2.38 (s, 3H), 2.20-1.80 (m, 4H).

4'-Methyl-N—((R)-1-(6-methylpyridin-3-yl)ethyl)-5-((tetrahydrofuran-2-yl)methoxy)biphenyl-3-carboxamide To a stirred solution of 4'-methyl-5-((tetrahydrofuran-2-yl)methoxy)biphenyl-3-carboxylic acid (40 mg, 0.13 mmol) in N,N-dimethylformamide (1 mL) were added (R)-1-(6-methylpyridin-3-yl)ethanamine dihydrochloride (60 mg, 0.29 mmol), N,N,N',N'-tetramethyl-O-(7-azabenzotriazol-1-yl)uronium hexafluorophosphate (120 mg, 0.32 mmol), and N,N-diisopropylethylamine (400 µL, 2.3 mmol). The reaction mixture was stirred for 16 hours at 25° C., and then purified by preparative HPLC to afford the final product as a light brown solid.

LC-MS: 430.9 [M+1]$^+$; $^1$H NMR (400 MHz, DMSO-d6): 8.90 (d, 1H, J=7.7 Hz), 8.47 (d, 1H, J=2.2 Hz), 7.71 (bs, 1H), 7.70-7.60 (m, 3H), 7.38 (bs, 1H), 7.33 (t, 1H, J=1.6 Hz), 7.29 (d, 2H, J=8.0 Hz), 7.21 (d, 1H, J=8.0 Hz), 5.18 (m, 1H), 4.19 (m, 1H), 4.15-3.95 (m, 2H), 3.79 (m, 1H), 3.67 (m, 1H), 2.43 (s, 3H), 2.35 (s, 3H), 2.02 (m, 1H), 1.85 (m, 2H), 1.70 (m, 1H), 1.51 (d, 3H, J=7.1 Hz).

Compound 315

2'-Cyano-5-(2,3-dihydroxypropoxy)-4'-methyl-N—((R)-1-(6-methylpyridin-3-yl)ethyl)biphenyl-3-carboxamide

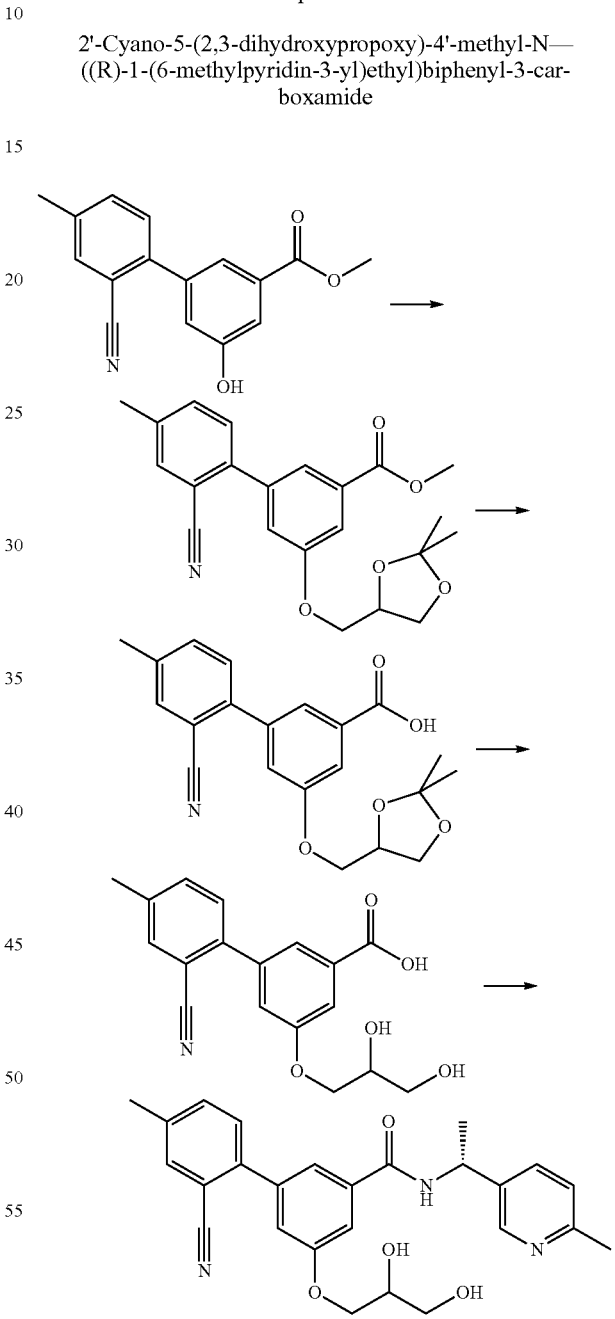

A) Methyl 2'-cyano-5-((2,2-dimethyl-1,3-dioxolan-4-yl)methoxy)-4'-methylbiphenyl-3-carboxylate To a stirred solution of methyl 2'-cyano-5-hydroxy-4'-methylbiphenyl-3-carboxylate (150 mg, 0.56 mmol), triphenylphosphine (220 mg, 0.84 mmol), 2,2-dimethyl-1,3-dioxolane-4-methanol (82 mg, 0.62 mmol) in CH₂Cl₂ (5 mL) at room temperature was slowly added a solution of diisopropyl azodicarboxylate (340 mg, 1.7 mmol) in CH₂Cl₂ (3 mL). The reaction mixture was stirred at room temperature overnight, and then concentrated in vacuo. The residue was purified by flash chromatography to afford the title compound.

B) 2'-Cyano-5-((2,2-dimethyl-1,3-dioxolan-4-yl)methoxy)-4'-methylbiphenyl-3-carboxylic acid To a solution of methyl 2'-cyano-5-((2,2-dimethyl-1,3-dioxolan-4-yl)methoxy)-4'-methylbiphenyl-3-carboxylate (72 mg, 0.19 mmol) in tetrahydrofuran (3 mL) was added 2.5 M of aq. lithium hydroxide solution (1 mL, 2.5 mmol). The reaction mixture was stirred at 60° C. overnight. The aqueous solution was acidified with 15% HCl (aq.) to pH=5, and extracted with EtOAc. The combined organic layers were concentrated in vacuo to get the title compound.

C) 2'-Cyano-5-(2,3-dihydroxypropoxy)-4'-methylbiphenyl-3-carboxylic acid

To a stirred solution of 2'-cyano-5-((2,2-dimethyl-1,3-dioxolan-4-yl)methoxy)-4'-methylbiphenyl-3-carboxylic acid (63 mg, 0.17 mmol) in THF (3 mL) was added 1 M of aq. HCl solution (3 mL, 3 mmol). The reaction mixture was stirred at room temperature for 4 hours, and then concentrated in vacuo. The residue was treated with water and extracted with EtOAc. The combined organic layers were dried over anhydrous MgSO₄ and concentrated to afford the title compound.
¹H NMR (CD₃OD, 400 MHz): 7.77 (t, 1H, J=1.6 Hz), 7.67 (m, 2H), 7.58 (dd, 1H, J=8.0, 2.0 Hz), 7.51 (d, 1H, J=8.0 Hz), 7.38 (t, 1H, J=2.0 Hz), 4.19 (dd, 1H, J=9.6, 4.0 Hz), 4.10 (dd, 1H, J=9.6, 6.0 Hz), 4.02 (m, 1H), 3.72 (dd, 1H, J=11.2, 5.6 Hz), 3.67 (dd, 1H, J=11.2, 5.6 Hz), 2.45 (s, 3H).

D) 2'-Cyano-5-(2,3-dihydroxypropoxy)-4'-methyl-N—((R)-1-(6-methylpyridin-3-yl)ethyl)biphenyl-3-carboxamide To a solution of 2'-cyano-5-(2,3-dihydroxypropoxy)-4'-methylbiphenyl-3-carboxylic acid (30 mg, 0.092 mmol) in N,N-dimethylformamide (1 mL) were added (R)-1-(6-methylpyridin-3-yl)ethanamine dihydrochloride (60 mg, 0.29 mmol), N,N,N',N'-tetramethyl-O-(7-azabenzotriazol-1-yl)uronium hexafluorophosphate (100 mg, 0.26 mmol), and N,N-diisopropylethylamine (400 μL, 2.3 mmol). The reaction mixture was stirred for 16 hours at 25° C., and then purified by preparative HPLC to afford the final product as a light color solid.
LC-MS: 446.6 [M+1]⁺; ¹H NMR (400 MHz, DMSO-d6): 8.92 (d, 1H, J=7.4 Hz), 8.46 (bs, 1H), 7.79 (bs, 1H), 7.70-7.55 (m, 4H), 7.53 (bs, 1H), 7.27 (bs, 1H), 7.20 (d, 1H, J=7.8 Hz), 5.17 (m, 1H), 5.00 (m, 1H), 4.70 (t, 1H, J=3.8 Hz), 4.11 (m, 1H), 3.97 (m, 1H), 3.83 (m, 1H), 3.46 (t, 2H, J=4.8 Hz), 2.43 (s, 3H), 2.41 (s, 3H), 1.49 (d, 3H, J=6.2 Hz).

Compound 324

2'-Cyano-4'-methyl-N—((R)-1-(6-methylpyridin-3-yl)ethyl)-5-(morpholin-2-ylmethoxy)biphenyl-3-carboxamide

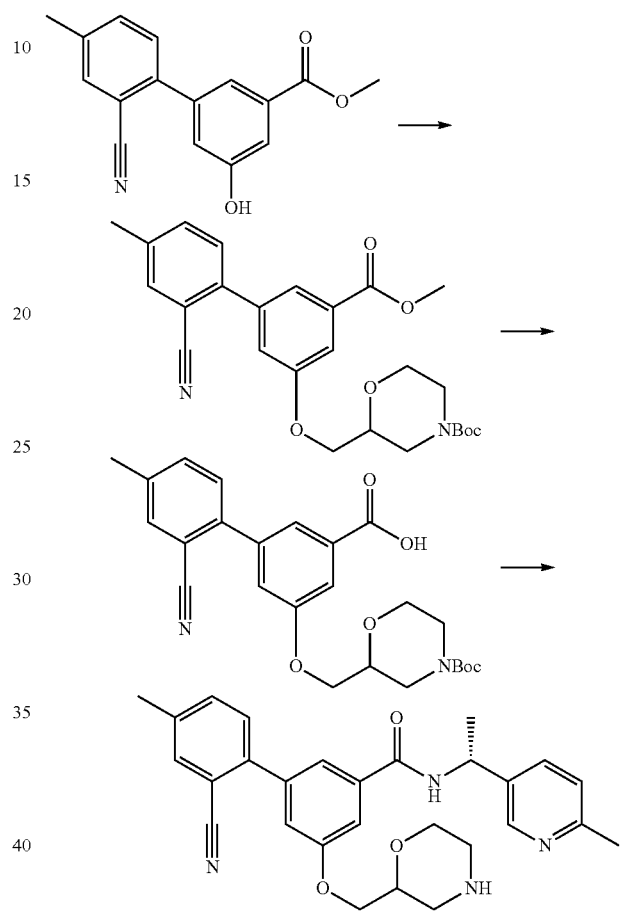

A) tert-Butyl 2-((2'-cyano-5-(methoxycarbonyl)-4'-methylbiphenyl-3-yloxy)methyl)morpholine-4-carboxylate To a stirred solution of methyl 2'-cyano-5-hydroxy-4'-methylbiphenyl-3-carboxylate (150 mg, 0.56 mmol), triphenylphosphine (220 mg, 0.84 mmol), tert-butyl 2-(hydroxymethyl)morpholine-4-carboxylate (130 mg, 0.62 mmol) (*Bioorg. Med. Chem. Lett.* 2007, 17, 533) in CH₂Cl₂ (5 mL) at room temperature under nitrogen was slowly added a solution of diisopropyl azodicarboxylate (340 mg, 1.7 mmol) in CH₂Cl₂ (3 mL). The mixture was stirred at room temperature overnight, and then concentrated in vacuo. The residue was purified by flash chromatography to afford the title compound.

B) 5-((4-(tert-Butoxycarbonyl)morpholin-2-yl)methoxy)-2'-cyano-4'-methylbiphenyl-3-carboxylic acid To a stirred solution of tert-butyl 2-((2'-cyano-5-(methoxycarbonyl)-4'-methylbiphenyl-3-yloxy)methyl)morpholine-4-carboxylate (107 mg, 0.23 mmol) in THF (2 mL) was added 2.5 M of aq. lithium hydroxide solution (0.52 mL, 1.3 mmol). The reaction mixture was stirred at 60° C. overnight, and then acidified with 15% HCl (aq.) to pH=5, and extracted with EtOAc. The combined organic layers were concentrated in vacuo to get the title compound. $^1$H NMR (CDCl$_3$, 400 MHz): 7.86 (t, 1H, J=1.6 Hz), 7.70 (t, 1H, J=1.6 Hz), 7.59 (s, 1H), 7.47 (dd, 1H, J=8.0, 1.2 Hz), 7.42 (d, 1H, J=8.0 Hz), 7.37 (s, 1H), 4.20-3.56 (m, 7H), 3.10-2.90 (m, 2H), 2.45 (s, 3H), 1.49 (s, 9H).

C) 2'-Cyano-4'-methyl-N—((R)-1-(6-methylpyridin-3-yl)ethyl)-5-(morpholin-2-ylmethoxy)biphenyl-3-carboxamide To a solution of 5-((4-(tert-butoxycarbonyl)morpholin-2-yl)methoxy)-2'-cyano-4'-methylbiphenyl-3-carboxylic acid (50 mg, 0.11 mmol) in N,N-dimethylformamide (1 mL) were added (R)-1-(6-methylpyridin-3-yl)ethanamine dihydrochloride (60 mg, 0.29 mmol), N,N,N',N'-tetramethyl-O-(7-azabenzotriazol-1-yl)uronium hexafluorophosphate (120 mg, 0.32 mmol), and N,N-diisopropylethylamine (400 µL, 2.3 mmol). The reaction mixture was stirred for 16 hours at 25° C., and then purified by preparative HPLC to afford the Boc-protected product which was dissolved in CH$_2$Cl$_2$ (5 mL) and trifluoroacetic acid (1 mL) was added. The mixture was stirred overnight at room temperature and LC-MS indicated that the deprotection was complete. The mixture was concentrated in vacuo, and the residue was purified by preparative HPLC to afford the final product as a white solid.

LC-MS: 471.6 [M+1]$^+$; $^1$H NMR (400 MHz, DMSO-d6): 8.90 (d, 1H, J=7.7 Hz), 8.46 (d, 1H, J=2.1 Hz), 8.00 (bs, 1H), 7.70-7.55 (m, 4H), 7.53 (bs, 1H), 7.29 (bs, 1H), 7.21 (d, 1H, J=8.0 Hz), 5.17 (m, 1H), 4.05 (m, 2H), 3.75 (m, 2H), 3.49 (m, 1H), 2.92 (m, 1H), 2.65 (m, 2H), 2.53 (m, 1H), 2.43 (s, 3H), 2.41 (s, 3H), 1.50 (d, 3H, J=7.1 Hz).

Compound 336

5-(4-Hydroxytetrahydrofuran-3-yloxy)-4'-methyl-N—((R)-1-(6-methylpyridin-3-yl)ethyl)biphenyl-3-carboxamide

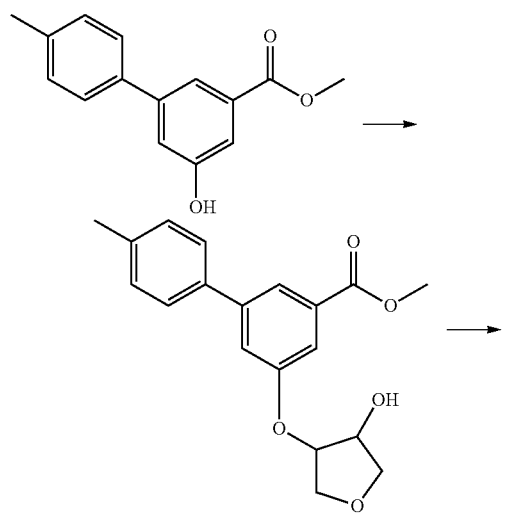

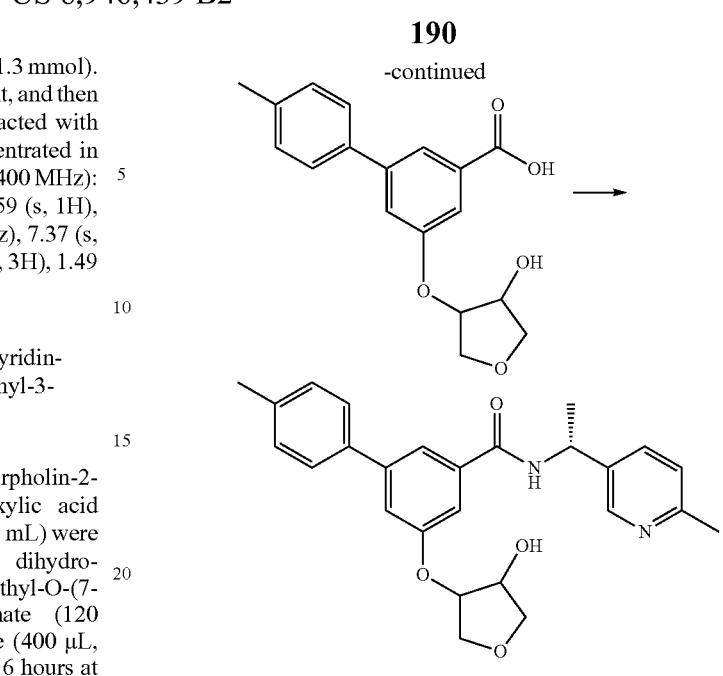

A) Methyl 5-(4-hydroxytetrahydrofuran-3-yloxy)-4'-methylbiphenyl-3-carboxylate

A stirred mixture of methyl 5-hydroxy-4'-methylbiphenyl-3-carboxylate (370 mg, 1.4 mmol), potassium carbonate (421 mg, 3.05 mmol), DMSO (8 mL), and 3,6-dioxabicyclo[3.1.0]hexane (260 mg, 3.0 mmol) was heated at 110° C. overnight. After cooling, the reaction mixture was diluted with EtOAc. The organic phase was washed with aq. NaHCO$_3$ (sat.), dried over anhydrous MgSO$_4$, filtered, and concentrated. The residue was purified by flash chromatography to afford the title compound.

B) 5-(4-Hydroxytetrahydrofuran-3-yloxy)-4'-methyl-biphenyl-3-carboxylic acid

To a stirred solution of methyl 5-(4-hydroxytetrahydrofuran-3-yloxy)-4'-methylbiphenyl-3-carboxylate (140 mg, 0.40 mmol) in 1,4-dioxane (2.8 mL) and water (2.8 mL) was added lithium hydroxide (50 mg, 2.1 mmol). The reaction mixture was stirred at room temperature for 2 hours, and then acidifized with 2N aq. H$_2$SO$_4$ to pH 4-5 and concentrated in vacuo. The residue was treated with water and extracted with EtOAc (10 mL×2). The combined organic layers were dried (MgSO$_4$) and concentrated to afford the title compound. $^1$H NMR (CD$_3$OD, 400 MHz): 7.87 (t, J=1.6 Hz, 1H), 7.55-7.51 (m, 3H), 7.42 (t, J=2.0 Hz, 1H), 7.28 (d, J=7.6 Hz, 2H), 4.84 (d, J=4.4 Hz, 1H), 4.38 (d, J=4.0 Hz, 1H), 4.23 (dd, J=10.4, 4.4 Hz, 1H), 4.05 (dd, J=9.6, 4.4 Hz, 1H), 3.94 (dd, J=10.4, 1.6 Hz, 1H), 3.77 (dd, J=9.6, 1.6 Hz, 1H), 2.38 (s, 3H).

C) 5-(4-Hydroxytetrahydrofuran-3-yloxy)-4'-methyl-N—((R)-1-(6-methylpyridin-3-yl)ethyl)biphenyl-3-carboxamide To a solution of 5-(4-hydroxytetrahydrofuran-3-yloxy)-4'-methylbiphenyl-3-carboxylic acid (35 mg, 0.11 mmol) in N,N-dimethylformamide (1 mL) were added (R)-1-(6-methylpyridin-3-yl)ethanamine dihydrochloride (60 mg, 0.29 mmol), N,N,N',N'-tetramethyl-O-(7-azabenzotriazol-1-yl)uronium hexafluorophosphate (100 mg, 0.26 mmol), and N,N-diisopropylethylamine (400 μL, 2.3 mmol). The reaction mixture was stirred for 16 hours at 25° C., and then purified by preparative HPLC to afford the final product as a white solid.

LC-MS: 432.8 [M+1]⁺; ¹H NMR (400 MHz, DMSO-d6): 8.90 (d, 1H, J=7.8 Hz), 8.47 (d, 1H, J=1.6 Hz), 7.73 (bs, 1H), 7.70-7.60 (m, 3H), 7.41 (bs, 1H), 7.38 (bs, 1H), 7.29 (d, 2H, J=7.9 Hz), 7.21 (d, 1H, J=8.0 Hz), 5.53 (bs, 1H), 5.17 (m, 1H), 4.85 (d, 1H, J=3.7 Hz), 4.24 (bs, 1H), 4.08 (dd, 1H, J=10.2, 4.1 Hz), 3.93 (dd, 1H, J=9.5, 4.4 Hz), 3.80 (d, 1H, J=10.2 Hz), 3.61 (d, 1H, J=9.4 Hz), 2.43 (s, 3H), 2.36 (s, 3H), 1.50 (d, 3H, J=7.0 Hz).

Compound 338

2'-Cyano-5-(4-hydroxypyrrolidin-3-yloxy)-4'-methyl-N—((R)-1-(6-methylpyridin-3-yl)ethyl)biphenyl-3-carboxamide

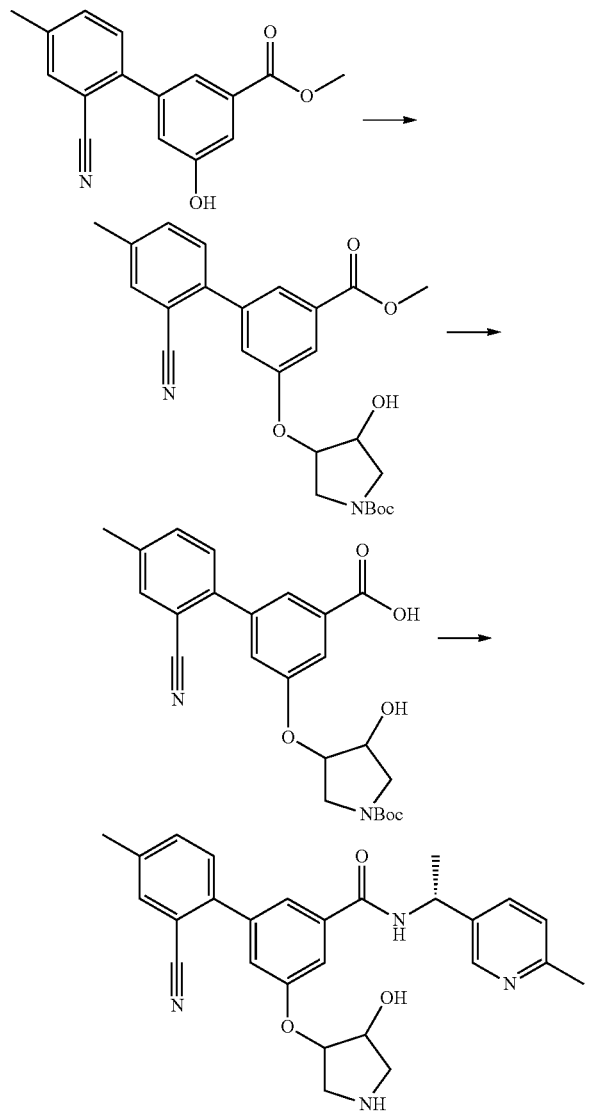

A) tert-Butyl 3-(2'-cyano-5-(methoxycarbonyl)-4'-methylbiphenyl-3-yloxy)-4-hydroxypyrrolidine-1-carboxylate A stirred mixture of methyl 2'-cyano-5-hydroxy-4'-methylbiphenyl-3-carboxylate (300 mg, 1.1 mol), potassium carbonate (320 mg, 2.4 mmol), DMSO (8 mL), and tert-butyl 6-oxa-3-aza-bicyclo[3.1.0]hexane-3-carboxylate (2.4 mmol) (J. Am. Chem. Soc. 2008, 130, 3900) was heated at 135° C. overnight. After cooling, the reaction mixture was diluted with EtOAc. The organic phase was washed with aq. NaHCO₃ (sat.), dried over anhydrous MgSO₄, filtered, and concentrated. The residue was purified by flash chromatography (0-50% EtOAc/hexane) to afford the title compound.

B) 5-(1-(tert-Butoxycarbonyl)-4-hydroxypyrrolidin-3-yloxy)-2'-cyano-4'-methylbiphenyl-3-carboxylic acid To a stirred solution of tert-butyl 3-(2'-cyano-5-(methoxycarbonyl)-4'-methylbiphenyl-3-yloxy)-4-hydroxypyrrolidine-1-carboxylate (310 mg, 0.68 mmol) in THF (3 mL) was added 2.5 M of aq. lithium hydroxide solution (1.5 mL, 3.8 mmol). The reaction mixture was stirred at 60° C. overnight. The aqueous solution was acidified with 15% HCl (aq.) to pH=5, and extracted with EtOAc. The combined organic layers were concentrated in vacuo to afford the title compound.

C) 2'-Cyano-5-(4-hydroxypyrrolidin-3-yloxy)-4'-methyl-N—((R)-1-(6-methylpyridin-3-yl)ethyl)biphenyl-3-carboxamide To a solution of 5-(1-(tert-butoxycarbonyl)-4-hydroxypyrrolidin-3-yloxy)-2'-cyano-4'-methylbiphenyl-3-carboxylic acid (60 mg, 0.14 mol) in N,N-dimethylformamide (1 mL) were added (R)-1-(6-methylpyridin-3-yl)ethanamine dihydrochloride (60 mg, 0.29 mmol), N,N,N',N'-tetramethyl-O-(7-azabenzotriazol-1-yl)uronium hexafluorophosphate (120 mg, 0.32 mmol), and N,N-diisopropylethylamine (400 μL, 2.3 mmol). The reaction mixture was stirred for 16 hours at 25° C., and then purified by preparative HPLC to afford the Boc-protected product which was dissolved in CH₂Cl₂ (5 mL) and trifluoroacetic acid (1 mL) was added. The mixture was stirred for 2 hrs at room temperature, and then concentrated in vacuo. The residue was purified by preparative HPLC to afford the final product as a light color solid.

LC-MS: 457.3 [M+1]⁺; ¹H NMR (400 MHz, DMSO-d6): 8.90 (d, 1H, J=7.6 Hz), 8.46 (bs, 1H), 7.80 (bs, 1H), 7.70-7.55 (m, 4H), 7.52 (bs, 1H), 7.33 (bs, 1H), 7.20 (d, 1H, J=8.2 Hz), 5.28 (bs, 1H), 5.16 (m, 1H), 4.65 (bs, 1H), 4.16 (bs, 1H), 3.50-3.25 (m, 2H), 3.05 (dd, 1H, J=11.7, 4.4 Hz), 2.88 (d, 1H, J=12.6 Hz), 2.73 (d, 1H, J=11.7 Hz), 2.43 (s, 3H), 2.41 (s, 3H), 1.49 (d, 3H, J=6.9 Hz).

Compound 340

(R)-5-((Dimethylamino)methyl)-4'-methyl-N-(1-(6-methylpyridin-3-yl)ethyl)biphenyl-3-carboxamide

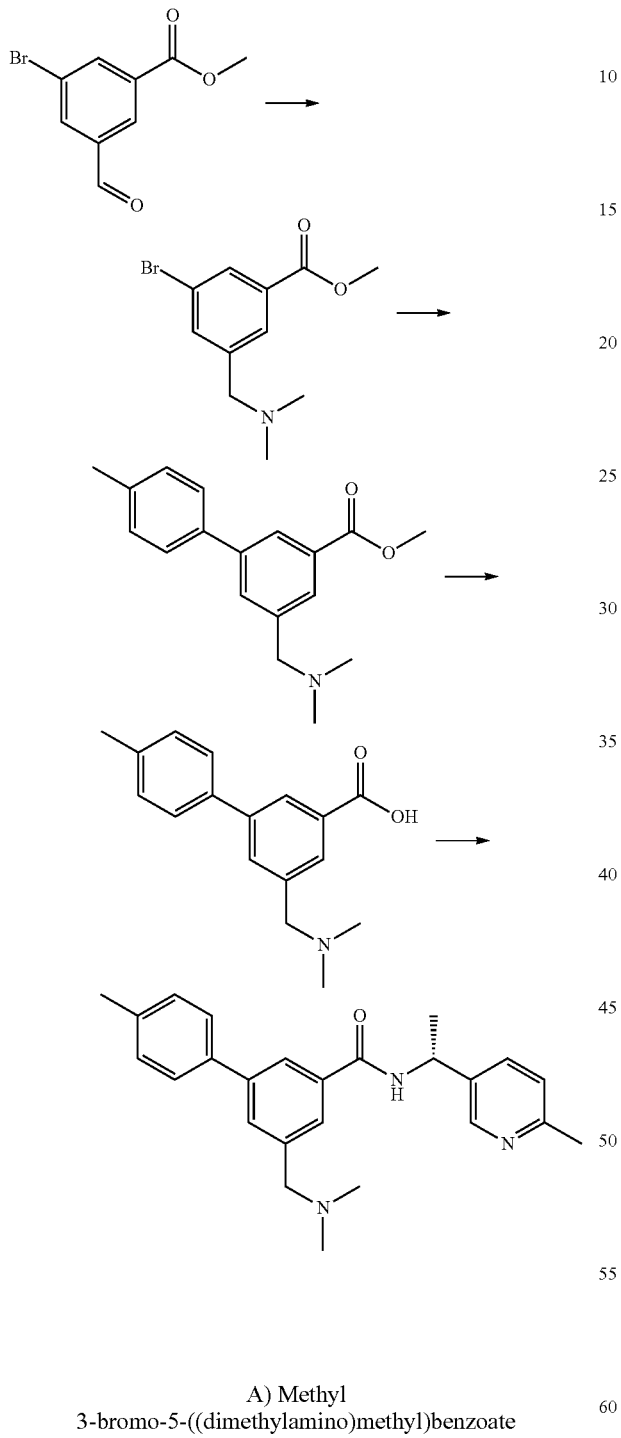

A) Methyl 3-bromo-5-((dimethylamino)methyl)benzoate

A mixture of methyl 3-bromo-5-formylbenzoate (200 mg, 0.82 mmol), methanol (3 mL), 2.0 M dimethylamine solution in THF (0.3 mL, 6 mmol), zinc dichloride (30 mg, 0.22 mmol), and sodium cyanoborohydride (200 mg, 3.2 mmol) was stirred at 0° C. for 1 h. The mixture was diluted with water (10 mL) and the aqueous layer was extracted with EtOAc (15 mL×3). The combined organic layers were dried over anhydrous MgSO$_4$ and concentrated. The residue was purified by silica gel chromatography to afford the title compound.

B) 5-((Dimethylamino)methyl)-4'-methylbiphenyl-3-carboxylate

A mixture of methyl 3-bromo-5-((dimethylamino)methyl) benzoate (50 mg, 0.18 mmol), p-tolylboronic acid (30 mg, 0.22 mmol), tetrakis(triphenylphosphine)-palladium(0) (10 mg, 0.009 mmol), N,N-dimethylformamide (0.5 mL), and toluene (1.5 mL) under nitrogen was subjected to microwave irradiation at 110° C. for 1 h. After cooling, the mixture was diluted with water (15 mL) and extracted with EtOAc (15 mL×3). The combined organic layers were dried over anhydrous MgSO$_4$, and concentrated in vacuo. The residue was purified by flash chromatography to afford the title compound.

C) 5-((Dimethylamino)methyl)-4'-methylbiphenyl-3-carboxylic acid

To a stirred solution of methyl 5-((dimethylamino)methyl)-4'-methylbiphenyl-3-carboxylate (90 mg, 0.32 mmol) in 1,4-dioxane (1.5 mL) and water (1.5 mL) was added lithium hydroxide (20 mg, 0.83 mmol). The reaction mixture was stirred at room temperature for 2 h, and then treated with aq. NH$_4$Cl and extracted with EtOAc (15 mL×3). The combined organic layers were dried over anhydrous MgSO$_4$, and concentrated. The residue was purified by silica gel chromatography to afford the title compound. $^1$H NMR (CD$_3$OD, 400 MHz): 8.29 (s, 1H), 7.79 (s, 1H), 7.60 (s, 1H), 7.59 (d, J=8.0 Hz, 2H), 7.28 (d, J=8.0 Hz, 2H), 4.27 (s, 2H), 2.81 (s, 6H), 2.38 (s, 3H).

D) (R)-5-((Dimethylamino)methyl)-4'-methyl-N-(1-(6-methylpyridin-3-yl)ethyl)biphenyl-3-carboxamide To a solution of 5-((dimethylamino)methyl)-4'-methylbiphenyl-3-carboxylic acid (20 mg, 0.074 mmol) in N,N-dimethylformamide (1 mL) were added (R)-1-(6-methylpyridin-3-yl)ethanamine dihydrochloride (40 mg, 0.19 mmol), N,N,N',N'-tetramethyl-O-(7-azabenzotriazol-1-yl)uronium hexafluorophosphate (60 mg, 0.16 mmol), and N,N-diisopropylethylamine (200 µL, 1.15 mmol). The reaction mixture was stirred for 16 hours at 25° C., and then purified by preparative HPLC to afford the final product.

LC-MS: 388.3 [M+1]$^+$; $^1$H NMR (400 MHz, DMSO-d6): 8.93 (d, 1H, J=7.8 Hz), 8.48 (d, 1H, J=2.2 Hz), 8.01 (t, 1H, J=1.4 Hz), 7.75 (bs, 1H), 7.70-7.65 (m, 2H), 7.62 (d, 2H, J=8.1 Hz), 7.31 (d, 2H, J=8.0 Hz), 7.21 (d, 1H, J=8.0 Hz), 5.19 (m, 1H), 3.48 (s, 2H), 2.43 (s, 3H), 2.36 (s, 3H), 2.17 (s, 6H), 1.52 (d, 3H, J=7.1 Hz).

Compound 342

3-(2-(Diethylamino)-1-hydroxyethyl)-5-(5-methylpyridin-2-yl)-N—((R)-1-(6-methylpyridin-3-yl)ethyl)benzamide

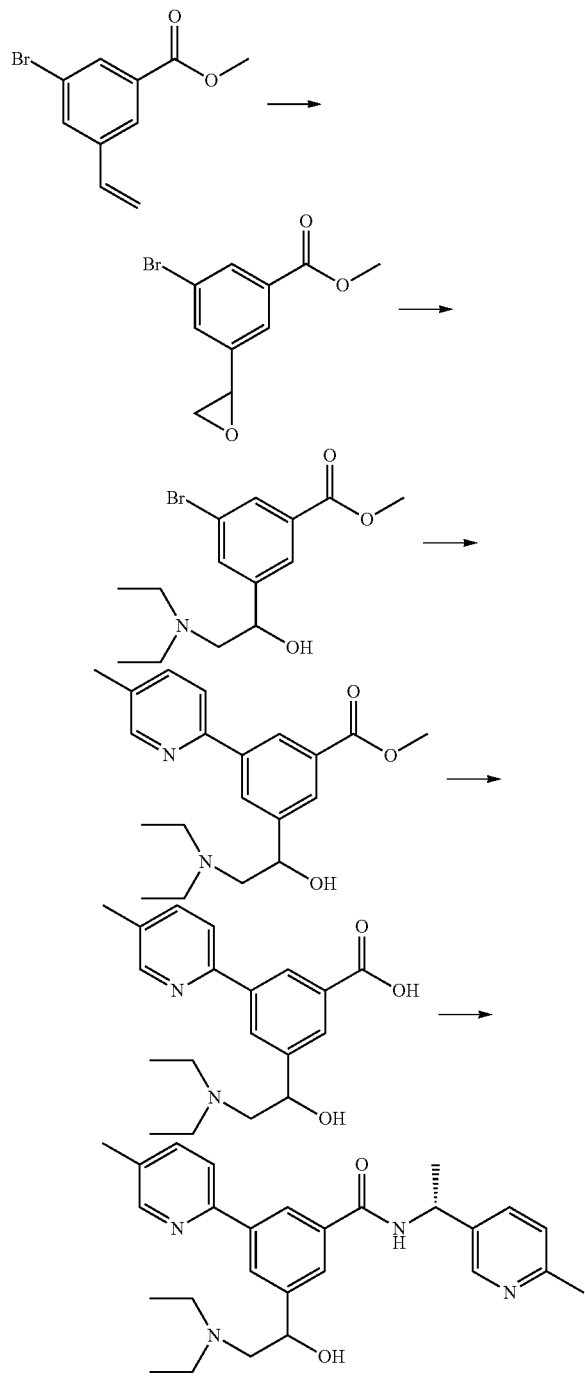

A) Methyl 3-bromo-5-(oxiran-2-yl)benzoate

To a stirred solution of methyl 3-bromo-5-vinylbenzoate (1.00 g, 4.15 mmol) in $CH_2Cl_2$ (40 mL) at 0° C. was added m-chloroperbenzoic acid (70% purity, 1.43 g, 5.80 mmol) in portions over a 10 minute period. The mixture was warmed to room temperature and stirred for 2 hours upon which it was poured onto saturated sodium bicarbonate (250 mL). The mixture was extracted with ethyl acetate (3×100 mL) and the combined extracts were dried over $Na_2SO_4$ and concentrated. The residue was purified by column chromatography (0-50% EtOAc/hexane) to afford the title compound as a yellow oil. $^1$H NMR (400 MHz, DMSO-d6): 7.92 (t, 1H, J=1.7 Hz), 7.86 (t, 1H, J=1.5 Hz), 7.78 (t, 1H, J=1.7 Hz), 4.09 (q, 1H, J=2.5 Hz), 3.87 (s, 3H), 3.17-3.14 (m, 1H), 2.92-2.90 (m, 1H).

B) Methyl 3-bromo-5-(1-(diethylamino)-2-hydroxyethyl)benzoate

Into a 20 mL reaction vessel were combined methyl 3-bromo-5-(oxiran-2-yl)benzoate (0.10 g, 0.39 mmol), ethanol (10 mL), and diethylamine (120 μL, 1.2 mmol). The mixture was heated at 50° C. overnight, and then concentrated. The residue was purified by preparative HPLC (100× 21.2 mm C18 column, $CH_3CN$/water[10 mM $Et_2NH$]) to afford the title compound.
LC-MS: 331.7 [M+1]$^+$; $^1$H NMR (400 MHz, DMSO-d6): 7.95 (t, 1H, J=1.7 Hz), 7.91 (t, 1H, J=1.7 Hz), 7.80 (t, 1H, J=1.7 Hz), 5.28 (brs, 1H), 4.66 (t, 1H, J=6.5 Hz), 3.86 (s, 3H), 2.57-2.51 (m, 2H), 2.48-2.43 (m, 4H), 0.86 (t, 6H, J=7.0 Hz).

C) Methyl 3-(2-(diethylamino)-1-hydroxyethyl)-5-(5-methylpyridin-2-yl)benzoate

A mixture of methyl 3-bromo-5-(2-(diethylamino)-1-hydroxyethyl)benzoate (80 mg, 0.24 mmol), 5-methyl-2-(tributylstannyl)pyridine (100 μL, 0.30 mmol), tetrakis(triphenylphosphine)-palladium(0) (14 mg, 0.012 mmol) and toluene (2.6 mL) under argon was subjected to microwave irradiation at 120° C. for 2 hours. The mixture was cooled to room temperature, poured into brine (20 mL) and extracted with ethyl acetate (3×20 mL). The combined extracts were dried over $Na_2SO_4$ and concentrated in vacuo. The residue was purified by column chromatography (0-100% EtOAc/hexane) to yield the title compound as a yellow oil. LC-MS: 343.7 [M+1]$^+$.

D) 3-(2-(Diethylamino)-1-hydroxyethyl)-5-(5-methylpyridin-2-yl)benzoic acid

Into a 20 mL reaction vessel were combined methyl 3-(2-(diethylamino)-1-hydroxyethyl)-5-(5-methylpyridin-2-yl)benzoate (50 mg, 0.15 mmol), tetrahydrofuran (10 mL) and lithium hydroxide (8.7 mg, 0.36 mmol). The mixture was heated at 50° C. for 3 hours. After cooling, the mixture was treated with 7 M aq. HCl (52 μL, 0.36 mmol), and concentrated to afford the crude compound which was used directly in the next step.

E) 3-(2-(Diethylamino)-1-hydroxyethyl)-5-(5-methylpyridin-2-yl)-N—((R)-1-(6-methylpyridin-3-yl)ethyl)benzamide To a solution of 3-(2-(diethylamino)-1-hydroxyethyl)-5-(5-methylpyridin-2-yl)benzoic acid (30 mg, 0.075 mmol) in N,N-dimethylformamide (5 mL) were added (R)-1-(6-methylpyridin-3-yl)ethanamine dihydrochloride (100 mg, 0.48 mmol), N,N,N',N'-tetramethyl-O-(7-azabenzotriazol-1-yl)uronium hexafluorophosphate (160 mg, 0.42 mmol) and N,N-diisopropylethylamine (300 μL, 1.7 mmol). The reaction mixture was stirred for 16 hours at 25° C. and purified by preparative HPLC (100×21.2 mm C18 column, CH₃CN/water[10 mM Et₂NH]) to afford the title product.

LC-MS: 447.6 [M+1]⁺; ¹H NMR (400 MHz, DMSO-d6): 8.96 (d, 1H, J=8.0 Hz), 8.54 (bs, 1H), 8.49 (bs, 1H), 8.38 (bs, 1H), 8.19 (bs, 1H), 7.93 (d, 1H, J=8.1 Hz), 7.87 (bs, 1H), 7.77-7.65 (m, 2H), 7.22 (d, 1H, J=8.1 Hz), 5.21 (m, 1H), 5.06 (bs, 1H), 4.72 (bs, 1H), 3.40-3.30 (m, 2H), 2.65-2.50 (m, 4H), 2.43 (s, 3H), 2.35 (s, 3H), 1.53 (d, 3H, J=7.0 Hz), 0.92 (t, 6H, J=7.1 Hz).

Compound 365

5-(1-Hydroxy-2-morpholinoethyl)-4'-methyl-N-((6-methylpyridin-3-yl)methyl)biphenyl-3-carboxamide

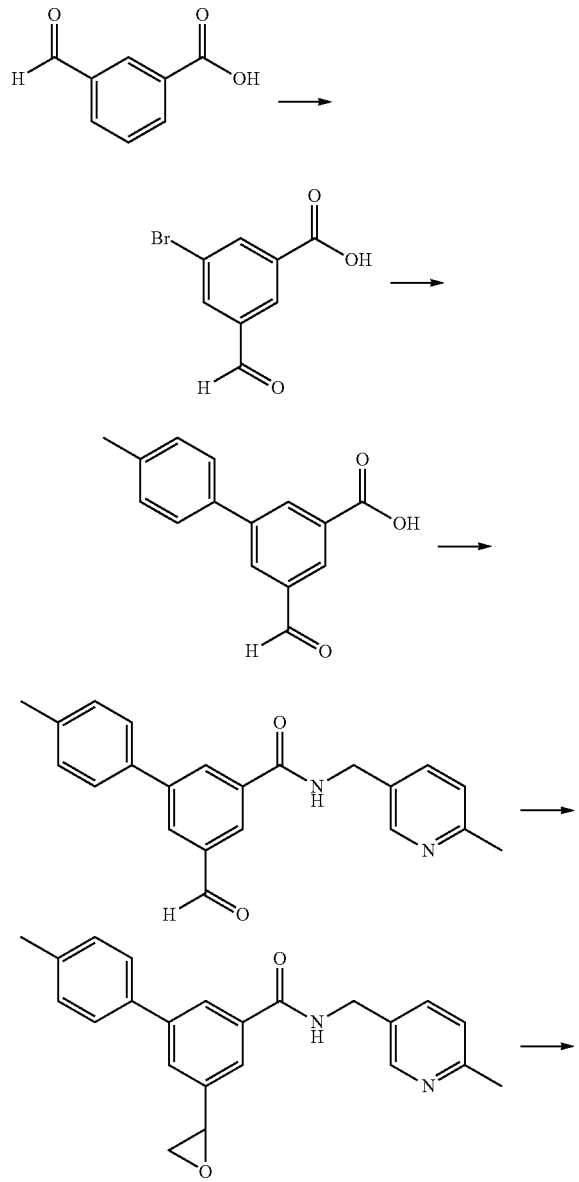

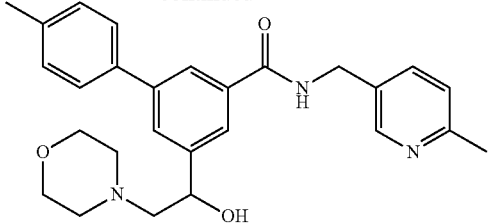

A) 3-Bromo-5-formylbenzoic acid

Into a round bottom flask were combined 3-formylbenzoic acid (10.0 g, 66.6 mmol) and sulfuric acid (653 g, 6.66 mol). N-Bromosuccinimide (14.23 g, 79.9 mmol) was added portion wise over a 10 minute period and the reaction was stirred at room temperature for 3 h upon which the mixture was poured over ice. The white precipitate that formed was filtered, washed with cold water (5×100 mL), and recrystallized from water-ethanol to afford the title compound as a white solid (12.98 g, 76.6%). LC-MS: 227.0 [M−1]⁻; ¹H NMR (400 MHz, DMSO-d6): 10.05 (s, 1H), 8.40 (t, 1H, J=1.5 Hz), 8.3 (d, 2H, J=1.5 Hz).

B) 5-Formyl-4'-methylbiphenyl-3-carboxylic acid

To a mixture of 3-bromo-5-formylbenzoic acid (8.0 g, 34.9 mmol), p-tolylboronic acid (9.5 g, 70 mmol), toluene (300 mL), cesium carbonate (28 g, 87 mmol), and water (25 mL) under nitrogen was added tetrakis(triphenylphosphine)palladium(0) (2.0 g, 1.7 mmol). The mixture was heated under reflux for 5 h. After cooling, the mixture was filtered through Celite and the filter cake was washed with EtOAc. The filtrate was washed with brine, dried, and concentrated. The residue was purified by column chromatography using methylene chloride:methanol gradient (0-5%) to afford the title compound (4.8 g, 51%). LC-MS: 239.0 [M−1]⁻.

C) 5-Formyl-4'-methyl-N-((6-methylpyridin-3-yl)methyl)biphenyl-3-carboxamide

Into a round bottom flask were combined 5-formyl-4'-methylbiphenyl-3-carboxylic acid (3.00 g, 12.5 mmol), (6-methylpyridin-3-yl)methanamine (1.91 g, 15.6 mmol), N,N-diisopropylethylamine (6.46 g, 49.9 mmol) and N,N-dimethylformamide (97 mL). N,N,N',N'-Tetramethyl-O-(7-azabenzotriazol-1-yl)uronium hexafluorophosphate (9.50 g, 25.0 mmol) was added in one portion and the mixture was heated at 60° C. for 2 h. After cooling, the mixture was poured onto saturated sodium bicarbonate (200 mL) and extracted with ethyl acetate (3×100 mL). The combined extracts were dried over sodium sulfate and concentrated in vacuo. The residue was purified by column chromatography using methylene chloride:methanol gradient (0-10%) to afford the title compound. LC-MS: 346.2 [M+1]⁺; ¹H NMR (400 MHz, DMSO-d6): 10.14 (s, 1H), 8.46-8.43 (m, 2H), 8.37-8.33 (m, 2H), 7.72 (d, 2H, J=8.0 Hz), 7.64 (dd, 1H, J=8.0 Hz), 7.34 (d, 2H, J=7.9 Hz), 7.22 (d, 2H, J=7.9 Hz), 4.51 (d, 2H, J=5.9 Hz), 2.44 (s, 3H), 2.37 (s, 3H).

D) 4'-Methyl-N-((6-methylpyridin-3-yl)methyl)-5-(oxiran-2-yl)biphenyl-3-carboxamide A mixture of sodium hydride (60% in mineral oil, 0.85 g, 21.2 mmol) in dimethyl sulfoxide (75 mL) was cooled to −10°

C. Trimethylsufoxonium iodide (4.66 g, 21.2 mmol) in DMSO (25 mL) was added dropwise over a 10 mM period. The mixture was warmed to room temperature and stirred for an additional hour. The mixture was cooled to 0° C. and 5-formyl-4'-methyl-N-((6-methylpyridin-3-yl)methyl)biphenyl-3-carboxamide (3.65 g, 10.6 mmol) in DMSO (25 mL) was added dropwise over a 10 minute period. The mixture was warmed to room temperature and stirred for 1 hour. The mixture was poured onto ice and extracted with ethyl acetate (3×150 mL). The combined extracts were dried over sodium sulfate and concentrated in vacuo. The mixture was purified by column chromatography using methylene chloride:methanol gradient (2-10%) to afford the title compound as a yellow oil. LC-MS: 358.8 [M+1]$^+$.

E) 5-(1-Hydroxy-2-morpholinoethyl)-4'-methyl-N-((6-methylpyridin-3-yl)methyl)biphenyl-3-carboxamide Into a 20 mL reaction vessel were combined 4'-methyl-N-((6-methylpyridin-3-yl)methyl)-5-(oxiran-2-yl)biphenyl-3-carboxamide (15 mg, 0.042 mmol), ethanol (2 mL), and morpholine (13 mg, 0.15 mmol). The mixture was heated at 50° C. overnight. The volatiles were removed under reduced pressure and the residue was purified by preparative HPLC (100× 21.2 mm C18 column, $CH_3CN$/water[10 mM $Et_2NH$]) to afford the title product.

LC-MS: 446.2 [M+1]$^+$; $^1$H NMR (400 MHz, DMSO-d6): 9.13 (t, 1H, J=5.8 Hz), 8.40 (d, 1H, J=2.3 Hz), 8.00 (t, 1H, J=1.7 Hz), 7.80 (s, 1H), 7.76 (s, 1H), 7.62 (d, 3H, J=8.2 Hz), 7.30 (d, 2H, J=7.8 Hz), 7.26 (d, 1H, J=7.8 Hz), 5.21 (d, 1H, J=4.0 Hz), 4.87-4.80 (m, 1H), 4.47 (d, 2H, J=5.8 Hz), 3.56 (t, 4H, J=4.6 Hz), 2.57-2.52 (m, 2H), 2.48-2.44 (m, 4H), 2.43 (s, 3H), 2.35 (s, 3H).

The syntheses of representative compounds of this invention can be carried out in accordance with the methods set forth above and using the appropriate reagents, starting materials, and purification methods known to those skilled in the art.

ASSAYS

Compounds provided herein can be evaluated using cell-based assays, such as calcium influx or electrophysiological assays, using biochemical assays, such as binding assays to $P2X_2$ and $P2X_3$ receptors, or can be evaluated in animal models of pain or urinary function. Examples of assays are described below.

The purinergic receptors $P2X_2$ and $P2X_3$ are expressed in a variety of tissues including various sensory and sympathetic ganglia, such as the dorsal root (DRG), nodose (ND), trigeminal (TG), and superior cervical ganglia (SCG) and also in smooth muscle cells (Burnstock, *Trends Pharmacol. Sci.* 27:166-76, 2006). In several regions, $P2X_2$ and $P2X_3$ receptors are coexpressed and functional studies have demonstrated the presence of heteromeric $P2X_{2/3}$ receptors whose properties differ from those of either homomeric receptor. In addition, chimeric $P2X_{2/3}$ receptors, containing the N-terminal cytoplasmic domain of $P2X_2$ fused to the first transmembrane domain of $P2X_3$ have been described; these chimeric channels retain the pharmacological profile of homomeric $P2X_3$ receptors, while gaining the non-desensitizing phenotype of the homomeric $P2X_2$ receptor (Neelands et al., *Br. J. Pharmacol.* 140:202-10, 2003). The non-desensitizing behavior of the chimeric receptor is especially useful for screening.

Members of the P2X family are ligand-gated non-selective cation channels whose activity can be characterized by using electrophysiological methods, or by measuring calcium ion influx using calcium-sensitive fluorescent dyes. Applications of agonists such as ATP, or an ATP analog such as α,β-Methyleneadenosine 5'-triphosphate (αβMeATP, Sigma-Aldrich), causes channel opening, resulting in current flow and calcium influx (Bianchi et al., *Eur. J. Pharmacol.* 376:127-38, 1999).

The compounds provided herein can be tested for antagonist activity at $P2X_3$ and $P2X_{2/3}$ receptors by measuring their ability to affect channel opening by ATP, αβMeATP, or other agonists. Functional tests of receptor activity include but are not limited to: (i) calcium ion influx measured by fluorescence of a calcium-sensitive dye and; (ii) ion flux resulting from channel opening measured by electrophysiological methods. These methods can be used to evaluate channel function when the relevant receptor is heterologously expressed in mammalian or amphibian cells. These methods can also be used to evaluate compounds provided herein in rodent primary neurons and other mammalian primary cells and cell lines that normally express the receptor of interest.

Compounds can further be evaluated for their ability to bind $P2X_3$ and $P2X_{2/3}$ receptors using biochemical approaches.

Compounds can also be evaluated for their ability to modify sensory and autonomic nervous system signaling where the receptors are known to have a role (e.g., urinary bladder afferent signaling, sensory nerve pain sensation). Finally, compounds provided herein can be tested in vivo in relevant animal models known to one skilled in the art, such as, for example, models of neuropathic, inflammatory, or visceral pain, or models of urinary incontinence.

The following biological examples are offered to illustrate the compounds, pharmaceutical compositions and methods provided herein and are not to be construed in any way as limiting the scope thereof.

Calcium Uptake Assay

Clones and Cell Lines:

Human $P2X_3$ (Accession no. NM__002559), $P2X_2$ (Accession no. NM__170682) and Rat $P2X_3$ (Accession no. NM__031075) and $P2X_2$ (Accession no. NM__053656) are cloned into a mammalian expression vector (e.g., pcDNA5/TO or pcDNA3 Invitrogen). The human $P2X_{2/3}$ chimera clone is created as described by Neelands et al, and then cloned into an expression vector as above. Receptors are expressed in cells (e.g., HEK293 or 1321N1 (obtained from the ECACC)) via transient transfection using standard lipid mediated transfection, or by creation of stable transfectants for each receptor. For expression of the $P2X_{2/3}$ heteromeric receptor, the $P2X_3$ expression vector is stably transfected into a cell line already stably expressing $P2X_2$. $P2X_{2/3}$ heteromer function is isolated using pharmacological methods. Cell lines are maintained in DMEM+5% Glutamax, the appropriate level of selective antibiotic, and 10% heat inactivated FBS.

P2X Antagonist Assay:

Functional activity of compounds at the P2X receptor is determined by measuring their ability to inhibit agonist-induced calcium influx. Compounds are tested for antagonist activity against the $P2X_{2/3}$ chimera, the $P2X_3$ homomer, or the $P2X_{2/3}$ heteromer. At the start of each screening day, the agonist $EC_{50}$ is determined. Compound % inhibition or $IC_{50}$s are subsequently determined using a predetermined agonist concentration ($EC_{50-90}$ depending on cell line) as a stimulus.

The agonists used are αβMeATP, ATP, or other ATP analogs. Compounds may be tested at concentrations ranging from 1 pM to 10 μM.

To test for antagonist activity, cells expressing the appropriate receptor are seeded onto 96 or 384 well plates 18-24 hours prior to assay. On the day of the assay, cells are loaded with calcium-sensitive fluorescent dye (e.g., Fluo-4 no wash reagent-Invitrogen cat# F36206, or the BD™ PBX Calcium Assay Kit-BD cat #640175) in Hank's Buffered Salt Solution (HBSS) with up to 10 mM supplemental $CaCl_2$. Plates are incubated at 37° C. and then equilibrated at room temperature. Antagonism of agonist-induced calcium influx is measured using a fluorescent imaging plate reader (e.g. FLIP-$R^{TETRA}$, Molecular Devices, Sunnyvale, Calif.). The assay comprises two stages: a pre-treatment phase followed by a treatment phase. Compounds may be tested as follows: For the pre-treatment phase, 50 μL of 3× concentration of test compound in HBSS is added to cells containing 100 μA, of dye loading media to achieve a final concentration of 1× test compound. For the treatment phase, at a set interval after pre-treatment (1-30 minutes), 50 μL of 1× test compound plus 4× agonist solution is added, resulting in a final concentration of 1× compound and 1× agonist. Fluorescence is measured at 0.1-3 second intervals—with an excitation wavelength of 494 nM and an emission wavelength of 515 nM. Responses are measured as (peak fluorescence after agonist addition) minus (baseline fluorescence prior to treatment). Percent inhibition is calculated as follows:

$$\text{Percentage inhibition} = 1 - \frac{\left(\begin{array}{c}\text{Compound Response} -\\ \text{Control Response}\end{array}\right)}{\left(\begin{array}{c}\text{Agonist Response} -\\ \text{Control Response}\end{array}\right)} \times 100$$

$IC_{50}$ values are determined by analyzing dose response data in a 4 parameter logistic fit using GraphPad Prizm.

Electrophysiological Experiments

Whole Cell Patch Clamp:

Whole cell recordings are made using the Multiclamp700A patch-clamp amplifier and Clampex acquisition program (Molecular Devices Corporation). Whole-cell recordings are obtained from 1321N1 or HEK cells stably or transiently transfected with $P2X_3$ and/or $P2X_2$ expression vectors. Solutions are either applied for periods of 1 to 3s by a gravity flow, 8-valve delivery system, or for periods of milliseconds using the quick-change Dynaflow perfusion system (Cellectricon Inc.). The internal pipette solution may include 140 mM Cesium-Chloride, 10 mM EGTA, and 5 mM Hepes at pH 7.2; normal external solution is 140 mM NaCl, 5 mM KCl, 1 mM $CaCl_2$, 2 mM $MgCl_2$, 25 mM Hepes, and 10 mM glucose. Concentration-response curves are obtained by recording currents in response to brief applications of agonist at 1-3 min intervals where regular external solution is perfused during the intervals. To obtain inhibition curves, antagonists are pre-applied to the cells for a defined time period before a short application of the agonist+antagonist. The periods of antagonist pre-application and agonist+antagonist applications are constant for the entire test concentration series. Agonist evoked currents are measured in cells that are voltage clamped at −60 or −80 millivolts. $IC_{50}$ values are determined by analyzing dose response data in a 4 parameter logistic fit using GraphPad Prizm or Origin.

Automated Two-Electrode Voltage Clamp Recording:

Xenopus oocytes (Nalco) are isolated by enzymatic dissociation using collagenase (Worthington, 2 mg/ml). Oocytes are then individually injected with $P2X_3$, $P2X_2$, or a combination of $P2X_2$ and $P2X_3$ mRNA. Each oocyte receives ~64 nl of RNA solution in water at a concentration of ~0.01 μg/μl. Injected oocytes are stored in standard oocyte incubation solution, ND96, containing (in mM) 96 NaCl, 2 KCl, 1 $MgCl_2$, 1-5 $CaCl_2$ and 50 μg/ml Gentamicin at 16° C. Agonist-induced-current caused by P2X channel opening is observed in oocytes 1-5 days after injection. For automated recordings, 8 oocytes are placed in the recording chambers. Each oocyte is impaled by 2 glass electrodes having resistances of 0.5 to 1 MOhm when filled with a 3 M KCl solution. Electrode advancement and oocyte impalement are under software control (OPUSXPRESS 1.1, Molecular devices Corporation). The solutions are prepared in 96 well plates and robotically pipetted into the oocyte recording chambers by an 8 channel pipettor. Inhibition by antagonists is determined by calculating % current remaining when oocytes are stimulated with agonist in the presence of test compound compared to the peak current in the presence of agonist alone. The sequence of solution application to the oocyte is as follows: a specific concentration (e.g., $EC_{50}$, $EC_{80}$, or $EC_{90}$) of the agonist is added first to elicit the maximal response. After the pulse, oocytes are washed for several minutes with ND96. The test compound is then added at a particular concentration, followed by the compound at the same concentration along with the agonist. Concentrations for the compounds may range from 0.3 to 10,000 nM. $IC_{50}$ values are determined by analyzing dose response data using a 4 parameter logistic fit using GraphPad Prizm or Origin software.

Manual Two-Electrode Voltage Clamp:

Individual oocytes are impaled manually with 2 electrodes and agonist evoked current are measured using an Oocyte clamp amplifier (Warner Instrument Corp.) and Clampex (Molecular Devices Corporation) acquisition software. Solutions are delivered using gravity flow and applied as above. The agonist induced current is measured in the absence and presence of antagonist. Antagonists are tested in a concentration series to obtain an inhibition curve as described above.

Selectivity Screens:

Compounds that inhibit $P2X_3$ and/or $P2X_{2/3}$ activation will be tested for activity against other P2X receptors to determine their selectivity for specific P2X family members. The list of receptors to be assayed includes, but is not restricted to P2X1, $P2X_2$, P2X4, P2X5, P2X6, and P2X7. The types of assay used for selectivity determination may include: 1) Agonist-induced Calcium influx in cells heterologously expressing the relevant receptor, 2) Electrophysiological determination of receptor inhibition in either mammalian cells or Xenopus oocytes heterologously expressing the receptor of interest. Methods and data analysis are similar to those described above for $P2X_3$ and $P2X_{2/3}$.

Radioligand Binding:

Radioligand experiments are done to determine the affinity of test compounds for $P2X_3$ homomeric and $P2X_{2/3}$ heteromeric receptors. These studies also provide valuable insights into the mechanism of action of antagonism. The general methodologies used for radioligand binding experiments for $P2X_3$ and $P2X_{2/3}$ receptors are described by Jarvis et al., *J. Pharmacol. Exp. Ther.* 10:407-16, 2004.

Briefly, cell membranes are prepared from cells transiently or stably expressing $P2X_3$ or $P2X_{2/3}$ receptors. Cells are grown to confluence, washed, isolated, and stored as pellets at −80° C. until use. Some studies may require the addition of Apyrase or hexokinase (Sigma-Aldrich) during membrane preparation to minimize ATP-mediated receptor desensitization during membrane preparation. Membranes are prepared by resuspending the cell pellet in homogenization buffer, homogenizing, and centrifuging to obtain a membrane pellet. Total protein concentrations are determined using standard methods.

Displacement binding studies are conducted using procedures adapted from Jarvis et al. Under optimized conditions, ligand competition experiments are conducted using radioligand ([3H]A-317491, Abbott), or other high affinity radioligands and a range of different concentrations of test compounds in binding buffer. Ligand saturation studies are conducted using a range of concentrations of radioligand. All binding reactions are terminated by rapid filtration through a glass fiber filter. Membranes are washed, incubated in scintillant, and counted in a scintillation counter. $IC_{50}$ values are determined using a four-parameter logistic Hill equation.

Drug Metabolism and Pharmacokinetics

Caco-2 Permeability:

Caco-2 permeability is measured according to the method described in Yee, *Pharm. Res.* 14:763-6, 1997. Caco-2 cells are grown on filter supports (Falcon HTS multiwell insert system) for 14 days. Culture medium is removed from both the apical and basolateral compartments and the monolayers are preincubated with pre-warmed 0.3 ml apical buffer and 1.0 ml basolateral buffer for 0.75 hour at 37° C. in a shaker water bath at 50 cycles/min. The apical buffer consists of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consists of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media is removed and test compound solution (10 µM) in buffer is added to the apical compartment. The inserts are moved to wells containing fresh basolateral buffer and incubated for 1 hr. Drug concentration in the buffer is measured by LC/MS analysis.

Flux rate (F, mass/time) is calculated from the slope of cumulative appearance of substrate on the receiver side and apparent permeability coefficient (Papp) is calculated from the following equation:

$$Papp\ (cm/sec) = (F*VD)/(SA*MD)$$

where SA is surface area for transport (0.3 cm$^2$), VD is the donor volume (0.3 ml), MD is the total amount of drug on the donor side at t=0. All data represent the mean of 2 inserts. Monolayer integrity is determined by Lucifer Yellow transport.

Human Dofetilide Binding:

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells are homogenized using a Polytron homogenizer (at the maximum power for 20 seconds) and centrifuged at 48,000 g for 20 minutes at 4° C. The pellet is resuspended, homogenized and centrifuged once more in the same manner. The resultant supernatant is discarded and the final pellet was resuspended (10-fold volume of 50 mM Tris buffer) and homogenized at the maximum power for 20 seconds. The membrane homogenate is aliquoted and stored at −80° C. until use. An aliquot is used for protein concentration determination using a Protein Assay Rapid Kit and ARVO SX plate reader (Wallac). All the manipulation, stock solution and equipment are kept on ice at all time. For saturation assays, experiments are conducted in a total volume of 2004 Saturation is determined by incubating 20 µl of [$^3$H]-dofetilide and 160 µl of membrane homogenates (20-30 µg protein per well) for 60 min at room temperature in the absence or presence of 10 µM dofetilide at final concentrations (20 µl) for total or nonspecific binding, respectively. All incubations are terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity is quantified by liquid scintillation counting using Packard LS counter.

For the competition assay, compounds are diluted in 96 well polypropylene plates as 4-point dilutions in semi-log format. All dilutions are performed in DMSO first and then transferred into 50 mM Tris buffer (pH 7.5 at 25° C.) containing 1 mM $MgCl_2$, 10 mM KCl so that the final DMSO concentration became equal to 1%. Compounds are dispensed in triplicate in assay plates (4 µl). Total binding and nonspecific binding wells are set up in 6 wells as vehicle and 10 µM dofetilide at final concentration, respectively. The radioligand was prepared at 5.6× final concentration and this solution is added to each well (36 µl). The assay is initiated by addition of YSi poly-L-lysine Scintillation Proximity Assay (SPA) beads (50 µl, 1 mg/well) and membranes (110 µl, 20 µg/well). Incubation is continued for 60 min at room temperature. Plates are incubated for a further 3 hours at room temperature for beads to settle. Receptor-bound radioactivity is quantified by counting WALLAC MICROBETA plate counter.

HERG Assay:

HEK 293 cells which stably express the HERG potassium channel are used for electrophysiological study. The methodology for stable transfection of this channel in HEK cells can be found elsewhere (Zhou et al., *Biophys. J.* 74:230-41, 1998). Before the day of experimentation, the cells are harvested from culture flasks and plated onto glass coverslips in a standard Minimum Essential Medium (MEM) medium with 10% Fetal Calf Serum (FCS). The plated cells are stored in an incubator at 37° C. maintained in an atmosphere of 95% $O_2$/5% $CO_2$. Cells are studied between 15-28 hrs after harvest.

HERG currents are studied using standard patch clamp techniques in the whole-cell mode. During the experiment the cells are superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings are made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MOhm and seal resistances >1 GOhm are accepted for further experimentation. Series resistance compensation was applied up to a maximum of 80%. No leak subtraction is done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol is applied to the cell to evoke membrane currents. The voltage protocol is as follows. The membrane is depolarized from a holding potential of −80 mV to +40 mV for 1000 ms. This was followed by a descending voltage ramp (rate 0.5 mV msec-1) back to the holding potential. The voltage protocol is applied to a cell continuously throughout the experiment every 4 seconds (0.25 Hz). The amplitude of the peak current elicited around −40 mV during the ramp is measured. Once stable evoked current responses are obtained in the external solution, vehicle (0.5% DMSO in the standard external solution) is applied for 10-20 min by a peristalic pump. Provided there were minimal changes in the amplitude of the evoked current response in the vehicle control condition, the test compound of either 0.3, 1, 3, or 10 mM is applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There is a subsequent wash period of a 10-20 min to assess reversibility. Finally, the cells is exposed to high dose of dofetilide (5 mM), a specific IKr blocker, to evaluate the insensitive endogenous current.

All experiments are performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, is measured off line on the computer.

The arithmetic mean of the ten values of amplitude is calculated under vehicle control conditions and in the presence of drug. Percent decrease of IN in each experiment was obtained by the normalized current value using the following formula: IN=(1−ID/IC)×100, where ID is the mean current value in the presence of drug and IC is the mean current value under control conditions. Separate experiments are performed for each drug concentration or time-matched control, and arithmetic mean in each experiment is defined as the result of the study.

Half-Life in Human Liver Microsomes (HLM):

Test compounds (1 µM) are incubated with 3.3 mM $MgCl_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of P450 group is collected at 0, 10, 30, and 60 min time point, where 0 mM time point indicated the time when NADPH was added into the reaction mixture of P450 group. An aliquot of samples of non-P450 group is collected at −10 and 65 mM time point. Collected aliquots are extracted with acetonitrile solution containing an internal standard. The precipitated protein is spun down in centrifuge (2000 rpm, 15 mM). The compound concentration in supernatant is measured by LC/MS/MS system. The half-life value is obtained by plotting the natural logarithm of the peak area ratio of compounds/internal standard versus time. The slope of the line of best fit through the points yields the rate of metabolism (k). This is converted to a half-life value using following equation:

Half-life=ln 2/k.

In Vivo Efficacy Assays $P2X_3$, $P2X_{2/3}$ antagonists may be tested in various animal models of human diseases, including models of neuropathic, inflammatory, and visceral pain, and models of bladder function. $P2X_3$ antagonists may be administered prior to or post-induction of the model depending upon the specific model and the compound PK characteristics. The route of administration may include intraperitoneal, (i.p.), subcutaneous (s.c.), oral (p.o.), intravenous (i.v.), intrathecal (i.t.), or intraplantar. The endpoints for these studies may include mechanical allodynia, thermal hyperalgesia, cold allodynia, decreased formalin-induced pain responses, decreased writhing and contractions or altered bladder mechanosensation as appropriate for the model as described below.

Formalin Model:

Test compounds are administered at various times prior to intraplantar administration of formalin. A dilute solution of formalin (25-50 µL of 1-2.5% formaldehyde/saline) is administered s.c. into the plantar surface of the left hind paw under light restraint. Immediately following injection, animals are placed on a mesh stand inside a clear observation chamber large enough to allow for free movement of the animals during the study. Behaviors are scored using manual scoring or automated scoring.

Manual scoring: Using a three channel timer, the observer records the time (t in seconds) of decreased weight-bearing ($t_1$), paw lifting ($t_2$), and licking/biting/shaking ($t_3$). Results are weighted according to the method of Dubuisson and Dennis, Pain, 4:161-174, 1977, using the formula $t_1+2t_2+3t_3/180$ where 180 s is the evaluation time for each increment. Behaviors are acquired in alternating 3 min increments starting at time=0 min (i.e. 0-3 min, 6-9 min etc.) and ending at 60 min.

Automated scoring: A small metal band weighing 0.5 g is placed on the left paw. Formalin is administered and the animal placed unrestrained inside an observation chamber over an electromagnetic detector system (Automated Nociception Analyzer, University of California, San Diego). The number of paw flinches is electronically recorded.

ATP and αβ-methylene ATP (αβ meATP)-Induced Inflammatory Pain:

Rats are administered up to 1 µMol αβmeATP, ATP, adenosine, or PBS in a volume up to 100 µL subcutaneously into the dorsal surface of the hindpaw. Immediately after injection, animals are placed on a stand inside a clear observation chamber large enough to allow for free movement of the animals. The duration of flinching and licking are recorded over a 20 minute interval to evaluate nocifensive behavior. Responses are measured using the either the manual or automated methods described above for the Formalin test. Additional behavioral testing may include assessment of mechanical allodynia and thermal hyperalgesia. For testing, compounds are administered prior to agonist injection.

Complete Freund's Adjuvant Model (CFA):

Animals receive an s.c. injection of 100 µL complete Freund's adjuvant containing 100 µg Mycobacterium tuberculosis strain H37Ra into the plantar surface of the right hind paw under isoflurane anesthesia. Swelling and inflammation are visible within 1 h after administration. Nociceptive testing may begin 24 h post CFA administration. Compounds are generally administered 0.5-12 hrs before testing.

Carageenan Induced Acute Pain:

Animals receive a subcutaneous injection of 100 µL of 2% carrageenan into the plantar surface of the right hind paw under isoflurane anesthesia. Swelling and inflammation are visible within 1 h after administration. Nociceptive testing may start 3-24 h post carageenan administration (Hargreaves et al., Pain, 32:77-88, 1988). Compounds are generally administered 0.5-12 hrs before testing.

Chronic Constriction Injury Model (CCI or Bennett Model):

The CCI model is performed according to the method described by Bennett and Xie, Pain, 33:87-107, 1988. Briefly, under isoflurane anesthesia, the right sciatic nerve is exposed at mid-thigh level via blunt dissection through the biceps femoris. Proximal to the bifurcation of the sciatic nerve, about 7 mm of nerve is freed of adhering tissue and 4 loose ligatures of 4.0 chromic gut are tied around the nerve. Spacing between ligatures is approximately 1 mm. The wound is closed in layers, and the skin closed with staples or non-silk sutures. Sham operated animals are treated identically with the exception that the sciatic nerve will not be ligated. Nociceptive testing can be done 7-21 days post surgery. Compounds are generally administered 0.5-12 hrs before testing.

Spinal Nerve Transection (SNT or Chung Model):

Under anesthesia, rats are placed in a prone position on a flat, sterile surface. A midline incision from L4-S2 is made and the left paraspinal muscles are separated from the spinous processes. The L5 and L6 spinal nerves are tightly ligated with a 4-0 silicon-treated silk suture, according to the method described by Kim and Chung, *Pain,* 50:355-363, 1992. The L4 spinal nerve is carefully preserved from being surgically injured. The skin is closed with wound clips and animals are returned to their home cages. Rats exhibiting prolonged post-operative neurological deficits or poor grooming are excluded from the experiments. The animals are assessed for nociceptive responses prior to surgery (baseline), then at various timepoints after administration of test compounds. Nociceptive testing can be done 7-21 days post surgery. Compounds are generally administered 0.5-12 hrs before testing.

Chemotherapy-Induced Painful Neuropathy:

Chemotherapy neuropathy is induced by i.p. administration of 1 mg/kg Taxol administered once/day on 4 alternating days (total dose=4 mg/kg) (Polomano et al., *Pain,* 94:293-304, 2001). Nociceptive testing can be done 9-30 days after the start of Taxol administration. Compounds are generally administered 0.5-12 hrs before testing.

Nociceptive Testing:

Mechanical Allodynia: Mechanical allodynia testing is performed using the up-down method of Dixon, *Ann. Rev. Pharmacol. Toxicol.* 20:441-462, 1980, modified for mechanical thresholds by Chaplan et al., *J. Neurosci. Methods* 53:55-63, 1994. To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. Each presentation lasts for a period of 4-8 seconds or until a nociceptive withdrawal behavior is observed. Flinching, paw withdrawal or licking of the paw are considered nociceptive behavioral responses. The 50% withdrawal threshold will be calculated using the method described by Chaplan et al., *J. Neurosci. Methods* 53:55-63, 1994

Thermal Hyperalgesia: Hind paw withdrawal latencies to a noxious thermal stimulus are determined using a plantar test apparatus (Ugo Basile) following the technique described by Hargreaves et al., *Pain* 32: 77-88, 1988. The radiant heat sourced is focused onto the plantar surface of the ipsilateral paw, and the paw withdrawal latency is determined. An increase latency of paw withdrawal demonstrates reversal of hyperalgesia.

Mechanical Hyperalgesia: The paw pressure assay can be used to assess mechanical hyperalgesia. For this assay, hind paw withdrawal thresholds (PWT) to a noxious mechanical stimulus are determined using an analgesymeter (Ugo Basile) as described in Stein et al., *Pharmacol. Biochem. Behav.* 31:451-455, 1988. The maximum weight that can be applied to the hind paw is set at 250 g and the end point is taken as complete withdrawal of the paw. PWT is determined once for each rat at each time point.

Cold allodynia: To measure cold allodynia, a drop of acetone is applied to the plantar surface of the paw through the underside of the grating on which the animals are standing using a 50 µL Hamilton syringe. The process is performed 5 times with a 3 min interval between each time. Vigorous shaking will be recorded as a positive response, and the time spent shaking is recorded. Alternatively, cold allodynia may be tested using the cold water bath method in which animals are placed into a cold water bath with water at a depth of 1.5-2.0 cm and at a temperature of 3-4 degrees centigrade and the number of paw lifts counted.

Colo-Rectal Distension (CRD):

Prior to induction of the model, animals are deprived of food but allowed access to water ad libitum for 16 h prior to the induction of the model. A 5 cm latex balloon is attached to a barostat system composed of a flow meter and pressure control program by a length of tubing. Under isoflurane anesthesia, the balloon is inserted into the distal colon via the anus at a distance of 5 cm from the anus and taped to the base of the tail. Post-anesthesia, the animal is placed unrestrained into a clean polypropylene cage and allowed to acclimate for 30 mins. The balloon is progressively inflated from 0-75 mmHg in 5 mm increments every 30 s. The colonic reaction threshold is defined as the pressure inducing the first abdominal contraction. Abdominal contraction indicative of visceral pain correlates with hunching, hump-backed position, licking of the lower abdomen, repeated waves of contraction of the ipsilateral oblique musculature with inward turning of the ipsilateral hindlimb, stretching, squashing of the lower abdomen against the floor (Wesselman, *Neurosci. Lett.,* 246:73-76, 1998). Alternatively, electrodes may be placed into the external oblique musculature for eletromyographic recordings of abdominal contractions. In this case, EMG activity is quantified during colonic balloon inflation. Compounds are generally administered 0.5-12 hrs before testing.

Acetic Acid WrithingTest:

A 0.6% solution of acetic acid (10 ml/kg) is administered i.p. to rats and the number of abdominal constrictions within 30 min are counted. Compounds are generally administered 0.5-12 hrs before testing.

Bladder Afferent Nerve Recordings:

In order to determine the precise role of inhibition of $P2X_3$ and $P2X_{2/3}$ receptors in the micturition response, test compounds will be examined for their ability to modulate afferent signaling from the urinary bladder. Compounds are evaluated in the urinary bladder/pelvic nerve preparation described by Vlaskovska et al., *J. Neuroscience,* 21:5670-7, 2001, and Cockayne et al., *J. Physiol.* 567:621-39, 2005. Briefly, the whole urinary tract attached to the lower vertebrae and surrounding tissues is isolated en bloc and superfused in a recording chamber with oxygenated (5% $CO_2$ and 95% $O_2$) Krebs solution. The bladder is catheterized through the urethra for intraluminal infusion. A second double lumen catheter is inserted into the bladder to measure intraluminal pressure and to drain the bladder. After the bladder is prepared, the pelvic nerve exiting the vertebrae is dissected and impaled with a suction glass electrode. Nerve activity is measured using standard electrophysiological methods. Following a 60 min stabilization period, repeated ramp distensions are performed until the afferent response stabilizes. This stabilized afferent response was used for comparing mechanosensitivity of bladder afferents between different treatment groups.

Isovolumetric Bladder Contraction Assay:

Female Sprague dawley rats are anesthetized, tracheotomized, and cannulated in the carotid artery and femoral vein. The urinary bladder is accessed via an abdominal incision, and the ureters ligated and transected. For fluid infusion and pressure measurements, the urinary bladder is cannulated.

Post surgery, the bladder is infused with saline until stable volume-induced bladder contractions are elicited. Once stable threshold volumes and contraction frequencies are obtained, the animal is dosed with compound and contraction frequency is measured.

Refill and Cystitis Models of Bladder Function:

Animals are anaesthetized, and transurethral closed cystometry was conducted as previously described (Dmitrieva et al., *Neuroscience* 78:449-59, 1997; Cockayne et al., *Nature* 407:1011-5, 2000). The bladder is catheterized transurethrally with a PE-10 polypropylene catheter. Each cystometrogram consists of slowly filling the bladder with normal saline via the transurethral catheter, and then recording the pressure associated with filling via a pressure transducer. Contractions greater than a predetermined threshold value are interpreted as micturition contractions. For each cystometrogram, the volume at which active contractions occurred (micturition threshold) and the number of contractions per cystometrogram are recorded. The effects of compounds are then determined.

Cystometrograms may also be obtained in animals cystitis models in which bladders are irritated by injection of cyclophosphamide (150 mg/kg, i.p.) 24 hrs prior to cystometry, or by infusion of up to 1% acetic acid during cystometry.

The synthetic and biological examples described in this application are offered to illustrate the compounds, pharmaceutical compositions and methods provided herein and are not to be construed in any way as limiting their scope. In the examples, all temperatures are in degrees Celsius (unless otherwise indicated). Compounds that can be prepared in accordance with the methods provided herein along with their biological activity data are presented in following Table. The syntheses of these representative compounds are carried out in accordance with the methods set forth above.

Exemplary Compounds Provided Herein

The following compounds have been or can be prepared according to the synthetic methods described herein. A calcium uptake assay was performed as described above and the activity of each compound is expressed as follows:

+ compound exhibited hP2X$_{2/3}$H IC$_{50}$>1000 nM
++ compound exhibited hP2X$_{2/3}$H IC$_{50}$ 501-1000 nM
+++ compound exhibited hP2X$_{2/3}$H IC$_{50}$ 100-500 nM
++++ compound exhibited hP2X$_{2/3}$H IC$_{50}$<100
\* compound exhibited hP2X$_3$ IC$_{50}$>1000 nM
\*\* compound exhibited hP2X$_3$ IC$_{50}$ 501-1000 nM
\*\*\* compound exhibited hP2X$_3$ IC$_{50}$ 100-500 nM
\*\*\*\* compound exhibited hP2X$_3$IC$_{50}$<100

TABLE 1

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 1 | 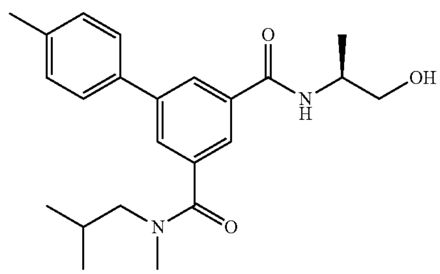 [SMILES: Cc1ccc(-c2cc(C(=O)N[C@@H](C)CO)cc(C(=O)N(C)CC(C)C)c2)cc1] | 382.5 | 383.3 | +++ | \*\*\*\* |
| 2 | 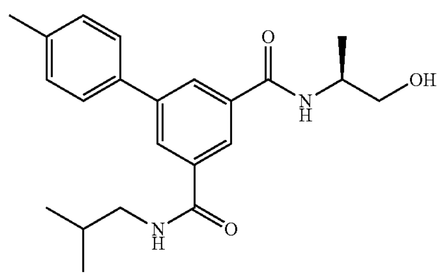 [SMILES: Cc1ccc(-c2cc(C(=O)NCC(C)C)cc(C(=O)N[C@@H](C)CO)c2)cc1] | 368.47 | 369.1 | + | \*\* |
| 3 | 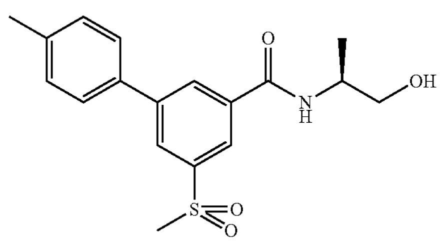 [SMILES: Cc1ccc(-c2cc(C(=O)N[C@@H](C)CO)cc(S(C)(=O)=O)c2)cc1] | 347.43 | 348.2 | + | \*\*\* |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 4 | 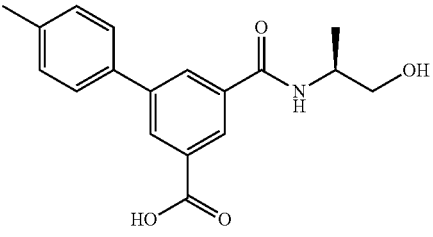 [SMILES: Cc1ccc(-c2cc(C(=O)O)cc(C(=O)N[C@@H](C)CO)c2)cc1] | 313.35 | 314.4 | + | * |
| 5 | 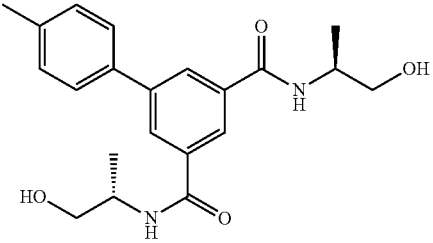 [SMILES: Cc1ccc(-c2cc(C(=O)N[C@@H](C)CO)cc(C(=O)N[C@@H](C)CO)c2)cc1] | 370.45 | 371.3 | ++ | * |
| 6 | 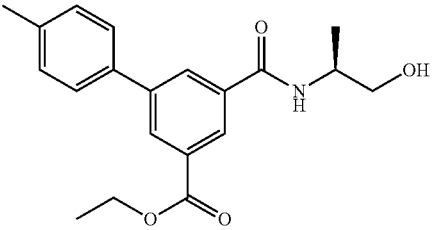 [SMILES: CCOC(=O)c1cc(C(=O)N[C@@H](C)CO)cc(-c2ccc(C)cc2)c1] | 341.4 | 342.4 | ++ | *** |
| 7 | 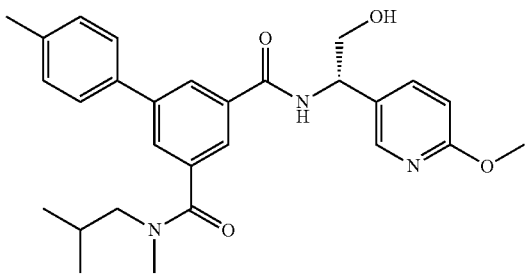 | 475.59 | 476.4 | +++ | *** |
| 8 | 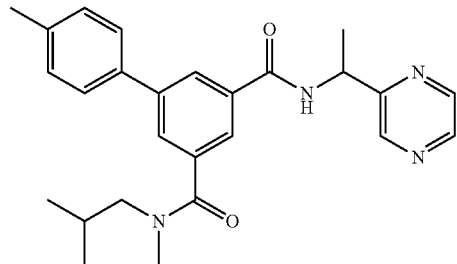 [SMILES: Cc1ccc(-c2cc(C(=O)NC(C)c3cnccn3)cc(C(=O)N(C)CC(C)C)c2)cc1] | 430.55 | 431.1 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 9 | 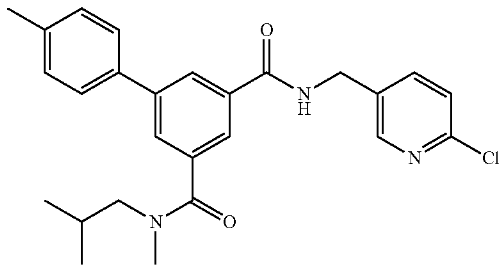 [SMILES: Cc1ccc(-c2cc(C(=O)NCc3ccc(Cl)nc3)cc(C(=O)N(C)CC(C)C)c2)cc1] | 449.98 | 450.4 | ++++ | **** |
| 10 | 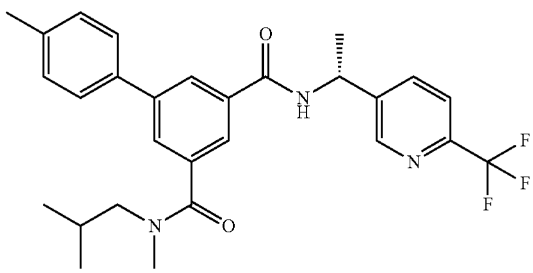 [SMILES: Cc1ccc(-c2cc(C(=O)N[C@H](C)c3ccc(C(F)(F)F)nc3)cc(C(=O)N(C)CC(C)C)c2)cc1] | 497.56 | 498.6 | +++ | *** |
| 11 | 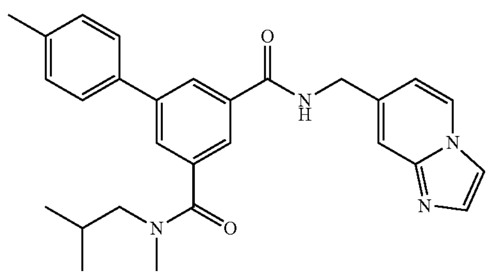 [SMILES: Cc1ccc(-c2cc(C(=O)NCc3ccn4ccnc4c3)cc(C(=O)N(C)CC(C)C)c2)cc1] | 454.57 | 455.4 | +++ | **** |
| 12 | 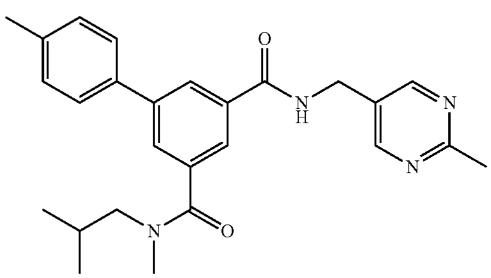 | 430.55 | 431.3 | ++++ | **** |
| 13 | 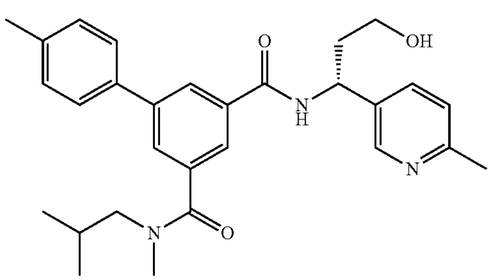 | 473.61 | 474.6 | +++ | *** |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 14 | 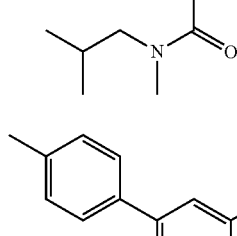 | 444.58 | 445.6 | ++++ | **** |
| 15 | 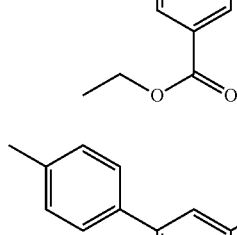 | 389.45 | 390.4 | ++++ | **** |
| 16 | 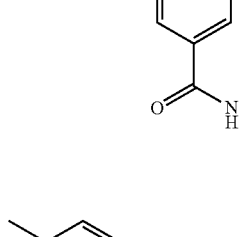 | 466.54 | 467.4 | +++ | *** |
| 17 | 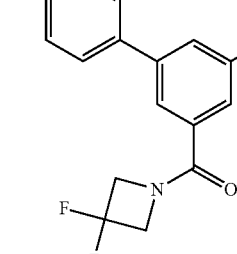 | 436.46 | 437.3 | ++++ | **** |
| 18 | 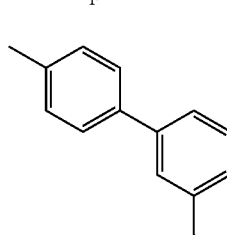 | 428.53 | 429.3 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 19 | 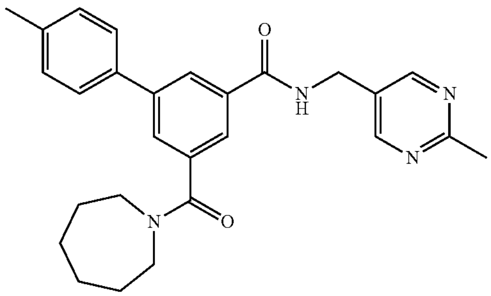 | 442.56 | 443.5 | ++++ | **** |
| 20 | 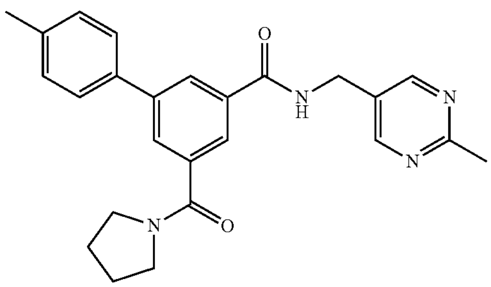 | 414.51 | 415.2 | ++++ | **** |
| 21 | 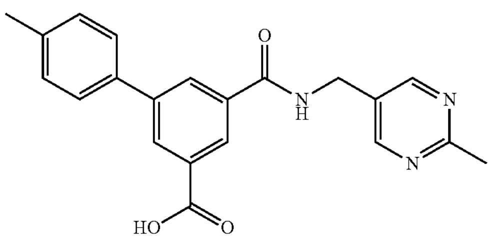 | 361.4 | 362.4 | + | *** |
| 22 | 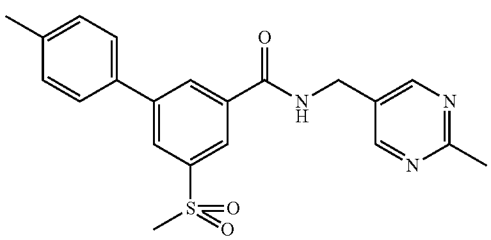 | 395.48 | 396.3 | +++ | **** |
| 23 | 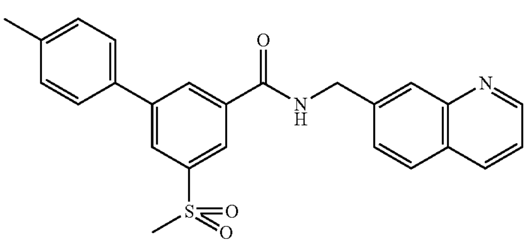 [SMILES: Cc1ccc(-c2cc(C(=O)NCc3ccc4cccnc4c3)cc(S(C)(=O)=O)c2)cc1] | 430.53 | 431.2 | +++ | *** |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 24 | 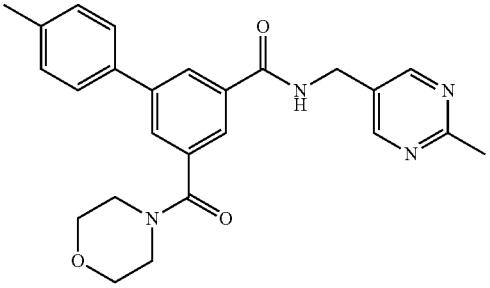 | 430.51 | 431.2 | +++ | **** |
| 25 | 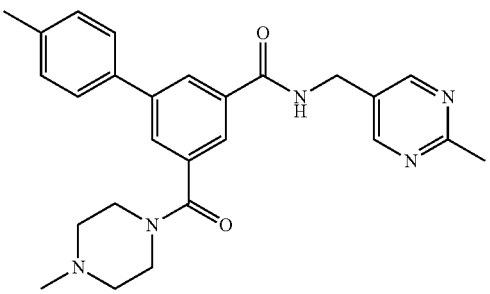 | 443.55 | 444.5 | +++ | **** |
| 26 | 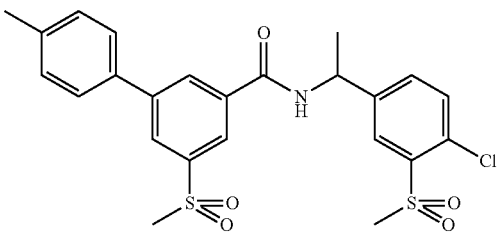 [SMILES: Cc1ccc(-c2cc(C(=O)NC(C)c3ccc(Cl)c(S(C)(=O)=O)c3)cc(S(C)(=O)=O)c2)cc1] | 506.04 | 506.3 | ++++ | **** |
| 27 | 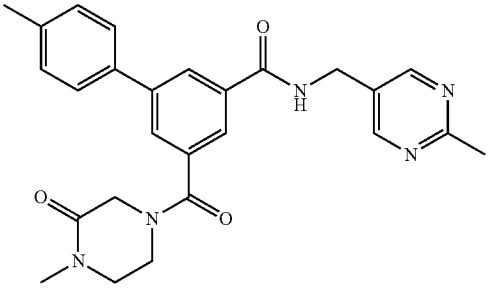 | 457.53 | 458.2 | ++ | **** |
| 28 | 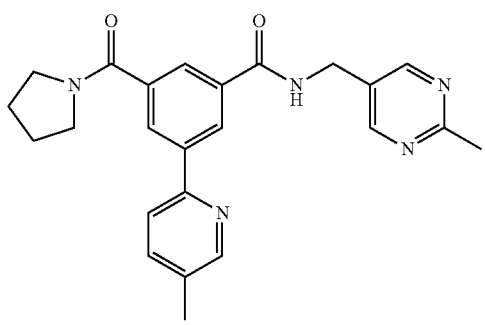 [SMILES: Cc1ccc(-c2cc(C(=O)NCc3cnc(C)nc3)cc(C(=O)N3CCCC3)c2)nc1] | 415.49 | 416.3 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 29 | 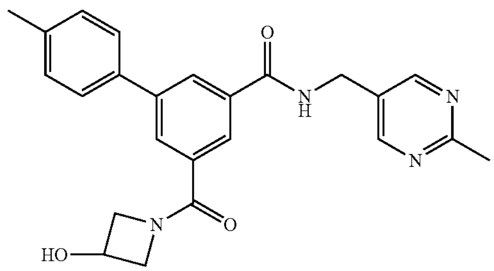 | 416.48 | 417.5 | ++++ | **** |
| 30 | 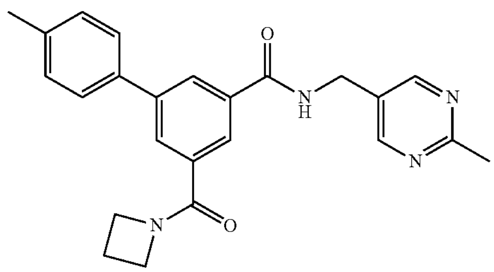 | 400.48 | 401.4 | ++++ | **** |
| 31 | 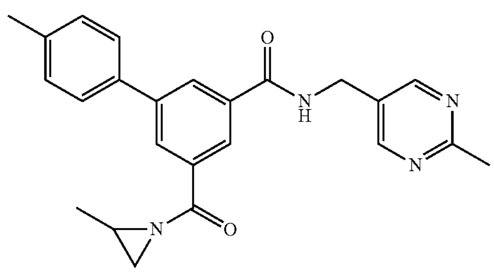 | 400.48 | 401.3 | ++ | **** |
| 32 | 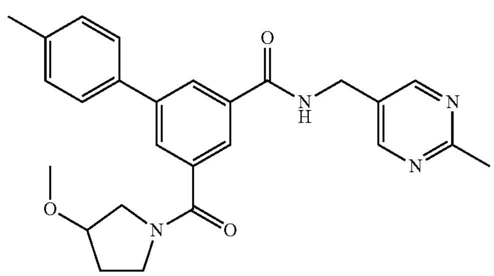 | 444.53 | 445.6 | ++++ | **** |
| 33 | 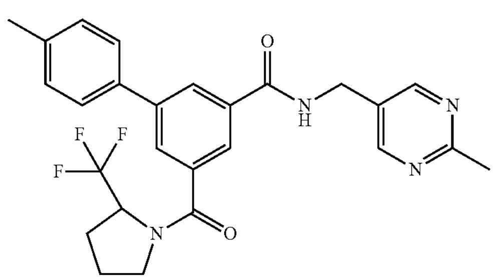 | 482.5 | 483.3 | ++++ | **** |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 34 | 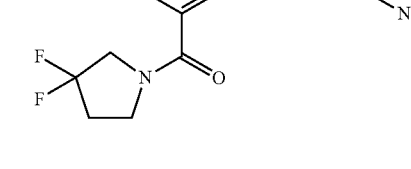 | 450.49 | 451.2 | ++++ | **** |
| 35 | 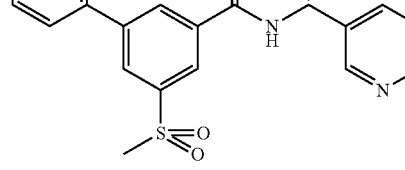 | 462.49 | 463.2 | ++++ | **** |
| 36 | 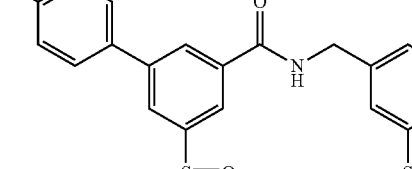 | 471.6 | 472.5 | ++++ | **** |
| 37 | 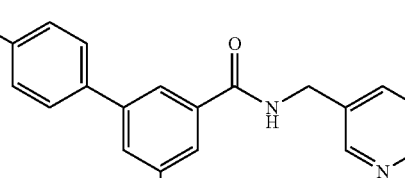 | 448.46 | 449.4 | +++ | *** |
| 38 | 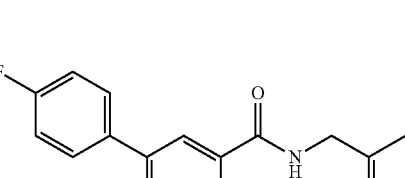 | 418.47 | 419.4 | + | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 39 | 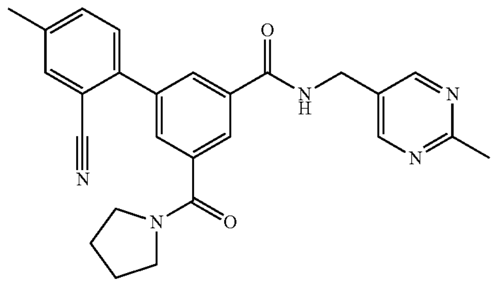 | 439.52 | 440.3 | ++++ | **** |
| 40 | 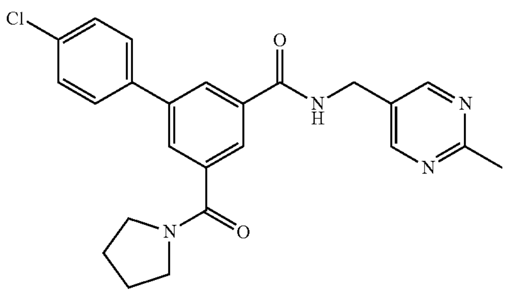 [SMILES: Cc1ncc(CNC(=O)c2cc(C(=O)N3CCCC3)cc(-c3ccc(Cl)cc3)c2)cn1] | 434.92 | 435.3 | +++ | **** |
| 41 | 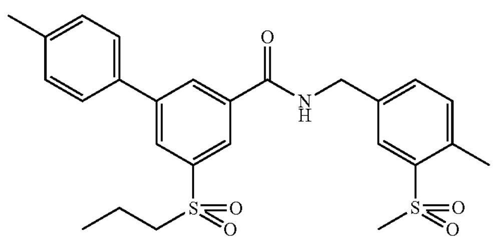 | 499.65 | 500.5 | ++++ | **** |
| 42 | 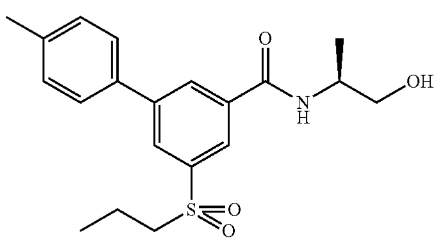 [SMILES: CCCS(=O)(=O)c1cc(C(=O)N[C@@H](C)CO)cc(-c2ccc(C)cc2)c1] | 375.49 | 376.1 | + | **** |
| 43 | 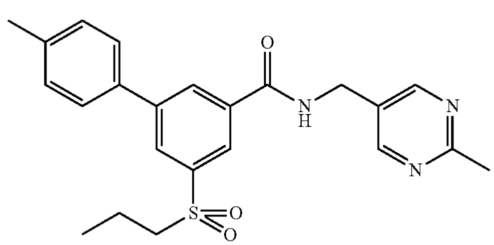 | 423.53 | 424.3 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 44 | 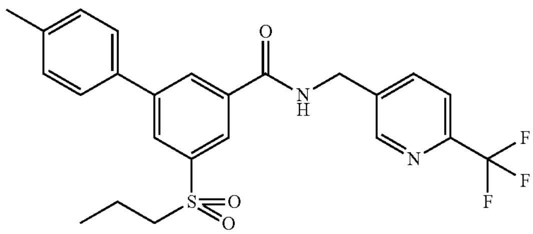 [SMILES: CCCS(=O)(=O)c1cc(C(=O)NCc2ccc(C(F)(F)F)nc2)cc(-c2ccc(C)cc2)c1] | 476.52 | 477.4 | +++ | *** |
| 45 | 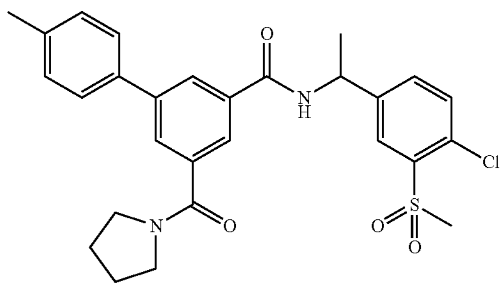 [SMILES: Cc1ccc(-c2cc(C(=O)NC(C)c3ccc(Cl)c(S(C)(=O)=O)c3)cc(C(=O)N3CCCC3)c2)cc1] | 525.07 | 525.6 | ++++ | *** |
| 46 | 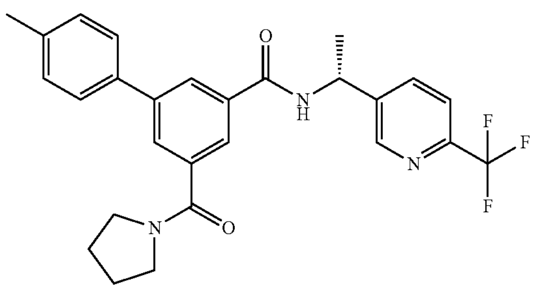 [SMILES: Cc1ccc(-c2cc(C(=O)N[C@H](C)c3ccc(C(F)(F)F)nc3)cc(C(=O)N3CCCC3)c2)cc1] | 481.52 | 482.4 | ++++ | *** |
| 47 | 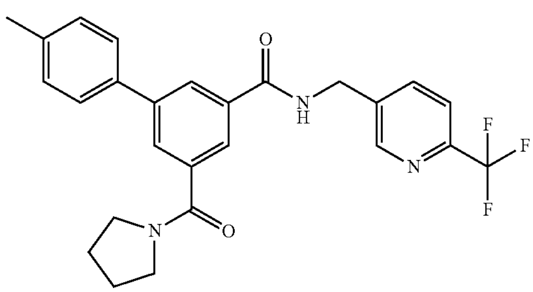 [SMILES: Cc1ccc(-c2cc(C(=O)NCc3ccc(C(F)(F)F)nc3)cc(C(=O)N3CCCC3)c2)cc1] | 467.49 | 468.5 | +++ | *** |
| 48 | 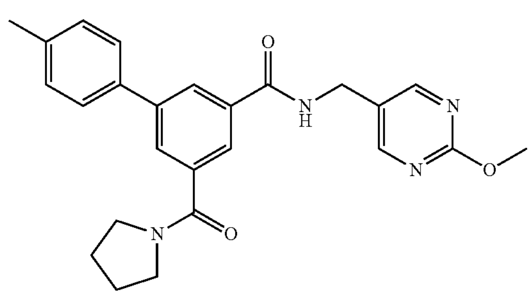 | 430.51 | 431.3 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 49 | 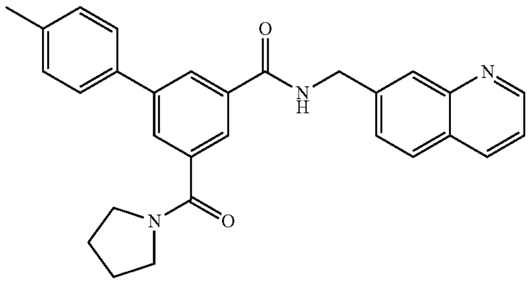 [SMILES: Cc1ccc(-c2cc(C(=O)NCc3ccc4cccnc4c3)cc(C(=O)N3CCCC3)c2)cc1] | 449.55 | 450.5 | +++ | *** |
| 50 | 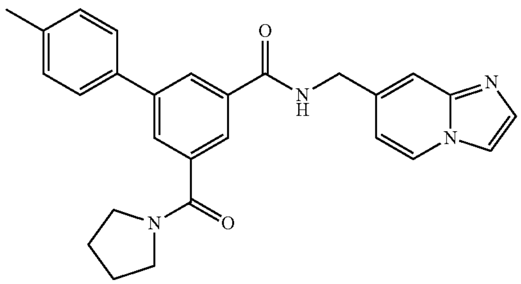 [SMILES: Cc1ccc(-c2cc(C(=O)NCc3ccn4ccnc4c3)cc(C(=O)N3CCCC3)c2)cc1] | 438.53 | 439.4 | ++++ | **** |
| 51 | 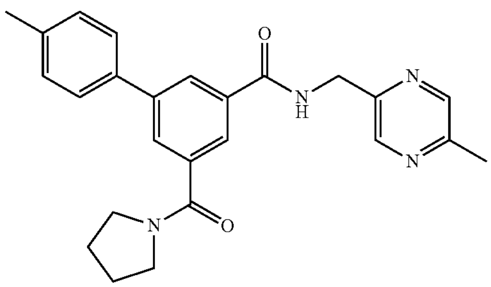 | 414.51 | 415.4 | ++++ | **** |
| 52 | 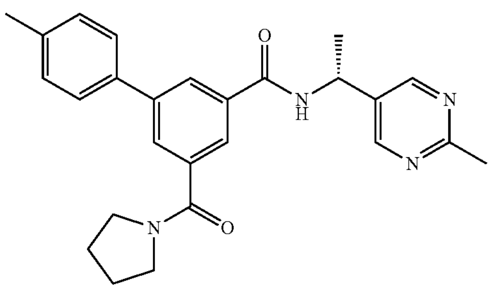 | 428.53 | 429.3 | ++++ | **** |
| 53 | 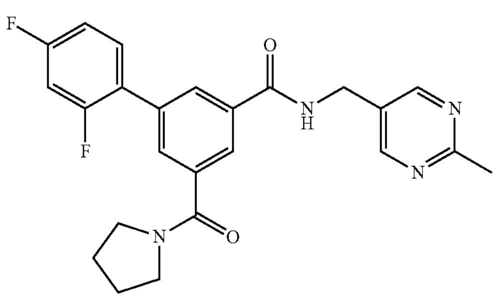 | 436.46 | 437.3 | + | *** |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 54 | 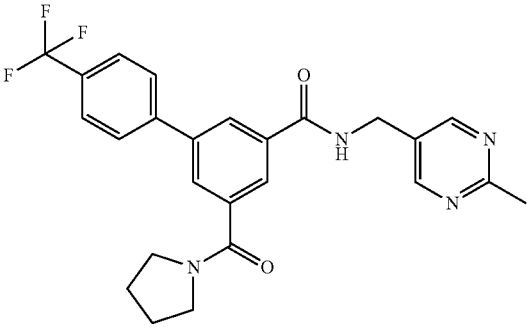 [SMILES: Cc1ncc(CNC(=O)c2cc(C(=O)N3CCCC3)cc(-c3ccc(C(F)(F)F)cc3)c2)cn1] | 468.48 | 469.4 | + | * |
| 55 | 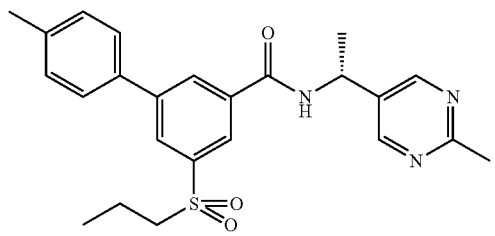 | 437.56 | 438.3 | ++++ | **** |
| 56 | 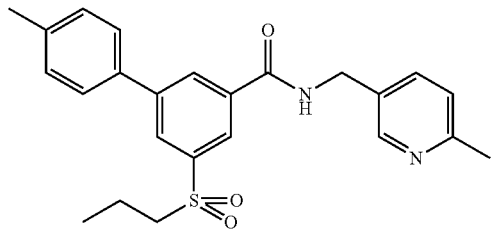 | 422.55 | 423.4 | ++++ | **** |
| 57 | 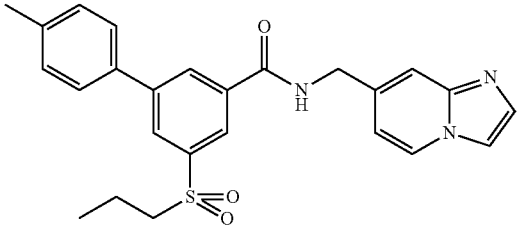 [SMILES: CCCS(=O)(=O)c1cc(C(=O)NCc2ccn3ccnc3c2)cc(-c2ccc(C)cc2)c1] | 447.56 | 448.4 | ++++ | **** |
| 58 | 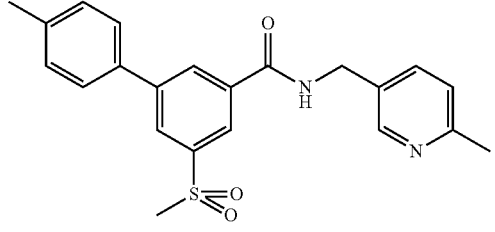 | 394.49 | 395.5 | ++++ | **** |
| 59 | 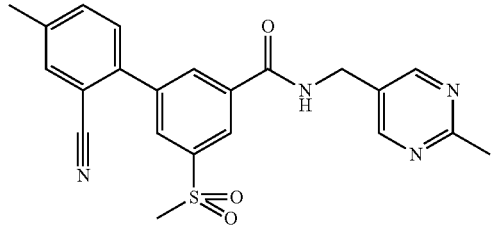 | 420.49 | 421.4 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 60 | 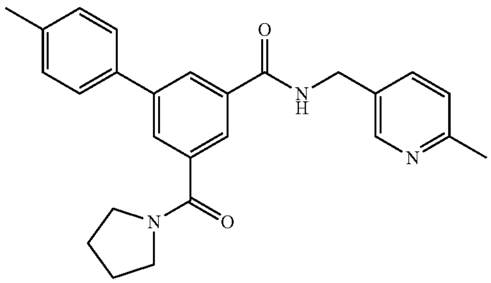 | 413.52 | 414.5 | ++++ | **** |
| 61 | 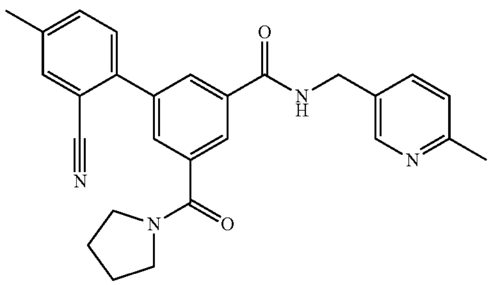 | 438.53 | 439.4 | ++++ | **** |
| 62 | 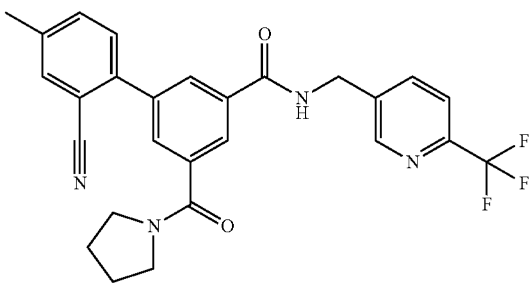 [SMILES: Cc1ccc(-c2cc(C(=O)NCc3ccc(C(F)(F)F)nc3)cc(C(=O)N3CCCC3)c2)c(C#N)c1] | 492.5 | 493.2 | +++ | **** |
| 63 | 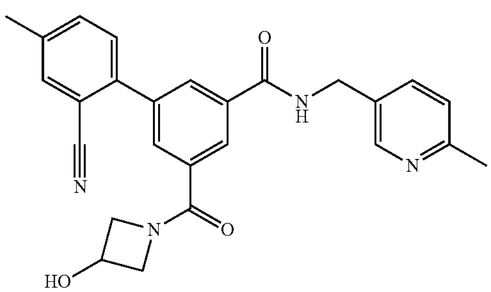 | 440.5 | 441.5 | ++++ | **** |
| 64 | 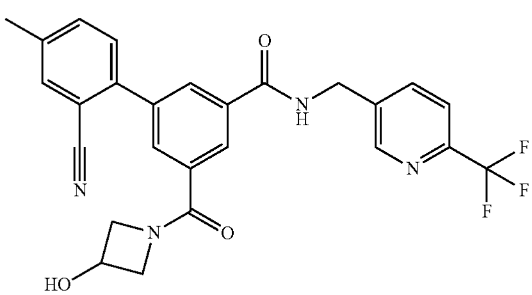 [SMILES: Cc1ccc(-c2cc(C(=O)NCc3ccc(C(F)(F)F)nc3)cc(C(=O)N3CC(O)C3)c2)c(C#N)c1] | 494.47 | 495.5 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
| --- | --- | --- | --- | --- | --- |
| 65 | 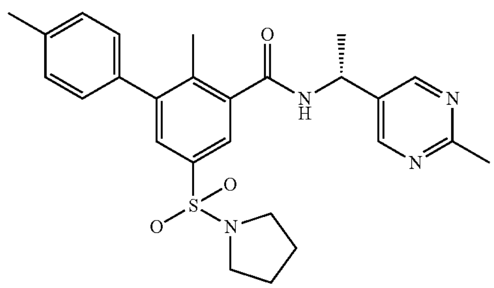 | 478.61 | 479.4 | + | *** |
| 66 | 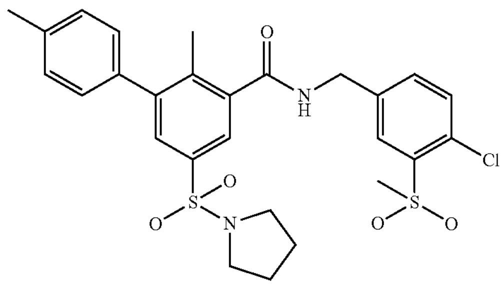 [SMILES: Cc1ccc(-c2cc(S(O)(O)N3CCCC3)cc(C(=O)NCc3ccc(Cl)c(S(C)(O)O)c3)c2C)cc1] | 561.12 | 561.6 | + | *** |
| 67 | 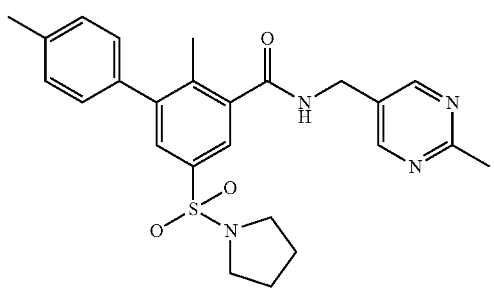 | 464.59 | 465.3 | + | **** |
| 68 | 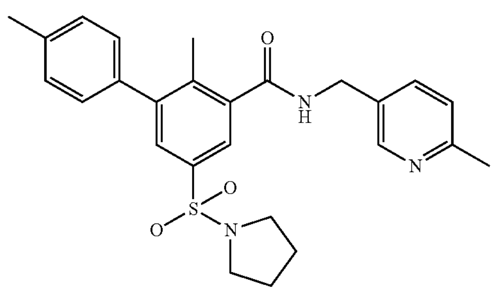 | 463.6 | 464.5 | + | *** |
| 69 | 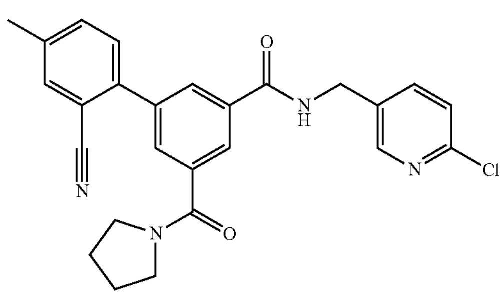 [SMILES: Cc1ccc(-c2cc(C(=O)NCc3ccc(Cl)nc3)cc(C(=O)N3CCCC3)c2)c(C#N)c1] | 458.95 | 459.2 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 70 | 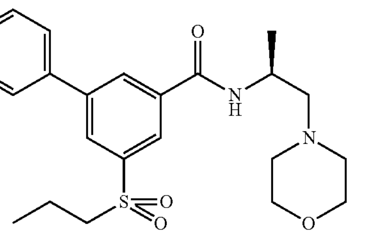 | 444.59 | 445.6 | +++ | **** |
| 71 | 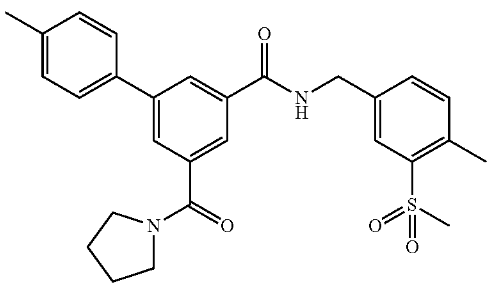 | 490.62 | 491.4 | ++++ | **** |
| 72 | 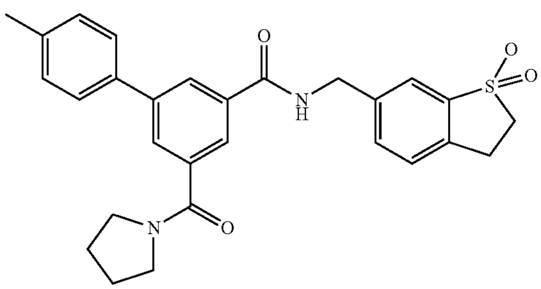 | 488.61 | 489.4 | ++++ | **** |
| 73 | 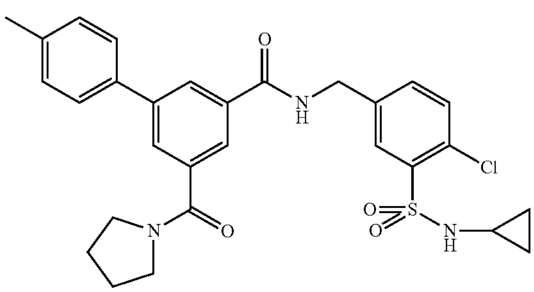 [SMILES: Cc1ccc(-c2cc(C(=O)NCc3ccc(Cl)c(S(=O)(=O)NC4CC4)c3)cc(C(=O)N3CCCC3)c2)cc1] | 552.09 | 552.6 | ++ | *** |
| 74 | 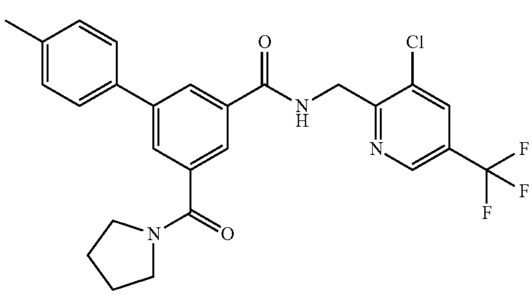 [SMILES: Cc1ccc(-c2cc(C(=O)NCc3ncc(C(F)(F)F)cc3Cl)cc(C(=O)N3CCCC3)c2)cc1] | 501.93 | 502.6 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 75 | 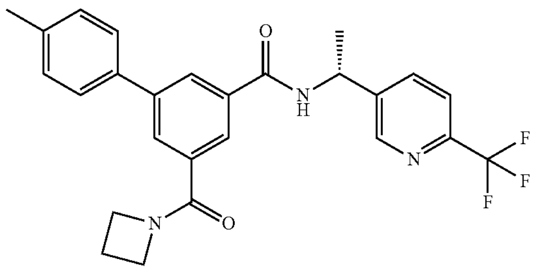 [SMILES: Cc1ccc(-c2cc(C(=O)N[C@H](C)c3ccc(C(F)(F)F)nc3)cc(C(=O)N3CCC3)c2)cc1] | 467.49 | 468.5 | ++++ | **** |
| 76 | 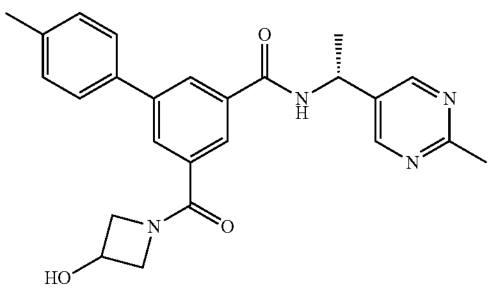 | 430.51 | 431.3 | ++++ | **** |
| 77 | 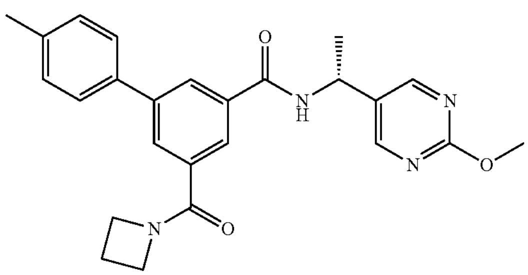 | 430.51 | 431.3 | ++++ | **** |
| 78 | 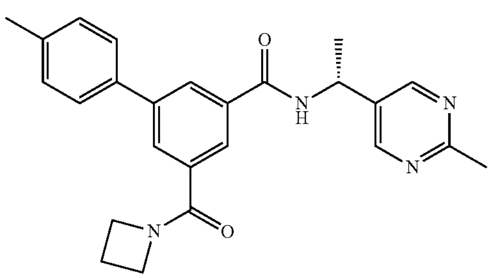 | 414.51 | 415.5 | ++++ | **** |
| 79 | 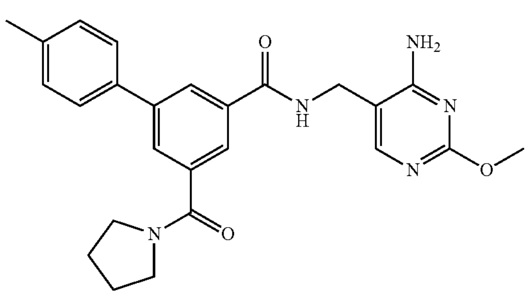 | 445.52 | 446.6 | ++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 80 | 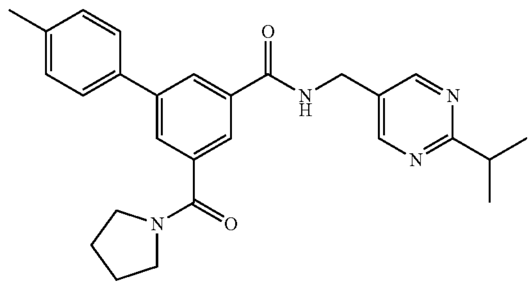 [SMILES: Cc1ccc(-c2cc(C(=O)NCc3cnc(C(C)C)nc3)cc(C(=O)N3CCCC3)c2)cc1] | 442.56 | 443.6 | + | ** |
| 81 | 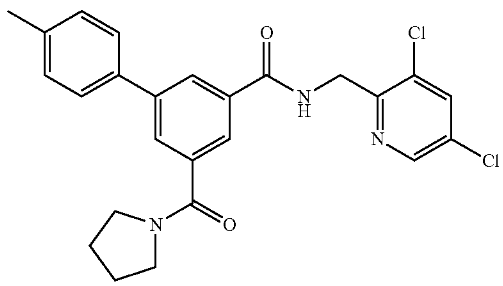 [SMILES: Cc1ccc(-c2cc(C(=O)NCc3ncc(Cl)cc3Cl)cc(C(=O)N3CCCC3)c2)cc1] | 468.38 | 468.4 | ++++ | **** |
| 82 | 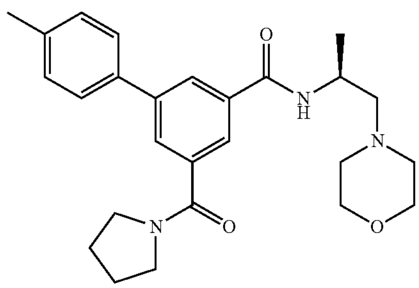 [SMILES: Cc1ccc(-c2cc(C(=O)N[C@@H](C)CN3CCOCC3)cc(C(=O)N3CCCC3)c2)cc1] | 435.56 | 436.4 | ++ | **** |
| 83 | 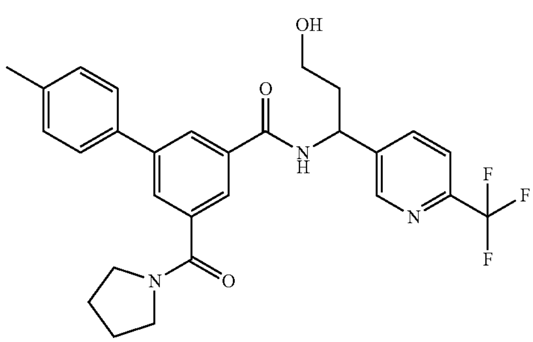 [SMILES: Cc1ccc(-c2cc(C(=O)NC(CCO)c3ccc(C(F)(F)F)nc3)cc(C(=O)N3CCCC3)c2)cc1] | 511.54 | 512.4 | +++ | *** |
| 84 | 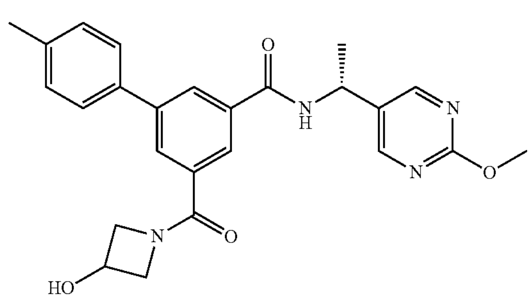 | 446.5 | 447.6 | +++ | **** |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 85 | 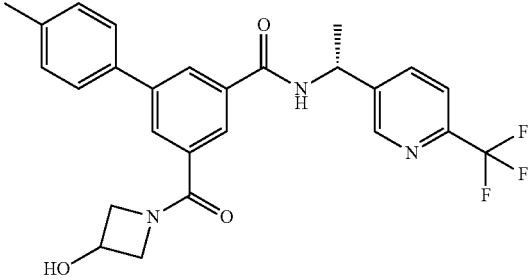 [SMILES: Cc1ccc(-c2cc(C(=O)N[C@H](C)c3ccc(C(F)(F)F)nc3)cc(C(=O)N3CC(O)C3)c2)cc1] | 483.49 | 484.3 | ++++ | **** |
| 86 | 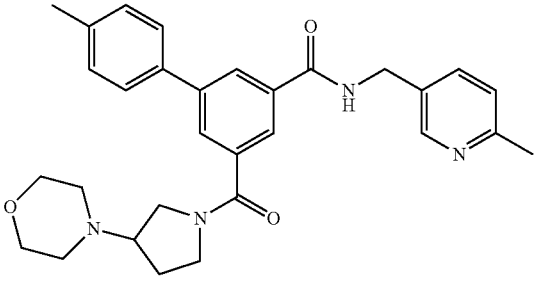 [SMILES: Cc1ccc(-c2cc(C(=O)NCc3ccc(C)nc3)cc(C(=O)N3CCC(N4CCOCC4)C3)c2)cc1] | 498.62 | 499.7 | +++ | *** |
| 87 | 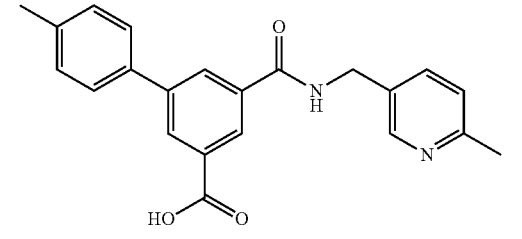 | 360.41 | 361.3 | +++ | *** |
| 88 | 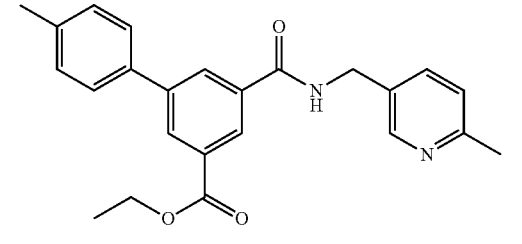 | 388.46 | 389.4 | ++++ | *** |
| 89 | 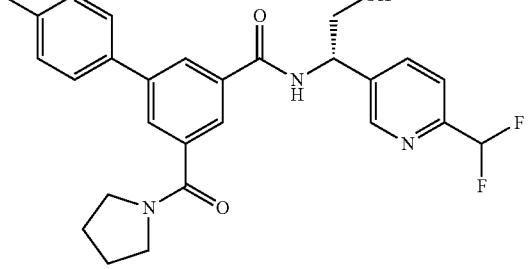 | 479.52 | 480.4 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 90 | 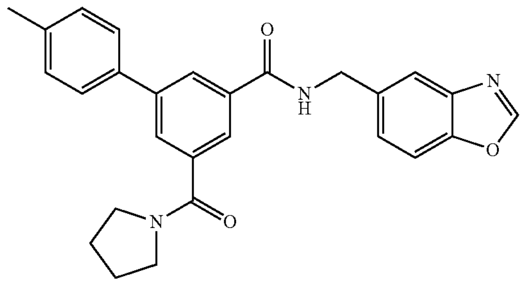 [SMILES: Cc1ccc(-c2cc(C(=O)NCc3ccc4ocnc4c3)cc(C(=O)N3CCCC3)c2)cc1] | 439.51 | 440.4 | ++++ | **** |
| 91 | 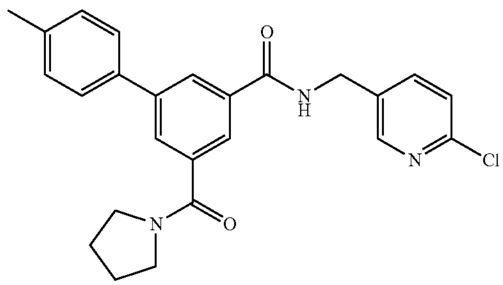 [SMILES: Cc1ccc(-c2cc(C(=O)NCc3ccc(Cl)nc3)cc(C(=O)N3CCCC3)c2)cc1] | 433.94 | 434.3 | ++++ | **** |
| 92 | 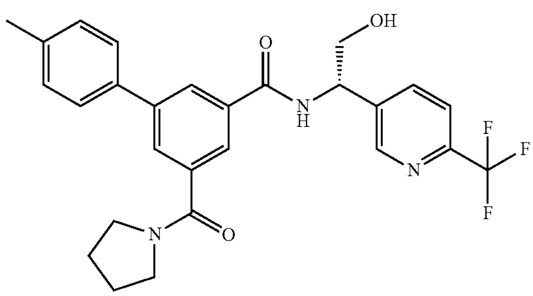 [SMILES: Cc1ccc(-c2cc(C(=O)N[C@H](CO)c3ccc(C(F)(F)F)nc3)cc(C(=O)N3CCCC3)c2)cc1] | 497.51 | 498.6 | ++++ | **** |
| 93 | 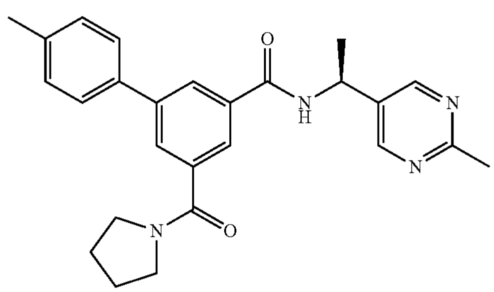 | 428.53 | 429.3 | ++ | *** |
| 94 | 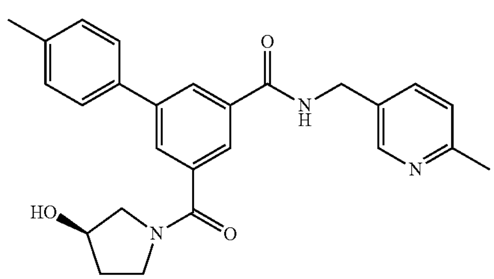 | 429.52 | 430.3 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 95 | 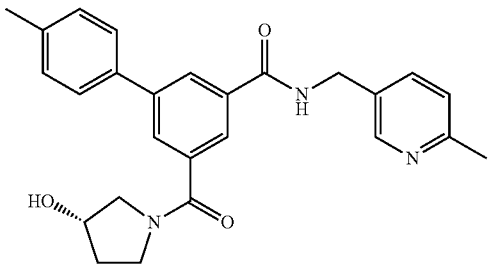 | 429.52 | 430.3 | +++ | **** |
| 96 | 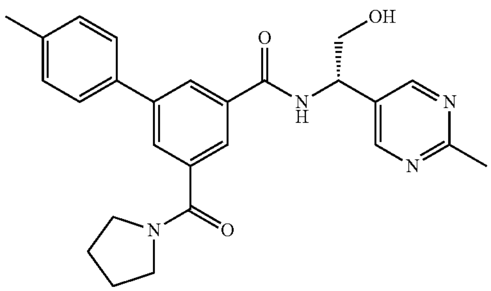 | 444.53 | 445.6 | ++++ | **** |
| 97 | 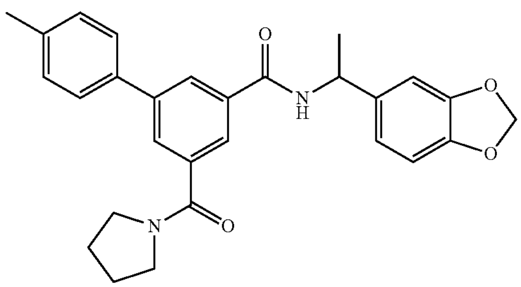 [SMILES: Cc1ccc(-c2cc(C(=O)NC(C)c3ccc4c(c3)OCO4)cc(C(=O)N3CCCC3)c2)cc1] | 456.54 | 457.3 | +++ | *** |
| 98 | 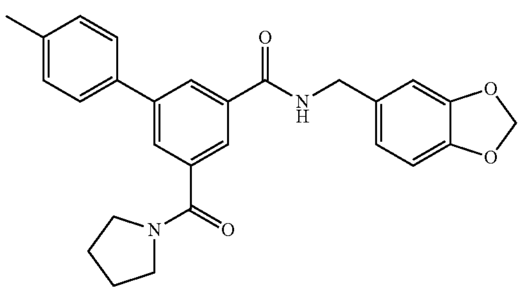 [SMILES: Cc1ccc(-c2cc(C(=O)NCc3ccc4c(c3)OCO4)cc(C(=O)N3CCCC3)c2)cc1] | 442.51 | 443.5 | +++ | *** |
| 99 | 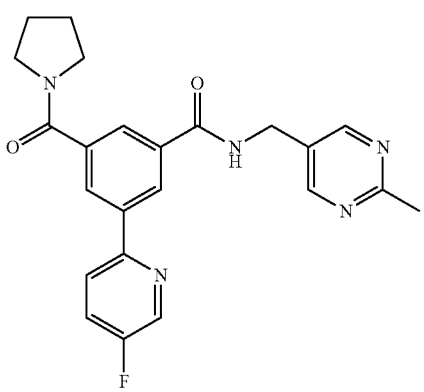 [SMILES: Cc1ncc(CNC(=O)c2cc(C(=O)N3CCCC3)cc(-c3ccc(F)cn3)c2)cn1] | 419.46 | 420.5 | + | * |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
| --- | --- | --- | --- | --- | --- |
| 100 | 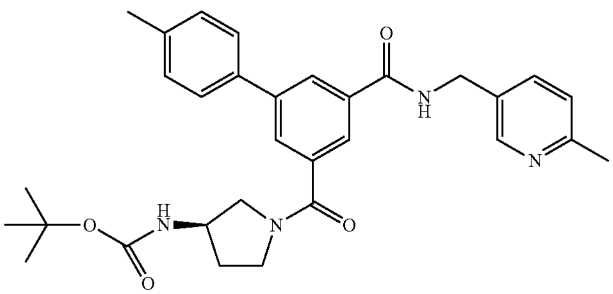 [SMILES: Cc1ccc(-c2cc(C(=O)NCc3ccc(C)nc3)cc(C(=O)N3CC[C@@H](NC(=O)OC(C)(C)C)C3)c2)cc1] | 528.65 | 529.6 | +++ | ** |
| 101 | 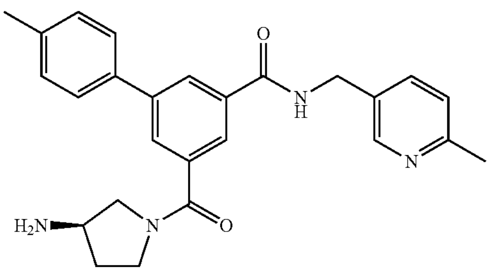 | 428.53 | 429.4 | ++ | *** |
| 102 | 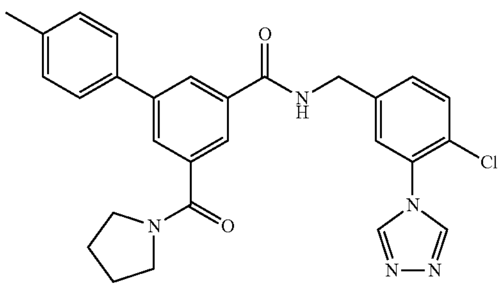 [SMILES: Cc1ccc(-c2cc(C(=O)NCc3ccc(Cl)c(-n4cnnc4)c3)cc(C(=O)N3CCCC3)c2)cc1] | 500 | 500.6 | ++++ | **** |
| 103 | 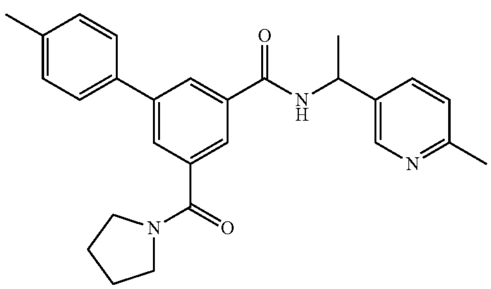 | 427.55 | 428.4 | ++++ | **** |
| 104 | 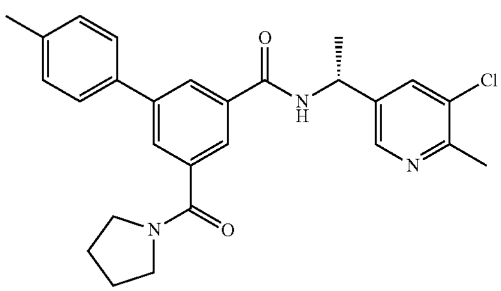 [SMILES: Cc1ccc(-c2cc(C(=O)N[C@H](C)c3cnc(C)c(Cl)c3)cc(C(=O)N3CCCC3)c2)cc1] | 461.99 | 462.3 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 105 | 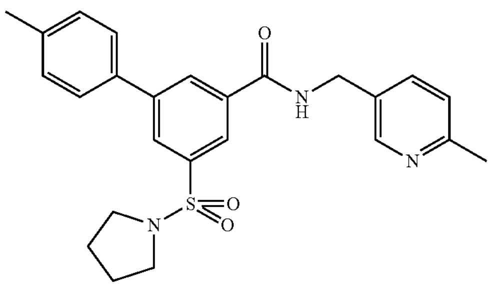 | 449.57 | 450.5 | ++++ | **** |
| 106 | 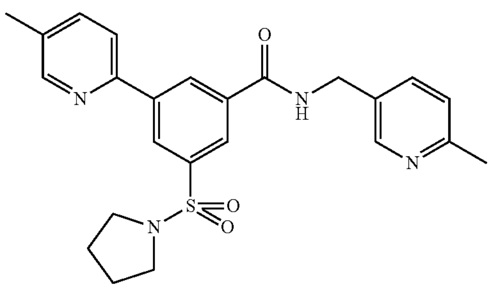 | 450.56 | 451.5 | ++++ | **** |
| 107 | 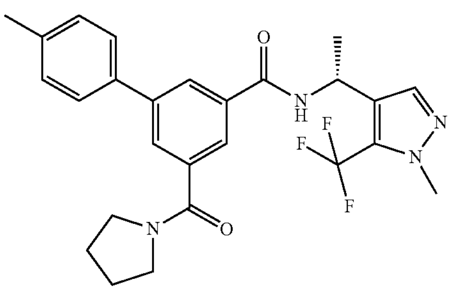 [SMILES: Cc1ccc(-c2cc(C(=O)N[C@H](C)c3cnn(C)c3C(F)(F)F)cc(C(=O)N3CCCC3)c2)cc1] | 484.52 | 485.2 | ++ | *** |
| 108 | 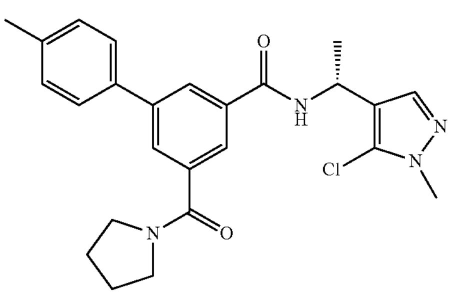 [SMILES: Cc1ccc(-c2cc(C(=O)N[C@H](C)c3cnn(C)c3Cl)cc(C(=O)N3CCCC3)c2)cc1] | 450.97 | 451.3 | ++++ | **** |
| 109 | 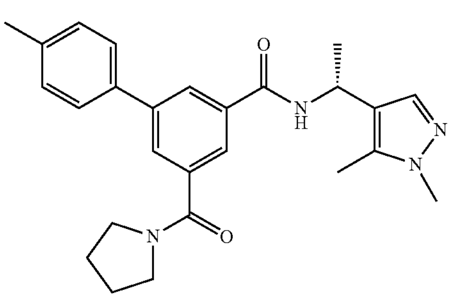 [SMILES: Cc1ccc(-c2cc(C(=O)N[C@H](C)c3cnn(C)c3C)cc(C(=O)N3CCCC3)c2)cc1] | 430.55 | 431.3 | ++ | *** |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 110 | 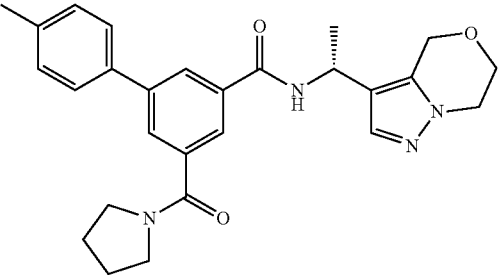 [SMILES: Cc1ccc(-c2cc(C(=O)N[C@H](C)c3cnn4c3COCC4)cc(C(=O)N3CCCC3)c2)cc1] | 458.56 | 459.3 | + | *** |
| 111 | 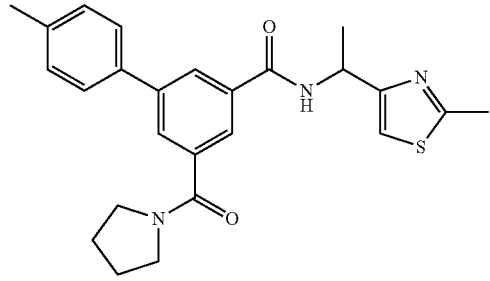 | 433.57 | 434.4 | +++ | **** |
| 112 | 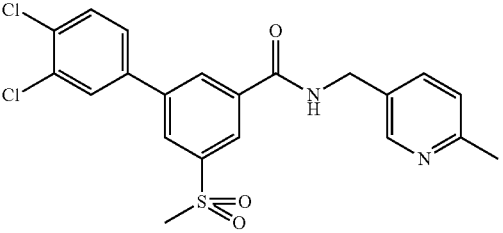 [SMILES: Cc1ccc(CNC(=O)c2cc(-c3ccc(Cl)c(Cl)c3)cc(S(C)(=O)=O)c2)cn1] | 449.36 | 449.3 | + | * |
| 113 | 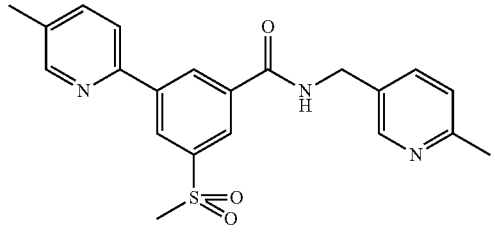 | 395.48 | 396.4 | +++ | **** |
| 114 | 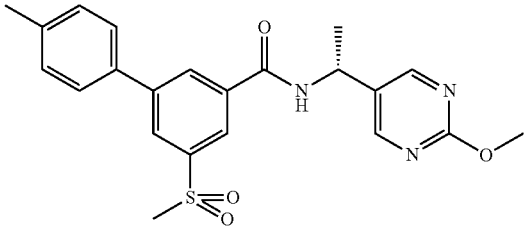 | 425.51 | 426.3 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 115 | 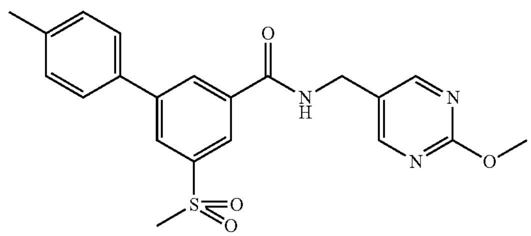 | 411.48 | 412.4 | +++ | **** |
| 116 | 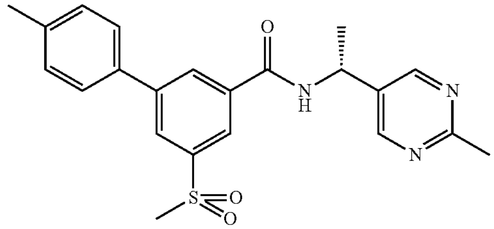 | 409.51 | 410.1 | ++++ | **** |
| 117 | 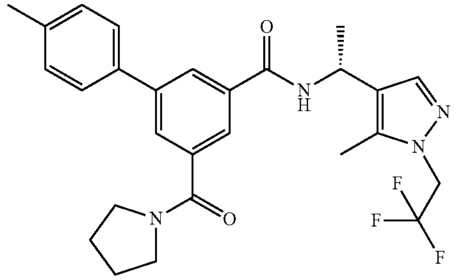 [SMILES: Cc1ccc(-c2cc(C(=O)N[C@H](C)c3cnn(CC(F)(F)F)c3C)cc(C(=O)N3CCCC3)c2)cc1] | 498.55 | 499.2 | + | ** |
| 118 | 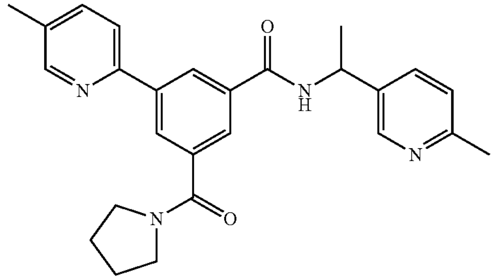 | 428.53 | 429.2 | ++++ | **** |
| 119 | 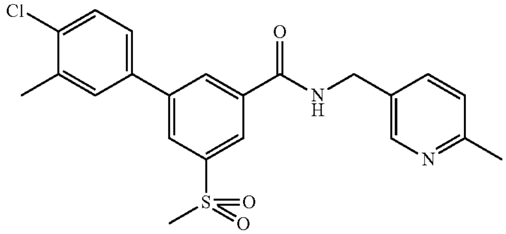 [SMILES: Cc1ccc(CNC(=O)c2cc(-c3ccc(Cl)c(C)c3)cc(S(C)(=O)=O)c2)cn1] | 428.94 | 429.3 | + | * |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 120 | 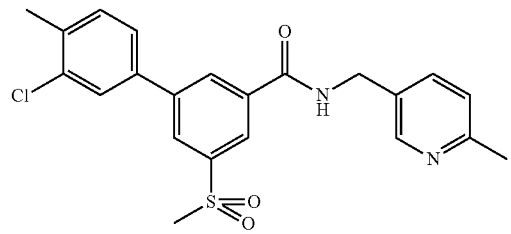 | 428.94 | 429.2 | + | * |
| 121 | 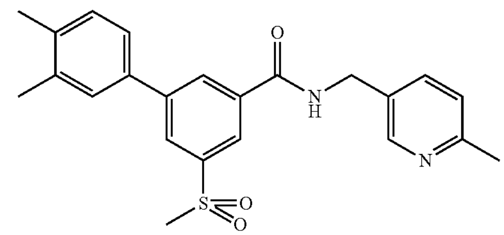 | 408.52 | 409.4 | + | * |
| 122 | 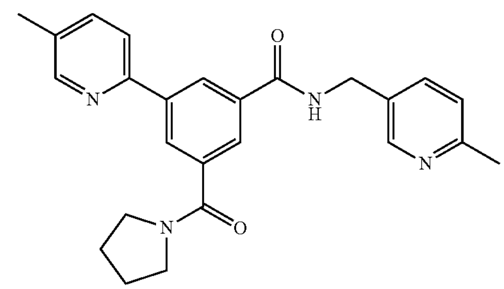 | 414.51 | 415.5 | ++++ | **** |
| 123 | 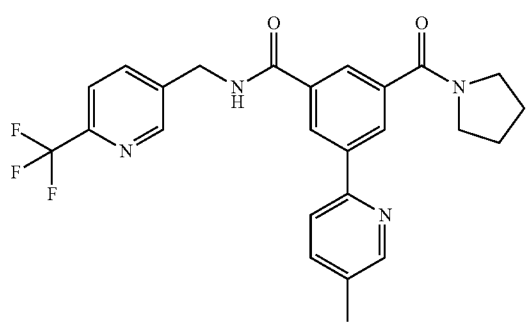 [SMILES: Cc1ccc(-c2cc(C(=O)NCc3ccc(C(F)(F)F)nc3)cc(C(=O)N3CCCC3)c2)nc1] | 468.48 | 469.4 | ++++ | **** |
| 124 | 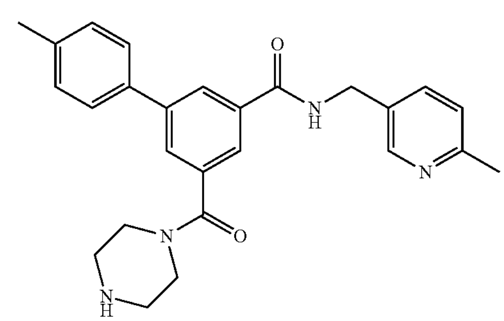 | 428.53 | 428.9 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 125 | 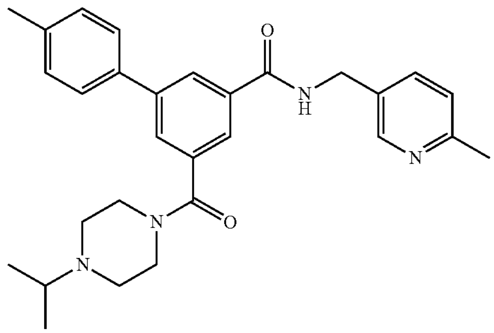 | 470.61 | 471.7 | +++ | **** |
| 126 | 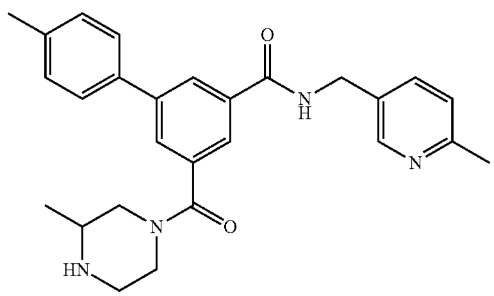 | 442.56 | 443.7 | +++ | **** |
| 127 | 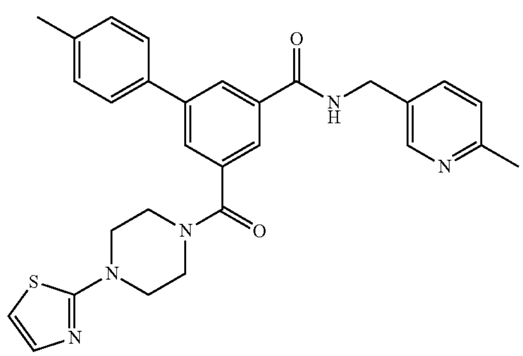 [SMILES: Cc1ccc(-c2cc(C(=O)NCc3ccc(C)nc3)cc(C(=O)N3CCN(c4nccs4)CC3)c2)cc1] | 511.65 | 512.4 | +++ | **** |
| 128 | 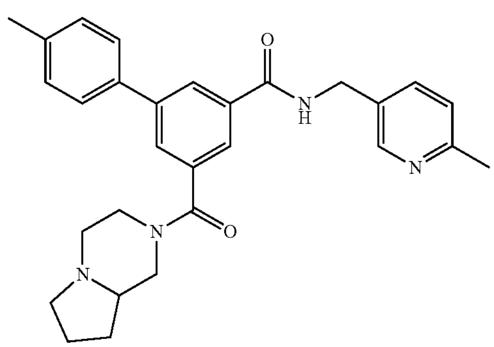 | 468.6 | 469.4 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 129 | 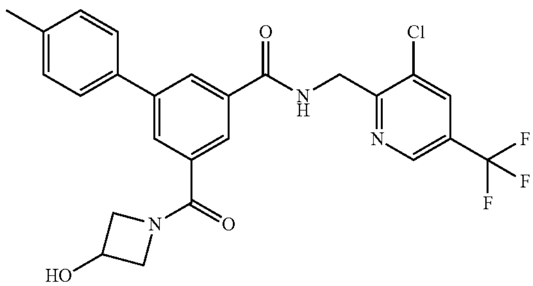 [SMILES: Cc1ccc(-c2cc(C(=O)NCc3ncc(C(F)(F)F)cc3Cl)cc(C(=O)N3CC(O)C3)c2)cc1] | 503.91 | 504.4 | ++++ | **** |
| 130 | 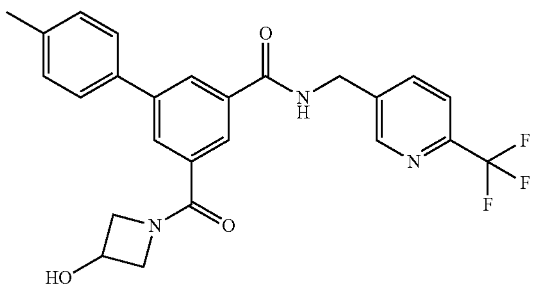 [SMILES: Cc1ccc(-c2cc(C(=O)NCc3ccc(C(F)(F)F)nc3)cc(C(=O)N3CC(O)C3)c2)cc1] | 469.46 | 470.5 | ++++ | **** |
| 131 | 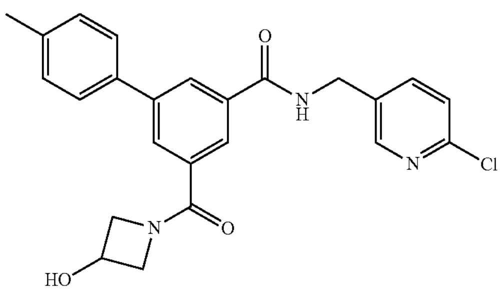 [SMILES: Cc1ccc(-c2cc(C(=O)NCc3ccc(Cl)nc3)cc(C(=O)N3CC(O)C3)c2)cc1] | 435.91 | 436.3 | ++++ | **** |
| 132 | 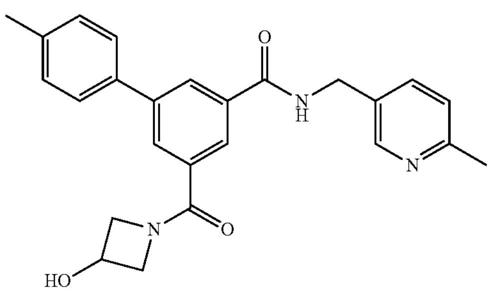 | 415.49 | 416.4 | ++++ | **** |
| 133 | 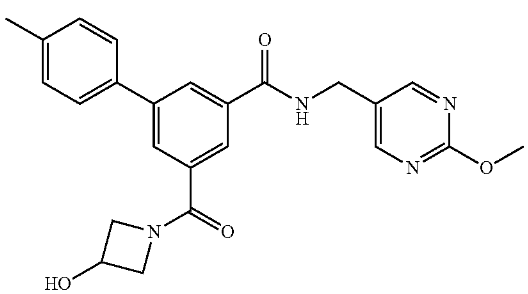 | 432.48 | 433.3 | +++ | **** |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 134 | 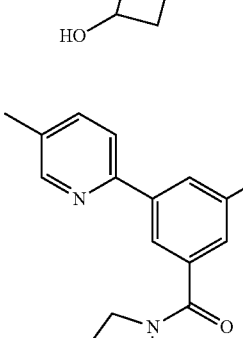 | 470.35 | 470.4 | ++++ | **** |
| 135 | 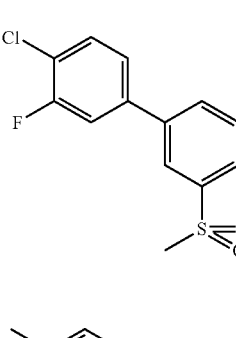 | 482.5 | 483.2 | ++++ | **** |
| 136 | 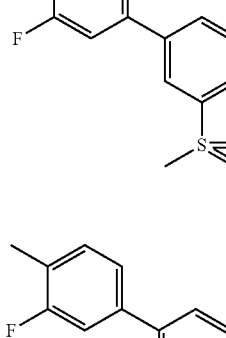 | 432.9 | 433.1 | + | ** |
| 137 | 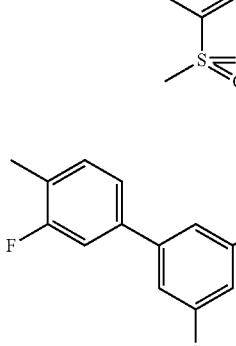 | 412.48 | 413.4 | +++ | *** |
| 138 | 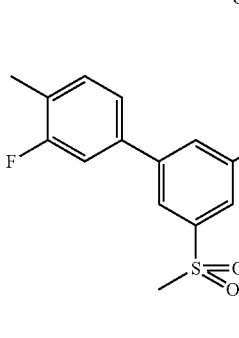 | 414.91 | 415.3 | +++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 139 | 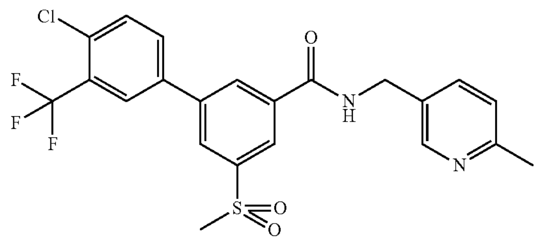 [SMILES: Cc1ccc(CNC(=O)c2cc(-c3ccc(Cl)c(C(F)(F)F)c3)cc(S(C)(=O)=O)c2)cn1] | 482.91 | 483.2 | + | * |
| 140 | 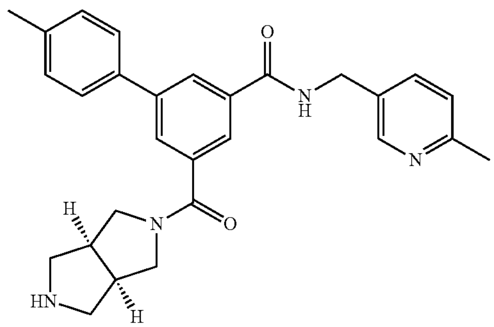 | 454.57 | 455.4 | +++ | *** |
| 141 | 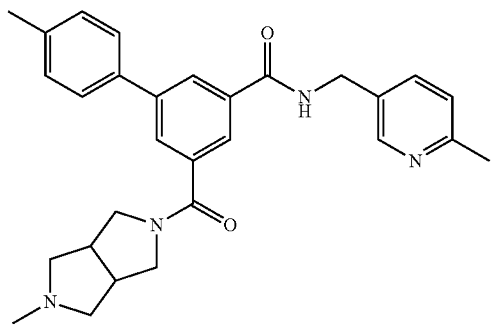 | 468.6 | 469.5 | +++ | **** |
| 142 | 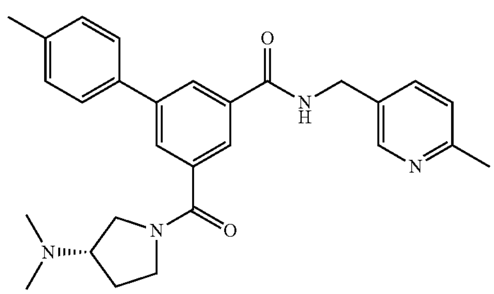 | 456.59 | 457.2 | +++ | **** |
| 143 | 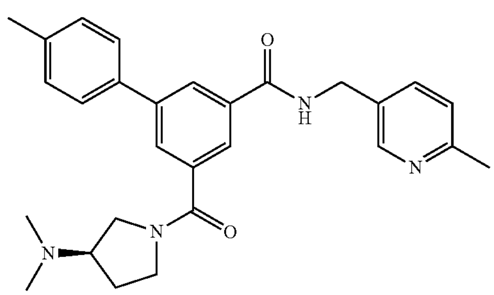 | 456.59 | 457.1 | ++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 144 | 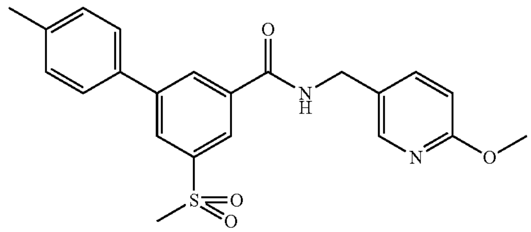 | 410.49 | 411.3 | ++++ | *** |
| 145 | 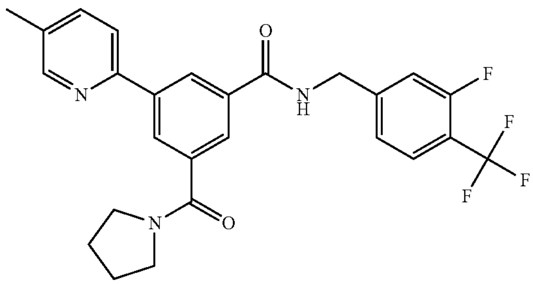 [SMILES: Cc1ccc(-c2cc(C(=O)NCc3ccc(C(F)(F)F)c(F)c3)cc(C(=O)N3CCCC3)c2)nc1] | 485.48 | 486.4 | +++ | *** |
| 146 | 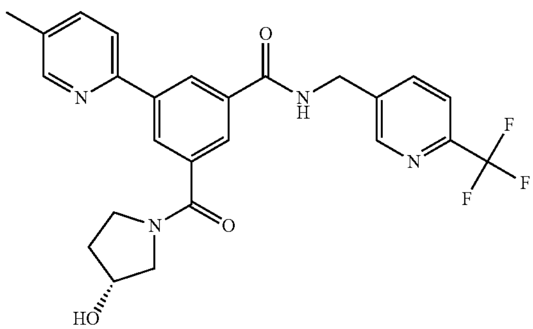 [SMILES: Cc1ccc(-c2cc(C(=O)NCc3ccc(C(F)(F)F)nc3)cc(C(=O)N3CC[C@@H](O)C3)c2)nc1] | 484.48 | 485.4 | ++++ | **** |
| 147 | 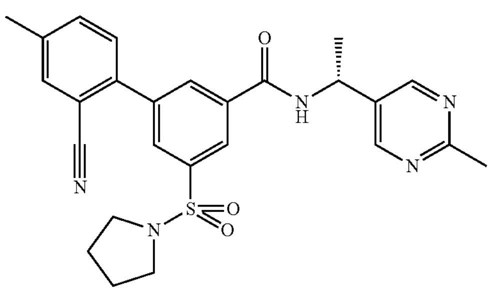 | 489.6 | 490.4 | + | **** |
| 148 | 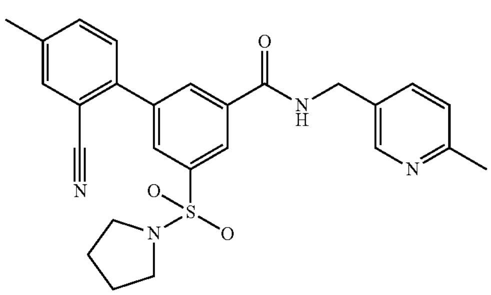 | 474.58 | 475.6 | + | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 149 | 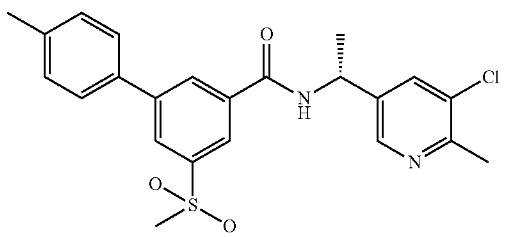 [SMILES: Cc1ccc(-c2cc(C(=O)N[C@H](C)c3cnc(C)c(Cl)c3)cc(S(C)(O)O)c2)cc1] | 442.96 | 443.4 | +++ | *** |
| 150 | 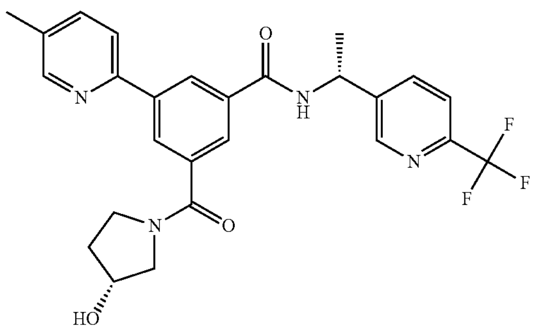 [SMILES: Cc1ccc(-c2cc(C(=O)N[C@H](C)c3ccc(C(F)(F)F)nc3)cc(C(=O)N3CC[C@@H](O)C3)c2)nc1] | 498.5 | 499.5 | ++++ | **** |
| 151 | 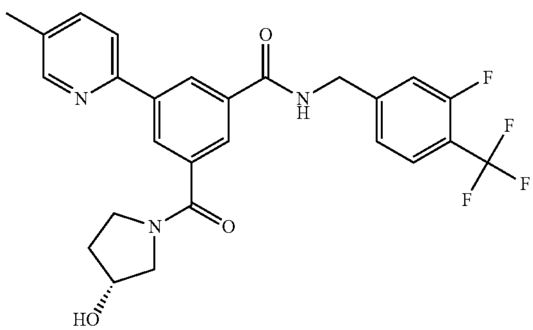 [SMILES: Cc1ccc(-c2cc(C(=O)NCc3ccc(C(F)(F)F)c(F)c3)cc(C(=O)N3CC[C@@H](O)C3)c2)nc1] | 501.48 | 502.5 | +++ | **** |
| 152 | 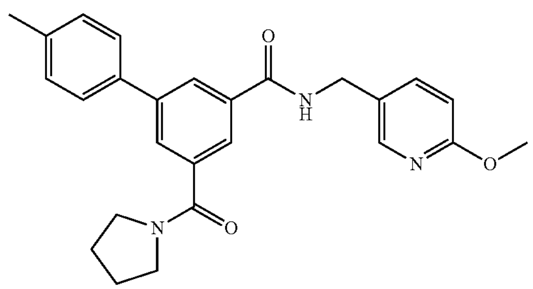 | 429.52 | 430.4 | ++++ | **** |
| 153 | 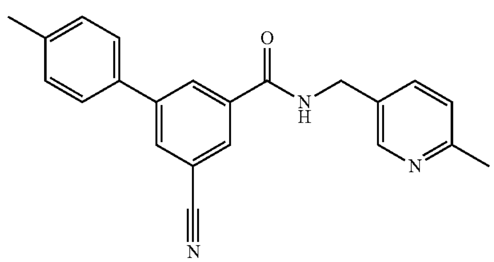 | 341.41 | 342.1 | +++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 154 | 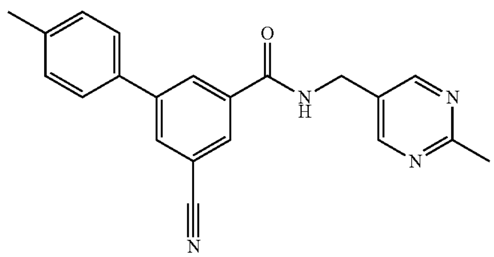 | 342.4 | 343.2 | +++ | *** |
| 155 | 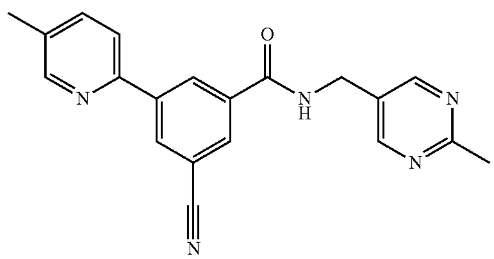 | 343.39 | 344.2 | + | * |
| 156 | 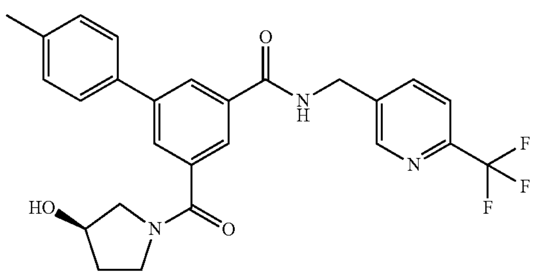 [SMILES: Cc1ccc(-c2cc(C(=O)NCc3ccc(C(F)(F)F)nc3)cc(C(=O)N3CC[C@@H](O)C3)c2)cc1] | 483.49 | 484.4 | +++ | **** |
| 157 | 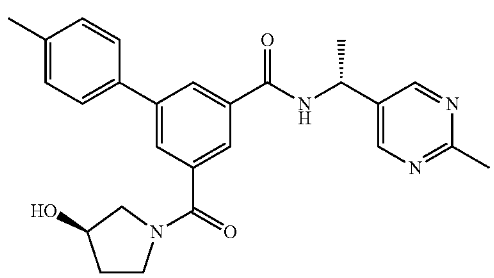 | 444.53 | 445.7 | ++++ | **** |
| 158 | 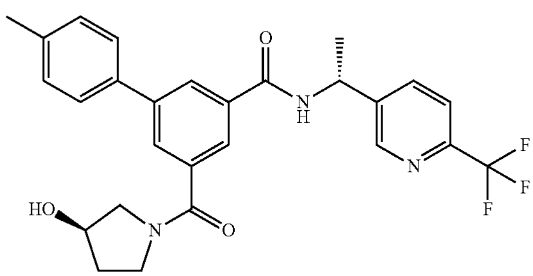 [SMILES: Cc1ccc(-c2cc(C(=O)N[C@H](C)c3ccc(C(F)(F)F)nc3)cc(C(=O)N3CC[C@@H](O)C3)c2)cc1] | 497.51 | 498.6 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 159 | 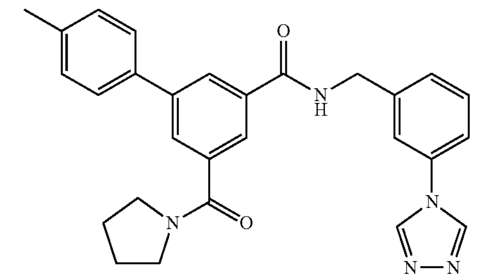 [SMILES: Cc1ccc(-c2cc(C(=O)NCc3cccc(-n4cnnc4)c3)cc(C(=O)N3CCCC3)c2)cc1] | 465.55 | 466.4 | +++ | *** |
| 160 | 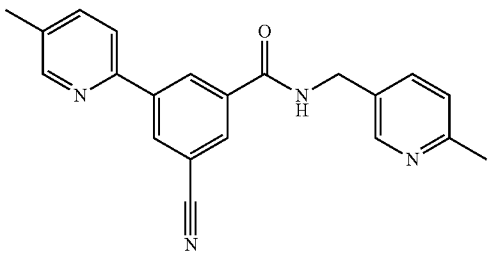 | 342.4 | 343.3 | ++ | *** |
| 161 | 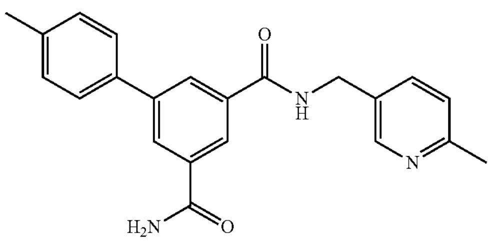 | 359.43 | 360.4 | +++ | **** |
| 162 | 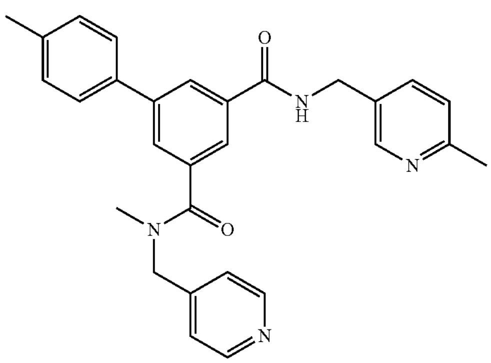 | 464.57 | 465.5 | ++++ | **** |
| 163 | 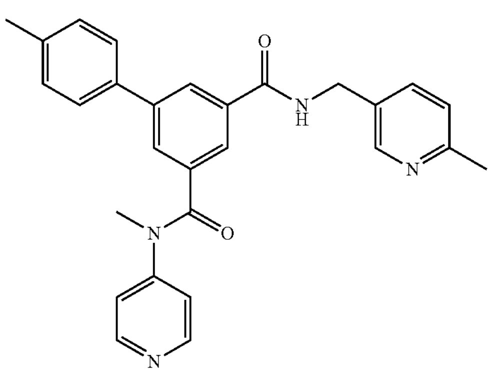 | 450.54 | 451.6 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 164 | 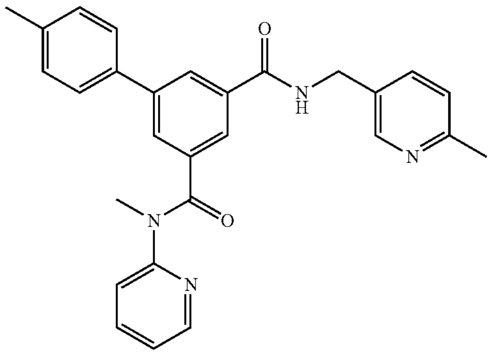 | 450.54 | 451.3 | +++ | **** |
| 165 | 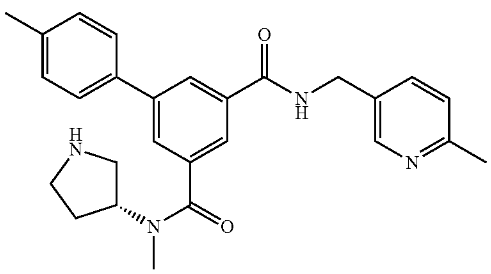 | 442.56 | 443.5 | ++ | *** |
| 166 | 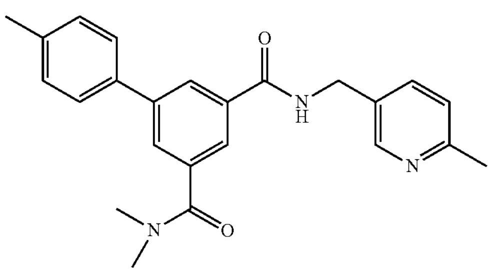 | 387.48 | 388.5 | +++ | **** |
| 167 | 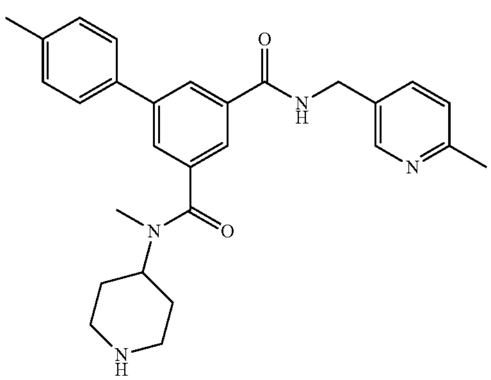 | 456.59 | 457.4 | + | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 168 | 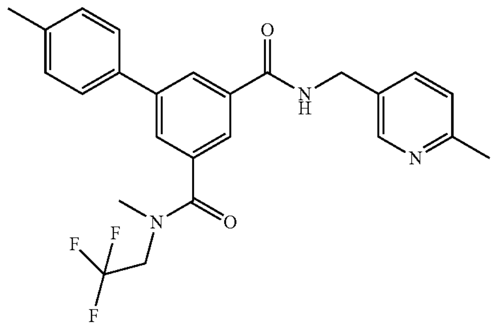 | 455.48 | 456.3 | ++++ | **** |
| 169 | 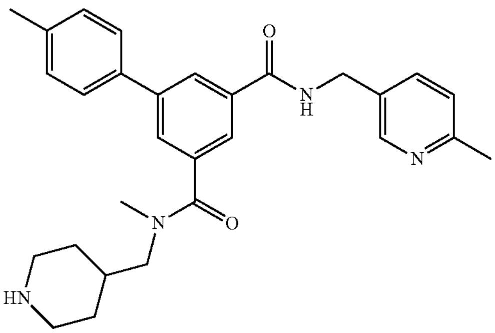 | 470.61 | 471.6 | +++ | *** |
| 170 | 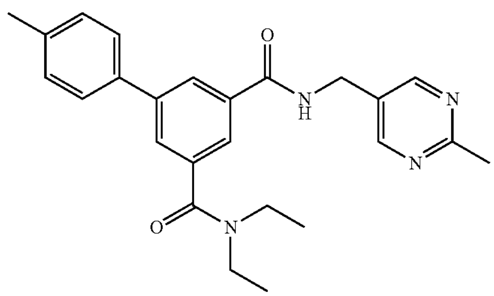 | 416.52 | 417.2 | +++ | **** |
| 171 | 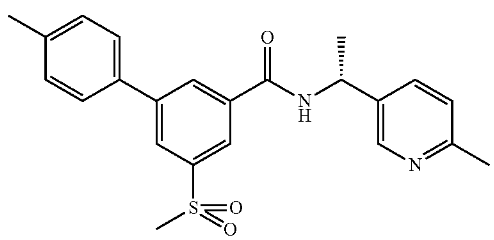 | 408.52 | 409.4 | ++++ | **** |
| 172 | 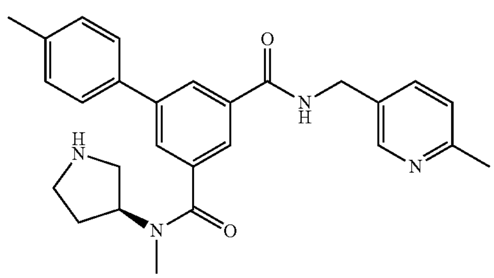 | 442.56 | 443.6 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 173 | 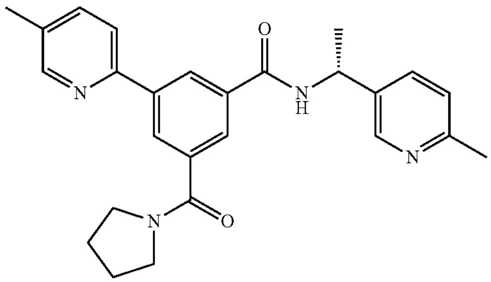 | 428.53 | 429.3 | ++++ | **** |
| 174 | 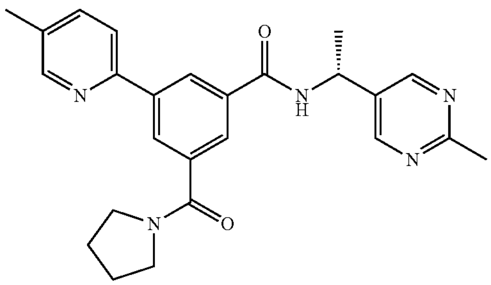 | 429.52 | 430.4 | ++++ | **** |
| 175 | 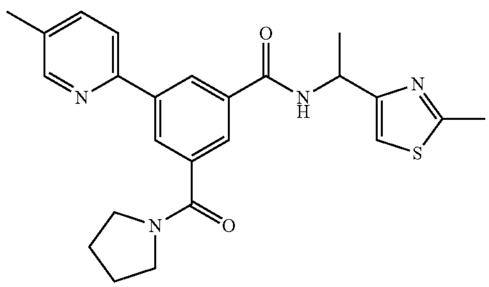 | 434.56 | 435.4 | +++ | **** |
| 176 | 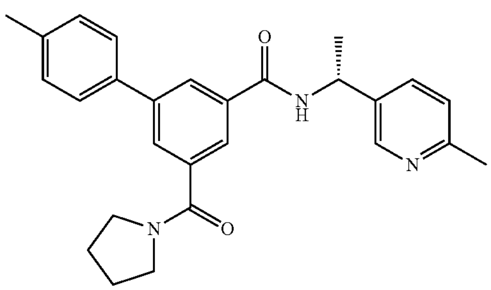 | 427.55 | 428.4 | ++++ | **** |
| 177 | 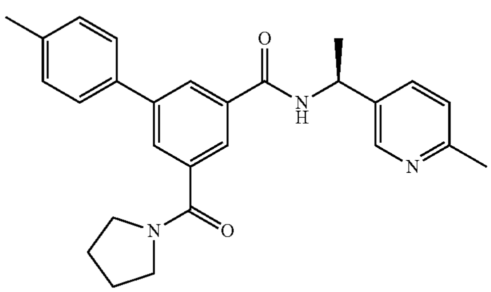 | 427.55 | 428.4 | + | * |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 178 | 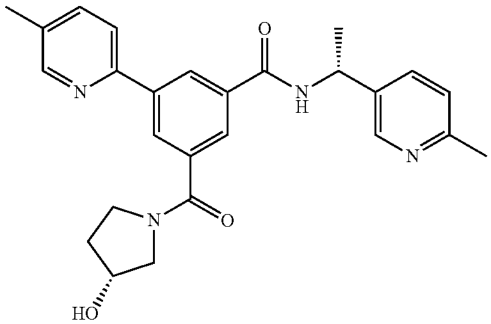 | 444.53 | 445.6 | ++++ | **** |
| 179 | 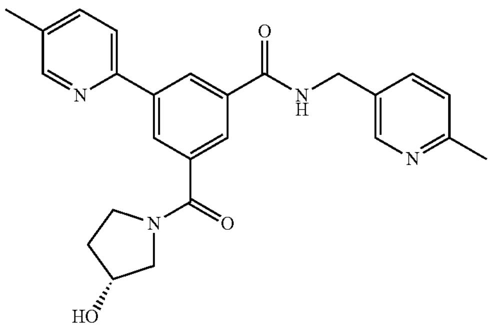 | 430.51 | 431.4 | ++++ | **** |
| 180 | 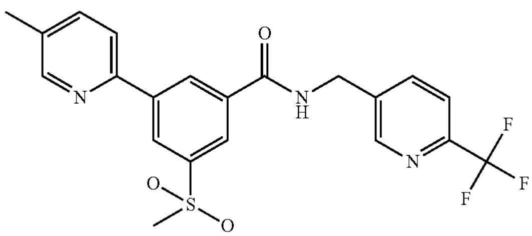 [SMILES: Cc1ccc(-c2cc(C(=O)NCc3ccc(C(F)(F)F)nc3)cc(S(C)(O)O)c2)nc1] | 449.45 | 450.7 | +++ | **** |
| 181 | 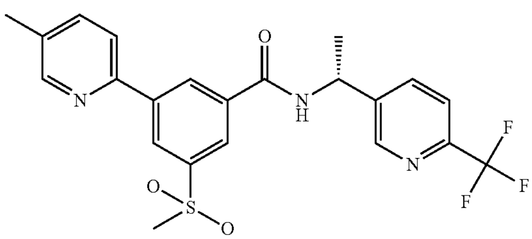 [SMILES: Cc1ccc(-c2cc(C(=O)N[C@H](C)c3ccc(C(F)(F)F)nc3)cc(S(C)(O)O)c2)nc1] | 463.48 | 464.8 | +++ | **** |
| 182 | 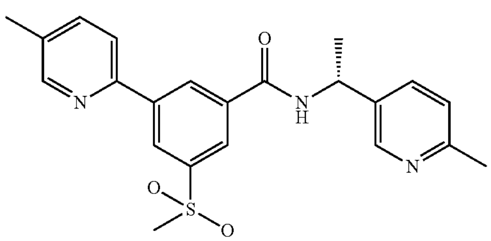 | 409.51 | 411.1 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
| --- | --- | --- | --- | --- | --- |
| 183 | 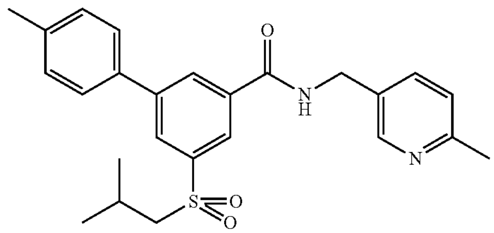 | 436.57 | 436.9 | ++++ | **** |
| 184 | 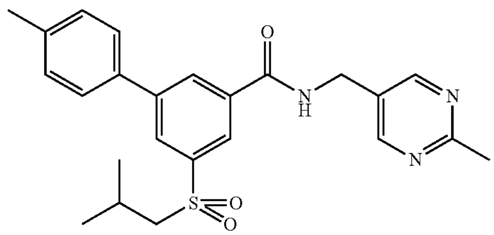 | 437.56 | 438 | ++++ | **** |
| 185 | 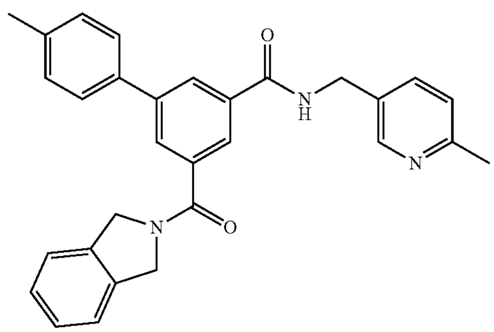 | 461.56 | 461.9 | +++ | *** |
| 186 | 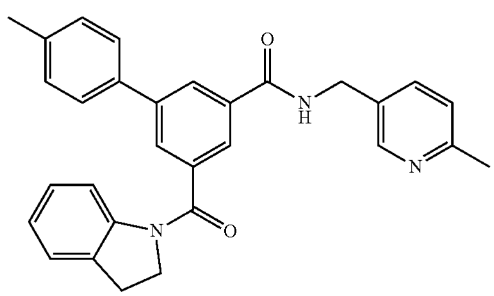 | 461.56 | 461.9 | ++++ | *** |
| 187 | 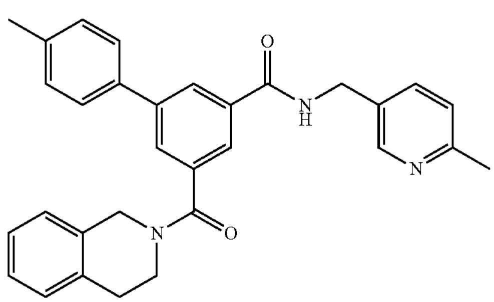 | 475.59 | 476 | +++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 188 | 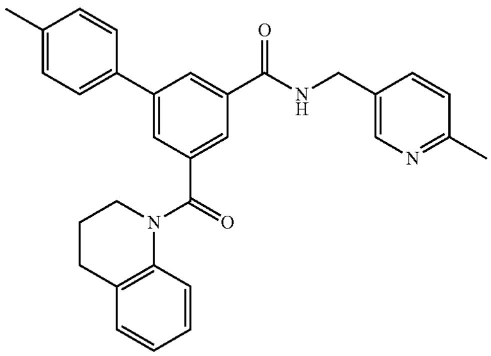 | 475.59 | 476.1 | +++ | *** |
| 189 | 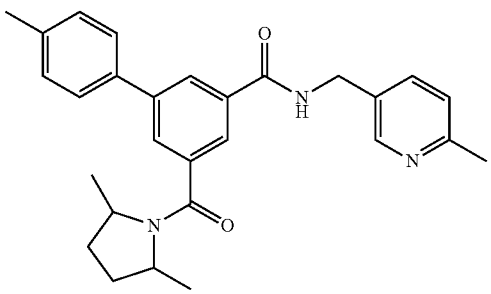 | 441.57 | 442.2 | ++++ | **** |
| 190 | 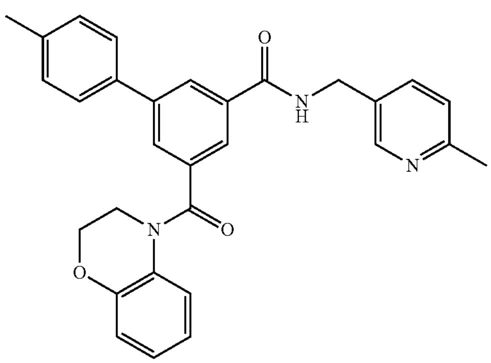 | 477.56 | 478.2 | ++++ | *** |
| 191 | 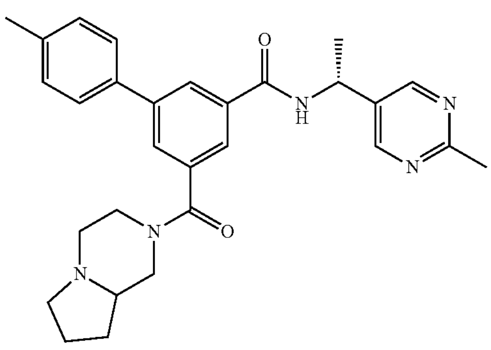 | 483.61 | 484.1 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 192 | 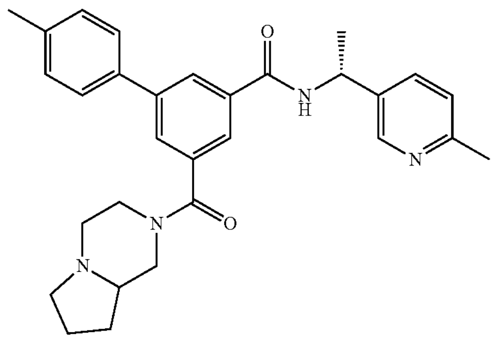 | 482.62 | 483.1 | ++++ | **** |
| 193 | 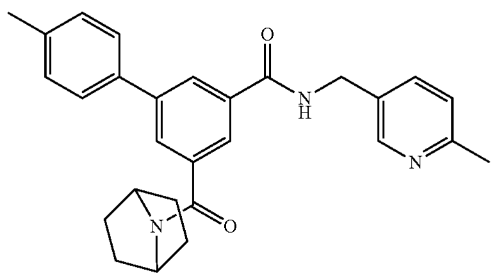 | 439.56 | 440 | ++++ | **** |
| 194 | 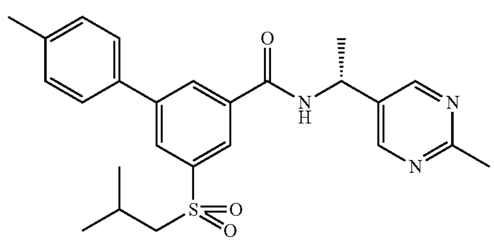 | 451.59 | 451.9 | ++++ | **** |
| 195 | 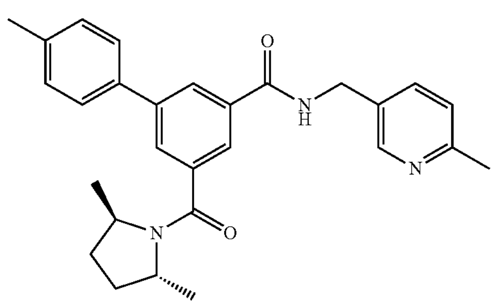 | 441.57 | 442.2 | ++++ | **** |
| 196 | 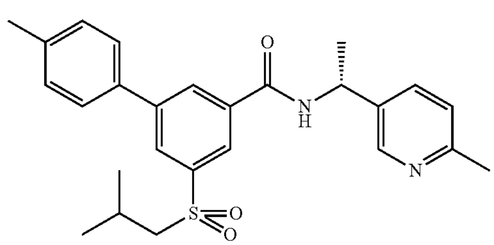 | 450.6 | 451 | ++++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 197 | 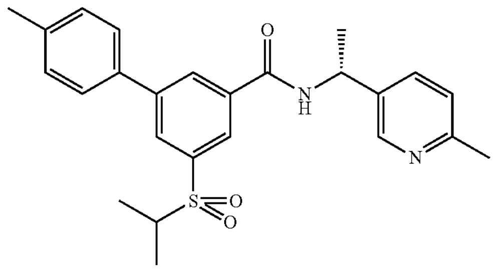 | 436.57 | 437.1 | ++++ | **** |
| 198 | 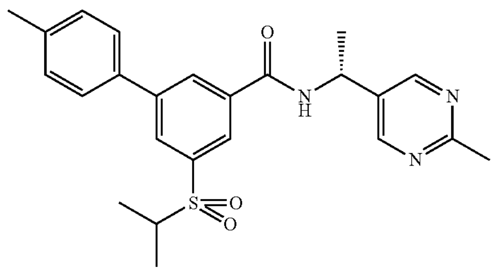 | 437.56 | 438 | ++++ | **** |
| 199 | 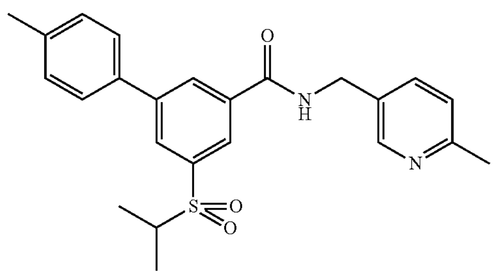 | 422.55 | 423 | ++++ | **** |
| 200 | 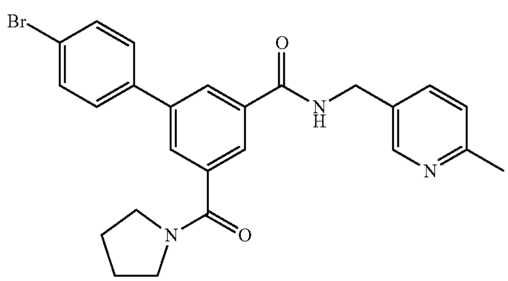 [SMILES: Cc1ccc(CNC(=O)c2cc(C(=O)N3CCCC3)cc(-c3ccc(Br)cc3)c2)cn1] | 478.39 | 480.1 | ++++ | **** |
| 201 | 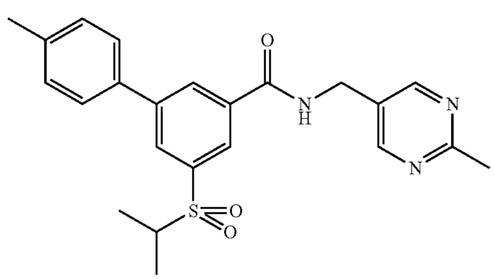 | 423.53 | 424.2 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 202 | 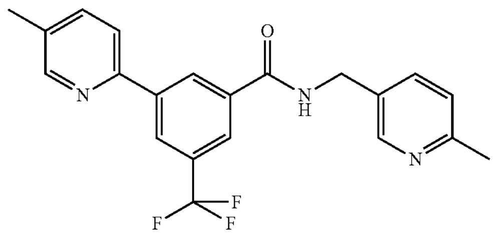 | 385.39 | 386 | + | *** |
| 203 | 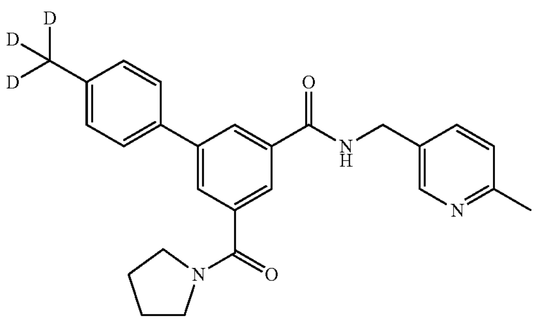 [SMILES: [2H]C([2H])([2H])c1ccc(-c2cc(C(=O)NCc3ccc(C)nc3)cc(C(=O)N3CCCC3)c2)cc1] | 416.54 | 417.2 | ++++ | **** |
| 204 | 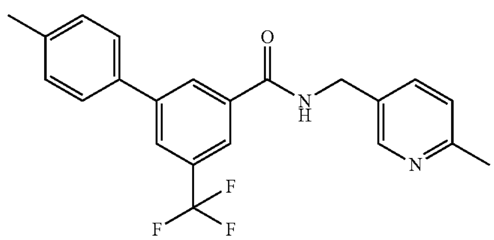 | 384.4 | 384.9 | ++ | * |
| 205 | 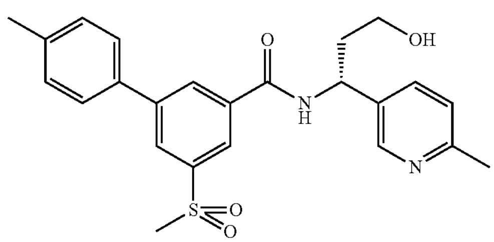 | 438.55 | 438.9 | ++++ | **** |
| 206 | 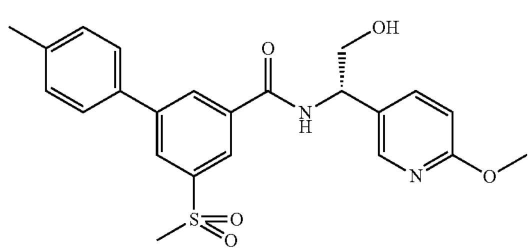 | 440.52 | 440.9 | ++++ | **** |
| 207 | 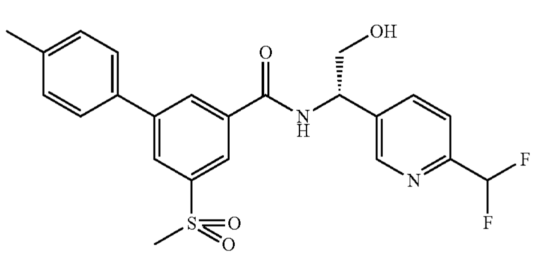 [SMILES: Cc1ccc(-c2cc(C(=O)N[C@H](CO)c3ccc(C(F)F)nc3)cc(S(C)(=O)=O)c2)cc1] | 460.5 | 460.9 | ++++ | **** |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_{3}$ (nM) |
|---|---|---|---|---|---|
| 208 | 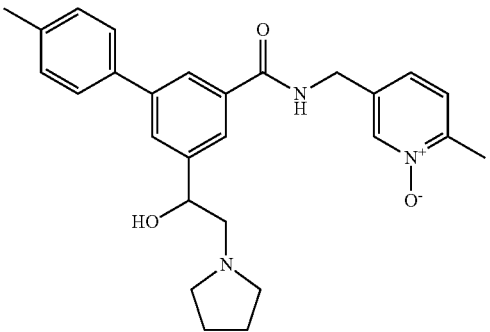 | 445.56 | 446.2 | +++ | **** |
| 209 | 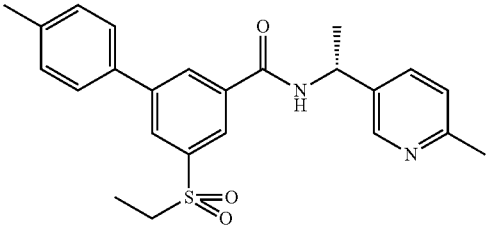 | 422.55 | 423 | ++++ | **** |
| 210 | 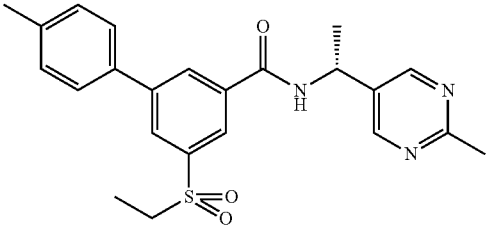 | 423.53 | 424.1 | ++++ | **** |
| 211 | 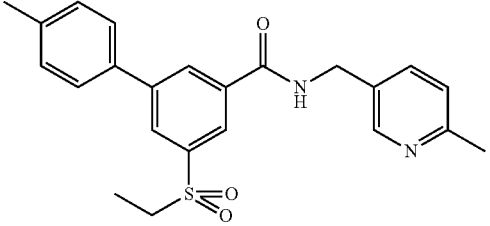 | 408.52 | 409 | ++++ | **** |
| 212 | 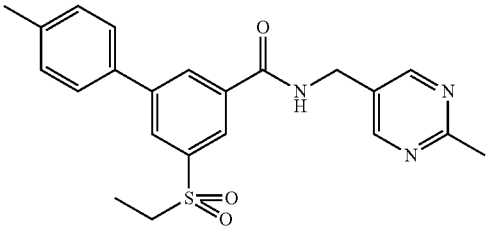 | 409.51 | 410.2 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 213 | 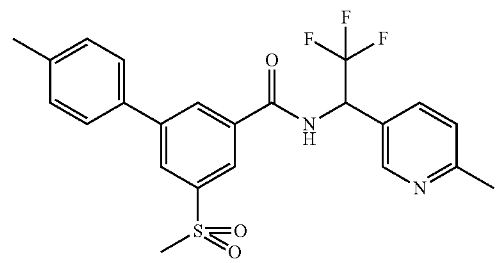 | 462.49 | 462.9 | + | * |
| 214 | 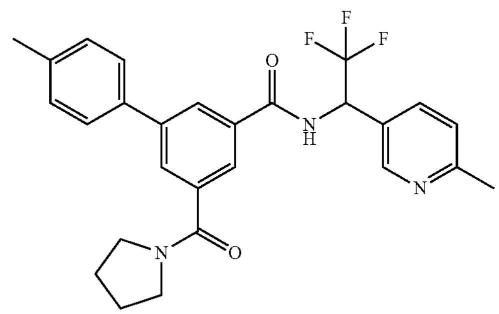 | 481.52 | 481.9 | + | * |
| 215 | 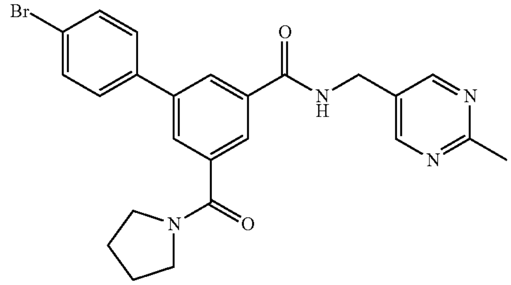 [SMILES: Cc1ncc(CNC(=O)c2cc(C(=O)N3CCCC3)cc(-c3ccc(Br)cc3)c2)cn1] | 479.38 | 481.1 | +++ | **** |
| 216 | 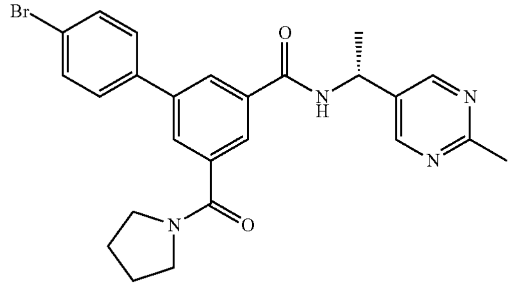 [SMILES: Cc1ncc([C@@H](C)NC(=O)c2cc(C(=O)N3CCCC3)cc(-c3ccc(Br)cc3)c2)cn1] | 493.4 | 493.3 | ++++ | **** |
| 217 | 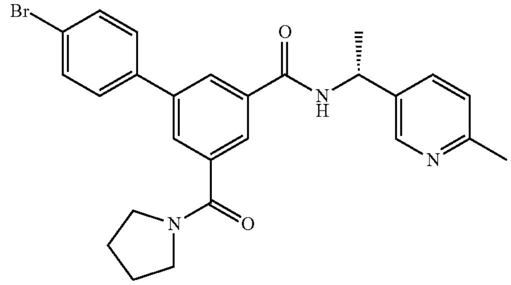 [SMILES: Cc1ccc([C@@H](C)NC(=O)c2cc(C(=O)N3CCCC3)cc(-c3ccc(Br)cc3)c2)cn1] | 492.41 | 494.3 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 218 | 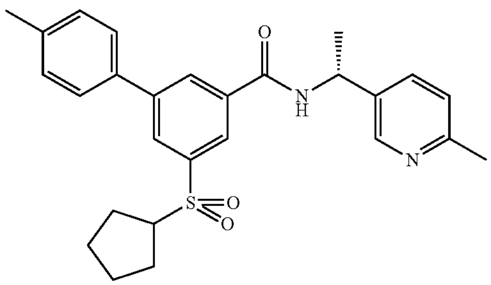 | 462.61 | 463 | ++++ | **** |
| 219 | 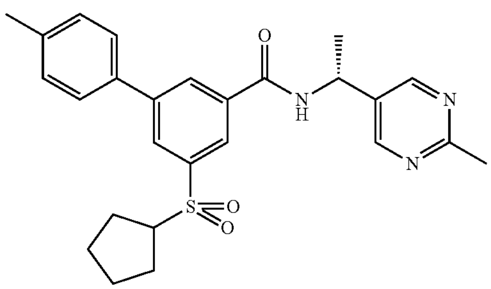 | 463.6 | 464.1 | ++++ | **** |
| 220 | 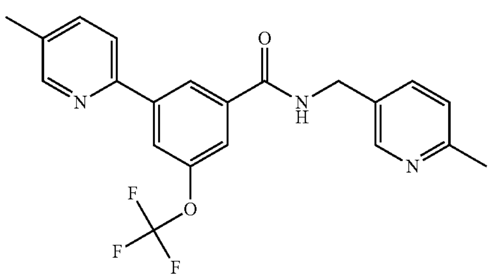 | 401.39 | 401.7 | + | *** |
| 221 | 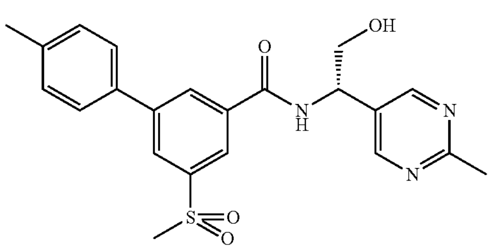 | 425.51 | 426 | ++++ | **** |
| 222 | 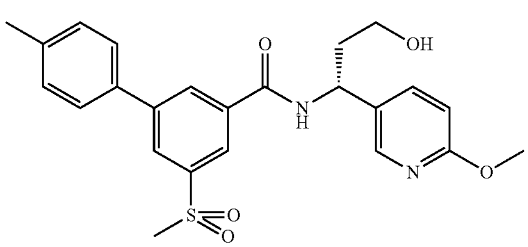 | 454.54 | 455.2 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 223 | 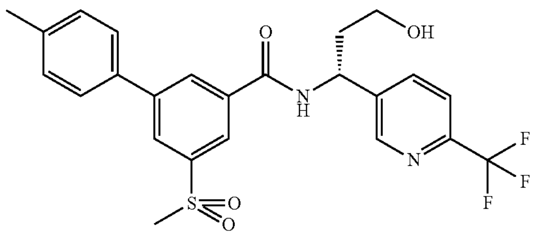 [SMILES: Cc1ccc(-c2cc(C(=O)N[C@H](CCO)c3ccc(C(F)(F)F)nc3)cc(S(C)(=O)=O)c2)cc1] | 492.52 | 493 | +++ | **** |
| 224 | 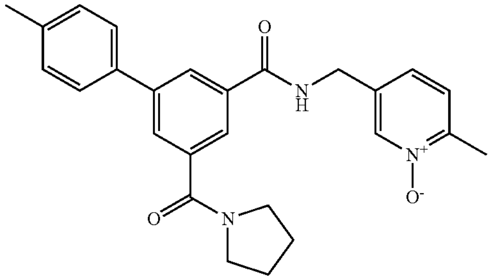 | 429.52 | 429.6 | ++++ | **** |
| 225 | 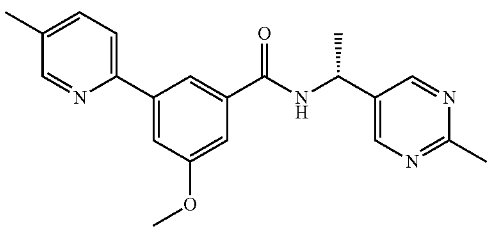 | 362.43 | 363.1 | +++ | **** |
| 226 | 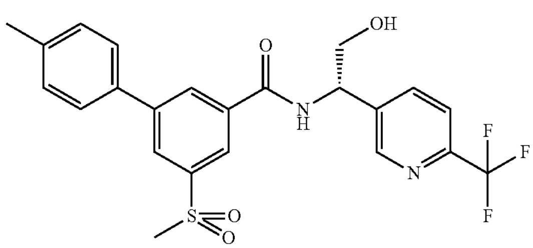 [SMILES: Cc1ccc(-c2cc(C(=O)N[C@H](CO)c3ccc(C(F)(F)F)nc3)cc(S(C)(=O)=O)c2)cc1] | 478.49 | 479.2 | +++ | **** |
| 227 | 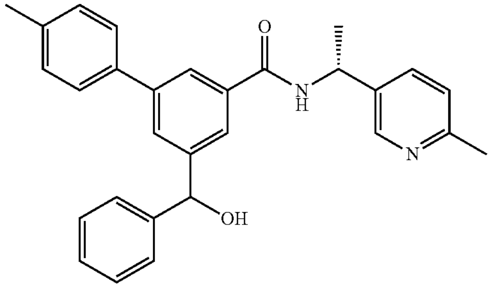 | 436.55 | 437.2 | ++++ | *** |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 228 | 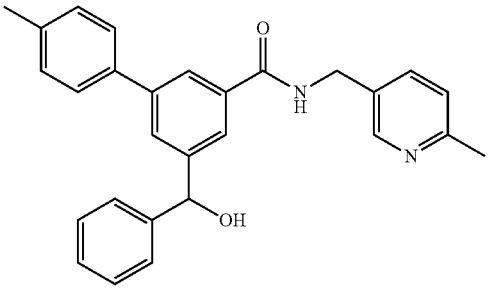 | 422.53 | 423.4 | +++ | *** |
| 229 | 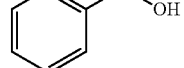 | 434.54 | 435.3 | ++++ | *** |
| 230 | 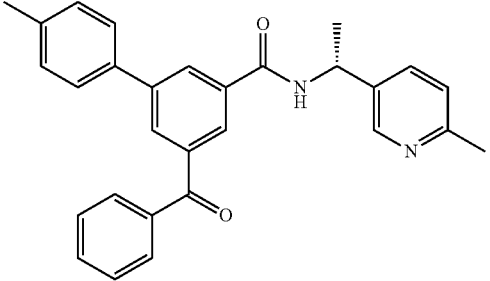 | 429.56 | 430.2 | +++ | **** |
| 231 | 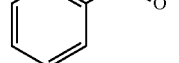 | 438.53 | 439 | + | * |
| 232 | 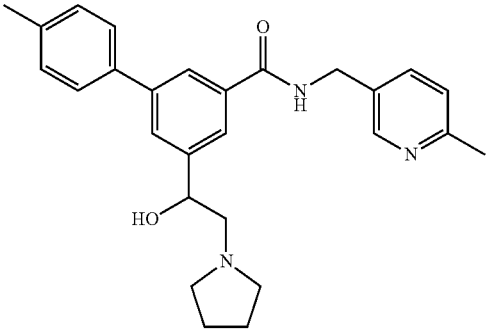 | 424.5 | 425.1 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 233 | 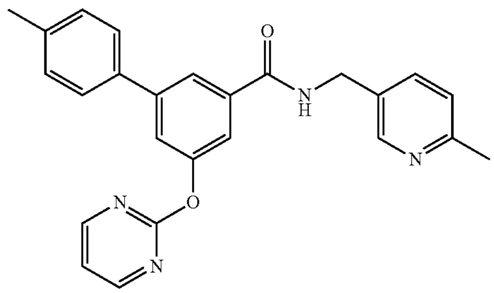 | 410.47 | 411.2 | +++ | *** |
| 234 | 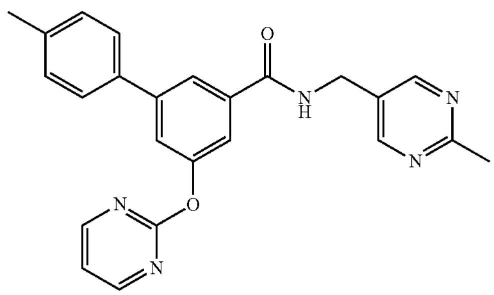 | 411.46 | 412.2 | ++ | *** |
| 235 | 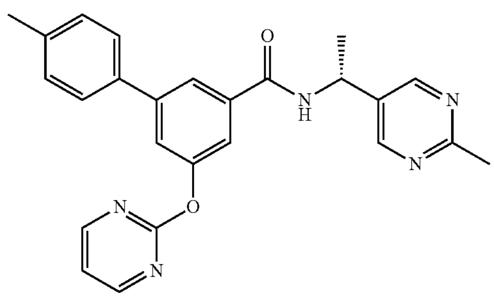 | 425.49 | 426.3 | +++ | **** |
| 236 | 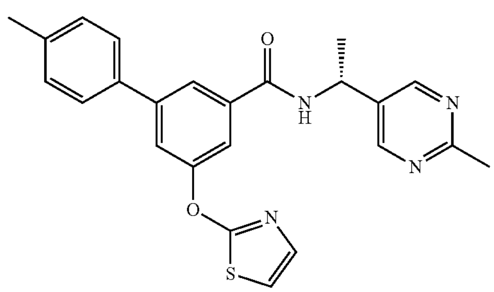 | 430.53 | 431.2 | ++++ | **** |
| 237 | 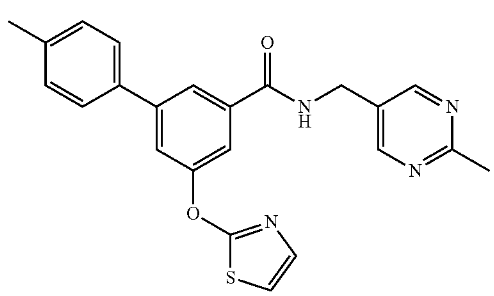 | 416.5 | 417 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 238 | 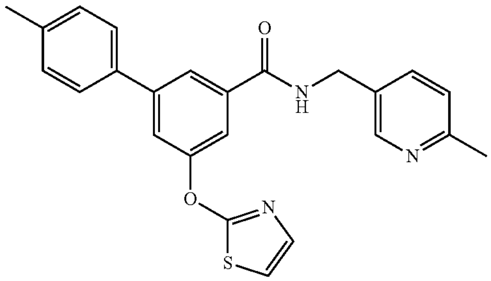 | 415.51 | 416 | +++ | *** |
| 239 | 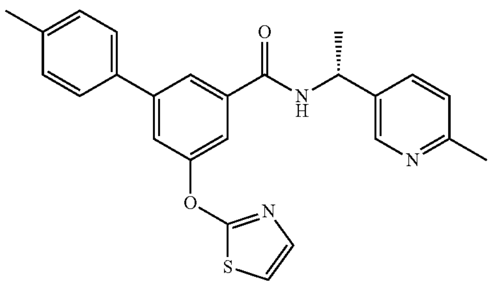 | 429.54 | 430.2 | ++++ | **** |
| 240 | 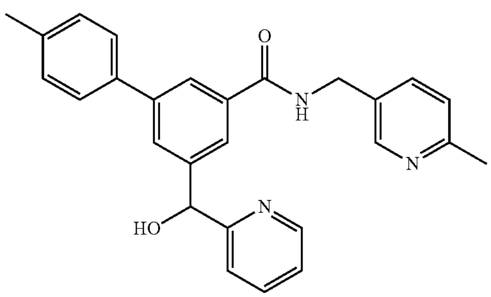 | 423.51 | 424.1 | ++++ | **** |
| 241 | 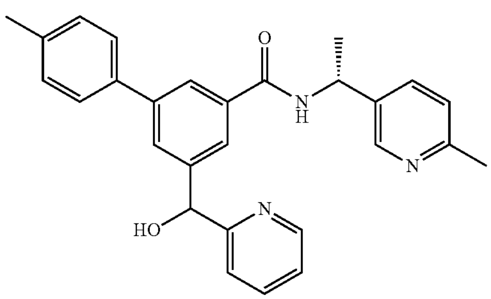 | 437.54 | 438.1 | ++++ | **** |
| 242 | 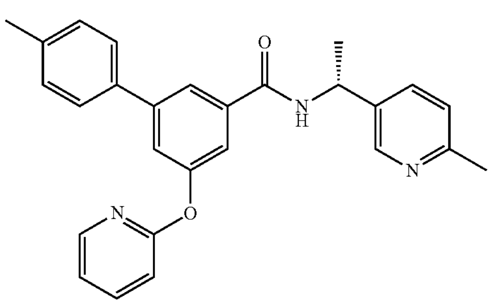 | 423.51 | 424 | ++++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 243 | 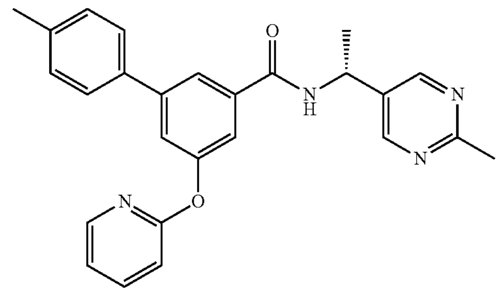 | 424.5 | 425.1 | ++++ | *** |
| 244 | 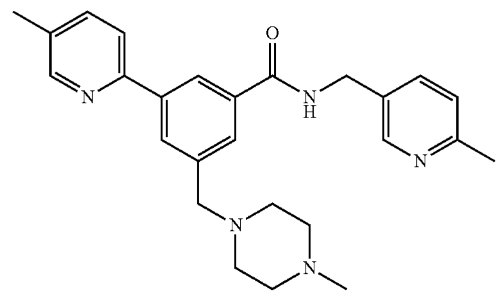 | 429.56 | 430.2 | ++ | *** |
| 245 | 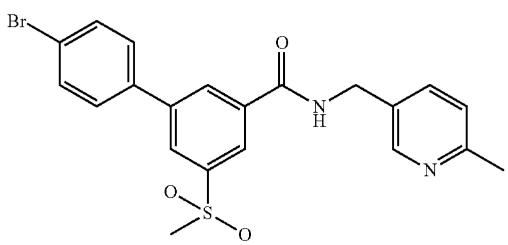 [SMILES: Cc1ccc(CNC(=O)c2cc(-c3ccc(Br)cc3)cc(S(C)(O)O)c2)cn1] | 459.36 | 461.1 | ++ | *** |
| 246 | 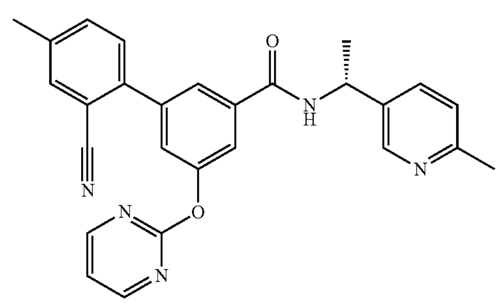 | 449.51 | 450.1 | +++ | **** |
| 247 | 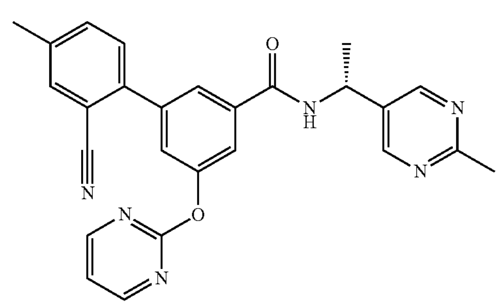 | 450.5 | 451 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 248 | 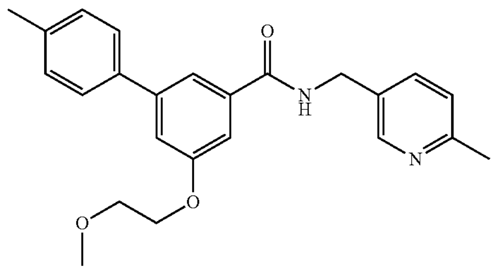 | 390.48 | 391.5 | ++++ | **** |
| 249 | 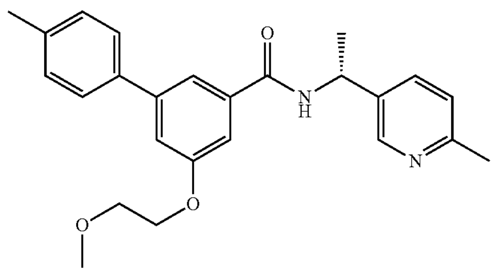 | 404.51 | 405 | ++++ | **** |
| 250 | 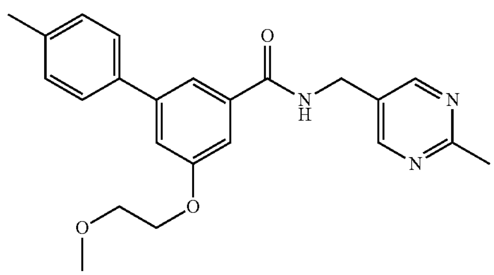 | 391.47 | 392.5 | +++ | **** |
| 251 | 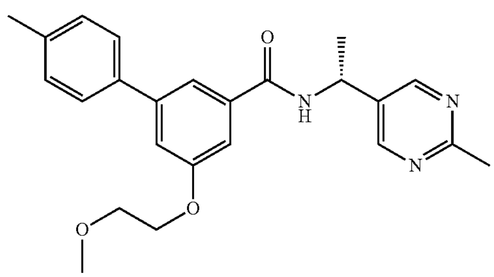 | 405.5 | 405.9 | ++++ | **** |
| 252 | 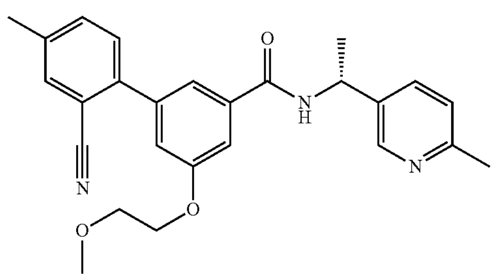 | 429.52 | 429.9 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 253 | 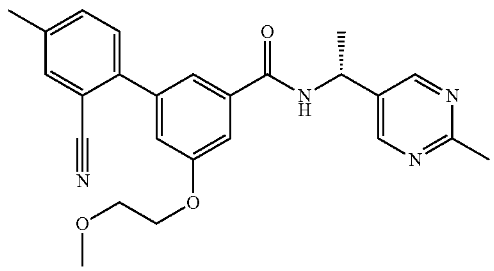 | 430.51 | 430.8 | ++++ | **** |
| 254 | 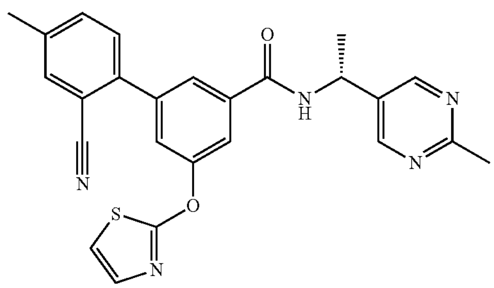 | 455.54 | 455.9 | ++++ | **** |
| 255 | 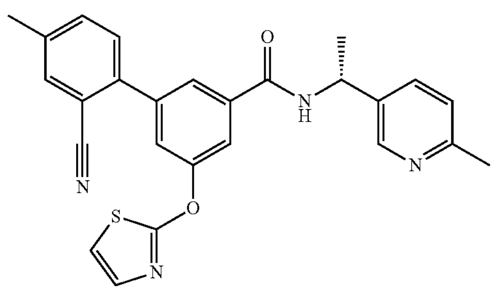 | 454.55 | 455.1 | ++++ | **** |
| 256 | 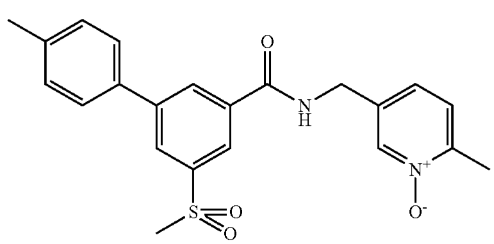 | 410.49 | 411.2 | ++++ | **** |
| 257 | 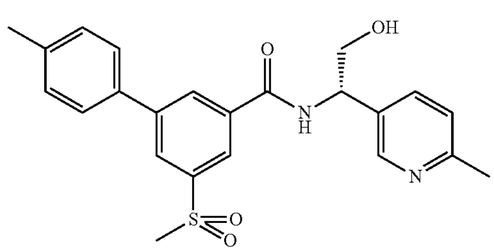 | 424.52 | 425 | ++++ | **** |

TABLE 1-continued
Ca Influx IC$_{50}$ of Exemplary Compounds
| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 258 | 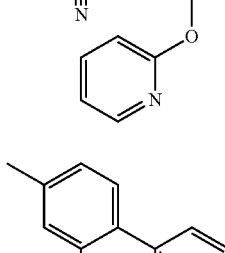 | 449.51 | 450.1 | +++ | **** |
| 259 | 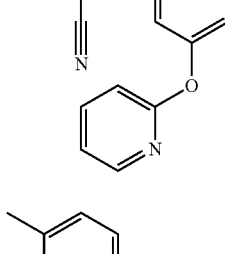 | 448.52 | 449.3 | ++++ | **** |
| 260 | 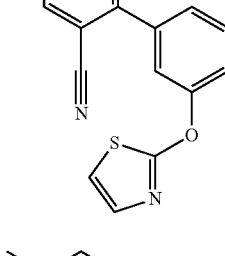 | 440.53 | 441.4 | +++ | **** |
| 261 | 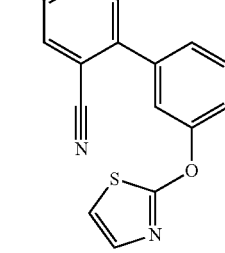 | 441.51 | 442.1 | +++ | **** |
| 262 | 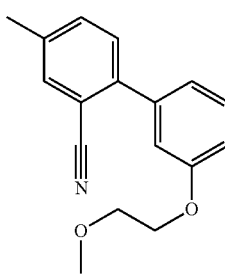 | 416.48 | 417.5 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 263 | 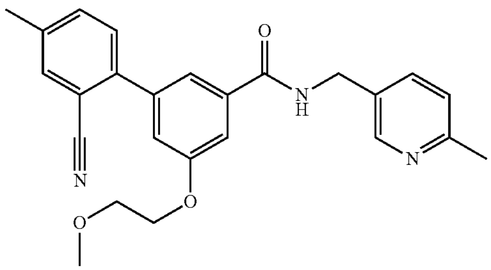 | 415.49 | 416.5 | +++ | **** |
| 264 | 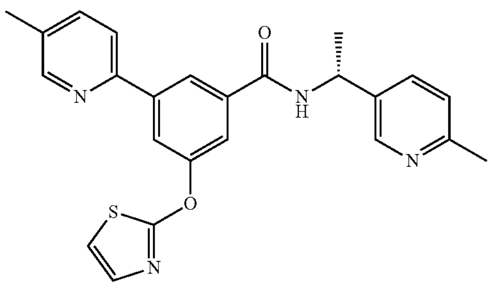 | 430.53 | 431 | ++++ | **** |
| 265 | 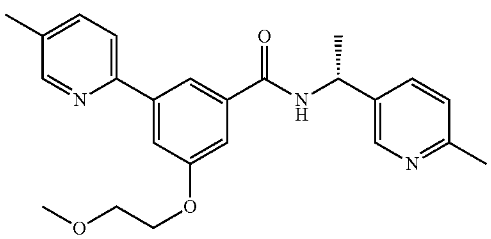 | 405.5 | 406.4 | +++ | **** |
| 266 | 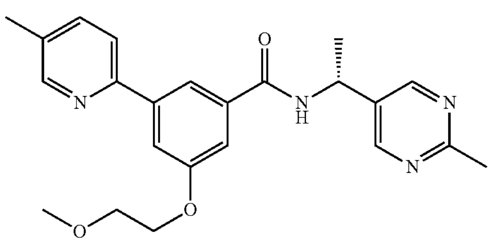 | 406.48 | 407.2 | +++ | **** |
| 267 | 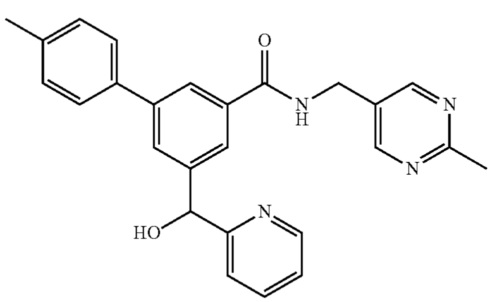 | 424.5 | 425.3 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 268 | 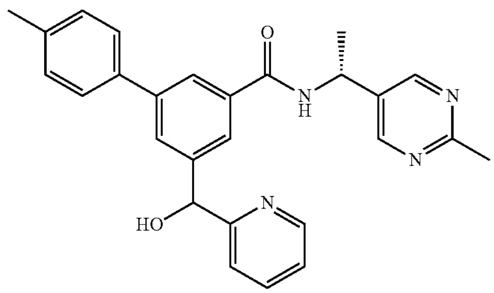 | 438.53 | 439.2 | ++++ | **** |
| 269 | 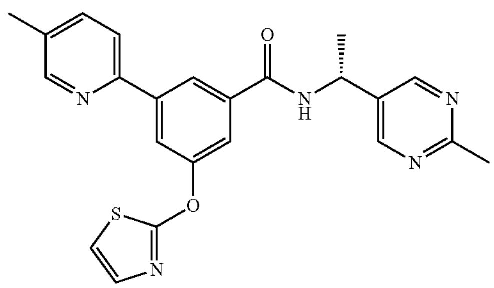 | 431.52 | 432.2 | ++++ | **** |
| 270 | 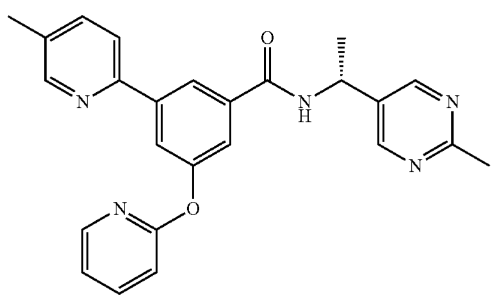 | 425.49 | 426.3 | ++++ | **** |
| 271 | 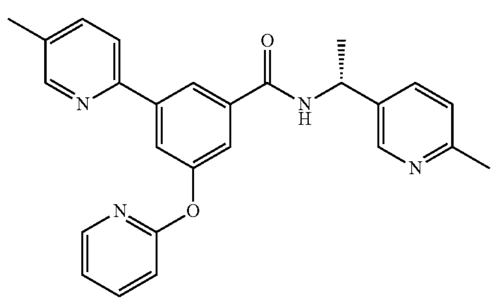 | 424.5 | 425.1 | ++++ | **** |
| 272 | 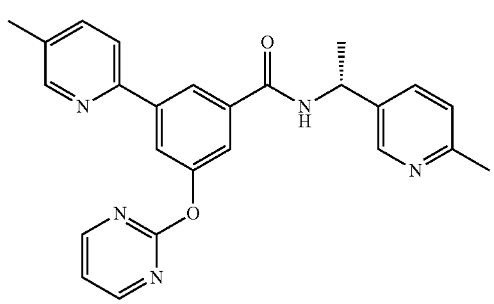 | 425.49 | 426.3 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
| --- | --- | --- | --- | --- | --- |
| 273 | 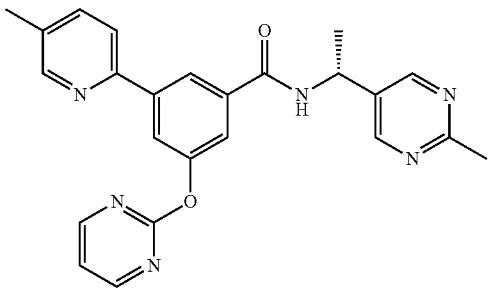 | 426.48 | 427.2 | ++ | *** |
| 274 | 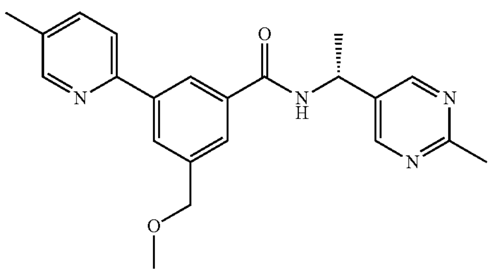 | 376.46 | 377.2 | +++ | *** |
| 275 | 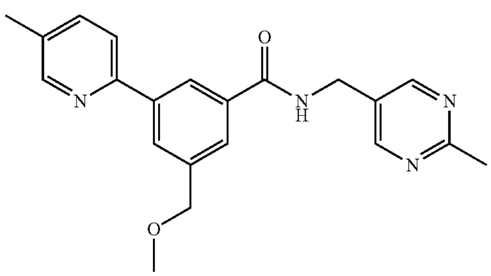 | 362.43 | 363.4 | ++ | *** |
| 276 | 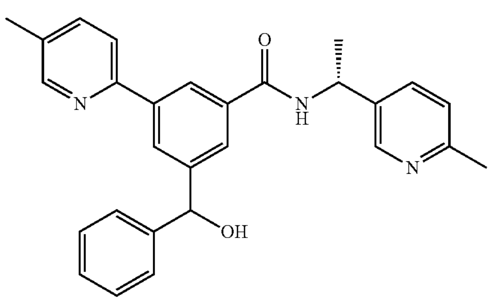 | 437.54 | 438 | ++++ | **** |
| 277 | 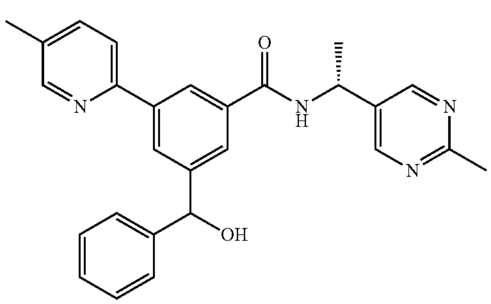 | 438.53 | 439.2 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 278 | 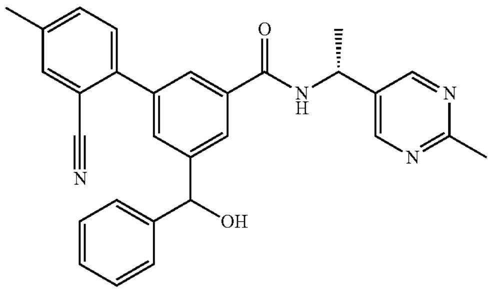 | 462.55 | 463.3 | ++++ | **** |
| 279 | 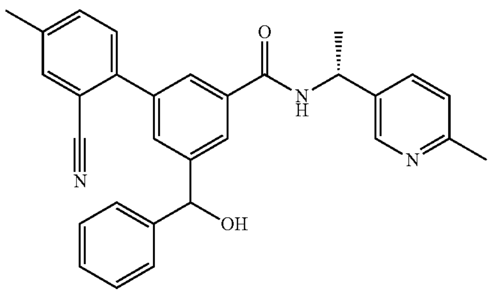 | 461.56 | 461.9 | ++++ | **** |
| 280 | 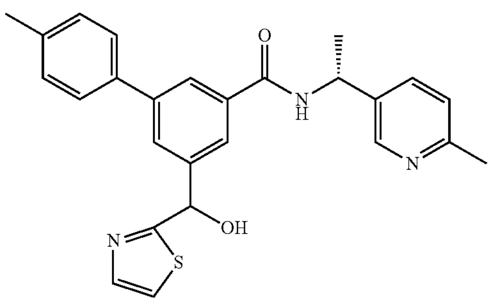 | 443.57 | 444.1 | ++++ | **** |
| 281 | 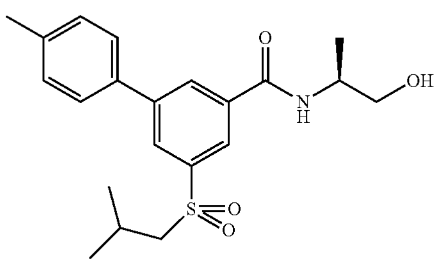 [SMILES: Cc1ccc(-c2cc(C(=O)N[C@@H](C)CO)cc(S(=O)(=O)CC(C)C)c2)cc1] | 389.51 | 390.5 | + | **** |
| 282 | 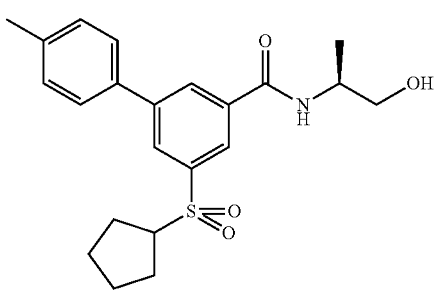 [SMILES: Cc1ccc(-c2cc(C(=O)N[C@@H](C)CO)cc(S(=O)(=O)C3CCCC3)c2)cc1] | 401.52 | 402 | + | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 283 | 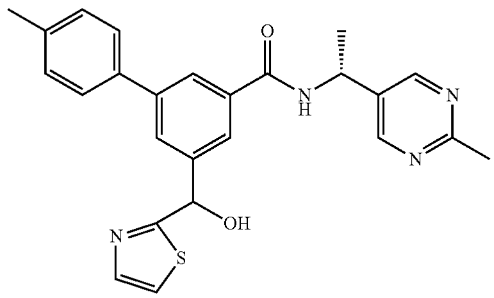 | 444.56 | 445.1 | ++++ | **** |
| 284 | 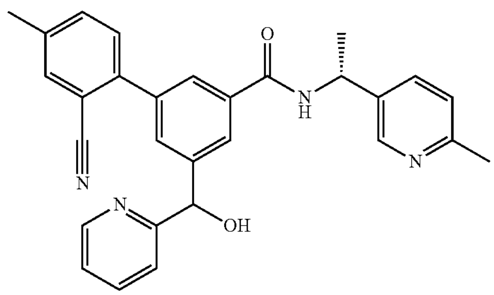 | 462.55 | 463.3 | ++++ | **** |
| 285 | 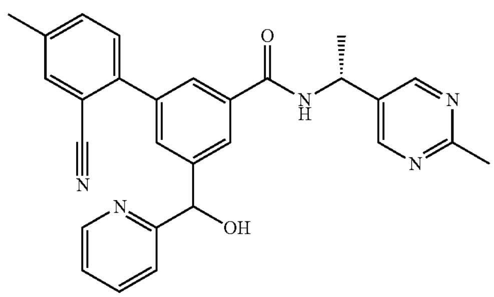 | 463.54 | 464.4 | ++++ | **** |
| 286 | 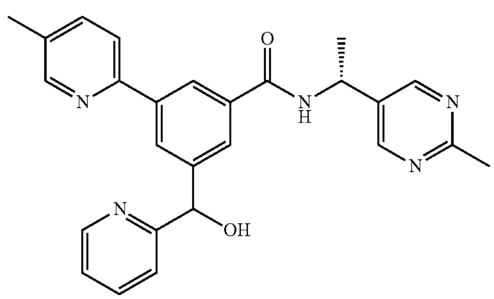 | 439.52 | 440.1 | ++++ | **** |
| 287 | 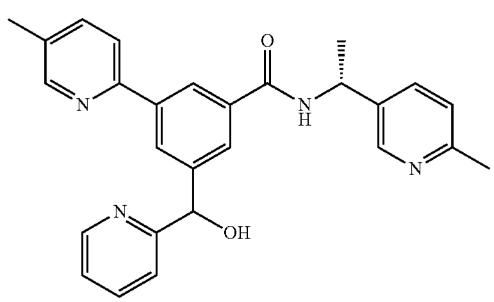 | 438.53 | 439.3 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 288 | 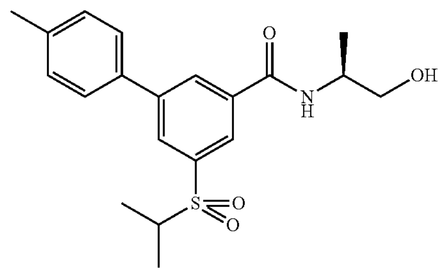 [SMILES: Cc1ccc(-c2cc(C(=O)N[C@@H](C)CO)cc(S(=O)(=O)C(C)C)c2)cc1] | 375.49 | 376.1 | + | **** |
| 289 | 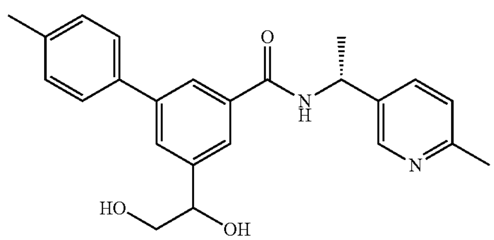 | 390.48 | 391.4 | ++++ | **** |
| 290 | 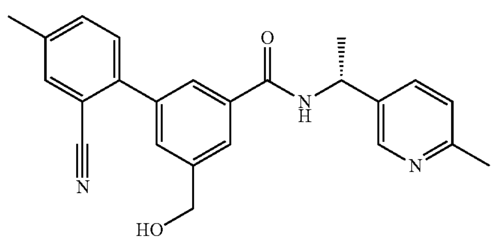 | 385.46 | 386.4 | ++++ | **** |
| 291 | 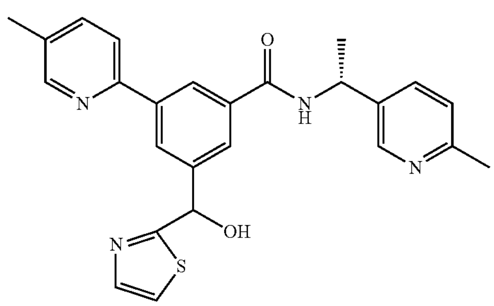 | 444.56 | 445.5 | ++++ | **** |
| 292 | 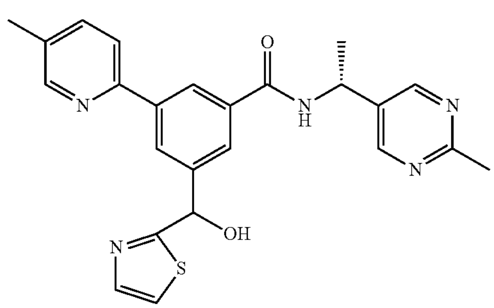 | 445.54 | 446.2 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 293 | 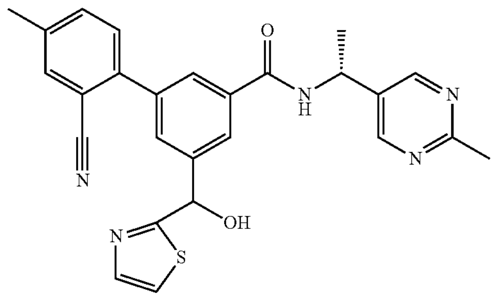 | 469.57 | 470 | ++++ | **** |
| 294 | 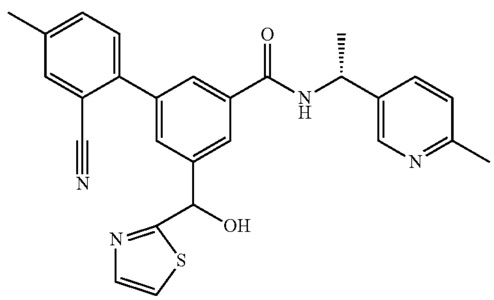 | 468.58 | 469.1 | ++++ | **** |
| 295 | 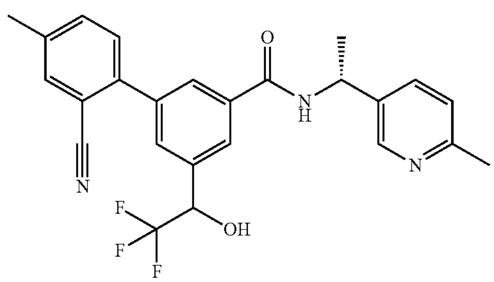 | 453.46 | 454.3 | ++++ | **** |
| 296 | 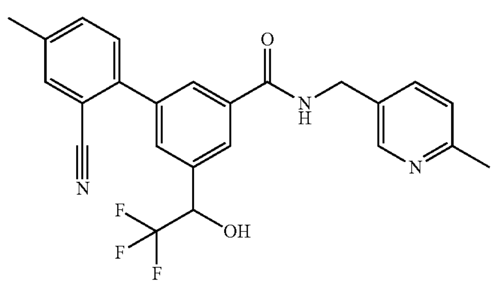 | 439.44 | 439.9 | ++++ | **** |
| 297 | 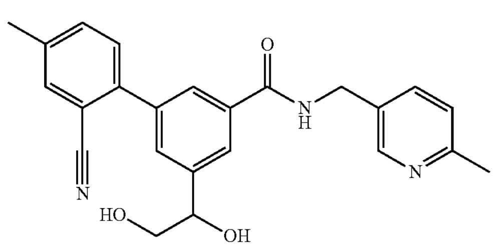 | 401.46 | 402.1 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 298 | 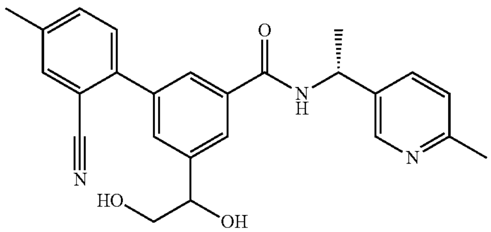 | 415.49 | 416.5 | ++++ | **** |
| 299 | 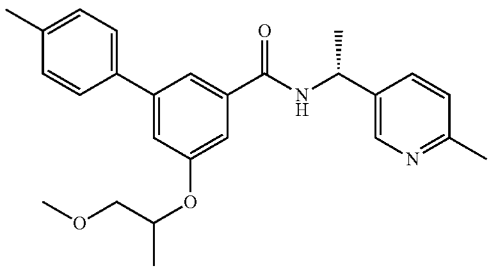 | 418.53 | 419.6 | ++++ | **** |
| 300 | 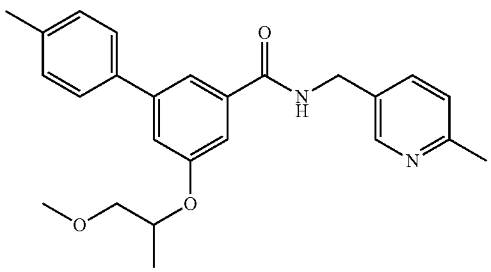 | 404.51 | 405.2 | ++++ | **** |
| 301 | 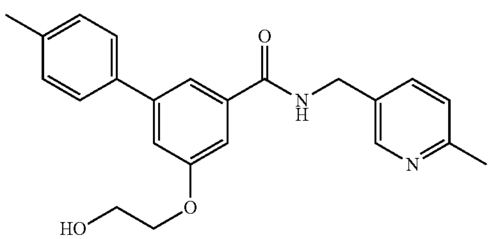 | 376.45 | 377.2 | +++ | **** |
| 302 | 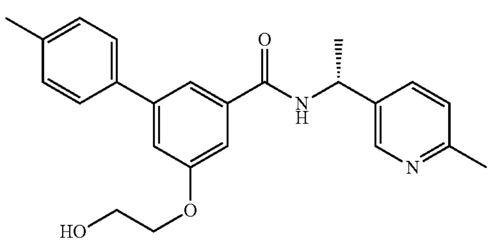 | 390.48 | 391.3 | ++++ | **** |
| 303 | 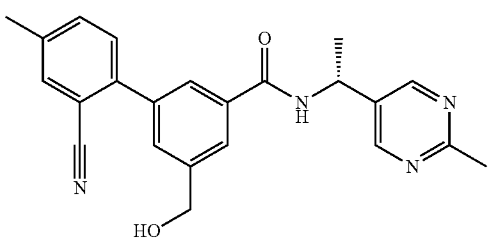 | 386.45 | 387.4 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 304 | 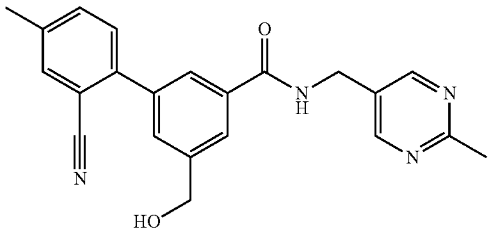 | 372.43 | 373.2 | +++ | **** |
| 305 | 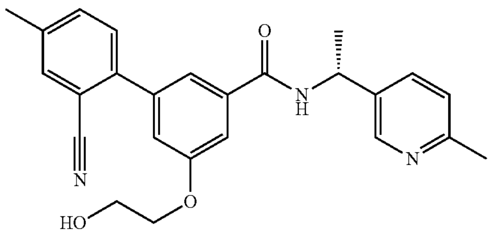 | 415.49 | 416.1 | ++++ | **** |
| 306 | 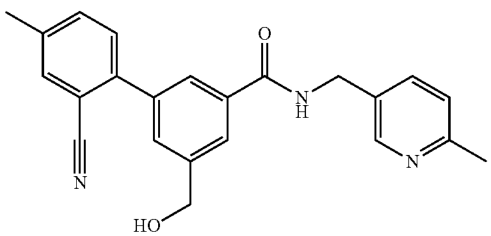 | 371.44 | 372.2 | +++ | **** |
| 307 | 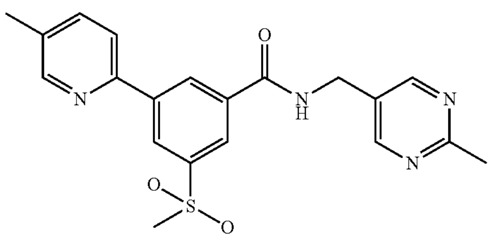 | 396.47 | 397 | + | **** |
| 308 | 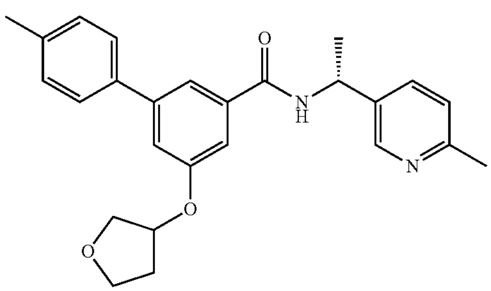 | 416.52 | 417.1 | ++++ | **** |
| 309 | 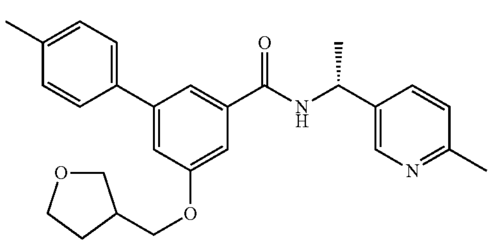 | 430.55 | 431.3 | ++++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 310 | 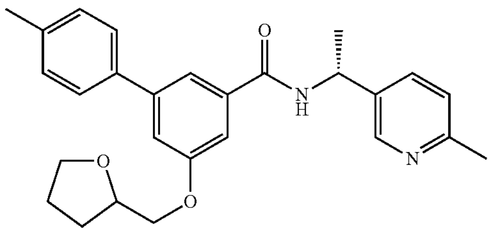 | 430.55 | 430.9 | ++++ | **** |
| 311 | 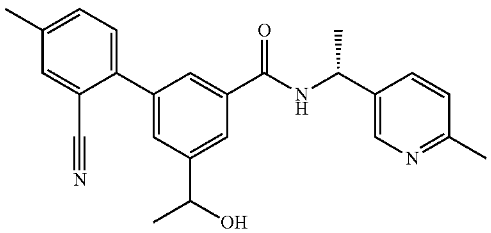 | 399.49 | 400.3 | ++++ | **** |
| 312 | 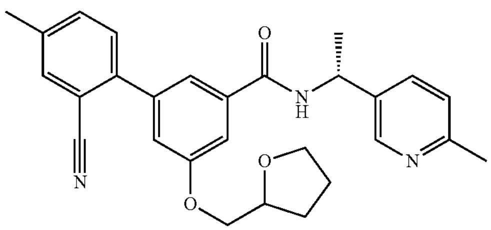 | 455.56 | 455.9 | ++++ | **** |
| 313 | 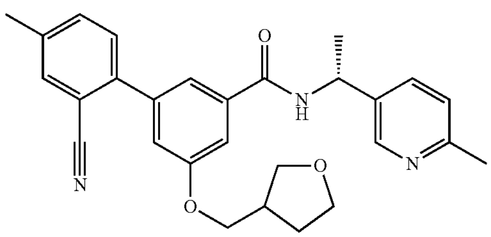 | 455.56 | 456.1 | ++++ | **** |
| 314 | 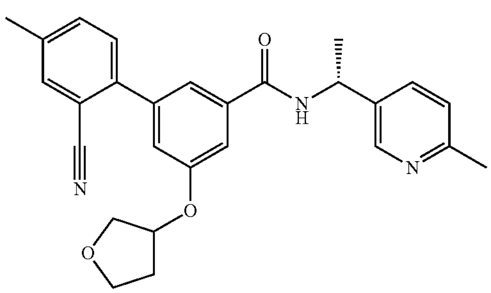 | 441.53 | 442.2 | ++++ | **** |
| 315 | 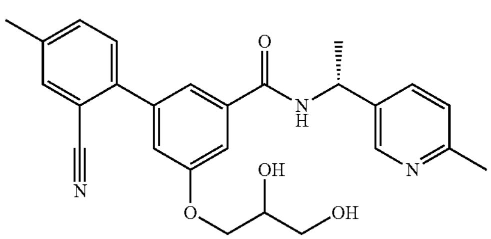 | 445.52 | 446.6 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 316 | 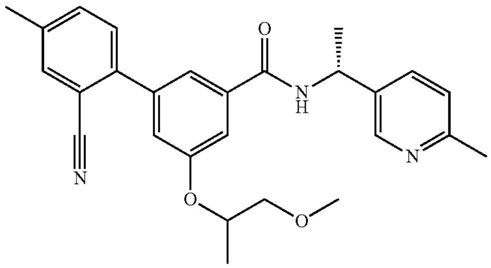 | 443.54 | 444.2 | ++++ | **** |
| 317 | 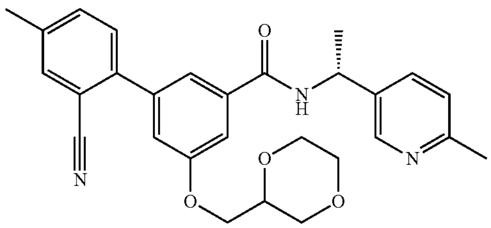 | 471.55 | 471.9 | ++++ | **** |
| 318 | 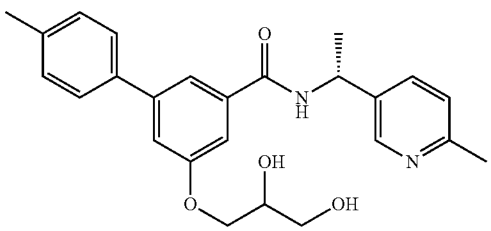 | 420.51 | 421.1 | ++++ | **** |
| 319 | 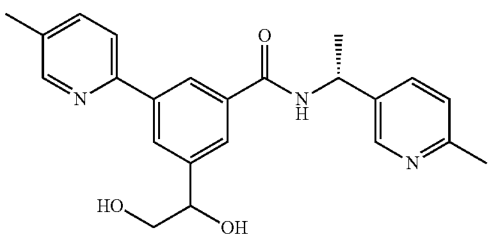 | 391.47 | 392.5 | +++ | **** |
| 320 | 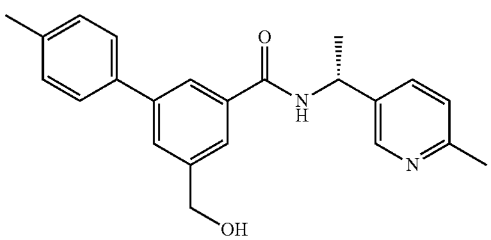 | 360.45 | 361.2 | +++ | **** |
| 321 | 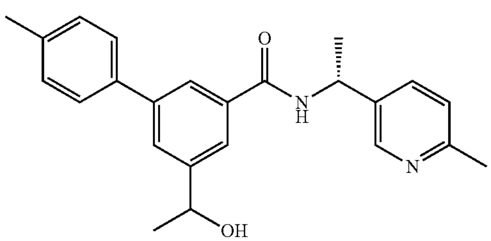 | 374.48 | 375 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|----|-----------|------------|----------|------------------------------|-------------------------|
| 322 | 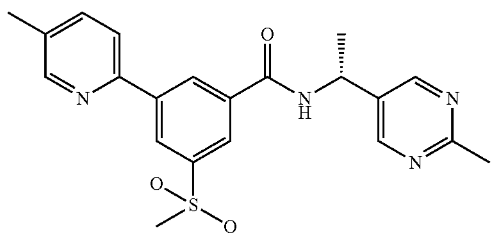 | 410.5 | 411.1 | +++ | **** |
| 323 | 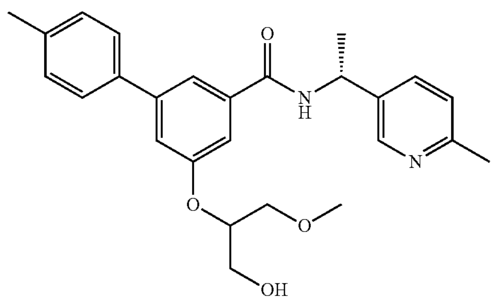 | 434.53 | 434.9 | ++++ | **** |
| 324 | 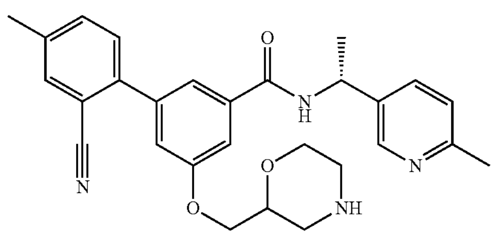 | 470.57 | 471.6 | +++ | **** |
| 325 | 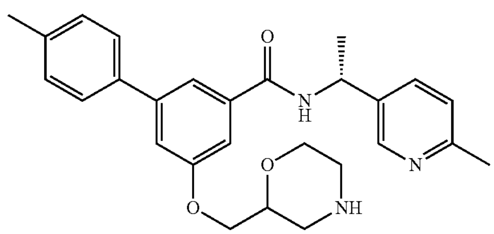 | 445.56 | 446.5 | +++ | **** |
| 326 | 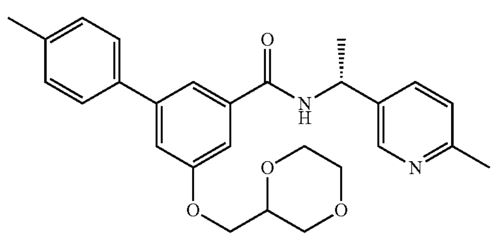 | 446.54 | 447.2 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 327 | 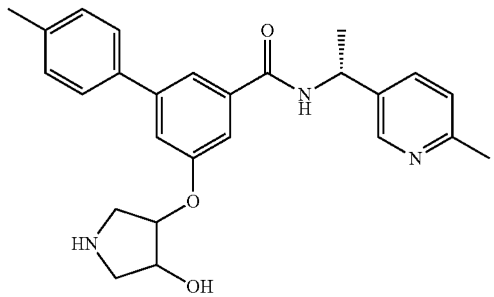 | 431.53 | 432.2 | +++ | **** |
| 328 | 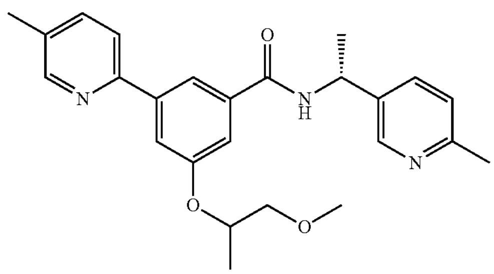 | 419.52 | 420.4 | ++++ | **** |
| 329 | 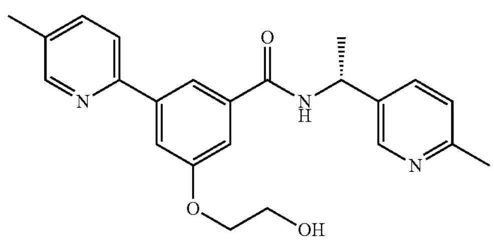 | 391.47 | 392.3 | +++ | **** |
| 330 | 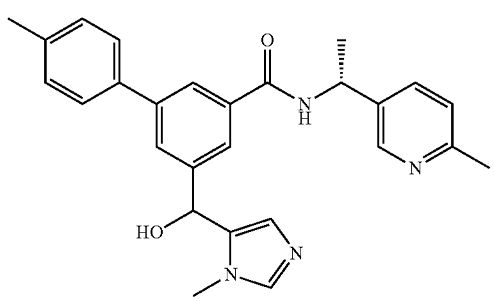 | 440.54 | 441.1 | ++++ | **** |
| 331 | 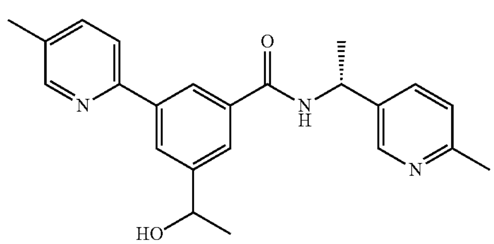 | 375.47 | 376.3 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 332 | 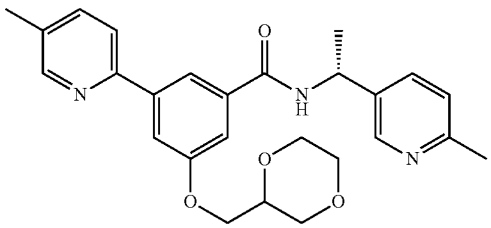 | 447.53 | 448.6 | +++ | **** |
| 333 | 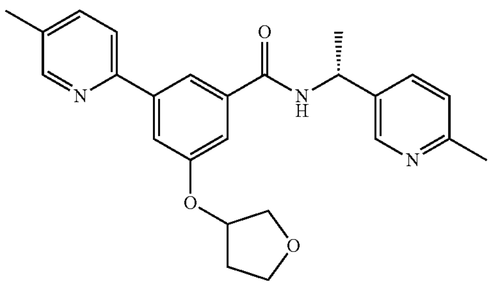 | 417.51 | 418.6 | ++++ | **** |
| 334 | 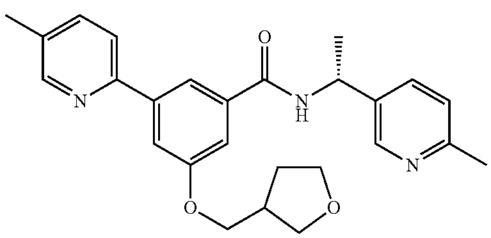 | 431.53 | 432.2 | ++++ | **** |
| 335 | 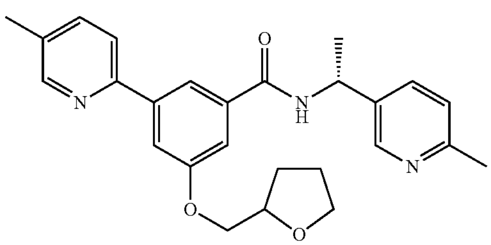 | 431.53 | 432.3 | ++++ | **** |
| 336 | 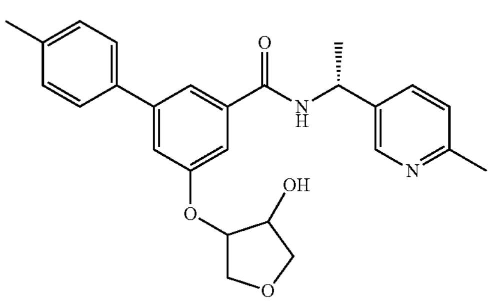 | 432.52 | 432.8 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 337 | 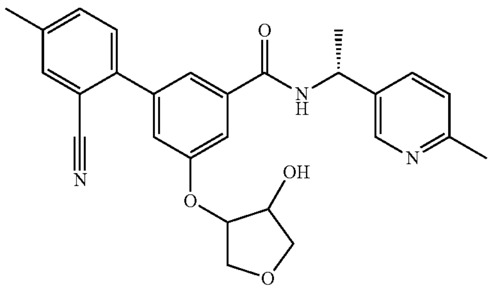 | 457.53 | 457.8 | ++++ | **** |
| 338 | 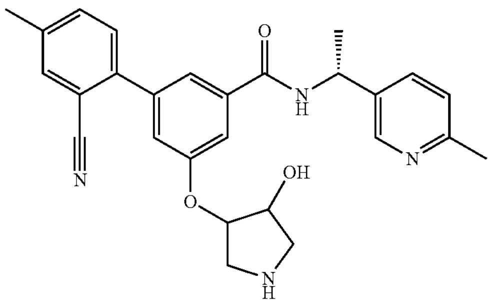 | 456.54 | 457.3 | +++ | **** |
| 339 | 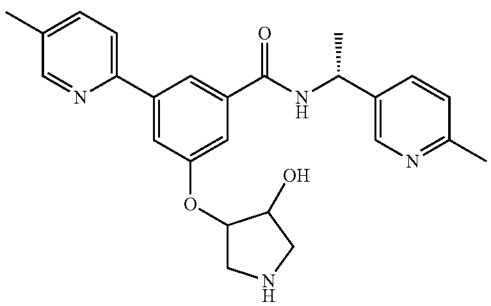 | 432.52 | 433.2 | +++ | **** |
| 340 | 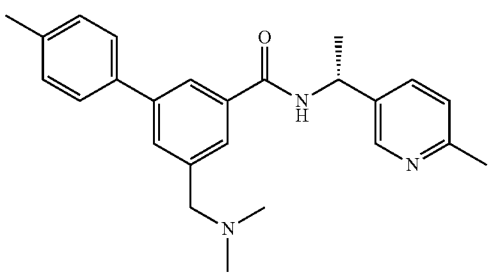 | 387.52 | 388.3 | +++ | **** |
| 341 | 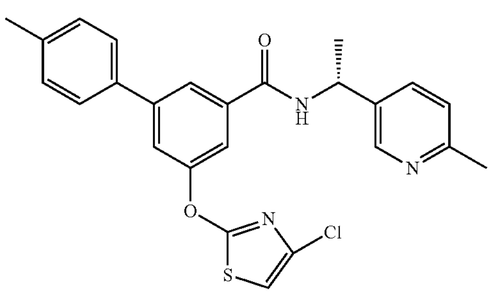 | 463.99 | 464.2 | ++++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 342 | 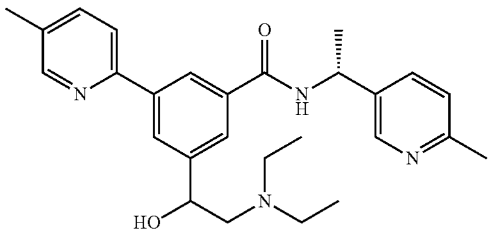 | 446.59 | 447.5 | +++ | **** |
| 343 | 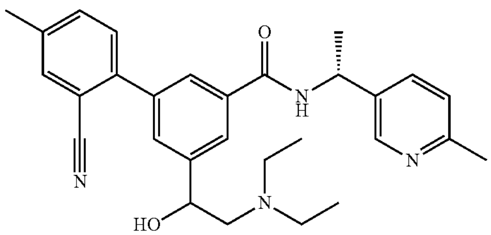 | 470.61 | 471.4 | +++ | **** |
| 344 | 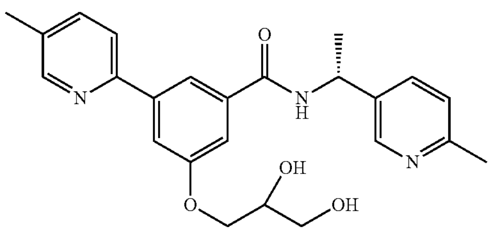 | 421.49 | 422.3 | +++ | **** |
| 345 | 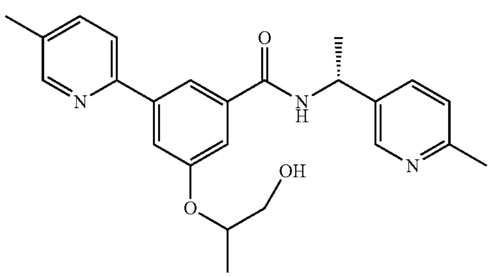 | 405.5 | 406 | ++++ | **** |
| 346 | 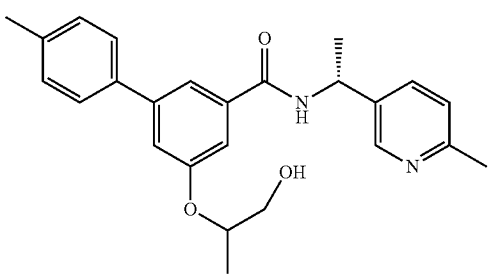 | 404.51 | 404.8 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 347 | 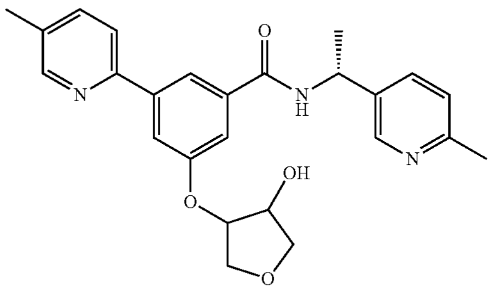 | 433.51 | 434.1 | +++ | **** |
| 348 | 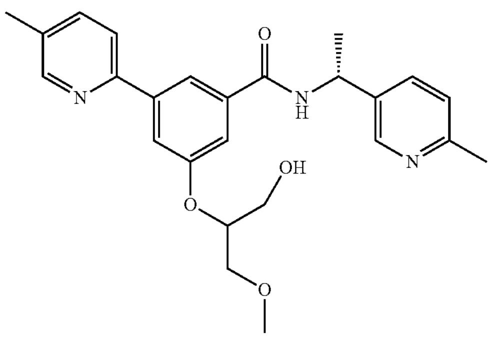 | 435.52 | 436.3 | ++++ | **** |
| 349 | 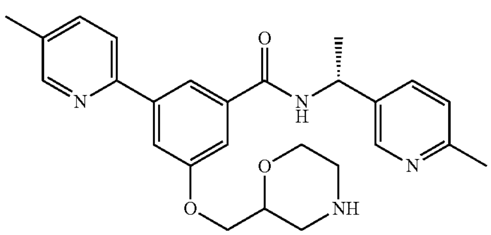 | 446.55 | 447.4 | +++ | **** |
| 350 | 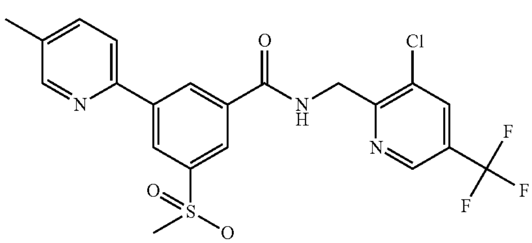 | 483.9 | 483.6 | +++ | **** |
| 351 | 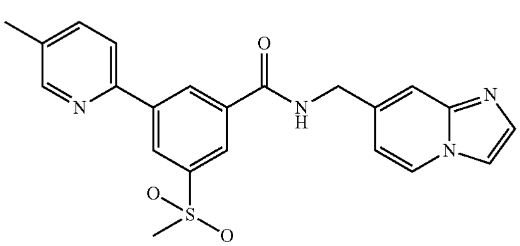 [SMILES: Cc1ccc(-c2cc(C(=O)NCc3ccn4ccnc4c3)cc(S(C)(O)O)c2)nc1] | 420.49 | 420.9 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 352 | 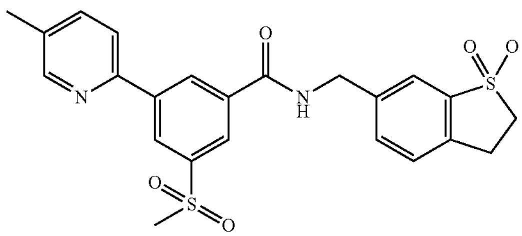 | 470.57 | 471.3 | +++ | **** |
| 353 | 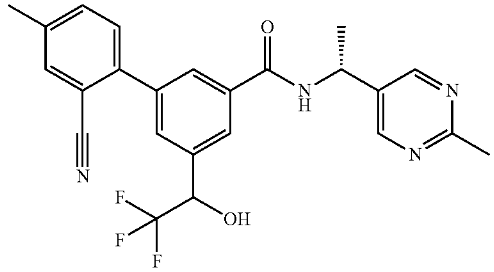 | 454.45 | 455 | ++++ | **** |
| 354 | 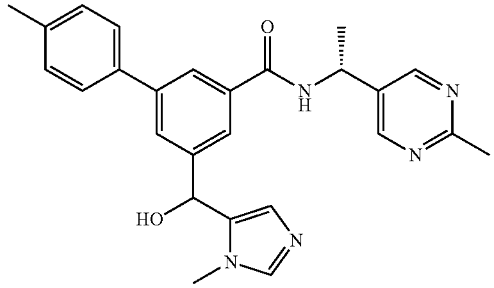 | 441.53 | 442.5 | ++++ | **** |
| 355 | 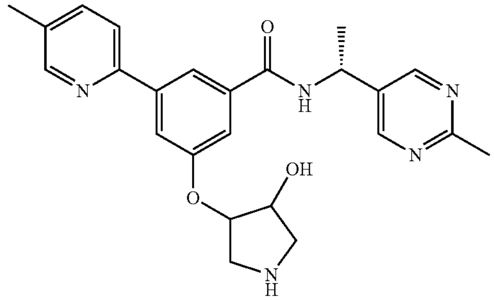 | 433.51 | 434.2 | + | **** |
| 356 | 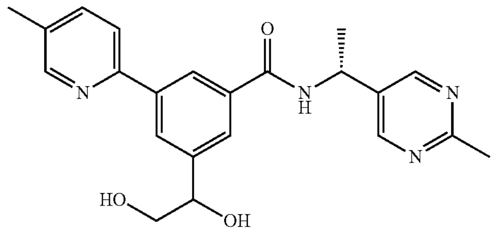 | 392.46 | 393.1 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 357 | 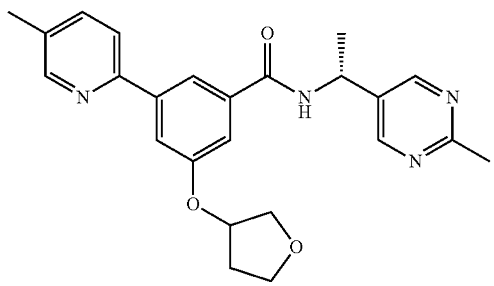 | 418.49 | 419.1 | +++ | **** |
| 358 | 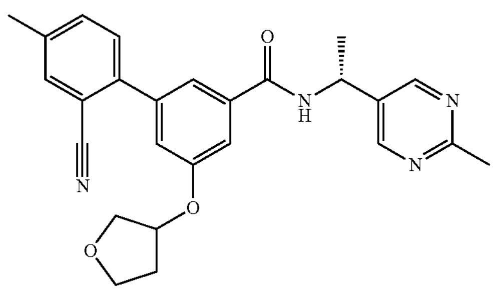 | 442.52 | 443.1 | ++++ | **** |
| 359 | 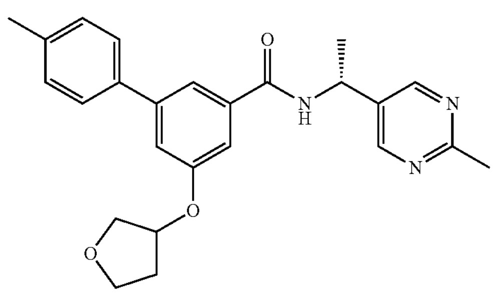 | 417.51 | 418.1 | ++++ | **** |
| 360 | 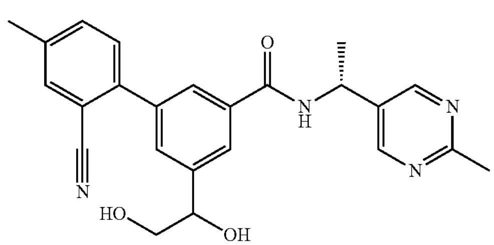 | 416.48 | 417.2 | +++ | **** |
| 361 | 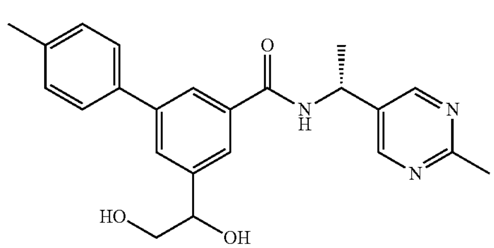 | 391.47 | 392.3 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 362 | 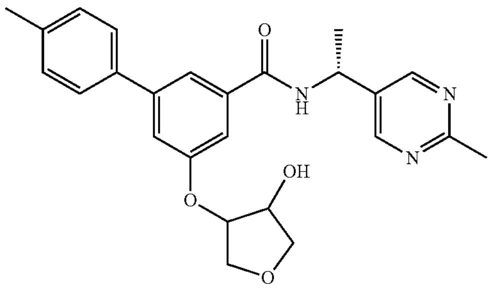 | 433.51 | 433.8 | ++++ | **** |
| 363 | 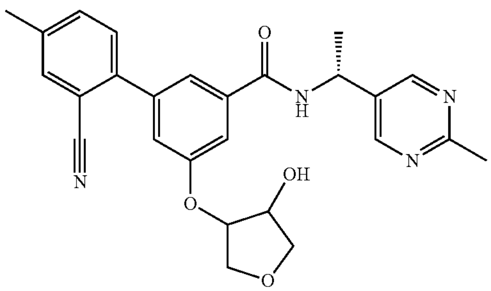 | 458.52 | 459 | ++++ | **** |
| 364 | 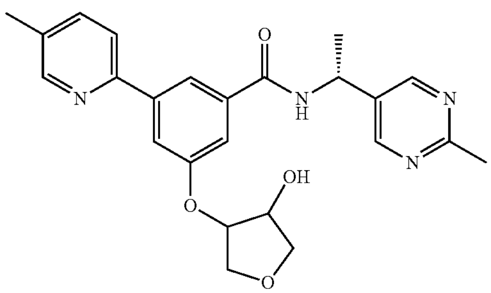 | 434.49 | 435.2 | +++ | **** |
| 365 | 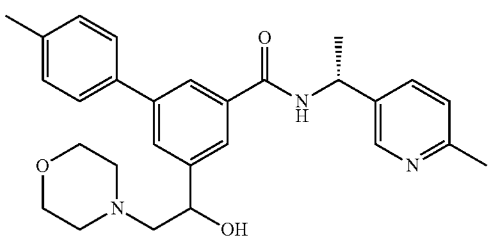 | 445.56 | 446.1 | ++++ | **** |
| 366 | 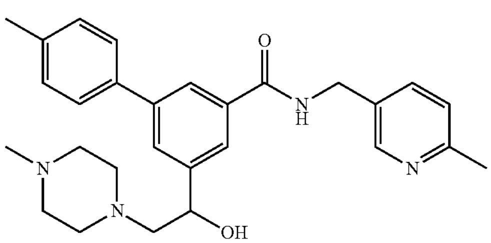 | 458.6 | 459.1 | ++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 367 | 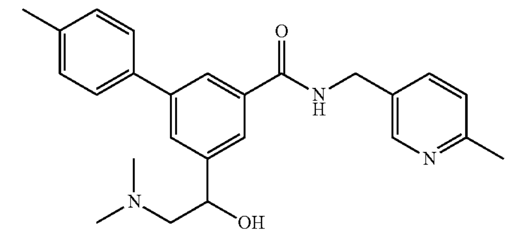 | 403.52 | 404.1 | + | **** |
| 368 | 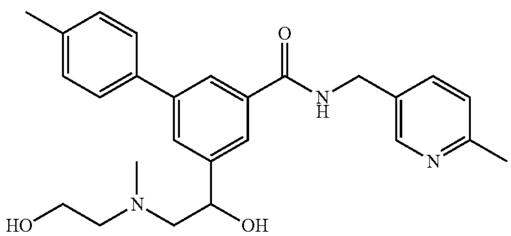 | 433.55 | 434.2 | ++ | **** |
| 369 | 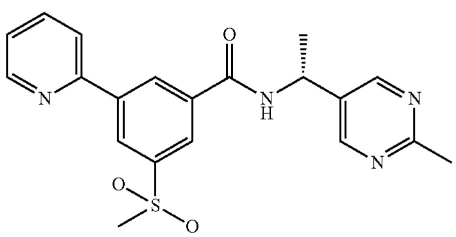 [SMILES: Cc1ncc([C@@H](C)NC(=O)c2cc(-c3ccccn3)cc(S(C)(O)O)c2)cn1] | 396.47 | 396.8 | | |
| 370 | 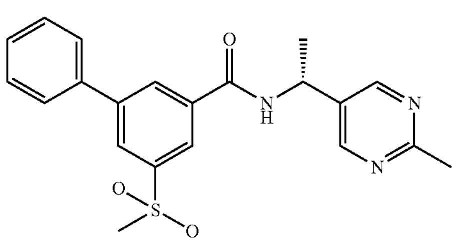 [SMILES: Cc1ncc([C@@H](C)NC(=O)c2cc(-c3ccccc3)cc(S(C)(O)O)c2)cn1] | 395.48 | 395.9 | ++ | **** |
| 371 | 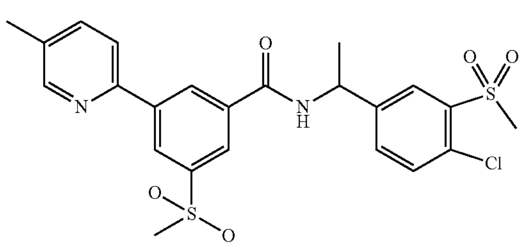 | 507.03 | 506.8 | +++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 372 | 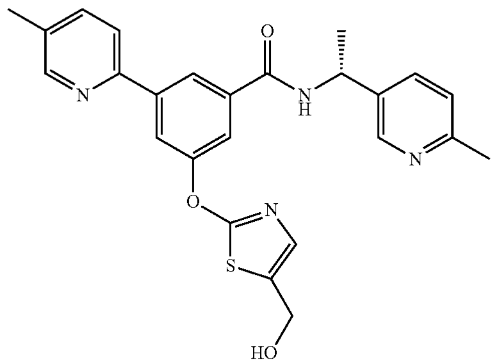 | 460.56 | 461.1 | ++++ | **** |
| 373 | 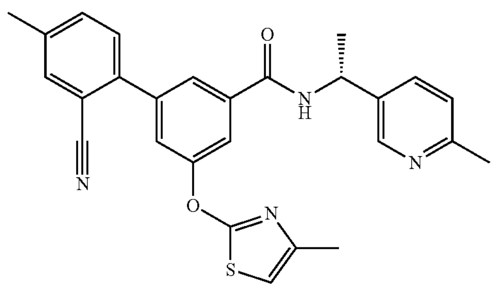 | 468.58 | 469.4 | ++++ | **** |
| 374 | 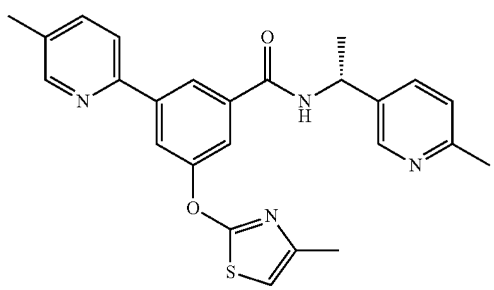 | 444.56 | 445.4 | ++++ | **** |
| 375 | 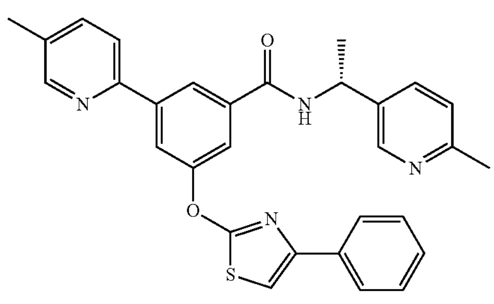 | 506.63 | 507.4 | +++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 376 | 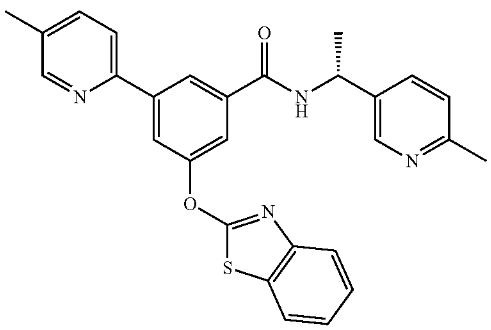 | 480.59 | 481.3 | ++++ | **** |
| 377 | 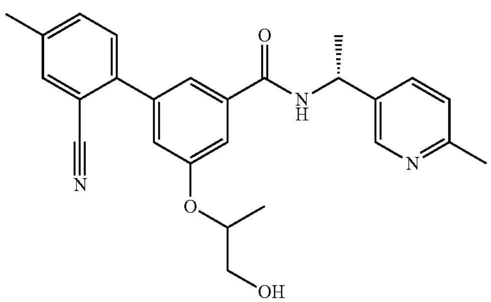 | 429.52 | 430.1 | ++++ | **** |
| 378 | 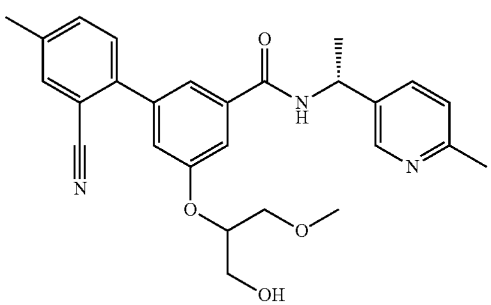 | 459.54 | 460.1 | ++++ | **** |
| 379 | 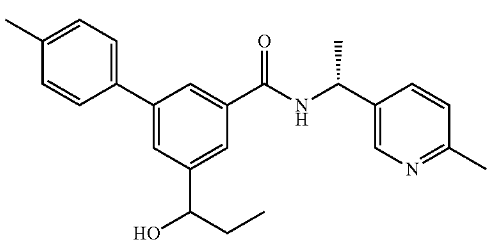 | 388.51 | 389.1 | ++++ | **** |
| 380 | 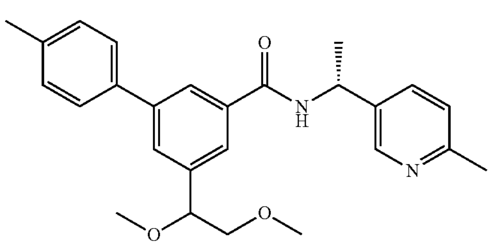 | 418.53 | 419.3 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 381 | 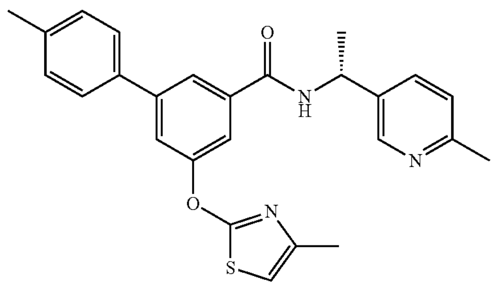 | 443.57 | 444.2 | ++++ | **** |
| 382 | 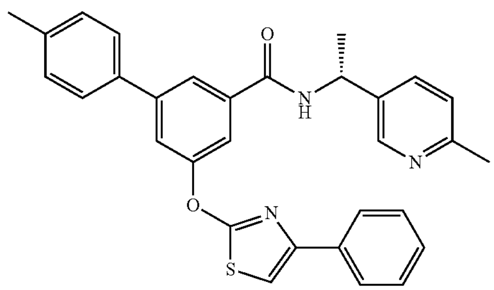 | 505.64 | 506.2 | | |
| 383 | 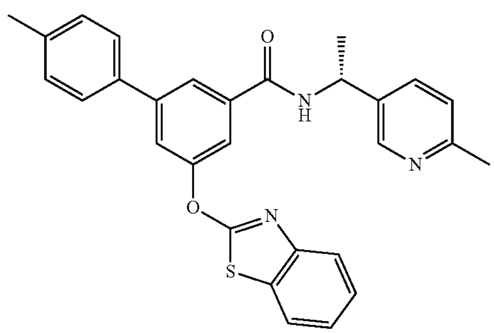 | 479.6 | 480.2 | | |
| 384 | 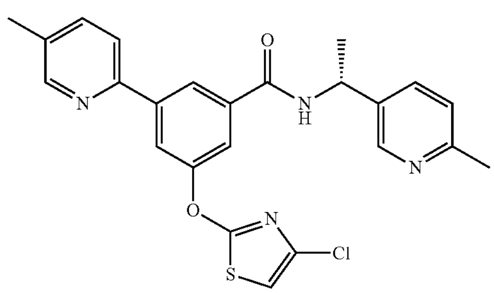 | 464.97 | 465.2 | ++++ | **** |
| 385 | 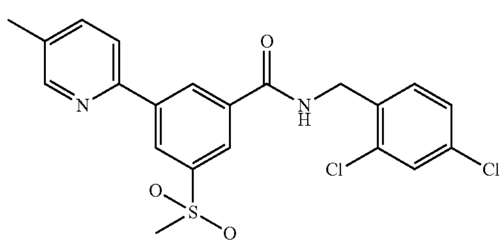 [SMILES: Cc1ccc(-c2cc(C(=O)NCc3ccc(Cl)cc3Cl)cc(S(C)(O)O)c2)nc1] | 449.36 | 449 | +++ | *** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 386 | 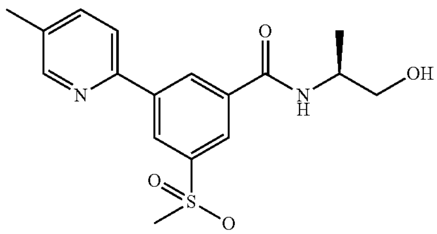 | 348.42 | 349 | | |
| 387 | 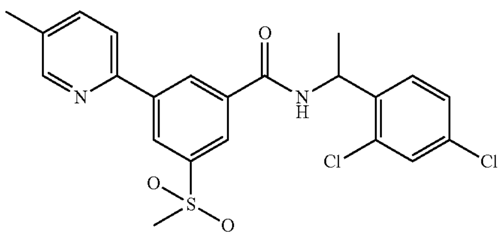 [SMILES: Cc1ccc(-c2cc(C(=O)NC(C)c3ccc(Cl)cc3Cl)cc(S(C)(O)O)c2)nc1] | 463.38 | 463 | + | *** |
| 388 | 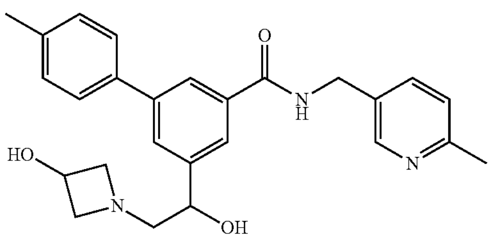 | 431.53 | 432.1 | +++ | **** |
| 389 | 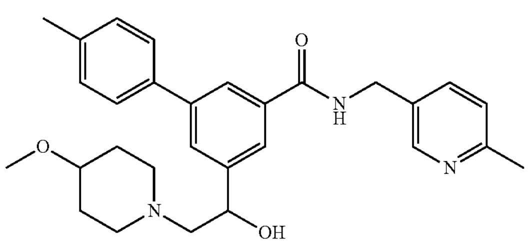 | 473.61 | 474.4 | +++ | **** |
| 390 | 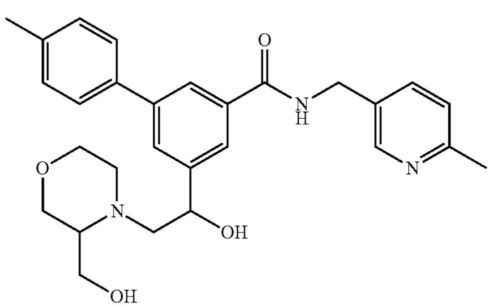 | 475.59 | 476.2 | ++++ | **** |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 391 | 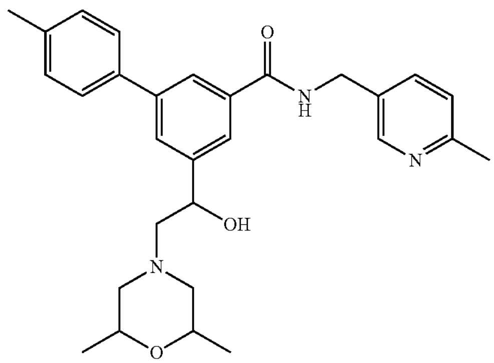 | 473.61 | 474.4 | ++++ | **** |
| 392 | 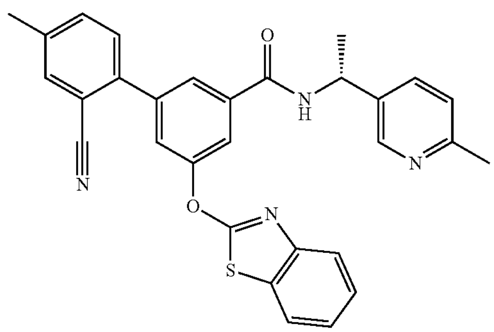 | 504.61 | 505.2 | +++ | *** |
| 393 | 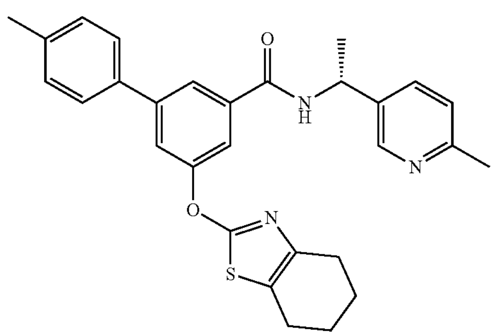 | 483.63 | 484.1 | +++ | *** |
| 394 | 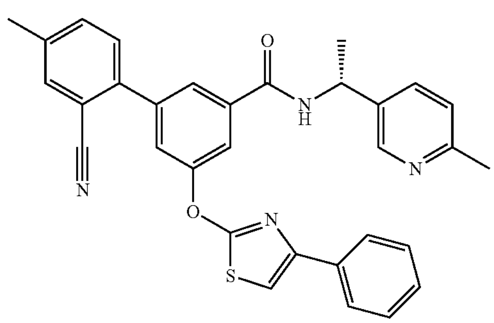 | 530.65 | 531.2 | | |

TABLE 1-continued

Ca Influx IC$_{50}$ of Exemplary Compounds

| ID | Structure | MW (Calcd) | MW (Obs) | IC$_{50}$ hP2X$_{2/3}$H (nM) | IC$_{50}$ hP2X$_3$ (nM) |
|---|---|---|---|---|---|
| 395 | 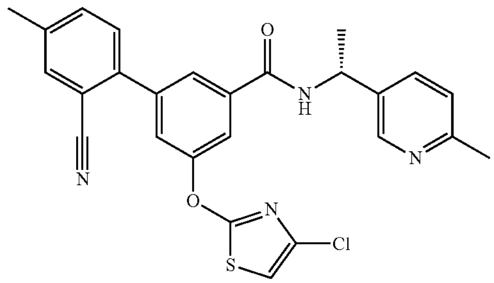 | 489 | 489.1 | ++++ | **** |
| 396 | 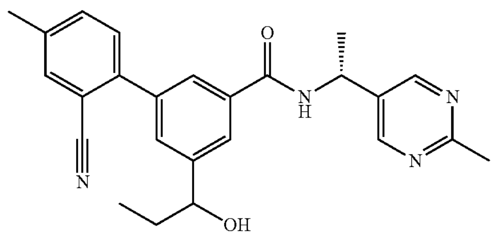 | 414.51 | 415.4 | ++++ | **** |
| 397 | 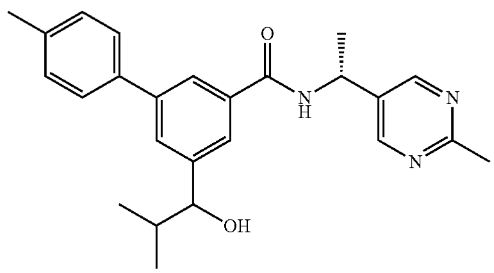 | 403.52 | 404.2 | ++++ | **** |
| 398 | 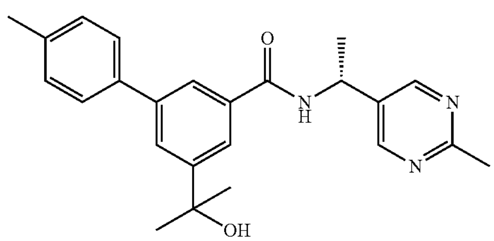 | 389.5 | 390.4 | ++++ | **** |
| 399 | 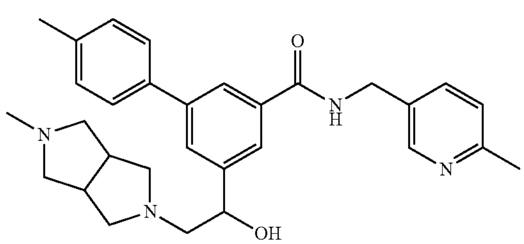 | 484.64 | 485.4 | ++ | *** |

From the foregoing description, various modifications and changes in the compositions and methods provided herein will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software

What is claimed is:

1. A compound having a formula 1:

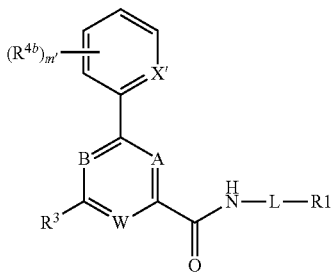

1 wherein
each of A, B, and W are independently selected from $CR^4$;
X' is N;
L is $-C(R^{2a}R^{2b})-$;
$R^1$ is selected from substituted or unsubstituted aryl, substituted or unsubstituted heteroaryl, hydroxy $C_1$-$C_4$ alkyl, $C_3$-$C_7$ cycloalkyl-$C_1$-$C_4$ alkyl, or 4-7 membered heterocycloalkyl-$C_1$-$C_4$ alkyl;
each of $R^{2a}$ and $R^{2b}$ is independently selected from hydrogen, $C_1$-$C_4$ alkyl, or hydroxy $C_1$-$C_4$ alkyl;
$R^3$ is $OR^{3a}$, CN, $COR^{3a}$, $COOR^{3a}$, $SOR^{3a}$, $CONR^{3a}R^{3b}$, $SONR^{3a}R^{3b}$, or $SO_2NR^{3a}R^{3b}$;
$R^{3a}$ is substituted or unsubstituted alkyl, substituted or unsubstituted cycloalkyl, substituted or unsubstituted heterocycloalkyl, substituted or unsubstituted aryl, or substituted or unsubstituted heteroaryl;
$R^{3b}$ is H, substituted or unsubstituted $C_1$-$C_6$ alkyl; or $R^{3a}$ and $R^{3b}$ join together to form a cycloheteroalkyl ring of 3-7 atoms;
each $R^4$ is independently selected from H, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, halo, nitro, and thiol;
each $R^{4b}$ is independently selected from H, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxy, substituted or unsubstituted alkoxycarbonyl, substituted or unsubstituted alkylarylamino, substituted or unsubstituted arylalkyloxy, substituted or unsubstituted amino, substituted or unsubstituted aryl, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol;

and subscript m' is selected from 0-4;
provided that
i) when $R^3$ is $CO_2Me$, or $OR^{3a}$; then $R^1$ is other than unsubstituted phenyl;
and
ii) when $R^1$ is 5-6 membered heterocycloalkylmethyl, and $R^3$ is $CO_2Me$; then $R^{4b}$ is other than Cl or 4-F;
or a pharmaceutically acceptable salt, N-oxide, stereoisomer or tautomer thereof.

2. A compound according to claim 1, wherein the compound is according to formula 2c, 2d, 2e, 2f, 2h, 2i, 2j, or 2k:

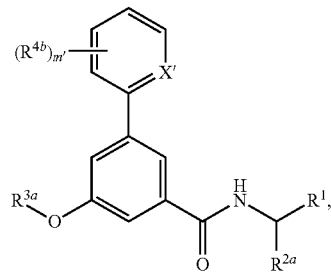

2c

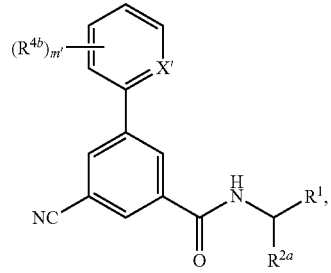

2d

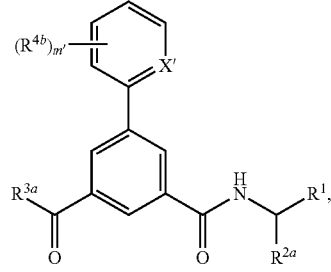

2e

-continued
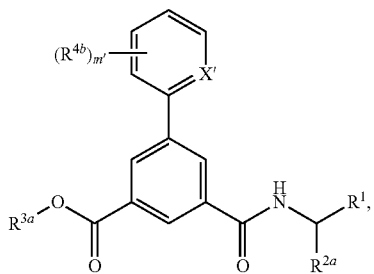
2f
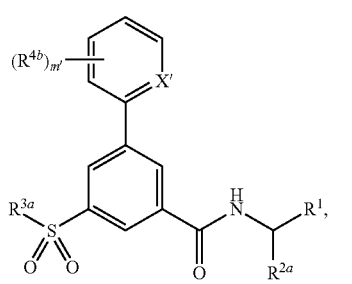
2g
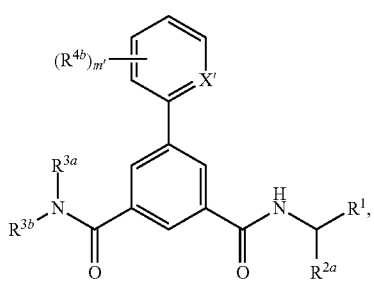
2h
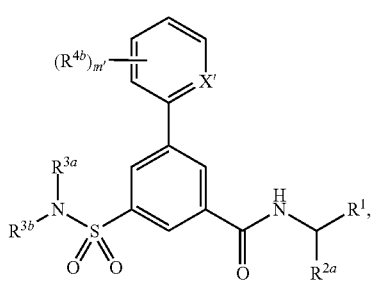
2i
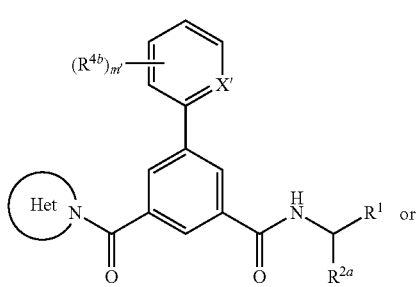
2j
-continued
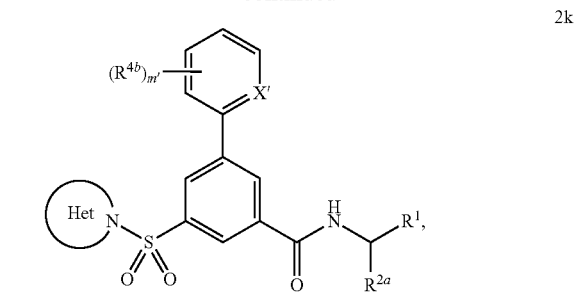
2k
wherein
X', R¹, R³ᵃ, R³ᵇ, R⁴ᵇ, and m' are as in claim 1; R²ᵃ is H, Me, $CH_2OH$, or $CH_2CH_2OH$; and Het is substituted or unsubstituted heterocycloalkyl; or a pharmaceutically acceptable salt, N-oxide, stereoisomer or tautomer thereof.
3. A compound according to claim 1, wherein the compound is according to formula 3c, 3d, 3e, 3f, 3h, 3i, 3j, or 3k:
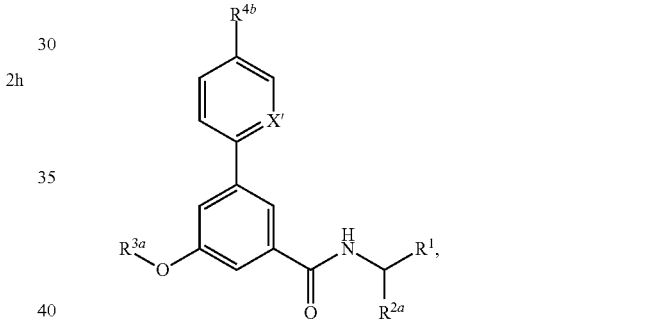
3c
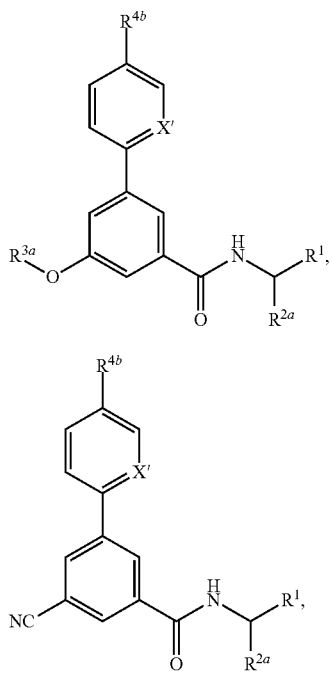
3d
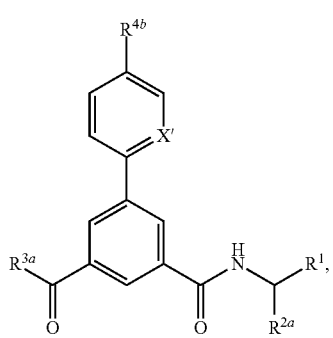
3e

373

-continued

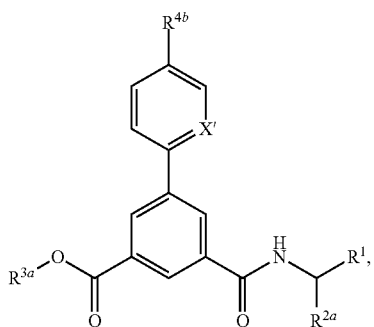
3f

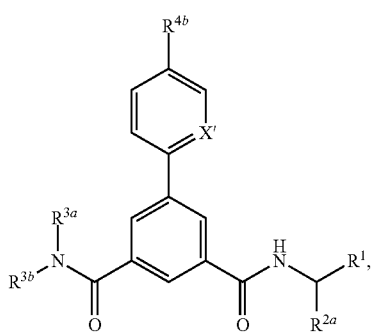
3h

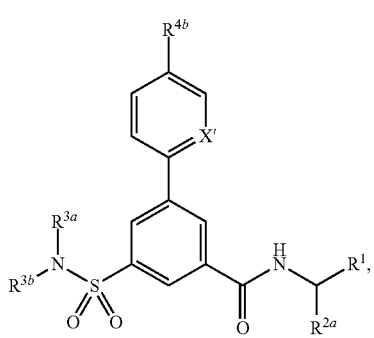
3i

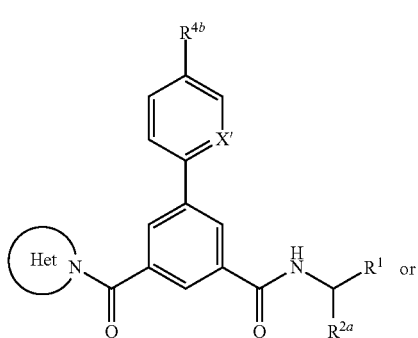
3j

374

-continued

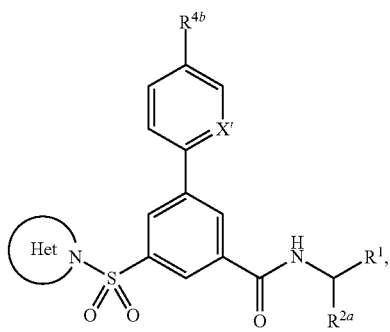
3k wherein
X', R¹, R³ᵃ, R³ᵇ, and R⁴ᵇ, are as in claim 1;
R²ᵃ is H, Me, CH₂OH, or CH₂CH₂OH; and Het is substituted or unsubstituted heterocycloalkyl; or a pharmaceutically acceptable salt, N-oxide, stereoisomer or tautomer thereof.

4. A compound according to any one of claims 1, 2, and 3, wherein R³ᵃ is substituted or unsubstituted alkyl.

5. A compound according to any one of claims 1, 2, and 3, wherein R³ᵃ is pyridylmethyl, piperidinylmethyl, piperazinylmethyl, pyrrolidinylmethyl, morpholinylmethyl, pyridylethyl, piperidinylethyl, piperazinylethyl, pyrrolidinylethyl, or morpholinylethyl.

6. A compound according to any one of claims 1, 2, and 3, wherein R³ᵃ is cyclopropyl, cyclopentyl, cyclopropylmethyl, or cyclopentylmethyl.

7. A compound according to any one of claims 1, 2, and 3, wherein R³ᵃ is substituted or unsubstituted heteroaryl.

8. A compound according to any one of claims 1, 2, and 3, wherein R³ᵃ is pyrrolyl, furanyl, thiophenyl, pyrazolyl, imidazolyl, oxazolyl, thiazolyl, triazolyl, thiadiazolyl, unsubstituted or substituted with alkyl or haloalkyl.

9. A compound according to any one of claims 1, 2, and 3, wherein R³ᵃ is selected from substituted or unsubstituted phenyl, pyridyl, pyrazinyl, pyrimidinyl, quinolinyl, isoquinolinyl, methylenedioxyphenyl, imidazopyridyl, benzoxazolyl, benzothiazolyl, and indolyl.

10. A compound according to any one of claims 1, 2, and 3, wherein R³ᵃ is

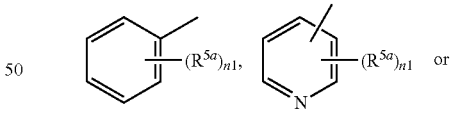

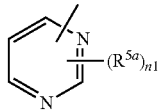

and wherein subscript n1 is selected from 1-5 and each R⁵ᵃ is independently selected from hydrogen, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, sulfo, substituted sulfo, substituted sulfinyl, substituted sulfonyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol.

11. A compound according to either of claim 2, or 3, wherein $R^{3b}$ is H or alkyl.

12. A compound according to either of claim 2, or 3, wherein Het is azetidin-1-yl, pyrrolidin-1-yl, piperidin-1-yl, morpholin-1-yl, piperazin-1-yl, and azepin-1-yl, unsubstituted or substituted with one or more groups selected from alkyl, alkoxy, dialkylamino, halo, haloalkyl, hydroxy, or hydroxyalkyl.

13. A compound according to claim 1, wherein the compound is according to formula 4, 5, 6, 7, 8, or 9:

4

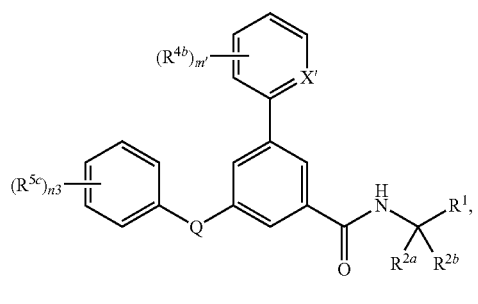

5

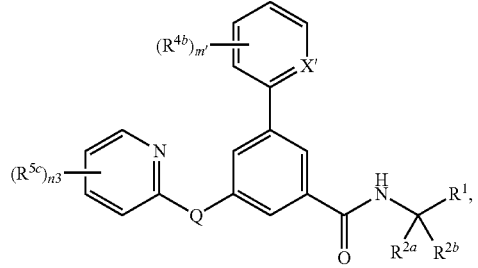

6

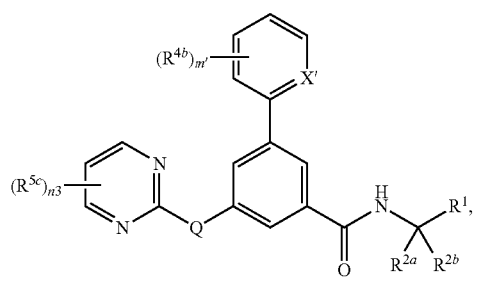

7

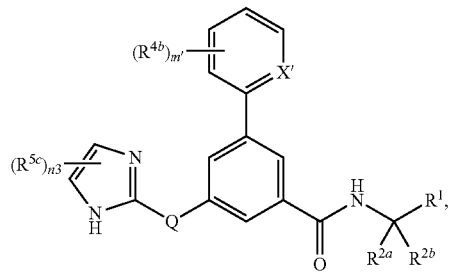

8

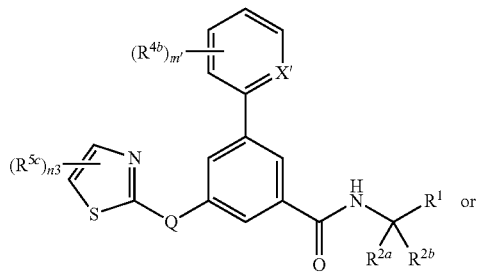

9

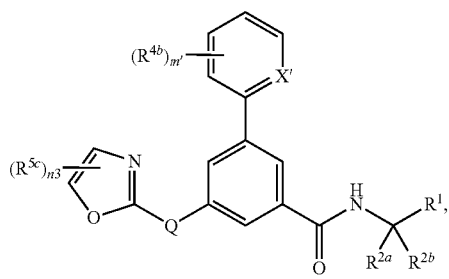

wherein

X', $R^1$, $R^{4b}$; and m' are as in claim 1; $R^{5c}$ is $R^{5a}$; the subscript n3 is 1, 2, or 3; and $R^{5a}$ is selected from hydrogen, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, sulfo, substituted sulfo, substituted sulfinyl, substituted sulfonyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol;

$R^{2a}$ is H, Me, $CH_2OH$, or $CH_2CH_2OH$; $R^{2b}$ is H; and Q is —O— or a pharmaceutically acceptable salt, stereoisomer or tautomer thereof.

14. A compound according to claim 1, wherein the compound is according to formula 10, 11, 12, 13, 14, or 15:

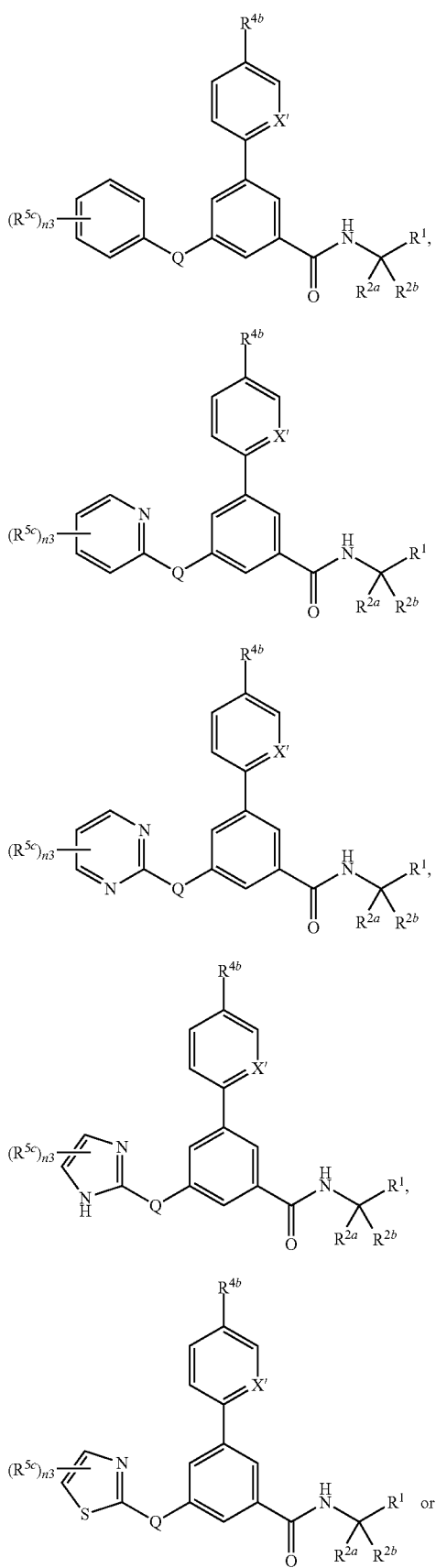

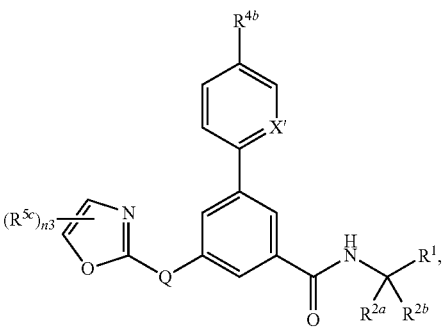

wherein
X', R¹, and R⁴ᵇ are as in claim 1; R⁵ᶜ is H, Cl, F, Me, OMe, or CF₃; and the subscript n3 is 1 or 2;
R²ᵃ is H, Me, CH₂OH, or CH₂CH₂OH; R²ᵇ is H; and Q is —O—;
or a pharmaceutically acceptable salt, stereoisomer or tautomer thereof.

15. A compound according to any one of claims 1, 2, 3, and 14, wherein R⁴ᵇ is H, C₁-C₄ alkyl, halo C₁-C₄ alkyl or halo.

16. A compound according to any one of claims 1, 2, 3, and 14, wherein R¹ is substituted or unsubstituted aryl or heteroaryl.

17. A compound according to any one of claims 1, 2, 3, and 14, wherein R¹ is selected from substituted or unsubstituted phenyl, pyridyl, pyrazinyl, thiazolyl, pyrimidinyl, quinolinyl, isoquinolinyl, methylenedioxyphenyl, imidazopyridyl, benzoxazolyl, benzothiazolyl, and indolyl.

18. A compound according to any one of claims 1, 2, 3, and 14, wherein R¹ is

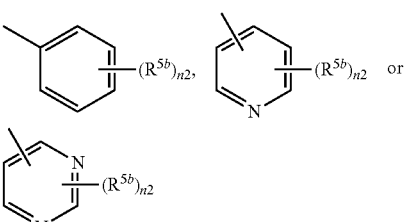

and wherein subscript n2 is selected from 1-5 and each R⁵ᵇ is independently selected from hydrogen, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, sulfo, substituted sulfo, substituted sulfinyl, substituted sulfonyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol.

19. A compound according to any one of claims 1, 2, 3, and 14, wherein R¹ is

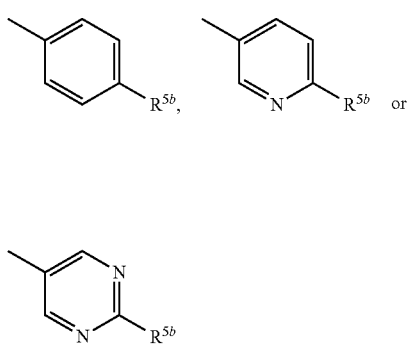

and wherein $R^{5b}$ is selected from hydrogen, substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxy, aryloxy, alkoxycarbonyl, substituted alkoxycarbonyl, substituted or unsubstituted alkylarylamino, arylalkyloxy, substituted arylalkyloxy, amino, aryl, substituted aryl, arylalkyl, sulfo, substituted sulfo, substituted sulfinyl, substituted sulfonyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol.

20. A compound according to claim 19, wherein each $R^{5b}$ is independently selected from H, alkyl, halo, cyano, alkoxy, and haloalkyl.

21. A compound according to claim 1, wherein $R^{2a}$ is methyl, hydroxymethyl or hydroxyethyl.

22. A compound according to claim 1, selected from
3-(4-Hydroxy-pyrrolidin-3-yloxy)-5-(5-methyl-pyridin-2-yl)-N—[(R)-1-(2-methyl-pyrimidin-5-yl)-ethyl]-benzamide;

| ID | Structure |
|---|---|
| 28 | 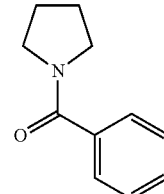 |
| 99 | 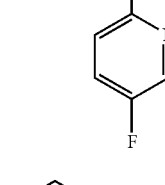 |
| 106 | 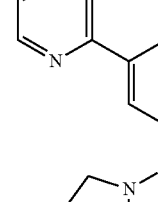 |
| 118 | 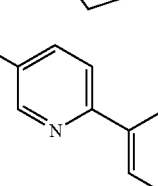 |
| 122 | 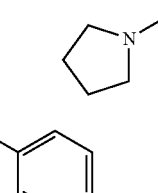 |
| 123 | 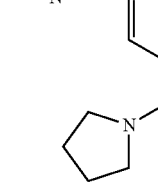 |

381
-continued
| ID | Structure |
|---|---|
| 135 | 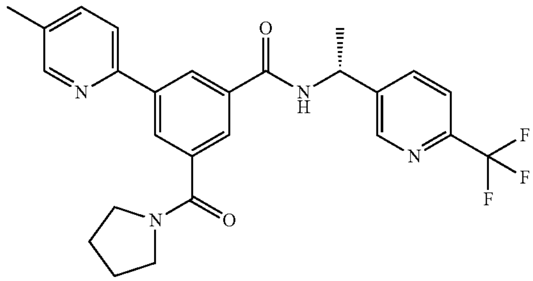 [SMILES: Cc1ccc(-c2cc(C(=O)N[C@H](C)c3ccc(C(F)(F)F)nc3)cc(C(=O)N3CCCC3)c2)nc1] |
| 145 | 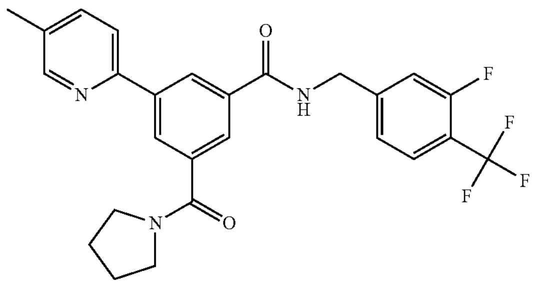 [SMILES: Cc1ccc(-c2cc(C(=O)NCc3ccc(C(F)(F)F)c(F)c3)cc(C(=O)N3CCCC3)c2)nc1] |
| 146 | 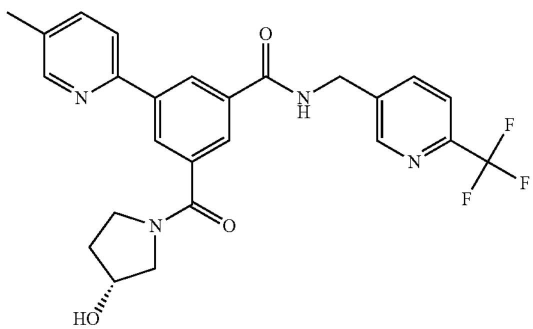 [SMILES: Cc1ccc(-c2cc(C(=O)NCc3ccc(C(F)(F)F)nc3)cc(C(=O)N3CC[C@@H](O)C3)c2)nc1] |
| 150 | 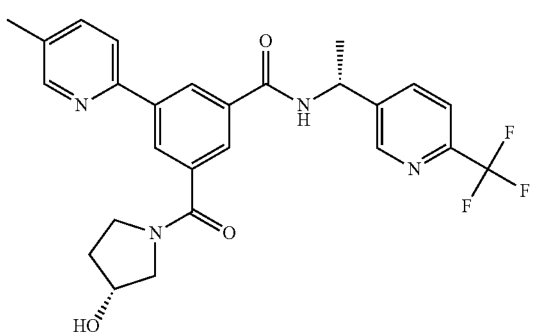 [SMILES: Cc1ccc(-c2cc(C(=O)N[C@H](C)c3ccc(C(F)(F)F)nc3)cc(C(=O)N3CC[C@@H](O)C3)c2)nc1] |
| 151 | 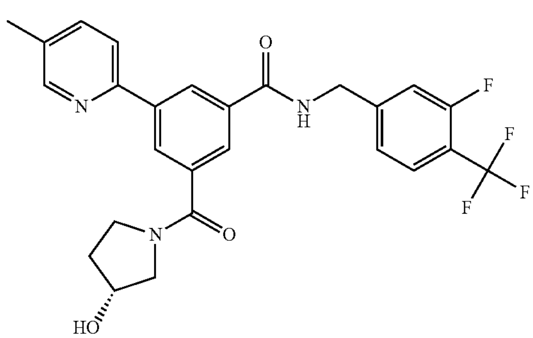 [SMILES: Cc1ccc(-c2cc(C(=O)NCc3ccc(C(F)(F)F)c(F)c3)cc(C(=O)N3CC[C@@H](O)C3)c2)nc1] |
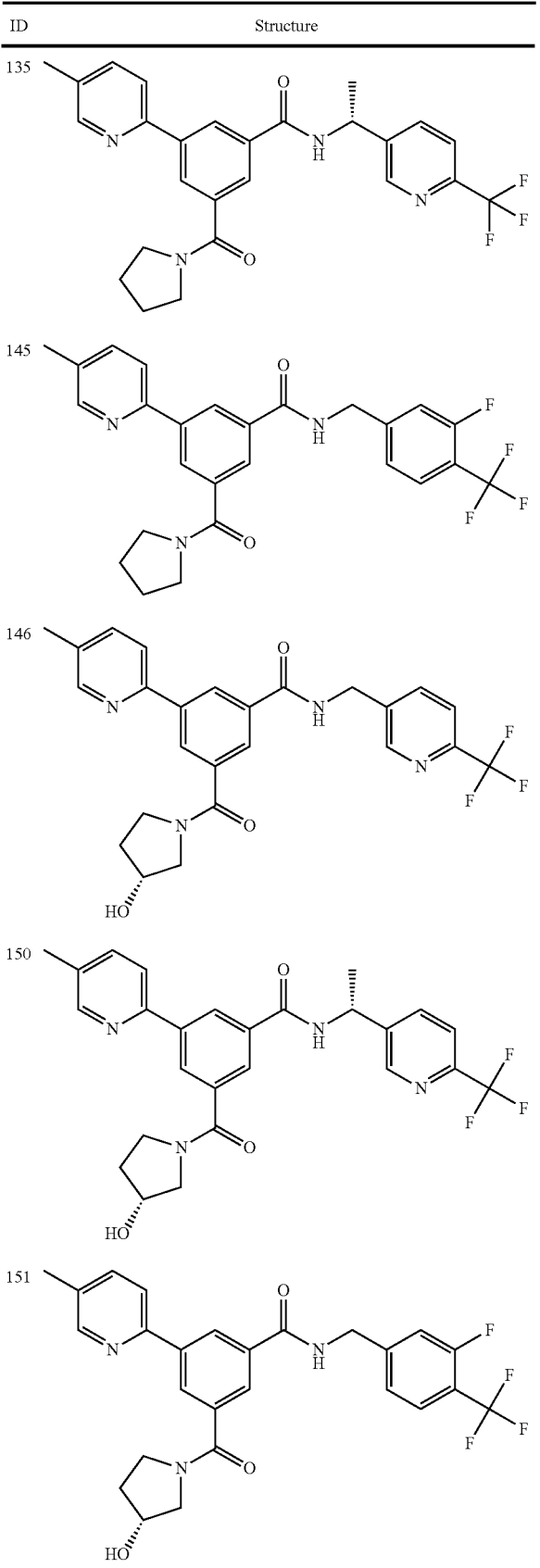
382
-continued
| ID | Structure |
|---|---|
| 155 | 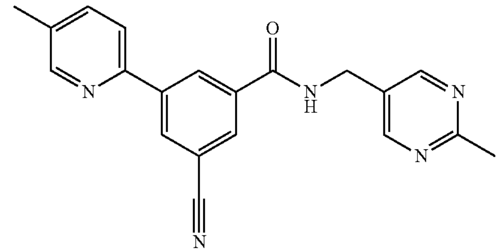 |
| 160 | 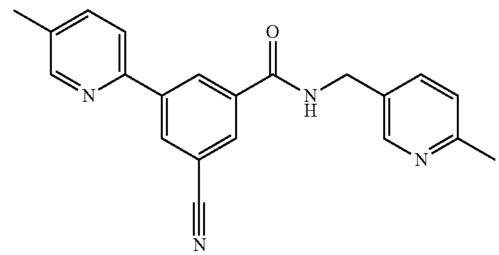 |
| 173 | 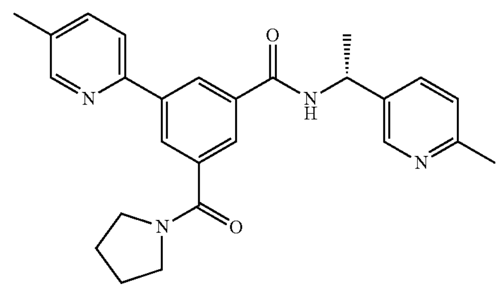 |
| 174 | 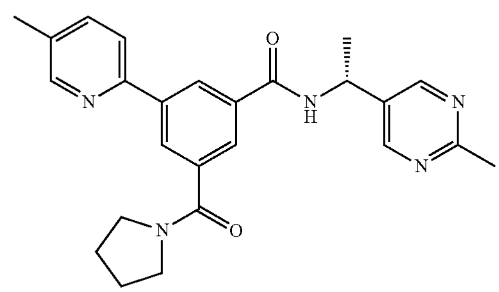 |
| 175 | 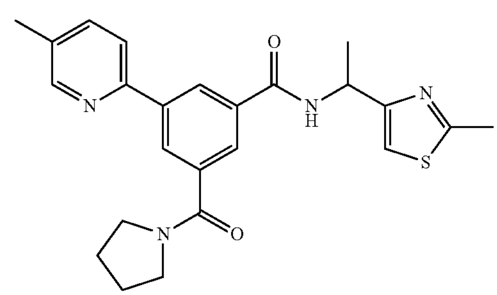 |
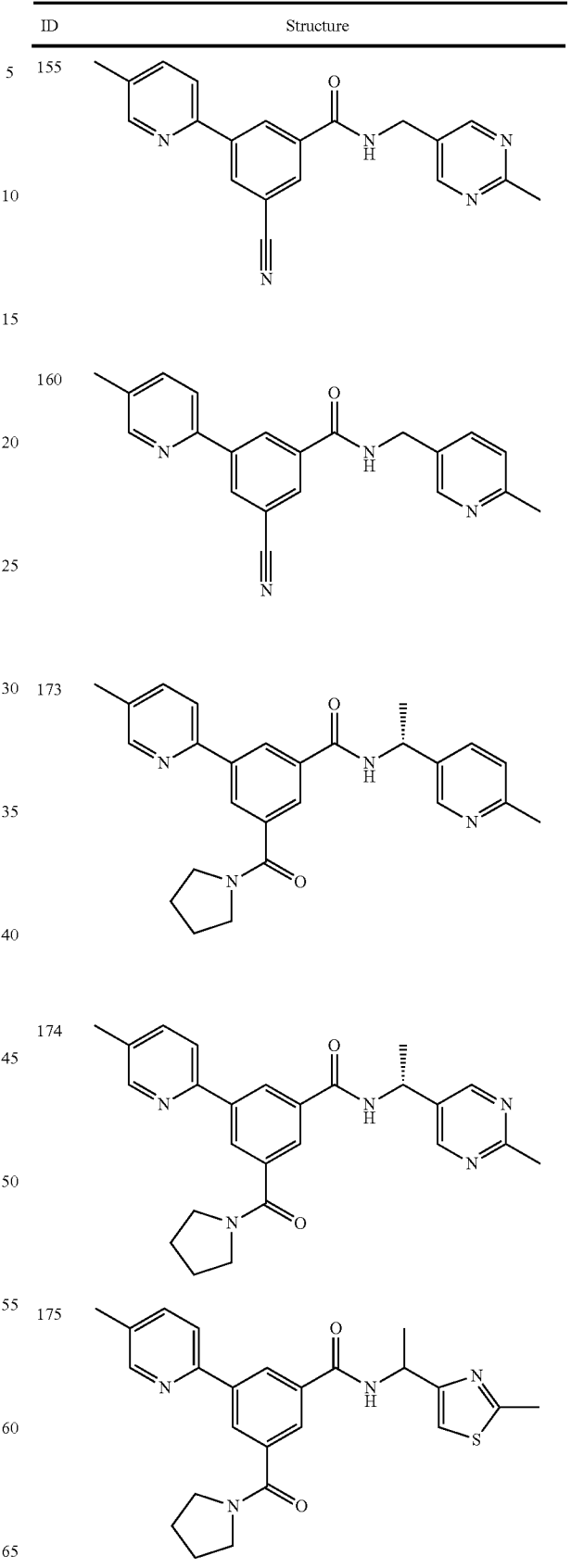

383
-continued
| ID | Structure |
|---|---|
| 178 | 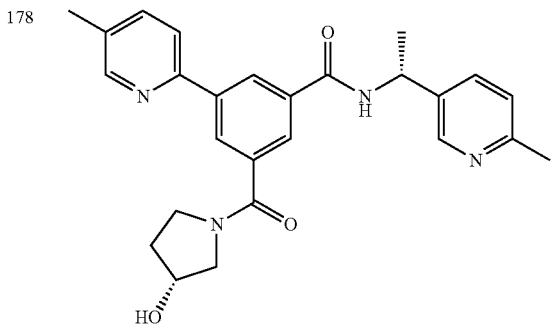 |
| 179 | 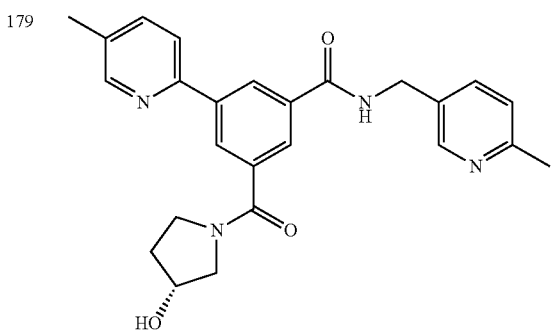 |
| 220 | 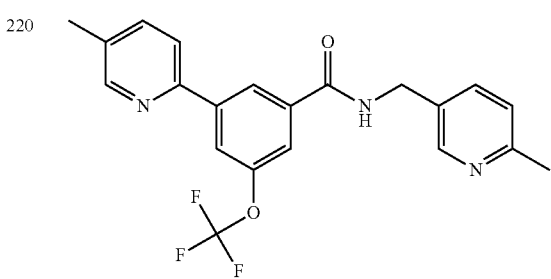 |
| 225 | 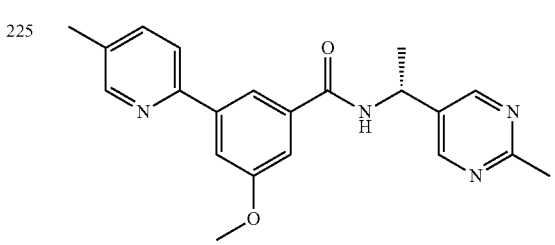 |
| 264 | 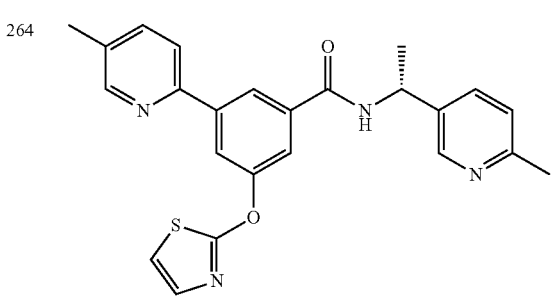 |
384
-continued
| ID | Structure |
|---|---|
| 265 | 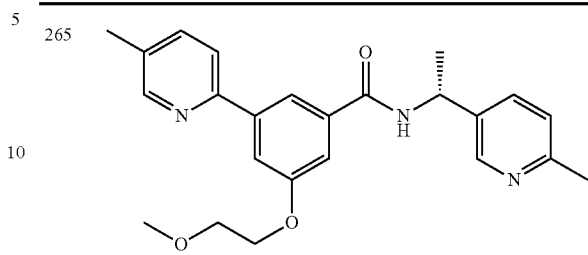 |
| 266 | 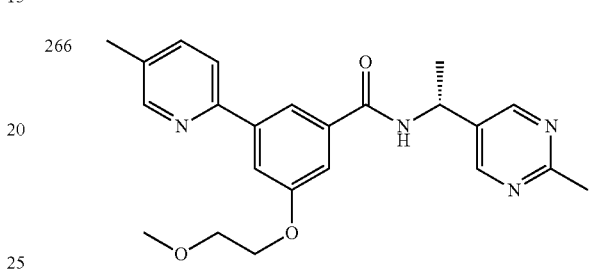 |
| 269 | 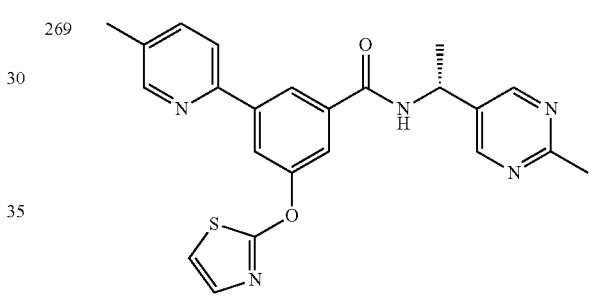 |
| 270 | 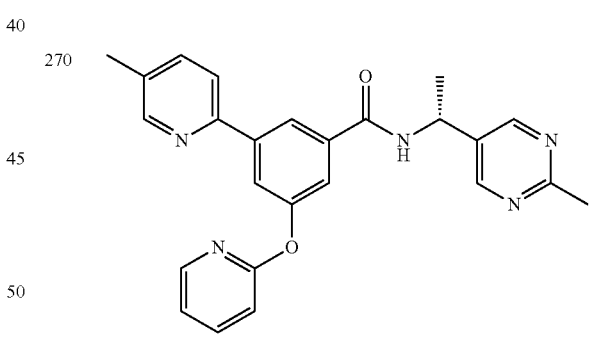 |
| 271 | 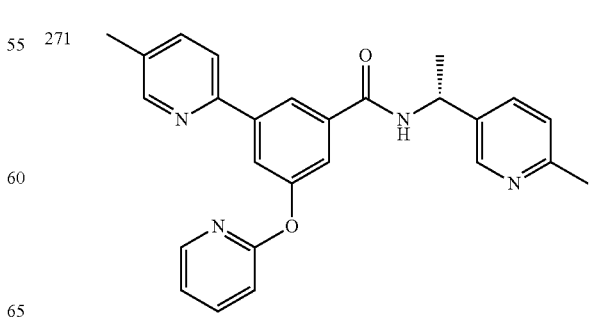 |

| ID | Structure |
|---|---|
| 272 | 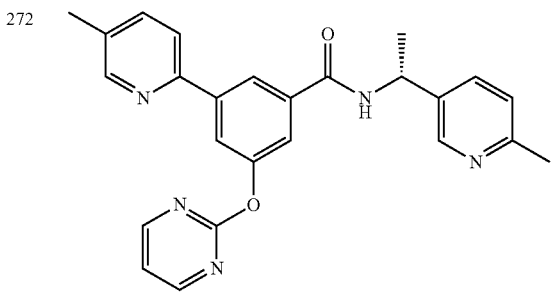 |
| 273 | 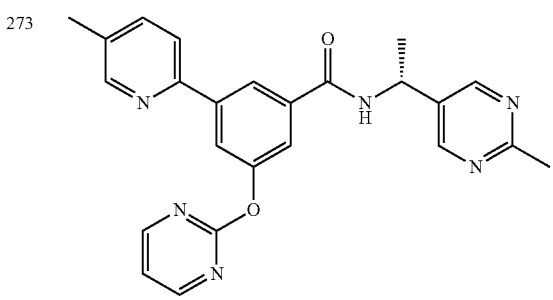 |
| 328 | 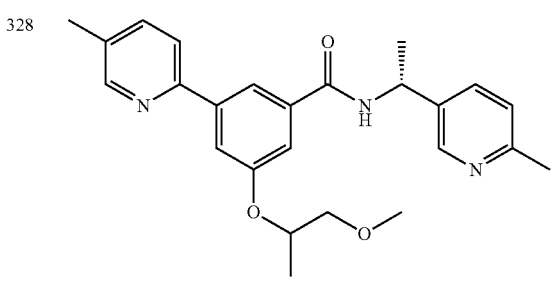 |
| 329 | 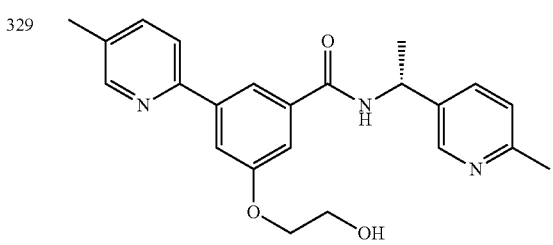 |
| 332 | 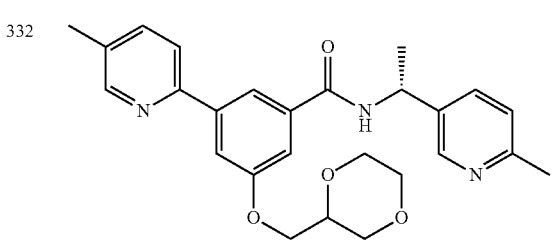 |
| ID | Structure |
|---|---|
| 333 | 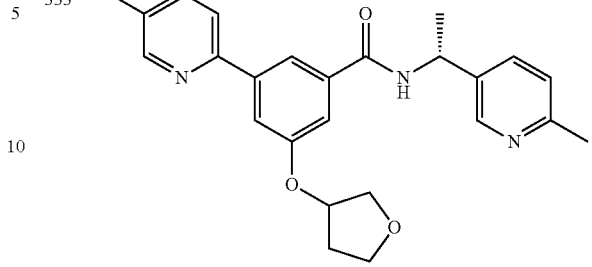 |
| 334 | 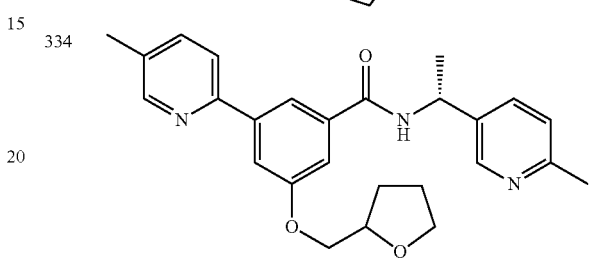 |
| 335 | 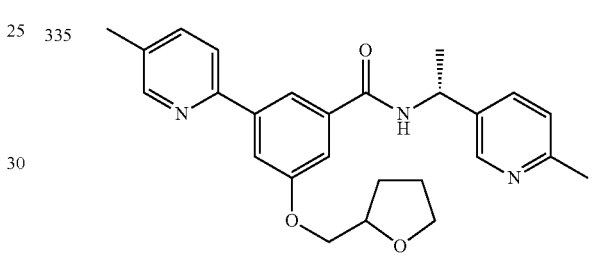 |
| 339 | 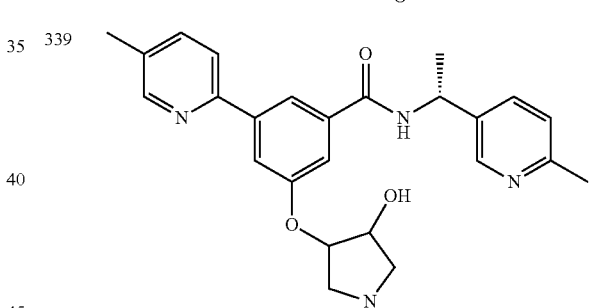 |
| 344 | 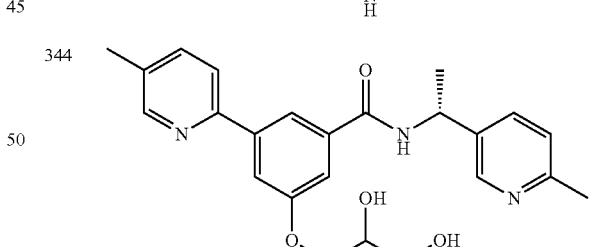 |
| 345 | 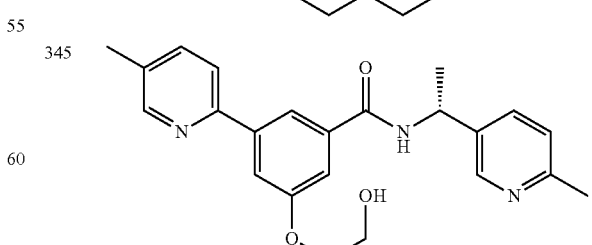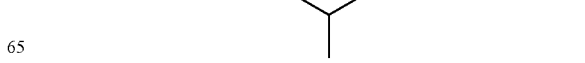 |

| ID | Structure |
|---|---|
| 347 | 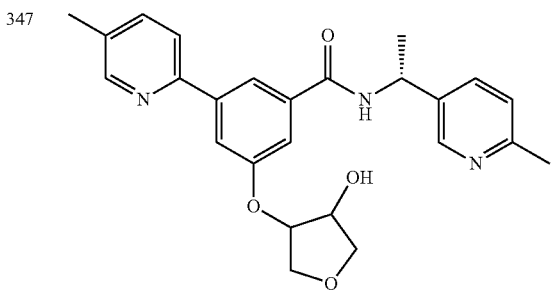 |
| 348 | 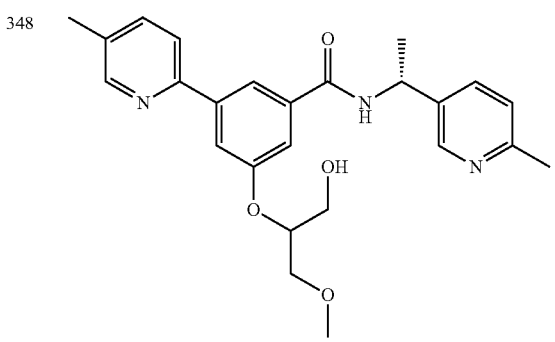 |
| 349 | 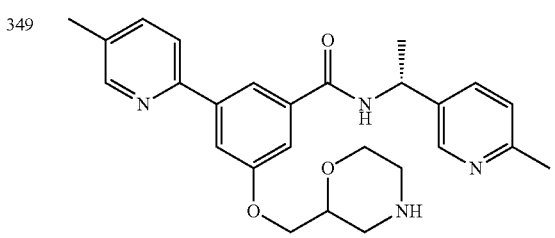 |
| 355 | 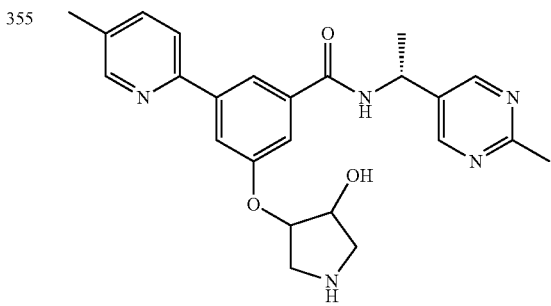 |
| 357 | 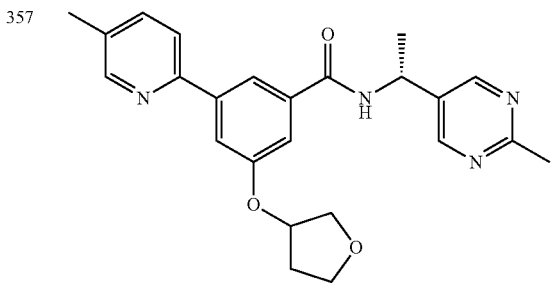 |
| ID | Structure |
|---|---|
| 364 | 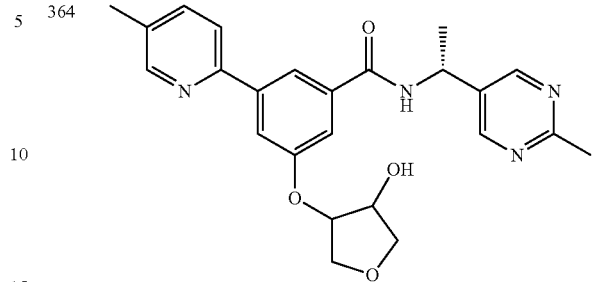 |
| 372 | 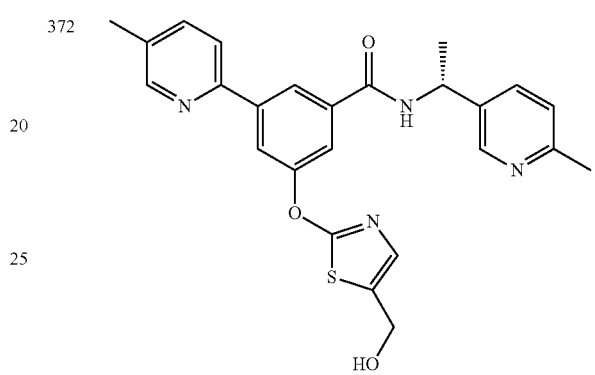 |
| 374 | 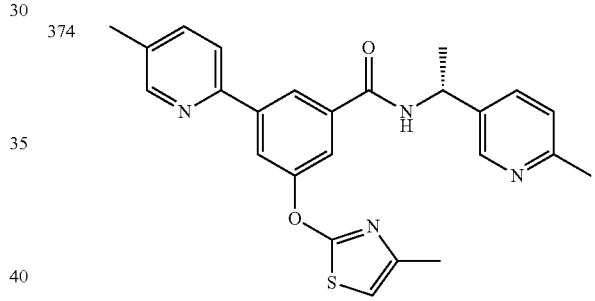 |
| 375 | 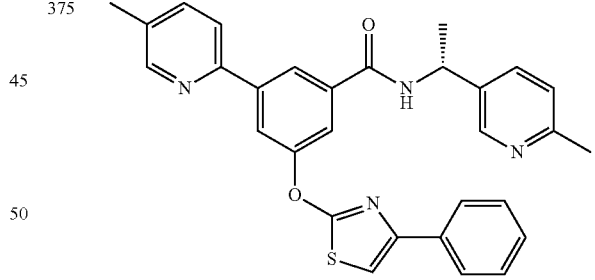 |
| 376 | 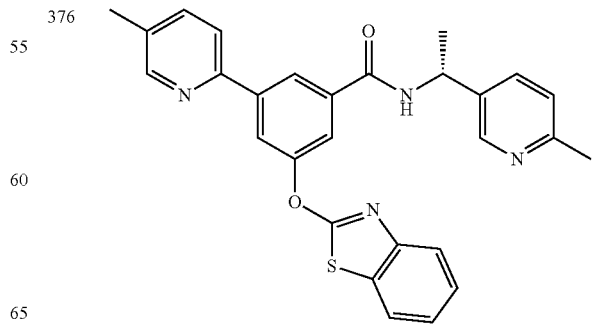 |

| ID | Structure |
|---|---|
| 384 | ![Structure 384: 5-methylpyridin-2-yl substituted benzamide with (S)-1-(6-methylpyridin-3-yl)ethylamide and 4-chlorothiazol-2-yloxy groups] | or a pharmaceutically acceptable salt, stereoisomer or tautomer thereof.

23. A pharmaceutical composition comprising a pharmaceutically acceptable carrier and a pharmaceutically effective amount of a compound of claim 1.

24. The pharmaceutical composition of claim 23, wherein the carrier is suitable for parenteral, oral, or topical administration.

25. A method for treating in a mammal in need thereof a disease or condition which comprises administering to the mammal an effective disease-treating or condition-treating amount of a compound according to claim 1, or a pharmaceutical composition according to any one of claims 23-24, wherein the disease or condition is selected from: rheumatoid arthritis.

* * * * *